United States Patent [19]
Kim et al.

[11] Patent Number: 5,856,134
[45] Date of Patent: Jan. 5, 1999

[54] HEPATITIS G VIRUS AND MOLECULAR CLONING THEREOF

[75] Inventors: Jungsuh P. Kim; Kirk E. Fry; LaVonne Marie Young, all of Palo Alto; Jeffrey M. Linnen, Foster City, all of Calif.; John Wages, Corvallis, Oreg.

[73] Assignee: Genelabs Technologies, Inc., Redwood City, Calif.

[21] Appl. No.: 461,361

[22] Filed: Jun. 5, 1995

Related U.S. Application Data

[60] Division of Ser. No. 444,733, May 19, 1995, which is a continuation-in-part of Ser. No. 344,271, Nov. 23, 1994, abandoned, which is a continuation-in-part of Ser. No. 285,561, Aug. 3, 1994, abandoned, which is a continuation-in-part of Ser. No. 246,985, May 20, 1994, abandoned, said Ser. No. 444,733, is a continuation-in-part of Ser. No. 389,886, Feb. 15, 1995, abandoned, which is a continuation-in-part of Ser. No. 357,509, Dec. 16, 1994, abandoned, which is a continuation-in-part of Ser. No. 329,729, Oct. 26, 1994, abandoned, which is a continuation-in-part of Ser. No. 285,558, Aug. 3, 1994, abandoned, and Ser. No. 285,543, Aug. 3, 1994, abandoned, said Ser. No. 285,558, and Ser. No. 285,543, each is a continuation-in-part of Ser. No.246, 985.

[51] Int. Cl.⁶ .............................. C12P 21/02; A61K 39/29
[52] U.S. Cl. ........................................ 435/69.3; 424/189.1
[58] Field of Search ................................ 530/324, 388.3, 530/387.1; 536/23.1; 435/5; 424/184.1

[56] References Cited

U.S. PATENT DOCUMENTS

| | | | |
|---|---|---|---|
| 4,810,492 | 3/1989 | Fujita et al. | 424/88 |
| 4,870,026 | 9/1989 | Wands et al. | 436/548 |
| 5,032,511 | 7/1991 | Takahashi et al. | 435/69.1 |
| 5,077,193 | 12/1991 | Mishiro et al. | 435/5 |
| 5,218,099 | 6/1993 | Reyes et al. | 536/23.72 |
| 5,275,947 | 1/1994 | Arima et al. | 435/252.33 |

FOREIGN PATENT DOCUMENTS

| | | |
|---|---|---|
| 0 318 216 | 5/1989 | European Pat. Off. . |
| 363 025 | 4/1990 | European Pat. Off. . |
| WO 90/00597 | 1/1990 | WIPO . |
| WO 91/06562 | 5/1991 | WIPO . |
| WO 91/15603 | 10/1991 | WIPO . |
| WO 94/18217 | 8/1994 | WIPO . |
| WO 95/21922 | 8/1995 | WIPO . |

OTHER PUBLICATIONS

Murphy, F.A., "Virus taxonomy", pp. 15–57 in Fields Virology, vol. 1, Lippincott–Raven Publishers, Philadelphia, 1996.

Farci et al., Lack of protective Immunity against reinfection with hepatits C virus, Science, vol. 258, pp. 135–140, Oct. 2, 1992.

U.S. application No. 08/196,030, Simons et al., filed Feb. 14, 1994.

U.S. application No. 08/242,654, Simons et al., filed May 13, 1994.

Bradley, D.W.., et al., "Posttransfusion Non–A, Non–B Hepatitis: Physicochemical Properties of Two Distinct Agents," *The Journal of Infectious Diseases*, 148(2):254–265 (1983).

Buti, M., et al., "Non–A, Non–B, Non–C, Non–E Acute Hepatitis: Does It Really Exist?" *Journal of Hepatology, The Journal of the European Association for the Study of the Liver*, in Abstracts of the 28th Annual Meeting of the European Association for the Study of the Liver, 1–4 Sep. 1993, Paris, France. 18(Suppl 1):S25 (1993).

Chan, S.W., et al., "Analysis of a new hepatitis C virus type and its phylogenetic relationship to existing variants," *Journal of General Virology*, 73(5):1131–1141 (1992).

Choo, Q–L., et al., "Isolation of a cDNA Clone Derived from a Blood–Borne Non–A, Non–B Viral Hepatitis Genome," *Science*, 244:359–362 (1989).

Jiang, X., et al., "Norwalk Virus Genome Cloning and Characterization," *Science*, 250:1580–1583 (1990).

Jones, W.F., et al., "The Role of Hepatitis C Virus (HCV) and Hepatitis E Virus (HEV) in Acute Hepatitis: Evidence for a Non–A,B,C,D,E Syndrome," *The American Association for the Study of Liver Diseases*, 16(2 Pt. 2):77A (1992).

Karayiannis, P., et al., "Studies of GB Hepatitis Agent in Tamarins," *Hepatology*, 9(2):186–192 (1989).

Matsui, S.M., et al., "The Isolation and Characterization of a Norwalk Virus–specific cDNA," *J. Clin. Invest.*, 87:1456–1461 (1991).

Matsuura, Y., et al., "Expression of the S–coded Genes of Lymphocytic Choriomeningitis Arenavirus using a Baculovirus Vector," *J. Gen Virol.*, 67:1515–1529 (1986).

Overton, H.A., et al., "Identification of the N and $NS_s$ Proteins Coded by the Ambisense S RNA of Punta Toro Phlebovirus Using Monospecific Antisera Raised to Baculovirus Expressed N and NSs Proteins," *Virology*, 157:338–350 (1987).

Reyes, G.R., et al., "Molecular Biology of Non–A, Non–B Hepatitis Agents: Hepatitis C and Hepatitis E Viruses," *Advances in Virus Research*, 40:57–103 (1991).

(List continued on next page.)

*Primary Examiner*—Michael P. Woodward
*Assistant Examiner*—Brenda Glass Brumback
*Attorney, Agent, or Firm*—Gary R. Fabian; Susan T. Evans; Peter J. Dehlinger

[57] ABSTRACT

Polypeptide antigens are disclosed which are immunoreactive with sera from individuals having a non-A, non-B, non-C, non-D, non-E Hepatitis, herein designated Hepatitis G Virus (HGV). Corresponding genomic-fragment clones containing polynucleotides encoding the open reading frame sequences for the antigenic polypeptides are taught. The antigens are useful in diagnostic methods for detecting the presence of HGV in test subjects. The antigens are also useful in vaccine and antibody preparations. In addition, the entire coding sequences of two HGV isolates are disclosed. Methods are presented for nucleic acid-based detection of HGV in samples and also methods for the isolation of further genomic sequences corresponding to HGV.

6 Claims, 17 Drawing Sheets

OTHER PUBLICATIONS

Reyes, G.R., "New Strategies for Isolation of Low Abundance Viral and Host cDNAs: Application to Cloning of the Hepatitis E Virus and Analysis of Tissue–Specific Transcription," *Seminars in Liver Diseases*, 12(3):289–300 (1992).

Reyes, G.R., et al., "Hepatitis E virus (HEV): epitope mapping and detection of strain variation," in Viral Hepatitus C, D, and E. Proceedings of the International Meeting on Non–A, Non–B Hepatitus, Tokyo, 27–30 Sep. 1989, T. Shikata, et al., eds., Elsevier Science Publishers, Amsterdam, NL. Chapter 43:237–245 (1989).

```
HGV
HoCV    ykwvkqkpvvipgyegktplfqifdkvkkewdqfgnpvavsfDtkawDdtqvttndlelik
              3490          3500          3510          3520          3530          3540
                     10            20            30

```
                                            10        20        30
                                                 *....*
HGV                              lweskktpcaicvDatcfDssiteedvalet
                                 :.:::.: ... :. ::::..::.:. .:.
HCV  vvstlpqvvmgssygfqyspgqrveflvntwkskknpmgfsyDtrcfDstvtendirvee
     2600      2610      2620      2630      2640      2650

40        50        60        70        80
                                           *.**...*...*
HGV  elya---lasdhpewvra-pgkyyasgtmvtpegvpvgerycRsSGvltTsasNcltcyi
     ..:.   ::.. .. ... ... : .:......:   : : ::.:::::::: .: ::::.
HCV  siyqccdlapearqaikslterlyiggpltnskgqncgyrrcRaSGvltTscgNtltcyl
     2660      2670      2680      2690      2700      2710

90       100       110       120       130       140
                        ***
HGV  kvkaacervglknvslliaGDDcliicerpvcdpsdalgralasygyacepsyhasldta
     :..:::  . :.. ..:..::: ..:::..   . ..:  :....
HCV  kasaacraaklqdctmlvnGDDlvvicesagtqedaaslrvfteamtrysappgdppqpe
     2720      2730      2740      2750      2760      2770
```

Fig. 5B

```
               Thrombin cleavage
  #j26         |    \/    |    |GE3-2- - - - - - - - - - - - - - - - - - - - ->
    K   S   D   L   V   P   R   G   S   M   V   S   W   D   A   D   A   R   A   P
   *           *           *           *           *           *
   1          11          21          31          41          51
   CAAAATCGGATCTGGTTCCGCGTGGTTCCATGGTCTCATGGGACGCGGACGCTCGTGCGC
                                   C^CATGG(NcoI)

- - - - - - - - - - - - - - - - - - - - - - - - - - - - - - - - - - - - - - - ->
    A   M   V   Y   G   P   G   Q   S   V   T   I   D   G   E   R   Y   T   L   P
   *           *           *           *           *           *
  61          71          81          91         101         111
   CCGCGATGGTCTATGGCCCTGGGCAAAGTGTTACCATTGACGGGGAGCGCTACACCTTGC
        ^Base mutated to remove NcoI site            AGC^GCT(Eco47III)

- - - - - - - - - - - - - - - - - - - - - - - - - - - - - - - - - - - - - - - ->
    H   Q   L   R   L   R   N   V   A   P   S   E   V   S   S   E   V   S   I   D
   *           *           *           *           *           *
  121         131         141         151         161         171
   CTCATCAACTGAGGCTCAGGAATGTGGCACCCTCTGAGGTTTCATCCGAGGTGTCCATTG

- - - - - - - - - - - - - - - - - - - - - - - - - - - - - - - - - - - - - - - ->
    I   G   T   E   T   E   D   S   E   L   T   E   A   D   L   P   P   A   A   A
   *           *           *           *           *           *
  181         191         201         211         221         231
   ACATTGGGACGGAGACTGAAGACTCAGAACTGACTGAGGCCGATCTGCCGCCGGCGGCTG
                  CTGAAG(Eco57I_16/14->)                 GCC^GGC(NaeI)
     CTTCAG(<-14/16_Eco57I)

- - - - - - - - - - - - - - - - - - - - - - - - - - - - - - - - - - - - - - - ->
    A   L   Q   A   I   E   N   A   A   R   I   L   E   P   H   I   D   V   I   M
   *           *           *           *           *           *
  241         251         261         271         281         291
   CTGCTCTCCAAGCGATCGAGAATGCTGCGAGGATTCTTGAACCGCACATTGATGTCATCA
                      CGAT^CG(PvuI)
              GAATGCN^(BsmI)

- - - - - - - - - - - - - - - - - - - - - - - - - - - - - - - - - - - - - - - ->
    E   D   C   S   T   P   S   L   C   G   S   S   R   E   M   P   V   W   G   E
   *           *           *           *           *           *
  301         311         321         331         341         351
   TGGAGGACTGCAGTACACCCTCTCTTTGTGGTAGTAGCCGAGAGATGCCTGTATGGGGAG
         CTGCA^G(PstI)

- - - - - - - - - - - - -END-GE3-2>|         poly His for IMAC
    D   I   P   R   T   P   S   P   A   L   I   G   S   H   H   H   H   H   Z    <- - - -NOTE
   *           *           *           *           *           *
  361         371         381         391         401         411
   AAGACATCCCCCGTACTCCATCGCCAGCACTTATCGGATCCCACCATCACCATCACCATT
                                       G^GATCC(BamHI)

|pGEX- - - - - - - - - - - - - - - - ->
    N   S   S   Z   L   T   D   D   L   P
   *           *           *           *
  421         431         441         451                Fig. 6
   AGAATTCATCGTGACTGACTGACGATCTACCT
    G^AATTC(EcoR1)
```

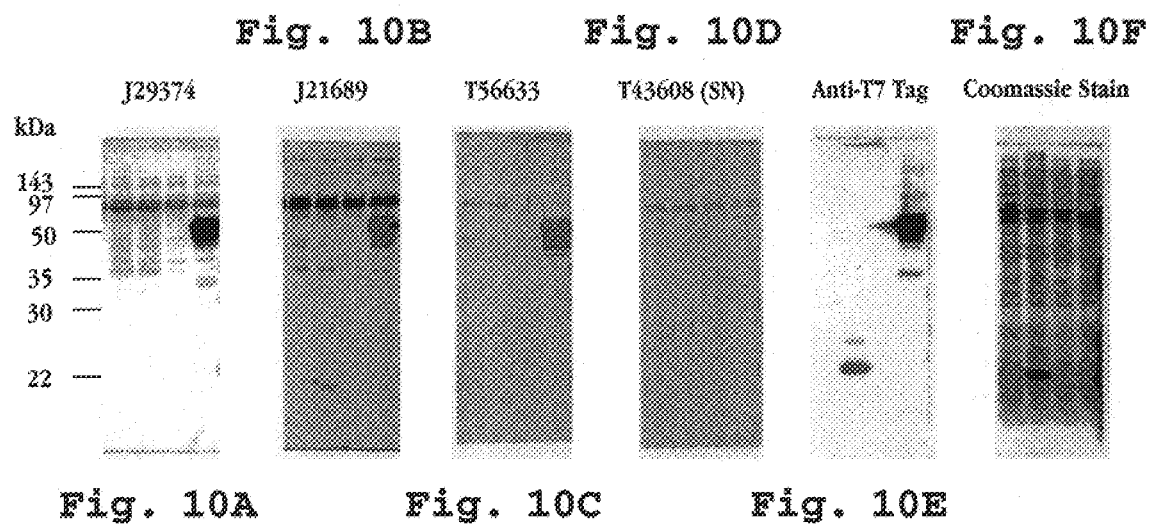

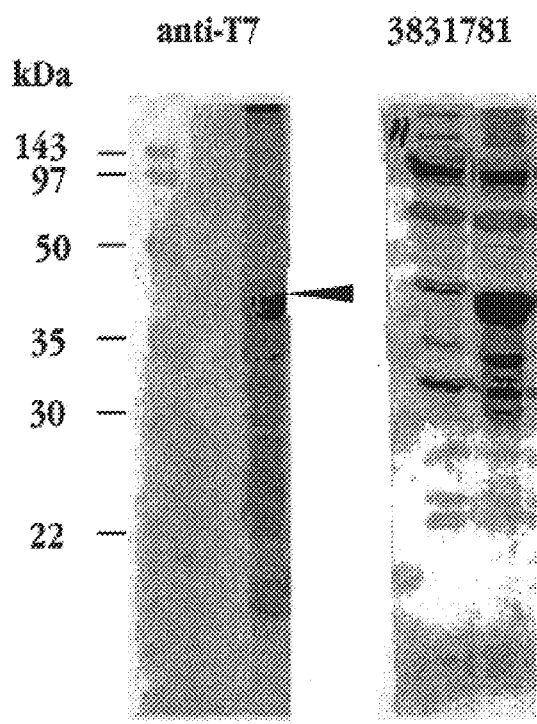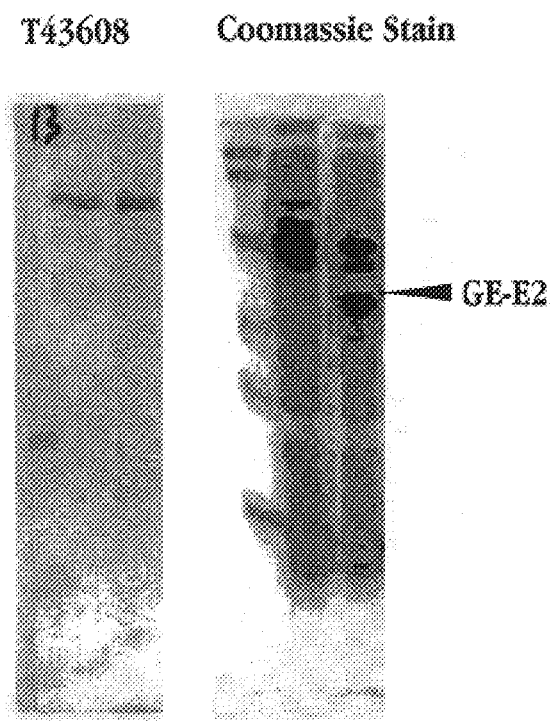
Fig. 14A, Fig. 14B, Fig. 14C, Fig. 14D

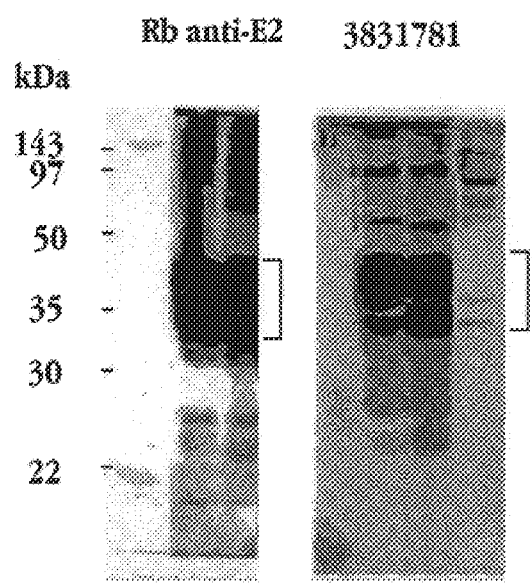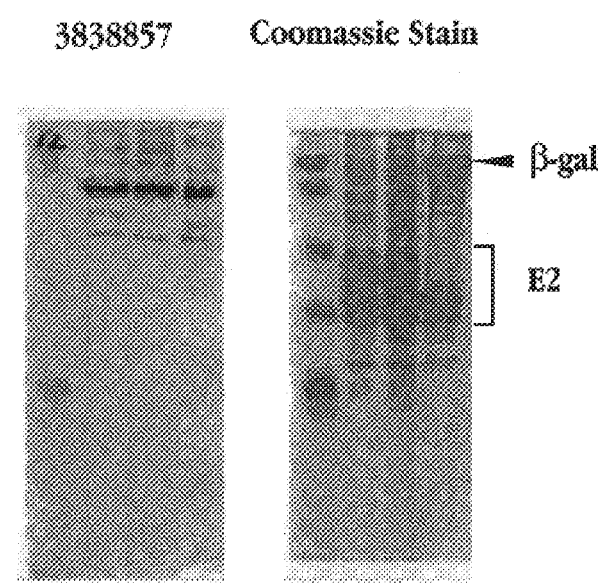
Fig. 15A  Fig. 15B  Fig. 15C  Fig. 15D ns# HEPATITIS G VIRUS AND MOLECULAR CLONING THEREOF This application is a divisional of U.S. application Ser. No. 08/444,733, filed 19 May 1995 which is a continuation-in-part of U.S. application Ser. No. 08/344,271, filed 23 Nov. 1994, abandoned, which is a continuation-in-part of U.S. application Ser. No. 08/285,561, abandoned, filed on 3 Aug. 1994, which is a continuation-in-part of U.S. application Ser. No. 08/246,985 filed on 20 May 1994, abandoned, and is a continuation-in-part of U.S. patent application Ser. No. 08/389,886, filed 15 Feb. 1995, abandoned, herein incorporated by reference, which is a continuation-in-part of Ser. No. 08/357,509, filed 16 Dec. 1994, abandoned, herein incorporated by reference, which is a continuation-in-part of U.S. patent application Ser. No. 08/329,729, filed 26 Oct. 1994, abandoned, herein incorporated by reference, which is a continuation-in-part of U.S. patent application Ser. No. 08/285,558, filed 3 Aug. 1994, and U.S. patent application Ser. No. 08/285,543, filed 3 Aug. 1994, both abandoned, herein incorporated by reference, which are continuations-in-part of U.S. patent application Ser. No. 08/246,985, filed 20 May 1994, herein incorporated by reference.

FIELD OF INVENTION

This invention relates to nucleic acid, polypeptide, antigen, epitope, vaccine and antibody compositions related to a NonA/NonB/NonC/NonD/NonE (N(ABCDE)) hepatitis-associated viral agent (HGV). The invention also relates to diagnostic and therapeutic methods.

REFERENCES

Abstracts, *The 1992 San Diego Conf.: Genetic Recognition, Clin. Chem.* 39(4):705 (1993).
Alexander, W. A., et al., *J. Virol.* 66:2934–2942 (1992).
Alter, H. J., et al., *New Eng. J. Med.* 321:1494–1500 (1989a).
Alter. M. J., et al., *N. Engl. J. Med.* 327:1899 (1989b).
Alter, H. J., *Abstracts of Int. Symp. on Viral Hepatitis and Liver Dis.*, p. 47 (1993).
Altschul, S., et al., *J. Mol. Biol.* 215:403–10 (1990).
Ascadi, G., et al., *Nature* 352:815 (1991).
Ausubel, F. M., et al., *CURRENT PROTOCOLS IN MOLECULAR BIOLOGY*, John Wiley and Sons, Inc., Media Pa.
Barany, F., *PCR Methods Appl.* 1:5 (1991).
Barham, W. B., et al., *J. Med. Virol.* 42:129–132 (1994).
Baron, S., et al., *JAMA* 266:1375 (1991).
Bazan, J. F., et al., *Virology* 171:637–639 (1989).
Beames, et al., *Biotechniques* 11:378 (1991).
Belyavsky, A., et al., *Nuc. Acids Res.* 17:2919–2932 (1989).
Blackburn, G. F., et al., *Clin. Chem.* 37:1534–1539 (1991).
Bradley, D. W., et al., *J. Infec. Dis.*, 148:2 (1983).
Bradley, D. W., et al., *J Gen. Virol.*, 69:1 (1988).
Bradley, D. W. et al., *Proc. Nat. Acad. Sci., USA*, 84:6277 (1987).
Briand, J.-P., et al., *J. Immunol. Meth.* 156:255 (1992).
Cahill, P., et al., *Clin. Chem.* 37:1482 (1991).
Carter, J. M., et al., *Methods Mol. Biol.* 36:207–223 (1994).
Chambers, T. J., et al., *Ann. Rev. Microbiol.* 44:649 (1990a).
Chambers, T. J., et al., *PNAS* 87:8898 (1990b).
Chomczynski et al, *Anal. Biochem.* 162:159 (1987).
Christian, R. B., et al., *J. Mol. Biol.* 227:771 (1992).
Commandaeur, et al., *Virology* 198:282–287 (1994).
Crea, R., U.S. Pat. No. 4,888,286, issued Dec. 19, 1989.
DeGraaf, M. E., et al., *Gene* 128:13 (1993).
DiBisceglie, A. M., et al., *Hepatology* 16:649 (1992).
DiBisceglie, A. M., et al., *NEJM* 321:1506 (1989).
DiCesare, J., et al., *Biotechniques* 15:152–157 (1993).
Dienstag, J. L., et al, *Sem Liver Disease* 6:67 (1986).
Earl, P. L., et al., "Expression of proteins in mammalian cells using vaccinia" In *Current Protocols in Molecular Biology* (F. M. Ausubel, et al. Eds.), Greene Publishing Associates & Wiley Interscience, New York (1991).
Eaton, M. A. W., et al., U.S. Pat. No. 4,719,180, issued Jan. 12, 1988.
Egholm, et al., *Nature* 365:566 (1993).
Elroy-Stein, O., et al., *Proc. Natl. Acad. Sci. USA.* 86:6126–6130 (1989).
EPO patent application 88310922.5, filed Nov. 18, 1988.
Falkner, F. G., et al., *J. Virol.* 62:1849–1854 (1988).
Farci, P., et al., *NEJM* 330:88 (1994).
Feigner and Rhodes, *Nature* 349:251 (1991).
Fickett, J. W., *Nuc. Acids Res.* 10:5303–5318 (1982).
Fling, S. P., et al., *Analytical Biochem.* 155:83–88 (1986).
Folgori, A., et al., *EMBO J.* 13:2236 (1994).
Francki, R. I. B., et al., *Arch. Virol.* Suppl2:223 (1991).
Frank, R., and Doring, R., *Tetrahedron* 44:6031–6040 (1988).
Frohinan, M. A., et al., *Proc. Natl. Acad. Sci. USA* 85:8998–9002 (1988).
Fuerst, T. R., et al., *Proc. Natl. Acad. Sci. USA* 83:8122–8126 (1986).
Gellissen, G., et al., *Antonie Van Leeuwenhoek*, 62(1–2): 79–93 (1992).
Geysen, M., et al., *Proc. Natl. Acad. Sci. USA* 81:3998–4002 (1984).
Gingeras, T. R., et al., *Ann. Biol. Clin.* 48:498 (1990).
Gingeras, T. R., et al., *J. Inf. Dis.* 164:1066 (1991).
Goeddel, D. V., *Methods in Enzymology* 185 (1990).
Grakoui, A., et al., *J. Virol.* 67:2832 (1993).
Grakoui, A., et al., *J. Virol.* 67:1385–1395 (1993).
Guatelli, J. C., et al., *Proc. Natl. Acad. Sci. USA* 87:1874 (1990).
Gubler, U., et al, Gene, 25:263 (1983).
Guthrie, C., and G. R. Fink, *Methods in Enzymology* 194 (1991).
Gutterman, J. U., *PNAS* 91:1198 (1994).
Harlow, E., et al., *ANTIBODIES: A LABORATORY MANUAL*, Cold Spring Harbor Laboratory Press (1988).
Haynes, J., et al., *Nuc. Acid. Res.* 11:687–706 (1983).
Hieter, P. A., et al., *Cell* 22:197–207 (1980).
Hijikata, M., et al., *PNAS* 88:5547 (1991).
Hochuli, E., in *GENETIC ENGINEERING, PRINCIPALS AND PRACTICE. VOL.* 12 (J. Stelow Ed.) Plenum, New York, pp. 87–98 (1990).
Holodniy, M., et al., *Biotechniques* 12:36 (1992).
Hopp, T. P., et al., *Proc. Natl. Acad. Sci. USA* 78:3824–3828 (1981).
Horn, T., and Urdea, M. S., *Nuc. Acids. Res.* 17:6959 (1989).
Houghten, R. A., *Proc. Natl. Acad. Sci. USA* 82:5131 (1985).
Hudson, D., *J. Org. Chem.* 53:617 (1988).
Irwin, M. J., et al., *J. Virol.* 58:5036 (1994).
Jacob, J. R., et al., in *THE MOLECULAR BIOLOGY OF HCV*, Section 4, pages 387–392 (1991).
Jacob, J. R., et al., *Hepatology* 10:921–927 (1989).
Jacob, J. R., et al., *J. Infect. Dis.* 161:1121–1127 (1990).
Janknecht, R., et al., *Proc. Natl. Acad. Sci. USA* 88:8972–8976 (1991).

Kaufman, R. J., "Selection and coamplification of heterologous genes in mammalian cells," in *Methods in Enzymology*, vol. 185, pp537–566. Academic Press, Inc., San Diego, Calif. (1991).

Kakumu, S., et al., *Gastroenterol.* 105:507 (1993).

Katz, E. D., and Dong, M., *Biotechniques* 8:546 (1990).

Kawasaki, E. S., et al., in *PCR TECHNOLOGY: PRINCIPLES AND APPLICATIONS OF DNA AMPLIFICATION* (H. A. Erlich, ed.) Stockton Press (1989).

King, L. A., et al., *The baculovirus expression system. A laboratory guide*, Chapman & Hall, London, New York, Tokyo, Melbourne, Madras, 1992.

Kyte, J., & Doolittle, R. F., *J. Mol. Biol.* 157:105–132 (1982).

Koonin, E. V., and Dolja, V. V., *Critical Reviews in Biochem. & Mol. Biol.* 28:375–430 (1993).

Krausslich, H. G. , et al., *VIRAL PROTEINASES AS TARGETS FOR CHEMOTHERAPY* (Cold Spring Harbor Press, Plainville, N.Y.) (1989).

Kumar, R., et al., *AIDS Res. Human Retroviruses* 5(3):345–354 (1989).

Lanford, R. E., et al., In Vitro *Cell. Dev. Biol.* 25:174–182 (1989).

Larder, B. A., and Kemp, S. D., *Science* 246:1155 (1989).

Lau, Y. F., et al., *Mol. Cell. Biol.* 4:1469–1475 (1984).

Lomell, H., et al., *Clin. Chem.* 48:492 (1990).

Maniatis, T., et al., *MOLECULAR CLONING: A LABORATORY MANUAL*, Cold Spring Harbor Laboratory (1982).

Marshall, W. S., and Caruthers, M. H., *Science* 259:1564 (1993).

Messing, J., *Methods in Enzymol.* 101:20 (1983).

Michelle, et al., *International Symposium on Viral Hepatitis*.

Miller, J. H., *EXPERIMENTS IN MOLECULAR GENETICS*, Cold Spring Harbor Laboratories, Cold Spring Harbor, N.Y. (1972).

Morrissey, D. V., et al., *Anal. Biochem.* 181:345 (1989).

Moss, B., et al., *CURRENT PROTOCOLS IN MOLECULAR BIOLOGY* (Section IV, Unit 16) (1991).

Moss, B., et al., U.S. Pat. No. 5,135,855, issued 4 Aug. 1992.

Mullis, K. B., U.S. Pat. No. 4,683,202, issued 28, Jul. 1987.

Mullis, K. B., et al., U.S. Pat. No. 4,683,195, issued 28, Jul. 1987.

Obeid, O. E., et al., *Virus Research* 32:69–84 (1994).

Osikowicz, G., et al., *Clin. Chem.* 36:1586 (1990).

Patterson, J. L., and Fernandez-Larsson, R., *Rev. Infect. Dis.* 12:1139 (1990).

Pearson, W. R. and Lipman, D. J., *PNAS* 85:2444–2448 (1988).

Pearson, W. R., *Methods in Enzymology* 183:63–98 (1990).

Pitha, *Biochem Biophys Acta*, 204:39 (1970a).

Pitha, *Biopolymers*, 9:965 (1970b).

Porath, J., *Protein Exp. and Purif.* 3:263 (1992).

Pritchard, C. G., and Stefano, J. E., *Ann. Biol. Chem.* 48:492 (1990).

Reichard, O., et al., *Lancet* 337:1058 (1991).

Reilly, P. R., et al., *BACULOVIRUS EXPRESSION VECTORS: A LABORATORY MANUAL* (1992).

Reyes, G., et al, *Science*, 247:1335 (1990).

Reyes, G., et al., *Molecular and Cellular Probes* 5:473–481 (1991).

Rice, C. M., et al., *New Biol.* 1:285–296 (1989).

Roberts, N. A., et al., *Science* 248:358 (1990).

Romanos, M. A., et al., *Yeast* 8(6):423–488 (1992).

Sanger, et al., *Proc. Natl. Acad. Sci.* 74:5463 (1977).

Sambrook, J., et al., In *MOLECULAR CLONING: A LABORATORY MANUAL*, Cold Spring Harbor Laboratory Press, Vol. 2 (1989).

Saiki, R. K., et al., *Science* 239:487–491 (1988).

Schagger, H., et al., *Anal. Biochem.* 166:368–379 (1987).

Scharf, S. J., et al., *Science* 233:1076 (1986).

Schuler, G. D., et al., *Proteins: Struc., Func. and Genet.* 9:180 (1989).

Scott, J. K., and Smith, G. P., *Science* 249:386 (1990).

Scott, J. K., et al., *Proc. Natl. Acad. Sci. USA* 89:5398 (1992).

Smith, D. B., et al., *Gene* 67:31 (1988).

Smith, J. P., *Curr. Opin. Biotechnol.* 2:668 (1991).

Sreenivasan, M. A., et al., *J. Gen. Virol.* 65:1005 (1984).

Sumiyoshi, H., et al., *J. Virol.* 66:5425–5431 (1992).

Summerton, J., et al., U.S. Pat. No. 5,142,047, issued Aug. 25, 1992.

Summerton, J., et al., U.S. Pat. No. 5,185,444 issued Feb. 9, 1993.

Tam, A., et al., *Virology* 185:120 (1991).

Tam, J. P., *Proc. Natl. Acad. Sci. USA* 85:5409 (1988).

Tessier, D. C., *Gene* 98:177–183 (1991).

Tonkinson, J. L., and Stein, C. A., *Antiviral Chem. and Chemother.* 4(4):193–200 (1993).

Ulmer, et al., *Science* 259:1745 (1993).

Urdea, M., *Clin. Chem.* 39:725 (1993).

Urdea, M., et al., *AIDS* 7:S11 (1993).

Wages, J. M., et al., *Amplifications* 10:1–6 (1993).

Walker, G. T., *PCR Methods Appl.* 3:1–6 (1993).

Wang, A. M., et al. in *PCR PROTOCOLS: A GUIDE TO METHODS AND APPLICATIONS* (M. A. Innis, et al., eds.) Academic Press (1990).

Wang, B., et al., *Proc. Natl. Acad. Sci. USA* 90:4156 (1993).

Whetsell, A. J., et al., *J. Clin. Micro.* 30:845 (1992).

Wolf, J. A., et al., *Nature* 247:1465 (1990).

Vacca, J. P., et al., *PNAS* 91:4096 (1994).

VanGemen, B., et al., *J. Virol. Methods* 43:177 (1993).

Valenzuela, P., et al., *Nature* 298:344 (1982).

Valenzuela, P., et al., in *HEPATITIS B*, eds. I. Millman, et al., Plenum Press, pages 225–236 (1984).

Yarbrough, et al., *J. Virol.* 65:5790 (1991).

Yoo, B. J., et al., *J. Virol.* 69:32–38 (1995).

Yoshio, T., et al., U.S. Pat. No. 4,849,350, issued Jul. 18, 1989.

Zhang, Y., et al., *J. Virol.* 65:6101–6110 (1991).

BACKGROUND OF THE INVENTION

Viral hepatitis resulting from a virus other than hepatitis A virus (HAV) and hepatitis B virus (HBV) has been referred to as non-A, non-B hepatitis (NANBH). NANBH can be further defined based on the mode of transmission of an individual type, for example, enteric versus parenteral.

One form of NANBH, known as enterically transmitted NANBH or ET-NANBH, is contracted predominantly in poor-sanitation areas where food and drinking water have been contaminated by fecal matter. The molecular cloning of the causative agent, referred to as the hepatitis E virus (HEV), has recently been described (Reyes et al., 1990; Tam et al.).

A second form of NANB, known as parenterally transmitted NANBH, or PT-NANBH, is transmitted by parenteral routes, typically by exposure to blood or blood products. The rate of this hepatitis varied by (i) locale, (ii) whether ALT testing was done in blood banks, and (iii) elimination of high-risk patients for AIDS. Approximately 10% of transfusions caused PT-NANBH infection and about half of those went on to a chronic disease state (Dienstag). After implementation of anti-HCV testing, HCV seroconversion per unit transfused was decreased to less than 1% among heart surgery patients (Alter).

Human plasma samples documented as having produced post-transfusion NANBH in human recipients have been used successfully to produce PT-NANBH infection in chimpanzees (Bradley). RNA isolated from infected chimpanzee plasma has been used to construct cDNA libraries in an expression vector for immunoscreening with serum from human subjects with chronic PT-NANBH infection. This procedure identified a PT-NANBH specific cDNA clone and the viral sequence was then used as a probe to identify a set of overlapping fragments making up 7,300 contiguous basepairs of a PT-NANBH viral agent. The sequenced viral agent has been named the hepatitis C virus (HCV) (for example, the sequence of HCV is presented in EPO patent application 88310922.5, filed Nov. 18, 1988). The full-length sequence (~9,500 nt) of HCV is now available.

Primate transmission studies conducted at the Centers for Disease Control (CDC; Phoenix, Ariz., 1973–1975; 1978–1983) originally provided substantial evidence for the existence of multiple agents of non-A, non-B hepatitis (NANBH): the primary agents associated with the majority of cases of NANBH are now recognized to be HCV and HEV (see above), for PT-NANBH and ET-NANBH, respectively. Later epidemiologic studies conducted at the CDC (Atlanta, Ga., 1989-present) using both research (prototype) and commercial tests for anti-HCV antibody showed that approximately 20% of all community-acquired NANBH was also non-C. Further testing of these samples for the presence of HEV (Reyes, et al., WO A 9115603 (Genelabs Inc.) 17, Oct. 1991) have indicated that these cases of community-acquired non-A, non-B, non-C hepatitis were also non-E.

Liver biopsy specimens, sera and plasma of Sentinel County patients (study of Drs. Miriam Alter and Kris Krawczynski) also showed that many bona fide cases of NANBH were also non-C hepatitis (serologically and by Reverse Transcriptase-Polymerase Chain Reaction (RT-PCR; Kawasaki, et al.; Wang, et al., 1990) negative for all markers of HCV infection) developed subsequently into chronic hepatitis with presentation of chronic persistent hepatitis (CPH) or chronic active hepatitis (CAH) consistent with a viral infection.

SUMMARY OF THE INVENTION

The invention pertains to the characterization and isolation of a newly discovered NonA/NonB/NonC/NonD/NonE (N-(ABCDE)) hepatitis-associated viral agent, herein designated Hepatitis G Virus (HGV). Disclosed here is a family of cDNA replicas of portions of HGV genome. Also disclosed are methods for the isolation and characterization of further HGV sequences and sequences of HGV variants.

The present invention includes HGV genomic polynucleotides, cDNAs thereto and complements thereof. With respect to polynucleotides, some aspects of the invention include: a purified Hepatitis G Virus genomic polynucleotide; HGV derived RNA and DNA polynucleotides; recombinant HGV polynucleotides; a recombinant polynucleotide making up a sequence derived from HGV or HGV variant cDNA or complementary sequences thereof; a recombinant polynucleotide encoding an epitope of HGV; a recombinant vector including any of the above recombinant polynucleotides, and a host cell transformed with any of these vectors. Another aspect of the invention is a polynucleotide probe for HGV and/or its variants.

Current studies on the nature of the genome of HGV, utilizing sequence information to compare HGV to other viral sequences, suggest that HGV is a member of the Flaviviridae family of viruses.

Portions of the HGV-derived cDNA sequences are effective as probes to isolate variants of the virus which occur naturally, or to determine the presence of virus in samples. These cDNAs also make available HGV-encoded polypeptide sequences, including HGV-specific polypeptide antigens. These coding sequences allow the production of polypeptides which are useful as reagents in diagnostic tests and/or as components of vaccines, or as standards. Further, it is possible to isolate and sequence other portions of the HGV genome by utilizing probes derived from these cDNAs, therefore giving rise to additional probes and polypeptides useful in the prophylactic, therapeutic and diagnosis applications.

Other aspects of the invention include: a recombinant expression system which incorporates an open reading frame (ORF) derived from HGV cDNA or complements thereof, wherein the ORF is linked operably to a control sequence which is compatible with a desired host, a cell transformed with the recombinant expression system, and a polypeptide produced by the transformed cell.

Yet another aspect of the invention are purified HGV particles; a preparation of polypeptides from the purified HGV; a purified HGV polypeptide; a purified HGV peptide; and a purified polypeptide which comprises an epitope immunologically identifiable with an epitope contained in HGV or an HGV variant.

Included aspects of the invention are an HGV polypeptide; a recombinant polypeptide consisting of a sequence derived from a HGV genome, HGV cDNA or complements thereof; a recombinant polypeptide made of an HGV epitope; and a fusion polypeptide comprised of an HGV polypeptide.

Both polyclonal and monoclonal antibodies directed against HGV epitopes contained within the polypeptide sequences are also useful as therapeutic agents, for diagnostic tests, for the isolation of the HGV agent from which these cDNAs derive, and for screening of antiviral agents.

Also included in the invention are a purified preparation of polyclonal antibodies directed against an HGV epitope; and monoclonal antibodies directed against HGV epitopes.

Some aspects of the invention pertaining to kits are those for: investigating samples for the presence of polynucleotides derived from HGV which comprise a polynucleotide probe including a nucleotide sequence from HGV of approximately 8 or more nucleotides, in an appropriate container; analyzing samples for the presence of antibodies directed against an HGV antigen made up of a polypeptide which contains an HGV epitope present in the HGV antigen, in a suitable container; and analyzing samples for the presence of HGV antigens made up of an anti-HGV antibody, in a suitable container.

Still other aspects of the invention include a polypeptide comprised of an HGV epitope, which is attached to a solid substrate; and an antibody to an HGV epitope, which is attached to a solid substrate.

Other aspects of the invention are: a technique for the production of an HGV polypeptide, which includes incubating host cells which are transformed with an expression vector, containing a sequence encoding an HGV polypeptide, under conditions which allow expression of said polypeptide; and a polypeptide which has been produced by this method (containing, for example, an HGV epitope).

Also included in the invention are a method for the detection of HGV nucleic acids in samples comprising reacting nucleic acids of the sample with a probe for an HGV polynucleotide, under conditions allowing the creation of a polynucleotide duplex between the probe and the HGV nucleic acid from the sample; as well as detecting a polynucleotide duplex containing the probe. The invention includes the following hybridization based detection methods: reporter labeling; polymerase chain reaction; self-sustained sequence replication; ligase chain reaction; and strand displacement amplification. Further, detection methods include signal amplification (e.g., branch-chained DNA probes and the Q-beta replicase method).

The invention also includes immunoassays, including an immunoassay for detecting HGV, comprising the incubation of a sample (which is suspected of being infected with HGV) with a probe antibody directed against an antigen/epitope of HGV, to be detected under conditions allowing the formation of an antigen-antibody complex; and detecting the antigen-antibody complex which contains the probe antibody. An immunoassay for the detection of antibodies which are directed against an HGV antigen comprising the incubation of a sample suspected of containing HGV with a probe polypeptide including an epitope of HGV, under conditions that allow the formation of an antibody-antigen complex; and distinguishing the antibody-antigen complex which contains the probe antigen.

Also forming part of the invention are HGV vaccines, for the treatment and/or prevention of HGV infection, comprising an immunogenic peptide containing an HGV epitope, or an inactivated preparation of HGV, or a reduced preparation of HGV.

In still another aspect, the invention includes a tissue culture grown cell, infected with HGV. In one embodiment, the tissue culture grown cells are primate liver cells.

Another aspect of the invention is a method for producing antibodies to HGV, comprising administering to a test subject an immunogenic polypeptide containing HGV epitopes in an adequate amount to elicit an immune response.

The present invention also includes an HGV mosaic polypeptide, where the mosaic polypeptide contains at least two epitopes of HGV, and, where the polypeptide substantially lacks amino acids normally intervening between the epitopes in the native HGV coding sequence. Such mosaic polypeptides are useful in the applications and methods discussed above.

The present invention further includes a random peptide epitope (mimitope) that mimics a natural HGV antigenic epitope during epitope presentation. Such mimitopes are useful in the applications and methods discussed above. Also included in the present invention is a method of identifying a random peptide HGV epitope. In the method, a library of random peptide epitopes is generated or selected. The library is contacted with an anti-HGV antibody. Mimitopes are identified that are specifically immunoreactive with the antibody. Sera (containing anti-HGV antibodies) or antibodies generated by the methods of the present invention can be used. Random peptide libraries can, for example, be displayed on phage or generated as combinatorial libraries.

In another aspect, the present invention includes therapeutic compounds and methods for the prevention and/or treatment of HGV infection.

These and other objects and features of the invention will be more fully appreciated when the following detailed description of the invention is read in conjunction with the accompanying drawings.

BRIEF DESCRIPTION OF THE FIGURES

FIGS. 5A and 5B: amino acid alignments of HGV with two other members of Flaviviridae family—Hog Cholera Virus and Hepatitis C Virus.

FIG. 6 shows a map of a portion of the vector pGEX-Hisb-GE3-2, a bacterial expression plasmid carrying an HGV epitope.

FIGS. 10A to 10F show scanned images of Western blot analyses of antigens GE-NS2b and GE-NS5a.

FIGS. 14A to 14C show scanned images of Western blot analyses of HGV pET clone GE-E2. FIG. 14D shows a scanned image of a corresponding coomassie stained gel.

FIGS. 15A to 15C show scanned images of Western blot analyses of HGV pET clone GE-NS5b. FIG. 15D shows a scanned image of a corresponding coomassie stained gel.

DETAILED DESCRIPTION OF THE INVENTION

I. DEFINITIONS

Figure 1:
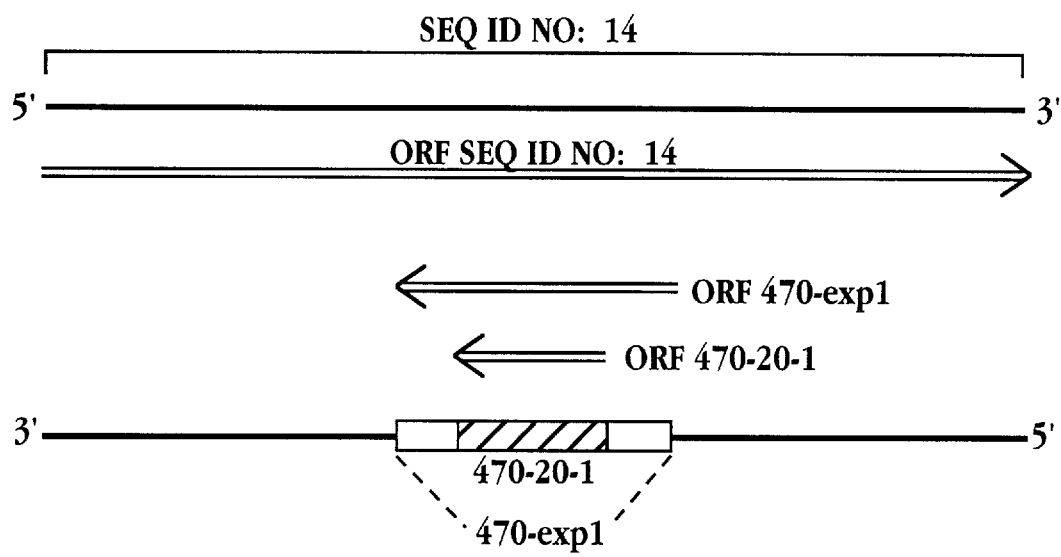
FIG. 1: the relationship of the SEQ ID NO:14 open reading frame to the 470-20-1 clone.

The terms defined below have the following meaning herein:

1. "nonA/nonB/nonC/nonD/nonE hepatitis viral agent {N-(ABCDE)}," herein provisionally designated HGV, means a virus, virus type, or virus class which (i) is transmissible in some primates, including, mystax, chimpanzees or humans as characterized by elevated serum alanine amino-transferase levels in an infected primate, (ii) is serologically distinct from hepatitis A virus (HAV), hepatitis B virus (HBV), hepatitis C virus (HCV), hepatitis D virus, and hepatitis E (HEV) (although HGV may co-infect a subject with these viruses), and (iii) is a member of the virus family Flaviviridae.

2. "HGV variants" are defined as viral isolates that have at least about 40%, preferably 55% or 65%, or more preferably 80% global sequence homology, that is, sequence identity over a length of the viral genome polynucleotide sequence, to the HGV polynucleotide sequences disclosed herein (e.g., SEQ ID NO:14).

"Sequence homology" is determined essentially as follows. Two polynucleotide sequences of similar length (preferably, the entire viral genome) are considered to be homologous to one another, if, when they are aligned using the ALIGN program, over 40%, preferably 55% or 65%, or more preferably 80% of the nucleic acids in the highest scoring alignment are identically aligned using a ktup of 1, the default parameters and the default PAM matrix.

The ALIGN program is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.).

In determining whether two viruses are "highly homologous" to each other, the complete sequence of all the viral proteins (or the polyprotein) for one virus are optimally, globally aligned with the viral proteins or polyprotein of the other virus using the ALIGN program of the above suite using a ktup of 1, the default parameters and the default PAM matrix. Regions of dissimilarity or similarity are not excluded from the analyses. Differences in lengths between the two sequences are considered as mismatches. Alternatively, viral structural protein regions are typically used to determine relatedness between viral isolates. Highly homologous viruses have over 40%, or preferably 55% or 65%, or more preferably 80% global polypeptide sequence identity.

3. Two nucleic acid fragments are considered to be "selectively hybridizable" to an HGV polynucleotide, if they are capable of specifically hybridizing to HGV or a variant thereof (e.g., a probe that hybridizes to HGV nucleic acid but not to polynucleotides from other members of the virus family Flaviviridae) or specifically priming a polymerase chain reaction: (i) under typical hybridization and wash conditions, as described, for example, in Maniatis, et al., pages 320–328, and 382–389, (ii) using reduced stringency wash conditions that allow at most about 25–30% basepair mismatches, for example: 2× SSC, 0.1% SDS, room temperature twice, 30 minutes each; then 2× SSC, 0.1% SDS, 37° C. once, 30 minutes; then 2× SSC room temperature twice, 10 minutes each, or (iii) selecting primers for use in typical polymerase chain reactions (PCR) under standard conditions (for example, in Saiki, R. K, et al.), which result in specific amplification of sequences of HGV or its variants.

Preferably, highly homologous nucleic acid strands contain less than 20–30% basepair mismatches, even more preferably less than 5–20% basepair mismatches. These degrees of homology can be selected by using wash conditions of appropriate stringency for identification of clones from gene libraries (or other sources of genetic material), as is well known in the art.

4. An "HGV polynucleotide," as used herein, is defined as follows. For polynucleotides greater than about 100 nucleotides, HGV polynucleotides encompass polynucleotide sequences encoded by HGV variants and homologous sequences as defined in "2" above. For polynucleotides less than about 100 nucleotides in length, HGV polynucleotide encompasses sequences that selectively hybridizes to sequences of HGV or its variants. Further, HGV polynucleotides include polynucleotides encoding HGV polypeptides (see below).

The term "polynucleotide" as used herein refers to a polymeric molecule having a backbone that supports bases capable of hydrogen bonding to typical nucleic acids, where the polymer backbone presents the bases in a manner to permit such hydrogen bonding in a sequence specific fashion between the polymeric molecule and a typically nucleic acid (e.g., single-stranded DNA). Such bases are typically inosine, adenosine, guanosine, cytosine, uracil and thymidine. Numerous polynucleotide modifications are known in the art, for example, labels, methylation, and substitution of one or more of the naturally occurring nucleotides with an analog.

Polymeric molecules include double and single stranded RNA and DNA, and backbone modifications thereof, for example, methylphosphonate linkages. Further, such polymeric molecules include alternative polymer backbone structures such as, but not limited to, polyvinyl backbones (Pitha, 1970a/b), morpholino backbones (Summerton, et al., 1992, 1993). A variety of other charged and uncharged polynucleotide analogs have been reported. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates). In addition linkages may contain the following exemplary modifications: pendant moieties, such as, proteins (including, for example, nucleases, toxins, antibodies, signal peptides and poly-L-lysine); intercalators (e.g., acridine and psoralen), chelators (e.g., metals, radioactive metals, boron and oxidative metals), alkylators, and other modified linkages (e.g., alpha anomeric nucleic acids).

5. An "HGV polypeptide" is defined herein as any polypeptide homologous to an HGV polypeptide. "Homology," as used herein, is defined as follows. In one embodiment, a polypeptide is homologous to an HGV polypeptide if it is encoded by nucleic acid that selectively hybridizes to sequences of HGV or its variants.

In another embodiment, a polypeptide is homologous to an HGV polypeptide if it is encoded by HGV or its variants, as defined above, polypeptides of this group are typically larger than 15, preferable 25, or more preferable 35, contiguous amino acids. Further, for polypeptides longer than about 60 amino acids, sequence comparisons for the purpose of determining "polypeptide homology" are performed using the local alignment program LALIGN. The polypeptide sequence, is compared against the HGV amino acid sequence or any of its variants, as defined above, using the LALIGN program with a ktup of 1, default parameters and the default PAM.

Any polypeptide (typically a polypeptide not specifically immunoreactive with HGV antibodies) with an optimal alignment longer than 60 amino acids and greater than 60%, preferably 70%, or more preferably 80% of identically aligned amino acids is considered to be a "homologous polypeptide." The LALIGN program is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.).

6. A polynucleotide is "derived from" HGV if it has the same or substantially the same basepair sequence as a region of an HGV genome, cDNA of HGV or complements thereof, or if it displays homology as noted under "2", "3" or "4" above.

A polypeptide or polypeptide "fragment" is "derived from" HGV if it is (i) encoded by an open reading frame of an HGV polynucleotide, or (ii) displays homology to HGV polypeptides as noted under "2" and "5" above, or (iii) is specifically immunoreactive with HGV positive sera.

7. "Substantially isolated" and "purified" are used in several contexts and typically refer to at least partial purification of an HGV virus particle, component (e.g., polynucleotide or polypeptide), or related compound (e.g., anti-HGV antibodies) away from unrelated or contaminating components (e.g., serum cells, proteins, non-HGV polynucleotides and non-anti-HGV antibodies). Methods and procedures for the isolation or purification of compounds or components of interest are described below (e.g., affinity purification of fusion proteins and recombinant production of HGV polypeptides).

8. In the context of the present invention, the phrase "nucleic acid sequences," when referring to sequences which encode a protein, polypeptide, or peptide, is meant to include degenerative nucleic acid sequences which encode homologous protein, polypeptide or peptide sequences as well as the disclosed sequence.

9. An "epitope" is the antigenic determinant defined as the specific portion of an antigen with which the antigen binding portion of a specific antibody interacts.

10. An antigen or epitope is "specifically immunoreactive" with HGV positive sera when the epitope/antigen binds to antibodies present in the HGV infected sera but does not bind to antibodies present in the majority (greater than about 90%, preferably greater than 95%) of sera from individuals who are not or have not been infected with HGV. "Specifically immunoreactive" antigens or epitopes may also be immunoreactive with monoclonal or polyclonal antibodies generated against specific HGV epitopes or antigens.

An antibody or antibody composition (e.g., polyclonal antibodies) is "specifically immunoreactive" with HGV when the antibody or antibody composition is immunoreactive with an HGV antigen but not with HAV, HBV, HCV, HDV or HEV antigens. Further, "specifically immunoreactive antibodies" are not immunoreactive with antigens typically present in normal sera obtained from subjects not infected with or exposed to HGV, HAV, HBV, HCV, HDV or HEV.

II. N-(ABCDE) SERA

Availability of a serologic test for anti-HCV and the development of an RT-PCR assay for HCV-RNA (Kawasaki, et al.; Wang, et al., 1990) allowed the identification of several cases of both post-transfusion and community acquired non-HCV hepatitis. The human hepatitis case, PNF 2161, was originally identified as having NANB hepatitis (NANBH) through the Sentinel Counties Study of community acquired hepatitis, sponsored by the Centers for Disease Control and Prevention (Alter, et al., 1989b). PNF 2161 was a sample obtained from an elderly Caucasian male patient who developed acute hepatitis approximately 8 weeks following a blood transfusion, with a peak serum ALT level of 1141 IU (normal, $\leq 45$ IU). Following resolution of the episode of acute hepatitis, he had fluctuating, but persistently elevated ALT levels over the next seven years, consistent with chronic hepatitis, although histopathologic confirmation of this diagnosis was not obtained.

The plasma specimen used to clone HGV (as described herein) was obtained in June 1989, approximately $4^{1/2}$ years following the episode of acute hepatitis, and cryo-preserved. Patient PNF 2161 was initially believed not to be infected with HCV, based on consistently negative results with a first generation immunoassay test (Ortho HCV ELISA Test System; Ortho Diagnostics, Raritan, N.J.). However, subsequent testing using a second generation HCV immunoassay (Ortho) and PCR with HCV 5'-non-coding region primers demonstrated that the patient was infected with HCV.

III. ISOLATION OF HGV ASSOCIATED SEQUENCES

As one approach toward identifying clones containing HGV sequences, a cDNA library was prepared from infected-HGV sera in the expression vector lambda gt11 (Example 1). Polynucleotide sequences were then selected for the expression of peptides which are immunoreactive with serum PNF 2161. First round screening was typically performed using the PNF 2161 serum (used to generate the phage library). It is also possible to screen with other suspected N-(ABCDE) sera.

Recombinant proteins identified by this approach provide candidates for peptides which can serve as substrates in diagnostic tests. Further, the nucleic acid coding sequences identified by this approach serve as useful hybridization probes for the identification of additional HGV coding sequences.

The sera described above were used to generate cDNA libraries in lambda gt11 (Example 1). In the method illustrated in Example 1, infected serum was precipitated in 8% PEG without dilution, and the libraries were generated from the resulting pelleted virus. Sera from infected human sources were treated in the same fashion.

As an advantageous alternative to PEG precipitation, ultracentrifugation can be used to pellet particulate agents from infected sera or other biological specimens. To isolate viral particles from which nucleic acids could be extracted, serum, ranging up to 2 ml, is diluted to approximately 10 ml with PBS, spun at 3K for 10 minutes, and the supernatant is centrifuged for a minimum of 2 hours at 40,000 rpm (approximately 110,000×g) in a Ti70.1 rotor (Beckman Instruments, Fullerton, Calif.) at 4° C. The supernatant is then aspirated and the pellet extracted by standard nucleic acid extraction techniques.

cDNA libraries were generated using random primers in reverse transcription reactions with RNA extracted from pelleted sera as starting material. The resulting molecules were ligated to Sequence Independent Single Primer Amplification (SISPA; Reyes, et al., 1991) linker primers and expanded in a non-selective manner, and then cloned into a suitable vector, for example, lambda gt11, for expression and screening of peptide antigens. Alternatively, the lambda gt10 vector may also be used.

Lambda gt11 is a particularly useful expression vector which contains a unique EcoRI insertion site 53 base pairs upstream of the translation termination codon of the β-galactosidase gene. Thus, an inserted sequence is expressed as a β-galactosidase fusion protein which contains the N-terminal portion of the β-galactosidase gene product, the heterologous peptide, and optionally the C-terminal region of the β-galactosidase peptide (the C-terminal portion being expressed when the heterologous peptide coding sequence does not contain a translation termination codon).

This vector also produces a temperature-sensitive repressor (cI857) which causes viral lysogeny at permissive temperatures, e.g., 32° C., and leads to viral lysis at elevated temperatures, e.g., 42° C. Advantages of this vector include: (1) highly efficient recombinant clone generation, (2) ability to select lysogenized host cells on the basis of host-cell growth at permissive, but not non-permissive, temperatures, and (3) production of recombinant fusion protein. Further, since phage containing a heterologous insert produces an inactive β-galactosidase enzyme, phage with inserts are typically identified using a colorimetric substrate conversion reaction employing β-galactosidase.

Example 1 describes the preparation of a cDNA library for the N-(ABCDE) hepatitis sera PNF 2161. The library was immunoscreened using PNF 2161 (Example 3). A number of lambda gt11 clones were identified which were immunoreactive. Immunopositive clones were plaque-purified and their immunoreactivity retested. Also, the immunoreactivity of the clones with normal human sera was also tested.

These clones were also examined for the "exogenous" nature of the cloned insert sequence. This basic test establishes that the cloned fragment does not represent a portion of human or other potentially contaminating nucleic acids (e.g., *E. coli, S. cerevisiea* and mitochondrial). The clone inserts were isolated by EcoRI digestion following polymerase chain reaction amplification. The inserts were purified then radiolabelled and used as hybridization probes against membrane bound normal human DNA, normal mystax DNA and bacterial DNA (control DNAs) (Example 4A).

Clone 470-20-1 (PNF211 cDNA source) was one of the clones isolated by immunoscreening with the PNF 2161 serum. The clone was not reactive with normal human sera. The clone has a large open reading frame (203 base pairs; SEQ ID NO:3), in-frame with the β-galactosidase gene of the lambda gt11 vector. The clone is exogenous by genomic DNA hybridization analyses and genomic PCR analyses, using human, yeast and *E. coli* genomic DNAs (Example 4B).

The sequence was present in PNF2161 serum as determined by RT-PCR (Example 4C). RT-PCR of serially diluted PNF 2161 RNA suggested at least about 105 copies of 470-20-1 specific sequence per ml. The sequence was also detected in sucrose density gradient fractions at densities consistent with the sequence banding in association with a virus-like particle (Example 5).

Bacterial lysates of *E. coli* expressing a second clone, clone 470-exp1, (SEQ ID NO:37) were also shown to be specifically immunoreactive with PNF 2161 serum at comparable levels to clone 470-20-1. The coding sequence of 470-exp1 was flanked by termination codons (based on sequence comparisons to SEQ ID NO:14, also see FIG. 1) and had an internal methionine.

Further sequences contained in SEQ ID NO:14, adjacent to clone 470-20-1, were obtained by anchor polymerase chain reaction (Anchor PCR) using primers from clone 470-20-1 (Example 6). In this case a PNF 2161 2-cDNA source library was used as template, where the cDNA/ complement double-stranded DNA products were ligated to lambda arms, but the mixture was not packaged.

470-20-1 specific primers were used in amplification reactions with SISPA-amplified PNF 2161 cDNA as a template (Example 4). The identity of the amplified DNA fragments were confirmed by (i) size and (ii) hybridization with a 470-20-1 specific oligonucleotide probe (SEQ ID NO:16). The 470-20-1 specific signal was detected in cDNA amplified by PCR from SISPA-amplified PNF 2161, demonstrating the presence of the 470-20-1 sequences in the source material.

The 470-20-1 specific primers were also used in amplification reactions with the following RNA sources as substrate: normal mystax liver RNA, normal tamarin (*Sanguins laboriatis*) liver RNA, and MY131 liver RNA (Example 4). The results from these experiments demonstrate the 470-20-1 sequences are present in the parent serum sample (PNF 2161) and in an RNA liver sample from an animal challenged with the PNF 2161 sample (MY131). Both normal control RNAs were negative for the presence of 470-20-1 sequences.

Further, PNF 2161 serum and other cloning source or related source materials were directly tested by PCR using primers from selected cloned sequences. Specific amplification products were detected by hybridization to a specific oligonucleotide probe 470-20-1-152F (SEQ ID NO:16). A specific signal was reproducibly detected in multiple extracts of PNF 2161, with the 470-20-1 specific primers.

The disease association between HGV and liver disease is further supported by the data presented in Example 4F. Sera from hepatitis patients and from blood donors with abnormal liver function were assessed for the presence of HGV by RT-PCR screening, using HGV specific primers. HGV specific sequence were detected in 6/152 of these sera samples. No HGV positives were detected among the control samples (n=11).

The results presented above indicate the isolation of a viral agent associated with N-(ABCDE) viral infection of liver (i.e., hepatitis) and/or infection, and resulting disease, of other tissue and cell types.

IV. FURTHER CHARACTERIZATION OF HGV RECOMBINANT ANTIGENS

A. Screening Recombinant Libraries.

Further candidate HGV antigens can be obtained from the libraries of the present invention using the screening methods described above. The cDNA library described above has been deposited with the American Type Culture Collection, 12301 Parklawn Dr., Rockville, Md., 20852, and has been assigned the following designation: PNF 2161 cDNA source, ATCC 75268. The deposit was accepted by the International Depository Authority on Jul. 16, 1992.

A second PNF 2161 cDNA library has been generated essentially as described for the first PNF 2161 cDNA library, except that second PNF 2161 cDNA source library was ligated to lambda gt11 arms but was not packaged. This non-packaged library was used to obtain the extension clones described below. A packaged version of this second library (PNF 2161 2-cDNA source library) has been deposited with the American Type Culture Collection, 12301 Parklawn Drive, Rockville, Md., 20852, and has been assigned the following designation: PNF 2161 2-cDNA source, ATCC 75837. The deposit was accepted by the International Depository Authority on Jul. 22, 1994.

In addition to the recombinant libraries generated above, other recombinant libraries from N-(ABCDE) hepatitis sera can likewise be generated and screened as described herein.

B. Epitope Mapping, Cross Hybridization and Isolation of Genomic Sequences.

Antigen encoding DNA fragments can be identified by (i) immunoscreening, as described above, or (ii) computer analyses of coding sequences (e.g., SEQ ID NO:14) using an algorithm (such as, "ANTIGEN," Intelligenetics, Mountain View, Calif.) to identify potential antigenic regions. An antigen-encoding DNA fragment can be subcloned. The subcloned insert can then be fragmented by partial DNase I digestion to generate random fragments or by specific restriction endonuclease digestion to produce specific sub-fragments. The resulting DNA fragments can be inserted into the lambda gt11 vector and subjected to immunoscreening in order to provide an epitope map of the cloned insert.

In addition, the DNA fragments can be employed as probes in hybridization experiments to identify overlapping HGV sequences, and these in turn can be further used as probes to identify a set of contiguous clones. The generation of sets of contiguous clones allows the elucidation of the sequence of the HGV's genome.

Any of the above-described clone sequences (e.g., derived from SEQ ID NO:14 or clone 470-20-1) can be used to probe the cDNA and DNA libraries, generated in a vector such as lambda gt10 or "LAMBDA ZAP II" (Stratagene, San Diego, Calif.). Specific subfragments of known sequence may be isolated by polymerase chain reaction or after restriction endonuclease cleavage of vectors carrying such sequences. The resulting DNA fragments can be used as radiolabelled probes against any selected library. In particular, the 5' and 3' terminal sequences of the clone inserts are useful as probes to identify additional clones.

Further, the sequences provided by the 5' end of cloned inserts are useful as sequence specific primers in first-strand cDNA or DNA synthesis reactions (Maniatis et al.; Scharf et al.). For example, specifically primed PNF 2161 cDNA and DNA libraries can be prepared by using specific primers derived from SEQ ID NO:14 on PNF 2161 nucleic acids as a template. The second-strand of the new cDNA is synthesized using RNase H and DNA polymerase I. The above procedures identify or produce DNA/cDNA molecules corresponding to nucleic acid regions that are 5' adjacent to the known clone insert sequences. These newly isolated sequences can in turn be used to identify further flanking sequences, and so on, to identify the sequences composing the entire genome for HGV. As described above, after new HGV sequences are isolated, the polynucleotides can be cloned and immunoscreened to identify specific sequences encoding HGV antigens.

Extension clone sequences (SEQ ID NO:14), containing further sequences of interest, have been obtained for clone PNF 470-20-1 (SEQ ID NO:3) using the "Anchor PCR" method described in Example 6. Briefly, the strategy consists of ligating PNF 2161 SISPA cDNA to lambda gt11 arms and amplifying the ligation reaction with a gt11-specific primer and one of two 470-20-1 specific primers.

The amplification products are electrophoretically separated, transferred to filters and the DNA bound to the filters is probed with a 470-20-1 specific probe. Bands corresponding to hybridization positive band signals were gel purified, cloned and sequenced.

C. Preparation of Antigenic Polypeptides and Antibodies.

The recombinant peptides of the present invention can be purified by standard protein purification procedures which may include differential precipitation, molecular sieve chromatography, ion-exchange chromatography, isoelectric focusing, gel electrophoresis and affinity chromatography.

In one embodiment of the present invention, the polynucleotide sequences of the antigens of the present invention have been cloned in the plasmid p-GEX (Example 7A) or various derivatives thereof (pGEX-GLI). The plasmid pGEX (Smith, et al., 1988) and its derivatives express the polypeptide sequences of a cloned insert fused in-frame to the protein glutathione-S-transferase (sj26). In one vector construction, plasmid pGEX-hisB, an amino acid sequence of 6 histidines is introduced at the carboxy terminus of the fusion protein.

The various recombinant pGEX plasmids can be transformed into appropriate strains of $E.$ $coli$ and fusion protein production can be induced by the addition of IPTG (isopropyl-thio galactopyranoside) as described in Example 7A. Solubilized recombinant fusion protein can then be purified from cell lysates of the induced cultures using glutathione agarose affinity chromatography (Example 7A).

Insoluble fusion protein expressed by the plasmid pGEX-hisB can be purified by means of immobilized metal ion affinity chromatography (Porath) in buffers containing 6M Urea or 6M guanidinium isothiocyanate, both of which are useful for the solubilization of proteins. Alternatively insoluble proteins expressed in pGEX-GLI or derivatives thereof can be purified using combinations of centrifugation to remove soluble proteins followed by solubilization of insoluble proteins and standard chromatographic methodologies, such as ion exchange or size exclusion chromatography, and other such methods are known in the art.

In the case of β-galactosidase fusion proteins (such as those produced by lambda gt11 clones) the fused protein can be isolated readily by affinity chromatography, by passing cell lysis material over a solid support having surface-bound anti-β-galactosidase antibody. For example, purification of a β-galactosidase/fusion protein, derived from 470-20-1 coding sequences, by affinity chromatography is described in Example 7B.

Also included in the invention is an expression vector, such as the lambda gt11 or pGEX vectors described above, containing HGV coding sequences and expression control elements which allow expression of the coding regions in a suitable host. The control elements generally include a promoter, translation initiation codon, and translation and transcription termination sequences, and an insertion site for introducing the insert into the vector.

The DNA encoding the desired antigenic polypeptide can be cloned into any number of commercially available vectors to generate expression of the polypeptide in the appropriate host system. These systems include, but are not limited to, the following: baculovirus expression (Reilly, et al.; Beames, et al.; Pharmingen; Clontech, Palo Alto, Calif.), vaccinia expression (Earl, 1991; Moss, et al.), expression in bacteria (Ausubel, et al.; Clontech), expression in yeast (Gellissen, 1992; Romanos, 1992; Goeddel; Guthrie and Fink), expression in mammalian cells (Clontech; Gibco-BRL, Ground Island, N.Y.), e.g., Chinese hamster ovary (CHO) cell lines (Haynes, 1983, Lau, 1984, Kaufman, 1990). These recombinant polypeptide antigens can be expressed directly or as fusion proteins. A number of features can be engineered into the expression vectors, such as leader sequences which promote the secretion of the expressed sequences into culture medium.

Expression of large HGV polypeptides using several of these systems is described in Example 16.

Expression in yeast systems has the advantage of commercial production. Recombinant protein production by vaccinia and CHO cell line have the advantage of being mammalian expression systems. Further, vaccinia virus expression has several advantages including the following: (i) its wide host range; (ii) faithful post-transcriptional modification, processing, folding, transport, secretion, and assembly of recombinant proteins; (iii) high level expression of relatively soluble recombinant proteins; and (iv) a large capacity to accommodate foreign DNA.

The recombinant expressed polypeptide produced HGV polypeptide antigens are typically isolated from lysed cells or culture media. Purification can be carried out by methods known in the art including salt fractionation, ion exchange chromatography, and affinity chromatography. Immunoaffinity chromatography can be employed using antibodies generated based on the HGV antigens identified by the methods of the present invention.

HGV polypeptide antigens may also be isolated from HGV particles (see below).

Continuous antigenic determinants of polypeptides are generally relatively small, typically 6 to 10 amino acids in length. Smaller fragments have been identified as antigenic regions, for example, in conformational epitopes. HGV polypeptide antigens are identified as described above. The resulting DNA coding regions of either strand can be expressed recombinantly either as fusion proteins or isolated polypeptides. In addition, amino acid sequences can be conveniently chemically synthesized using commercially available synthesizer (Applied Biosystems, Foster City, Calif.) or "PIN" technology (Applied Biosytems).

In another embodiment, the present invention includes mosaic proteins that are composed of multiple epitopes. An HGV mosaic polypeptide typically contains at least two epitopes of HGV, where the polypeptide substantially lacks amino acids normally intervening between the epitopes in the native HGV coding sequence. Synthetic genes (Crea; Yoshio et al.; Eaton et al.) encoding multiple, tandem epitopes can be constructed that will produce mosaic proteins using standard recombinant DNA technology using polypeptide expression vector/host system described above.

Further, multiple antigen peptides can be synthesized chemically by methods described previously (Tam, J. P., 1988; Briand et al.). For example, a small immunologically inert core matrix of lysine residues with α- and e-amino groups can be used to anchor multiple copies of the same or different synthetic peptides (typically 6–15 residues long) representing epitopes of interest. Mosaic proteins or multiple antigen peptide antigens give higher sensitivity and specificity in immunoassays due to the signal amplification resulting from distribution of multiple epitopes.

Antigens obtained by any of these methods can be used for antibody generation, diagnostic tests and vaccine development.

In another aspect, the invention includes specific antibodies directed against the polypeptide antigens of the present invention. Antigens obtained by any of these methods may be directly used for the generation of antibodies or they may be coupled to appropriate carrier molecules. Many such carriers are known in the art and are commercially available (e.g., Pierce, Rockford Ill.). Typically, to prepare antibodies, a host animal, such as a rabbit, is immunized with the purified antigen or fused protein antigen. Hybrid, or fused, proteins may be generated using a variety of coding sequence derived from other proteins, such as glutathione-s-transferase or β-galactosidase. The host serum or plasma is collected following an appropriate time interval, and this serum is tested for antibodies specific against the antigen. Example 8 describes the production of rabbit serum antibodies which are specific against the 470-20-1 antigen in the Sj26/470-20-1 hybrid protein. These techniques are equally applicable to all immunogenic sequences derived from HGV, including, but not limited to, those derived from the coding sequence presented as SEQ ID NO:14.

The gamma globulin fraction or the IgG antibodies of immunized animals can be obtained, for example, by use of saturated ammonium sulfate precipitation or DEAE Sephadex chromatography, affinity chromatography, or other techniques known to those skilled in the art for producing polyclonal antibodies.

Alternatively, purified antigen or fused antigen protein may be used for producing monoclonal antibodies. Here the spleen or lymphocytes from an immunized animal are removed and immortalized or used to prepare hybridomas by methods known to those skilled in the art. To produce a human-derived hybridoma, a human lymphocyte donor is selected. A donor known to be infected with a HGV may serve as a suitable lymphocyte donor. Lymphocytes can be isolated from a peripheral blood sample. Epstein-Barr virus (EBV) can be used to immortalize human lymphocytes or a suitable fusion partner can be used to produce human-derived hybridomas. Primary in vitro sensitization with viral specific polypeptides can also be used in the generation of human monoclonal antibodies.

Antibodies secreted by the immortalized cells are screened to determine the clones that secrete antibodies of the desired specificity, for example, by using the ELISA or Western blot method (Example 10; Ausubel et al.).

Using HGV-positive serum or plasma, or the antibodies of the present invention, other antigenic peptides and epitopes can be isolated. For example, a number of different techniques have been developed for the simultaneous synthesis of many peptides (Geysen, et al.; Houghten; Frank and Doring; Hudson). The method developed by Geysen, et al., is especially useful because of the relative simplicity with which large numbers of different peptide sequences can be generated and tested for antigenicity. In the Geysen method (also referred to as MULTI-PIN peptide synthesis), the peptides are synthesized on polyacrylamide acid grafted polyethylene rods attached to a micro-titer plate. The MULTI-PIN strategy allows large numbers of syntheses (96 peptides per plate) to be immunologically screened using the polyclonal or monoclonal antibodies of the present invention and commercially available reagents and instrumentation. Immunoreactive peptides are identified and characterized.

It has been reported that up to 6,000 oligopeptides can be synthesized in a two week period, thus making it practical (by synthesizing all of the possible overlapping amino acid sequences of a particular antigen) to screen viral antigen sequences for epitopes to the resolution of a single amino acid (Geysen, et al.).

An alternative method of scanning for immunodominate peptides is to synthesize longer peptides (e.g., 10 to 30 amino acids) corresponding to HGV coding sequences using conventional automated peptide synthesis (Carter, et al., 1994; Obeid, et al., 1994; Commandaeur, et al., 1994). This method has the advantage that the longer peptides can fold into shapes that mimic conformational epitopes.

Also, HGV antibodies, in particular, monoclonals, can be used to identify random polypeptides that mimic their virus-encoded target polypeptides (Scott and Smith, 1990; Smith, 1991). For example, random peptide libraries displayed on phage (RPL) (Scott and Smith, 1990) can be used as a source of peptide ligands for antibody generation or for vaccine development. RPL approach allows the expression of peptide-ligand containing fusion proteins on the phage surface and enrichment of these ligand encoding phages by affinity selection using antibodies (Smith, J. P., 1991; Christian, et al.; Scott, et al., 1992; Folgori, et al.). These random peptide epitopes detected by specific antibodies mimic the natural antigenic epitopes (mimotopes) during epitope presentation. HGV antigenic mimics (mimotopes) can be isolated from RPL. Hexa- to decapeptide phagotope (mimotope displayed on phage) expressing RPL can be made by published methods (Scott and Smith; Smith, J. P, 1991; Christian, et al.; Scott, et al.; DeGraaf, et al.; Folgori, et al.) and screened by HGV-associated human sera or the antibodies of the present invention.

One example of the use of RPL for isolation of 470-20-1 mimotopes is as follows. The random decapeptide-pIII fusion phage display library is constructed according to the methods described previously (DeGraaf, et al., 1993).

Briefly, a chemically synthesized single-stranded degenerate insert is annealed to shorter oligonucleotides which generate SfiI restriction overhangs. Annealed DNA is ligated into SfiI-cut fUSE-5 vector DNA.

E. coli MC1061 is transformed with the ligated DNA. The library is amplified through approximately ten population doublings in LB medium with 20 mg/ml tetracycline. This library is affinity selected using one or more of 470-20-1 immunoreactive sera (or antibodies of the present invention). Polystyrene beads (Precision Plastic Ball Company, Chicago. Ill.) are coated with ammonium sulfate fractionated positive serum (e.g., PNF 2161) in 50 mM NaHCO3, pH 9.6 overnight at 4° C. Antibody coated beads are thoroughly washed with PBS and blocked with BSA.

These serum coated, blocked beads are pre-incubated with an excess of M13K07-UV killed phage for 4 hours at 4° C. Library phage are then added to the above pre-incubation mixture and incubated for 12 hours at 4° C. Unbound phage are removed and the beads are washed extensively with TTB (50 mM Tris, pH 7.5, 150 mM NaCl, 0.5% "TWEEN 20"(v/v), 1 mg/ml BSA) buffer. Bound phage are eluted with elution buffer (0.1M HCl adjusted to pH 2.2 with 2M Tris-HCl, pH 9.0). Eluted, enriched phage are screened with a second positive serum (e.g., Mys 136 sera) by plaque immunoscreening.

Further screening of the selected phagotopes can be carried out using large panels of positive and negative sera or specific HGV monoclonal antibodies. Selected phagotopes can be used directly in ELISA assay or antibody generation. Alternatively, the sequences of the phagotope encoding nucleotides can be determined and expressed in conventional vector/host system and used as antigen.

Mimic polypeptides identified as described above can in turn can serve as antigens in detection assays or can be used for the generation of antigen-specific antibodies.

D. ELISA and Protein Blot Screening.

When HGV antigens are identified, typically through plaque immunoscreening as described above, the antigens can be expressed and purified. The antigens can then be screened rapidly against a large number of suspected HGV hepatitis sera using alternative immunoassays, such as, ELISAs or Protein Blot Assays (Western blots) employing the isolated antigen peptide. The antigen polypeptides fusion can be isolated as described above, usually by affinity chromatography to the fusion partner such as β-galactosidase or glutathione-S-transferase. Alternatively, the antigen itself can be purified using antibodies generated against it (see below).

A general ELISA assay format is presented in Example 10. Harlow, et al., describe a number of useful techniques for immunoassays and antibody/antigen screening.

The purified antigen polypeptide or fusion polypeptide containing the antigen of interest, is attached to a solid support, for example, a multiwell polystyrene plate. Sera to be tested are diluted and added to the wells. After a period of time sufficient for the binding of antibodies to the bound antigens, the sera are washed out of the wells. A labelled reporter antibody is added to each well along with an appropriate substrate: wells containing antibodies bound to the purified antigen polypeptide or fusion polypeptide containing the antigen are detected by a positive signal.

A typical format for protein blot analyses using the polypeptide antigens of the present invention is presented in Example 10. General protein blotting methods are described by Ausubel, et al. In Example 10, the 470-20-1/sj26 fusion protein was used to screen a number of sera samples. The results presented in Example 10 demonstrate that several different source N-(ABCDE) hepatitis sera are immunoreactive with the polypeptide antigen.

The results presented above demonstrate that the polypeptide antigens of the present invention can, by these methods, be rapidly screened against panels of suspected HGV infected serum samples for the detection of HGV.

E. Cell Culture Systems, Animal Models and Isolation of HGV.

HGV infectivity studies have been carried out in chimpanzees, cynomolgus monkey and-four mystax subjects (Example 4H). These studies have yielded further information about HGV infectivity in these animal models. The HGV described in the present specification have the advantage of being capable of infecting tamarins, cynomologous monkeys and chimpanzees.

Alternatively, primary hepatocytes obtained from infected animals (chimpanzees, baboons, monkeys, or humans) can be cultured in vitro. A serum-free medium, supplemented with growth factors and hormones, has been described which permits the long-term maintenance of differentiated primate hepatocytes (Lanford, et al.; Jacob, et al., 1989, 1990, 1991). In addition to primary hepatocyte cultures, immortalized cultures of infected cells may also be generated. For example, primary liver cultures may be fused to a variety of cells (like HepG2) to provide stable immortalized cell lines. Primary hepatocyte cell cultures may also be immortalized by introduction of oncogenes or genes causing a transformed phenotype. Such oncogenes or genes can be derived from a number of sources known in the art including SV40, human cellular oncogenes and Epstein Barr Virus.

Further, the un-infected hepatocytes (e.g., primary or continuous hepatoma cell lines) may be infected by exposing the cells in culture to the HGV either as partially purified particle preparations (prepared, for example, from infected sera by differential centrifugation and/or molecular sieving) or in infectious sera. These infected cells can then be propagated and the virus passaged by methods known in the art. In addition, other cell types, such as lymphoid cell lines, may be useful for the propagation of HGV.

Protein similarity studies of HGV have detected amino acid regions similar to other viruses in the family Flaviviridae. It is known that members of this family of viruses can be propagated in a variety of tissue culture systems (ATCC-Viruses catalogue, 1990). By analogy it is likely that HGV can be propagated in one or more of the following tissue culture systems: Hela cells, primary hamster kidney cells, monkey kidney cells, vero cells, LLC-MK2 (rhesus monkey kidney cells), KB cells(human oral epidermoid carcinoma cells), duck embryo cells, primary sheep leptomeningeal cells, primary sheep choroid plexus cells, pig kidney cells, bovine embryonic kidney cells, bovine turbinate cells, chick embryo cells, primary rabbit kidney cells, BHD-21 cells, or PK-13 cells.

In addition to expression of HGV, regions of HGV polynucleotide sequences, cDNA or in vitro transcribed RNA can be introduced by recombinant means into tissue culture cells. Such recombinant manipulations allow the individual expression of individual components of the HGV.

RNA samples can be prepared from infected tissue or, in particular, from infected cell cultures. The RNA samples can be fractionated on gels and transferred to membranes for hybridization analyses using probes derived from the cloned HGV sequences.

HGV particles may be isolated from infected sera, infected tissue, the above-described cell culture media, or the cultured infected cells by methods known in the art. Such methods include techniques based on size fractionation (i.e., ultrafiltration, precipitation, sedimentation), using anionic and/or cationic exchange materials, separation on the basis of density, hydrophilic properties, and affinity chromatography. During the isolation procedure the HGV can be identified (i) using the anti-HGV hepatitis associated agent antibodies of the present invention, (ii) by using hybridization probes based on identified HGV nucleic acid sequences (e.g., Example 5) or (iii) by RT-PCR.

Antibodies directed against HGV can be used in purification of HGV particles through immunoaffinity chromatography (Harlow, et al.; Pierce). Antibodies directed against HGV polypeptides or fusion polypeptides (such as 470-20-1) are fixed to solid supports in such a manner that the antibodies maintain their immunoselectivity. To accomplish such attachment of antibodies to solid support bifunctional coupling agents (Pierce; Pharmacia, Piscataway, N.J.) containing spacer groups are frequently used to retain accessibility of the antigen binding site of the antibody.

HGV particles can be further characterized by standard procedures including, but not limited to, immunofluorescence microscopy, electron microscopy, Western blot analyses of proteins composing the particles, infection studies in animal and/or cell systems utilizing the partially purified particles, and sedimentation characteristics. The results presented in Example 5 suggest that the viral particle of the present invention is more similar to an enveloped viral particle than to a non-enveloped viral particle.

HGV particles can be disrupted to obtain HGV genomes. Disruption of the particles can be achieved by, for example, treatment with detergents in the presence of chelating agents. The genomic nucleic acid can then be further characterized. Characterization may include analyses of DNase and RNase sensitivity. The strandedness (Example 4I) and conformation (e.g., circular) of the genome can be determined by techniques known in the art, including visualization by electron microscopy and sedimentation characteristics.

The isolated genomes also make it possible to sequence the entire genome whether it is segmented or not, and whether it is an RNA or DNA genome (using, for example RT-PCR, chromosome walking techniques, or PCR which utilizes primers from adjacent cloned sequences). Determination of the entire sequence of HGV allows genomic organization studies and the comparison of the HGV sequences to the coding and regulatory sequences of known viral agents.

F. Screening for Agents Having Anti-HGV Hepatitis Activity.

The use of cell culture and animal model systems for propagation of HGV provides the ability to screen for anti-hepatitis agents which inhibit the production of infectious HGV: in particular, drugs that inhibit the replication of HGV. Cell culture and animal models allow the evaluation of the effect of such anti-hepatitis drugs on normal cellular functions and viability. Potential anti-viral agents (including natural products or synthetic compounds; for example, small molecules, complex mixtures such as fungal extracts, and anti-sense oligonucleotides) are typically screened for antiviral activity over a range of concentrations. The effect on HGV replication and/or antigen production is then evaluated, typically by monitering viral macromolecular synthesis or accumulation of macromolecules (e.g., DNA, RNA or protein). This evaluation is often made relative to the effect of the anti-viral agent on normal cellular function (DNA replication, RNA transcription, general protein translation, etc.).

The detection of the HGV can be accomplished by many methods including those described in the present specification. For example, antibodies can be generated against the antigens of the present invention and these antibodies used in antibody-based assays (Harlow, et al.) to identify and quantitate HGV antigens in cell culture. HGV antigens can be quantitated in culture using competition assays: polypeptides encoded by the cloned HGV sequences can be used in such assays. Typically, a recombinantly produced HGV antigenic polypeptide is produced and used to generate a monoclonal or polyclonal antibody. The recombinant HGV polypeptide is labelled using a reporter molecule. The inhibition of binding of this labelled polypeptide to its cognate antibody is then evaluated in the presence of samples (e.g., cell culture media or sera) that contain HGV antigens. The level of HGV antigens in the sample is determined by comparison of levels of inhibition to a standard curve generated using unlabelled recombinant proteins at known concentrations.

The HGV sequences of the present invention are particularly useful for the generation of polynucleotide probes/primers that may be used to quantitate the amount of HGV nucleic acid sequences produced in a cell culture system. Such quantification can be accomplished in a number of ways. For example, probes labelled with reporter molecules can be used in standard dot-blot hybridizations or competition assays of labelled probes with infected cell nucleic acids. Further, there are a number of methods using the polymerase chain reaction to quantitate target nucleic acid levels in a sample (Osikowicz, et al.).

Protective antibodies can also be identified using the cell culture and animal model systems described above. For example, polyclonal or monoclonal antibodies are generated against the antigens of the present invention. These antibodies are then used to pre-treat an infectious HGV-containing inoculum (e.g., serum) before infection of cell cultures or animals. The ability of a single antibody or mixtures of antibodies to protect the cell culture or animal from infection is evaluated. For example, in cell culture and animals the absence of viral antigen and/or nucleic acid production serves as a screen. Further in animals, the absence of HGV hepatitis disease symptoms, e.g., elevated ALT values, is also indicative of the presence of protective antibodies.

Alternatively, convalescent sera can be screened for the presence of protective antibodies and then these sera used to identify HGV hepatitis associated agent antigens that bind with the antibodies. The identified HGV antigen is then recombinantly or synthetically produced. The ability of the antigen to generate protective antibodies is tested as above.

After initial screening, the antigen or antigens identified as capable of generating protective antibodies, either singly or in combination, can be used as a vaccine to inoculate test animals. The animals are then challenged with infectious HGV. Protection from infection indicates the ability of the animals to generate antibodies that protect them from infection. Further, use of the animal models allows identification of antigens that activate cellular immunity.

In animal model studies, a protective immune response in response to challenge by a viral preparation (e.g., infected serum) (i) protects the animal from infection or (ii) prevents manifestation of disease.

G. Vaccines and the Generation of Protective Immunity.

Vaccines can be prepared from one or more of the immunogenic polypeptides identified by the method of the present invention. Genomic organization similarities between the isolated sequences from HGV and other known viral proteins may provide information concerning the polypeptides that are likely to be candidates for effective vaccines. In addition, a number of computer programs can be used for to identify likely regions of isolated sequences that encode protein antigenic determinant regions (for example, Hopp, et al.; "ANTIGEN," Intelligenetics, Mountain View, Calif.).

Vaccines containing immunogenic polypeptides as active ingredients are typically prepared as injectables either as solutions or suspensions. Further, the immunogenic polypeptides may be prepared in a solid or lyophilized state that is suitable for resuspension, prior to injection, in an aqueous form. The immunogenic polypeptides may also be emulsified or encapsulated in liposomes. The polypeptides are frequently mixed with pharmaceutically acceptable excipients that are compatible with the polypeptides. Such excipients include, but are not limited to, the following and combinations of the following: saline, water, sugars (such as dextrose and sorbitol), glycerol, alcohols (such as ethanol [EtOH]), and others known in the art. Further, vaccine preparations may contain minor amounts of other auxiliary substances such as wetting agents, emulsifying agents (e.g., detergents), and pH buffering agents. In addition, a number of adjuvants are available which may enhance the effectiveness of vaccine preparations. Examples of such adjuvants include, but are not limited to, the following: the group of related compounds including N-acetyl-muranyl-L-threonyl-D-isoglutamine and N-acetyl-nor-muranyl-L-alanyl-D-isoglutamine, and aluminum hydroxide.

The immunogenic polypeptides used in the vaccines of the present invention may be recombinant, synthetic or isolated from, for example, attenuated HGV particles. The polypeptides are commonly formulated into vaccines in neutral or salt forms. Pharmaceutically acceptable organic and inorganic salts are well known in the art.

HGV hepatitis associated agent vaccines are parenterally administered, typically by subcutaneous or intramuscular injection. Other possible formulations include oral and suppository formulations. Oral formulations commonly employ excipients (e.g., pharmaceutical grade sugars, saccharine, cellulose, and the like) and usually contain within 10–98% immunogenic polypeptide. Oral compositions take the form of pills, capsules, tablets, solutions, suspensions, powders, etc., and may be formulated to allow sustained or long-term release. Suppository formulations use traditional binders and carriers and typically contain between 0.1% and 10% of the immunogenic polypeptide.

In view of the above information, multivalent vaccines against HGV hepatitis associated agents can be generated which are composed of one or more structural or non-structural viral-agent polypeptide(s). These vaccines can contain, for example, recombinant expressed HGV polypeptides, polypeptides isolated from HGV virions, synthetic polypeptides or assembled epitopes in the form of mosaic polypeptides. In addition, it may be possible to prepare vaccines, which confer protection against HGV hepatitis infection through the use of inactivated HGV. Such inactivation might be achieved by preparation of viral lysates followed by treatment of the lysates with appropriate organic solvents, detergents or formalin.

Vaccines may also be prepared from attenuated HGV strains. Such attenuated HGV may be obtained utilizing the above described cell culture and/or animal model systems. Typically, attenuated strains are isolated after multiple passages in vitro or in vivo. Detection of attenuated strains is accomplished by methods known in the art. One method for detecting attenuated HGV is the use of antibody probes against HGV antigens, sequence-specific hybridization probes, or amplification with sequence-specific primers for infected animals or assay of HGV-infected in vitro cultures.

Alternatively, or in addition to the above methods, attenuated HGV strains may be constructed based on the genomic information that can be obtained from the information presented in the present specification. Typically, a region of the infectious agent genome that encodes, for example, a polypeptide that is related to viral pathogenesis can be deleted. The deletion should not interfere with viral replication. Further, the recombinant attenuated HGV construct allows the expression of an epitope or epitopes that are capable of giving rise to protective immune responses against the HGV. The desired immune response may include both humeral and cellular immunity.The genome of the attenuated HGV is then used to transform cells and the cells grown under conditions that allow viral replication. Such attenuated strains are useful not only as vaccines, but also as production sources of viral antigens and/or HGV particles.

Hybrid particle immunogens that contain HGV epitopes can also be generated. The immunogenicity of HGV epitopes may be enhanced by expressing the epitope in eucaryotic systems (e.g., mammalian or yeast systems) where the epitope is fused or assembled with known particle forming proteins. One such protein is the hepatitis B surface antigen. Recombinant constructs where the HGV epitope is directly linked to coding sequence for the particle forming protein will produce hybrid proteins that are immunogenic with respect to the HGV epitope and the particle forming protein. Alternatively, selected portions of the particle-forming protein coding sequence, which are not involved in particle formation, may be replaced with coding sequences corresponding to HGV epitopes. For example, regions of specific immunoreactivity to the particle-forming protein can be replaced by HGV epitope sequences.

The hepatitis B surface antigen has been shown to be expressed and assembled into particles in the yeast *Saccharomyces cerevisiea* and in mammalian cells (Valenzuela, et al., 1982 and 1984; Michelle, et al.). These particles have been shown to have enhanced immunoreactivity. Formation of these particles using hybrid proteins, i.e., recombinant constructs with heterologous viral sequences, has been previously disclosed (EPO 175,261, published 26, Mar. 1986). Such hybrid particles containing HGV epitopes may also be useful in vaccine applications.

The vaccines of the present invention are administered in dosages compatible with the method of formulation, and in such amounts that will be pharmacologically effective for prophylactic or therapeutic treatments. The quantity of immunogen administered depends on the subject being treated, the capacity of the treatment subject's immune system for generation of protective immune response, and the desired level of protection.

HGV vaccines of the present invention can be administered in single or multiple doses. Dosage regimens are also determined relative to the treatment subject's needs and tolerances. In addition to the HGV immunogenic polypeptides, vaccine formulations may be administered in conjunction with other immunoregulatory agents.

In an additional approach to HGV vaccination, DNA constructs encoding HGV proteins under appropriate regulatory control are introduced directly into mammalian tissue, in vivo. Introduction of such constructs produces "genetic immunization". Similar DNA constructs have been shown to be taken up by cells and the encoded proteins expressed (Wolf, et al.; Ascadi, et al.). Injected DNA does not appear to integrate into host cells chromatin or replicate. This expression gives rise to substantial humoral and cellular immune responses, including protection from in vivo viral challenge in animal systems (Wang, et al., 1993; Ulmer, et al.). In one embodiment, the DNA construct is injected into skeletal muscle following pre-treatment with local anesthetics, such as, bupivicaine hydrochloride with methylparaben in isotonic saline, to facilitate cellular DNA uptake. The injected DNA constructs are taken up by muscle cells and the encoded proteins expressed.

Compared to vaccination with soluble viral subunit proteins, genetic immunization has the advantage of authentic in vivo expression of the viral proteins. These viral proteins are expressed in association with host cell histocompatibility antigens, and other proteins, as would occur with natural viral infection. This type of immunization is capable of inducing both humoral and cellular immune responses, in contrast to many soluble subunit protein vaccines. Accordingly, this type of immunization retains many of the beneficial features of live attenuated vaccines, without the use of infectious agents for vaccination and attendant safety concerns.

Direct injection of plasmid or other DNA constructs encoding the desired vaccine antigens into in vivo tissues is one delivery means. Other means of delivery of the DNA constructs can be employed as well. These include a variety of lipid-based approaches in which the DNA is packaged using liposomes, cationic lipid reagents or cytofectins (such as, lipofectin). These approaches facilitate in vivo uptake and expression, as summarized by Felgner and Rhodes (1991). Various modifications to these basic approaches include the following: incorporation of peptides, or other moieties, to facilitate (i) targeting to particular cells, (ii) the intracellular disposition of the DNA construct following uptake, or (iii) to facilitate expression. Alternatively, the sequences encoding the desired vaccine antigens may be inserted into a suitable retroviral vector. The resulting recombinant retroviral vector inoculated into the subject for in vivo expression of the vaccine antigen. The antigen then induces the immune responses. As noted above, this approach has been shown to induce both humoral and cellular immunity to viral antigens (Irwin, et al.).

Further, the HGV vaccines of the present invention may be administered in combination with other vaccine agents, for example, with other hepatitis vaccines.

H. Synthetic Peptides.

Using the coding sequences of HGV polypeptide, synthetic peptides can be generated which correspond to these polypeptides. Synthetic peptides can be commercially synthesized or prepared using standard methods and apparatus in the art (Applied Biosystems, Foster City, Calif.).

Alternatively, oligonucleotide sequences encoding peptides can be either synthesized directly by standard methods of oligonucleotide synthesis, or, in the case of large coding sequences, synthesized by a series of cloning steps involving a tandem array of multiple oligonucleotide fragments corresponding to the coding sequence (Crea; Yoshio et al.; Eaton et al.). oligonucleotide coding sequences can be expressed by standard recombinant procedures (Maniatis et al.; Ausubel et al.).

V. CHARACTERIZATION OF THE VIRAL GENOME

As shown in Example 4, the HGV genome appears to be an RNA molecule and has the closest sequence similarity to viral sequences that are catagorized in the Flaviviridae family of viruses. This family includes the Flaviviruses, Pestiviruses and an unclassified Genus made up of one member, Hepatitis C virus. The HGV virus does not have significant global (i.e., over the length of the virus) sequence identity with other recognized members of the Flaviviridae—with the exception of the protein motifs discussed below.

In general members of the Flaviviridae are enveloped viruses that have densities in sucrose gradients between 1.1 and 1.23 g/ml and are sensitive to heat, organic solvents and detergents. As shown in Example 5, HGV has density characteristics similar to an enveloped Flaviviridae virus (HCV). The integrity of the HGV virion also appears to be sensitive to organic solvents (Example 5).

Flaviviridae virions contain a single molecule of linear single-stranded (ss) RNA which also serves as the only mRNA that codes for the viral proteins. The ssRNA molecule is typically between the size of 9 and 12 kilobases long.

Viral proteins are derived from one polyprotein precursor that is subsequently processed to the mature viral proteins. Most members of the Flaviviridae do not contain poly(A) tails at their 3' ends. Virions are about 15–20% lipid by weight.

Members in the Flaviviridae family have a core protein and two or three membrane-associated proteins. The analogous structural proteins of members in the three genera Flavivirus family show little similarity to one another at the sequence level. The nonstructural proteins contain conserved motifs for RNA dependent RNA polymerase (RDRP), helicase, and a serine protease. These short blocks of conserved amino acids or motifs can be detected using computer algorithms known in the art such as "MACAW" (Schuler, et al.). These motifs are presumably related to constraints imposed by substrates processed by these proteins (Koonin and Dolja). The order of these motifs is conserved in all members of the Flaviviridae family. The genome of HGV contains protein motifs found in members of the Flaviviridae family, for example, (i) the helicase gene, (ii) the serine-like protease domain, and (iii) the RNA dependent RNA polymerase (RDRP) of (see FIG. 5, "GDD" sequence);

Sequence information is disclosed herein on several different strains/isolates of HGV. This information can be used by one skilled in the art to isolate new stains/isolates using the techniques of hybridization, primer extension, and RT-PCR as described herein (e.g., using degenerate primers based on the disclosed HGV variant sequences).

In the present case, HGV is an new isolate believed to be a member of the family Flaviviridae. Within this virus family, examination of the structural proteins encoded by a virus allows the most definitive determination of whether a viral isolate is a member of a distinct species of virus. Non-structural proteins are most conserved between different species of viruses within a family of virus species. This is believed to be the result of the necessity for preserving enzymatic functions, such as, the following: the proteolytic cleavage of a viral polyprotein, and replication of the RNA genome by viral helicase and RNA dependent RNA polymerase of the virus.

Examination of several species within any genus of the Flaviviridae family, e.g., the flavivirus genus, demonstrates that the genes for these conserved functions are more highly conserved between species than the structural proteins. Accordingly, one of the major determining factors of whether a virus isolate represents a new species, versus a "variant isolate" of a known species, is a determination of global homology of the structural proteins between known viral species and the new virus isolate.

Local homologies found within regions about 200 amino acids or less which are found in non-structural proteins are indeterminant indicators of whether an isolate is a variant or a new species. Typically, virus isolates having global structural protein homologies of less than or about 40% are classified as either different species (viruses) or different genuses. The structural regions of HGV each have homologies lower than 40% compared with any virus described in "GENBANK" (comparisons carried out by methods standard in the art). Accordingly, HGV is considered to be a new species and possibly a new genus of positive strand RNA virus.

Another important region that is examined in determining the phylogenetic placement of a viral isolate is the 5' and 3' untranslated regions (UTRs). These regions are compared between viral isolates. For example, all the members HCV, an unclassified genus of Flaviviridae, have 5' untranslated regions that are greater than about 90% conserved with all other members in the genus. Further, the members of the HCV share 3' untranslated regions between about 24 and about 50 nucleotides long.

No significant alignments are found with any virus in "GENBANK" (Ver. 86) when the 5'-untranslated region is used as a query sequence with FASTA on BLASTN. Further, HGV contains a 3' untranslated region that is at least about 250 nucleotides long that also contains little homology to any other known virus.

Members of the Flaviviridae family are known to replicate in a wide variety of animals ranging from (i) hematophagous arthropod vectors (ticks and mosquitoes), where they do not cause disease, to (ii) a large range of vertebrate hosts (humans, primates, other mammals, marsupials, and birds). Over 30 members of the Flaviviridae family cause diseases in man, ranging from febrile illness, or rash, to potentially fatal diseases such as hemorrhagic fever, encephalitis, or hepatitis. At least 10 members of the Flaviviridae family cause severe and economically important diseases in domestic animals.

VI. UTILITY

A. The Invention.

In one aspect, the invention pertains to polynucleotides derived from a Hepatitis G Virus (HGV) polynucleotide in substantially isolated form. In one embodiment the HGV polynucleotide is characterized by (i) transmission in primates, (ii) serologically distinguishable from hepatitis A virus (HAV), hepatitis B virus (HBV), hepatitis C virus (HCV), hepatitis D virus, and hepatitis E virus (HEV), and (iii) membership of the virus family Flaviviridae. Polynucleotides of the invention may be comprised of DNA or RNA (or analogs or variants thereof) and may be produced recombinantly, isolated, or synthesized according to methods known in the art.

Generally, HGV polynucleotides of the invention will be at least 10 nucleotides in length. In an alternative embodiment, the HGV polynucleotide will be at least 15 nucleotides in length. In still a further alternative embodiment, the HGV polynucleotide will be at least 20 nucleotides in length.

In a more specific embodiment, polynucleotides of the invention include cDNA or cDNA complements of the HGV genome. In a more specific embodiment, such a cDNA or cDNA complement will have at least a 40% sequence homology to a polynucleotide selected from the group consisting of SEQ ID NO:14, SEQ ID NO:37, and SEQ ID NO:19, or complements thereof. In yet another embodiment such cDNA's will exhibit at least 55% sequence homology to a polynucleotide selected from the group consisting of SEQ ID NO:14, SEQ ID NO:37, and SEQ ID NO:19, or complements thereof. In more specific embodiments, cDNA or cDNA complement polynucleotides of the invention will have sequences derived from sequences selected from the group consisting of SEQ ID NO:14, SEQ ID NO:37, and SEQ ID NO:19, or complements thereof.

In another general embodiment, polynucleotides of the invention are polynucleotide probes that specifically hybridize with HGV. In yet another general embodiment, polynucleotides of the invention will encode an epitope of HGV. More specifically, such epitope encoding polynucleotides may include sequences derived from SEQ ID NO:14, SEQ ID NO:19 or SEQ ID NO:37.

In another general embodiment, the polynucleotide of the invention includes a contiguous sequence of nucleotides that is capable of selectively hybridizing to an HGV polynucleotide. In this regard, HGV is characterized as a genome comprising an open reading frame (ORF) encoding an amino acid sequence having at least 40% sequence homology to one of the following amino acid sequences: the 2873 amino acid sequence of SEQ ID NO:15, the 190 amino acid sequence of SEQ ID NO:38, or the 67 amino acid sequence of SEQ ID NO:20. More particularly, the polynucleotide probe will specifically hybridize with HGV. Such a polynucleotide probe may carry detection labels or other modifications or be fixed to a solid support.

DNA polynucleotides as described above may also encode an HGV specifically immunoreactive antigenic determinants. In this regard, HGV is characterized as having a genome, cDNA or complements thereof comprising an open reading frame (ORF) encoding an amino acid sequence. Such, an amino acid sequence having at least 40% sequence homology to one of the following amino acid sequences: the 2873 amino acid sequence of SEQ ID NO:15, the 190 amino acid sequence of SEQ ID NO:38, or the 67 amino acid sequence of SEQ ID NO:20.

In another specific embodiment, an HGV-encoding DNA polynucleotide that is specifically reactive with an HGV antigenic determinant will, in accordance with the invention, include an amino acid sequence having at least 55% sequence homology to the 2873 amino acid sequence of SEQ ID NO:15 or to the 190 amino acid sequence of SEQ ID NO:38 or to the 67 amino acid sequence of SEQ ID NO:20.

In yet another specific embodiment, the DNA polynucleotide may exhibit at least 40% sequence homology to a polynucleotide selected from the group consisting of SEQ ID NO:14, SEQ ID NO:37, and SEQ ID NO:19, or complements thereof.

In still a further embodiment, the invention includes a DNA polynucleotide that encodes an HGV-derived polypeptide. More particularly, the polypeptide encoded by the polynucleotide will include a contiguous sequence of at least 15–60 amino acids having 55% sequence homology to a contiguous sequence of at least 15–60 amino acids encoded by an HGV genome, cDNA or complements thereof.

In a specific embodiment, HGV-polypeptide encoding polynucleotides may be encoded within the PNF 2161 cDNA source lambda gt11 library. In yet another specific embodiment, the DNA polynucleotide may encode an epitope of HGV. In still a further embodiment, the polynucleotide may be a probe that specifically hybridizes with HGV.

In a related aspect, the invention includes a recombinant vector that contains a DNA polynucleotide that encodes an HGV polypeptide. In another related aspect, the invention includes a cell transformed with such a vector.

In still another related aspect, the invention includes a polynucleotide probe that specifically hybridizes with an HGV hepatitis virus genome, cDNA or complements thereof. In a more specific embodiment, the polynucleotide probe sequence has at least 40% homology to a sequence derived from SEQ ID NO:19, SEQ ID NO:37, or SEQ ID NO:14, or complements thereof. In another specific embodiment, the polynucleotide probe is derived from SEQ ID NO:19, SEQ ID NO:37, or SEQ ID NO:14, or complements thereof.

In another related aspect, the invention includes a method of detecting an HGV hepatitis virus nucleic acid in a test subject. According to the method a nucleic acid-containing sample is obtained from the subject. The sample is then combined with and at least one polynucleotide probe that specifically hybridizes with the HGV hepatitis viral genome. HGV nucleic acid/probe complexes, formed by hybridization of the HGV nucleic acid with probe, are then detected. Such detecting may be accomplished by hybridization of a probe containing at least one reporter moiety to the HGV nucleic acid.

In a more specific embodiment, the above-described method includes the use of HGV nucleic acid specific probes where the two probes (primers) define an internal region of the HGV nucleic acid. In this embodiment, each probe has one strand containing a 3'-end internal to the HGV nucleic acid internal region. The nucleic acid/probe hybridization complexes are then converted to double-strand probe containing fragments by primer extension reactions. Probe-containing fragments are amplified by successively repeating the steps of (i) denaturing the double-strand fragments to produce single-strand fragments, (ii) hybridizing the single strands with the probes to form strand/probe complexes, (iii) generating double-strand fragments from the strand/probe complexes in the presence of DNA polymerase and all four deoxyribonucleotides, and (iv) repeating steps (i) to (iii) until a desired degree of amplification has been achieved. Amplification products are then identified according to established procedures. The method of the invention may further include a third polynucleotide probe capable of selectively hybridizing to the internal region described above but not to the specific probe/primer sequences used for amplification.

In another specific embodiment, detection of HGV nucleic acid/probe complexes is accomplished by a target amplification method, such as by self-sustained sequence replication, ligase chain reaction, or strand displacement amplification. In a further specific embodiment detection is accomplished employing a signal amplification technique such as branch-chained DNA probes or the Q-beta replicase method.

In still another related aspect, the invention includes a kit for analyzing samples for the presence of polynucleotides derived HGV hepatitis virus. In a general embodiment, the kit includes at least one polynucleotide probe containing a nucleotide sequence that will specifically hybridize with an HGV polynucleotide and a suitable container. In a specific embodiment, the kit includes two polynucleotide probes defining an internal region of the HGV polynucleotide, where each probe has one strand containing a 3'-end internal to the region. In a further embodiment, the probes may be useful as primers for polymerase chain reaction amplification.

In still a further related aspect, the invention includes the HGV hepatitis virus particle in substantially isolated form.

The invention also includes a polypeptide or a preparation of polypeptides from the HGV hepatitis virus in substantially isolated form. In this regard, the HGV virus is characterized as follows: (i) it is transmissible in primates; (ii) it is serologically distinct from hepatitis A virus (HAV), hepatitis B virus (HBV), hepatitis C virus (HCV), hepatitis D virus, and hepatitis E virus (HEV); and (iii) it is a member of the virus family Flaviviridae. HGV polypeptides, as defined above, may be prepared by conventional means, including chemical synthesis and recombinant DNA expression. Such polypeptides may also be fixed to a solid phase.

In a specific embodiment the polypeptide is specifically immunoreactive with at least one anti-HGV antibody. In still a further specific embodiment, the polypeptide comprises an antigenic determinant specifically immunoreactive with HGV. In this context, HGV is characterized by having a genome comprising an open reading frame (ORF) encoding an amino acid sequence having at least 40% sequence homology to the 2873 amino acid sequence of SEQ ID NO:15 or to the 190 amino acid sequence of SEQ ID NO:38 or to the 67 amino acid sequence of SEQ ID NO:20. In a more specific embodiment, the ORF encodes amino acid sequence has at least 55% sequence homology to one of the aforementioned amino acid sequences. In still a further embodiment, the polypeptide sequence is derived from the 2873 amino acid sequence of SEQ ID NO:15, or fragments thereof, the 190 amino acid sequence of SEQ ID NO:38, or fragments thereof, or the 67 amino acid sequence of SEQ ID NO:20, or fragments thereof.

In another specific embodiment, the polypeptide from the HGV hepatitis virus includes a contiguous sequence of at least about 60 amino acids encoded by an HGV genome, cDNA or complements thereof. More specifically, such peptide sequence may be encoded by the PNF 2161 cDNA source lambda gt11 library.

Recombinantly expressed HGV polypeptides may, in a more specific embodiment, include a polypeptide sequence derived from SEQ ID NO:20, SEQ ID NO:38, or SEQ ID NO:15. In another embodiment such a polypeptide may be encoded by a sequence derived from SEQ ID NO:14, or from the complement of SEQ ID NO:14.

In a further related embodiment, in accordance with the invention, an HGV hepatitis virus polypeptide may be a fusion polypeptide comprising an HGV polypeptide and a second polypeptide. More specifically, such a fusion polypeptide may include, as a second polypeptide signal sequences, β-galactosidase or glutathione-S-transferase protein sequences. Alternatively, the second polypeptide may comprise a particle forming protein.

The above-described polypeptides may be derived from structural or non-structural viral proteins.

In still a further related aspect, the invention includes a cloning vector capable of expressing, under suitable conditions, an open reading frame (ORF) of cDNA derived from HGV hepatitis virus genome, cDNA or complements thereof. In this aspect of the invention, the ORF is operably linked to a control sequence compatible with a desired host. In a related aspect, the invention includes a cell transformed with such a vector. In a more specific embodiment of the vector, the ORF may be derived from SEQ ID NO:14 or its complement. In yet further specific embodiments, the ORF may be derived from SEQ ID NO:37 or SEQ ID NO:19.

In a related aspect, the invention includes a method of producing an HGV hepatitis virus polypeptide. The method includes culturing cells containing the above-described vectors under conditions suitable to achieve expression of the open reading frame (ORF) sequence. In a more specific embodiment, the ORF sequence encodes a polypeptide sequence selected from the group of polypeptide sequences, or fragments thereof, consisting of SEQ ID NO:15, SEQ ID NO:38 and SEQ ID NO:20. Further, the ORF sequences may be derived from an HGV cDNA, or complement thereof. In yet another specific embodiment, the vector is a lambda gt11 phage vector expressed in *Escherichia coli* cells.

In a further related aspect, the invention includes a diagnostic kit for use in screening serum containing antibodies specific against HGV hepatitis virus infection. Such a kit may include a substantially isolated HGV polypeptide antigen comprising an epitope which is specifically immunoreactive with at least one anti-HGV antibody. Such a kit also includes means for detecting the binding of said antibody to the antigen. In regard to such a kit, HGV is characterized by having a genome, cDNA or complements thereof comprising an open reading frame (ORF) encoding an amino acid sequence. Such an amino acid sequence typically having at least 40% sequence homology to the 2873 amino acid sequence of SEQ ID NO:15 or to the 190 amino acid sequence of SEQ ID NO:38 or to the 67 amino acid sequence of SEQ ID NO:20. In specific embodiments, the kit may include a recombinantly produced or chemically synthesized polypeptide antigen. The polypeptide antigen of the kit may also be attached to a solid support.

In a more specific embodiment, the detecting means of the above-described kit includes a solid support to which said polypeptide antigen is attached. Such a kit may also include a non-attached reporter-labelled anti-human antibody. In this embodiment, binding of the antibody to the HGV polypeptide antigen can be detected by binding of the reporter-labelled antibody the antibody.

In a related aspect, the invention includes a method of detecting HGV hepatitis virus infection in a test subject. This detection method includes reacting serum from an HGV test subject with a substantially isolated HGV polypeptide antigen, and examining the antigen for the presence of bound antibody. In a specific embodiment, the method includes a polypeptide antigen attached to a solid support, and the serum is reacted with the support. Subsequently, the support is reacted with a reporter-labelled anti-human antibody. The solid support is then examined for the presence of reporter-labelled antibody.

In a further related aspect, the invention includes an HGV hepatitis virus vaccine composition. The composition includes a substantially isolated HGV polypeptide antigen, where the antigen includes an epitope which is specifically immunoreactive with at least one anti-HGV antibody. The peptide antigen may be produced according to methods known in the art, including recombinant expression or chemical synthesis. The peptide antigen is preferably present in a pharmacologically effective dose in a pharmaceutically acceptable carrier.

In still a further related aspect, the invention includes a monoclonal antibody that is specifically immunoreactive with the HGV hepatitis virus epitope. In another related aspect, the invention includes a substantially isolated preparation of polyclonal antibodies specifically immunoreactive with HGV. In a more specific embodiment, such polyclonal antibodies are prepared by affinity chromatography.

In a related aspect, the invention includes a method for producing antibodies to HGV. The method includes administering to a test subject a substantially isolated HGV polypeptide antigen, where the antigen includes an epitope which is specifically immunoreactive with at least one anti-HGV antibody. The antigen is administered in an amount sufficient to produce an immune response in the subject.

In yet another related aspect, the invention includes a diagnostic kit for use in screening serum containing HGV antigens. The diagnostic kit includes a substantially isolated antibody specifically immunoreactive with an HGV polypeptide antigen, and means for detecting the binding of the polypeptide antigen to the antibody. In one embodiment, the antibody is attached to a solid support. In a specific embodiment, the antibody may be a monoclonal antibody. The detecting means of the kit may include a second, labelled monoclonal antibody. Alternatively, or in addition, the detecting means may include a labelled, competing antigen.

In another, related aspect, the invention includes a method of detecting HGV infection in a test subject. According to this aspect of the invention, serum from a test subject is reacted with a substantially isolated HGV specific antibody of the kit described above. The HGV specific antibody is then examined for the presence of bound antigen.

In still a further related aspect, the invention includes an in vitro grown cell infected with HGV. In a specific embodiment, the cell is a hepatocyte grown in tissue culture. More specifically, the tissue culture cell may be an immortalized hepatocyte, or it may be a from a cell line derived from liver of an HGV infected primate.

In a related aspect, the invention includes a method of propagating HGV. The method includes culturing in vitro grown, HGV-infected cells, as described above, under conditions effective to promote the propagation of HGV. In another related aspect, the invention includes HGV particles produced by such a propagation method.

In still a further aspect, the invention includes a mosaic polypeptide. Such a polypeptide may include at least two epitopes of HGV, where the polypeptide substantially lacks amino acids normally intervening between the epitopes in the native HGV coding sequence. In a more specific embodiment, the mosaic polypeptide is attached to a solid support. In still a further related aspect, the invention includes a nucleic acid that encodes the above-described mosaic polypeptide.

In another related aspect, the invention includes a method of detecting HGV infection in a test subject. The method includes contacting an antibody-containing sample from the subject with a mosaic polypeptide, as described above, and examining the antigen for the presence of bound antibody.

In still a further related aspect, the invention includes an HGV vaccine composition. The vaccine composition includes mosaic polypeptide that includes more than one HGV epitope. The mosaic polypeptide is present in a pharmacologically effective dose in a pharmaceutically acceptable carrier.

B. Immunoassays for HGV.

One utility for the antigens obtained by the methods of the present invention is their use as diagnostic reagents for the detection of antibodies present in the sera of test subjects infected with HGV hepatitis virus, thereby indicating infection in the subject; for example, 470-20-1 antigen, antigens encoded by SEQ ID NO:14 or its complement, and antigens encoded by portions of either strand of the complete viral sequence. The antigens of the present invention can be used singly, or in combination with each other, in order to detect HGV. The antigens of the present invention may also be coupled with diagnostic assays for other hepatitis agents such as HAV, HBV, HCV, and HEV.

In one diagnostic configuration, test serum is reacted with a solid phase reagent having a surface-bound antigen obtained by the methods of the present invention, e.g., the 470-20-1 antigen. After binding with anti-HGV antibody to the reagent and removing unbound serum components by washing, the reagent is reacted with reporter-labelled anti-human antibody to bind reporter to the reagent in proportion to the amount of bound anti-HGV antibody on the solid support. The reagent is again washed to remove unbound labelled antibody, and the amount of reporter associated with the reagent is determined. Typically, the reporter is an enzyme which is detected by incubating the solid phase in the presence of a suitable fluorometric or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Also forming part of the invention is an assay system or kit for carrying out this diagnostic method. The kit generally includes a support with surface-bound recombinant HGV antigen (e.g., the 470-20-1 antigen, as above), and a reporter-labelled anti-human antibody for detecting surface-bound anti-HGV antigen antibody.

In a second diagnostic configuration, known as a homogeneous assay, antibody binding to a solid support produces some change in the reaction medium which can be directly detected in the medium. Known general types of homogeneous assays proposed heretofore include (a) spin-labelled reporters, where antibody binding to the antigen is detected by a change in reported mobility (broadening of the spin splitting peaks), (b) fluorescent reporters, where binding is detected by a change in fluorescence efficiency or polarization, (c) enzyme reporters, where antibody binding causes enzyme/substrate interactions, and (d) liposome-bound reporters, where binding leads to liposome lysis and release of encapsulated reporter. The adaptation of these methods to the protein antigen of the present invention follows conventional methods for preparing homogeneous assay reagents.

In each of the assays described above, the assay method involves reacting the serum from a test individual with the protein antigen and examining the antigen for the presence of bound antibody. The examining may involve attaching a labelled anti-human antibody to the antibody being examined (for example from acute, chronic or convalescent phase) and measuring the amount of reporter bound to the solid support, as in the first method, or may involve observing the effect of antibody binding on a homogeneous assay reagent, as in the second method.

A third diagnostic configuration involves use of HGV antibodies capable of detecting HGV-specific antigens. The HGV antigens may be detected, for example, using an antigen capture assay where HGV antigens present in candidate serum samples are reacted with a HGV specific monoclonal or polyclonal antibody. The antibody is bound to a solid substrate and the antigen is then detected by a second, different labelled anti-HGV antibody. Antibodies can be prepared, utilizing the peptides of the present invention, by standard methods. Further, substantially isolated antibodies (essentially free of serum proteins which may affect reactivity) can be generated (e.g., affinity purification (Harlow et al.)).

C. Hybridization Assays for HGV.

One utility for the nucleic acid sequences obtained by the methods of the present invention is their use as diagnostic agents for HGV sequences present in sera, thereby indicating infection in the individual. Primers and/or probes derived from the coding sequences of the present invention, in particular, Clone 470-20-1 and SEQ ID NO:14, can be used singly, or in combination with each other, in order to detect HGV.

In one diagnostic configuration, test serum is reacted under PCR or RT-PCR conditions using primers derived from, for example, 470-20-1 sequences. The presence of HGV, in the serum used in the amplification reaction, can be detected by specific amplification of the sequences targeted by the primers. Example 4 describes the use of polymerase chain amplification reactions, employing primers derived from the clones of the present invention, to screen different source material. The results of these amplification reactions demonstrate the ability of primers derived from the clones of the present invention (for example, 470-20-1), to detect homologous sequences by amplification reactions employing a variety of different source templates. The amplification reactions in Example 4 included use of nucleic acids obtained directly from sera as template material.

Alternatively, probes can be derived from the HGV sequences of the present invention. These probes can then be labelled and used as hybridization probes against nucleic acids obtained from test serum or tissue samples. The probes can be labelled using a variety of reporter molecules and detected accordingly: for example, radioactive isotopic labelling and chemiluminescent detection reporter systems (Tropix, Bedford, Mass.).

Target amplification methods, embodied by the polymerase chain reaction, the self-sustained sequence replication technique ["3SR," (Guatelli, et al.; Gingeras, et al., 1990) also known as "NASBA" (VanGemen, et al.)], the ligase chain reaction (Barany), strand-displacement amplification ["SDA," (Walker)], and other techniques, multiply the number of copies of the target sequence. Signal amplification techniques, exemplified by branched-chain DNA probes (Horn and Urdea; Urdea; Urdea, et al.) and the Q-beta replicase method (Cahill, et al.; Lomell, et al.), first bind a specific molecular probe, then replicate all of or part of this probe or in some other manner amplify the probe signal.

For the detection of the specific nucleic acid sequences disclosed in the present invention or contiguous sequences in the same or a similar (related) viral genome, amplification and detection methodologies may be employed, as alternatives to amplification by the PCR. A number of such techniques are known to the field of nucleic acid diagnostics (The 1992 San Diego Conference: Genetic Recognition, *Clin. Chem.* 39(4):705 (1993)).

1. Self-Sustained Sequence Replication.

The Self-Sustained Sequence Replication (3SR) technique results in amplification to a similar magnitude as PCR, but isothermally. Rather than thermal cycle-driven PCR, the 3SR operates as a concerted three-enzyme reaction of a) cDNA synthesis by reverse transcriptase, b) RNA strand degradation by RNase H, and c) RNA transcription by T7 RNA polymerase.

As the entire reaction sequence occurs isothermally (typically at 42° C.), expensive temperature-cycling instrumentation is not required. In the absence of duplex denaturation via heating, organic solvents, or other mechanism, only single-stranded templates (i.e., predominantly RNA) are amplified.

Suitable primers for use in 3SR amplification can be selected from the viral sequences of the present invention by those having ordinary skill in the art. For example, for isothermal amplification of viral sequences by the 3SR technique, primer 470-20-1-77F (SEQ ID NO:9) is modified by the addition of the T7 promoter sequence and a preferred T7 transcription initiation site to the 5'-end of the oligonucleotide. This modification results in a suitable 3SR primer T7-470-20-1-77F (SEQ ID NO:9). Primer 470-20-1-211R (SEQ ID NO:10) can be used in these reactions either without modification or T7 promoter.

RNA extracted from PNF 2161 is incubated with AMV reverse transcriptase (30 U), RNase H (3 U), T7 RNA polymerase (100 U), in 100 ul reactions containing 20 mM Tris-HCl, pH 8.1 (at room temperature), 15 mM MgCl$_2$, 10 mM KCl, 2 mM spermidine HCl, 5 mM dithiothreitol (DTT), 1 mM each of dATP, dCTP, dGTP, and TTP, 7 mM each of ATP, CTP, GTP, and UTP, and 0.15 uM each primer. Amplification takes place during incubation at 42° C. for 1–2 h.

Initially, primer T7-470-20-1-77F anneals to the target RNA, and is extended by AMV reverse transcriptase to form cDNA complementary to the starting RNA strand. Following degradation of the RNA strand by RNase H, reverse transcriptase catalyzes the synthesis of the second strand DNA, resulting in a double-stranded template containing the (double-stranded) T7 promoter sequence. RNA transcription results in production of single-stranded RNA. This RNA then serves to re-enter the cycle for additional rounds of amplification, finally resulting in a pool of high-concentration product RNA. The product is predominantly single-stranded RNA of the same strand as the primer containing the T7 promoter (T7-470-20-177F), with much smaller amounts of cDNA.

Alternatively, the other primer (470-20-1-211R) may contain the T7 promoter, or both primers may contain the promoter, resulting in production of both strands of RNA as products of the reaction. Products of the 3SR reaction may be detected, characterized, or quantitated by standard techniques for the analyses of RNA (e.g., Northern blots, RNA slot or dot blots, direct gel electrophoresis with RNA-staining dyes). Further, the products may be detected by methods making use of biotin-avidin affinity interactions or specific hybridizations of nucleic acid probes.

In one technique for rapid and specific analyses of 3SR products, solution hybridization of the product to radiolabelled oligonucleotide 470-20-1-152R (SEQ ID NO:21) is followed by non-denaturing polyacrylamide gel electrophoresis. This assay (a gel mobility shift-type assay) results in the detection of specific probeproduct hybrid as a slower-moving band than the band corresponding to unhybridized oligonucleotide.

2. Ligase Chain Reaction (LCR)

As another example of a detection system, the HGV sequence may form the basis for design of ligase chain reaction (LCR) primers. LCR makes use of the nickclosing activity of DNA ligase to join two immediately adjacent oligonucleotides possessing adjacent 5'-phosphate ("donor" oligo) and 3'-hydroxyl ("acceptor" oligo) terminii. The property of DNA ligase to join only fully complementary ends in a template-dependent way, leads to a high degree of specificity, in that ligation will not occur unless the terminii to be linked are perfectly matched in sequence to the target strand.

As an alternative to PCR, with some advantages in terms of specificity for discrimination of single base mismatches between primer and target nucleic acid, the LCR may be used to detect or "type" strains of virus possessing homology to HGV sequences. These techniques are suitable for assessing the presence of specific mutations when such base changes are known to confer drug resistance (e.g., Larder and Kemp; Gingeras, et al., 1991).

In the presence of template-complementary donor and acceptor oligonucleotides and oligonucleotides complementary to the donor and acceptor, exponential amplification by LCR is possible. In this embodiment, each round of ligation generates additional template for subsequent rounds, in a cyclic reaction.

For example, primer 470-20-1-211R (SEQ ID NO:10), an adjacent oligonucleotide (B, SEQ ID NO:22) and cognate oligos (211R', SEQ ID NO:23, and B', SEQ ID NO:24), can be used to perform LCR amplification of the sequence of this invention. Reverse transcription is first performed by standard methods to generate cDNA, which is then amplified in reactions containing 0.1–1 $\mu$M each of the four LCR primers, 20 mM Tris-HCl, pH 8.3 (room temperature), 25 mM KCl, 10 mM MgCl$_2$, 10 mM dithiothreitol (DTT), 0.5 mM NAD+, 0.01% Triton X-100, and 5 Units of DNA ligase (Ampligase, Epicentre Technologies, Madison, Wis., or other commercial supplier of thermostable DNA ligase), in 25 ul reactions.

Thermal cycling is performed at 94° C. for 1 min. 30 s; 94° C. for 1 min., 65° C. for 2 min., repeated for 25–40 cycles. Specificity of product synthesis depends on primer-template match at the 3'-terminal position. Products are detected by polyacrylamide gel electrophoresis, followed by ethidium bromide staining; alternatively, one of the acceptor oligos (211R' or B) is 5'-radiolabelled for visualization by autoradiography following gel electrophoresis.

Alternatively, a donor oligo is 3'-end-labelled with a specific bindable moiety (e.g., biotin), and the acceptor is 5'-labelled with a specific detectable group (e.g., a fluorescent dye), for solid phase capture and detection.

3. Methods for Analysis of Amplified DNA

Numerous techniques have been described for the analyses of amplified DNA. Several such techniques are advantageous for high-throughput applications, where gel electrophoresis is impractical, for example, rapid and high-resolution HPLC techniques (Katz and Dong). However, in general, methods for infectious disease organism screening using nucleic acid probes involve a separate post-amplification hybridization step in order to assure requisite specificity for pathogen detection.

One such detection embodiment is an affinity-based hybrid capture technique (Holodniy, et al.). In this embodiment the PCR is conducted with one biotinylated primer. Following amplification, the double-stranded product is denatured then hybridized to a peroxidase-labelled probe complementary to the strand having incorporated the biotinylated primer. The hybridized product is then incubated in a buffer which is in contact with an avidin (or streptavidin) coated surface (e.g., membrane filter, microwell, latex or paramagnetic beads).

The mass of coated solid phase which contacts the volume of PCR product to be analyzed by this method must contain sufficient biotin-binding sites to capture essentially all of the free biotinylated primer, as well as the much lower concentration of biotinylated PCR product. Following three to four washes of the solid phase, bound hybridized product is detected by incubation with o-phenylenediamine in citrate buffer containing hydrogen peroxide.

Alternatively, capture may be mediated by probe-coated surfaces, followed by affinity-based detection via the biotinylated primer and an avidin-reporter enzyme conjugate (Whetsell, et al.).

4. Additional Methods

Viral sequences of the present invention may also form the basis for a signal amplification approach to detection, using branched-chain DNA probes. Branched-chain probes (Horn and Urdea; Urdea) have been described for detection and quantification of rare RNA and DNA sequences (Urdea, et al.). In this method, an oligonucleotide probe (RNA, DNA, or nucleic acid analogue) is synthesized with a sequence complementary to the target RNA or DNA. The probe also contains a unique branching sequence or sequences not complementary to the target RNA or DNA.

This unique sequence constitutes a target for hybridization of branched secondary detector probes, each of which contains one or more other unique sequences, serving as targets for tertiary probes. At each branch point in the signal amplification pathway, a different unique sequence directs hybridization of secondary, tertiary, etc., detection probes. The last probe in the series typically is linked to an enzyme useful for detection (e.g., alkaline phosphatase). The sequential hybridization of primers eventually results in the buildup of a highly-branched structure, the arms of which terminate in enzyme-linked probes.

Enzymatic turnover provides a final amplification, and the choice of highly sensitive chemiluminescent substrates (e.g., LumiPhos, Lumigen, Detroit, Mich., as a substrate for alkaline phosphatase labels) results in exquisite sensitivity, on the order of 10,000 molecules or less of original target sequence per assay. In such a detection method, amplification depends only on molecular hybridization, rather than enzymatic mechanisms, and is thus far less susceptible to inhibitory substances in clinical specimens than, for example, PCR. Thus, this detection method allows the use of crude techniques for nucleic acid release in test samples, without extensive purification before assay.

Amplification for sensitive detection of the viral sequences of the present invention may also be accomplished by the Q-β replicase technique (Cahill, et al.; Lomell, et al.; Pritchard, et al.). In this method, a specific probe is designed to be complementary to the target sequence. This probe is then inserted by standard molecular cloning techniques into the sequence of the replicatable RNA from Q-β phage. Insertion into a specific region of the replicon does not prevent replication by Q-β replicase.

Following molecular hybridization, and several cycles of washing, the replicase is added and amplification of the probe RNA ensues. "Reversible target capture" is one known technique for reducing the potential background from replication of unhybridized probes (Morrissey, et al.). Amplified replicons are detectable by standard molecular hybridization techniques employing DNA, RNA or nucleic acid analogue probes.

Additional methods for amplification and detection of rare DNA or RNA sequences are known in the literature and preferred to the PCR for some applications in the field of molecular diagnostics. These alternative techniques may form the basis for detection, characterization (e.g., sequence diversity existing as multiple related strains of the sequence described herein, genotypic changes characteristic of drug resistance), or quantification of the sequence disclosed in the present invention.

Also forming part of the invention are assay systems or kits for carrying out the amplification/hybridization assay methods just described. Such kits generally include either specific primers for use in amplification reactions or hybridization probes.

D. Therapeutic Uses.

As discussed above, the HGV antigens of the present invention can be used in vaccine preparation.

Further, antibodies generated against the polypeptide antigens of the present invention can be used for passive immunotherapy or passive immunoprophylaxis. The antibodies can be administered in amounts similar to those used for other therapeutic administrations of antibody. For example, pooled gamma globulin is administered at 0.02–0.1 ml/lb body weight during the early incubation of other viral diseases such as rabies, measles and hepatitis B to interfere with establishment of infection. Thus, antibodies reactive with the HGV antigens can be passively administered alone or in conjunction with another anti-viral agent to a host infected with HGV to enhance the ability of the host to deal with the infection.

The HGV sequences disclosed herein identify HGV as a member of the Flaviviridae family (see above). The Flaviviridae are classified into 3 genera, flaviviruses, petstiviruses, and the hepatitis C virus genera (Francki, et al.). All Flaviviridae possess a positive strand RNA genome of 9.0–12 kb in length which encodes a single long polypeptide of 3000–4000 amino acids. This polypeptide is proteolytically cleaved into approximately 10 proteins, including, a viral capsid protein, viral envelope protein(s), and a minimum of 5 non-structural proteins (NS). The nonstructural proteins include a chymotrypsin like serine protease, RNA helicase (NS3), and an RNA-dependent RNA polymerase (NS5). The NS3 protein of Flaviviridae is required for proteolytic cleavage of the viral polypeptide. The NS5 protein is required for replication of the viral genome (Chambers, et al., 1990a).

Additionally, several cellular proteins have been identified as being involved in the replication of the Flaviviridae. For example, cellular signal peptidase enzyme may be required to cleave the viral polypeptide at several cleavage sites, to allow for expression of the viral protease (Hijikata, et al.).

Inhibitors which prevent these proteins from carrying out their required functions in flavivirus replication may also have therapeutic value at treating infection with HGV. Finally cytokines or other polypeptides which are known to have antiviral activity and/or modulate the human immune system may be efficacious at treating HGV infection.

One compound known to inhibit Flaviviridae RNA dependent RNA polymerases, which by analogy may be expected to inhibit the activity of the NS5 protein of HGV, is the nucleotide analogue 1-B-D-ribofuranosyl-1-2,4-triazole, 3-carboxamide, also known as ribavirin (Patterson, et al.). The method of action of ribavirin is thought to involve depletion of intercellular guanine pools and interference with the capping of viral RNAs (Patterson et al.).

In individuals infected with HCV, significant reductions in viral titer and in serum levels of alanine aminotransferase (ALT—an indicator enzyme for liver dysfunction) were observed while ribavirin was administered (Reichard, et al.; Di Bisceglie, et al., 1992). Ribavirin appears to have broad efficacy for treating Flaviviridae infections, accordingly, beneficial results are expected after administration of ribavirin to individuals suffering from HGV derived liver disease.

Another class of compounds known to be efficacious for treating Flaviviridae infections include the cytokines interferon α, interferon β, and interferon γ (Baron, et al.; Gutterman). Interferons are thought to act as antivirals by both (i) inducing the expression of cellular proteins that interfere with the replication and translation of viral RNAs, and (ii) by the activation of components of the human cellular immune system (Baron, et al.). The interferons have broad applicability to the treatment of viral infections including infection with HBV, HDV, and HCV (Gutterman; Farci, et al.). In particular, multiple studies have indicated that the interferons, either alone or in combination with other antiviral therapies, are effective at treating infection with hepatitis C virus (Di Bisceglie, et al., 1989; Kakumu, et al.). Due to both the apparent hepatotropic nature of HGV and its classification in the family Flaviviridae, HGV infection may be expected to respond to similar interferon therapy.

Still another class of compounds with potent anti-viral activity are inhibitors of viral proteases (Krausslich, et al.). All Flaviviridae encode a chymotrypsin-like serine protease which is required to cleave multiple sites of the genome polypeptide at multiple sites in the non-structural region. The amino acid residues that make up the catalytic site of this protease are well described and include a Histidine, an Aspartic acid, and a Serine residue (Grakoui, et al.). Furthermore studies of the flavivirus, Yellow Fever Virus have indicated that mutation of the Serine residue of the active site inhibits viral replication (Chambers, et al., 1990b).

Inhibitors of the HGV NS3 protein can be designed to mimic the transition state of enzymatic cleavage. Alternatively, such inhibitors may be isolated by mass screening of previously synthesized compounds. The activity of putative HGV NS3 proteinase inhibitors can be determined through the use of in vitro transcription/translation systems, which are widely used in Flaviviridae research (Hijikata, et al.; Grakoui, et al.).

Alternatively, the HGV genome can be cloned into a suitable vector for eukaryotic protein expression, such a bacculovirus or vaccinia, and the efficacy of the compounds can be determined in tissue culture systems (Grakoui, et al.). Similar approaches have been employed successfully to obtain potent inhibitors of the HIV protease (Vacca, et al.; Roberts, et al.).

Another approach to treating disease caused by infection with the HGV relies on the synthesis of antisense oligonucleotides (Tonkinson and Stein) or oligonucleotide analogs which encode portions of the sequences of HGV disclosed in the present invention. As is true for all Flaviviridae, it would be expected that the genome of HGV is a positive strand RNA molecule of 9–12 kb in size. The single stranded nature of the viral genome should make HGV exquisitely sensitive to antisense oligonucleotides. Possible target sequences which might be employed to inhibit viral replication include the 5' untranslated region of HGV, the ribosome binding site of HGV or other sequences which would interfere with the translation of the HGV genome.

Antisense oligonucleotides can be synthesized using commercially available synthesizers. Preferably the oligonucleotides are synthesized using phosphorodithioate backbones which have the advantage of being resistant to nuclease cleavage (Marshall & Caruthers). Additionally other oligonucleotide analogues, such as those having a uncharged or amide type backbone (Egholm, et al.) may be employed. These oligonucleotides are commercially available (Biosearch, Millipore, Bedford, Mass.) and advantageous in that their lack of charge allows them to cross biological membranes, which are typically resist the passage of charged macromolecules.

Oligonucleotides (or analogs thereof) for antisense applications are typically greater than 8 nucleotides in length to facilitate hybridization to a target sequence within the HGV genome. Upon hybridization of, for example, DNA oligomers to viral RNA target sequences, the hybridization complex can be degraded by a cellular enzyme such as RNAse H. The reduction in HGV templates then lessens the severity of HGV associated disease.

The usefulness and efficacy of the above described therapeutic methods can be evaluated in vitro, using the cell systems described above, and in vivo, using the animal model systems described above.

The following examples illustrate, but in no way are intended to limit the present invention.

MATERIALS AND METHODS

Synthetic oligonucleotide linkers and primers were prepared using commercially available automated oligonucleotide synthesizers. Alternatively, custom designed synthetic oligonucleotides may be purchased from commercial suppliers.

Standard molecular biology and cloning techniques were performed essentially as previously described in Ausubel, et al., Sambrook, et al., and Maniatis, et al.

Common manipulations relevant to employing antisera and/or antibodies for screening and detection of immunoreactive protein antigens were performed essentially as described (Harlow, et al.). Similarly ELISA and Western blot assays for the detection of anti viral antibodies were performed either as described by their manufacturer (Abbott, N. Chicago, Ill., Genelabs Diagnostics, Singapore) or using standard techniques known in the art (Harlow, et al).

EXAMPLES

Example 1

Construction of PNF2161 cDNA Libraries

A. Isolation of RNA from Sera.

One milliliter of undiluted PNF 2161 serum was precipitated by the addition of PEG (MW 6,000) to 8% and centrifugation at 12K, for 15 minutes in a microfuge, at 4° C. RNA was extracted from the resulting serum pellet essentially as described by Chomczynski.

The pellet was treated with a solution containing 4M guanidinium isothiocyanate, 0.18% 2-mercaptoethanol, and 0.5% sarcosyl. The treated pellet was extracted several times with acidic phenolchloroform, and the RNA was precipitated with ethanol. This solution was held at −70° C. for approximately 10 minutes and then spun in a microfuge at 4° C. for 10 minutes. The resulting pellet was resuspended in 100 $\mu$l of DEPC-treated (diethyl pyrocarbonate) water, and 10 $\mu$l of 3M NaOAc, pH=5.2, two volumes of 100% ethanol and one volume of 100% isopropanol were added to the solution. The solution was held at −70° C. for at least 10 minutes. The RNA pellet was recovered by centrifugation in a microfuge at 12,000×g for 15 minutes at 5° C. The pellet was washed in 70% ethanol and dried under vacuum.

B. Synthesis of cDNA (i) FIRST STRAND SYNTHESIS

The synthesis of cDNA molecules was accomplished as follows. The above described RNA preparations were transcribed into cDNA, according to the method of Gubler et al. using random nucleotide hexamer primers (cDNA Synthesis Kit, BMB, Indianapolis, Ind, or GIBCO/BRL).

After the second-strand cDNA synthesis, T4 DNA polymerase was added to the mixture to maximize the number of blunt-ends of cDNA molecules. The reaction mixture was incubated at room temperature for 10 minutes. The reaction mixture was extracted with phenol/chloroform and chloroform isoamyl alcohol.

The cDNA was precipitated by the addition of two volumes of 100% ethanol and chilling at −70° C. for 15 minutes. The cDNA was collected by centrifugation, the pellet washed with 70% ethanol and dried under vacuum.

C. Amplification of the Double Stranded cDNA Molecules.

The cDNA pellet was resuspended in 12 $\mu$l distilled water. To the resuspended cDNA molecules the following components were added: 5 μl phosphorylated linkers (Linker AB, a double strand linker comprised of SEQ ID NO:1 and SEQ ID NO:2, where SEQ ID NO:2 is in a 3' to 5' orientation relative to SEQ ID NO:1—as a partially complementary sequence to SEQ ID NO:1), 2 μl 10× ligation buffer (0.66M Tris.Cl pH=7.6, 50 mM $MgCl_{21}$, 50 mM DTT, 10 mM ATP) and 1 μl T4 DNA ligase (0.3 to 0.6 Weiss Units). Typically, the cDNA and linker were mixed at a 1:100 ratio. The reaction was incubated at 14° C. overnight. The following morning the reaction was incubated at 70° C. for three minutes to inactivate the ligase.

To 100 μl of 10 mM Tris-Cl buffer, pH 8.3, containing 1.5 mM $MgCl_2$ and 50 mM KCl (Buffer A) was added about 1 μl of the linker-ligated cDNA preparation, 2 μM of a primer having the sequence shown as SEQ ID NO:1, 200 μM each of dATP, dCTP, dGTP, and dTTP, and 2.5 units of *Thermus aquaticus* DNA polymerase (Taq polymerase). The reaction mixture was heated to 94° C. for 30 sec for denaturation, allowed to cool to 50° C. for 30 sec for primer annealing, and then heated to 72° C. for 0.5–3 minutes to allow for primer extension by Taq polymerase. The amplification reaction, involving successive heating, cooling, and polymerase reaction, was repeated an additional 25–40 times with the aid of a Perkin-Elmer Cetus DNA thermal cycler (Mullis; Mullis, et al.; Reyes, et al., 1991; Perkin-Elmer Cetus, Norwalk, Conn.).

After the amplification reactions, the solution was then phenol/chloroform, chloroform/isoamyl alcohol extracted and precipitated with two volumes of ethanol. The resulting amplified cDNA pellets were resuspended in 20 μl TE (pH=7.5).

D. Cloning of the cDNA into Lambda Vectors.

The linkers used in the construction of the cDNAs contained an EcoRI site which allowed for direct insertion of the amplified cDNAs into lambda gt11 vectors (Promega, Madison Wis. or Stratagene, La Jolla, Calif.). Lambda vectors were purchased from the manufacturer (Promega) which were already digested with EcoRI and treated with alkaline phosphatase, to remove the 5' phosphate and prevent self-ligation of the vector.

The EcoRI-digested cDNA preparations were ligated into lambda gt11 (Promega). The conditions of the ligation reactions were as follows: 1 μl vector DNA (Promega, 0.5 mg/ml); 0.5 or 3 μl of the PCR amplified insert cDNA; 0.5 μl 10× ligation buffer (0.5M Tris-HCl, pH=7.8; 0.1M $MgCl_2$; 0.2M DTT; 10 mM ATP; 0.5 mg/ml bovine serum albumin (BSA)), 0.5 μl T4 DNA ligase (0.3 to 0.6 Weiss units) and distilled water to a final reaction volume of 5 μl.

The ligation reactions were incubated at 14° C. overnight (12–18 hours). The ligated cDNA was packaged by standard procedures using a lambda DNA packaging system ("GIGAPAK", Stratagene, LaJolla, Calif.), and then plated at various dilutions to determine the titer. A standard X-gal blue/white assay was used to determine recombinant frequency of the libraries (Miller; Maniatis et al.).

Percent recombination in each library was also determined as follows. A number of random clones were selected and corresponding phage DNA isolated. Polymerase chain reaction (Mullis; Mullis, et al.) was then performed using isolated phage DNA as template and lambda DNA sequences, derived from lambda sequences flanking the EcoRI insert site for the cDNA molecules, as primers. The presence or absence of insert was evident from gel analyses of the polymerase chain reaction products.

The cDNA-insert phage libraries generated from serum sample PNF 2161 was deposited with the American Type Culture Collection, 12301 Parklawn Dr., Rockville Md. 20852, and has been assigned the deposit designation ATCC 75268 (PNF 2161 cDNA source).

Example 2

Immunoscreening of Recombinant Libraries

The lambda gt11 libraries generated in Example 1 were IMMUNOSCREENING for the production of antigens recognizable by the PNF 2161 serum from which the libraries were generated. The phage were plated for plaque formation using the *Escherichia coli* bacterial plating strain *E. coli* KM392. Alternatively, *E. coli* Y1090R (Promega, Madison Wis.) may be used.

The fusion proteins expressed by the lambda gt11 clones were screened with serum antibodies essentially as described by Ausubel, et al.

Each library was plated at approximately $2 \times 10^4$ phages per 150 mm plate. Plates were overlaid with nitrocellulose filters overnight. Filters were washed with TBS (10 mM, Tris pH 7.5; 150 mM NaCl), blocked with AIB (TBS buffer with 1% gelatin) and incubated with a primary antibody diluted 100 times in AIB.

After washing with TBS, filters were incubated with a second antibody, goat-anti-human IgG conjugated to alkaline phosphatase (Promega). Reactive plaques were developed with a substrate (for example, BCIP, 5-bromo-4-chloro-3-indolyl-phosphate), with NBT (nitro blue tetrazolium salt (Sigma)). Positive areas from the primary screening were replated and IMMUNOSCREENING until pure plaques were obtained.

Example 3

Screening of the PNF 2161 Library

The cDNA library of PNF 2161 in lambda gt11 was screened, as described in Example 2, with PNF 2161 sera. The results of the screening are presented in Table 1.

TABLE 1

| | PNF2161 Libraries | | | |
|---|---|---|---|---|
| Library[1] | % Recomb.[2] | Antibody[3] | # Screened | # Clones Plaque-Purified |
| PNF/RNA | 85 | PNF | $5.5 \times 10^5$ | 4 |
| PNF/RNA | 90 | PNF | $8 \times 10^4$ | 7 |
| TOTALS: | | | | 11 |

[1]-cDNA library constructed from the indicated human source.
[2]-Percent recombinant clones in the indicated λgt11 library as determined by blue/white plaque assay and confirmed by PCR amplification of randomly selected clones.
[3]-Antisera source used for the immunoscreening of each indicated library.

One of the clones isolated by the above screen (PNF 2161 clone 470-20-1, SEQ ID NO:3; β-galactosidase in-frame fusion translated sequence, SEQ ID NO:4), was used to generate extension clones, as described in Example 6. Clone 470-20-1 nucleic acid sequence is presented as SEQ ID NO:3 (protein sequence SEQ ID NO:4). The isolated nucleic acid sequence without the SISPA cloning linkers is presented as SEQ ID NO:19 (protein SEQ ID NO:20).

Example 4

Characterization of the Immunoreactive 470-20-1 Clone

A. Southern Blot Analysis of Immunoreactive Clones.

The inserts of immunoreactive clones were screened for their ability to hybridize to the following control DNA sources: normal human peripheral blood lymphocyte (purchased from Stanford University Blood Bank, Stanford, Calif.) DNA, and *Escherichia coli* KM392 genomic DNA (Ausubel, et al.; Maniatis, et al.; Sambrook, et al.). Ten micrograms of human lymphocyte DNA and 2 micrograms of *E. Coli* genomic DNA-were digested with EcoRI and HindIII. The restriction digestion products were electrophoretically fractionated on an agarose gel (Ausubel, et al.) and transferred to nylon or nitrocellulose membranes (Schleicher and Schuell, Keene, N.H.) as per the manufacturer's instructions.

Probes from the immunoreactive clones were prepared as follows. Each clone was amplified using primers corresponding to lambda gt11 sequences that flank the EcoRI cloning site of the gt11 vector. Amplification was carried out by polymerase chain reactions utilizing each immunoreactive clone as template. The resulting amplification products were digested with EcORI, the amplified fragments gel purified and eluted from the gel (Ausubel, et al.). The resulting amplified fragments, derived from the immunoreactive clones, were then random prime labelled using a commercially available kit (BMB) employing $^{32}$P-dNTPs.

The random primed probes were then hybridized to the above-prepared nylon membrane to test for hybridization of the insert sequences to the control DNAS. The 470-20-1 insert did not hybridize with any of the control DNAs.

As positive hybridization controls, a probe derivative from a human C-kappa gene fragment (Hieter) was used as single gene copy control for human DNA and a *E. coli* polymerase gene fragment was similarly used for *E. coli* DNA.

B. Genomic PCR.

PCR detection was developed first to verify exogenicity with respect to several genomic DNAs which could have been inadvertently cloned during library construction, then to test for the presence of the cloned sequence in the cloning source and related specimen materials. Several different types of specimens, including SISPA-amplified nucleic acids and nucleic acids extracted from the primary source, and nucleic acids extracted from related source materials (e.g., from animal passage studies), were tested.

The term "genomic PCR" refers to testing for the presence of specific sequences in genomic DNA from relevant organisms. For example, a genomic PCR for a Mystax-derived clone would include genomic DNAs as follows:

1. human DNA (1 µg/rxn.)
2. Mystax DNA (0.1–1 µg/rxn.)
3. *E. coil* (10–100 ng/rxn.)
4. yeast (10–100 ng/rxn.)

Human and Mystax DNAs are tested, as the immediate and ultimate source for the agent. *E. coli* genomic DNA, as a frequent contaminant of commercial enzyme preparations, is tested. Yeast is also tested, as a ubiquitous organism, whose DNA can contaminate reagents and thus, be cloned.

In addition, a negative control (i.e., buffer or water only), and positive controls to include approximately $10^5$ c/rxn., are also amplified.

Amplification conditions vary, as may be determined for individual sequences, but follow closely the following standard PCR protocol: PCR was performed in reactions containing 10 mM Tris, pH 8.3, 50 mM KCl, 1.75 mM $MgCl_2$, 1.0 uM each primer, 200 uM each DATP, dCTP, and dGTP, and 300 µM dUTP, 2.5 units Taq DNA polymerase, and 0.2 units uracil-N-glycosylase per 100 ul reaction. Cycling was for at least 1 minute at 94° C., followed by 30 to 40 repetitions of denaturation (92°–94° C. for 15 seconds), annealing (55°–56° C. for 30 seconds), and extension (72° C. for 30 seconds). PCR reagents were assembled, and amplification reactions were constituted, in a specially-designated laboratory maintained free of amplified DNA.

As a further barrier to contamination by amplified sequences and thus compromise of the test by "false positives," the PCR was performed with dUTP replacing TTP, in order to render the amplified sequences biochemically distinguishable from native DNA. To enzymatically render unamplifiable any contaminating PCR product, the enzyme uracil-N-glycosylase was included in all genomic PCR reactions. Upon conclusion of thermal cycling, the reactions were held at 72° C. to prevent renaturation of uracil-N-glycosylase and possible degradation of amplified U-containing sequences.

A "HOT START PCR" was performed, using standard techniques ("AMPLIWAX", Perkin-Elmer Biotechnology; alternatively, manual techniques were used), in order to make the above general protocol more robust for amplification of diverse sequences, which ideally require different amplification conditions for maximal sensitivity and specificity.

Detection of amplified DNA was performed by hybridization to specific oligonucleotide probes located internal to the two PCR primer sequences and having no or minimal overlap with the primers. In some cases, direct visualization of electrophoresed PCR products was performed, using ethidium bromide fluorescence, but probe hybridization was in each case also performed, to help ensure discrimination between specific and non-specific amplification products. Hybridization to radiolabelled probes in solution was followed by electrophoresis in 8–15% polyacrylamide gels (as appropriate to the size of the amplified sequence) and autoradiography.

Clone 470-20-1 was tested by genomic PCR, against human, *E. coli*, and yeast DNAs. No specific sequence was detected in negative control reactions, nor in any genomic DNA which was tested, and $10^5$ copies of DNA/reaction resulted in a readily-detectable signal. This sensitivity (i.e., $10^5$/reaction) is adequate for detection of single-copy human sequences in reactions containing 1 ug total DNA, representing the DNA from approximately $1.5 \times 10^5$ cells.

C. Direct Serum PCR

Serum or other cloning source or related source materials were directly tested by PCR using primers from selected cloned sequences. In these experiments, HGV viral particles were directly precipitated from sera with polyethylene glycol (PEG), or, in the case of PNF and certain other sera, were pelleted by ultracentrifugation. For purification of RNA, the pelleted materials were dissolved in guanidinium thiocyanate and extracted by the acid guanidinium phenol technique (Chomczynski, et al.).

Alternatively, a modification of this method afforded through and implemented by the use of commercially available reagents, e.g., "TRIREAGENT" (Molecular Research Center, Cincinnati, Ohio) or "TRIZOL" (Life Technologies, Gaithersburg, Md.), and associated protocols was used to isolate RNA. In addition, RNA suitable for PCR analyses was isolated directly from serum or other fluids containing virus, without prior concentration or pelleting of virus particles, through the use of "PURESCRIPT" reagents and protocols (Gentra Systems, Minneapolis, Minn.).

Isolated DNA was used directly as a template for the PCR. RNA was reverse transcribed using reverse transcriptase (Gibco/BRL), and the cDNA product was then used as a template for subsequent PCR amplification.

In the case of 470-20-1, nucleic acid from the equivalent of 20–50 ul of PNF serum was used as the input template into each RT-PCR or PCR reaction. Primers were designed based on the 470-20-1 sequence, as follows: 470-20-1-77F (SEQ ID NO:9) and 470-20-1-211R (SEQ ID NO:10). Reverse transcription was performed using MMLV-RT (Gibco/BRL) and random hexamers (Promega) by incubation at room temperature for approximately 10 minutes, 42° C. for 15 minutes, and 99° C. for 5 minutes, with rapid cooling to 4° C. The synthesized cDNA was amplified directly, without purification, by PCR, in reactions containing 1.75 mM $MgCl_2$, 0.2–1 $\mu$M each primer, 200 uM each dATP, dCTP, dGTP, and dTTP, and 2.5–5.0 units Taq DNA polymerase ("AMPLITAQ", Perkin-Elmer) per 100 ul reaction. Cycling was for at least one minute at 94° C., followed by 40–45 repetitions of denaturation (94° C. for 15 seconds for 10 cycles; 92° C. or 94° C. for 15 seconds for the succeeding cycles), annealing (55° C. for 30 seconds), and extension (72° C. for 30 seconds), in the "GENEAMP SYSTEM 9600" thermal cycler (Perkin-Elmer) or comparable cycling conditions in other thermal cyclers (Perkin-Elmer; MJ Research, Watertown, Mass).

Positive controls consisted of (i) previously amplified PCR product whose concentration was estimated using the Hoechst 33258 fluoescence assay, (ii) purified plasmid DNA containing the DNA sequence of interest, or (iii) purified RNA transcripts derived from plasmid clones in which the DNA sequence of interest is disposed under the transcriptional control of phage RNA promoters such as T7, T3, or SP6 and RNA prepared through the use of commercially available in vitro transcription kits. In addition, an aliquot of positive control DNA corresponding to approximately 10–100 copies/rxn. can be spiked into reactions containing nucleic acids extracted from the cloning source specimen, as a control for the presence of inhibitors of DNA amplification reactions. Each separate extract was tested with at least one positive control.

Specific products were detected by hybridization to a specific oligonucleotide probe 470-20-1-152F (SEQ ID NO:16), for confirmation of specificity. Hybridization of 10 ul of PCR product was performed in solution in 20 ul reaction containing approximately $1\times10^6$ cpm of $^{32}$P-labelled 470-20-1-152F. Specific hybrids were detected following electrophoretic separation from unhybridized oligo in polyacrylamide gels, and autoradiography.

In addition to PNF, extracted nucleic acids from normal serum was also reverse transcribed and amplified, using the "serum PCR" protocol sequence. No signal was detected in normal human serum. The specific signal in PNF serum was reproducibly detected in multiple extracts, with the 470-20-1 specific primers.

D. Amplification from SISPA Uncloned Nucleic Acids

SISPA (Sequence-Independent Single Primer Amplification) amplified cDNA was used as templates (Example 1). Sequence-specific primers designed from selected cloned sequences were used to amplify DNA fragments of interest from the templates. Typically, the templates were the SISPA-amplified samples used in the cloning manipulations. For example, amplification primers 470-20-1-77F (SEQ ID NO:9) and 470-20-1-211R (SEQ ID NO:10) were selected from the clone 470-20-1 sequence (SEQ ID NO:3). These primers were used in amplification reactions with the SISPA-amplified PNF2161 cDNA as a template.

The identity of the amplified DNA fragments were confirmed by (i) hybridization with the specific oligonucleotide probe 470-20-1-152F (SEQ ID NO:16), designed based on the 470-20-1 sequence (SEQ ID NO:3) and/or (ii) size. The probe used for DNA blot detection was labelled with digoxygenin using terminal transferase according to the manufacturer's recommendations (BMB). Hybridization to the amplified DNA was then performed using either Southern blot or liquid hybridization (Kumar, et al., 1989) analyses.

Positive control DNA used in the amplification reactions was previously amplified PCR product whose concentration was estimated by the Hoechst 33258 fluorescence assay, or, alternatively, purified plasmid DNA containing the cloned inserts of interest.

The 470-20-1 specific signal was detected in cDNA amplified by PCR from SISPA-amplified PNF2161. Negative control reactions were nonreactive, and positive control DNA templates were detected.

E. Amplification from Liver RNA Samples.

RNA was prepared from liver biopsy material following the methods of Cathal, et al., wherein tissue was extracted in 5M guanidine thiocyanate followed by direct precipitation of RNA by 4M LiCl. After washing of the RNA pellet with 2M LiCl, residual contaminating protein was removed by extraction with phenol:chloroform and the RNA recovered by ethanol precipitation.

The 470-20-1 specific primers were also used in amplification reactions with the following RNA sources as substrate: normal mystax liver RNA, normal tamarin (*Sanguinus labiatus*) liver RNA, and MY131 liver RNA. MY131 is a mystax that was inoculated intravenously with 1 ml of PNF 2161 plasma. There were obvious elevations of a liver enzyme (SCID) and histological evidence of an apparent viral infection. The histological correlation was most obvious in the liver of MY131, whose liver was obtained at or near the peak of SCID activity. Mystax 131 liver RNA did not give amplified products with the non-coding primers (SEQ ID NO:7 and SEQ ID N0:8) of HCV.

The amplification reactions were carried out in duplicate for two experiments. The results of these amplification reactions are presented in Table 2.

TABLE 2

| PCR with 470-20-1 Primers | | | | |
|---|---|---|---|---|
| | Exp. 1 | | Exp. 2 | |
| | A | B | A | B |
| Normal My liver RNA | – | – | – | – |
| Normal tamarin liver RNA | – | – | – | – |
| My131 liver RNA | + | + | + | + |
| PNF 2161 | ++ | ++ | ++ | ++ |

These results demonstrate the 470-20-1 sequences are present in the parent serum sample (PNF 2161) and in a liver RNA sample from a passage animal of the PNF 2161 sample (MY131). However, both control RNAs were negative for the presence of 470-20-1 sequences.

F. Screening of a Serum Panel for HGV Sequences by Polymerase Chain Reaction Using RNA Templates.

1. High-Alt Donors

The disease association between HGV and liver disease was assessed by polymerase chain reaction screening, using HGV specific primers, of sera from hepatitis patients and from blood donors with abnormal liver function. The latter consisted of serum from blood donations with serum ALT levels greater than 45 International Units per ml.

A serum panel consisting of 152 total sera was selected. The following sera were selected for the serum panel: 104 high-ALT sera from screened blood donations at the Stanford University Blood Bank (SUBB); 34 N-(ABCDE) hepatitis sera from northern California, Egypt, and Peru; and 14 sera from other donors suspected of having liver disease and/or hepatitis virus infection. The negative controls for the panel were as follows: 9 highly-screened blood donors (SUBB) notable for the absence of risk factors for viral infections ("supernormal" sera, e.g., O-negative, Rh-negative; negative for HIV, known hepatitis agents, and CMV; whose multiple previous blood donations had been transfused without causing disease); and 2 random blood donors. These sera were assayed for the presence of HGV specific sequences by RT-PCR using the 470-20-1 primers 77F (SEQ ID NO:9) and 211R (SEQ ID NO:10).

RNA extraction and RT-PCR were performed essentially as described in Example 4C, except that the primer 470-20-1-211R was 5'-biotinylated to facilitate rapid screening of amplified products by a method involving hybridization in solution, followed by affinity capture of hybridized probe using streptavidin-coated paramagnetic beads. Methods for the analysis of nucleic acids by hybridization to specific labelled probes with capture of the hybridized sequences through affinity interactions are well known in the art of nucleic acid analysis.

Depending on the amount of serum available for testing, RNA from 30 to 50 µl of serum was used per RT/PCR reaction. Each serum was tested in duplicate, with positive controls corresponding to 10, 100, or 1000 copies of RNA transcript per reaction and with appropriate negative (buffer) controls. No negative controls were reactive, and at least 10 copies per reaction were detectable in each PCR run. Indeterminate results were defined as specific hybridizing signal being present in only one of two duplicate reactions.

Efficient, highly sensitive analysis of the products from the amplification analysis of this serum panel was performed using an instrument specifically designed for affinity-based hybrid capture using electrochemiluminscent oligonucleotide probes (QPCR System 5000™, Perkin-Elmer). Assays utilizing the QPCR 5000™ have been described (DiCesare, et al; Wages, et al).

The products of each reaction were assayed by hybridization to probe 470-20-1-152F (5'-end-labelled with an electrochemiluminscent ruthenium chelate), and measurement using the "QPCR 5000." Based on a cutoff of the sum of the mean and three times the standard deviation of negative controls in a given amplification run, a total of 34 possible positives were selected for confirmatory testing.

The 34 samples were analyzed by solution hybridization and electrophoresis (Example 4C). Out of these 34 samples, 6 sera (i.e., 6/152) were shown to have specific hybridizing sequences in duplicate reactions. Of these six samples, three were strongly reactive by comparison with positive controls: one High-ALT serum from SUBB, and two N-(ABCDE) sera from Egypt.

A second blood sample was obtained from the highly positive SUBB serum donor one year after the initial sample was taken. The second serum sample was confirmed to be HGV positive by the PCR methods described above. This result confirms persistant infection by HGV in a human. The serum was designated "JC." Further, the serum donor was HCV negative (determined by seroreactivity tests and PCR) and antibody negative for HAV and HBV.

In addition, a third N-(ABCDE) serum from Egypt, a northern California blood donor with N-(ABCDE) hepatitis, and a N-(ABCDE) hepatitis serum, were also shown to be weakly positive by this method. Two other sera gave indeterminate results, defined as the presence of specific sequences in one of two amplification reactions.

Subsequent PCR analysis of replicate serum aliquots from these HGV-positive and indeterminate sera resulted in HGV-positive results in 6 of 8 sera tested and indeterminate results in the remaining 2 sera.

A second primer set was used for the confirmation of HGV positive samples. This primer set (GV57-4512MF, SEQ ID NO:121, and GV57-4657MR, SEQ ID NO:122) for diagnostic amplification, was selected from a conserved region of HGV derived from the putative NS5 coding region. An approximately 2.2 kb fragment was amplified from each of 5 separate HGV isolates. The primers used for the amplification reactions were 470EXT4-2189R (SEQ ID NO:119) and 470EXT4-29F (SEQ ID NO:120). The amplified DNA fragments were sequenced and the sequences aligned. Highly conserved regions were identified from the alignment and optimal primer sequences were designed incorporating mixed base synthesis at those positions that remained divergent throughout the five sequences. The resulting NS5 primers were as follows: GV57-4512MF, SEQ ID NO:121, and GV57-4657MR, SEQ ID NO:122. These primers were used to amplify a diagnostic fragment of 165 bp from test samples.

An internal probe sequence, GV22dc-89MF (SEQ ID NO:123) was derived from another highly conserved region for detection of the specifically amplified product. The probe is also of sufficient length to allow for detection of minimally divergent HGV sequences under lowered stringency conditions.

Analysis of specimens for the presence of the diagnostic NS5 sequence followed the same conditions for sample preparation, amplification, and liquid hybridization as described for the 470-20-1 primers (Example 4C). The concordance of results for sera samples analyzed by PCR using both the 470-20-1 and NS5 primer pairs are shown in Table 3.

TABLE 3

| | 470-20-1 Primer Pair | | |
|---|---|---|---|
| | + | − | Indeterminant |
| NS5-Region Primer Pair (GV57) + | 71 | 0 | 1 |
| − | 6 | 13 | 2 |
| Indeterminant | 2 | 1 | 0 |

Further PCR analyses of additional aliquots obtained from the 8 sera identified above as being HGV-positive were carried out using the 470-20-1 primer set (SEQ ID NO:9 and SEQ ID NO:10) and the NS5 primer set. In these assays, the HGV PCR analyses gave consistently positive results in 5 of the 8 sera. These results are presented in Table 4.

In contrast, none of the two random donors or nine highly-screened "supernormal" sera was positive in either set of PCR analysis.

These results reinforce the disease association between HGV and liver disease.

TABLE 4

| Specimen Group | Number Tested | Number Positive |
| --- | --- | --- |
| High-ALT Donor | 104 | 1 |
| Non-ABCDE, other | 48 | 4 |
| Normal Donor | 2 | 0 |
| "Supernormal" | 9 | 0 |
| Totals | 163 | 5 |

Further testing of sera from High-ALT donors has yielded the following results. A total of 495 sera have been tested, in addition to the initial panel of 104 sera described above. Of these 495 specimens, 6 were identified as HGV positive using the primer pair 470-20-1-77F (SEQ ID NO:9) and 470-20-1-211R (SEQ ID NO:10). These six sera have the following HCV profiles: R25342, HCV negative; R17749, HCV positive; J53171, HCV positive, HBV positive; J54406, HCV negative; R08074, HCV negative; and X31049, HCV negative. Positive scores are based on repeated reactivity in at least 2 separate reactions. R25342 was tested and confirmed positive by PCR using the NS5 primer pair. Accordingly, a detection rate of approximately 1.2% has been observed (7 of 599 tested).

Freshly-obtained plasma samples from blood donors with elevated ALT were also obtained from SUBB, the Peninsula Blood Bank (Burlingame, Calif.), and the New York Blood Center (New York, N.Y.), for testing for HGV RNA by PCR (470-20-1 primer pair). Of 214 total donations which were tested, a total of 5 (approximately 2.3%) were HGV RNA positive. These five sera have the following HCV profiles: T55806, HCV positive; T55875, HCV negative; T56633, HCV negative; R38730, HCV negative; and 3831781, HCV negative. Subsequent donations from two of these donors, T55806 and T55875, were also HGV RNA positive. T55806, T55875 and T56633 were tested and confirmed positive by PCR using the NS5 primer pair.

2. Screening of Accepted Blood Donors

To assess the prevalence of HGV in the normal blood donor population, serum was collected from screened blood donors for transfusion at SUBB. A total of 968 specimens, representing 769 unique donors, was tested for HGV RNA. The samples were screened by PCR using the 470-20-1 primer pair.

A total of 16 sera were identified as having detectable HGV RNA. Of these, 6 represent duplicates from 3 donors, such that a total of 13 unique donors of 769 tested were HGV positive by RNA PCR. All positive samples were tested and confirmed positive by PCR using the NS5 primer pair. These donors were characterized by normal ALT levels, as well as otherwise normal serology. Accordingly, approximately 1.7% of the sera tested in the normal blood donor population are HGV positive. Therefore, the presence of HGV was detected in both accepted and rejected blood donors.

3. Specimens from Various Geographic Locales.

The presence of HGV infection in populations of hepatitis patients from geographically widespread sources was assessed by PCR. The PCR reactions were carried out essentially as described in Example 4C using the 470-20-1 PCR primer pairs. Serum samples from Egypt, Greece, Australia (see Example 4F-4), Peru, England, Italy, Germany, South Korea, United States and Japan were tested. HGV RNA was detectable in subsets of all populations tested.

4. Post-Transfusion Associated HGV Infection and Parenteral Transmission.

HGV RNA was detected in several post-transfusion hepatitis cases (those of Japanese and European origin were included in Example 4F-3). For 4 total cases, one from Japan, two from the U.S. and one from Australia, multiple time-points were assayed for the presence of HGV RNA. For 3 of these cases, (i) pre-transfusion samples were available to estabish previous HGV status of the patient, and (ii) samples were available from individual blood donors to those three cases, to establish donor HGV status.

The first case was a Japanese patient transfused on Dec. 2, 1980. Following the transfusion the patient developed Non-B Non-C hepatitis. A total of 5 sera from this patient were tested for HGV RNA by PCR using the 470-20-1 primer pair. HGV RNA was detectable from about 2 weeks to about 8 months following transfusion. A sample taken greater than 1 year post-transfusion was indeterminate (i.e., positive in one duplicate reaction only). No pre-transfusion sample was available for testing.

Cases BIZ and STO (Tables 5 and 6, respectively) were from a prospectively-followed heart surgery study (Alter, et al., 1989) conducted at the NIH. For each of these patients, pre-transfusion sera were available and were determined to be negative for HGV RNA by PCR using the 470-20-1 primer pair. BIZ tested positive for HGV RNA from day one post-transfusion to week 198 post-transfusion. Of 9 total blood donors to BIZ, 2 out of 8 tested were found to be HGV positive. STO tested positive for HGV RNA from week 5 post-transfusion through week 92 post-transfusion.

TABLE 5

Transfusion-Associated Transmission of HGV: Case BIZ

| Draw Date | Time | ALT in IU/L | 470 PCR Result |
| --- | --- | --- | --- |
| 10/30/78 | −4 days | 23 | − |
| 11/01/78 | −1 day | 31 | − |
| 11/03/78 | +1 day | 29 | + |
| 11/17/78 | +2 weeks | 51 | + |
| 03/22/79 | +20 weeks | 135 | + |
| 06/28/79 | +34 weeks | 133 | + |
| 04/06/81 | +127 weeks | 141 | + |
| 08/20/82 | +198 weeks | 39 | + |

TABLE 6

Transfusion-Associated Transmission of HGV: Case STO

| Draw Date | Time | ALT in IU/L | 470 PCR Result |
| --- | --- | --- | --- |
| 06/15/83 | −1 day | 23 | − |
| 07/18/83 | +5 weeks | 80 | + |
| 10/31/83 | +20 weeks | 75 | + |
| 12/31/83 | +28 weeks | 30 | + |
| 01/02/85 | +81 weeks | 90 | − |
| 03/20/85 | +92 weeks | 23 | + |

The fourth case, also prospectively-defined, was a cardiac surgery patient who participated in a post-transfusion hepatitis study conducted in Sydney, Australia. The patient (PA-124), having no other identifiable risk factors, received 14 units of blood during surgery (4 units packed red cells, 10 units of platelets). Of these 14 units one was HGV positive; the other 13 were HGV negative. HBV and HCV serologies of the 14 blood donors were negative with the exception of a reactive HCV EIA (first generation test). No other HCV test confirmed the positive finding.

In patient PA-124 (Table 7), serum ALT was elevated beginning with a sample taken two weeks postoperation, and was observed to be at least 10 times the pre-operation level for a period of 14 weeks. PCR results for HCV performed on pre-transfusion, 4 week, and 8 week sera from PA-124, were all negative. Serum from this patient was tested for HGV RNA using the 470-20-1 PCR primers. A pre-transfusion sample was negative for HGV RNA. Positive results were demonstrated following transfusion, coinciding with and succeeding the ALT elevation. The presence of HGV RNA was detected out to one year post-transfusion. These data support the conclusion that HGV may be parenterally transmitted.

TABLE 7

Transfusion-Associated Transmission of HGV: Case PA-124

| Weeks Post-Operation | ALT in IU/L | 470 PCR Result |
| --- | --- | --- |
| pre-transfusion | 7 | − |
| 2 | 74 | + |
| 4 | 86 | + |
| 8 | 135 | + |
| 12 | 179 | + |
| 14 | 78 | + |
| 18 | 9 | + |
| 24 | 6 | + |
| 36 | 11 | + |
| 52 | 11 | + |
| 64 | 23 | − |
| 84 | 10 | − |

In addition to prospectively-defined post-transfusion transmission cases, additional cases of HGV infection were identified in risk groups defined by multiple transfusions and intravenous drug use (IVDU) (Table 8).

TABLE 8

HGV RT-PCR Testing of Coded Sera: Selected Hepatitis and Parenteral Risk Groups

| Group | Number Tested | Number Positive |
| --- | --- | --- |
| Autoimmune Hepatitis | 10 | 0 |
| Primary Biliary Cirrhosis | 20 | 0 |
| Suspected Acute NonA-E Hepatitis | 24 | 2 |
| Chronic Hepatitis (NonA-C) (confirmed by liver biopsy) | 34 | 3 |
| Hepatocellular Carcinoma | 20 | 2 |
| Chronic HBV | 20 | 2 |
| Chronic HCV | 50 | 6 |
| Hemophilia | 49 | 9 |
| IVDU | 54 | 15 |
| Multiply Transfused Anemia | 100 | 19 |

Among 100 multiply-transfused sickle cell anemia and thalassemia patients, 19 (19%) were found to have detectable serum HGV RNA. Similarly, 9 of 49 hemophilia patients (18%) were HGV positive with 470-20-1 and NS5 primers. Significantly, 15 of 54 (28%) IVDU were found to be PCR positive for HGV RNA. Infection rates in these parenteral risk groups (18–28%) appear to be higher than rates in blood donors with elevated ALT (1–2%). These results reinforce the significance of the parenteral route for HGV transmission.

5. PCR Screening of Selected Hepatitis Disease Groups

Sera from patients with acute and chronic hepatitis, hepatocellular carcinoma, HBV infection or HCV infection were tested for the presence of HGV using polymerase chain reaction (data presented in Table 8). In each of sets of specimens from patients with liver disease, HGV positive specimens were demonstrated (with the exception of specimens from patients with autoimmune hepatitis and primary biliary cirrhosis, both conditions not thought to be exclusively associated with an infectious agent).

As shown in the collections of sera from post-transfusion hepatitis patients (Example 4F-4), HGV infection is established during acute hepatitis, but circulating viral RNA continues to be detected during chronic infection for periods of time measured in months to years.

Approximately 10–20% co-infection rates were observed in patients with HBV and HCV infection. HGV infection is thus shown to be associated with hepatitis with or without co-infection with other hepatitis viruses. Co-infection may reflect similar risk factors and routes of transmission for these hepatitis viruses. As noted above, there is a higher prevalence of HGV in parenteral risk groups, such as hemophiliacs, IVDU's, and multiply transfused anemia patients (compared with other hepatitis risk groups).

6. Persistent Infection by HGV in Humans

Post-transfusion hepatitis cases BIZ, STO, and PA-124 were show to have PCR-detectable viral RNA up to 3.8, 1.8, and 1.0 years, respectively, following transfusion and acute infection. Additional serum samples were obtained from donor JC (Example 4F-1), one year and 1.5 years following the initial positive sample. These follow-up serum samples were also HGV positive. Additional sera from other high-ALT donors (T55806, T55875, R25342), obtained several months following the serum sample in which HGV infection was originally detected, were also positive. Similarly, when HGV infection was established in an experimental primate (CH1356, Example 4H), HGV RNA was detected over 1.5 years following inoculation. These data establish persistent HGV viremia in humans and experimental primates.

G. Amplification of Long Fragments from Patient RNA for Sequencing.

PCR primers were designed to amplify several informative regions of the HGV genome in order to obtain sequence information on varied HGV isolates. The primers 470EXT4-2189R (SEQ ID NO:119) and 470EXT4-29F (SEQ ID NO:120) were designed to amplify a 2.2 kb fragment that contained the original 470-20-1 sequence. RNA from samples was reverse-transcribed using "SUPERSCRIPT II" reverse transcriptase (Gibco/BRL, Gaithersburg, Md.). The resulting cDNA was amplified using reagents for efficient long-range PCR ("XL PCR BUFFERS" and "rTth-XL", Perkin Elmer/Applied Biosystems Div., Foster City, Calif.).

The amplification reaction was considered to be positive if a band of the correct size on agarose gel electrophoresis was detected. The sample was confirmed as positive by preliminary DNA sequencing of the amplification product. The following sera samples tested positive for HGV RNA by this amplification method: PNF2161; R10291 (JC); and specimens from each of the North American, Egyptian, and Japanese groups. However, no positive samples were detected from the Peruvian sera.

Successful amplification from a variety of HGV-positive specimens provides confirmation of the results obtained by PCR amplification using the 470-20-1 primer pair discussed above. Failure to obtain amplification, however, may reflect poor RNA quality or low copy number or local sequence differences among isolates such that the selected primer sets would not function universally.

In order to obtain sequence information from the putative 5'-untranslated region of the HGV genome, primers were designed to amplify fragments from the 5'-untranslated region (based on the HGV PNF 2161-variant). The two fragments were defined by the following primer sets: FV94-22F (SEQ ID NO:124) and FV94-724R (SEQ ID NO:125), yielding a 728 base pair fragment; and FV94-94F (SEQ ID NO:126) and FV94-912R (SEQ ID NO:127), yielding an 847 base pair fragment.

The conditions just described to promote efficient long-range PCR were used. Products were obtained from most of the samples tested, providing additional confirmation of the presence of HGV RNA in the samples.

H. Infectivity of HGV in Primates.

Two chimpanzees (designated CH1323 and CH1356), six cynomolgus monkeys (CY143, CY8904, CY8908, CY8912, CY8917, and CH8918), and six Mystax (MY29, MY131, MY98, MY187, MY229, MY254) subjects were inoculated with PNF 2161. Pre-inoculation and post-inoculation sera were monitored for ALT and for the presence of HGV RNA sequences (as determined by PCR screening—described above).

One cynomologous monkey (CY8904) showed a positive RNA PCR result (39 days post-inoculation) and one indeterminant result from a total of 17 seperate blood draws. In one chimpanzee, designated CH1356, was sustained viremia observed by RT-PCR. As shown in Table 9, no significant ALT elevation was observed, and circulating virus was detected only at time points considerably after inoculation. Viremia was observed at and following 118 days post-inoculation. Suggestive reactivity was also observed in the first post-inoculation time-point (8 days), which may indicate residual inoculum.

TABLE 9

ALT and PCR Results from CH1356 Following Inoculation with PNF 2161

| Days Post-Inoculation | ALT* | HGV PCR |
|---|---|---|
| 0 | 59 | − |
| 8 | 65 | ± |
| 15 | 85 | − |
| 22 | 89 | − |
| 29 | 89 | − |
| 36 | 86 | − |
| 39 | 31 | − |
| 47 | 74 | − |
| 54 | 40 | − |
| 61 | 57 | − |
| 84 | 65 | ± |
| 89 | 63 | + |
| 98 | 64 | − |
| 118 | 84 | + |
| 125 | 73 | + |
| 134 | 74 | + |
| 159 | 80 | + |
| 610 | (ALT not available) | + |

*average ALT base-line before inoculation was 50.

The data presented above indicate that HGV infection was persistent up to 1.7 years in an experimental primate.

I. Characterization of the Viral Genome.

The isolation of 470-20-1 from a cDNA library (Example 1) suggests that the viral genome detected in PNF 2161 is RNA. Further experiments to confirm the identity of the HGV viral genome as RNA include the following.

Selective degradation of either RNA or DNA (e.g., by DNase-free RNase or RNase-free DNase) in the original cloning source followed by amplification with HGV specific primers and detection of the amplification products serves to distinguish RNA from DNA templates.

An alternative method makes use of amplification reactions (nucleic acids from the original cloning source as template and HGV specific primers) that employ (i) a DNA-dependent DNA polymerase, in the absence of any RNA-dependent DNA polymerase (i.e., reverse transcripase) in the reactions, and (ii) a DNA-dependent DNA polymerase and an RNA-dependent DNA polymerase in the reactions. In this method, if the HGV genome is DNA or has a DNA intermediate, then amplified product is detected in both types of amplification reactions. If the HGV genome is only RNA, the amplified product is detected in only the reverse transcriptase-containing reactions.

Total nucleic acid (i.e., DNA or RNA) was extracted from PNF 2161, using proteinase K and SDS followed by phenol extraction, as described in Example 4C. The purified nucleic acid was then amplified using polymerase chain reaction (PCR) where either (i) the PCR was preceded by a reverse transcription step, or (ii) the reverse transcription step was omitted. Amplification was reproducibly obtained only when the PCR reactions were preceded by reverse transcription. As a control, DNA templates were successfully amplified in separate reactions. These results demonstrate that the nature of the HGV viral genome is RNA.

The strand of the cloned, double-stranded DNA sequence that was originally present in PNF 2161 may be deduced by various means, including the following. Northern or dot blotting of the unamplified genomic RNA from an infected source serum can be performed, followed by hybridization of duplicate blots to probes corresponding to each strand of the cloned sequence. Alternatively, single-stranded cDNA probes isolated from M13 vectors (Messing), or multiple strand-specific oligonucleotide probes are used for added sensitivity. If the source serum contains single-stranded RNA, only one probe (i.e., sequences from one strand of the 470-20-1 clones) yield a signal, under appropriate conditions of hybridization stringency. If the source serum contains double-stranded RNA, both strand-probes will yeild a signal.

The polymerase chain reaction, prefaced by reverse transcription using one or the other specific primer, represents a much more sensitive alternative to Northern blotting. Genomic RNA extracted from purified virions present in PNF 2161 serum is used as the input template into each RT/PCR. Rather than cDNA synthesis with random hexamers, HGV sequence-specific primers were used. One cDNA synthesis reaction was performed with a primer complementary to one strand of the cloned sequence (e.g., 470-20-1-77F); a second cDNA synthesis reaction was also performed using a primer derived from the opposite strand (e.g., 470-20-1-211R).

The resulting first strand cDNA was amplified in using two HGV specific primers. Controls were included for successful amplification by PCR (e.g., DNA controls). RNA transcripts from each strand of the cloned sequence was also used, to control also for the reverse transcription efficiency obtained when using the specific primers which are described.

Specific products were detected by agarose gel electrophoresis with ethidium bromide staining. DNA controls (i.e., double-stranded DNA controls for the PCR amplification) were successfully amplified regardless of the primer used for reverse transcription. Single-stranded RNA transcripts (i.e., controls for reverse transcription efficiency and strand specificity) were amplified only when the opposite-strand primer was used for cDNA synthesis.

The PNF-derived HGV polynucleotide gave rise to a specific amplified product only when the primer 470-20-1-211R was used for reverse transcription, thus indicating that the original HGV polynucleotide sequence present in the serum is complementary to 470-20-1-211R and is likely a single-strand RNA.

Example 5

Sucrose Density Gradient Separation of PNF2161

A. Bading of PNF-2161 Agent.

A continuous gradient of 10–60% sucrose ("ULTRAPURE", Gibco/BRL) in TNE (50 mM Tris-Cl, pH 7.5, 100 mM NaCl, 1 mM EDTA) was prepared using a gradient maker from Hoefer Scientific (San Francisco, Calif.). Approximately 12.5 ml of the gradient was overlaid with 0.4 ml of PNF serum which had been stored at −70° C., rapidly thawed at 37° C., then diluted in TNE.

The gradient was then centrifuged in the SW40 rotor (Beckman Instruments) at 40,000 rpm (approximately 200,000×g at $r_{av}$) at 4° C. for approximately 18 hours. Fractions of volume approximately 0.6 ml were collected from the bottom of the tube, and 0.5 ml was weighed directly into the ultracentrifuge tube, for calculation of density.

TABLE 10

Measured Densities of PNF Fractions and Presence of 470-20-1

| Fraction | Density | 470-20-1 Detected* |
|---|---|---|
| 1 | 1.274 | − |
| 2 | 1.274 | − |
| 3 | 1.266 | − |
| 4 | 1.266 | − |
| 5 | 1.260 | − |
| 6 | 1.254 | − |
| 7 | 1.248 | + |
| 8 | 1.206 | + |
| 9 | 1.146 | + |
| 10 | 1.126 | +++ |
| 11 | 1.098 | ++++ |
| 12 | 1.068 | +++ |
| 13 | 1.050 | + |
| 14 | 1.034 | + |
| 15 | 1.036 | + |
| 16 | 1.018 | − |
| 17 | 1.008 | + |
| 18 | 1.020 | + |

*"+" and "−" scores were initially based on 40-cycle PCR. In order to distinguish "+", "++", "+++", and "++++", fractions giving initial positive scores (7–18) were amplified with 30 cycles of PCR.

The putative viral particles were then pelleted by centrifugation at 40,000 rpm in the Ti70.1 rotor (approximately 110,000×g) at 4° C. for 2 hours, and RNA was extracted using the acid guanidinium phenol technique ("TRI REAGENT", Molecular Research Center, Cincinnati, Ohio.), and alcohol-precipitated using glycogen as a carrier to improve recovery. The purified nucleic acid was dissolved in an RNase-free buffer containing 2 mM DTT and 1 U/μl recombinant RNasin.

Analysis of the gradient fractions by RNA PCR (Example 4C) showed a distinct peak in the 470-20-1 specific signal, localized in fractions of density ranging from 1.126 to 1.068 g/ml (Table 10). The 470-20-1 signal was thus shown, under these conditions, to form a discrete band, consistent with the expected behavior of a viral particle in a sucrose gradient.

B. Relative Viral Particle Densities.

PNF 2161 has been demonstrated to be co-infected with HCV (see above). In order to compare the properties of the 470-20-1 viral particle to other known hepatitis viral particles, the serum PNF 2161 and a sample of purified Hepatitis A Virus were layered on a sucrose gradient (as described above). Fractions (0.6 ml) were collected, pelleted and the RNA extracted. The isolated RNA from each fraction was subjected to amplification reactions (PCR) using HAV (SEQ ID NO:5; SEQ ID NO:6), HCV (SEQ ID NO:7; SEQ ID NO:8) and 470-20-1 (SEQ ID NO:9, SEQ ID NO:10) specific primers.

Product bands were identified by electrophoretic separation of the amplification reactions on agarose gels followed by ethidium bromide staining. The results of this analysis are presented in Table 11.

TABLE 11

| Average Density | HAV | HCV | 470-20-1 |
|---|---|---|---|
| 1.269 | − | − | − |
| 1.263 | + | − | − |
| 1.260 | + | − | − |
| 1.246 | ++ | − | − |
| 1.238 | ++ | − | − |
| 1.240 | + | − | − |
| 1.207 | + | − | − |
| 1.193 | + | − | − |
| 1.172 | + | ± | − |
| 1.150 | + | ± | ± |
| 1.134 | + | + | ± |
| 1.118 | + | + | + |
| 1.103 | + | + | + |
| 1.118 | + | + | + |
| 1.103 | + | + | + |
| 1.088 | ± | + | + |
| 1.084 | − | + | + |
| 1.080 | − | + | + |
| 1.070 | − | + | + |
| 1.057 | − | + | ± |
| 1.035 | − | ± | − |
| 1.017 | − | − | − |
| 1.009 | − | − | − |

These results suggest that 470-20-1 particles are more similar to HCV particles than to HAV.

Further, serum PNF 2161 and HAV particles were treated with chloroform before sucrose gradient centrifugation. The results of these experiments suggest that 470-20-1 agent may be an enveloped virus since it has more similar properties to an enveloped Flaviviridae member (HCV) than a non-enveloped virus (HAV).

Example 6

Generation of 470-20-1 Extension Clones

A. Anchor PCR.

RNA was extracted directly from PNF2161 serum as described in Example 1. The RNA was passed through a "CHROMA SPIN" 100 gel filtration column (Clontech) to remove small molecular weight impurities. cDNA was synthesized using a BMB cDNA synthesis kit. After cDNA synthesis, the PNF cDNA was ligated to a 50 to 100 fold excess of KL-1/KL-2 SISPA or JML-A/JML-B linkers (SEQ ID NO:11/SEQ ID NO:12, and SEQ ID NO:17/SEQ ID NO:18, respectively) and amplified for 35 cycles using either the primer KL-1 or the primer JML-A.

The 470 extension clones were generated by anchored PCR of a 1 μl aliquot from a 10 μl ligation reaction containing EcoRI digested (dephosphorylated) lambda gt11 arms (1 μg) and EcoRI digested PNF cDNA (0.2 μg). PCR amplification (40 cycles) of the ligation reaction was carried out using the lambda gt11 reverse primer (SEQ ID NO:13) in combination with either 470-20-77F (SEQ ID NO:9) or 470-20-1-211R (SEQ ID NO:10). All primer concentrations for PCR were 0.2 μM.

The amplification products (9 μl/100 μl) were separated on a 1.5% agarose gel, blotted to "NYTRAN" (Schleicher and Schuell, Keene, N.H.), and probed with a digoxygenin labelled oligonucleotide probe specific for 470-20-1. The digoxygenin labeling was performed according to the manufacturer's recommendations using terminal transferase (BMB). Bands that hybridized were gel-purified, cloned into the "TA CLONING VECTOR pCR II" (Invitrogen), and sequenced.

Numerous clones having both 5' and 3' extensions to 470-20-1 were identified. All sequences are based on a consensus sequence from the sequencing of at least two independent isolates. This Anchor PCR approach was repeated in a similar manner to obtain further 5' and 3' extension sequences. These PCR amplification reactions were carried out using the lambda gt11 reverse primer (SEQ ID NO:13) in combination with HGV specific primers derived from sequences obtained from previous extension clones. The substrate for these reactions was unpackaged PNF 2161 2-cDNA source DNA.

Sequencing was carried out using "DYEDEOXY TERMINATOR CYCLE SEQUENCING" (a modification of the procedure of Sanger, et al.) on an Applied Biosystems model 373A DNA sequencing system according to the manufacturer's recommendations (Applied Biosystems, Foster City, Calif.). Sequence data is presented in the Sequence Listing. Sequences were compared with "GENBANK", EMBL database and dbEST (National Library of Medicine) sequences at both nucleic acid and amino acid levels. Search programs FASTA, BLASTP, BLASTN and BLASTX (Altschul, et al.) indicated that these sequences were novel as both nucleic acid and amino acid sequences.

Individual clones obtained using a selected primer pair were aligned to yield a consensus sequence. The series of consensus sequences used to construct the sequence for the HGV-PNF 2161 variant was as follows: 4E3, SEQ ID NO:26; 3E3, SEQ ID NO:27; 2E5, SEQ ID NO:28 1E5, SEQ ID NO:29 4E5, SEQ ID NO:30 3E5, SEQ ID NO:31 2E3, SEQ ID NO:32 1E3, SEQ ID NO:33 4E5-20, SEQ ID NO:34 5E3, SEQ ID NO:39 6E3, SEQ ID NO:40 7E3, SEQ ID NO:42 5E5, SEQ ID NO:43; 6E5(44F), SEQ ID NO:44; 8E3, SEQ ID NO:98; 9E3, SEQ ID NO:109; 10E3, SEQ ID NO:110; 11E3, SEQ ID NO:116; 12E3, SEQ ID NO:118; 5'-end, SEQ ID NO:175; and 3'-END, SEQ ID NO:167.

The individual consensus sequences were aligned, overlapping sequences identified and a consensus sequence for the HGV-PNF 2161 variant was determined. This consensus sequence was compared with the sequences obtained for four other HGV variants: JC (SEQ ID NO:182), BG34 (SEQ ID NO:176), T55806 (SEQ ID NO:178), and EB20-2 (SEQ ID NO:180).

Figure 11:
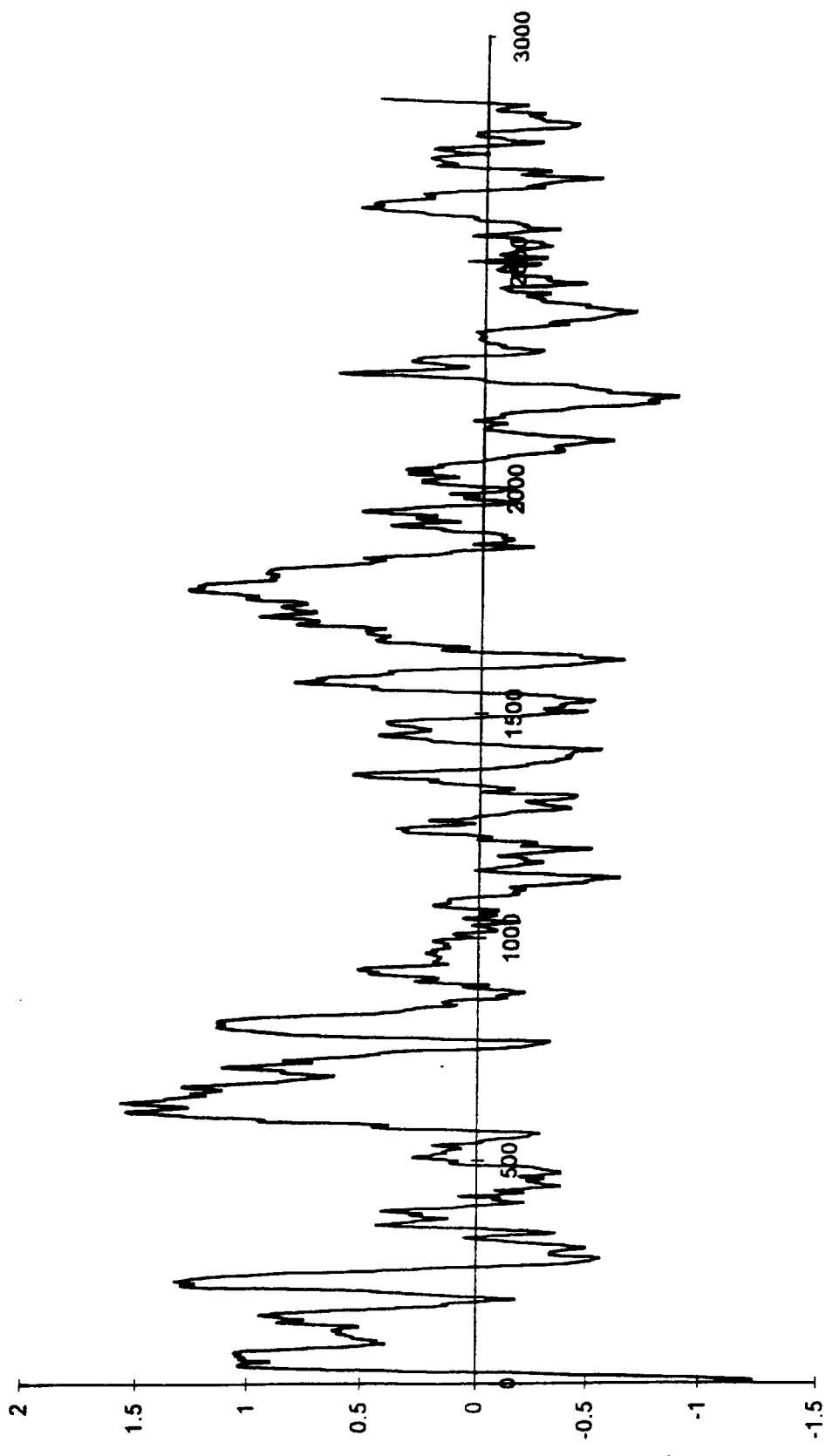
FIG. 11 presents a Kyte-Doolittle hydrophobicity plot of the coding sequence of HGV.

The consensus sequence of the HGV-PNF 2161 variant consists of 9391 base pairs presented as SEQ ID NO:14. This sequence represents a continuous open reading frame (SEQ ID NO:15). A Kyte-Doolittle hydrophobicity plot of the polyprotein is presented as FIG. 11.

The relationship between the original 470-20-1 clone and the sequences obtained by extension is shown schematically in FIG. 1. As seen in the figure, the DNA strand having opposite polarity to the protein coding sequence of 470-20-1 comprising a long continuous open reading frame.

The amino acid sequence of HGV was compared against the sequences of all viral sequence in the PIR database (IntelliGenetics, Inc., Mountain View, Calif.) of protein sequences. The comparison was carried out using the "SSEARCH" program of the "FASTA" suite of programs version 1.7 (Pearson, et al.). Regions of local sequence similarities were found between the HGV sequences and two viruses in the Flaviviridae family of viruses. The similarity alignments are presented in FIGS. 5A and 5B.

Present in these alignments are motifs for the RNA dependent RNA polymerase (RDRP) of these viruses. Conserved RDRP amino acid motifs are indicated in FIGS. 5A and 5B by stars and uppercase, bold letters (Koonin and Dolja). These alignments demonstrate that this portion of the HGV coding sequence correspond to RDRP. This alignment data combined with the data concerning the RNA genome of HGV supports the placement of HGV as a member of the Flaviviridae family.

The global amino acid sequence identities of the HGV polyprotein (SEQ ID NO:15) with HOCV (Hog Cholera Virus) and HCV are 17.1% and 25.5%, respectively. Such levels of global sequence identity demonstrates that HGV is a separate viral entity from both HOCV and HCV. To illustrate, in two members of the Flaviviridae family of viruses BVDV (Bovine Diarrhea Virus) and HCV, 16.2% of the amino acids can be globally aligned with HGV.

Members within a genus generally show high homology when aligned globally, for example, BVDV vs. HOCV show 71.2% identity. Various members (variants) of the un-named genus of which HCV is a member are between 65% and 100% identical when globally aligned.

B. Race PCR: 5' End Cloning.

Clones representing the 5'-end of the HGV genome were obtained by a modified Anchor PCR approach that utilized RACE (Rapid Amplification of cDNA Ends) technology. The RACE method was originally described by Frohman, et al., (1988) and Belyausky, et al., (1989). Briefly, the 5'-end clones of HGV were obtained as follows.

First-strand cDNA synthesis was primed using random hexamers and synthesis was carried out using either "SUPERSCRIPT II" or "rTth" reverse transcriptase (GIBCO/BRL). After first-strand synthesis, the RNA template was degraded by base hydrolysis (NaOH). The cDNA sample was neutralized by the addition of acetic acid and purified by absorption to a glass matrix support ("GENOBIND," Clontech, Palo Alto, Calif.). Following purification, the cDNA was concentrated by ethanol precipitation and washed twice with 80% ethanol.

The originally described RACE method was modified as follows. A single-stranded oligonucleotide anchor (SEQ ID NO:174) (Clontech) was ligated to the 3' end of the first-strand cDNA using T4 RNA ligase in the presence of cobalt chloride. The oligonucleotide anchor was obtained from the manufacturer with two modifications: (i) the 3'-end of the anchor was modified with an amino group which prevents concatamer formation, and (ii) the 5'-end contains a phosphate group which allows ligation to the first-strand cDNA.

After ligation of the anchor, the cDNA was used as a template for PCR amplification using several HGV-specific primers in combination with a primer complementary to the anchor sequence (AP primer, SEQ ID NO:134). The resulting amplification products were separated by agarose gel electrophoresis, transferred to filters and hybridized with a nested, HGV-specific oligonucleotide probe. Bands that hybridized to the HGV-probe were isolated, cloned into "pCR-II" (Invitrogen, San Diego, Calif.) and sequenced.

C. HGV 3' End Cloning.

Clones representing the 3'-end of the HGV genome were obtained by a modified anchored RT-PCR method. Briefly, poly A polymerase (GIBCO/BRL, Gaithersburg, Md.) was used to catalyze the addition of a poly(A) tail to PNF 2161 RNA prior to cDNA synthesis. The poly(A) addition was performed according to the manufacturer's recommendations. Following purification of the poly(A) modified RNA, reverse transcription with "SUPERSCRIPT II" (GIBCO/BRL) was carried out using primer GV-5446IRT (SEQ ID NO:184). The resulting cDNA was amplified by PCR using the following primer set: GV59-5446F (SEQ ID NO:171) and GV-5446IR (SEQ ID NO:172).

After amplification, the products were separated by agarose gel electrophoresis, transferred to filters and hybridized with a digoxigenin-labelled oligonucleotide probe (E5-7-PRB, SEQ ID NO:173). Products that hybridized with the oligonucleotide were isolated, purified, cloned into "pCR-II" and sequenced. The two clones isolated by this method were MP3-3 (SEQ ID NO:168) and MP3-7 (SEQ ID NO:169).

Example 7

Isolation of 470-20-1 Fusion Protein

A. Expression and Purification of 470-20-1/Glutathione-S-Transferase Fusion Protein Expression of a glutathione-S-transferase (sj26) fused protein containing the 470-20-1 peptide was achieved as follows. A 237 base pair insert (containing 17 nucleotides of SISPA linkers on both sides) corresponding to the original lambda gt11 470-20-1 clone was isolated from the lambda gt11 470-20-1 clone by polymerase chain reaction using primers gt11 F(SEQ ID NO:25) and gt11 R(SEQ ID NO:13) followed by Eco RI digestion.

The insert was cloned into a modified pGEX vector, pGEX MOV. pGEX MOV encodes sj26 protein fused with six histidines at the carboxy terminal end (sj26his). The 470-20-1 polypeptide coding sequences were introduced into the vector at a cloning site located downstream of sj26his coding sequence in the vector. Thus, the 470-20-1 polypeptide is expressed as sj26his/470-20-1 fusion protein. The sj26 protein and six histidine region of the fusion protein allow the affinity purification of the fusion protein by dual chromatographic methods employing glutathioneconjugated beads (Smith, D. B., et al.) and immobilized metal ion beads (Hochula; Porath).

*E. coli* strain W3110 (ATCC catalogue number 27352) was transformed with pGEX MOV and pGEX MOV containing 470-20-1 insert. Sj26his protein and 470-20-1 fusion protein were induced by the addition of 2 mM isopropyl-β-thiogalactopyranoside (IPTG). The fusion proteins were purified either by glutathione-affinity chromatography or by immobilized metal ion chromatography (IMAC) according to the published methods (Smith, D. B., et al.; Porath) in conjunction with conventional ion-exchange chromatography.

The purified 470-20-1 fusion protein was immunoreactive with PNF 2161. However, purified sj26his protein was not immunoreactive with PNF 2161, indicating the presence of specific immunoreaction between the 470-20-1 peptide and PNF 2161.

B. Isolation of 470-20-1/B-Galactosidase Fusion Protein

KM392 lysogens infected either with lambda phage gt11 or with gt11/470-20-1 are incubated in 32° C. until the culture reaches to an O. D. of 0.4. Then the culture is incubated in a 43° C. water bath for 15 minutes to induce gt11 peptide synthesis, and further incubated at 37° C. for 1 hour. Bacterial cells are pelleted and lysed in lysis buffer (10 mM Tris, pH 7.4, 2% "TRITON X-100" and 1% aprotinin). Bacterial lysates are clarified by centrifugation (10K, for 10 minutes, Sorvall JA20 rotor) and the clarified lysates are incubated with Sepharose 4B beads conjugated with anti-β-galactosidase (Promega).

Binding and elution of β-galactosidase fusion proteins are performed according to the manufacturer's instruction. Typically binding of the proteins and washing of the column are done with lysis buffer. Bound proteins are eluted with 0.1M carbonate/bicarbonate buffer, pH 10. The purified 470-20-1/b-galactosidase protein is immunoreactive with both PNF2161 and anti-b-galactosidase antibody. However, β-galactosidase, expressed by gt11 lysogen and purified, is not immunoreactive with PNF2161 but immunoreactive with anti-β-galactosidase antibody.

Example 8

Purification of the 470-20-1 Fusion Protein and Preparation of Anti-470-20-1 Antibody A. Glutathione Affinity Purification Materials included 50 ml glutathione affinity matrix reduced form (Sigma), XK 26/30 Pharmacia column, 2.5×10 cm Bio-Rad "ECONO-COLUMN" (Richmond, Calif.), Gilson (Middleton, Wis.) HPLC, DTT (Sigma), glutathione reduced form (Sigma), urea, and sodium phosphate dibasic.

The following solutions were used in purification of the fusion protein:

Buffer A: phosphate buffer saline, pH 7.4, and

Buffer B: 50 mM Tris Ph 8.5, 8 mM glutathione, (reduced form glutathione)

Strip buffer: 8M urea, 100 mM Tris pH 8.8, 10 mM glutathione, 1.5 NaCl.

*E. coli* carrying the plasmid pGEX MOV containing 470-20-1 insert, were grown in a fermentor (20 liters). The bacteria were collected and lysed in phosphate buffered saline (PBS) containing 2 mM phenylmethyl sulfonyl fluoride (PMSF) using a micro-fluidizer. Unless otherwise noted, all of the following procedures were carried out at 4° C.

The crude lysate was prepared for loading by placing lysed bacteria into "OAKRIDGE" tubes and spinning at 20K rpms (40k×g) in a Beckman model JA-20 rotor. The supernatant was filtered through a 0.4 μm filter and then through a 0.2 μm filter.

The 2.5×10 cm "ECONO-COLUMN" was packed with the glutathione affinity matrix that was swelled in PBS for two hours at room temperature. The column was brought into equilibrium by washing with 4 bed volumes of PBS.

The column was loaded with the crude lysate at a flow rate of 8 ml per minute. Subsequently, the column was washed with 5 column volumes of PBS at the same flow rate.

Figure 2:
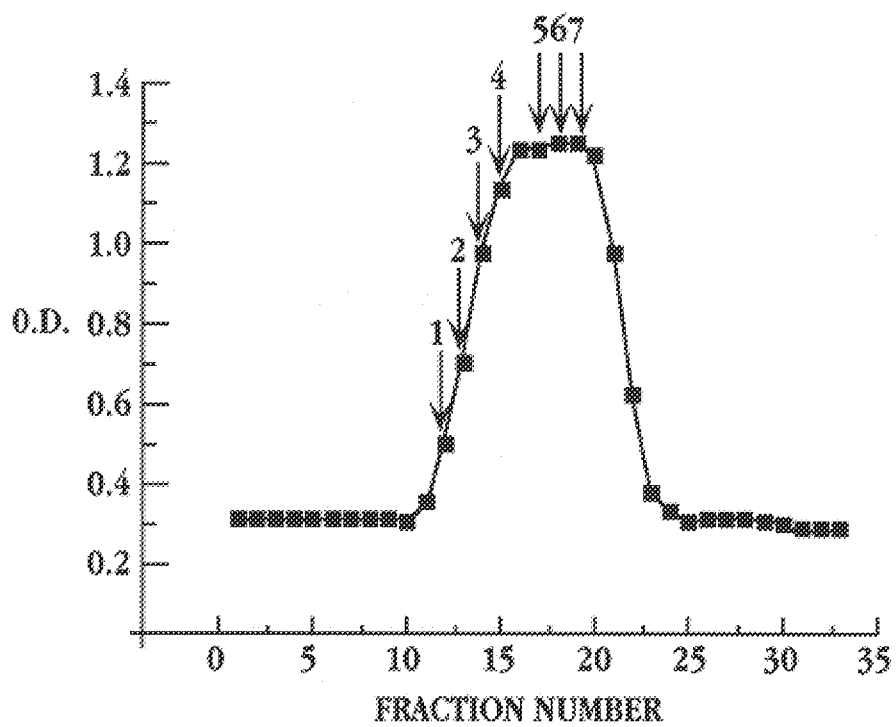
FIG. 2: shows an exemplary protein profile from gradient fractions eluted from a glutathione affinity column.
Figure 3:
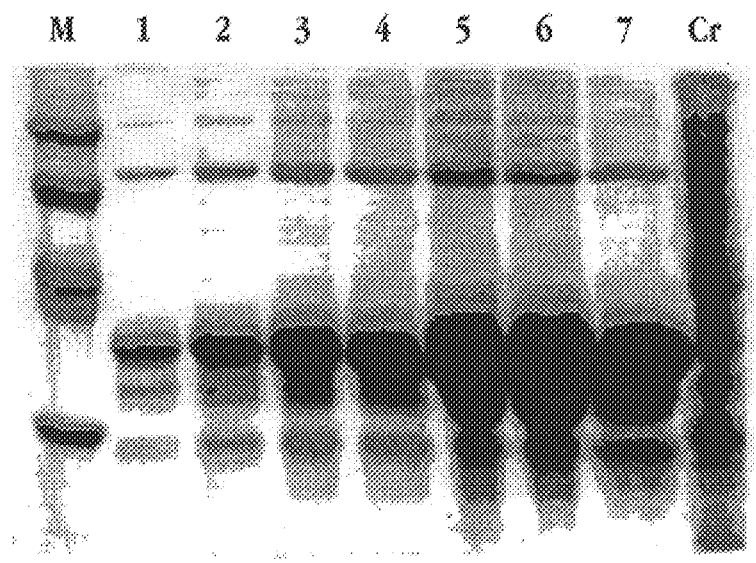
FIG. 3: shows a scanned image of an exemplary Sodium dodecyl sulfate polyacrylamide gel electrophoresis analysis of fraction samples from FIG. 2.

The column was eluted by setting the flow rate to 0.75–1 ml/min. and introducing Buffer B. Buffer B was pumped through the column for 5 column volumes and two-minute fractions were collected. An exemplary elution profile is shown in FIG. 2. The content and purity of the proteins present in the fractions were assessed by standard SDS PAGE (FIG. 3). The 470-20-1/sj26his fusion protein was identified based on its predicted molecular weight and its immunoreactivity to PNF 2161 serum. For further manipulations, the protein can be isolated from fractions containing the fusion protein or from the gel by extraction of gel regions containing the fusion protein.

B. Purification of Clone 470-20-1 Fusion Protein by Anion Exchange.

Solutions include the following:

Buffer A (10 mM sodium phosphate pH 8.0, 4M urea, 10 mM DTT);

Buffer B (10 mM sodium phosphate pH 8.0, 4M urea, 10 mM DTT, 2.0M NaCl); and

Strip Buffer (8M urea, 100 mM Tris pH 8.8, 10 mM glutathione, 1.5 NaCl).

Crude lysate (or other protein source, such as pooled fractions from above) was loaded onto "HIGH-Q-50" (Biorad, Richmond, Calif.) column at a flow rate of 4.0 ml/min. The column was then washed with Buffer A for 5 column volumes at a flow rate of 4.0 ml/min.

Figure 4A:
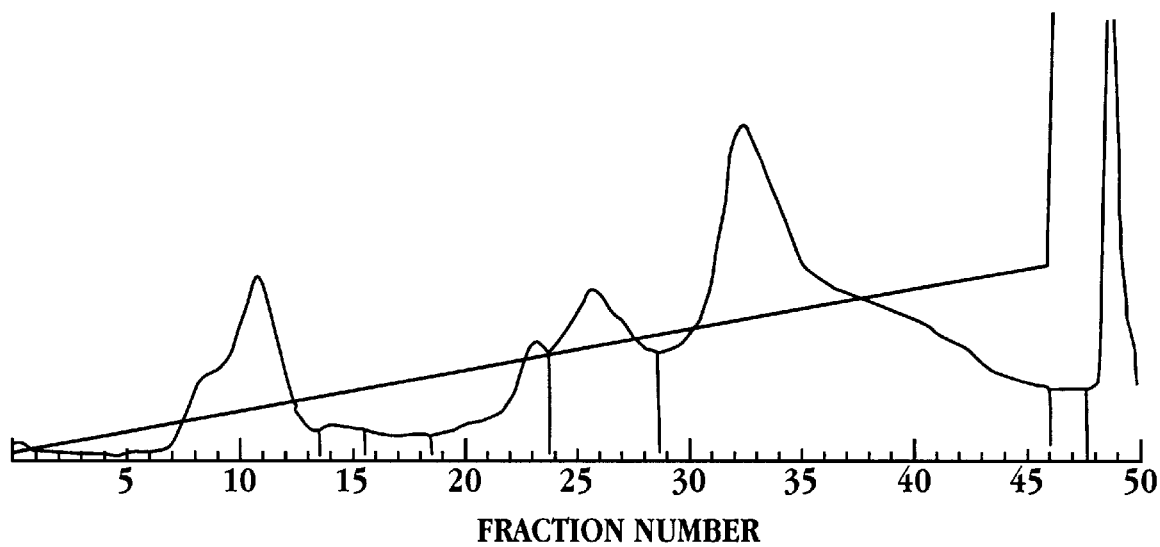
FIG. 4A: shows an exemplary protein profile from gradient fractions eluted from an anion exchange column.
Figure 4B:
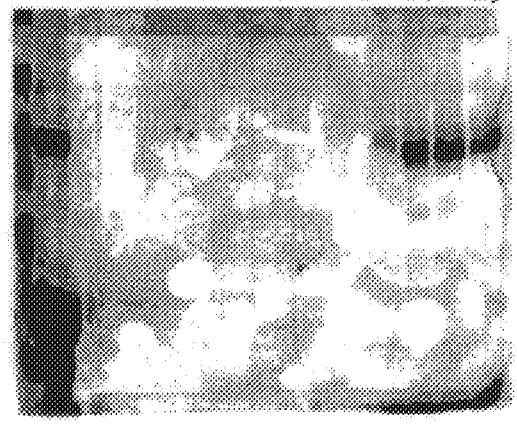
FIGS. 4B and 4C: show scanned images of exemplary Sodium dodecyl sulfate polyacrylamide gel electrophoresis analysis of fraction samples from FIG. 4A.
Figure 4C:
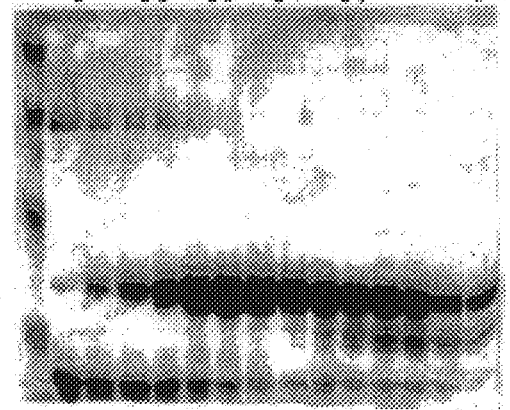

After these washes, a gradient was started and ran from Buffer A to Buffer B in 15 column volumes. The gradient then stepped to 100% Buffer B for one column volume. An exemplary gradient is shown in FIG. 4A. Fractions were collected every 10 minutes. Purity of the 470-20-1/sj26his fusion protein was assessed by standard SDS-PAGE (FIGS. 4B and 4C) and relevant fractions were pooled (approximately fractions 34 through 37, FIG. 4C).

C. Preparation of Anti-470-20-1 Antibody

The purified 470-20-1/sj26his fusion protein is injected subcutaneously in Freund's adjuvant in a rabbit. Approximately 1 mg of fusion protein is injected at days 0 and 21, and rabbit serum is typically collected at 6 and 8 weeks.

A second rabbit is similarly immunized with purified sj26his protein.

Minilysates are prepared from bacteria expressing the 470-20-1/sj26his fusion protein, sj26his protein, and β-galactosidase/470-20-1 fusion protein. The lysates are fractionated on a gel and transfered to a membrane. Separate Western blots are performed using the sera from the two rabbits.

Serum from the animal immunized with 470-20-1 fusion protein is immunoreactive with all sj26his fusion protein in minilysates of IPTG induced *E. coli* W3110 that are transformed either with PGEX MOV or with pGEX MOV containing 470-20-1 insert. This serum is also immunoreactive with the fusion protein in the minilysate from the 470-20-1 lambda gt11 construct.

The second rabbit serum is immunoreactive with both sj26his and 470-20-1/sj26his fusion proteins in the minilysates. This serum is not expected to immunoreactive with 470-20-1/β-galactosidase fusion protein in the minilysate from the 470-20-1 lambda gt11 construct. None of the sera are expected to be immunoreactive with β-galactosidase.

Anti-470-20-1 antibody present in the sera from the animal immunized with the fusion protein is purified by affinity chromatography (using the 470-20-1 ligand).

Alternatively, the fusion protein can be cleaved to provide the 470-20-1 antigen free of the sj-26 protein sequences. The 470-20-1 antigen alone is then used to generate antibodies as described above.

Example 9

Rabbit Anti-Peptide Sera

Peptides were designed to cover the entire HGV sequence, in particular, to cover each of the functional groups in the non-structural and structural genes. Peptides were synthesized commercially by conventional techniques. Representative peptides are presented in Table 12.

TABLE 12

| Desgination | Size of Peptide (aa) | End Points Relative to SEQ ID NO: 14 |
|---|---|---|
| PEP1/NS2a | 30 | 2674/2763 |
| PEP2/E1 | 16 | 733/780 |
| PEP3/E2 | 18 | 1219/1272 |
| PEP4/NS2B | 18 | 3061/3114 |
| PEP5/NS3 | 21 | 3571/3633 |

TABLE 12-continued

| Desgination | Size of Peptide (aa) | End Points Relative to SEQ ID NO: 14 |
|---|---|---|
| PEP6/NS3** | 18 | 4909/4959 |
| PEP7/NS4A | 18 | 5275/5328 |
| PEP8/NS4B | 16 | 6097/6144 |
| PEP9/NS5A | 16 | 7033/7080 |
| PEP10/NS5B | 18 | 7783/7836 |

**The NS3 peptide has an extraneous Cysteine on the C terminal end that is not in the HGV-PNF 2161 variant polypeptide sequence; the actual sequence was a Q.

The peptides were coupled to KLH. Using rabbits as host, the conjugated peptides were injected subcutaneously at multiple sites. Anti-peptide rabbit serum were generated by a commercial facility. A two-week immunization protocol was used with bleeds taken at alternate weeks.

Rabbit anti-peptide sera were shown to be peptide specific and to have high titer. Rabbit anti-peptide sera also recognize corresponding recombinant proteins expressed in *E. coli* and baculovirus. Antibody endpoint titers range from 1:50,000 dilution to 1:625,000 dilution. Rabbit anti-peptide 7 (NS4a) had low end point titers of only 1:1,000. Accordingly, rabbit anti-serum to the NS4a protein expressed in, for example, the baculovirus system may be a more useful reagent.

Rabbit anti-peptide sera are useful for immunoprecipitating corresponding HGV proteins expressed, for example, in baculovirus and vaccinia. Rabbit anti-peptide sera are also useful as capture antibody in EIAs to detect HGV antigen. Rabbit anti-peptide sera are further useful in the characterization of the HGV proteins.

Example 10

Serology

A. Western Blot Analysis of Sera Panels

The 470-20-1 fusion antigen (described above) was used to screen panels of sera. Many of the panels were of human sera derived both from individuals suffering from hepatitis and uninfected controls.

Affinity purified 470-20-1 fusion antigen (Example 8) was loaded onto a 12% SDS-PAGE at 2 μg/cm. The gel was run for two hours at 200 V. The antigen was transfered from the gel to a nitrocellulose filter.

The membrane was then blocked for 2 hours using a solution of 1% bovine serum albumin, 3% normal goat serum, 0.25% gelatin, 100 mM NaPO$_4$, 100 mM NaCl, and 1% nonfat dry milk. The membrane was then dried and cut into 1–2 mm strips; each strip contained the 470-20-1 fusion antigen. The strip was typically rehydrated with TBS (150 mM NaCl; 20 mM Tris HCl, pH 7.5) and incubated in panel sera (1:100) overnight with rocking at room temperature.

The strips were washed twice for five minutes each time in TBS plus "TWEEN 20" (0.05%), and then washed twice for five minutes each time in TBS. The strips were then incubated in secondary antibody (Promega anti-human IgG-Alkaline Phosphatase conjugate, 1:7500), for 1 hour with rocking at room temperature. The strips were then washed twice×5 minutes in TBS+"TWEEN 20", then twice×5 minutes in TBS.

Bound antibody was detected by incubating the strips in a substrate solution containing BCIP (Example 2) and NBT (Example 2) in pH 9.5 buffer (100 mM Tris, 100 mM NaCl, 5 mM MgCl$_2$). Color development was allowed to proceed for approximately 15 minutes at which point color development was halted by 3 washes in distilled H₂O.

Test sera were derived from the following groups of individuals: (i) blood donors, negative for HBV Ab, surface Ag, negative for HCV, HIV, HTLV-1 Abs; (ii) HBV, sera from individuals who are infected with Hepatitis B virus; (iii) HCV, sera from individuals infected with Hepatitis C virus by virtue of being reactive in a second-generation HCV ELISA assay; and (iv) HXV, individuals serologically negative for HAV, HBV, HCV, or HEV.

The results of these screens are presented in Table 13.

TABLE 13

470-20-1 Sera Panelling Result Summary

| Sample | No. Human* Sera Tested | + | IND* | − |
|---|---|---|---|---|
| blood donor | 30 | 1 (3.3%) | 2 (6.7%) | 27 (90.0%) |
| HBV | 40 | 7 (17.5%) | 4 (10.0%) | 29 (72.5%) |
| HCV | 38 | 11 (28.95%) | 11 (28.95%) | 16 (42.1%) |
| HXV | 122 | 20 (16.4%) | 12 (9.8%) | 90 (73.8%) |

*Indeterminate, weak reactivity

These results suggest the presence of the 470-20-1 antigen in a number of different sera samples. The antigen is not immunoreactive with normal human sera.

B. General ELISA Protocol for Detection of Antibodies

Polystyrene 96 well plates ("IMMULON II" (PGC)) are coated with 5 μg/ml (100 μL per well) antigen in 0.1M sodium bicarbonate buffer, pH 9.5. Plates are sealed with "PARAFILM" and stored at 4° C. overnight.

Plates are aspirated and blocked with 300 uL 10% normal goat serum and incubated at 37° C. for 1 hr.

Plates are washed 5 times with PBS 0.5% "TWEEN-20".

Antisera is diluted in 1× PBS, pH 7.2. The desired dilution(s) of antisera (0.1 mL) are added to each well and the plate incubated 1 hour at 37° C. The plates are then washed 5 times with PBS 0.5% "TWEEN-20".

Horseradish peroxidase (HRP) conjugated goat anti-human antiserum (Cappel) is diluted 1/5,000 in PBS. 0.1 mL of this solution is added to each well. The plate is incubated 30 min at 37° C., then washed 5 times with PBS.

Sigma ABTS (substrate) is prepared just prior to addition to the plate.

The reagent consists of 50 ml 0.05M citric acid, pH 4.2, 0.078 ml 30% hydrogen peroxide solution and 15 mg ABTS. 0.1 ml of the substrate is added to each well, then incubated for 30 min at room temperature. The reaction is stopped with the addition of 0.050 mL 5% SDS (w/v). The relative absorbance is determined at 410 nm.

Example 11

Expression of Selected HGV Antigens

The entire coding sequence of HGV was subcloned into greater than 50 distinct overlapping cDNA fragments. The length of most cDNA fragments ranged from about 200 bp to about 500 bp. The cDNA fragments were cloned separately into the expression vector, pGEX-HisB. This vector is similar to pGEX-MOV, described above.

pGEX-hisB is a modification of pGEX-2T (Genbank accession number A01438; a commercially available expression vector). The vector pGEX-2T has been modified by insertion of a NcoI site directly downstream from the thrombin cleavage site. This site is followed by a BamHI site, which is followed by a poly-histidine (six histidines) encoding sequence, followed by the EcoRI site found in pGEX-2T. Coding sequences of interest are typically inserted between the NcoI site and the BamHI site. In FIG. 6 (SEQ ID NO:115), the inserted sequence encodes the GE3-2 antigen. The rest of the vector sequence is identical to pGEX-2T. Expression of fusion protein is carried out essentially as described above with other pGEX-derived expression vectors.

Cloning of all 50 fragments was carried out essentially as described below, where specific primers were selected for each of the 50 coding regions. Each HGV insert DNA is PCR amplified from RNA extracted from PNF 2161 or other HGV(+) sera using a specific set of primers as described in Example 4C. Typically, the 5' primer contained a NcoI restriction site and the 3' primer contained a BamHI restriction site. The NcoI primers in the amplified fragments allowed in-frame fusion of amplified coding sequences to the GST-Sj26 coding sequence in the expression vectors pGEX-Hisb or pGEX MOV.

Amplified HGV insert DNA is digested with restriction enzymes NcoI and Bam HI. Digested insert DNA is gel purified and ligated with NcoI and BamHI digested pGEX hisB or pGEX MOV. E. coli strain W3110 (ATCC #27325, American Type Culture Collection, Rockville, Md.) was transformed with the ligation product. Ampicillin resistant colonies were selected. Presence of the insert was confirmed by the PCR amplification of the insert from the ampicillin resistant colony using primers homologous to pGEX vector sequences flanking the inserted molecules (primers GLI F (SEQ ID NO:235) and GLI R (SEQ ID NO:236).

The size of the PCR amplification product is the insert size plus approximately 160 bp derived from vector. Transformants with appropriate inserts were selected and subjected to protein induction by IPTG as described in Example 7. Expressed recombinant proteins were analyzed for specific immunoreactivity against putative HGV-infected human sera by Western blot.

Eight fragments designated GE3, GE9, GE15, GE17, GE4, EXP3, GE1-N and GE-57 encoded antigens that gave a clear immunogenic response when reacted with putative HGV-infected human sera.

A. Cloning of GE3, GE9, GE15, GE17, GE4, EXP3, GEL-N and GE57.

The coding sequence inserts for clones GE3, GE9, GE15, GE17, GE4, EXP3, GE1-N and GE57 were generated by polymerase chain reaction from SISPA-amplified double-stranded cDNA or RNA obtained from PNF 2161 or T55806 using PCR primers specific for each fragment. Following Table 14 lists the coordinates of each clone relative to SEQ ID NO:14 and the primer sets used for generation of each clone insert.

TABLE 14

| Clone | Serum Source | Coordinate on SEQ ID NO: 14 | F Primer (SEQ ID NO:) | R Primer (SEQ ID NO:) |
|---|---|---|---|---|
| GE3 | PNF 2161 | 6615–6977 | GE-3F (SEQ ID NO: 46) | GE-3R (SEQ ID NO: 47) |
| GE9 | PNF 2161 | 8154–8441 | GE-9F (SEQ ID NO: 48) | GE-9R (SEQ ID NO: 49) |
| GE15 | PNF 2161 | 3615–3935 | GE-15F (SEQ ID NO: 111) | GE-15R (SEQ ID NO: 112) |

TABLE 14-continued

| Clone | Serum Source | Coordinate on SEQ ID NO: 14 | F Primer (SEQ ID NO:) | R Primer (SEQ ID NO:) |
|---|---|---|---|---|
| GE17 | PNF 2161 | 3168–3305 | GE-17F (SEQ ID NO: 113) | GE-17R (SEQ ID NO: 114) |
| GE4 | PNF 2161 | 6825–7226 | GE4F (SEQ ID NO: 149) | GE4R (SEQ ID NO: 150) |
| EXP3 | PNF 2161 | 6648–7658 | 470EXP3F (SEQ ID NO: 151) | 470EXP3R (SEQ ID NO: 152) |
| GE1-N | PNF 2161 | 5850–6239 | GE1-NF (SEQ ID NO: 237) | GE1-NR (SEQ ID NO: 238) |
| GE57 | T55806 | 271*–456* | GE57F (SEQ ID NO: 239) | GE57R (SEQ ID NO: 240) |

*These sequences are given relative to SEQ ID NO: 178.

The amino acid sequence of GE57 is presented as SEQ ID NO:241.

In the GE3-5' primer (GE-3F, SEQ ID NO:46) a silent point mutation was introduced to modify a natural NcoI restriction site. Using the above-described primers, PCR amplification products were generated. The amplification products were gel purified, digested with NcoI and BamHI, and gel purified again. The purified NcoI/BamHI GE3, GE9, GE15, GE17, GE4, GE1-N and GE57 fragments were independently ligated into dephosphorylated, NcoI/BamHI cut pGEX-HisB vectors. The purified NcoI/BamHI EXP3 fragment was ligated into dephosphorylated, NcoI/BamHI cut pGEX-MOV vector.

Each ligation mixture was transformed into *E. coli* W3110 strain and ampicillin resistant colonies were selected. The ampicillin resistant colonies were resuspended in a Tris/EDTA buffer and analyzed by PCR, using primers GLI F (SEQ ID NO:235) and GLI R (SEQ ID NO:236) to confirm the presence of insert sequences. Eight candidate clones were designated GE3-2, GE9-2, GE15-1, GE17-2, GE4-8, EXP3-7, GE1-N and GE57, respectively.

B. Expression of the GE3-2, GE9-2, GE15-1, GE172, GE4-8, EXP3-7, GE1-N and GE57 Fusion Proteins.

Colonies of ampicillin resistant bacteria carrying GE3-2, GE9-2, GE15-1, and GE17-2, GE4-8, EXP3-7, GE1-N and GE57 containing-vectors were individually inoculated into LB medium containing ampicillin. The cultures were grown to OD of 0.8 to 0.9 at which time IPTG (isopropylthio-beta-galactoside; Gibco-BRL) was added to a final concentration of 0.3 to 1 mM, for the induction of protein expression. Incubation in the presence of IPTG was continued for 3 to 4 hours.

Bacterial cells were harvested by centrifugation and resuspended in SDS sample buffer (0.0625M Tris, pH 6.8, 10% glycerol, 5% mercaptoethanol, 2.3% SDS). The resuspended pellet was boiled for 5 min. and then cleared of insoluble cellular debris by centrifugation. The supernatants obtained from IPTG-induced cultures of GE3-2, GE9-2, GE15-1, GE17-2, GE4-8, EXP3-7, GE1-N and GE57 were analyzed by SDS-polyacrylamide gel electrophoresis (PAGE) together with uninduced lysates. The proteins from these gels were then transferred to nitrocellulose filters (i.e., by Western blotting).

The filters were first incubated with rabbit polyclonal antibody or mouse monoclonal antibody (RM001 from Sierra Biosource, Calif.) directed to GST protein to detect the expression of appropriate size GST-fusion protein expression. Expected protein sizes of above clones are 40, 38, 39, 32, 42, 64, 42 and 33 KDa, respectively. Immunoreactivity of RM001 with bands at the appropriate molecular weight for the fusion proteins demonstrated the successful expression of the fusion proteins of above clones by the bacterial cells. Expression of the clone proteins were also monitored by the appearance of over-expressed proteins of appropriate sizes upon IPTG induction on the Coomassie brilliant blue stained gel.

C. Western Blot Analysis of HGV Proteins.

Once the expression of the HGV clone protein was confirmed by Western blot analysis with anti-GST antibody a second set of filters, prepared as above, were then exposed to several HGV(+) and HGV(−) human sera. Human sera used for Western blot analyses of whole cell lysates were pre-absorbed with the lambda-gt11-nitrocellulose filters. Lambda-gt11-nitrocellulose filters were prepared as follows. Briefly, an overnight culture of KM392 culture was prepared in LB. The culture was diluted 10 fold in fresh LB containing 0.2% maltose and incubated for 1 hour at 37° C. with shaking.

After 1 hour the culture was mixed with an equal volume of MgCa solution (0.01M $MgCl_2$ and 0.01M $CaCl_2$). To this mixture lambda gt11 was added to a titer of $2 \times 10^4$ PFU/ml and incubated for 30 min without shaking. After 30 minutes (per each ml of this phage/*E.coli* mixture) 15 ml of molten (55° C.) LB top agar (LB with 0.8% agar) was added: 8 ml of this mixture was spread onto each 15 cm LB agar plate. After the top agar solidified the plate was incubated at 37° C. for 3–5 hr.

After plaques developed, a nitrocellulose filter was placed on the plate and the plate further incubated at 37° C. overnight. The nitrocellulose filter was removed and washed thoroughly with TBS (50 mM Tris-HCl, pH 7.5, 150 mM NaCl) plus 0.05% "TWEEN 20." The washed filter was then blocked with 1% gelatin in TBS overnight. The filter was washed three times (5 minutes each wash) with TBS.

For the pre-absorption of human sera each serum was diluted 100 fold in blocking solution (described in Example 10). Ten mls. of diluted serum was then incubated overnight with two lambda gt11 filters prepared as above. Lambda gt11 filters were removed and the pre-absorbed serum used for Western blot analysis.

Western blot analyses demonstrated that clones GE3-2, GE9-2, GE15-1, GE17-2, GE4-8, EXP3-7, GE1-N and GE57 showed specific immunoreactivity toward HGV(+) sera. The GE-4-8 protein was immunoreactive with J21689 serum. J21689 is HGV (+) serum as determined by HGV PCR (Example 4) and HCV (+) as determined by HCV PCR and serological analyses. The EXP3-7 protein was immunoreactive with JC and T55806. JC is the HGV-positive serum identified in Example 4F that was rejected by the blood bank for being high ALT. A second JC sample, taken one year after the initial serum sample, was also positive for HGV by PCR analysis. T55806 is also the HGV-positive serum identified in Example 4F that was rejected by the blood bank for being High ALT. This serum is co-positive with HCV.

Further, GE15-1 and GE-17 showed weak but specific immunoreactivity toward PNF 2161 and T55806. GE1-N was immunoreactive with PNF2161, JC, T55806, T56633, T27034 and R0001. T56633, T27034 and R0001 are HGV (+) sera identified in Example 4F. GE57 was immunoreactive with E57963 and R0001. E57963 is HGV and HCV co-positive serum. GE3-2 and GE9-2 were also immunoreactive with HGV sera specifically. However, none of the eight antigens were immunoreactive with HGV negative sera T43608 and R05072.

The GE3-2 and GE9-2 fusion proteins were purified from bacterial cell lysates essentially as in Example 7 using dual chromatographic methods employing glutathione-conjugated beads (Smith, D. B., et al.) and immobilized metal ion beads (Hochuli; Porath). The purified proteins were subjected to Western blot analysis as follows.

Various amounts of the purified HGV proteins (e.g., GE3-2 and GE9-2 proteins) were loaded on 12% acrylamide gels. Following PAGE, proteins were transferred from the gels to nitrocellulose membranes, using standard procedures. Individual membranes were incubated with one of a number of human or mouse sera. Excess sera were removed by washing the membranes.

These membranes were incubated with alkaline phosphatase-conjugated goat anti-human antibody (Promega) or alkaline phosphatase-conjugated goat anti-mouse antibodies (Sigma), depending on the serum being used for screening. The membranes were washed again, to remove excess goat anti-human IgG antibody, and exposed to NBT/BCIP. Photographs of exemplary stained membranes having the GE3 fusion protein are shown in FIGS. 7A to 7D.

Figures 7A, 7B, 7C, 7D:
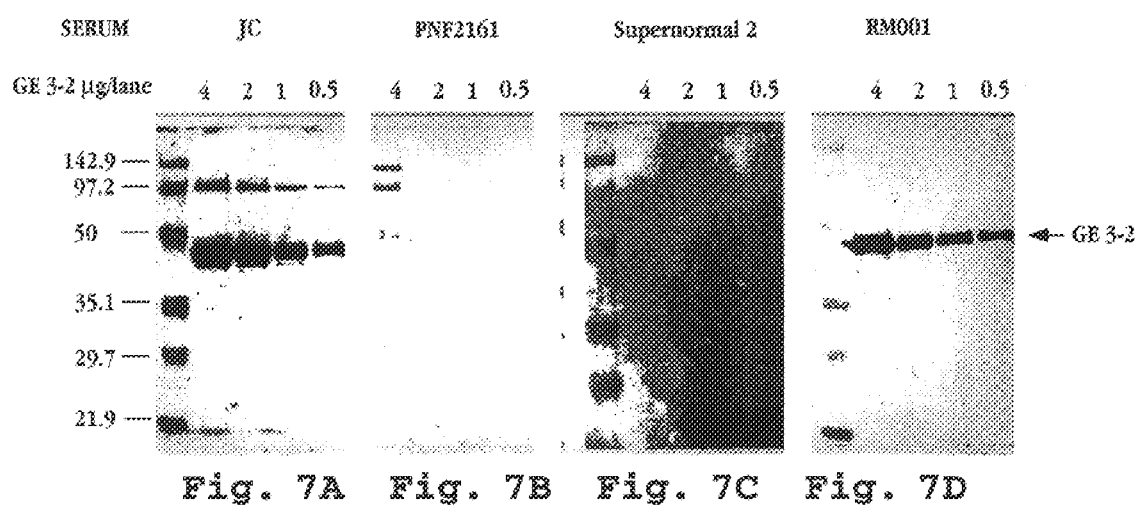
FIGS. 7A to 7D show scanned images of Western blot analyses of the purified HGV GE3-2 protein.

The Figures show the results of Western blot analysis of the purified GE3-2 protein using the following sera: N-(ABCDE) human (JC) serum (FIG. 7A), N-(ABDE) human (PNF 2161) serum (FIG. 7B), a super normal (SN2) serum (FIG. 7C), and mouse monoclonal antibody (RM001) directed against GST-Sj26 protein (FIG. 7D).

In each of the figures, lane 1 contains prestained molecular weight standards(Bio-Rad), and lanes 2–5 contain, respectively, the following amounts of the GE3-2 fusion protein: 4 μg, 2 μg, 1 μg, and 0.5 μg. Numbers represent loading amounts in micrograms per 0.6 centimeter of gel (well size). Dilutions of the human JC, PNF 2161 and Super Normal 2 sera were 1:100. The anti-sj26 dilution was 1:1000. The band seen at about 97K in the JC blot is reactivity against a minor contaminant in the GE3.2 fusion protein preparation.

Protein marker sizes are 142.9, 97.2, 50, 35.1, 29.7 and 21.9 KD.

As shown in FIGS. 7A to 7D, GE3-2 showed specific immunoreactivity with JC serum. GE3-2 reacted weakly with PNF 2161 serum and would be scored as an indeterminant or negative.

In parallel experiments, GE9-2 showed weak but specific immunoreactivity toward PNF 2161 serum.

Example 12

Construction of Exemplary Epitope Libraries
A. The Y5 Library.

Polymerase Chain Reactions were employed to amplify 3 overlapping DNA fragments from PNF 2161 SISPA-amplified cDNA. The PNF 2161 SISPA-amplified cDNA was prepared using the JML-A/B linkers (SEQ ID NO:54 and SEQ ID NO:55). One microliter of this material was re-amplified for 30 cycles (1 minute at 94° C., 1.5 minutes at 55° C. and 2 minutes at 72° C.) using 1 μM of the JML-A primers. The total reaction volume was 100 μl. The products from 3 of these amplifications were combined and separated from excess PCR primers by a single pass through a "WIZARD PCR COLUMN" (Promega) following the manufacturer's instructions. The "WIZARD PCR COLUMN" is a silica based resin that binds DNA in high ionic strength buffers and will release DNA in low ionic strength buffers. The amplified DNA was eluted from the column with 100 μl distilled H20.

The eluted DNA was fractionated on a 1.5% Agarose TBE gel (Maniatis, et al.) and visualized with UV light following ethidium bromide staining. A strong smear of DNA fragments between 150 and 1000 bp was observed. One microliter of the re-amplified cDNA was used as for template in PCR reactions with each primer pair presented in Table 15.

TABLE 15

| Primers | SEQ ID NO: | Size of Amplified Fragment |
|---|---|---|
| 470ep-F1 | SEQ ID NO: 56 | 810 |
| 470ep-R1 | SEQ ID NO: 57 | |
| 470ep-F2 | SEQ ID NO: 58 | 750 |
| 470ep-R3 | SEQ ID NO: 59 | |
| 470ep-F4 | SEQ ID NO: 60 | 669 |
| 470ep-R4 | SEQ ID NO: 61 | |

The primers were designed to result in the amplification of HGV specific DNA fragments of the sizes indicated in Table 15. In the amplification reactions, the primer pairs were used at a concentration of 1 μM. Amplifications were for 30 cycles of 1 minute at 94, 1.5 minutes at 54° C. and 3 minutes at 72° C. in a total reaction volume of 100 μl. Each of the three different primer pair PCR reactions resulted in the specific amplification of products having the expected sizes. For each primer pair reaction, amplification products from 3 independent PCR reactions were combined and purified using a "WIZARD PCR COLUMN" as described above. The purified products were eluted in 50 μl dH20.

Samples from each purified product (14 μl, containing approximately 1–2 μg of each primer-pair amplified DNA fragment) were combined. The combined sample of all three different amplified fragments was added to 5 μl of 10× DNAse Digestion buffer (500 mM Tris PH 7.5, 100 mM MnCl$_2$) and 2 μl of dH20. From this digestion mixture, a 10 μl sample was removed and placed in a tube containing 5 μl of Stop solution (100 mM EDTA, pH 8.0). This sample was the 0 "minutes of digestion" time point. The rest of the digestion reaction was placed at 25° C. To the digestion mixture 1 μl of 1/25 diluted RNase-free DNAse I (Stratagene) was added. At various time points 10 μl aliquots were withdrawn and mixed with 5 μl of Stop solution. The DNAse I digested DNA products were analyzed on a 1.5% Agarose TBE gel.

The results of several digestion experiments showed that 40 minutes of digestion provided a good distribution of DNA fragments in the size range of 100–300 bp. A DNAse I digestion was then repeated with the entire digestion being left for 40 minutes at room is temperature. The digestion was stopped by the addition of 18 μl of Stop Buffer and the digested DNA products were purified using a "WIZARD PCR COLUMN." The "WIZARD-PCR COLUMN" was eluted with 50 μl of dH20 and the eluted DNA added to the following reaction mixture: 7 μl of Restriction Enzyme Buffer C (Promega, 10 mM MgCl$_2$, 1 mM DTT, 50 mM NaCl, 10 mM Tris, pH 7.9, 1× concentration); 11 μl of 1.25 mM dNTPs; and 2 μl T4 DNA Polymerase (Boehringer-Mannhiem). This reaction mixture was held at 37° C. for 30 minutes, at which point 70 μl of pH 8.0 phenol/CHCl$_3$ was added and mixed. The phenol/CHCl$_3$ was removed and extracted once to yield a total aqueous volume of 150 μl containing the DNA sample. The DNA was ethanol precipitated using 2 volumes of absolute ethanol and 0.5 volume of 7.5M NH$_4$-acetate. The DNA was pelleted by centrifugation for 15 minutes at 14,000 rpm in an "EPPENDORF MICROFUGE", dried for 5 minutes at 42° C. and resuspended in 25 μl of dH20.

The DNA was ligated to 5' phosphorylated SISPA linkers KL1 (SEQ ID NO:62) and KL2 (SEQ ID NO:63). Several different concentrations of SISPA linkers and DNA was tested. The highest level of ligation (assessed as described below) occurred under the following ligation reaction conditions: 6 µl of DNA, 2 µl of 5.0×10–12M KL1/KL2 linkers, 1 µl of 10× ligase buffer (New England Biolabs), and 1 µl of 400 Units/µl T4 DNA Ligase (New England Biolabs) in a total reaction volume of 10 µl. Ligations were carried out overnight at 16° C.

Two reactions were run in parallel as follows. A 2 µl sample of the ligated material was amplified using the KL1 SISPA primer in a total reaction volume of 100 µl (25 cycles of 1 minute at 94° C., 1.5 minutes at 55° C. and 2 minutes at 72° C.). The degree of ligation was assessed by separating ⅕ of the PCR reaction amplified products by electrophoresis using a 1.5% agarose TBE gel. The gel was stained with ethidium bromide and the bands visualized with UV light.

The amplification products from the duplicate reactions were purified using "WIZARD PCR COLUMNS" and the purified DNA eluted in 50 µl of dH20. A twenty-five microliter aliquot of the PCR KL1/KL2 amplified DNA was digested with 36 Units of EcoRI (Promega) in a total volume of 30 µl. The reaction was carried out overnight at 37° C. The Digested DNA was purified using a "SEPHADEX G25" spin column.

The EcoRI digested DNA was ligated in overnight reactions to λgt11 arms that were pre-digested with EcoRI and treated with calf intestinal alkaline phosphatase (Stratagene, La Jolla, Calif.). The ligation mixture was packaged using a "GIGAPACK GOLD PACKAGING EXTRACT" (Stratagene) following manufacturer's instructions. Titration of the amount of recombinant phage obtained was performed by plating a 1/10 dilution of the packaged phage on a lawn of KM-392, where the plate contained 20 µl of a 100 mg/ml solution of x-gal (5-Bromo-4-chloro-3-indolyl-β-D-galactoside; Sigma) and 20 µl of a 0.1M solution of IPTG (Isopropyl-1-thio-β-D-galactoside; Sigma). A titer was obtained of $1.2 \times 10^6$ phage/ml containing over 75% recombinant phage.

The percentage of recombinant plaques was confirmed by PCR analysis of 8 randomly picked plaques using primers 11F (SEQ ID NO:25) and 11R (SEQ ID NO:13). This packaged library containing the DNA fragments derived from the digestion of the amplified DNAs F1/R1, F2/R3, and F4/R4 amplified DNAs and was designated library Y5.

B. The ENV Library.

An expression library, designated the ENV library, was generated as follows. One microliter of PNF 2161 SISPA amplified DNA was used as the template in polymerase chain amplification reactions utilizing the following primer pairs: GEP-F15 (SEQ ID NO:128) and GEP-R15 (SEQ ID NO:129), which generate a 525 nucleotide HGV fragment; and GEP-F17 (SEQ ID NO:130) and GEP-R16 (SEQ ID NO:131), which generate a 765 nucleotide HGV fragment.

PCR amplification was for 35 cycles of 94° C. for 1 min, 52° C. for 1.5 minutes, and 72° C. for 3 minutes. The amplified products were purified and digested with DNAse I. Ligation of KL1 and KL2 linkers to cDNA, amplification of DNA fragments and construction of libraries in lambda gt11 were performed essentially as described in Example 12A. The recombinant frequency of the library was greater than 70%. Analysis of the inserts by polymerase chain reaction using primers derived from the flanking regions of lambda gt11 confirmed the recombinant frequency and indicated that the insert size range was 150–500 nucleotides.

C. The NS3 Library.

An expression library designated NS3 was constructed as follows. A first fragment was amplified by polymerase chain reaction using the primers 470ep-F9 (SEQ ID NO:132) and 470ep-R9 (SEQ ID NO:133) and, as template, PNF 2161 SISPA amplified nucleic acids. The predicted product of this amplification reaction was 777 base pairs. The amplified fragment was gel purified by separation on a TAE gel. The fragment was further purified using "GENECLEAN" (Bio 101, La Jolla, Calif.).

Fragment F9/R9 was also amplified using the extension clone GE3L-11 (SEQ ID NO:41) as source material. Approximately 25 ng of GE3L-11 was used as template with the F9 and R9 primers in amplification reactions.

Both of the F9/R9 amplifications were for 30 cycles of 94° C., for 1 minute, 52° C. for two minutes, and 72° C. for 3 minutes, using "TAQ START" (Clonetech, Palo Alto, Calif.). The amplification products from both reactions were combined. The products were digested with DNAse I (10 µl GE3L product and 25 ul of PNF SISPA product). The GE3L-based amplification product represented the majority of the amplification product starting material. Ligation of KL1 and KL2 linkers to cDNA, amplification of DNA fragments and construction of libraries in lambda gt11 were performed essentially as described in Example 12A.

The titer obtained was $2.5 \times 10^6$ phage/ml and the percent recombinant phage was determined to be greater than 99%. Polymerase chain reaction analysis of the insert sizes confirmed the recombinant frequency and indicated an insert size range of 150 to 550 nucleotides.

In addition, a second fragment was also amplified using the GEP-F10/GEP-R10 primers (SEQ ID NO:135 and SEQ ID NO:136, respectively). One microliter of PNF 2161 SISPA amplified nucleic acids was used as template. The predicted fragment size of 570 nucleotides was obtained. The resulting amplification products were manipulated as just described for the F9/R9 amplifications. The titer obtained for this fragment when inserted in lambda gt11 was $1.47 \times 10^6$ phage/ml, with a recombinant frequency of 90%.

D. The NS2 Library.

The NS2 epitope library was constructed using the methodologies described in Example 12A. Four DNA fragments containing all or part of the HGV proteins NS2, NS3, and NS5b were amplified from 1 ul of PNF 2161 SISPA DNA (prepared essentially as described in Example 12A). The library was generated using the primers given in Table 16 and SISPA amplified PNF 2162 DNA as template.

TABLE 16

| Fragments | | nt | |
|---|---|---|---|
| 9E3-REV | (SEQ ID NO: 264) | 592aa | 358 (of 389) of |
| E394-R | (SEQ ID NO: 265) | | E2 to aa 166 of NS-2 |
| GEP-F12 | (SEQ ID NO: 266) | 663 | aa 144 (of 313) of |
| GEP-R12 | (SEQ ID NO: 267) | | NS-2 to aa 51 of NS-3 |
| GEP-F14 | (SEQ ID NO: 268) | 715 | aa 357–594 of NS-3 |
| GEP-R13 | (SEQ ID NO: 269) | | |
| 470epF8 | (SEQ ID NO: 270) | 648 | aa 716–847 of NS-5 |
| GEP-R14 | (SEQ ID NO: 271) | | (716 to end) |

All amplifications were for 35 cycles of 94° C./1 minute, 48° C./2 minutes, and 73° C./3 minutes. All amplifications yielded at least a fragment of the expected size. The amplified products were mixed and in an approximately 1:1:1:1 ratio and partially digested with DNase I. As above, the digestion products were ligated to KL1 SISPA linkers, amplified and EcoRI digested. The digested fragments were ligated into lambda gt11. The ligation reactions were packaged.

The packaged ligation products were plated. The resulting library was determined to contain ~70% recombinant phage with an observed insert size of 150 to 500 nucleotides.

E. The VNS5a Library.

Primers 470EXT4-2189R (SEQ ID NO:119) and 470EXT4-29F (SEQ ID NO:120) were used to isolate a 2.1 kb DNA fragment that contains the entire coding sequences for the HGV proteins NS4b and NS5a, as well as the 3' end of NS4a and the 5' end of NS5b. PCR amplifications using these primers were performed as described in Example 4G. Successful amplification was observed with multiple HGV-infected sera including the following: T56633 was from a blood donor whose donation was rejected due to an ALT value above the cutoff; samples E21-A and E20 were derived from Egyptian individuals suffering from hepatitis; and sample AH0591 is derived from an Australian individual who developed fulminant hepatitis.

The amplified products of E21-A and E20 were cloned into the T overhang site of the vector T/A (obtained from InVitrogen, San Diego, Calif.) essentially as described in Example 6. The 2.1 kb HGV inserts from these 2 plasmids were then isolated by the digestion of approximately 20 ug of plasmid DNA with approximately 150 units of the restriction enzyme EcoRI. After incubation overnight at 37° C., the products of the digestion were separated by TAE agarose gel electrophoresis. The products were excised from the section of the agarose gel containing the fragment of interest. The agarose was melted and extraction of the liberated DNA was carried out using the "GENECLEAN II" kit according to the manufacturers instructions (Bio 101, La Jolla, Calif.).

The purified 2.1 kb fragments derived from the E21-A and E20 samples, as well as the DNA fragments obtained from PCR amplification of samples T56633 and AH0591, were digested separately with DNAse I as described in Example 12A. For all 4 samples digestion conditions were determined that resulted in the isolation of fragments of between 100 to 1000 nts in size. After purification and trimming (Example 12A) the fragments derived from each of the 4 HGV infected samples were ligated separately to different sets of SISPA linkers. After ligation the DNAs were SISPA amplified.

The amplified DNAs were separately digested overnight at 37° C. with approximately 100 units of EcoRI. The digested DNAs were then purified by spin column chromatography using G25 resin (5'3' Inc, Boulder, Colo.). Digested DNA from the samples T56633, AH0591, and E21-A were combined at a ratio of 1:1:1 and the mixture of DNAs was ligated into the EcoRI site of λgt11 as described in Example 12A. After packaging using the "GIGAPACK III XL" extract (Stratagene, LaJolla, Calif.), the resulting library was plated in the presence of IPTG and XGAL and determined to have a titer of approximately $1.0 \times 10^6$ phage/ml and a recombinant frequency of approximately 70%.

Example 13

Immunoscreening of the Epitope Libraries
A. Isolation of Immunoreactive Y5 Clones.

Two HGV positive sera, PNF2161 and JC, were used for immunoscreening of the Y5 library, essentially as described in Example 2. The Y5 phage library was plated onto 20 plates at approximately 15,000 phage per plate. The plates were incubated for approximately 5 hours and were overlaid with nitrocellulose filters (Schleicher and Schuell) overnight. The filters were blocked by incubation in AIB (1% gelatin plus 0.02% Na azide) for approximately 6 hours. The blocked filters were washed once with TBS.

Ten Y5 library filters were incubated overnight, with agitation, with PNF2161 serum and ten filters with JC serum. Both sera were diluted 1:10 in AIB. In order to reduce non-specific antibody binding, the diluted sera had been pre-treated by incubation overnight with nitrocellulose filters to which wild type λgt11 were adsorbed.

The filters were removed from the sera, washed 3 times with TBS and incubated with goat anti-human alkaline phosphatase-conjugated secondary antibody (Promega; diluted 1/7500 in AIB) for one hour. The filters were washed 4 times with TBS. Bound secondary antibody was detected by incubation of the filters in AP buffer (100 mM NaCl, 5 mM $MgCl_2$, 100 mM Tris pH 9.5) containing NBT and BCIP.

Plaques that tested positive in the initial screen were picked and eluted in 500 μl of PDB (100 mM NaCl, 8.1 mM $MgSO_4$, 50 mM Tris pH 7.5, 0.02% Gelatin). The immunoreactive phage were purified by replating the eluted phage at a total density of 100–500 plaques per 100 mm plate. The plates were re-Immunoscreening with the appropriate HGV-positive sera, essentially as described above. After color development several isolated, positive plaques were picked and put into 500 μl of PDB. After 1 hour of incubation, 2 μl of the repurified phage PDB solution was used as template in a PCR reaction containing the 11F (SEQ ID NO:25) and 11R (SEQ ID NO:13) PCR primers. These primers are homologous to sequences located 70 nucleotides (nt) 5' and 90 nt 3' of the EcoRI site of λgt11. The PCR reactions were amplified through 30 cycles of 94° C. for 1 minute, 55° C. for 1.5 minutes and 72° C. for 2 minutes.

The PCR amplification reactions were size-fractionated on agarose gels. PCR amplification of purified plaques resulted in a single band for each single-plaque amplification reaction, where the amplified fragment contained the DNA insert plus approximately 140 bp of 5' and 3' phage flanking sequences. The amplified products, from PCR reactions resulting in single bands, were purified using a "S-300 HR" spin column (Pharmacia), following manufacturers instructions. The DNA was quantitated and DNA sequenced employing an Applied Biosystems automated sequencer 373A and appropriate protocols.

The above-described screening of the Y5 library with JC sera resulted in the purification and DNA sequencing of the positive-strand clones presented in Table 17. Positive-strand clones correspond to the 5' to 3' translation of the HGV sequence presented in SEQ ID NO:14—the polyprotein reading frame.

TABLE 17

| Clone | Screening Sera | Insert Size (base pairs) | Insert Size (amino acids) | Nucleic Acid SEQ ID NO. | Encoded Protein SEQ ID NO. |
|---|---|---|---|---|---|
| Y5-10 | JC | 210 | 62 | 64 | 65 |
| Y5-12 | JC | 333 | 94 | 66 | 67 |
| Y5-26 | JC | 303 | 93 | 68 | 69 |
| Y5-5 | JC | 153 | 36 | 70 | 71 |
| Y5-3 | JC | 162 | 44 | 72 | 73 |
| Y5-27 | JC | 288 | 86 | 74 | 75 |
| Y5-25 | JC | 165 | 36 | 76 | 77 |
| Y5-20 | JC | 165 | 19[1] | 78 | 79 |
| Y5-16 | JC | 234 | 56 | 80 | 81 |

[1]the clone contained a double insert, nt 69 to 126 of the clone insert correspond to HGV sequences.

These clones delineated 2 immunogenic regions within the putative NS5 protein of HGV. The se two region, relative to the sequence presented as SEQ ID NO:14 are positions 6636 to 6821 and 7278 to 7385.

Further, screening of the Y5 library with PNF 2161 sera resulted in the purification and DNA sequencing of the following negative-strand clones presented in Table 18. Negative-strand clones correspond to the 5' to 3' translation of the sequence complementary to the HGV sequence presented in SEQ ID NO:14.

TABLE 18

| Clone | Screening Sera | Insert Size (base pairs) | Insert Size (amino acids) | Nucleic Acid SEQ ID NO. | Encoded Protein SEQ ID NO. |
|---|---|---|---|---|---|
| Y5-50 | PNF 2161 | 349 | 104 | 82 | 83 |
| Y5-52 | PNF 2161 | 119 | 20[1] | 84 | 85 |
| Y5-53 | PNF 2161 | 250 | 33[2] | 86 | 87 |
| Y5-55 | PNF 2161 | 143 | 20[3] | 88 | 89 |
| Y5-56 | PNF 2161 | 366 | 110 | 90 | 91 |
| Y5-57 | PNF 2161 | 231 | 65 | 92 | 93 |
| Y5-60 | PNF 2161 | 151 | 38 | 94 | 95 |
| Y5-63 | PNF 2161 | 125[4] | 25 | 96 | 97 |

[1] the clone contained a double insert, nt 46 to 105 of the clone insert correspond to HGV sequences.
[2] the clone contained a double insert, nt 19 to 118 of the clone insert correspond to HGV sequences.
[3] the clone contained a double insert, nt 70 to 126 of the clone insert correspond to HGV sequences.
[4] the insert contains an extra, non-HGV sequence between nucleotides 19 and 35.

All of these sequences contain portions of the original HGV clone 470-20-1 isolated using the PNF 2161 serum.

Additional epitope clones from the Y5 library were isolated as follows. The Y5 library was screened with the HGV infected sera J21689 and T56633 using the methods described in Example 13. Greater than 400 positive plaques were obtained, indicating the presence of a strongly immunogenic sequence recognized by both of these HGV infected sera. Ten of these positive plaques were purified and DNA sequenced. The results obtained from the DNA sequencing are delineated in Table 19.

TABLE 19

| CLONE | HGV VAR | SERA | START* | STOP |
|---|---|---|---|---|
| Y5-114-1A | PNF | J21689 | 6636 | 6827 |
| Y5-114-2B | PNF | J21689 | 6678 | 6935 |
| Y5-121-19A | PNF | T56633 | 6678 | 7063 |
| Y5-121-11A | PNF | T56633 | 6636 | 6917 |
| Y5-121-12A | PNF | T56633 | 6636 | 6959 |
| Y5-121-15A | PNF | T56633 | 6636 | 6917 |
| Y5-121-16A | PNF | T56633 | 6636 | 6989 |
| Y5-121-17A | PNF | T56633 | 6636 | 7082 |
| Y5-121-20A | PNF | T56633 | 6636 | 6929 |
| Y5-121-18A | PNF | T56633 | 6636 | 6896 |

*start/stop locations are given relative to SEQ ID NO: 14.

Comparison of these sequences with those obtained previously from screening this library indicated that these clones all contained the same epitope(s) that are contained in the previously isolated epitope clone Y5-10. Two of the clones, Y5-114-2B and Y5-121-19A are distinguished by the fact that their 5' ends are located 14 amino acids closer to the carboxy terminal of NS5a than the previously observed start of clones Y5-10, Y5-12, and Y5-26. None of the above clones has its 3' end interior to that observed in the clone Y5-10. Thus a minimal sequence of this epitope is contained within amino acid sequence (SEQ ID NO:272).

B. Antigenic Clones from the ENV Library.

The ENV library was screened with HGV serum J21094. This serum (J21094) was identified as HCV positive based on the first generation (c-100) HCV test. Subsequent testing of the initial J21094 serum sample, and of subsequently obtained J21094 samples, by PCR and with other HCV antigens confirmed that the source individual for the serum was HCV infected. Evidence for the presence of HGV nucleic acid was obtained via PCR analysis using the 470-20-1 and NS5 primer sets.

A number of phage clones were identified as immunoreactive with J21094 serum. The phage were plaque purified and sequenced. Seven of the clones (Q7-12-1, Q7-16-2-2, Q7-15-2, Q7-17-2-1, Q7-19-1, and Q7-19-2-1) contained the same insert. The nucleotide sequence for Q7-12-1 is presented as SEQ ID NO:143 (polypeptide sequence, SEQ ID NO:144).

One additional clone, Q7-16-1, obtained by the method just described, has the same 5' end as Q7-12-1, but is 26 amino acids shorter at the 3' end.

C. Antigenic Clones from the NS3 Library.

A one to one mixture of the F9/R9 phage and F10/R10 phage were screened using the following sera: PNF 2161, J21689 and E57963. Both J21689 and E57963 are sera that test co-positive for HCV and HGV by PCR (using multiple primers). Each immunoscreening was of 10 plates or approximately 150,000 phage. Some of the immunopositive clones identified in these screens are as follows.

Clone Y12-10-3 (polynucleotide sequence, SEQ ID NO:145; polypeptide sequence, SEQ ID NO:146) was identified by its immunoreactivity with J21689 serum. The clone expresses an 88 amino acid insert from HGV NS3.

Clone Y12-15-1 (polynucleotide sequence, SEQ ID NO:147; polypeptide sequence, SEQ ID NO:148) was identified by its immunoreactivity with E57963 serum. The clone expresses a 64 amino acid insert from the NS3 protein of HGV. This sequence is located approximately 70 amino acids 5' to clone Y12-10-3.

D. Antigenic Clones from the NS2 Library.

Multiple positive plaques were isolated by screening the NS2 library with HGV-positive serum T56633. Eleven of these plaques were subsequently purified and DNA sequenced. The locations of the inserts contained within these plaques (relative to SEQ ID NO:14) are delineated in Table 20.

TABLE 20

| CLONE | HGV VAR | SERA | START* | STOP |
|---|---|---|---|---|
| Q9-18-5 | PNF | T56633 | 3071 | 2778 |
| Q9-18-3 | PNF | T56633 | 2951 | 2745 |
| Q9-20-4 | PNF | T56633 | 3002 | 2745 |
| Q9-18-2 | PNF | T56633 | 2990 | 2745 |
| Q9-20-8 | PNF | T56633 | 3062 | 2745 |
| Q9-20-5 | PNF | T56633 | 2972 | 2787 |
| Q9-17-1 | PNF | T56633 | 2990 | 2745 |
| Q9-19-3 | PNF | T56633 | 2982 | 2745 |
| Q9-19-1 | PNF | T56633 | 2982 | 2745 |
| Q9-19-5 | PNF | T56633 | 2984 | 2745 |
| Q9-20-2 | PNF | T56633 | 3027 | 2745 |

*in this table the locations are given with respect to SEQ ID NO: 14. The actual sequence of the clones are the complement of the indicated fragment.

All of the immunoclones express portions of the same open reading frame (ORF). This reading frame is encoded by the HGV polynucleotide strand that is complementary to the sequence encoding the polyprotein. This ORF extends between nts 6322 and 6865 of the sequence complementary to SEQ ID NO:14. There is a Methionine that could serve as a site of translation initiation located at nt 6388 of the complementary strand that would allow for the production of a 159 amino acid protein.

The smallest amino acid sequence common to all of the 11 sequenced clones is located between nts 6342 to 6606 (relative to the complementary strand of SEQ ID NO:14). The amino acid sequence encoded by this region of the negative strand of HGV-PNF 2161 is presented as SEQ ID NO:273.

The subcloning and subsequent Western blot analysis of immunoreactive negative strand regions is described below.

E. Antigenic Clones from the VNS5a Library.

Approximately 1.5×10$^5$ phage from the VNS5a library was plated out and subsequently screened with the HGV-positive serum J29374 using the procedures described in Example 13. Immunoscreening of the VNS5a library with J29374 resulted in the isolation of multiple positive plaques. Six of these plaques were purified and subsequently DNA sequenced. The original strain of the DNA sequence obtained could be determined by which of the SISPA linker sequences was present at the 5' and 3' ends of the clones. The locations of the starts and stops of the obtained clones (relative to SEQ ID NO:14) and their source sera are summarized in Table 21.

TABLE 21

| Clone | HGV Variant Source | Sera | Start* | Stop |
|---|---|---|---|---|
| Q11-14-2 | AH0591 | J29374 | 6525 | 6749 |
| Q11-16-1 | E21-A | J29374 | 6432 | 6935 |
| Q11-10-2 | T56633 | J29374 | 6579 | 6710 |
| Q11-18-2 | T56633 | J29374 | 6579 | 6758 |
| Q11-22-1 | T56633 | J29374 | 6576 | 6680 |
| Q11-9-1 | T56633 | J29374 | 6531 | 6851 |

All of these clones contain the sequence of the clone Q11-22-1 in common (SEQ ID NO:274). This amino acid sequence is located immediately 5' to the minimal sequence of the Y5-10 epitope. Thus it defines an additional unique epitope in HGV NS5a (along with Y5-10 and Y5-5). Comparison of the observed amino acid sequence of these 3 HGV variants with the sequence of the PNF-2161 and JC isolates reveals few amino acid substitutions.

Example 14

Further Characterization of Immunoreactive Clones
A. Subcloning.
1. Y5 Clones.

Clones Y5-10, Y5-16, and Y5-5 were selected for subcloning into the expression vector pGEX-HisB. PCR primers were designed which removed the extraneous linker sequences at the end of these clones. These primers also introduced (i) a NcoI site at the 5' end (relative to the coding sequence) of each insert, and (ii) a BamHI site at the 3' end of each insert. Using these primers (see Table 22), the DNA fragments were amplified from 2 μl of the plaque pure stocks.

TABLE 22

| Clone | Primer Set | |
|---|---|---|
| Y5-10 | Y5-10-F1 | SEQ ID NO: 99 |
| | Y5-10-R1 | SEQ ID NO: 100 |
| Y5-16 | Y5-16F1 | SEQ ID NO: 101 |
| | 470ep-R3 | SEQ ID NO: 102 |
| Y5-5 | Y5-5-F1 | SEQ ID NO: 103 |
| | 470ep-R3 | SEQ ID NO: 102 |

Amplifications were performed as follows: 30 cycles of 94° C. for 1 minute, 50° C. for 1.5 minutes, and 72° C. for 2 minutes. After amplification the resulting DNAs were purified using "WIZARD PCR," spin columns, the samples elated in 50 μl, and digested overnight with NcoI and BamHI. A minimum of 30 units of each enzyme was used in the restriction endonuclease digestions (NcoI, Boehringer Mannhiem; BamHI, Promega).

The digested PCR fragments were ligated overnight to expression vector pGEX-HisB that had been digested with NcoI and BamHI. Each set of ligated plasmids was independently used to transform E. coli strain W3110, using a heat shock protocol (Ausubel, et al.; Maniatis, et al.). Transformants were selected on LB plates containing 100 μg/ml ampicillin and resistant colonies were used to inoculate 2 mls of LB containing 100 μg/ml ampicillin. Cultures expressing non-recombinant sj26/his protein were also prepared.

After incubation overnight at 37° C. the cultures were diluted 1/10 into 2 mls of fresh LB plus ampicillin and grown for an additional 1 hour at 37° C. IPTG was added to a final concentration of 0.2 mM and the cultures were grown for an additional 3 hours at 37° C. The bacteria were pelleted by centrifugation and the bacterial pellet was resuspended in 100 μl PBS. To the pellet, 100 μl of 2× SDS sample buffer (0.125M Tris, pH 6.8, 10% glycine, 5% β-mercaptoethanol, 2.3% SDS) was added. The resulting lysates were vortexed and heated to 100° C. for 5 minutes. Aliquots (15 μl) of each lysate were loaded onto a 12% acrylamide SDS-PAGE gel.

The expressed proteins were size-fractionated by electrophoresis. The separated proteins were transferred from the gel to nitrocellulose filters using standard techniques (Harlow, et al.). An additional gel containing the expressed proteins was stained using coomasie blue protein stain.

Transformants carrying plasmids Y5-10, Y5-5 and 5-16 expressed significant amounts of correctly sized recombinant fusion proteins. The identity of the recombinant fusions were confirmed by incubating a Western blot (prepared above) with a murine monoclonal antibody that is specifically immunoreactive with sj26 (Sierra BioSource, Gilroy, Calif.).

Additional confirmation that the picked colonies contained the appropriate insert was obtained as follows. A phage solution for each colony was prepared by inoculating 40 μl of TE solution with a toothpick containing a small amount of bacteria putatively expressing a recombinant clone had been inoculated. A 5 μl sample was taken from each solution and separately PCR amplified.

The amplifications employed the appropriate forward primer, (e.g., Y5-10 F for a colony putatively expressing Y5-10) and a reverse primer (SEQ ID NO:104) homologous to a sequence located 3' to the cloning sites of the plasmid pGEX-HisB. The PCR amplifications were for 25 cycles as follows: 94° C. for 1 minute, 50° C. for 1.5 minutes and 72° C. for 2 minutes. All of the colonies selected for further analysis produced a correctly sized DNA band with no other obvious bands under these conditions.

The immunoreactivity of the antigens expressed from the Y5-10, Y5-16, & Y5-5 inserts (expressed as sj26-his fusion proteins) was determined as follows. Aliquots (15 μl) of the crude lysates prepared above were size-fractionated by SDS-PAGE using a 12% acrylamide gel. The proteins were electro-blotted ("NOVEX MINICELL MINIBLOT II," San Diego, Calif.) onto nitrocellulose filters. The filters were then individually incubated with one of the following sera: JC, PNF 2161, and super normal serum 4 (SN4) (R05072) as a negative control. In addition, one filter was incubated with anti-sj26 monoclonal antibodies (RM001; Sierra BioSource).

As expected, the recombinant protein produced by the bacteria expressing the antigens encoded by the Y5-10, Y5-5, and Y5-16 inserts all reacted with JC sera. No reactivity was observed with either PNF 2161 or SN4 sera. All proteins appeared to be expressed at similar levels as determined by their reactivity to the anti-sj26 monoclonal antibody. The Y5-5 and Y5-10 encoded proteins were selected for further purification.

E. coli carrying Y5-5- and Y5-10-containing pGEX-HisB vectors were cultured and expression of the fusion protein induced as described above. The cells were lysed in PBS, containing 2 mM PMSF, using a French Press at 1500 psi. The crude lysate was spun to remove cellular debris. The supernatant was loaded onto the glutathione affinity column at a high flow rate and the column was washed with 10 column volumes of PBS. The Y5-5 and Y5-10 fusion proteins were eluted with 10 mM Tris pH 8.8 containing 10 mM glutathione.

Each of the fusion protein samples was diluted 1/10 with Buffer A (10 mM Tris pH 8.8, containing 8M urea) and loaded onto a nickel charged-chelating "SEPHAROSE" fast flow column. Each column was repeatedly washed with Buffer A until no further contaminants were eluted. The fusion proteins were eluted using a gradient of imidazole in buffer A. An imidazole gradient was run from 0 to 0.5M imidazole in 20 column volumes. Fractions were collected.

Each set of fractions was analyzed by standard SDS-PAGE using 12% polyacrylamide gels. Pools of the Y5-5 and Y5-10 fusion protein-containing fractions were separately made.

Figures 8A, 8B, 8C, 8D:
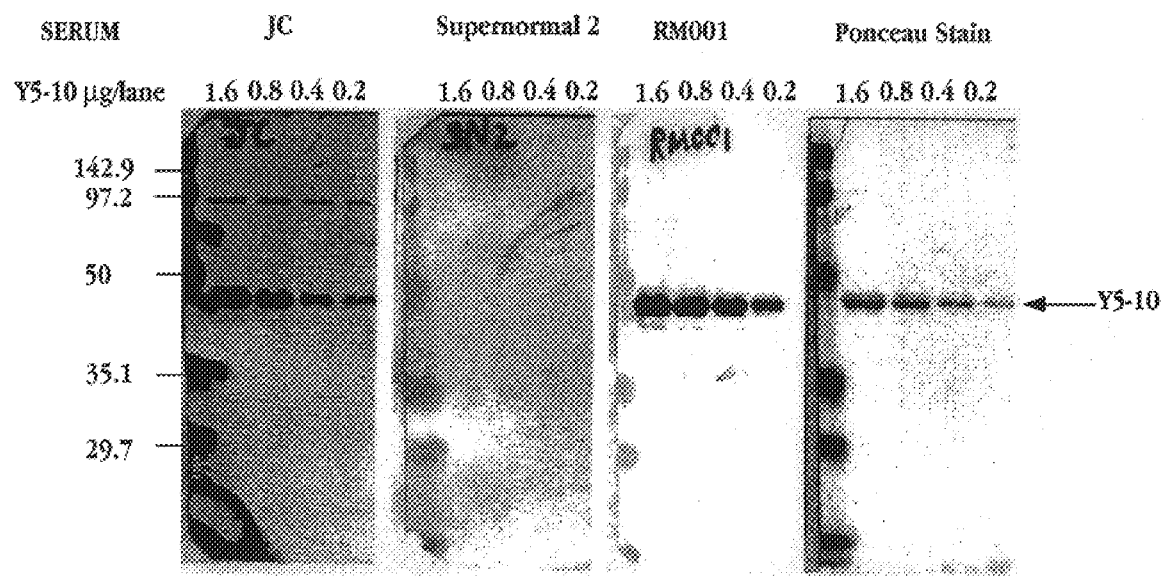
FIGS. 8A to 8D show scanned images of Western blot analyses of the purified HGV Y5-10 antigen.
Figures 9A, 9B, 9C, 9D:
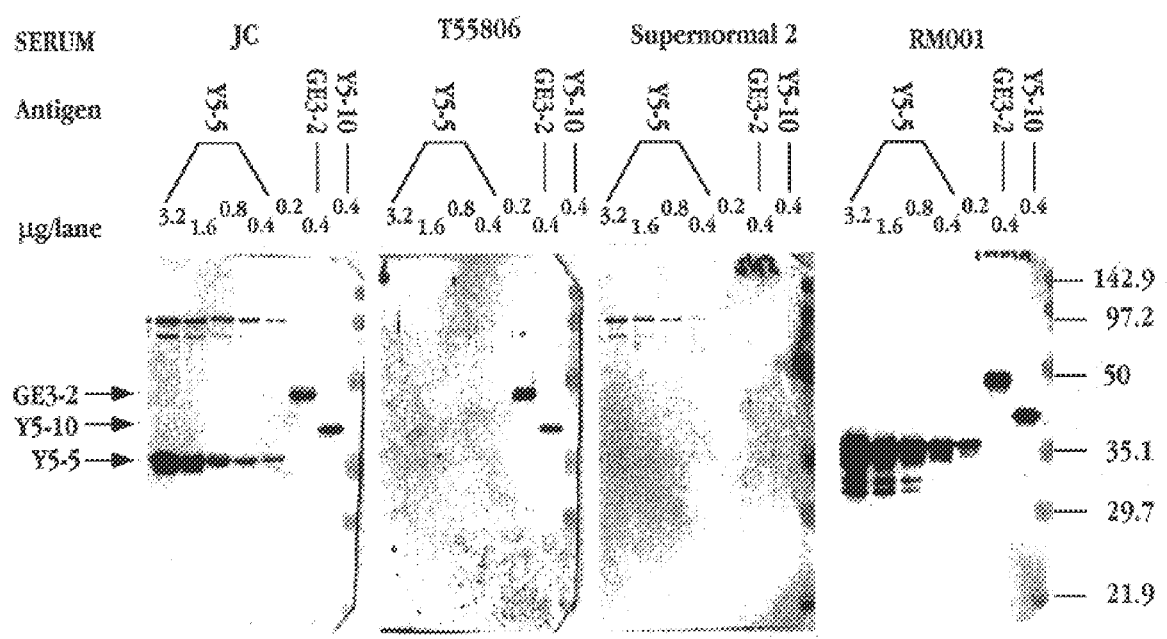
FIGS. 9A to 9D show scanned images of Western blot analyses of the following antigens: Y5-5, GE3-2 and Y5-10.

FIGS. 8A to 8D show the results of Western blot analysis of the following samples (μg/lane): lane 1, Y5-10 antigen 1.6 μg; lane 2, Y5-10 antigen 0.8 μg; lane 3, Y5-10 antigen 0.4 μg; and lane 4, Y5-10 antigen 0.2 μg. Human serum JC (FIG. 8A) and Super Normal 2 serum (FIG. 8B) were diluted 1:100. The anti-GST mouse monoclonal antibody RM001 (FIG. 8C) was diluted 1:1000. FIG. 8D shows the Y5-10 antigen resolved by SDS-PAGE, transferred onto the nitrocellulose membrane and stained with Ponceau S protein stain (Kodak, Rochester, N.Y.; Sigma). Arrow indicates the location of Y5.10 antigen. These results demonstrate that Y5-10 is specifically immunoreactive with N-(ABCDE) human serum JC.

FIGS. 9A to 9D show the results of Western blot analysis of the following samples: lane 1, Y5-5 antigen 3.2 μg; lane 2, Y5-5 antigen 1.6 μg; lane 3, Y5-5 antigen 0.8 μg; lane 4, Y5-5 antigen 0.4 μg; lane 5, Y5-5 antigen 0.2 μg; lane 6, GE3-2 antigen 0.4 μg; and lane 7, Y5-10 antigen 0.4 μg. Human serum JC (FIG. 9A), T55806 (FIG. 9B), and Super Normal 2 serum (FIG. 9C) were diluted 1:100. RM001, the anti-GST mouse monoclonal antibody, (FIG. 9D) was diluted 1:1000. Arrows indicate the locations of antigens Y5.5, GE3.2 and Y5.10. These results show specific immunoreactivity of the Y5-5 antigen with the JC serum. Further, the antigens GE3-2 and Y5-10 were reactive with T55806. However, the Y5-5 antigen was not reactive with the HGV-positive sera T55806.

The Y5-10 antigen was also size-fractionated by SDS polyacrylamide gel electrophoresis. The gel was stained using coomasie blue protein stain. The gel was scanned for purity with a laser densitometer. The purity of the Y5-10 fusion protein was approximately 95%.

2. ENV Clones.

The immunoclone Q7-12-1 was originally isolated by screening the ENV epitope library with the HCV positive sera J21094. Sequence specific primers were employed to isolate the HGV insert contained within the Q7-12-1 λgt11 clone. The Q7-12-1 insert was excised and cloned into pGEX-Nde. The sequence of the insert was confirmed by the DNA sequencing (SEQ ID NO:275).

3. NS3 Clones.

The immunoclone Y12-15-1 was originally isolated by screening the NS3 epitope library with the HGV positive sera E57963. Sequence specific primers were employed to isolate the HGV insert contained within the Y12-15-1 λgt11 clone. The Y12-15-1 insert was excised and cloned into pGEX-Nde. The sequence of the insert was confirmed by the DNA sequencing (SEQ ID NO:276).

The immunoclone Y12-10-3 was originally isolated by screening the NS3 epitope library with the HGV positive sera J21689. Sequence specific primers were employed to isolate the HGV insert contained within the Y12-10-3 λgt11 clone. The Y12-10-3 insert was excised and cloned into pGEX-Nde. Production of fusion proteins by selected clone was evaluated by Western blot analysis. The sequence of the insert was confirmed by the DNA sequencing (SEQ ID NO:277).

4. NS2 Clones.

Multiple negative strand immunoclones derived from sequences complementary to the sequences of the NS2 region of SEQ ID NO:14 were isolated. There are at least 2 significant ORFs encoded by the negative strand of HGV. The first of these ORFs, represented by the Q9 series of clones was described above. The second of these ORFs is located between nts 6723 and 7259 of the complement of SEQ ID NO:14 and also possess a 5' methionine at nt 6774. The second ORF encodes a 162 amino acid protein.

Selected portions of the sequences of both of these negative strand ORFs were cloned into the expression vector pGEX-Nde. All of these subclones were obtained by the PCR amplification of PNF 2161 SISPA material using appropriate oligonucleotide primers, thus they contain the sequence of the HGV-PNF 2161 variant. Table 23 indicates the names, size of the ORF and locations relative to the complement of SEQ ID NO:14.

TABLE 23

| NAME/ORF | ORF | FROM NT (ATG) | TO NT |
|---|---|---|---|
| 5' NEG ORF | 159 AA | 6388 | 6865 |
| 3' NEG ORF | 162 AA | 6722 | 7258 |
| NORF-F1/R1 | 3' | 7107 | 7259 |
| NORF-F4/R1 | 3' | 6900 | 7259 |
| NORF-F4/KR2 | 3' | 6901 | 7172 |
| NORF-F2/R1 | 3' | 6744 | 7259 |
| NORF-KF2/R4 | 5' | 6684 | 6865 |
| NORF-KF1/R2 | 5' | 6881 | 6742 |
| NORF-F3/R2 | 5' | 6389 | 6742 |
| NORF-F2/R3 | 3' | 6744 | 6899 |
| K3P-KF2/KR1 | 5' | 6684 | 6772 |
|  | 3' | 6744 | 6791 |

The first 2 lines of this table identify the locations of the NS2 region 5' and 3' negative strand ORFs relative to the complement of SEQ ID NO:14. The remaining lines indicate the specific nucleotide sequences expressed by all of the 9 clones. Note that several of the clones express amino acids located 5' to the hypothetical HGV initiating methionine of the ORF. Also note that the last clone listed, K3p-KF2/KR1, is a chimera expressing the indicated portions of the 5' ORF followed by the indicated portions of the 3' ORF.

All of the DNA fragments were subsequently cloned into pGEX-Nde. Insert containing clones were also identified and confirmed.

5. NS5a Clones.

Table 24 lists a number of NS5a clones and the regions of SEQ ID NO:14 to which they correspond.

TABLE 24

| Name | HGV Source | Start | Stop |
| --- | --- | --- | --- |
| EXY10-F2 | PNF | 6416 | 6827 |
| EXY10-F3 | PNF | 6537 | 6827 |
| Q11-F1-R1 | T56633 | 6537 | 6680 |
| Q11-F1-R2 | T56633 | 6537 | 6827 |
| Q11-F1-R1 | T56633 | 6576 | 6680 |
| Q11-F1-R2 | T56633 | 6576 | 6827 |
| Y5-12 | PNF | 6633 | 6917 |
| EXY12 | PNF | 6918 | 6977 |
| EXY10F14 | PNF | 6822 | 6977 |

These sequences were cloned into the vector pGEX-Nde for expression of the encoded protein antigens.

B. Western Blot Analysis of Selected HGV Subclones.

To determine the reactivity of both the negative and positive strand constructs described above whole cell lysates from bacteria expressing the various HGV subclones were prepared essentially as described in Example 13B. Aliquots of the expressed proteins were then fractionated by SDS-PAGE, the proteins transferred to nitrocellulose filters, and the filters probed with HGV-positive or control sera (e.g., anti-SJ26 MAB RM01). The blots were incubated with an appropriate reporter antibody.

With respect to the HGV proteins tested, clear immunoreactivity to the protein NORF-F3/R2 was detected with the HGV sera J21689 and T56633. The NORF-F3/R2 subclone expresses the amino acid sequences that were also encoded by the Q9 series of negative strand epitope clones. The observed strong reactivity with HGV sera T56633 confirms the immunoreactivity of this region of the negative strand of HGV. Reactivity to the NORF-F3/R2 protein was not observed with the sera from the HGV negative individual R04316 or any of 5 other HGV negative supernormal sera tested.

Additional blots indicated that the other major 5' ORF clone NORF KF2-R4, which expresses amino acids of the carboxy terminal half of the 5' negative strand ORF located does not react with the HGV-positive sera T56633. This observation in conjunction with the locations of the Q9 epitope clones described above suggest that the immunogenic epitope of this portion of the negative strand is contained within the 55amino acid delineated above (SEQ ID NO:273). The fact that this sequence is recognized by other HGV antisera, including J21689, indicates that immunoreactivity towards this sequence is relatively widespread among HGV infected individuals.

Further, clear immunoreactivity with the Y12-10-3 protein was observed with the HGV-infected sera J21689, J29374, and E57963. The specificity of this reactivity is additionally supported by the failure to observe immunoreactivity with the HGV antisera J29374 or E57963 in the absence of the induction of Y12-10-3 protein expression by IPTG. No reactivity to Y12-10-3 was observed with any of 7 supernormal sera tested.

Example 15

A Multi-Antigen HGV Diagnostic Assay

Although the epitope clones described above do not appear to be reactive with all HGV PCR-positive sera, many of these clones react with a substantial fraction of the HGV infected sera they have been tested against. Additionally these proteins have not exhibited substantial cross reactivity with HGV-negative sera. It is therefore possible to construct a diagnostic assay in which several of these proteins are combined so that the individual reactivities of the protein are summed. Such an assay is expected to have a relatively high sensitivity for the detection of HGV-positive sera and a relatively low background reactivity with HGV-negative sera.

Exemplary epitopes/antigens useful in such an assay include, but are not limited to, NORF-F3/R2 (NS2-Neg strand), Y12-10-3 (NS3), Q11-F2-R1 (NS5a), Y5-10 (NS5a), Y5-5 (NS5a), Q11-F2-R2 (combines 2 epitopes of NS5a).

For this assay, individual antigens are typically selected that contain different unique epitopes that recognized different subset of HGV-positive sera. Further, such antigens typically do not significantly react with HGV-negative sera. Following the guidance of the present invention, additional useful immunogenic clones can be isolated.

A multi-antigen diagnostic assay can take many formats. In one embodiment, the assay might entail immobilizing each of, et al., 5 HGV proteins and control proteins at separate locations on a nitrocellulose strip or other convenient solid phase format. Alternatively the non-viral portions of, for example, an HGV-fusion protein could be modified, either by insertions or deletions such that they would naturally migrate to easily distinguishable locations upon SDS PAGE and subsequent Western blot analysis. Strips are then incubated in test sera. After detection of bound antibody, a serum may then be scored based on (i) the number of antigens with which it is immunoreactive, and (ii) the strength of the immunological reactions. Reactivity to a non-HGV control protein would render a serum un-typeable. Reactivity with no HGV protein would classify a serum as HGV-negative.

ELISA-based screening assay can be formed by combining purified antigen proteins in a single reaction zone or by creating protein constructs that express 2 or more of the reactive epitopes as a single protein (e.g., a HGV mosaic polypeptide). The methods to construct mosaic polypeptides is described herein. Q11-F2-R2 construct described above, in fact, represents a "matrix protein" that encodes 2 individual epitopes in a single polypeptide chain. Western blot assays may serve as a confirmatory assay for such an ELISA screening test.

Alternatively or in addition, full length HGV proteins, such as E2, NS5a and NS3 might be placed in a single reaction zone. Sera reactive with such proteins may also be confirmed as HGV positive by Western blot assay.

Example 16

Expression of Large HGV Polypeptides

A. Expression of Larger HGV Antigens in *E. coli*

1. Cloning and Expression.

To identify conformational HGV epitopes (not covered by small overlapping HGV constructs or by phage library screening) larger HGV protein constructs were generated in the pET-21a(+) vector (Novagen, Wis.) based on the prediction of cleavage sites (Bazan, et al., 1989; Chambers, et al., 1990b; Grakoui, et al., 1993; Kyte and Doolittle, 1982). Individual HGV protein constructs were generated in a similar fashion to HGV sequences cloned into pGEX vectors.

Briefly, selected HGV sequences were RT-PCR amplified from a HGV(+) human sera source using HGV sequence specific primers. The primers were engineered to contain appropriate restriction sites for cloning manipulations in the pET vector. Coding sequences of interest were typically inserted between the EcoRI site and the HindIII sites in the vector to produce 5' in-frame fusions with T7.Tag leader sequence and 3' in-frame fusion with a hexamer histidine sequence. T7.Tag (an 11 amino acid sequence) allows the detection of the fusion proteins using an anti-T7.Tag monoclonal antibody (Novagen, Wis.). The histidine hexamer at the carboxyl end of the fusion protein allows the purification of the protein using immobilized metal ion affinity chromatography.

HGV fragments were ligated into appropriately digested pET-21a(+) vectors. Ligated products were transformed into competent E.coli (HMS174; Novagen, Wis.). Plasmid DNA from transformed HMS174 was analyzed for the presence of HGV sequences by PCR, using primers T7F(SEQ ID NO:157) and T7R(SEQ ID NO:158), which are homologous to pET-21a(+) vector sequences flanking the inserted molecule. The size of the PCR product was the insert size plus approximately 260 bp derived from the vector.

For each construct the PCR results confirmed the presence of the insert sequences. Transformants with appropriate inserts were selected, plasmid DNAs with HGV inserts prepared and introduced into HMS174(DE3) competent E.coli (Novagen, Wis.) for the expression of HGV proteins.

Expression of HGV proteins was induced with 1 mM IPTG. Expression of the T7.Tag fusion proteins was monitored by the appearance of the predicted size proteins on the Coomassie blue stained gel. Expression of the fusion proteins was confirmed by Western blot analysis using anti-T7.Tag antibody (Novagen, Wis.). HGV proteins expressed in pET-21a(+) vector are shown in the Table 25. The start and end points of the expressed sequences are given relative to SEQ ID NO:14. The amino acid sequence of GE-Cap is shown in SEQ ID NO:185.

TABLE 25

| Name | Domain | Serum source | Start | End | HGV aa | Size (KDa) |
|---|---|---|---|---|---|---|
| GE-Cap | capsid | T55806 | 271* | 480* | 70 | 11 |
| GE-E1a | E1 | PNF | 594 | 1148 | 185 | 24 |
| GE-E2 | E2/NS1 | PNF | 1149 | 2183 | 345 | 41 |
| GE-Ns2b | NS2b | PNF | 2904 | 3254 | 117 | 16 |
| GE-NS3 | NS3 | PNF | 3255 | 5081 | 609 | 70 |
| GE-NS4a | NS4a | PNF | 5082 | 6083 | 334 | 40 |
| GE-NS4b | NS4b | PNF | 6084 | 6536 | 151 | 20 |
| GE-NS4 | NS4 | PNF | 5082 | 6536 | 485 | 57 |
| GE-NS5a | NS5a | PNF | 6537 | 7529 | 331 | 39 |
| GE-NS5b | NS5b | PNF | 7530 | 9044 | 505 | 59 |

*These sequences are given relative to SEQ ID NO: 178

Figure 12:
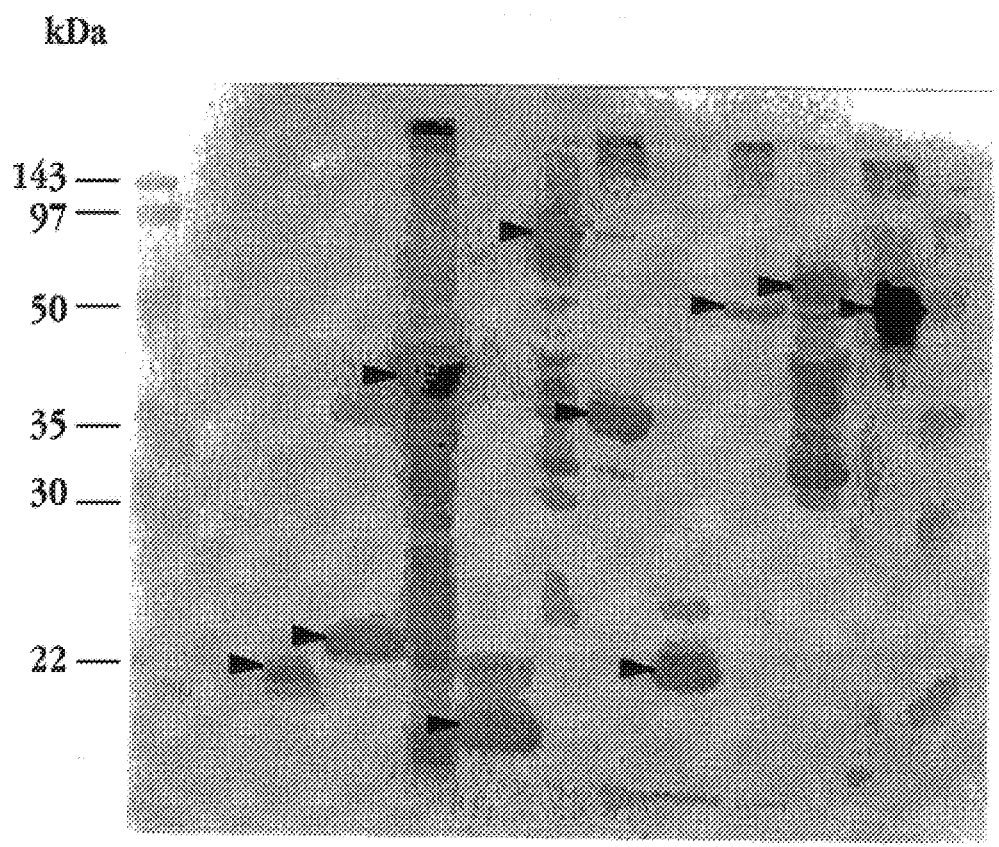
FIG. 12 shows a scanned image of a Western blot analyses of HGV pET clones with anti-T7.Tag monoclonal antibody.

FIG. 12 shows the expression of each HGV proteins demonstrated by Western blot analysis with T7.Tag monoclonal antibody. The lanes in FIG. 12 are as follows: Lane 1, pre-stained molecular weight marker (Bio-Rad); Lane 2, uninduced GE-Cap lysate; Lanes 3–11, IPTG induced lysates of GE-Cap, E1a, E2, NS2b, NS3, NS4a, NS4b, NS4, and NS5b lysate, respectively. Lane 12 contained 1 μg of purified NS5a. Locations of each antigen are marked with arrow heads. As shown in FIG. 12 all the HGV proteins were expressed in E.coli.

2. Western Blot Analyses of HGV proteins expressed in VET vector

Western blot analyses of the HGV protein expressed in pET vector were performed as described in Example 11C using E. coli whole cell lysates and pre-absorbed sera. The results of these analyses demonstrated that several of pET HGV proteins are specifically immunoreactive with HGV-positive human sera but not with HGV-negative human sera. GE-NS2b-1 protein was immunoreactive with J21689 serum. The GE-NS5a-3 protein was immunoreactivity with several HGV (+) sera on Western blot analysis, including JC, T55806, T56633, J21689, E57963 and R0001. Among these sera T55806, J21689 and E57963 are HCV co-positive (by the PCR analysis). Neither GE-NS2b-1 nor GE-NS5a-3 were immunoreactive with several HGV negative sera tested.

FIGS. 10A to 10F show the exemplary results of a series of Western blot experiments examining the reactivity of antigens GE-NS2b and GE-NS5a3. The lanes in each blot of FIGS. 10A to 10F are as follows: Lane 1, uninduced GE-NS2b lysate; Lane 2, IPTG induced GE-NS2b lysate; Lane 3, uninduced GE-NS5a lysate; and Lane 4, IPTG induced GE-NS5a lysate. Each blot was incubated with a human serum or mouse monoclonal antibody: FIG. 10A, J29374; FIG. 10B, J21689; FIG. 10C, T56633; FIG. 10D, T43608 (super normal serum); FIG. 10E, Anti-T7.Tag; and FIG. 10F, coomassie stained gel. The serum or monoclonal antibody that was used is indicated above each blot. Human sera were diluted 1:100 and anti-T7.Tag mouse monoclonal antibody was diluted 1:1000.

In addition to the sera listed above, additional HGV-PCR positive sera have been screened using GE-NS5a. The results of all these analyses have demonstrated the reactivity of the GE-NS5a antigen with multiple HGV-infected sera.

GE-NS5b was immunoreactive with HGV(+) sera JC and T55806 but was not immunoreactive with HGV(-) negative sera tested. FIGS. 13A to 13E show the results of a series of Western blot experiments examining the reactivity of antigen GE-NS5b. The lanes in each blot the figures are as follows: Lane 1, pre-stained molecular weight marker (Bio-Rad); Lane 2, uninduced GE-NS5b lysate; Lane 3, IPTG induced GE-NS5b lysate.

Figures 13A, 13B, 13C, 13D, 13E:
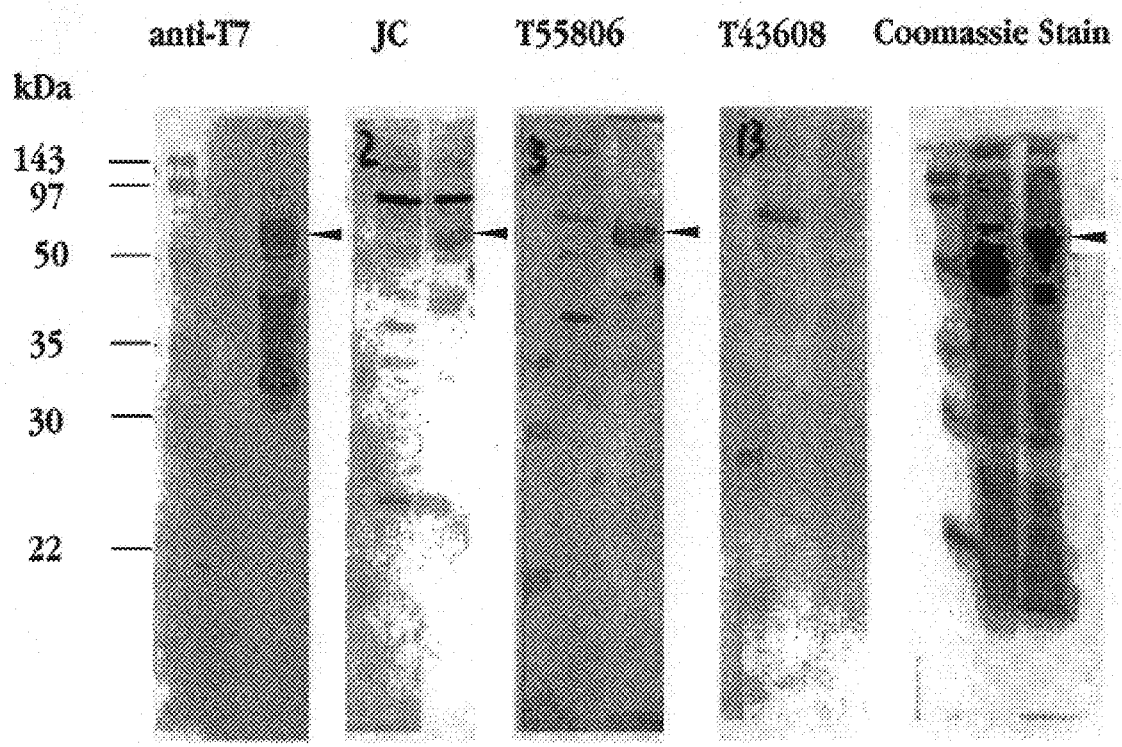
FIGS. 13A to 13D show scanned images of Western blot analyses of HGV pET clone GE-NS5b.
FIG. 13E shows a corresponding coomassie stained gel.
Figure 16:
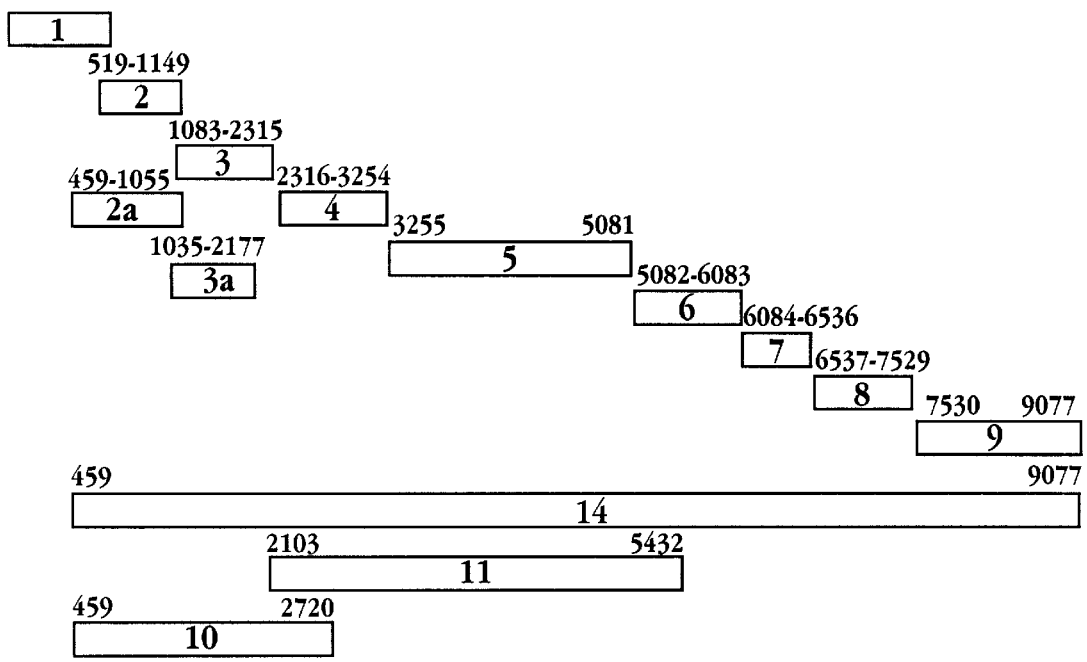
FIG. 16 shows a schematic representation of the coding regions of HGV.

Each blot was incubated with a human serum or mouse monoclonal antibody: FIG. 13A, anti-T7.Tag monoclonal antibody; FIG. 13B, JC; FIG. 13C, T55806; and FIG. 13D, T43608 (super normal serum). FIG. 13E is a Coomassie Stain.

FIGS. 14A to 14D show the results of a series of Western blot experiments examining the reactivity of antigen GE-E2. The lanes in each of FIGS. 14A to 14D are as follows: Lane 1, pre-stained molecular weight marker (Bio-Rad); Lane 2, uninduced GE-E2 lysate; Lane 3, IPTG induced GE-E2 lysate. Each blot was incubated with a human serum or mouse monoclonal antibody:

FIG. 14A, anti-T7.Tag monoclonal antibody; FIG. 14B, 3831781; and FIG. 14C, T43608 (super normal serum). FIG. 14D is Coomassie Stain. The serum or monoclonal antibody that was used is indicated above each blot. GE-E2 protein was immunoreactive with HGV-positive serum 3831781 but was not immunoreactive with supernormal serum T43608 (FIGS. 14B and 14C, respectively).

Antigens GE-Cap and GE-NS4a were also specifically immunoreactive with HGV(+) serum J21689.

B. Expression larger HGV Antigens in Insect Cells.

Expression of proteins using recombinant baculoviruses offers the following advantages (i) a high level of recombinant protein expression, and (ii) the benefits of a higher eucaryotic system, including efficient protein translocation and modification. This system is particularly useful for expression of translocated proteins, e.g., HGV E1, E2 and NS2a.

1. Cloning and Expression.

Spodoptera frugiperda insect cell culture Sf21 and a derivative of Autografa californica nuclear polyhedrosis virus "BACULOGOLD" (Pharmingen, San Diego, Calif.) were used for expression of HGV polypeptides. Established protocols were used for insect cell cultivation and for generation of recombinant baculoviruses by co-transfection of baculovirus plasmid transfer vectors with linearized baculovirus DNA (King, 1992). Conventional techniques were used for construction of baculovirus plasmid transfer vectors (Maniatis, et al.; Sambrook, et al.).

The baculovirus transfer vector pAcYM1 (King, et al., 1992) was modified by ligating a double-stranded oligonucleotide coding for a Histidine hexamer into the vector's BamHI cloning site (vector designated pAcYMIH). A stop codon (TAA) was placed after the Histidine hexamer sequence. This provides a histidine hexamer on the carboxy-termini of expressed proteins. The BamHI cloning site of the pAcYMI parent vector remained intact in the pAcYMIH and could be used for cloning various genes in-frame with the Histidine hexamer. The histidine hexamer provides a method of rapid and efficient purification of the expressed protein (Janknecht, et al., 1991).

A second baculovirus transfer vector, pVT-Bac, was also modified in a similar manner to provide a histidine hexamer on the carboxy-termini of expressed proteins. pVT-Bac like the pAcYMI vector contains a strong late polyhedrin promoter. In addition, pVT-Bac also provides a strong insect translocation signal sequence to ensure efficient translocation of the expressed proteins (Tessier, et al., 1991). The pVT-Bac vector was modified by ligating a double-stranded oligonucleotide coding for a histidine hexamer into the vector's BamHI cloning site (yielding the pVT-BacH vector). The BamHI cloning site of the pVT-Bac parent vector remains intact in the obtained pVT-BacH vector and can be used for cloning genes in-frame with the insect leader sequence and the histidine hexamer sequence.

DNA fragments coding for various HGV genes were obtained by reverse transcription PCR. Regions of the HGV genome were selected according to predicted cleavage sites (Bazan, et al., 1989; Chambers, et al., 1990b; Grakoui, et al., 1993; Kyte and Doolittle, 1982). The following primer pairs were used in RT-PCR amplification reactions using PNF 2161 source nucleic acid: E1, SEQ ID NO:242, SEQ ID NO:243; E2B (HGV signal sequence), SEQ ID NO:246, SEQ ID NO:247; E2C (insect signal sequence), SEQ ID NO:244, SEQ ID NO:245; NS2a, SEQ ID NO:248, SEQ ID NO:249; NS2b, SEQ ID NO:250, SEQ ID NO:251; NS3, SEQ ID NO:252, SEQ ID NO:253; NS4a, SEQ ID NO:254, SEQ ID NO:255; NS4b, SEQ ID NO:256, SEQ ID NO:257; NS5a, SEQ ID NO:258, SEQ ID NO:259; NS5b, SEQ ID NO:260, SEQ ID NO:261; and E1-E2-NS2a, SEQ ID NO:262, SEQ ID NO:263.

Amplified DNA fragments were digested with BamHI or BglII endonucleases and cloned into BamHI cut pAcYMI, pAcYMIH, pVT-Bac or pVT-BacH vectors. Sequences coding for the E1 and E2 carboxy-terminal anchors as well as a hydrophobic sequence at the carboxy-terminus of NS5b were deleted in order to facilitate subsequent protein purification.

The recombinant baculovirus plasmid transfer vectors containing HGV sequences were co-transfected with linearized baculovirus DNA and the recombinant viruses were selected as white foci in presence of X-gal (King, et al., 1992). Recombinant viruses were twice plaque-purified and propagated. Monolayers of Sf21 cells were infected with the recombinant baculoviruses at the multiplicity 5 p.f.u. per cell and incubated at 27° C. for 60 h. The cells were washed with PBS and lysed in TNN buffer (50 mM Tris-HCl pH 8.0, 150 mM NaCl, 0.5% "NONIDET-P40"). Inclusion bodies were isolated by spinning the cell samples at 14k for 5 minutes. The inclusion bodies were resuspended in protein dissociation buffer (10% 2-mercaptoethanol, 10% SDS, 25% glycerol, 10 mM Tris-HCl pH 6.8, 0.02% Bromphenol blue) and incubated at 100° C. for 10 minutes.

The protein expression patterns analyzed by SDS-PAGE. Proteins were separated by 0.1% SDS-18% PAGE and stained with Coomassie brilliant blue. The majority of the HGV proteins were expressed to a high level and could be easily detected on the Coomassie blue stained gels. NS5a and NS2a polypeptides were detected by $^{35}S$ methionine protein labeling (King, et al., 1992).

HGV E2 protein glycosylation was examined as follows. Sf21 cells were infected with recombinant baculoviruses and processed as described above. Proteins were separated by 0.1% SDS-12% PAGE, electroblotted onto an "IMMOBILON-P" (Millipore, Bedford Mass.) membrane and reacted with Galanthus nivalis agglutinin (Boehringer Mannheim DIG Glycan differentiation kit) which is specific for mannose residues. The HGV E2 protein that was expressed with its own signal sequence was extensively glycosylated, indicating that the predicted E2 signal sequence can function as such.

2. Immunofluorescence Assay Analysis.

SF21 insect cells were infected with the baculovirus-HGV constructs described above. Cells were harvested, spun at 1.5K rpm for 3 minutes, washed in 1× PBS, and spun again.

For Immunofluorescence Assay (IFA) (King, et al., 1992) the cells were resuspended in PBS and layered into the wells of glass slides such that the cells formed a sub-confluent layer in the wells of the slides. The slides were air-dried. The cells fixed with pre-chilled −70° C. acetone for 10 minutes and rehydrated with PBS for 5 minutes. The excess PBS was removed by blotting. The fixed cells were treated for one hour with the following "Blocking" buffer: 40 mM Tris HCl pH 7.5, 3% goat serum, 1% BSA, 1% nonfat milk and 0.1% gelatin.

Primary antibody was then added to the fixed cells. Primary antibodies included a series of human HGV-positive sera and a positive control monoclonal antibody. Before use, the sera were pre-absorbed for non-specific proteins using insect cell lysate. Preabsorption was carried out overnight at 4° C. Uninfected SF21 cells were used as a negative control. After addition of a selected primary antibody (sera), the slides were incubated for 2 hours then washed several times with PBS and excess buffer removed. A secondary antibody conjugated with fluorescein (0.5 $\mu$g/ml conc.) was then added to the samples on the slides. The incubation time and temperature for the secondary antibody was the same as for the primary antibody. After incubation, slides were washed in PBS and mounted with a cover slip. The fluorescence of the cells was then determined using a fluorescence microscope.

The results of this analysis were as follows. Cells expressing HGV antigen E1-E2-NS2a were immunoreactive with 4/10 HGV-positive sera and weakly immunoreactive with an additional 2/10 sera. Cells expressing E1 were weakly immunoreactive with 1/10 sera. Cells expressing E2 were immunoreactive with 3/10 sera and weakly immunoreactive with 1/10 sera. None of the cells carrying HGV antigens were immunoreactive with supernormal control sera.

3. Western Blot Analyses of HGV proteins expressed in baculo vector

Western blot analyses of the HGV proteins expressed in recombinant baculo virus infected Sf21 insect cells were also performed. Inclusion bodies were prepared as described above and subjected to Western blot analysis. Western blot analysis was performed using pre-absorbed sera. The results of the analyses demonstrated that E2 proteins (one variant having the endogenous HGV signal sequence, E2B, and a second variant carrying an insect signal sequence, E2C) were specifically immunoreactive with HGV(+) serum 3831781.

FIGS. 15A to 15D show the results of a series of Western blot experiments examining the reactivity of baculo antigens E2B and E2C. The lanes in each blot of FIGS. 15A to 15D were as follows: Lane 1, prestained molecular weight marker (Bio-Rad); Lane 2, E2B lysate; Lane 3, E2C lysate; Lane 4, β-galactosidase lysate. Each blot was incubated with a human or rabbit serum: FIG. 15A, rabbit anti-E2 antibody; FIG. 15B, 3831781 (an HGV-PCR-positive serum); FIG. 15C, 3838857 (an HGV-negative serum). FIG. 15D a Coomassie Stain. The serum or rabbit antibody that was used is indicated above each blot. Human sera were diluted 1:100 and rabbit serum was diluted 1:1000.

Further, HGV antigen NS2b protein expressed in insect cells was immunoreactive with J21689. These results are consistent with the results obtained with pET expressed HGV proteins.

C. Expression of Larger Antigens in Vaccinia.

1. Cloning and Expression.

Various regions of HGV genome were integrated into vaccinia virus genome for expression. An exemplary HGV polypeptide expression strategy is given in FIG. 16. HGV (PNF 2161 variant) proteins expressed in vaccinia virus are schematically illustrated in FIG. 16. Full length polyprotein is drawn (not to scale) by an open box indicating regions of predicted proteins: C=highly basic protein, 4A=NS4A, 4B=NS4B, 5a=NS5A, 5b=NS5B. The individual boxes with nucleotide locations (below the polyprotein) represents exemplary regions of HGV for expression in vaccinia virus. The number in the box stands for recombinant virus nomenclature. Virus #1 was derived from the highly basic protein region of HGV Stain T55806 (SEQ ID NO:185).

Two sets of recombinant viruses were generated. The first set contained HGV sequences that correspond to individual protein domains based on sequence analysis of HGV cDNA (FIG. 16, fragments #1 to #9). The second set contained HGV sequences that spanned multiple protein domains, up to full length of HGV genome (FIG. 16, #10, #11, #14).

The various regions of the HGV genome were cloned into the multicloning site of the vaccinia expression vector. A recombinant vaccinia virus expression system was used that included bacterial phage T7 system and *E. coli* lac repressor for high level inducible expression (Fuerst, 1986; Elroy-Stein, 1989; Alexander, 1992; Moss, et al.). Therefore, recombinant protein is expressed only in the presence of an inducer, such as isopropyl beta-D-thiogalactoside (IPTG). Both direct cloning and PCR were used for plasmid construction. In the latter, restriction endonuclease sites suitable for cloning into the vaccinia vector were incorporated into primers used to amplify individual DNA fragment.

A polyhistidine tag was also incorporated into every clone covering individual domains of HGV for use in purifying the expressed proteins. HGV-PCR amplification products were digested with the appropriate restriction enzymes and ligated into the vaccinia vector. Target HGV cDNA fragments were integrated into vaccinia virus genome through homologous recombination and drug (mycophenolic acid) selection (Falkner, 1988, Earl, 1991). Recombinant virus were plaque purified 4 times before a viral stock was generated.

The length of each clone in nucleotides is indicated in FIG. 16. The group of smaller clones (#1 to #9) are useful for HGV epitope mapping. The larger clones (e.g., #10, #11 and #14) are also useful for mapping the HGV polyprotein cleavage sites experimentally. In addition to the clones shown in FIG. 16, additional recombinant viruses covering multiple domains from NS3 to NS5b can be constructed.

Expression plasmids were transfected into mammalian cells which had been infected with a parent vaccinia virus. CV-1 and BS-C-1 cells were maintained in Minimum Essential Medium (MEM) supplemented with 10% fetal bovine serum. The cells were used for transfection (CV-1) and recombinant virus selection and propagation (BS-C-1).

2. Evaluation of recombinant protein expression.

BS-C-1 cells were infected with recombinant virus in the presence or absence of IPTG for 7 hours after which cells were labeled with $^{35}$S-methionine for another one hour (Zhang, 1991). Briefly, $1\times10^6$ BS-C-1 cells were infected with recombinant virus at a multiplicity of infection (MOI) of 10 plaque forming unit (PFU) per cell for 1 h and then supplemented with medium in the presence or absence of 5 mM IPTG for another 6 h. Cells were pulse-labeled with 600 ul Methionine-free medium supplemented with 2.5% dialyzed fetal bovine serum plus 60 uCi 35S-methionine ("TRAN $^{35}$S-LABEL", ICN, Costa Mesa, Calif.) in the presence or absence of 5 mM IPTG for another 60 min. Labeled cells were then lysed on ice for 10 min in the presence of 100 mM Tris pH8.0, 150 mM NaCl, and 1% "TRITON X-100." Nuclei were spun down and supernatant was collected for analysis.

Cell lysate was analyzed by SDS-polyacrylamide gel electrophoresis (Fling, 1986; Schagger, 1987). Gels were fixed with 50% methanol and 10% acetic acid before they were treated with a fluorograph solution "AMPLIFY" (Amersham, Arlington Heights, Ill.). Gels were dried and exposed to X-ray film.

Using this method, expression of HGV polypeptides by viruses containing inserts #4 to #11, and #14 (FIG. 16) has been confirmed. Expression of polypeptides corresponding to other regions is confirmed in a similar manner. For example, in a NS5a construct, upon induction by IPTG, a unique polypeptide was produced that migrated just below a 46 KDa protein standard. This protein was not seen in the infection in the absence of IPTG induction, establishing the identity of the protein as NS5a recombinant protein.

Further, limited immunoprecipitations using HGV region-specific antisera (for example, rabbit anti-sera raised against an isolated HGV polypeptide from the region of interest) against $^{35}$S-Met labeled cell lysate from individual virus infections was carried out to evaluate the protein expression from recombinant viruses. For example, expression of NS2, NS3, NS4B, NS5A and NS5B has been confirmed. An alternative method, to evaluate recombinant protein expression is to perform western blot analysis with HGV-region-specific antisera.

When the full length HGV polyprotein was expressed in #14 virus (FIG. 16), processed products of NS2, NS3and NS5A were detected using immunoprecipitation with HGV region-specific antisera, demonstrating the usefulness of the full length HGV clone to evaluate polyprotein processing.

Using an expression strategy similar to that shown in FIG. 16, candidate HGV proteins/antigens can be expressed in yeast or CHO cells. Yeast offers high level of expression, economical operation, and ease of scaling up for commercial production. CHO cell lines allow secretion of the recombinant proteins into growth media for large scale protein production and purification useful, for example, for vaccine development.

Example 17

HGV Encoded Highly Basic Proteins

A. Determination of the Methionine Used for Initiation in the Translation of HGV from PNF and T55806.

The methionine located at nucleotide (nt) 459 (relative to SEQ ID NO:14) in the HGV-PNF 2161 variant is in-frame with the polyprotein. The "capsid" region appears to be 32 amino acid long. In other HGV isolates, such as T55806, this region is longer (e.g., about 83 amino acids). The methionine located at nt 349 (relative to SEQ ID NO:14) in HGV-PNF 2161 variant is not in-frame with the polyprotein sequence, but a methionine at the same position in HGV-T55806 variant is in frame with the polyprotein. To see if there is a read-through or a ribosomal frame shift at this position in HGV-PNF 2161, the following experiments were carried out.

Constructs were made containing (i) HGV genomic sequences having all the MET codons upstream of the HGV E1 region (e.g., in HGV-PNF 2161 there are six such METs and five such in T55806), (ii) two different 3' ends for each construct to allow determination of whether a ribosome shift of read-through occurs. For a given genomic DNA, if both translated products are the same size, that suggests they are terminated prematurely at the stop codon. On the other hand, if read-through or frameshift occurs two products that differ by 55 amino acids are expected.

A total of 21 constructs containing sequences from variants HGV-PNF 2161 and HGV-T55806 were subcloned in a pGEX vector and corresponding proteins expressed in *E. coli*. Sizes of the resulting translation products were determined by both Coomassie stained gels and Westerns that were blotted with monoclonal anti-GST antibody. Induced and un-induced samples were prepared for each construct.

The results demonstrated that the size of the protein products corresponded to that expected by translation initiating at the first MET in-frame with the polyprotein. There was no evidence of frameshifting or read-through.

B. Alternative Encoded Highly Basic Proteins.

The method of Fickett (1982) was used to scan the genomic sequences HGV-PNF 2161 and HGV-JC for sequences that potentially encode proteins (i) alternative to the previously described polyprotein, (ii) showing conservation between HGV-PNF 2161 and HGV-JC, and (iii) having predicted isoelectric points in excess of pH 10. Two such potential proteins were identified.

The first protein is encoded by residues 628 through 882 (relative to SEQ ID NO:14) in HGV-PNF 2161 and by residues 556 through 810 (relative to SEQ ID NO:182) in HGV-JC. This protein is 85 amino acids long, is greater than 75% homologous between HFV94-1 and JC9B, and has a predicted pI of 11.6–12.3.

The second protein is encoded by residues 6844 through 7125 in HGV-PNF 2161 (relative to SEQ ID NO:14) and by 6772 to 7053 in HGV-JC (relative to SEQ ID NO:182). This protein is 94 amino acids long, is greater than 88% homologous between HGV-PNF 2161 and HGV-JC, and has a predicted pI of 12.4–12.7.

These exemplary two proteins represent potentially expressed highly basic proteins of HGV.

Example 18

Cloning Further HGV Isolates and Design of Diagnostic Primers

A. Construction of a cDNA Clone of HGV-PNF 2161.

A cDNA clone of the nearly full-length HGV genome from PNF 2161 was constructed by cloning three overlapping PCR products into the plasmid vector pGEM3Z (Promega, Madison, Wis.). The PCR products used in this construction were obtained by reverse transcription with "SUPERSCRIPT II" (Gibco/BRL, Gaithersburg, Md.) followed by PCR using reaction conditions that allowed for the amplification of long target sequences ("rTth-XL" polymerase and "XL PCR BUFFERS", Applied Biosystems, Foster City, Calif.). The rTth enzyme used for these "long-range" PCR reactions has proof-reading activity (i.e. 3' to 5' exonuclease activity) that corrects mis-incorporated nucleotides, thus providing for high fidelity PCR.

The three products used to construct the HGV genome included (i) an internal 6.7 kb product (nt 2101 to 8834 of SEQ ID NO:14) amplified using the primers GV75-36FE (SEQ ID NO:228) and GV75-7064RLE (SEQ ID NO:229), (ii) a 2.8 kb 5'-end product (nt 38 to 2899 of SEQ ID NO:14) amplified using 28F (SEQ ID NO:230) and FV94-2864R (SEQ ID NO:231), and (iii) a 2.9 kb 3'-end product (nt 6449 to 9366 of SEQ ID NO:14) amplified using FV94-6439F (SEQ ID NO:232) and FV94-9331R (SEQ ID NO:233).

Initially, the 6.7 kb internal fragment was cloned into the "TA-vector" PCRII to create the clone HGV7. Subsequently, a 6.1 kb KpnI/EcoRI fragment was removed from HGV7 and combined with the KpnI/XbaI digested 2.8 kb 5'-end product (the primer 28F contains an artificial XbaI site) and cloned into XbaI/EcoRI digested pGEM3Z. This 8.8 kb clone, which lacks about 0.6 kb of the 3' portion of the HGV genome, was designated HGV-KEX-2. To construct the nearly fulllength HGV genome, the 3'-end HGV product was digested with NheI and EcoRI (the primer FV94-9331R contains an artificial EcoRI site) and cloned into NheI/EcoRI digested HGV-KEX-2 plasmid creating a cloned HGV-PNF2161 sequence of 9329 nt (nt 38 to 9366 of SEQ ID NO:14) that is designated 3Z-HGV94-6. The complete sequence of 3Z-HGV94-6 is presented as SEQ ID NO:234.

The clone 3Z-HGV94-6 may be used to generate in vitro-transcribed full-length HGV RNA or portions thereof (e.g., using SP6 polymerase). The RNA molecules can be used to transfect human cell lines. This approach could be used to map the various regions of the viral genome, study its replication, and understand the mechanisms of HGV pathogenicity in human cells (Rice, et al., 1989; Sumiyoshi, et al., 1992; Yoo, et al., 1995).

B. Cloning the JC Variant.

One milliliter of JC serum was spun at 40,000 rpms (Beckman, Spinco Rotor 70.1Ti) for 2 hours. The resulting pellet was extracted using "TRIREAGENT" (MRC, Cincinnati, Ohio.), resulting in the formation of 3 phases. The upper phase contained RNA only. This phase was taken and RNA recovered by ethanol precipitation.

HGV cDNA molecules were generated from the JC sample by two methods. The first method was amplification (RT-PCR) of the JC nucleic acid sample using specific and nested primers. The primer sequences were based on the HGV sequence obtained from PNF 2161 serum. The criteria used to select the primers were (i) regions having a high G/C content, and (ii) no repetitious sequences.

The second method used to generate HGV cDNA molecules was amplification using HGV (PNF 2161) specific primers followed by identification of HGV specific sequences with $^{32}$P-labelled oligonucleotide probes. Such DNA hybridizations were carried out essentially as described by Sambrook, et al. (1989). The PCR derived clones were either (i) cloned into the "TA" vector (Invitrogen, San Diego, Calif.) and sequenced with vector primers (TAR and TAF), or (ii) sequenced directly after PCR amplification. Both the probe and primer sequences were based on the HGV variant obtained from the PNF 2161 serum.

These two approaches yielded multiply-overlapping HGV fragments from the JC serum. Each of these fragments were cloned and sequenced. The sequences were aligned to obtain the HGV (JC-variant) consensus sequence presented as SEQ ID NO:182 (polypeptide sequence, SEQ ID NO:183). The sequence of each region of the HGV (JC-variant) virus was based on a consensus from at least three different, overlapping, independent clones.

C. Other HGV Variants.

In addition to the HGV PNF 2161-variant and JC-variant sequences, three partial HGV isolates have been obtained from the sera BG34, T55806 and EB20 by methods similar to those described above. The partial sequences of these isolates are presented as SEQ ID NO:176 (BG34 nucleic acid), SEQ ID NO:177 (BG34 polypeptide), SEQ ID NO:178 (T55806 nucleic acid), SEQ ID NO:179 (T55806 polypeptide), SEQ ID NO:180 (EB20-2 nucleic acid) and SEQ ID NO:181 (EB20-2 polypeptide).

D. Alternative Primers for Diagnostic PCR.

PCR primers and corresponding assay development may be derived from regions of the HGV genome(s) typically based on the analysis of conserved regions. Based on comparisons of the HGV-JC variant and the HGV-PNF 2161 variant, the 5' untranslated region of HGV was selected as one such region for development of a further PCR-based diagnostic test for the detection of HGV isolates. Two exemplary primers are FV-94-22F (SEQ ID NO:124) and FV94-724R (SEQ ID NO:125). These primers amplify an approximately 728 bp fragment of the HGV genome.

Sequence analysis was performed on amplification products from reactions employing these two primers for 36 isolates of HGV (including PNF 2161 and JC, see Table 26). An approximately 400 bp region (nt 69 to 469 of SEQ ID NO:14) of the approximately 728 bp amplification product was used for multiple sequence alignments (Table 26) and further determination of conserved regions (see below).

TABLE 26

| SEQ ID NO: | Serum Code | Country | % ID PNF 2161 |
|---|---|---|---|
| 186 | S59 | England | 96.8 |
| 187 | S368 | England | 98.8 |
| 188 | S309 | England | 95.5 |
| 189 | FZ | Australia | 96 |
| 190 | G21 | Greece | 97.8 |
| 191 | G23 | Greece | 94.3 |
| 192 | G59 | Greece | 93.6 |
| 193 | E36 | Egypt | 94 |
| 194 | R38730 | USA | 94.8 |
| 195 | G281 | Greece | 97.8 |
| 196 | G157 | Greece | 94.3 |
| 197 | G154 | Greece | 96 |
| 198 | G213 | Greece | 94.8 |
| 199 | G204 | Greece | 98.3 |
| 200 | G191 | Greece | 94.8 |
| 201 | G299 | Greece | 94.8 |
| 202 | T56957 | USA | 95.3 |
| 203 | C01698 | USA | 98.8 |
| 204 | T27034 | USA | 93.5 |
| 205 | E57963 | USA | 98.5 |
| 206 | R37166 | USA | 97.5 |
| 207 | B5 | Germany | 95.5 |
| 208 | B33 | Germany | 95.5 |
| 209 | FH010 | Australia | 95 |
| 210 | PNF2161 | USA | 100 |
| 211 | JC | USA | 96.3 |
| 212 | 7155 | Peru | 89.8 |
| 213 | 7244 | Peru | 89 |
| 214 | K27 | Korea | 89.5 |
| 215 | K30 | Korea | 89.5 |
| 216 | T55875 | USA | 97.3 |

TABLE 26-continued

| SEQ ID NO: | Serum Code | Country | % ID PNF 2161 |
|---|---|---|---|
| 217 | T56633 | USA | 93.5 |
| 218 | EB20 | Egypt | 94.1 |
| 219 | T55806 | USA | 95.6 |
| 220 | BG34 | Greece | 94.8 |
| 221 | BE12 | Egypt | 95 |

The development of an amplification-based (e.g., PCR) or probe-based method/assay for the detection of HGV isolates in samples involves the selection of appropriate primer/probe sequences. Two criteria for such an assay are low copy sensitivity and specificity for HGV sequences. Alignments of sequences (such as just described) can help guide primer/probe selection and design.

Several criteria for selecting primers are as follows: (i) forward and reverse primers of a pair should not be significantly complementary in sequence, and (ii) primers should not have significant self complementary or the potential to form secondary structures. These precautions minimize the potential for generation of primer dimers or oligomers.

Primers may optimally be designed from sequence regions showing no variation among different isolates but may also be designed from regions of less homology by incorporating mixed base synthesis or neutral bases, such as inosine, at those positions to account for known isolate divergence. The following two groups of primers are examples of primers may be employed in development of a PCR-based assay for detection of HGV genomes: forward primers SEQ ID NO:222, SEQ ID NO:223 and SEQ ID NO:224; and reverse primers SEQ ID NO:225, SEQ ID NO:226 and SEQ ID NO:227.

Various combinations of primers, may be employed in development of an HGV diagnostic assay. Optimal combinations of primers are experimentally determined and typically address considerations for assay sensitivity and specificity. Such considerations include the following: (i) a PCR product length of 100–300 bp for efficient amplification and ease of product detection; (ii) an ability to reproducibly detect at least 10 copies of target HGV, and (iii) an ability to reproducibly detect a majority of HGV variants.

In addition, probe sequences may be similarly designed with mixed base or neutral base syntheses and/or may be used at reduced stringency so as to detect a majority of HGV variants.

While the invention has been described with reference to specific methods and embodiments, it will be appreciated that various modifications and changes may be made without departing from the invention.

SEQUENCE LISTING ( 1 ) GENERAL INFORMATION:

( i i i ) NUMBER OF SEQUENCES: 277

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: SISPA primer, top strand Linker AB ( x i ) SEQUENCE DESCRIPTION: SEQ ID NO:1:

GGAATTCGCG GCCGCTCG                                                                    1 8

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: Linker AB, bottom strand ( x i ) SEQUENCE DESCRIPTION: SEQ ID NO:2:

CGAGCGGCCG CGAATTCCTT                                                          2 0

( 2 ) INFORMATION FOR SEQ ID NO:3:

( i ) SEQUENCE CHARACTERISTICS:
        ( A ) LENGTH: 237 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: PNF 2161 CLONE 470-20-1

( i x ) FEATURE:
        ( A ) NAME/KEY: CDS
        ( B ) LOCATION: 1..237

( x i ) SEQUENCE DESCRIPTION: SEQ ID NO:3:

```
GAA  TTC  GCG  GCC  GCT  CGG  GCT  GTC  TCG  GAC  TCT  TGG  ATG  ACC  TCG  AAT       4 8
Glu  Phe  Ala  Ala  Ala  Arg  Ala  Val  Ser  Asp  Ser  Trp  Met  Thr  Ser  Asn
 1              5                        1 0                       1 5

GAG  TCA  GAG  GAC  GGG  GTA  TCC  TCC  TGC  GAG  GAG  GAC  ACC  GGC  GGG  GTC       9 6
Glu  Ser  Glu  Asp  Gly  Val  Ser  Ser  Cys  Glu  Glu  Asp  Thr  Gly  Gly  Val
              2 0                       2 5                       3 0

TTC  TCA  TCT  GAG  CTG  CTC  TCA  GTA  ACC  GAG  ATA  AGT  GCT  GGC  GAT  GGA      1 4 4
Phe  Ser  Ser  Glu  Leu  Leu  Ser  Val  Thr  Glu  Ile  Ser  Ala  Gly  Asp  Gly
         3 5                       4 0                       4 5
```

```
GTA  CGG  GGG  ATG  TCT  TCT  CCC  CAT  ACA  GGC  ATC  TCT  CGG  CTA  CTA  CCA       192
Val  Arg  Gly  Met  Ser  Ser  Pro  His  Thr  Gly  Ile  Ser  Arg  Leu  Leu  Pro
      50                      55                       60

CAA  AGA  GAG  GGT  GTA  CTG  CAG  TCC  TCC  ACG  AGC  GGC  CGC  GAA  TTC            237
Gln  Arg  Glu  Gly  Val  Leu  Gln  Ser  Ser  Thr  Ser  Gly  Arg  Glu  Phe
 65                      70                       75
```

( 2 ) INFORMATION FOR SEQ ID NO:4:

( i ) SEQUENCE CHARACTERISTICS:
        ( A ) LENGTH: 79 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Glu  Phe  Ala  Ala  Ala  Arg  Ala  Val  Ser  Asp  Ser  Trp  Met  Thr  Ser  Asn
 1                    5                    10                       15

Glu  Ser  Glu  Asp  Gly  Val  Ser  Ser  Cys  Glu  Glu  Asp  Thr  Gly  Gly  Val
               20                       25                       30

Phe  Ser  Ser  Glu  Leu  Leu  Ser  Val  Thr  Glu  Ile  Ser  Ala  Gly  Asp  Gly
           35                       40                       45

Val  Arg  Gly  Met  Ser  Ser  Pro  His  Thr  Gly  Ile  Ser  Arg  Leu  Leu  Pro
      50                      55                       60

Gln  Arg  Glu  Gly  Val  Leu  Gln  Ser  Ser  Thr  Ser  Gly  Arg  Glu  Phe
 65                      70                       75
```

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: HAV-R1

( x i ) SEQUENCE DESCRIPTION: SEQ ID NO:5:

```
GTTGACCAAC  TGAGTCTGAA  GC                                                            22
```

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: HAV-F1

( x i ) SEQUENCE DESCRIPTION: SEQ ID NO:6:

```
GATTGGAAAT  CTGATCCGTC  CC                                                            22
```

( 2 ) INFORMATION FOR SEQ ID NO:7:

( i ) SEQUENCE CHARACTERISTICS:

(A) LENGTH: 19 base pairs
(B) TYPE: nucleic acid
(C) STRANDEDNESS: single
(D) TOPOLOGY: linear (ii) MOLECULE TYPE: DNA (iii) HYPOTHETICAL: NO (vi) ORIGINAL SOURCE:
(C) INDIVIDUAL ISOLATE: HCV- LANR (xi) SEQUENCE DESCRIPTION: SEQ ID NO:7:

TCGCGACCCA ACACTACTC  19

(2) INFORMATION FOR SEQ ID NO:8:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (iii) HYPOTHETICAL: NO (vi) ORIGINAL SOURCE:
(C) INDIVIDUAL ISOLATE: HCV 1532

(xi) SEQUENCE DESCRIPTION: SEQ ID NO:8:

GGGGGCGACA CTCCACCA  18

(2) INFORMATION FOR SEQ ID NO:9:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer 470- 20-1-77F (xi) SEQUENCE DESCRIPTION: SEQ ID NO:9:

CTCTTTGTGG TAGTAGCCGA GAGAT  25

(2) INFORMATION FOR SEQ ID NO:10:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer 470- 20-1-211R (xi) SEQUENCE DESCRIPTION: SEQ ID NO:10:

CGAATGAGTC AGAGGACGGG GTAT  24

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer KL- 1

( x i ) SEQUENCE DESCRIPTION: SEQ ID NO:11:

GCAGGATCCG AATTCGCATC TAGAGAT        27

( 2 ) INFORMATION FOR SEQ ID NO:12:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer KL- 2

( x i ) SEQUENCE DESCRIPTION: SEQ ID NO:12:

ATCTCTAGAT GCGAATTCGG ATCCTGCGA        29

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: LAMBDA GT11, REVERSE PRIMER ( x i ) SEQUENCE DESCRIPTION: SEQ ID NO:13:

GGCAGACATG GCCTGCCCGG        20

( 2 ) INFORMATION FOR SEQ ID NO:14:

( i ) SEQUENCE CHARACTERISTICS:
        ( A ) LENGTH: 9392 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:

(C) INDIVIDUAL ISOLATE: HGV-PNF 2161 Variant (ix) FEATURE:
    (A) NAME/KEY: CDS
    (B) LOCATION: 459..9077

(xi) SEQUENCE DESCRIPTION: SEQ ID NO:14:

```
ACGTGGGGGA GTTGATCCCC CCCCCCCGGC ACTGGGTGCA AGCCCCAGAA ACCGACGCCT      60

ATCTAAGTAG ACGCAATGAC TCGGCGCCGA CTCGGCGACC GGCCAAAAGG TGGTGGATGG     120

GTGATGACAG GGTTGGTAGG TCGTAAATCC CGGTCACCTT GGTAGCCACT ATAGGTGGGT     180

CTTAAGAGAA GGTTAAGATT CCTCTTGTGC CTGCGGCGAG ACCGCGCACG GTCCACAGGT     240

GTTGGCCCTA CCGGTGGGAA TAAGGGCCCG ACGTCAGGCT CGTCGTTAAA CCGAGCCCGT     300

TACCCACCTG GGCAAACGAC GCCCACGTAC GGTCCACGTC GCCCTTCAAT GTCTCTCTTG     360

ACCAATAGGC GTAGCCGGCG AGTTGACAAG GACCAGTGGG GGCCGGGGGC TTGGAGAGGG     420

ACTCCAAGTC CCGCCCTTCC CGGTGGGCCG GGAAATGC ATG GGG CCA CCC AGC         473
                                            Met Gly Pro Pro Ser
                                              1               5

TCC GCG GCG GCC TGC AGC CGG GGT AGC CCA AGA ATC CTT CGG GTG AGG      521
Ser Ala Ala Ala Cys Ser Arg Gly Ser Pro Arg Ile Leu Arg Val Arg
             10                  15                      20

GCG GGT GGC ATT TCC TTT TTC TAT ACC ATC ATG GCA GTC CTT CTG CTC      569
Ala Gly Gly Ile Ser Phe Phe Tyr Thr Ile Met Ala Val Leu Leu Leu
                 25                  30                  35

CTT CTC GTG GTT GAG GCC GGG GCC ATT CTG GCC CCG GCC ACC CAC GCT      617
Leu Leu Val Val Glu Ala Gly Ala Ile Leu Ala Pro Ala Thr His Ala
             40                  45                  50

TGT CGA GCG AAT GGG CAA TAT TTC CTC ACA AAT TGT TGT GCC CCG GAG      665
Cys Arg Ala Asn Gly Gln Tyr Phe Leu Thr Asn Cys Cys Ala Pro Glu
         55                  60                  65

GAC ATC GGG TTC TGC CTG GAG GGT GGA TGC CTG GTG GCC CTG GGG TGC      713
Asp Ile Gly Phe Cys Leu Glu Gly Gly Cys Leu Val Ala Leu Gly Cys
 70                  75                  80                  85

ACG ATT TGC ACT GAC CAA TGC TGG CCA CTG TAT CAG GCG GGT TTG GCT      761
Thr Ile Cys Thr Asp Gln Cys Trp Pro Leu Tyr Gln Ala Gly Leu Ala
                 90                  95                 100

GTG CGG CCT GGC AAG TCC GCG GCC CAA CTG GTG GGG GAG CTG GGT AGC      809
Val Arg Pro Gly Lys Ser Ala Ala Gln Leu Val Gly Glu Leu Gly Ser
             105                 110                 115

CTA TAC GGG CCC CTG TCG GTC TCG GCC TAT GTG GCT GGG ATC CTG GGC      857
Leu Tyr Gly Pro Leu Ser Val Ser Ala Tyr Val Ala Gly Ile Leu Gly
         120                 125                 130

CTG GGT GAG GTG TAC TCG GGT GTC CTA ACG GTG GGA GTC GCG TTG ACG      905
Leu Gly Glu Val Tyr Ser Gly Val Leu Thr Val Gly Val Ala Leu Thr
 135                 140                 145

CGC CGG GTC TAC CCG GTG CCT AAC CTG ACG TGT GCA GTC GCG TGT GAG      953
Arg Arg Val Tyr Pro Val Pro Asn Leu Thr Cys Ala Val Ala Cys Glu
150                 155                 160                 165

CTA AAG TGG GAA AGT GAG TTT TGG AGA TGG ACT GAA CAG CTG GCC TCC     1001
Leu Lys Trp Glu Ser Glu Phe Trp Arg Trp Thr Glu Gln Leu Ala Ser
                 170                 175                 180

AAC TAC TGG ATT CTG GAA TAC CTC TGG AAG GTC CCA TTT GAT TTC TGG     1049
Asn Tyr Trp Ile Leu Glu Tyr Leu Trp Lys Val Pro Phe Asp Phe Trp
             185                 190                 195

AGA GGC GTG ATA AGC CTG ACC CCC TTG TTG GTT TGC GTG GCC GCA TTG     1097
Arg Gly Val Ile Ser Leu Thr Pro Leu Leu Val Cys Val Ala Ala Leu
         200                 205                 210

CTG CTG CTT GAG CAA CGG ATT GTC ATG GTC TTC CTG TTG GTG ACG ATG     1145
Leu Leu Leu Glu Gln Arg Ile Val Met Val Phe Leu Leu Val Thr Met
```

|  |  |  |  |  | 215 |  |  |  |  | 220 |  |  |  |  | 225 |  |  |  |
|---|---|---|---|---|---|---|---|---|---|---|---|---|---|---|---|---|---|---|

```
GCC  GGG  ATG  TCG  CAA  GGC  GCC  CCT  GCC  TCC  GTT  TTG  GGG  TCA  CGC  CCC       1193
Ala  Gly  Met  Ser  Gln  Gly  Ala  Pro  Ala  Ser  Val  Leu  Gly  Ser  Arg  Pro
230            	    235	                 240	                  245

TTT  GAC  TAC  GGG  TTG  ACT  TGG  CAG  ACC  TGC  TCT  TGC  AGG  GCC  AAC  GGT       1241
Phe  Asp  Tyr  Gly  Leu  Thr  Trp  Gln  Thr  Cys  Ser  Cys  Arg  Ala  Asn  Gly
                    250                      255                          260

TCG  CGT  TTT  TCG  ACT  GGG  GAG  AAG  GTG  TGG  GAC  CGT  GGG  AAC  GTT  ACG       1289
Ser  Arg  Phe  Ser  Thr  Gly  Glu  Lys  Val  Trp  Asp  Arg  Gly  Asn  Val  Thr
               265                      270                      275

CTT  CAG  TGT  GAC  TGC  CCT  AAC  GGC  CCC  TGG  GTG  TGG  TTG  CCA  GCC  TTT       1337
Leu  Gln  Cys  Asp  Cys  Pro  Asn  Gly  Pro  Trp  Val  Trp  Leu  Pro  Ala  Phe
          280                      285                          290

TGC  CAA  GCA  ATC  GGC  TGG  GGT  GAC  CCC  ATC  ACT  TAT  TGG  AGC  CAC  GGG       1385
Cys  Gln  Ala  Ile  Gly  Trp  Gly  Asp  Pro  Ile  Thr  Tyr  Trp  Ser  His  Gly
     295                           300                      305

CAA  AAT  CAG  TGG  CCC  CTT  TCA  TGC  CCC  CAG  TAT  GTC  TAT  GGG  TCT  GCT       1433
Gln  Asn  Gln  Trp  Pro  Leu  Ser  Cys  Pro  Gln  Tyr  Val  Tyr  Gly  Ser  Ala
310                      315                      320                      325

ACA  GTC  ACT  TGC  GTG  TGG  GGT  TCC  GCT  TCT  TGG  TTT  GCC  TCC  ACC  AGT       1481
Thr  Val  Thr  Cys  Val  Trp  Gly  Ser  Ala  Ser  Trp  Phe  Ala  Ser  Thr  Ser
                    330                      335                      340

GGT  CGC  GAC  TCG  AAG  ATA  GAT  GTG  TGG  AGT  TTA  GTG  CCA  GTT  GGC  TCT       1529
Gly  Arg  Asp  Ser  Lys  Ile  Asp  Val  Trp  Ser  Leu  Val  Pro  Val  Gly  Ser
               345                      350                      355

GCC  ACC  TGC  ACC  ATA  GCC  GCA  CTT  GGA  TCA  TCG  GAT  CGC  GAC  ACG  GTG       1577
Ala  Thr  Cys  Thr  Ile  Ala  Ala  Leu  Gly  Ser  Ser  Asp  Arg  Asp  Thr  Val
          360                      365                      370

CCT  GGG  CTC  TCC  GAG  TGG  GGA  ATC  CCG  TGC  GTG  ACG  TGT  GTT  CTG  GAC       1625
Pro  Gly  Leu  Ser  Glu  Trp  Gly  Ile  Pro  Cys  Val  Thr  Cys  Val  Leu  Asp
     375                      380                      385

CGT  CGG  CCT  GCC  TCC  TGC  GGC  ACC  TGT  GTG  AGG  GAC  TGC  TGG  CCC  GAG       1673
Arg  Arg  Pro  Ala  Ser  Cys  Gly  Thr  Cys  Val  Arg  Asp  Cys  Trp  Pro  Glu
390                      395                      400                      405

ACC  GGG  TCG  GTT  AGG  TTC  CCA  TTC  CAT  CGG  TGC  GGC  GTG  GGG  CCT  CGG       1721
Thr  Gly  Ser  Val  Arg  Phe  Pro  Phe  His  Arg  Cys  Gly  Val  Gly  Pro  Arg
                    410                      415                      420

CTG  ACA  AAG  GAC  TTG  GAA  GCT  GTG  CCC  TTC  GTC  AAC  AGG  ACA  ACT  CCC       1769
Leu  Thr  Lys  Asp  Leu  Glu  Ala  Val  Pro  Phe  Val  Asn  Arg  Thr  Thr  Pro
               425                      430                      435

TTC  ACC  ATT  AGG  GGG  CCC  CTG  GGC  AAC  CAG  GGC  CGA  GGC  AAC  CCG  GTG       1817
Phe  Thr  Ile  Arg  Gly  Pro  Leu  Gly  Asn  Gln  Gly  Arg  Gly  Asn  Pro  Val
          440                      445                      450

CGG  TCG  CCC  TTG  GGT  TTT  GGG  TCC  TAC  GCC  ATG  ACC  AGG  ATC  CGA  GAT       1865
Arg  Ser  Pro  Leu  Gly  Phe  Gly  Ser  Tyr  Ala  Met  Thr  Arg  Ile  Arg  Asp
455                      460                      465

ACC  CTA  CAT  CTG  GTG  GAG  TGT  CCC  ACA  CCA  GCC  ATT  GAG  CCT  CCC  ACC       1913
Thr  Leu  His  Leu  Val  Glu  Cys  Pro  Thr  Pro  Ala  Ile  Glu  Pro  Pro  Thr
470                      475                      480                      485

GGG  ACG  TTT  GGG  TTC  TTC  CCC  GGG  ACG  CCG  CCT  CTC  AAC  AAC  TGC  ATG       1961
Gly  Thr  Phe  Gly  Phe  Phe  Pro  Gly  Thr  Pro  Pro  Leu  Asn  Asn  Cys  Met
                    490                      495                      500

CTC  TTG  GGC  ACG  GAA  GTG  TCC  GAG  GCA  CTT  GGG  GGT  GCT  GGC  CTC  ACG       2009
Leu  Leu  Gly  Thr  Glu  Val  Ser  Glu  Ala  Leu  Gly  Gly  Ala  Gly  Leu  Thr
               505                      510                      515

GGG  GGG  TTC  TAT  GAA  CCC  CTG  GTG  CGC  AGG  TGT  TCG  AAG  CTG  ATG  GGA       2057
Gly  Gly  Phe  Tyr  Glu  Pro  Leu  Val  Arg  Arg  Cys  Ser  Lys  Leu  Met  Gly
          520                      525                      530

AGC  CGA  AAT  CCG  GTT  TGT  CCG  GGG  TTT  GCA  TGG  CTC  TCT  TCG  GGC  AGG       2105
Ser  Arg  Asn  Pro  Val  Cys  Pro  Gly  Phe  Ala  Trp  Leu  Ser  Ser  Gly  Arg
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 535 |     |     |     |     |     | 540 |     |     |     |     |     | 545 |     |      |
| CCT | GAT | GGG | TTT | ATA | CAT | GTC | CAG | GGT | CAC | TTG | CAG | GAG | GTG | GAT | GCA | 2153 |
| Pro | Asp | Gly | Phe | Ile | His | Val | Gln | Gly | His | Leu | Gln | Glu | Val | Asp | Ala |      |
| 550 |     |     |     |     | 555 |     |     |     |     | 560 |     |     |     |     | 565 |      |
| GGC | AAC | TTC | ATC | CCG | CCC | CCG | CGC | TGG | TTG | CTC | TTG | GAC | TTT | GTA | TTT | 2201 |
| Gly | Asn | Phe | Ile | Pro | Pro | Pro | Arg | Trp | Leu | Leu | Leu | Asp | Phe | Val | Phe |      |
|     |     |     |     | 570 |     |     |     |     | 575 |     |     |     |     | 580 |     |      |
| GTC | CTG | TTA | TAC | CTG | ATG | AAG | CTG | GCT | GAG | GCA | CGG | TTG | GTC | CCG | CTG | 2249 |
| Val | Leu | Leu | Tyr | Leu | Met | Lys | Leu | Ala | Glu | Ala | Arg | Leu | Val | Pro | Leu |      |
|     |     |     | 585 |     |     |     |     |     | 590 |     |     |     |     | 595 |     |      |
| ATC | TTG | CTG | CTG | CTA | TGG | TGG | TGG | GTG | AAC | CAG | CTG | GCA | GTC | CTA | GGG | 2297 |
| Ile | Leu | Leu | Leu | Leu | Trp | Trp | Trp | Val | Asn | Gln | Leu | Ala | Val | Leu | Gly |      |
|     |     | 600 |     |     |     |     | 605 |     |     |     |     | 610 |     |     |     |      |
| CTG | CCG | GCT | GTG | GAA | GCC | GCC | GTG | GCA | GGT | GAG | GTC | TTC | GCG | GGC | CCT | 2345 |
| Leu | Pro | Ala | Val | Glu | Ala | Ala | Val | Ala | Gly | Glu | Val | Phe | Ala | Gly | Pro |      |
|     | 615 |     |     |     |     | 620 |     |     |     |     | 625 |     |     |     |     |      |
| GCC | CTG | TCC | TGG | TGT | CTG | GGA | CTC | CCG | GTC | GTC | AGT | ATG | ATA | TTG | GGT | 2393 |
| Ala | Leu | Ser | Trp | Cys | Leu | Gly | Leu | Pro | Val | Val | Ser | Met | Ile | Leu | Gly |      |
| 630 |     |     |     |     | 635 |     |     |     |     | 640 |     |     |     |     | 645 |      |
| TTG | GCA | AAC | CTG | GTG | CTG | TAC | TTT | AGA | TGG | TTG | GGA | CCC | CAA | CGC | CTG | 2441 |
| Leu | Ala | Asn | Leu | Val | Leu | Tyr | Phe | Arg | Trp | Leu | Gly | Pro | Gln | Arg | Leu |      |
|     |     |     |     | 650 |     |     |     |     | 655 |     |     |     |     | 660 |     |      |
| ATG | TTC | CTC | GTG | TTG | TGG | AAG | CTT | GCT | CGG | GGA | GCT | TTC | CCG | CTG | GCC | 2489 |
| Met | Phe | Leu | Val | Leu | Trp | Lys | Leu | Ala | Arg | Gly | Ala | Phe | Pro | Leu | Ala |      |
|     |     |     | 665 |     |     |     |     |     | 670 |     |     |     |     | 675 |     |      |
| CTC | TTG | ATG | GGG | ATT | TCG | GCG | ACC | CGC | GGG | CGC | ACC | TCA | GTG | CTC | GGG | 2537 |
| Leu | Leu | Met | Gly | Ile | Ser | Ala | Thr | Arg | Gly | Arg | Thr | Ser | Val | Leu | Gly |      |
|     |     | 680 |     |     |     |     | 685 |     |     |     |     | 690 |     |     |     |      |
| GCC | GAG | TTC | TGC | TTC | GAT | GCT | ACA | TTC | GAG | GTG | GAC | ACT | TCG | GTG | TTG | 2585 |
| Ala | Glu | Phe | Cys | Phe | Asp | Ala | Thr | Phe | Glu | Val | Asp | Thr | Ser | Val | Leu |      |
|     | 695 |     |     |     |     | 700 |     |     |     |     | 705 |     |     |     |     |      |
| GGC | TGG | GTG | GTG | GCC | AGT | GTG | GTA | GCT | TGG | GCC | ATT | GCG | CTC | CTG | AGC | 2633 |
| Gly | Trp | Val | Val | Ala | Ser | Val | Val | Ala | Trp | Ala | Ile | Ala | Leu | Leu | Ser |      |
| 710 |     |     |     |     | 715 |     |     |     |     | 720 |     |     |     |     | 725 |      |
| TCG | ATG | AGC | GCA | GGG | GGG | TGG | AGG | CAC | AAA | GCC | GTG | ATC | TAT | AGG | ACG | 2681 |
| Ser | Met | Ser | Ala | Gly | Gly | Trp | Arg | His | Lys | Ala | Val | Ile | Tyr | Arg | Thr |      |
|     |     |     |     | 730 |     |     |     |     | 735 |     |     |     |     | 740 |     |      |
| TGG | TGT | AAG | GGG | TAC | CAG | GCA | ATC | CGT | CAA | AGG | GTG | GTG | AGG | AGC | CCC | 2729 |
| Trp | Cys | Lys | Gly | Tyr | Gln | Ala | Ile | Arg | Gln | Arg | Val | Val | Arg | Ser | Pro |      |
|     |     |     | 745 |     |     |     |     |     | 750 |     |     |     |     | 755 |     |      |
| CTC | GGG | GAG | GGG | CGG | CCT | GCC | AAA | CCC | CTG | ACC | TTT | GCC | TGG | TGC | TTG | 2777 |
| Leu | Gly | Glu | Gly | Arg | Pro | Ala | Lys | Pro | Leu | Thr | Phe | Ala | Trp | Cys | Leu |      |
|     |     | 760 |     |     |     |     | 765 |     |     |     |     | 770 |     |     |     |      |
| GCC | TCG | TAC | ATC | TGG | CCA | GAT | GCT | GTG | ATG | ATG | GTG | GTG | GTT | GCC | TTG | 2825 |
| Ala | Ser | Tyr | Ile | Trp | Pro | Asp | Ala | Val | Met | Met | Val | Val | Val | Ala | Leu |      |
|     | 775 |     |     |     |     | 780 |     |     |     |     | 785 |     |     |     |     |      |
| GTC | CTT | CTC | TTT | GGC | CTG | TTC | GAC | GCG | TTG | GAT | TGG | GCC | TTG | GAG | GAG | 2873 |
| Val | Leu | Leu | Phe | Gly | Leu | Phe | Asp | Ala | Leu | Asp | Trp | Ala | Leu | Glu | Glu |      |
| 790 |     |     |     |     | 795 |     |     |     |     | 800 |     |     |     |     | 805 |      |
| ATC | TTG | GTG | TCC | CGG | CCC | TCG | TTG | CGG | CGT | TTG | GCT | CGG | GTG | GTT | GAG | 2921 |
| Ile | Leu | Val | Ser | Arg | Pro | Ser | Leu | Arg | Arg | Leu | Ala | Arg | Val | Val | Glu |      |
|     |     |     |     | 810 |     |     |     |     | 815 |     |     |     |     | 820 |     |      |
| TGC | TGT | GTG | ATG | GCG | GGT | GAG | AAG | GCC | ACA | ACC | GTC | CGG | CTG | GTC | TCC | 2969 |
| Cys | Cys | Val | Met | Ala | Gly | Glu | Lys | Ala | Thr | Thr | Val | Arg | Leu | Val | Ser |      |
|     |     |     | 825 |     |     |     |     |     | 830 |     |     |     |     | 835 |     |      |
| AAG | ATG | TGT | GCG | AGA | GGA | GCT | TAT | TTG | TTC | GAT | CAT | ATG | GGC | TCT | TTT | 3017 |
| Lys | Met | Cys | Ala | Arg | Gly | Ala | Tyr | Leu | Phe | Asp | His | Met | Gly | Ser | Phe |      |
|     |     | 840 |     |     |     |     | 845 |     |     |     |     | 850 |     |     |     |      |
| TCG | CGT | GCT | GTC | AAG | GAG | CGC | CTG | TTG | GAA | TGG | GAC | GCA | GCT | CTT | GAA | 3065 |
| Ser | Arg | Ala | Val | Lys | Glu | Arg | Leu | Leu | Glu | Trp | Asp | Ala | Ala | Leu | Glu |      |

```
                855                      860                      865
CCT CTG TCA TTC ACT AGG ACG GAC TGT CGC ATC ATA CGG GAT GCC GCG         3113
Pro Leu Ser Phe Thr Arg Thr Asp Cys Arg Ile Ile Arg Asp Ala Ala
870             875                 880                 885

AGG ACT TTG TCC TGC GGG CAG TGC GTC ATG GGT TTA CCC GTG GTT GCG         3161
Arg Thr Leu Ser Cys Gly Gln Cys Val Met Gly Leu Pro Val Val Ala
                890                 895                 900

CGC CGT GGT GAT GAG GTT CTC ATC GGC GTC TTC CAG GAT GTG AAT CAT         3209
Arg Arg Gly Asp Glu Val Leu Ile Gly Val Phe Gln Asp Val Asn His
            905                 910                 915

TTG CCT CCC GGG TTT GTT CCG ACC GCG CCT GTT GTC ATC CGA CGG TGC         3257
Leu Pro Pro Gly Phe Val Pro Thr Ala Pro Val Val Ile Arg Arg Cys
        920                 925                 930

GGA AAG GGC TTC TTG GGG GTC ACA AAG GCT GCC TTG ACA GGT CGG GAT         3305
Gly Lys Gly Phe Leu Gly Val Thr Lys Ala Ala Leu Thr Gly Arg Asp
935                 940                 945

CCT GAC TTA CAT CCA GGG AAC GTC ATG GTG TTG GGG ACG GCT ACG TCG         3353
Pro Asp Leu His Pro Gly Asn Val Met Val Leu Gly Thr Ala Thr Ser
950                 955                 960                 965

CGA AGC ATG GGA ACA TGC TTG AAC GGC CTG CTG TTC ACG ACC TTC CAT         3401
Arg Ser Met Gly Thr Cys Leu Asn Gly Leu Leu Phe Thr Thr Phe His
                970                 975                 980

GGG GCT TCA TCC CGA ACC ATC GCC ACA CCC GTG GGG GCC CTT AAT CCC         3449
Gly Ala Ser Ser Arg Thr Ile Ala Thr Pro Val Gly Ala Leu Asn Pro
            985                 990                 995

AGA TGG TGG TCA GCC AGT GAT GAT GTC ACG GTG TAT CCA CTC CCG GAT         3497
Arg Trp Trp Ser Ala Ser Asp Asp Val Thr Val Tyr Pro Leu Pro Asp
        1000                1005                1010

GGG GCT ACT TCG TTA ACA CCT TGT ACT TGC CAG GCT GAG TCC TGT TGG         3545
Gly Ala Thr Ser Leu Thr Pro Cys Thr Cys Gln Ala Glu Ser Cys Trp
1015                1020                1025

GTC ATC AGA TCC GAC GGG GCC CTA TGC CAT GGC TTG AGC AAG GGG GAC         3593
Val Ile Arg Ser Asp Gly Ala Leu Cys His Gly Leu Ser Lys Gly Asp
1030                1035                1040                1045

AAG GTG GAG CTG GAT GTG GCC ATG GAG GTC TCT GAC TTC CGT GGC TCG         3641
Lys Val Glu Leu Asp Val Ala Met Glu Val Ser Asp Phe Arg Gly Ser
                1050                1055                1060

TCT GGC TCA CCG GTC CTA TGT GAC GAA GGG CAC GCA GTA GGA ATG CTC         3689
Ser Gly Ser Pro Val Leu Cys Asp Glu Gly His Ala Val Gly Met Leu
            1065                1070                1075

GTG TCT GTG CTT CAC TCC GGT GGT AGG GTC ACC GCG GCA CGG TTC ACT         3737
Val Ser Val Leu His Ser Gly Gly Arg Val Thr Ala Ala Arg Phe Thr
        1080                1085                1090

AGG CCG TGG ACC CAA GTG CCA ACA GAT GCC AAA ACC ACT ACT GAA CCC         3785
Arg Pro Trp Thr Gln Val Pro Thr Asp Ala Lys Thr Thr Thr Glu Pro
1095                1100                1105

CCT CCG GTG CCG GCC AAA GGA GTT TTC AAA GAG GCC CCG TTG TTT ATG         3833
Pro Pro Val Pro Ala Lys Gly Val Phe Lys Glu Ala Pro Leu Phe Met
1110                1115                1120                1125

CCT ACG GGA GCG GGA AAG AGC ACT CGC GTC CCG TTG GAG TAC GAT AAC         3881
Pro Thr Gly Ala Gly Lys Ser Thr Arg Val Pro Leu Glu Tyr Asp Asn
                1130                1135                1140

ATG GGG CAC AAG GTC TTA ATC TTG AAC CCC TCA GTG GCC ACT GTG CGG         3929
Met Gly His Lys Val Leu Ile Leu Asn Pro Ser Val Ala Thr Val Arg
            1145                1150                1155

GCC ATG GGC CCG TAC ATG GAG CGG CTG GCG GGT AAA CAT CCA AGT ATA         3977
Ala Met Gly Pro Tyr Met Glu Arg Leu Ala Gly Lys His Pro Ser Ile
        1160                1165                1170

TAC TGT GGG CAT GAT ACA ACT GCT TTC ACA AGG ATC ACT GAC TCC CCC         4025
Tyr Cys Gly His Asp Thr Thr Ala Phe Thr Arg Ile Thr Asp Ser Pro
```

-continued

```
              1175                          1180                           1185
CTG  ACG  TAT  TCA  ACC  TAT  GGG  AGG  TTT  TTG  GCC  AAC  CCT  AGG  CAG  ATG         4073
Leu  Thr  Tyr  Ser  Thr  Tyr  Gly  Arg  Phe  Leu  Ala  Asn  Pro  Arg  Gln  Met
1190                      1195                     1200                     1205

CTA  CGG  GGC  GTT  TCG  GTG  GTC  ATT  TGT  GAT  GAG  TGC  CAC  AGT  CAT  GAC         4121
Leu  Arg  Gly  Val  Ser  Val  Val  Ile  Cys  Asp  Glu  Cys  His  Ser  His  Asp
                          1210                     1215                     1220

TCA  ACC  GTG  CTG  TTA  GGC  ATT  GGG  AGA  GTC  CGG  GAG  CTG  GCG  CGT  GGG         4169
Ser  Thr  Val  Leu  Leu  Gly  Ile  Gly  Arg  Val  Arg  Glu  Leu  Ala  Arg  Gly
               1225                     1230                     1235

TGC  GGG  GTG  CAA  CTA  GTG  CTC  TAC  GCC  ACC  GCT  ACA  CCT  CCC  GGA  TCC         4217
Cys  Gly  Val  Gln  Leu  Val  Leu  Tyr  Ala  Thr  Ala  Thr  Pro  Pro  Gly  Ser
               1240                     1245                     1250

CCT  ATG  ACG  CAG  CAC  CCT  TCC  ATA  ATT  GAG  ACA  AAA  TTG  GAC  GTG  GGC         4265
Pro  Met  Thr  Gln  His  Pro  Ser  Ile  Ile  Glu  Thr  Lys  Leu  Asp  Val  Gly
          1255                     1260                     1265

GAG  ATT  CCC  TTT  TAT  GGG  CAT  GGA  ATA  CCC  CTC  GAG  CGG  ATG  CGA  ACC         4313
Glu  Ile  Pro  Phe  Tyr  Gly  His  Gly  Ile  Pro  Leu  Glu  Arg  Met  Arg  Thr
1270                     1275                     1280                     1285

GGA  AGG  CAC  CTC  GTG  TTC  TGC  CAT  TCT  AAG  GCT  GAG  TGC  GAG  CGC  CTT         4361
Gly  Arg  His  Leu  Val  Phe  Cys  His  Ser  Lys  Ala  Glu  Cys  Glu  Arg  Leu
                    1290                     1295                     1300

GCT  GGC  CAG  TTC  TCC  GCT  AGG  GGG  GTC  AAT  GCC  ATT  GCC  TAT  TAT  AGG         4409
Ala  Gly  Gln  Phe  Ser  Ala  Arg  Gly  Val  Asn  Ala  Ile  Ala  Tyr  Tyr  Arg
                    1305                     1310                     1315

GGT  AAA  GAC  AGT  TCT  ATC  ATC  AAG  GAT  GGG  GAC  CTG  GTG  GTC  TGT  GCT         4457
Gly  Lys  Asp  Ser  Ser  Ile  Ile  Lys  Asp  Gly  Asp  Leu  Val  Val  Cys  Ala
                    1320                     1325                     1330

ACA  GAC  GCG  CTT  TCC  ACT  GGG  TAC  ACT  GGA  AAT  TTC  GAC  TCC  GTC  ACC         4505
Thr  Asp  Ala  Leu  Ser  Thr  Gly  Tyr  Thr  Gly  Asn  Phe  Asp  Ser  Val  Thr
                    1335                     1340                     1345

GAC  TGT  GGA  TTA  GTG  GTG  GAG  GAG  GTC  GTT  GAG  GTG  ACC  CTT  GAT  CCC         4553
Asp  Cys  Gly  Leu  Val  Val  Glu  Glu  Val  Val  Glu  Val  Thr  Leu  Asp  Pro
1350                     1355                     1360                     1365

ACC  ATT  ACC  ATC  TCC  CTG  CGG  ACA  GTG  CCT  GCG  TCG  GCT  GAA  CTG  TCG         4601
Thr  Ile  Thr  Ile  Ser  Leu  Arg  Thr  Val  Pro  Ala  Ser  Ala  Glu  Leu  Ser
                    1370                     1375                     1380

ATG  CAA  AGA  CGA  GGA  CGC  ACG  GGT  AGG  GGC  AGG  TCT  GGA  CGC  TAC  TAC         4649
Met  Gln  Arg  Arg  Gly  Arg  Thr  Gly  Arg  Gly  Arg  Ser  Gly  Arg  Tyr  Tyr
                    1385                     1390                     1395

TAC  GCG  GGG  GTG  GGC  AAA  GCC  CCT  GCG  GGT  GTG  GTG  CGC  TCA  GGT  CCT         4697
Tyr  Ala  Gly  Val  Gly  Lys  Ala  Pro  Ala  Gly  Val  Val  Arg  Ser  Gly  Pro
               1400                     1405                     1410

GTC  TGG  TCG  GCG  GTG  GAA  GCT  GGA  GTG  ACC  TGG  TAC  GGA  ATG  GAA  CCT         4745
Val  Trp  Ser  Ala  Val  Glu  Ala  Gly  Val  Thr  Trp  Tyr  Gly  Met  Glu  Pro
               1415                     1420                     1425

GAC  TTG  ACA  GCT  AAC  CTA  CTG  AGA  CTT  TAC  GAC  GAC  TGC  CCT  TAC  ACC         4793
Asp  Leu  Thr  Ala  Asn  Leu  Leu  Arg  Leu  Tyr  Asp  Asp  Cys  Pro  Tyr  Thr
1430                     1435                     1440                     1445

GCA  GCC  GTC  GCG  GCT  GAT  ATC  GGA  GAA  GCC  GCG  GTG  TTC  TTC  TCT  GGG         4841
Ala  Ala  Val  Ala  Ala  Asp  Ile  Gly  Glu  Ala  Ala  Val  Phe  Phe  Ser  Gly
                         1450                     1455                     1460

CTC  GCC  CCA  TTG  AGG  ATG  CAC  CCT  GAT  GTC  AGC  TGG  GCA  AAA  GTT  CGC         4889
Leu  Ala  Pro  Leu  Arg  Met  His  Pro  Asp  Val  Ser  Trp  Ala  Lys  Val  Arg
                    1465                     1470                     1475

GGC  GTC  AAC  TGG  CCC  CTC  TTG  GTG  GGT  GTT  CAG  CGG  ACC  ATG  TGT  CGG         4937
Gly  Val  Asn  Trp  Pro  Leu  Leu  Val  Gly  Val  Gln  Arg  Thr  Met  Cys  Arg
                    1480                     1485                     1490

GAA  ACA  CTG  TCT  CCC  GGC  CCA  TCG  GAT  GAC  CCC  CAA  TGG  GCA  GGT  CTG         4985
Glu  Thr  Leu  Ser  Pro  Gly  Pro  Ser  Asp  Asp  Pro  Gln  Trp  Ala  Gly  Leu
```

-continued

| | | | | | | | | | | | | | | | | |
|---|---|---|---|---|---|---|---|---|---|---|---|---|---|---|---|---|
| | | | 1495 | | | | 1500 | | | | | 1505 | | | | |
| AAG | GGC | CCA | AAT | CCT | GTC | CCA | CTC | CTG | CTG | AGG | TGG | GGC | AAT | GAT | TTA | 5033 |
| Lys | Gly | Pro | Asn | Pro | Val | Pro | Leu | Leu | Leu | Arg | Trp | Gly | Asn | Asp | Leu | |
| 1510 | | | | 1515 | | | | | 1520 | | | | | | 1525 | |
| CCA | TCT | AAA | GTG | GCC | GGC | CAC | CAC | ATA | GTG | GAC | GAC | CTG | GTC | CGG | AGA | 5081 |
| Pro | Ser | Lys | Val | Ala | Gly | His | His | Ile | Val | Asp | Asp | Leu | Val | Arg | Arg | |
| | | | | 1530 | | | | 1535 | | | | | | 1540 | | |
| CTC | GGT | GTG | GCG | GAG | GGT | TAC | GTC | CGC | TGC | GAC | GCT | GGG | CCG | ATC | TTG | 5129 |
| Leu | Gly | Val | Ala | Glu | Gly | Tyr | Val | Arg | Cys | Asp | Ala | Gly | Pro | Ile | Leu | |
| | | | | 1545 | | | | 1550 | | | | | | 1555 | | |
| ATG | ATC | GGT | CTA | GCT | ATC | GCG | GGG | GGA | ATG | ATC | TAC | GCG | TCA | TAC | ACC | 5177 |
| Met | Ile | Gly | Leu | Ala | Ile | Ala | Gly | Gly | Met | Ile | Tyr | Ala | Ser | Tyr | Thr | |
| 1560 | | | | | 1565 | | | | | 1570 | | | | | | |
| GGG | TCG | CTA | GTG | GTG | GTG | ACA | GAC | TGG | GAT | GTG | AAG | GGG | GGT | GGC | GCC | 5225 |
| Gly | Ser | Leu | Val | Val | Val | Thr | Asp | Trp | Asp | Val | Lys | Gly | Gly | Gly | Ala | |
| 1575 | | | | | 1580 | | | | | | 1585 | | | | | |
| CCC | CTT | TAT | CGG | CAT | GGA | GAC | CAG | GCC | ACG | CCT | CAG | CCG | GTG | GTG | CAG | 5273 |
| Pro | Leu | Tyr | Arg | His | Gly | Asp | Gln | Ala | Thr | Pro | Gln | Pro | Val | Val | Gln | |
| 1590 | | | | | 1595 | | | | | 1600 | | | | | 1605 | |
| GTT | CCT | CCG | GTA | GAC | CAT | CGG | CCG | GGG | GGT | GAA | TCA | GCA | CCA | TCG | GAT | 5321 |
| Val | Pro | Pro | Val | Asp | His | Arg | Pro | Gly | Gly | Glu | Ser | Ala | Pro | Ser | Asp | |
| | | | | 1610 | | | | | 1615 | | | | | 1620 | | |
| GCC | AAG | ACA | GTG | ACA | GAT | GCG | GTG | GCA | GCC | ATC | CAG | GTG | GAC | TGC | GAT | 5369 |
| Ala | Lys | Thr | Val | Thr | Asp | Ala | Val | Ala | Ala | Ile | Gln | Val | Asp | Cys | Asp | |
| | | | | 1625 | | | | 1630 | | | | | | 1635 | | |
| TGG | ACT | ATC | ATG | ACT | CTG | TCG | ATC | GGA | GAA | GTG | TTG | TCC | TTG | GCT | CAG | 5417 |
| Trp | Thr | Ile | Met | Thr | Leu | Ser | Ile | Gly | Glu | Val | Leu | Ser | Leu | Ala | Gln | |
| | | | | 1640 | | | | | 1645 | | | | | 1650 | | |
| GCT | AAG | ACG | GCC | GAG | GCC | TAC | ACA | GCA | ACC | GCC | AAG | TGG | CTC | GCT | GGC | 5465 |
| Ala | Lys | Thr | Ala | Glu | Ala | Tyr | Thr | Ala | Thr | Ala | Lys | Trp | Leu | Ala | Gly | |
| | | | | 1655 | | | | 1660 | | | | | | 1665 | | |
| TGC | TAT | ACG | GGG | ACG | CGG | GCC | GTT | CCC | ACT | GTA | TCC | ATT | GTT | GAC | AAG | 5513 |
| Cys | Tyr | Thr | Gly | Thr | Arg | Ala | Val | Pro | Thr | Val | Ser | Ile | Val | Asp | Lys | |
| 1670 | | | | | 1675 | | | | | 1680 | | | | | 1685 | |
| CTC | TTC | GCC | GGA | GGG | TGG | GCG | GCT | GTG | GTG | GGC | CAT | TGC | CAC | AGC | GTG | 5561 |
| Leu | Phe | Ala | Gly | Gly | Trp | Ala | Ala | Val | Val | Gly | His | Cys | His | Ser | Val | |
| | | | | | 1690 | | | | | 1695 | | | | | 1700 | |
| ATT | GCT | GCG | GCG | GTG | GCG | GCC | TAC | GGG | GCT | TCA | AGG | AGC | CCG | CCG | TTG | 5609 |
| Ile | Ala | Ala | Ala | Val | Ala | Ala | Tyr | Gly | Ala | Ser | Arg | Ser | Pro | Pro | Leu | |
| | | | | 1705 | | | | 1710 | | | | | | 1715 | | |
| GCA | GCC | GCG | GCT | TCC | TAC | CTG | ATG | GGG | TTG | GGC | GTT | GGA | GGC | AAC | GCT | 5657 |
| Ala | Ala | Ala | Ala | Ser | Tyr | Leu | Met | Gly | Leu | Gly | Val | Gly | Gly | Asn | Ala | |
| | | | | 1720 | | | | | 1725 | | | | | 1730 | | |
| CAG | ACG | CGC | CTG | GCG | TCT | GCC | CTC | CTA | TTG | GGG | GCT | GCT | GGA | ACC | GCC | 5705 |
| Gln | Thr | Arg | Leu | Ala | Ser | Ala | Leu | Leu | Leu | Gly | Ala | Ala | Gly | Thr | Ala | |
| 1735 | | | | | 1740 | | | | | | 1745 | | | | | |
| TTG | GGC | ACT | CCT | GTC | GTG | GGC | TTG | ACC | ATG | GCA | GGT | GCG | TTC | ATG | GGG | 5753 |
| Leu | Gly | Thr | Pro | Val | Val | Gly | Leu | Thr | Met | Ala | Gly | Ala | Phe | Met | Gly | |
| 1750 | | | | | 1755 | | | | | 1760 | | | | | 1765 | |
| GGG | GCC | AGT | GTC | TCC | CCC | TCC | TTG | GTC | ACC | ATT | TTA | TTG | GGG | GCC | GTC | 5801 |
| Gly | Ala | Ser | Val | Ser | Pro | Ser | Leu | Val | Thr | Ile | Leu | Leu | Gly | Ala | Val | |
| | | | | 1770 | | | | | 1775 | | | | | 1780 | | |
| GGA | GGT | TGG | GAG | GGT | GTT | GTC | AAC | GCG | GCG | AGC | CTA | GTC | TTT | GAC | TTC | 5849 |
| Gly | Gly | Trp | Glu | Gly | Val | Val | Asn | Ala | Ala | Ser | Leu | Val | Phe | Asp | Phe | |
| | | | | 1785 | | | | | 1790 | | | | | 1795 | | |
| ATG | GCG | GGG | AAA | CTT | TCA | TCA | GAA | GAT | CTG | TGG | TAT | GCC | ATC | CCG | GTA | 5897 |
| Met | Ala | Gly | Lys | Leu | Ser | Ser | Glu | Asp | Leu | Trp | Tyr | Ala | Ile | Pro | Val | |
| | | | 1800 | | | | | 1805 | | | | | 1810 | | | |
| CTG | ACC | AGC | CCG | GGG | GCG | GGC | CTT | GCG | GGG | ATC | GCT | CTC | GGG | TTG | GTT | 5945 |
| Leu | Thr | Ser | Pro | Gly | Ala | Gly | Leu | Ala | Gly | Ile | Ala | Leu | Gly | Leu | Val | |

```
                 1815                         1820                         1825
TTG  TAT  TCA  GCT  AAC  AAC  TCT  GGC  ACT  ACC  ACT  TGG  TTG  AAC  CGT  CTG      5993
Leu  Tyr  Ser  Ala  Asn  Asn  Ser  Gly  Thr  Thr  Thr  Trp  Leu  Asn  Arg  Leu
1830                     1835                          1840                    1845

CTG  ACT  ACG  TTA  CCA  AGG  TCT  TCA  TGT  ATC  CCG  GAC  AGT  TAC  TTT  CAG      6041
Leu  Thr  Thr  Leu  Pro  Arg  Ser  Ser  Cys  Ile  Pro  Asp  Ser  Tyr  Phe  Gln
                         1850                     1855                         1860

CAA  GTT  GAC  TAT  TGC  GAC  AAG  GTC  TCA  GCC  GTG  CTC  CGG  CGC  CTG  AGC      6089
Gln  Val  Asp  Tyr  Cys  Asp  Lys  Val  Ser  Ala  Val  Leu  Arg  Arg  Leu  Ser
               1865                     1870                          1875

CTC  ACC  CGC  ACA  GTG  GTT  GCC  CTG  GTC  AAC  AGG  GAG  CCT  AAG  GTG  GAT      6137
Leu  Thr  Arg  Thr  Val  Val  Ala  Leu  Val  Asn  Arg  Glu  Pro  Lys  Val  Asp
          1880                     1885                          1890

GAG  GTA  CAG  GTG  GGG  TAT  GTC  TGG  GAC  CTG  TGG  GAG  TGG  ATC  ATG  CGC      6185
Glu  Val  Gln  Val  Gly  Tyr  Val  Trp  Asp  Leu  Trp  Glu  Trp  Ile  Met  Arg
1895                          1900                     1905

CAA  GTG  CGC  GTG  GTC  ATG  GCC  AGA  CTC  AGG  GCC  CTC  TGC  CCC  GTG  GTG      6233
Gln  Val  Arg  Val  Val  Met  Ala  Arg  Leu  Arg  Ala  Leu  Cys  Pro  Val  Val
1910                     1915                          1920                    1925

TCA  CTA  CCC  TTG  TGG  CAT  TGC  GGG  GAG  GGG  TGG  TCC  GGG  GAA  TGG  TTG      6281
Ser  Leu  Pro  Leu  Trp  His  Cys  Gly  Glu  Gly  Trp  Ser  Gly  Glu  Trp  Leu
                         1930                     1935                         1940

CTT  GAC  GGT  CAT  GTT  GAG  AGT  CGC  TGC  CTC  TGT  GGC  TGC  GTG  ATC  ACT      6329
Leu  Asp  Gly  His  Val  Glu  Ser  Arg  Cys  Leu  Cys  Gly  Cys  Val  Ile  Thr
               1945                     1950                          1955

GGT  GAC  GTT  CTG  AAT  GGG  CAA  CTC  AAA  GAA  CCA  GTT  TAC  TCT  ACC  AAG      6377
Gly  Asp  Val  Leu  Asn  Gly  Gln  Leu  Lys  Glu  Pro  Val  Tyr  Ser  Thr  Lys
          1960                     1965                          1970

CTG  TGC  CGG  CAC  TAT  TGG  ATG  GGG  ACT  GTC  CCT  GTG  AAC  ATG  CTG  GGT      6425
Leu  Cys  Arg  His  Tyr  Trp  Met  Gly  Thr  Val  Pro  Val  Asn  Met  Leu  Gly
1975                          1980                     1985

TAC  GGT  GAA  ACG  TCG  CCT  CTC  CTG  GCC  TCC  GAC  ACC  CCG  AAG  GTT  GTG      6473
Tyr  Gly  Glu  Thr  Ser  Pro  Leu  Leu  Ala  Ser  Asp  Thr  Pro  Lys  Val  Val
1990                     1995                          2000                    2005

CCC  TTC  GGG  ACG  TCT  GGC  TGG  GCT  GAG  GTG  GTG  GTG  ACC  ACT  ACC  CAC      6521
Pro  Phe  Gly  Thr  Ser  Gly  Trp  Ala  Glu  Val  Val  Val  Thr  Thr  Thr  His
                         2010                     2015                         2020

GTG  GTA  ATC  AGG  AGG  ACC  TCC  GCC  TAT  AAG  CTG  CTG  CGC  CAG  CAA  ATC      6569
Val  Val  Ile  Arg  Arg  Thr  Ser  Ala  Tyr  Lys  Leu  Leu  Arg  Gln  Gln  Ile
               2025                     2030                          2035

CTA  TCG  GCT  GCT  GTA  GCT  GAG  CCC  TAC  TAC  GTC  GAC  GGC  ATT  CCG  GTC      6617
Leu  Ser  Ala  Ala  Val  Ala  Glu  Pro  Tyr  Tyr  Val  Asp  Gly  Ile  Pro  Val
          2040                     2045                          2050

TCA  TGG  GAC  GCG  GAC  GCT  CGT  GCG  CCC  GCC  ATG  GTC  TAT  GGC  CCT  GGG      6665
Ser  Trp  Asp  Ala  Asp  Ala  Arg  Ala  Pro  Ala  Met  Val  Tyr  Gly  Pro  Gly
2055                          2060                     2065

CAA  AGT  GTT  ACC  ATT  GAC  GGG  GAG  CGC  TAC  ACC  TTG  CCT  CAT  CAA  CTG      6713
Gln  Ser  Val  Thr  Ile  Asp  Gly  Glu  Arg  Tyr  Thr  Leu  Pro  His  Gln  Leu
2070                     2075                          2080                    2085

AGG  CTC  AGG  AAT  GTG  GCA  CCC  TCT  GAG  GTT  TCA  TCC  GAG  GTG  TCC  ATT      6761
Arg  Leu  Arg  Asn  Val  Ala  Pro  Ser  Glu  Val  Ser  Ser  Glu  Val  Ser  Ile
                         2090                     2095                         2100

GAC  ATT  GGG  ACG  GAG  ACT  GAA  GAC  TCA  GAA  CTG  ACT  GAG  GCC  GAT  CTG      6809
Asp  Ile  Gly  Thr  Glu  Thr  Glu  Asp  Ser  Glu  Leu  Thr  Glu  Ala  Asp  Leu
               2105                     2110                          2115

CCG  CCG  GCG  GCT  GCT  GCT  CTC  CAA  GCG  ATC  GAG  AAT  GCT  GCG  AGG  ATT      6857
Pro  Pro  Ala  Ala  Ala  Ala  Leu  Gln  Ala  Ile  Glu  Asn  Ala  Ala  Arg  Ile
          2120                     2125                          2130

CTT  GAA  CCG  CAC  ATT  GAT  GTC  ATC  ATG  GAG  GAC  TGC  AGT  ACA  CCC  TCT      6905
Leu  Glu  Pro  His  Ile  Asp  Val  Ile  Met  Glu  Asp  Cys  Ser  Thr  Pro  Ser
```

```
            2135                         2140                         2145
CTT  TGT  GGT  AGT  AGC  CGA  GAG  ATG  CCT  GTA  TGG  GGA  GAA  GAC  ATC  CCC         6953
Leu  Cys  Gly  Ser  Ser  Arg  Glu  Met  Pro  Val  Trp  Gly  Glu  Asp  Ile  Pro
2150                2155                     2160                     2165

CGT  ACT  CCA  TCG  CCA  GCA  CTT  ATC  TCG  GTT  ACT  GAG  AGC  AGC  TCA  GAT         7001
Arg  Thr  Pro  Ser  Pro  Ala  Leu  Ile  Ser  Val  Thr  Glu  Ser  Ser  Ser  Asp
                    2170                     2175                     2180

GAG  AAG  ACC  CCG  TCG  GTG  TCC  TCC  TCG  CAG  GAG  GAT  ACC  CCG  TCC  TCT         7049
Glu  Lys  Thr  Pro  Ser  Val  Ser  Ser  Ser  Gln  Glu  Asp  Thr  Pro  Ser  Ser
                    2185                     2190                     2195

GAC  TCA  TTC  GAG  GTC  ATC  CAA  GAG  TCC  GAG  ACA  GCC  GAA  GGG  GAG  GAA         7097
Asp  Ser  Phe  Glu  Val  Ile  Gln  Glu  Ser  Glu  Thr  Ala  Glu  Gly  Glu  Glu
          2200                     2205                     2210

AGT  GTC  TTC  AAC  GTG  GCT  CTT  TCC  GTA  TTA  AAA  GCC  TTA  TTT  CCA  CAG         7145
Ser  Val  Phe  Asn  Val  Ala  Leu  Ser  Val  Leu  Lys  Ala  Leu  Phe  Pro  Gln
2215                     2220                     2225

AGC  GAC  GCG  ACC  AGG  AAG  CTT  ACC  GTC  AAG  ATG  TCG  TGC  TGC  GTT  GAA         7193
Ser  Asp  Ala  Thr  Arg  Lys  Leu  Thr  Val  Lys  Met  Ser  Cys  Cys  Val  Glu
2230                     2235                     2240                     2245

AAG  AGC  GTC  ACG  CGC  TTT  TTC  TCA  TTG  GGG  TTG  ACG  GTG  GCT  GAT  GTT         7241
Lys  Ser  Val  Thr  Arg  Phe  Phe  Ser  Leu  Gly  Leu  Thr  Val  Ala  Asp  Val
                    2250                     2255                     2260

GCT  AGC  CTG  TGT  GAG  ATG  GAA  ATC  CAG  AAC  CAT  ACA  GCC  TAT  TGT  GAC         7289
Ala  Ser  Leu  Cys  Glu  Met  Glu  Ile  Gln  Asn  His  Thr  Ala  Tyr  Cys  Asp
               2265                     2270                     2275

CAG  GTG  CGC  ACT  CCG  CTT  GAA  TTG  CAG  GTT  GGG  TGC  TTG  GTG  GGC  AAT         7337
Gln  Val  Arg  Thr  Pro  Leu  Glu  Leu  Gln  Val  Gly  Cys  Leu  Val  Gly  Asn
               2280                     2285                     2290

GAA  CTT  ACC  TTT  GAA  TGT  GAC  AAG  TGT  GAG  GCT  AGG  CAA  GAA  ACC  TTG         7385
Glu  Leu  Thr  Phe  Glu  Cys  Asp  Lys  Cys  Glu  Ala  Arg  Gln  Glu  Thr  Leu
2295                     2300                     2305

GCC  TCC  TTC  TCT  TAC  ATT  TGG  TCT  GGA  GTG  CCG  CTG  ACT  AGG  GCC  ACG         7433
Ala  Ser  Phe  Ser  Tyr  Ile  Trp  Ser  Gly  Val  Pro  Leu  Thr  Arg  Ala  Thr
2310                     2315                     2320                     2325

CCG  GCC  AAG  CCT  CCC  GTG  GTG  AGG  CCG  GTT  GGC  TCT  TTG  TTA  GTG  GCC         7481
Pro  Ala  Lys  Pro  Pro  Val  Val  Arg  Pro  Val  Gly  Ser  Leu  Leu  Val  Ala
                    2330                     2335                     2340

GAC  ACT  ACT  AAG  GTG  TAT  GTT  ACC  AAT  CCA  GAC  AAT  GTG  GGA  CGG  AGG         7529
Asp  Thr  Thr  Lys  Val  Tyr  Val  Thr  Asn  Pro  Asp  Asn  Val  Gly  Arg  Arg
               2345                     2350                     2355

GTG  GAC  AAG  GTG  ACC  TTC  TGG  CGT  GCT  CCT  AGG  GTT  CAT  GAT  AAG  TAC         7577
Val  Asp  Lys  Val  Thr  Phe  Trp  Arg  Ala  Pro  Arg  Val  His  Asp  Lys  Tyr
               2360                     2365                     2370

CTC  GTG  GAC  TCT  ATT  GAG  CGC  GCT  AAG  AGG  GCC  GCT  CAA  GCC  TGC  CTA         7625
Leu  Val  Asp  Ser  Ile  Glu  Arg  Ala  Lys  Arg  Ala  Ala  Gln  Ala  Cys  Leu
2375                     2380                     2385

AGC  ATG  GGT  TAC  ACT  TAT  GAG  GAA  GCA  ATA  AGG  ACT  GTA  AGG  CCA  CAT         7673
Ser  Met  Gly  Tyr  Thr  Tyr  Glu  Glu  Ala  Ile  Arg  Thr  Val  Arg  Pro  His
2390                     2395                     2400                     2405

GCT  GCC  ATG  GGC  TGG  GGA  TCT  AAG  GTG  TCG  GTT  AAG  GAC  TTA  GCC  ACC         7721
Ala  Ala  Met  Gly  Trp  Gly  Ser  Lys  Val  Ser  Val  Lys  Asp  Leu  Ala  Thr
                    2410                     2415                     2420

CCC  GCG  GGG  AAG  ATG  GCC  GTC  CAT  GAC  CGG  CTT  CAG  GAG  ATA  CTT  GAA         7769
Pro  Ala  Gly  Lys  Met  Ala  Val  His  Asp  Arg  Leu  Gln  Glu  Ile  Leu  Glu
               2425                     2430                     2435

GGG  ACT  CCG  GTC  CCC  TTT  ACT  CTT  ACT  GTG  AAA  AAG  GAG  GTG  TTC  TTC         7817
Gly  Thr  Pro  Val  Pro  Phe  Thr  Leu  Thr  Val  Lys  Lys  Glu  Val  Phe  Phe
               2440                     2445                     2450

AAA  GAC  CGG  AAG  GAG  GAG  AAG  GCC  CCC  CGC  CTC  ATT  GTG  TTC  CCC  CCC         7865
Lys  Asp  Arg  Lys  Glu  Glu  Lys  Ala  Pro  Arg  Leu  Ile  Val  Phe  Pro  Pro
```

-continued

```
                2455                          2460                          2465
CTG  GAC  TTC  CGG  ATA  GCT  GAA  AAG  CTC  ATC  TTG  GGA  GAC  CCA  GGC  CGG      7913
Leu  Asp  Phe  Arg  Ile  Ala  Glu  Lys  Leu  Ile  Leu  Gly  Asp  Pro  Gly  Arg
2470                2475                          2480                     2485

GTA  GCC  AAG  GCG  GTG  TTG  GGG  GGG  GCC  TAC  GCC  TTC  CAG  TAC  ACC  CCA      7961
Val  Ala  Lys  Ala  Val  Leu  Gly  Gly  Ala  Tyr  Ala  Phe  Gln  Tyr  Thr  Pro
                         2490                          2495                     2500

AAT  CAG  CGA  GTT  AAG  GAG  ATG  CTC  AAG  CTA  TGG  GAG  TCT  AAG  AAG  ACC      8009
Asn  Gln  Arg  Val  Lys  Glu  Met  Leu  Lys  Leu  Trp  Glu  Ser  Lys  Lys  Thr
                    2505                          2510                     2515

CCT  TGC  GCC  ATC  TGT  GTG  GAC  GCC  ACC  TGC  TTC  GAC  AGT  AGC  ATA  ACT      8057
Pro  Cys  Ala  Ile  Cys  Val  Asp  Ala  Thr  Cys  Phe  Asp  Ser  Ser  Ile  Thr
               2520                          2525                     2530

GAA  GAG  GAC  GTG  GCT  TTG  GAG  ACA  GAG  CTA  TAC  GCT  CTG  GCC  TCT  GAC      8105
Glu  Glu  Asp  Val  Ala  Leu  Glu  Thr  Glu  Leu  Tyr  Ala  Leu  Ala  Ser  Asp
2535                          2540                          2545

CAT  CCA  GAA  TGG  GTG  CGG  GCA  CTT  GGG  AAA  TAC  TAT  GCC  TCA  GGC  ACC      8153
His  Pro  Glu  Trp  Val  Arg  Ala  Leu  Gly  Lys  Tyr  Tyr  Ala  Ser  Gly  Thr
2550                          2555                          2560                2565

ATG  GTC  ACC  CCG  GAA  GGG  GTG  CCC  GTC  GGT  GAG  AGG  TAT  TGC  AGA  TCC      8201
Met  Val  Thr  Pro  Glu  Gly  Val  Pro  Val  Gly  Glu  Arg  Tyr  Cys  Arg  Ser
                         2570                          2575                2580

TCG  GGT  GTC  CTA  ACA  ACT  AGC  GCG  AGC  AAC  TGC  TTG  ACC  TGC  TAC  ATC      8249
Ser  Gly  Val  Leu  Thr  Thr  Ser  Ala  Ser  Asn  Cys  Leu  Thr  Cys  Tyr  Ile
                    2585                          2590                     2595

AAG  GTG  AAA  GCT  GCC  TGT  GAG  AGA  GTG  GGG  CTG  AAA  AAT  GTC  TCT  CTT      8297
Lys  Val  Lys  Ala  Ala  Cys  Glu  Arg  Val  Gly  Leu  Lys  Asn  Val  Ser  Leu
               2600                          2605                     2610

CTC  ATA  GCC  GGC  GAT  GAC  TGC  TTG  ATC  ATA  TGT  GAG  CGG  CCA  GTG  TGC      8345
Leu  Ile  Ala  Gly  Asp  Asp  Cys  Leu  Ile  Ile  Cys  Glu  Arg  Pro  Val  Cys
2615                          2620                          2625

GAC  CCA  AGC  GAC  GCT  TTG  GGC  AGA  GCC  CTA  GCG  AGC  TAT  GGG  TAC  GCG      8393
Asp  Pro  Ser  Asp  Ala  Leu  Gly  Arg  Ala  Leu  Ala  Ser  Tyr  Gly  Tyr  Ala
2630                          2635                          2640                2645

TGC  GAG  CCC  TCA  TAT  CAT  GCA  TCA  TTG  GAC  ACG  GCC  CCC  TTC  TGC  TCC      8441
Cys  Glu  Pro  Ser  Tyr  His  Ala  Ser  Leu  Asp  Thr  Ala  Pro  Phe  Cys  Ser
                         2650                          2655                2660

ACT  TGG  CTT  GCT  GAG  TGC  AAT  GCA  GAT  GGG  AAG  CGC  CAT  TTC  TTC  CTG      8489
Thr  Trp  Leu  Ala  Glu  Cys  Asn  Ala  Asp  Gly  Lys  Arg  His  Phe  Phe  Leu
                    2665                          2670                     2675

ACC  ACG  GAC  TTC  CGG  AGG  CCG  CTC  GCT  CGC  ATG  TCG  AGT  GAG  TAT  AGT      8537
Thr  Thr  Asp  Phe  Arg  Arg  Pro  Leu  Ala  Arg  Met  Ser  Ser  Glu  Tyr  Ser
               2680                          2685                     2690

GAC  CCG  ATG  GCT  TCG  GCG  ATC  GGT  TAC  ATC  CTC  CTT  TAT  CCT  TGG  CAC      8585
Asp  Pro  Met  Ala  Ser  Ala  Ile  Gly  Tyr  Ile  Leu  Leu  Tyr  Pro  Trp  His
2695                          2700                          2705

CCC  ATC  ACA  CGG  TGG  GTC  ATC  ATC  CCT  CAT  GTG  CTA  ACG  TGC  GCA  TTC      8633
Pro  Ile  Thr  Arg  Trp  Val  Ile  Ile  Pro  His  Val  Leu  Thr  Cys  Ala  Phe
2710                     2715                          2720                2725

AGG  GGT  GGA  GGC  ACA  CCG  TCT  GAT  CCG  GTT  TGG  TGC  CAG  GTG  CAT  GGT      8681
Arg  Gly  Gly  Gly  Thr  Pro  Ser  Asp  Pro  Val  Trp  Cys  Gln  Val  His  Gly
                         2730                          2735                2740

AAC  TAC  TAC  AAG  TTT  CCA  CTG  GAC  AAA  CTG  CCT  AAC  ATC  ATC  GTG  GCC      8729
Asn  Tyr  Tyr  Lys  Phe  Pro  Leu  Asp  Lys  Leu  Pro  Asn  Ile  Ile  Val  Ala
                    2745                          2750                     2755

CTC  CAC  GGA  CCA  GCA  GCG  TTG  AGG  GTT  ACC  GCA  GAC  ACA  ACT  AAA  ACA      8777
Leu  His  Gly  Pro  Ala  Ala  Leu  Arg  Val  Thr  Ala  Asp  Thr  Thr  Lys  Thr
               2760                          2765                     2770

AAG  ATG  GAG  GCT  GGT  AAG  GTT  CTG  AGC  GAC  CTC  AAG  CTC  CCT  GGC  TTA      8825
Lys  Met  Glu  Ala  Gly  Lys  Val  Leu  Ser  Asp  Leu  Lys  Leu  Pro  Gly  Leu
```

```
                    2775                         2780                          2785
GCA  GTC  CAC  CGA  AAG  AAG  GCC  GGG  GCG  TTG  CGA  ACA  CGC  ATG  CTC  CGC       8873
Ala  Val  His  Arg  Lys  Lys  Ala  Gly  Ala  Leu  Arg  Thr  Arg  Met  Leu  Arg
2790                2795                          2800                         2805

TCG  CGC  GGT  TGG  GCT  GAG  TTG  GCT  AGG  GGC  TTG  TTG  TGG  CAT  CCA  GGC       8921
Ser  Arg  Gly  Trp  Ala  Glu  Leu  Ala  Arg  Gly  Leu  Leu  Trp  His  Pro  Gly
                    2810                          2815                         2820

CTA  CGG  CTT  CCT  CCC  CCT  GAG  ATT  GCT  GGT  ATC  CCG  GGG  GGT  TTC  CCT       8969
Leu  Arg  Leu  Pro  Pro  Pro  Glu  Ile  Ala  Gly  Ile  Pro  Gly  Gly  Phe  Pro
                    2825                          2830                         2835

CTC  TCC  CCC  CCC  TAT  ATG  GGG  GTG  GTA  CAT  CAA  TTG  GAT  TTC  ACA  AGC       9017
Leu  Ser  Pro  Pro  Tyr  Met  Gly  Val  Val  His  Gln  Leu  Asp  Phe  Thr  Ser
                    2840                          2845                         2850

CAG  AGG  AGT  CGC  TGG  CGG  TGG  TTG  GGG  TTC  TTA  GCC  CTG  CTC  ATC  GTA       9065
Gln  Arg  Ser  Arg  Trp  Arg  Trp  Leu  Gly  Phe  Leu  Ala  Leu  Leu  Ile  Val
2855                          2860                          2865

GCC  CTC  TTC  GGG  TGAACTAAAT  TCATCTGTTG  CGGCAAGGTC  TGGTGACTGA                   9117
Ala  Leu  Phe  Gly
2870

TCATCACCGG  AGGAGGTTCC  CGCCCTCCCC  GCCCCAGGGG  TCTCCCCGCT  GGGTAAAAAG               9177

GGCCCGGCCT  TGGGAGGCAT  GGTGGTTACT  AACCCCCTGG  CAGGGTCAAA  GCCTGATGGT               9237

GCTAATGCAC  TGCCACTTCG  GTGGCGGGTC  GCTACCTTAT  AGCGTAATCC  GTGACTACGG               9297

GCTGCTCGCA  GAGCCCTCCC  CGGATGGGGC  ACAGTGCACT  GTGATCTGAA  GGGGTGCACC               9357

CCGGGAAGAG  CTCGGCCCGA  AGGCCGGSTT  CTACT                                            9392
```

( 2 ) INFORMATION FOR SEQ ID NO:15:

( i ) SEQUENCE CHARACTERISTICS:
        ( A ) LENGTH: 2873 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met  Gly  Pro  Pro  Ser  Ser  Ala  Ala  Ala  Cys  Ser  Arg  Gly  Ser  Pro  Arg
 1                      5                      10                      15

Ile  Leu  Arg  Val  Arg  Ala  Gly  Gly  Ile  Ser  Phe  Phe  Tyr  Thr  Ile  Met
                   20                      25                      30

Ala  Val  Leu  Leu  Leu  Leu  Leu  Val  Val  Glu  Ala  Gly  Ala  Ile  Leu  Ala
                   35                      40                      45

Pro  Ala  Thr  His  Ala  Cys  Arg  Ala  Asn  Gly  Gln  Tyr  Phe  Leu  Thr  Asn
              50                      55                      60

Cys  Cys  Ala  Pro  Glu  Asp  Ile  Gly  Phe  Cys  Leu  Glu  Gly  Gly  Cys  Leu
 65                     70                      75                      80

Val  Ala  Leu  Gly  Cys  Thr  Ile  Cys  Thr  Asp  Gln  Cys  Trp  Pro  Leu  Tyr
                   85                      90                      95

Gln  Ala  Gly  Leu  Ala  Val  Arg  Pro  Gly  Lys  Ser  Ala  Ala  Gln  Leu  Val
                   100                     105                     110

Gly  Glu  Leu  Gly  Ser  Leu  Tyr  Gly  Pro  Leu  Ser  Val  Ser  Ala  Tyr  Val
                   115                     120                     125

Ala  Gly  Ile  Leu  Gly  Leu  Gly  Glu  Val  Tyr  Ser  Gly  Val  Leu  Thr  Val
              130                     135                     140

Gly  Val  Ala  Leu  Thr  Arg  Arg  Val  Tyr  Pro  Val  Pro  Asn  Leu  Thr  Cys
145                     150                     155                     160

Ala  Val  Ala  Cys  Glu  Leu  Lys  Trp  Glu  Ser  Glu  Phe  Trp  Arg  Trp  Thr
                   165                     170                     175
```

-continued

```
Glu Gln Leu Ala Ser Asn Tyr Trp Ile Leu Glu Tyr Leu Trp Lys Val
                180                 185                 190

Pro Phe Asp Phe Trp Arg Gly Val Ile Ser Leu Thr Pro Leu Leu Val
            195                 200                 205

Cys Val Ala Ala Leu Leu Leu Glu Gln Arg Ile Val Met Val Phe
        210                 215                 220

Leu Leu Val Thr Met Ala Gly Met Ser Gln Gly Ala Pro Ala Ser Val
225                 230                 235                 240

Leu Gly Ser Arg Pro Phe Asp Tyr Gly Leu Thr Trp Gln Thr Cys Ser
                245                 250                 255

Cys Arg Ala Asn Gly Ser Arg Phe Ser Thr Gly Glu Lys Val Trp Asp
                260                 265                 270

Arg Gly Asn Val Thr Leu Gln Cys Asp Cys Pro Asn Gly Pro Trp Val
                275                 280                 285

Trp Leu Pro Ala Phe Cys Gln Ala Ile Gly Trp Gly Asp Pro Ile Thr
    290                 295                 300

Tyr Trp Ser His Gly Gln Asn Gln Trp Pro Leu Ser Cys Pro Gln Tyr
305                 310                 315                 320

Val Tyr Gly Ser Ala Thr Val Thr Cys Val Trp Gly Ser Ala Ser Trp
                325                 330                 335

Phe Ala Ser Thr Ser Gly Arg Asp Ser Lys Ile Asp Val Trp Ser Leu
            340                 345                 350

Val Pro Val Gly Ser Ala Thr Cys Thr Ile Ala Ala Leu Gly Ser Ser
            355                 360                 365

Asp Arg Asp Thr Val Pro Gly Leu Ser Glu Trp Gly Ile Pro Cys Val
    370                 375                 380

Thr Cys Val Leu Asp Arg Arg Pro Ala Ser Cys Gly Thr Cys Val Arg
385                 390                 395                 400

Asp Cys Trp Pro Glu Thr Gly Ser Val Arg Phe Pro Phe His Arg Cys
                405                 410                 415

Gly Val Gly Pro Arg Leu Thr Lys Asp Leu Glu Ala Val Pro Phe Val
            420                 425                 430

Asn Arg Thr Thr Pro Phe Thr Ile Arg Gly Pro Leu Gly Asn Gln Gly
        435                 440                 445

Arg Gly Asn Pro Val Arg Ser Pro Leu Gly Phe Gly Ser Tyr Ala Met
    450                 455                 460

Thr Arg Ile Arg Asp Thr Leu His Leu Val Glu Cys Pro Thr Pro Ala
465                 470                 475                 480

Ile Glu Pro Pro Thr Gly Thr Phe Gly Phe Phe Pro Gly Thr Pro Pro
            485                 490                 495

Leu Asn Asn Cys Met Leu Leu Gly Thr Glu Val Ser Glu Ala Leu Gly
            500                 505                 510

Gly Ala Gly Leu Thr Gly Gly Phe Tyr Glu Pro Leu Val Arg Arg Cys
        515                 520                 525

Ser Lys Leu Met Gly Ser Arg Asn Pro Val Cys Pro Gly Phe Ala Trp
    530                 535                 540

Leu Ser Ser Gly Arg Pro Asp Gly Phe Ile His Val Gln Gly His Leu
545                 550                 555                 560

Gln Glu Val Asp Ala Gly Asn Phe Ile Pro Pro Arg Trp Leu Leu
                565                 570                 575

Leu Asp Phe Val Phe Val Leu Leu Tyr Leu Met Lys Leu Ala Glu Ala
            580                 585                 590

Arg Leu Val Pro Leu Ile Leu Leu Leu Leu Trp Trp Trp Val Asn Gln
```

-continued

|  |  |  |  |  | 595 |  |  |  |  | 600 |  |  |  |  | 605 |  |  |
|---|---|---|---|---|---|---|---|---|---|---|---|---|---|---|---|---|---|

Leu Ala Val Leu Gly Leu Pro Ala Val Glu Ala Ala Val Ala Gly Glu
    610                     615                 620

Val Phe Ala Gly Pro Ala Leu Ser Trp Cys Leu Gly Leu Pro Val Val
625             630             635                         640

Ser Met Ile Leu Gly Leu Ala Asn Leu Val Leu Tyr Phe Arg Trp Leu
            645                 650                     655

Gly Pro Gln Arg Leu Met Phe Leu Val Leu Trp Lys Leu Ala Arg Gly
            660             665                     670

Ala Phe Pro Leu Ala Leu Leu Met Gly Ile Ser Ala Thr Arg Gly Arg
        675             680                 685

Thr Ser Val Leu Gly Ala Glu Phe Cys Phe Asp Ala Thr Phe Glu Val
    690             695                 700

Asp Thr Ser Val Leu Gly Trp Val Val Ala Ser Val Val Ala Trp Ala
705             710                 715                     720

Ile Ala Leu Leu Ser Ser Met Ser Ala Gly Gly Trp Arg His Lys Ala
                725             730                     735

Val Ile Tyr Arg Thr Trp Cys Lys Gly Tyr Gln Ala Ile Arg Gln Arg
            740             745                 750

Val Val Arg Ser Pro Leu Gly Glu Gly Arg Pro Ala Lys Pro Leu Thr
        755             760                 765

Phe Ala Trp Cys Leu Ala Ser Tyr Ile Trp Pro Asp Ala Val Met Met
    770             775                 780

Val Val Val Ala Leu Val Leu Leu Phe Gly Leu Phe Asp Ala Leu Asp
785                 790             795                     800

Trp Ala Leu Glu Glu Ile Leu Val Ser Arg Pro Ser Leu Arg Arg Leu
            805             810                 815

Ala Arg Val Val Glu Cys Cys Val Met Ala Gly Glu Lys Ala Thr Thr
            820             825                 830

Val Arg Leu Val Ser Lys Met Cys Ala Arg Gly Ala Tyr Leu Phe Asp
        835             840                 845

His Met Gly Ser Phe Ser Arg Ala Val Lys Glu Arg Leu Leu Glu Trp
    850             855                 860

Asp Ala Ala Leu Glu Pro Leu Ser Phe Thr Arg Thr Asp Cys Arg Ile
865             870             875                     880

Ile Arg Asp Ala Ala Arg Thr Leu Ser Cys Gly Gln Cys Val Met Gly
            885             890                 895

Leu Pro Val Val Ala Arg Arg Gly Asp Glu Val Leu Ile Gly Val Phe
            900             905                 910

Gln Asp Val Asn His Leu Pro Pro Gly Phe Val Pro Thr Ala Pro Val
        915             920                 925

Val Ile Arg Arg Cys Gly Lys Gly Phe Leu Gly Val Thr Lys Ala Ala
    930             935                 940

Leu Thr Gly Arg Asp Pro Asp Leu His Pro Gly Asn Val Met Val Leu
945             950             955                     960

Gly Thr Ala Thr Ser Arg Ser Met Gly Thr Cys Leu Asn Gly Leu Leu
            965             970                     975

Phe Thr Thr Phe His Gly Ala Ser Arg Thr Ile Ala Thr Pro Val
            980             985                 990

Gly Ala Leu Asn Pro Arg Trp Trp Ser Ala Ser Asp Asp Val Thr Val
        995             1000                1005

Tyr Pro Leu Pro Asp Gly Ala Thr Ser Leu Thr Pro Cys Thr Cys Gln
    1010            1015                1020

```
Ala Glu Ser Cys Trp Val Ile Arg Ser Asp Gly Ala Leu Cys His Gly
1025                1030                1035                1040

Leu Ser Lys Gly Asp Lys Val Glu Leu Asp Val Ala Met Glu Val Ser
                1045                1050                1055

Asp Phe Arg Gly Ser Ser Gly Ser Pro Val Leu Cys Asp Gly His
                1060                1065                1070

Ala Val Gly Met Leu Val Ser Val Leu His Ser Gly Gly Arg Val Thr
                1075                1080                1085

Ala Ala Arg Phe Thr Arg Pro Trp Thr Gln Val Pro Thr Asp Ala Lys
                1090                1095                1100

Thr Thr Thr Glu Pro Pro Pro Val Pro Ala Lys Gly Val Phe Lys Glu
1105                1110                1115                1120

Ala Pro Leu Phe Met Pro Thr Gly Ala Gly Lys Ser Thr Arg Val Pro
                1125                1130                1135

Leu Glu Tyr Asp Asn Met Gly His Lys Val Leu Ile Leu Asn Pro Ser
                1140                1145                1150

Val Ala Thr Val Arg Ala Met Gly Pro Tyr Met Glu Arg Leu Ala Gly
                1155                1160                1165

Lys His Pro Ser Ile Tyr Cys Gly His Asp Thr Thr Ala Phe Thr Arg
                1170                1175                1180

Ile Thr Asp Ser Pro Leu Thr Tyr Ser Thr Tyr Gly Arg Phe Leu Ala
1185                1190                1195                1200

Asn Pro Arg Gln Met Leu Arg Gly Val Ser Val Val Ile Cys Asp Glu
                1205                1210                1215

Cys His Ser His Asp Ser Thr Val Leu Leu Gly Ile Gly Arg Val Arg
                1220                1225                1230

Glu Leu Ala Arg Gly Cys Gly Val Gln Leu Val Leu Tyr Ala Thr Ala
                1235                1240                1245

Thr Pro Pro Gly Ser Pro Met Thr Gln His Pro Ser Ile Ile Glu Thr
                1250                1255                1260

Lys Leu Asp Val Gly Glu Ile Pro Phe Tyr Gly His Gly Ile Pro Leu
1265                1270                1275                1280

Glu Arg Met Arg Thr Gly Arg His Leu Val Phe Cys His Ser Lys Ala
                1285                1290                1295

Glu Cys Glu Arg Leu Ala Gly Gln Phe Ser Ala Arg Gly Val Asn Ala
                1300                1305                1310

Ile Ala Tyr Tyr Arg Gly Lys Asp Ser Ser Ile Ile Lys Asp Gly Asp
                1315                1320                1325

Leu Val Val Cys Ala Thr Asp Ala Leu Ser Thr Gly Tyr Thr Gly Asn
                1330                1335                1340

Phe Asp Ser Val Thr Asp Cys Gly Leu Val Val Glu Glu Val Val Glu
1345                1350                1355                1360

Val Thr Leu Asp Pro Thr Ile Thr Ile Ser Leu Arg Thr Val Pro Ala
                1365                1370                1375

Ser Ala Glu Leu Ser Met Gln Arg Arg Gly Arg Thr Gly Arg Gly Arg
                1380                1385                1390

Ser Gly Arg Tyr Tyr Tyr Ala Gly Val Gly Lys Ala Pro Ala Gly Val
                1395                1400                1405

Val Arg Ser Gly Pro Val Trp Ser Ala Val Glu Ala Gly Val Thr Trp
                1410                1415                1420

Tyr Gly Met Glu Pro Asp Leu Thr Ala Asn Leu Leu Arg Leu Tyr Asp
1425                1430                1435                1440

Asp Cys Pro Tyr Thr Ala Ala Val Ala Ala Asp Ile Gly Glu Ala Ala
                1445                1450                1455
```

```
Val Phe Phe Ser Gly Leu Ala Pro Leu Arg Met His Pro Asp Val Ser
            1460                1465                1470
Trp Ala Lys Val Arg Gly Val Asn Trp Pro Leu Leu Val Gly Val Gln
        1475                1480                1485
Arg Thr Met Cys Arg Glu Thr Leu Ser Pro Gly Pro Ser Asp Asp Pro
    1490                1495                1500
Gln Trp Ala Gly Leu Lys Gly Pro Asn Pro Val Pro Leu Leu Leu Arg
1505                1510                1515                1520
Trp Gly Asn Asp Leu Pro Ser Lys Val Ala Gly His His Ile Val Asp
                1525                1530                1535
Asp Leu Val Arg Arg Leu Gly Val Ala Glu Gly Tyr Val Arg Cys Asp
            1540                1545                1550
Ala Gly Pro Ile Leu Met Ile Gly Leu Ala Ile Ala Gly Gly Met Ile
        1555                1560                1565
Tyr Ala Ser Tyr Thr Gly Ser Leu Val Val Val Thr Asp Trp Asp Val
    1570                1575                1580
Lys Gly Gly Gly Ala Pro Leu Tyr Arg His Gly Asp Gln Ala Thr Pro
1585                1590                1595                1600
Gln Pro Val Val Gln Val Pro Pro Val Asp His Arg Pro Gly Gly Glu
                1605                1610                1615
Ser Ala Pro Ser Asp Ala Lys Thr Val Thr Asp Ala Val Ala Ala Ile
            1620                1625                1630
Gln Val Asp Cys Asp Trp Thr Ile Met Thr Leu Ser Ile Gly Glu Val
        1635                1640                1645
Leu Ser Leu Ala Gln Ala Lys Thr Ala Glu Ala Tyr Thr Ala Thr Ala
    1650                1655                1660
Lys Trp Leu Ala Gly Cys Tyr Thr Gly Thr Arg Ala Val Pro Thr Val
1665                1670                1675                1680
Ser Ile Val Asp Lys Leu Phe Ala Gly Gly Trp Ala Ala Val Val Gly
                1685                1690                1695
His Cys His Ser Val Ile Ala Ala Ala Val Ala Ala Tyr Gly Ala Ser
            1700                1705                1710
Arg Ser Pro Pro Leu Ala Ala Ala Ala Ser Tyr Leu Met Gly Leu Gly
        1715                1720                1725
Val Gly Gly Asn Ala Gln Thr Arg Leu Ala Ser Ala Leu Leu Leu Gly
    1730                1735                1740
Ala Ala Gly Thr Ala Leu Gly Thr Pro Val Val Gly Leu Thr Met Ala
1745                1750                1755                1760
Gly Ala Phe Met Gly Gly Ala Ser Val Ser Pro Ser Leu Val Thr Ile
                1765                1770                1775
Leu Leu Gly Ala Val Gly Gly Trp Glu Gly Val Val Asn Ala Ala Ser
            1780                1785                1790
Leu Val Phe Asp Phe Met Ala Gly Lys Leu Ser Ser Glu Asp Leu Trp
        1795                1800                1805
Tyr Ala Ile Pro Val Leu Thr Ser Pro Gly Ala Gly Leu Ala Gly Ile
    1810                1815                1820
Ala Leu Gly Leu Val Leu Tyr Ser Ala Asn Asn Ser Gly Thr Thr Thr
1825                1830                1835                1840
Trp Leu Asn Arg Leu Leu Thr Thr Leu Pro Arg Ser Ser Cys Ile Pro
                1845                1850                1855
Asp Ser Tyr Phe Gln Gln Val Asp Tyr Cys Asp Lys Val Ser Ala Val
            1860                1865                1870
Leu Arg Arg Leu Ser Leu Thr Arg Thr Val Val Ala Leu Val Asn Arg
```

```
                        1875                           1880                          1885
Glu  Pro  Lys  Val  Asp  Glu  Val  Gln  Val  Gly  Tyr  Val  Trp  Asp  Leu  Trp
              1890                         1895                     1900
Glu  Trp  Ile  Met  Arg  Gln  Val  Arg  Val  Val  Met  Ala  Arg  Leu  Arg  Ala
1905                           1910                        1915                     1920
Leu  Cys  Pro  Val  Val  Ser  Leu  Pro  Leu  Trp  His  Cys  Gly  Glu  Gly  Trp
              1925                         1930                          1935
Ser  Gly  Glu  Trp  Leu  Leu  Asp  Gly  His  Val  Glu  Ser  Arg  Cys  Leu  Cys
                   1940                         1945                          1950
Gly  Cys  Val  Ile  Thr  Gly  Asp  Val  Leu  Asn  Gly  Gln  Leu  Lys  Glu  Pro
              1955                         1960                          1965
Val  Tyr  Ser  Thr  Lys  Leu  Cys  Arg  His  Tyr  Trp  Met  Gly  Thr  Val  Pro
1970                           1975                        1980
Val  Asn  Met  Leu  Gly  Tyr  Gly  Glu  Thr  Ser  Pro  Leu  Leu  Ala  Ser  Asp
1985                           1990                        1995                     2000
Thr  Pro  Lys  Val  Val  Pro  Phe  Gly  Thr  Ser  Gly  Trp  Ala  Glu  Val  Val
                        2005                         2010                          2015
Val  Thr  Thr  Thr  His  Val  Val  Ile  Arg  Arg  Thr  Ser  Ala  Tyr  Lys  Leu
              2020                         2025                          2030
Leu  Arg  Gln  Gln  Ile  Leu  Ser  Ala  Ala  Val  Ala  Glu  Pro  Tyr  Tyr  Val
              2035                         2040                          2045
Asp  Gly  Ile  Pro  Val  Ser  Trp  Asp  Ala  Asp  Ala  Arg  Ala  Pro  Ala  Met
              2050                         2055                          2060
Val  Tyr  Gly  Pro  Gly  Gln  Ser  Val  Thr  Ile  Asp  Gly  Glu  Arg  Tyr  Thr
2065                           2070                        2075                     2080
Leu  Pro  His  Gln  Leu  Arg  Leu  Arg  Asn  Val  Ala  Pro  Ser  Glu  Val  Ser
                        2085                         2090                          2095
Ser  Glu  Val  Ser  Ile  Asp  Ile  Gly  Thr  Glu  Thr  Glu  Asp  Ser  Glu  Leu
                   2100                         2105                          2110
Thr  Glu  Ala  Asp  Leu  Pro  Pro  Ala  Ala  Ala  Leu  Gln  Ala  Ile  Glu
                   2115                         2120                          2125
Asn  Ala  Ala  Arg  Ile  Leu  Glu  Pro  His  Ile  Asp  Val  Ile  Met  Glu  Asp
              2130                         2135                          2140
Cys  Ser  Thr  Pro  Ser  Leu  Cys  Gly  Ser  Ser  Arg  Glu  Met  Pro  Val  Trp
2145                           2150                        2155                     2160
Gly  Glu  Asp  Ile  Pro  Arg  Thr  Pro  Ser  Pro  Ala  Leu  Ile  Ser  Val  Thr
                        2165                         2170                          2175
Glu  Ser  Ser  Ser  Asp  Glu  Lys  Thr  Pro  Ser  Val  Ser  Ser  Gln  Glu
                   2180                         2185                          2190
Asp  Thr  Pro  Ser  Ser  Asp  Ser  Phe  Glu  Val  Ile  Gln  Glu  Ser  Glu  Thr
              2195                         2200                          2205
Ala  Glu  Gly  Glu  Glu  Ser  Val  Phe  Asn  Val  Ala  Leu  Ser  Val  Leu  Lys
              2210                         2215                          2220
Ala  Leu  Phe  Pro  Gln  Ser  Asp  Ala  Thr  Arg  Lys  Leu  Thr  Val  Lys  Met
2225                           2230                        2235                     2240
Ser  Cys  Cys  Val  Glu  Lys  Ser  Val  Thr  Arg  Phe  Phe  Ser  Leu  Gly  Leu
                        2245                         2250                          2255
Thr  Val  Ala  Asp  Val  Ala  Ser  Leu  Cys  Glu  Met  Glu  Ile  Gln  Asn  His
                   2260                         2265                          2270
Thr  Ala  Tyr  Cys  Asp  Gln  Val  Arg  Thr  Pro  Leu  Glu  Leu  Gln  Val  Gly
                   2275                         2280                          2285
Cys  Leu  Val  Gly  Asn  Glu  Leu  Thr  Phe  Glu  Cys  Asp  Lys  Cys  Glu  Ala
              2290                         2295                          2300
```

```
Arg Gln Glu Thr Leu Ala Ser Phe Ser Tyr Ile Trp Ser Gly Val Pro
2305                2310                2315                2320

Leu Thr Arg Ala Thr Pro Ala Lys Pro Pro Val Val Arg Pro Val Gly
                2325                2330                2335

Ser Leu Leu Val Ala Asp Thr Thr Lys Val Tyr Val Thr Asn Pro Asp
                2340                2345                2350

Asn Val Gly Arg Arg Val Asp Lys Val Thr Phe Trp Arg Ala Pro Arg
                2355                2360                2365

Val His Asp Lys Tyr Leu Val Asp Ser Ile Glu Arg Ala Lys Arg Ala
                2370                2375                2380

Ala Gln Ala Cys Leu Ser Met Gly Tyr Thr Tyr Glu Glu Ala Ile Arg
2385                2390                2395                2400

Thr Val Arg Pro His Ala Ala Met Gly Trp Gly Ser Lys Val Ser Val
                2405                2410                2415

Lys Asp Leu Ala Thr Pro Ala Gly Lys Met Ala Val His Asp Arg Leu
                2420                2425                2430

Gln Glu Ile Leu Glu Gly Thr Pro Val Pro Phe Thr Leu Thr Val Lys
                2435                2440                2445

Lys Glu Val Phe Phe Lys Asp Arg Lys Glu Glu Lys Ala Pro Arg Leu
                2450                2455                2460

Ile Val Phe Pro Pro Leu Asp Phe Arg Ile Ala Glu Lys Leu Ile Leu
2465                2470                2475                2480

Gly Asp Pro Gly Arg Val Ala Lys Ala Val Leu Gly Gly Ala Tyr Ala
                2485                2490                2495

Phe Gln Tyr Thr Pro Asn Gln Arg Val Lys Glu Met Leu Lys Leu Trp
                2500                2505                2510

Glu Ser Lys Lys Thr Pro Cys Ala Ile Cys Val Asp Ala Thr Cys Phe
                2515                2520                2525

Asp Ser Ser Ile Thr Glu Glu Asp Val Ala Leu Glu Thr Glu Leu Tyr
                2530                2535                2540

Ala Leu Ala Ser Asp His Pro Glu Trp Val Arg Ala Leu Gly Lys Tyr
                2545                2550                2555                2560

Tyr Ala Ser Gly Thr Met Val Thr Pro Glu Gly Val Pro Val Gly Glu
                2565                2570                2575

Arg Tyr Cys Arg Ser Ser Gly Val Leu Thr Thr Ser Ala Ser Asn Cys
                2580                2585                2590

Leu Thr Cys Tyr Ile Lys Val Lys Ala Ala Cys Glu Arg Val Gly Leu
                2595                2600                2605

Lys Asn Val Ser Leu Leu Ile Ala Gly Asp Asp Cys Leu Ile Ile Cys
                2610                2615                2620

Glu Arg Pro Val Cys Asp Pro Ser Asp Ala Leu Gly Arg Ala Leu Ala
2625                2630                2635                2640

Ser Tyr Gly Tyr Ala Cys Glu Pro Ser Tyr His Ala Ser Leu Asp Thr
                2645                2650                2655

Ala Pro Phe Cys Ser Thr Trp Leu Ala Glu Cys Asn Ala Asp Gly Lys
                2660                2665                2670

Arg His Phe Phe Leu Thr Thr Asp Phe Arg Arg Pro Leu Ala Arg Met
                2675                2680                2685

Ser Ser Glu Tyr Ser Asp Pro Met Ala Ser Ala Ile Gly Tyr Ile Leu
                2690                2695                2700

Leu Tyr Pro Trp His Pro Ile Thr Arg Trp Val Ile Ile Pro His Val
                2705                2710                2715                2720

Leu Thr Cys Ala Phe Arg Gly Gly Gly Thr Pro Ser Asp Pro Val Trp
                2725                2730                2735
```

| Cys | Gln | Val | His | Gly | Asn | Tyr | Tyr | Lys | Phe | Pro | Leu | Asp | Lys | Leu | Pro |
|     |     |     | 2740|     |     |     | 2745|     |     |     |     |     | 2750|     |     |

| Asn | Ile | Ile | Val | Ala | Leu | His | Gly | Pro | Ala | Ala | Leu | Arg | Val | Thr | Ala |
|     |     |     | 2755|     |     |     | 2760|     |     |     |     |     | 2765|     |     |

| Asp | Thr | Thr | Lys | Thr | Lys | Met | Glu | Ala | Gly | Lys | Val | Leu | Ser | Asp | Leu |
|     | 2770|     |     |     |     | 2775|     |     |     |     | 2780|     |     |     |     |

| Lys | Leu | Pro | Gly | Leu | Ala | Val | His | Arg | Lys | Lys | Ala | Gly | Ala | Leu | Arg |
| 2785|     |     |     |     | 2790|     |     |     |     | 2795|     |     |     |     | 2800|

| Thr | Arg | Met | Leu | Arg | Ser | Arg | Gly | Trp | Ala | Glu | Leu | Ala | Arg | Gly | Leu |
|     |     |     |     | 2805|     |     |     |     | 2810|     |     |     |     |     | 2815|

| Leu | Trp | His | Pro | Gly | Leu | Arg | Leu | Pro | Pro | Pro | Glu | Ile | Ala | Gly | Ile |
|     |     |     | 2820|     |     |     |     | 2825|     |     |     |     | 2830|     |     |

| Pro | Gly | Gly | Phe | Pro | Leu | Ser | Pro | Pro | Tyr | Met | Gly | Val | Val | His | Gln |
|     |     | 2835|     |     |     |     | 2840|     |     |     |     | 2845|     |     |     |

| Leu | Asp | Phe | Thr | Ser | Gln | Arg | Ser | Arg | Trp | Arg | Trp | Leu | Gly | Phe | Leu |
|     |     | 2850|     |     |     |     | 2855|     |     |     |     | 2860|     |     |     |

| Ala | Leu | Leu | Ile | Val | Ala | Leu | Phe | Gly |
| 2865|     |     |     |     |     | 2870|     |     |

(2) INFORMATION FOR SEQ ID NO:16:

(i) SEQUENCE CHARACTERISTICS:
  (A) LENGTH: 27 base pairs
  (B) TYPE: nucleic acid
  (C) STRANDEDNESS: single
  (D) TOPOLOGY: linear (ii) MOLECULE TYPE: DNA (iii) HYPOTHETICAL: NO (iv) ANTI-SENSE: NO (vi) ORIGINAL SOURCE:
  (C) INDIVIDUAL ISOLATE: PROBE 470-20- 1-152F (xi) SEQUENCE DESCRIPTION: SEQ ID NO:16:

TCGGTTACTG AGAGCAGCTC AGATGAG     27

(2) INFORMATION FOR SEQ ID NO:17:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (iii) HYPOTHETICAL: NO (vi) ORIGINAL SOURCE:
  (C) INDIVIDUAL ISOLATE: JML-A, PRIMER (xi) SEQUENCE DESCRIPTION: SEQ ID NO:17:

AGGAATTCAG CGGCCGCGAG     20

(2) INFORMATION FOR SEQ ID NO:18:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: DNA ( i i i ) HYPOTHETICAL: NO ( v i ) ORIGINAL SOURCE:
   ( C ) INDIVIDUAL ISOLATE: JML-B, PRIMER ( x i ) SEQUENCE DESCRIPTION: SEQ ID NO:18:

```
CTCGCGGCCG CTGAATTCCT TT                                                22
```

( 2 ) INFORMATION FOR SEQ ID NO:19:

( i ) SEQUENCE CHARACTERISTICS:
      ( A ) LENGTH: 203 base pairs
      ( B ) TYPE: nucleic acid
      ( C ) STRANDEDNESS: double
      ( D ) TOPOLOGY: linear ( i i ) MOLECULE TYPE: cDNA ( i i i ) HYPOTHETICAL: NO ( v i ) ORIGINAL SOURCE:
      ( C ) INDIVIDUAL ISOLATE: 470-20-1 CLONE, WITHOUT SISPA
         LINKERS ( i x ) FEATURE:
      ( A ) NAME/KEY: CDS
      ( B ) LOCATION: 2..203

( x i ) SEQUENCE DESCRIPTION: SEQ ID NO:19:

```
G GCT GTC TCG GAC TCT TGG ATG ACC TCG AAT GAG TCA GAG GAC GGG          46
  Ala Val Ser Asp Ser Trp Met Thr Ser Asn Glu Ser Glu Asp Gly
  1               5                   10                  15

GTA TCC TCC TGC GAG GAG GAC ACC GGC GGG GTC TTC TCA TCT GAG CTG        94
Val Ser Ser Cys Glu Glu Asp Thr Gly Gly Val Phe Ser Ser Glu Leu
              20                  25                  30

CTC TCA GTA ACC GAG ATA AGT GCT GGC GAT GGA GTA CGG GGG ATG TCT        142
Leu Ser Val Thr Glu Ile Ser Ala Gly Asp Gly Val Arg Gly Met Ser
             35                  40                  45

TCT CCC CAT ACA GGC ATC TCT CGG CTA CTA CCA CAA AGA GAG GGT GTA        190
Ser Pro His Thr Gly Ile Ser Arg Leu Leu Pro Gln Arg Glu Gly Val
         50                  55                  60

CTG CAG TCC TCC A                                                      203
Leu Gln Ser Ser
        65
```

( 2 ) INFORMATION FOR SEQ ID NO:20:

( i ) SEQUENCE CHARACTERISTICS:
      ( A ) LENGTH: 67 amino acids
      ( B ) TYPE: amino acid
      ( D ) TOPOLOGY: linear ( i i ) MOLECULE TYPE: protein ( x i ) SEQUENCE DESCRIPTION: SEQ ID NO:20:

```
Ala Val Ser Asp Ser Trp Met Thr Ser Asn Glu Ser Glu Asp Gly Val
1               5                   10                  15

Ser Ser Cys Glu Glu Asp Thr Gly Gly Val Phe Ser Ser Glu Leu Leu
            20                  25                  30

Ser Val Thr Glu Ile Ser Ala Gly Asp Gly Val Arg Gly Met Ser Ser
         35                  40                  45

Pro His Thr Gly Ile Ser Arg Leu Leu Pro Gln Arg Glu Gly Val Leu
     50                  55                  60

Gln Ser Ser
65
```

( 2 ) INFORMATION FOR SEQ ID NO:21:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: 470-20-1- 152R ( x i ) SEQUENCE DESCRIPTION: SEQ ID NO:21:

CTCATCTGAG CTGCTCTCAG TAACCGA 27

( 2 ) INFORMATION FOR SEQ ID NO:22:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: OLIGONUCLEOTIDE B ( x i ) SEQUENCE DESCRIPTION: SEQ ID NO:22:

CTGTCTCGGA CTCTTGGATG ACCT 24

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: COGNATE OLIGONUCLEOTIDE 211R'

( x i ) SEQUENCE DESCRIPTION: SEQ ID NO:23:

ATACCCCGTC CTCTGACTCA TTCG 24

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: COGNATE OLIGONUCLEOTIDE B'

( x i ) SEQUENCE DESCRIPTION: SEQ ID NO:24:

AGGTCATCCA AGAGTCCGAG ACAG 24

( 2 ) INFORMATION FOR SEQ ID NO:25:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: LAMBDA GT 11 FORWARD PRIMER, 20mer ( x i ) SEQUENCE DESCRIPTION: SEQ ID NO:25:

CACATGGCTG AATATCGACG 20

( 2 ) INFORMATION FOR SEQ ID NO:26:

( i ) SEQUENCE CHARACTERISTICS:
    ( A ) LENGTH: 180 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( C ) INDIVIDUAL ISOLATE: Consensus Sequence 4E3

( x i ) SEQUENCE DESCRIPTION: SEQ ID NO:26:

GCGAGCCTAG TCTTTGACTT CATGGCGGGG AAACTTTCAT CAGAAGATCT GTGGTATGCC 60

ATCCCGGTAC TGACCAGCCC GGGGGCGGGC CTTGCGGGGA TCGCTCTCGG GTTGGTTTTG 120

TATTCAGCTA ACAACTCTGG CACTACCACT TGGTTGAACC GTCTGCTGAC TACGTTACCA 180

( 2 ) INFORMATION FOR SEQ ID NO:27:

( i ) SEQUENCE CHARACTERISTICS:
    ( A ) LENGTH: 430 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( C ) INDIVIDUAL ISOLATE: Consensus Sequence 3E3

( x i ) SEQUENCE DESCRIPTION: SEQ ID NO:27:

GGCACTACCA CTTGGTTGAA CCGTCTGCTG ACTACGTTAC CAAGGTCTTC ATGTATCCCG 60

GACAGTTACT TTCAGCAAGT TGACTATTGC GACAAGGTCT CAGCCGTGCT CCGGCGCCTG 120

-continued

| | | | | | | |
|---|---|---|---|---|---|---|
|AGCCTCACCC|GCACAGTGGT|TGCCCTGGTC|AACAGGGAGC|CTAAGGTGGA|TGAGGTACAG|180|
|GTGGGGTATG|TCTGGGACCT|GTGGGAGTGG|ATCATGCGCC|AAGTGCGCGT|GGTCATGGCC|240|
|AGACTCAGGG|CCCTCTGCCC|CGTGGTGTCA|CTACCCTTGT|GGCATTGCGG|GGAGGGGTGG|300|
|TCCGGGAAT|GGTTGCTTGA|CGGTCATGTT|GAGAGTCGCT|GCCTCTGTGG|CTGCGTGATC|360|
|ACTGGTGACG|TTCTGAATGG|GCAACTCAAA|GAACCAGTTT|ACTCTACCAA|GCTGTGCCGG|420|
|CACTATTGGA| | | | | |430|

( 2 ) INFORMATION FOR SEQ ID NO:28:

( i ) SEQUENCE CHARACTERISTICS:
        ( A ) LENGTH: 180 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 2E5

( x i ) SEQUENCE DESCRIPTION: SEQ ID NO:28:

| | | | | | | |
|---|---|---|---|---|---|---|
|CTTACCGTCA|AGATGTCGTG|CTGCGTTGAA|AAGAGCGTCA|CGCGCTTTTT|CTCATTGGGG|60|
|TTGACGGTGG|CTGATGTTGC|TAGCCTGTGT|GAGATGGAAA|TCCAGAACCA|TACAGCCTAT|120|
|TGTGACCAGG|TGCGCACTCC|GCTTGAATTG|CAGGTTGGGT|GCTTGGTGGG|CAATGAACTT|180|

( 2 ) INFORMATION FOR SEQ ID NO:29:

( i ) SEQUENCE CHARACTERISTICS:
        ( A ) LENGTH: 344 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 1E5

( x i ) SEQUENCE DESCRIPTION: SEQ ID NO:29:

| | | | | | | |
|---|---|---|---|---|---|---|
|CTTCTCTTTG|TGGTAGTAGC|CGAGAGATGC|CTGTATGGGG|AGAAGACATC|CCCCGTACTC|60|
|CATCGCCAGC|ACTTATCTCG|GTTACTGAGA|GCAGCTCAGA|TGAGAAGACC|CCGTCGGTGT|120|
|CCTCCTCGCA|GGAGGATACC|CCGTCCTCTG|ACTCATTCGA|GGTCATCCAA|GAGTCCGAGA|180|
|CAGCCGAAGG|GGAGGAAAGT|GTCTTCAACG|TGGCTCTTTC|CGTATTAAAA|GCCTTATTTC|240|
|CACAGAGCGA|CGCGACCAGG|AAGCTTACCG|TCAAGATGTC|GTGCTGCGTT|GAAAAGAGCG|300|
|TCACGCGCTT|TTTCTCATTG|GGGTTGACGG|TGGCTGATGT|TGCT| |344|

( 2 ) INFORMATION FOR SEQ ID NO:30:

( i ) SEQUENCE CHARACTERISTICS:
        ( A ) LENGTH: 423 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
  ( C ) INDIVIDUAL ISOLATE: Consensus Sequence 4E5

( x i ) SEQUENCE DESCRIPTION: SEQ ID NO:30:

| | | | | | | |
|---|---|---|---|---|---|---|
| GTAAGGCCAC | ATGCTGCCAT | GGGCTGGGGA | TCTAAGGTGT | CGGTTAAGGA | CTTAGCCACC | 60 |
| CCCGCGGGGA | AGATGGCCGT | CCATGACCGG | CTTCAGGAGA | TACTTGAAGG | GACTCCGGTC | 120 |
| CCCTTTACTC | TTACTGTGAA | AAAGGAGGTG | TTCTTCAAAG | ACCGGAAGGA | GGAGAAGGCC | 180 |
| CCCCGCCTCA | TTGTGTTCCC | CCCCCTGGAC | TTCCGGATAG | CTGAAAAGCT | CATCTTGGGA | 240 |
| GACCCAGGCC | GGGTAGCCAA | GGCGGTGTTG | GGGGGGGCCT | ACGCCTTCCA | GTACACCCCA | 300 |
| AATCAGCGAG | TTAAGGAGAT | GCTCAAGCTA | TGGGAGTCTA | AGAAGACCCC | TTGCGCCATC | 360 |
| TGTGTGGACG | CCACCTGCTT | CGACAGTAGC | ATAACTGAAG | AGGACGTGGC | TTTGGAGACA | 420 |
| GAG | | | | | | 423 |

( 2 ) INFORMATION FOR SEQ ID NO:31:

( i ) SEQUENCE CHARACTERISTICS:
    ( A ) LENGTH: 516 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( C ) INDIVIDUAL ISOLATE: Consensus Sequence 3E5

( x i ) SEQUENCE DESCRIPTION: SEQ ID NO:31:

| | | | | | | |
|---|---|---|---|---|---|---|
| TACAGCCTAT | TGTGACCAGG | TGCGCACTCC | GCTTGAATTG | CAGGTTGGGT | GCTTGGTGGG | 60 |
| CAATGAACTT | ACCTTTGAAT | GTGACAAGTG | TGAGGCTAGG | CAAGAAACCT | TGGCCTCCTT | 120 |
| CTCTTACATT | TGGTCTGGAG | TGCCGCTGAC | TAGGGCCACG | CCGGCCAAGC | CTCCCGTGGT | 180 |
| GAGGCCGGTT | GGCTCTTTGT | TAGTGGCCGA | CACTACTAAG | GTGTATGTTA | CCAATCCAGA | 240 |
| CAATGTGGGA | CGGAGGGTGG | ACAAGGTGAC | CTTCTGGCGT | GCTCCTAGGG | TTCATGATAA | 300 |
| GTACCTCGTG | GACTCTATTG | AGCGCGCTAA | GAGGGCCGCT | CAAGCCTGCC | TAAGCATGGG | 360 |
| TTACACTTAT | GAGGAAGCAA | TAAGGACTGT | AAGGCCACAT | GCTGCCATGG | GCTGGGGATC | 420 |
| TAAGGTGTCG | GTTAAGGACT | TAGCCACCCC | CGCGGGGAAG | ATGGCCGTCC | ATGACCGGCT | 480 |
| TCAGGAGATA | CTTGAAGGGA | CTCCGGTCCC | CTTTAC | | | 516 |

( 2 ) INFORMATION FOR SEQ ID NO:32:

( i ) SEQUENCE CHARACTERISTICS:
    ( A ) LENGTH: 518 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:

(C) INDIVIDUAL ISOLATE: Consensus Sequence 2E3

(x i) SEQUENCE DESCRIPTION: SEQ ID NO:32:

| | | | | | | |
|---|---|---|---|---|---|---|
| GAATGGGCAA | CTCAAAGAAC | CAGTTTACTC | TACCAAGCTG | TGCCGGCACT | ATTGGATGGG | 60 |
| GACTGTCCCT | GTGAACATGC | TGGGTTACGG | TGAAACGTCG | CCTCTCCTGG | CCTCCGACAC | 120 |
| CCCGAAGGTT | GTGCCCTTCG | GGACGTCTGG | CTGGGCTGAG | GTGGTGGTGA | CCACTACCCA | 180 |
| CGTGGTAATC | AGGAGGACCT | CCGCCTATAA | GCTGCTGCGC | CAGCAAATCC | TATCGGCTGC | 240 |
| TGTAGCTGAG | CCCTACTACG | TCGACGGCAT | TCCGGTCTCA | TGGGACGCGG | ACGCTCGTGC | 300 |
| GCCCGCCATG | GTCTATGGCC | CTGGGCAAAG | TGTTACCATT | GACGGGAGC | GCTACACCTT | 360 |
| GCCTCATCAA | CTGAGGCTCA | GGAATGTGGC | ACCCTCTGAG | GTTTCATCCG | AGGTGTCCAT | 420 |
| TGACATTGGG | ACGGAGACTG | AAGACTCAGA | ACTGACTGAG | GCCGATCTGC | CGCCGGCGGC | 480 |
| TGCTGCTCTC | CAAGCGATCG | AGAATGCTGC | GAGGATTC | | | 518 |

(2) INFORMATION FOR SEQ ID NO:33:

(i) SEQUENCE CHARACTERISTICS:
(A) LENGTH: 268 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (v) ORIGINAL SOURCE:
(C) INDIVIDUAL ISOLATE: Consensus Sequence 1E3

(x i) SEQUENCE DESCRIPTION: SEQ ID NO:33:

| | | | | | | |
|---|---|---|---|---|---|---|
| CTTACTGAGG | CCGATCTGCC | GCCGGCGGCT | GCTGCTCTCC | AAGCGATCGA | GAATGCTGCG | 60 |
| AGGATTCTTG | AACCGCACAT | TGATGTCATC | ATGGAGGACT | GCAGTACACC | CTCTCTTTGT | 120 |
| GGTAGTAGCC | GAGAGATGCC | TGTATGGGGA | GAAGACATCC | CCCGTACTCC | ATCGCCAGCA | 180 |
| CTTATCTCGG | TTACTGAGAG | CAGCTCAGAT | GAGAAGACCC | CGTCGGTGTC | CTCCTCGCAG | 240 |
| GAGGATACCC | CGTCCTCTGA | CTCATTCG | | | | 268 |

(2) INFORMATION FOR SEQ ID NO:34:

(i) SEQUENCE CHARACTERISTICS:
(A) LENGTH: 781 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (v) ORIGINAL SOURCE:
(C) INDIVIDUAL ISOLATE: INDIVIDUAL CLONE 4E5-20

(x i) SEQUENCE DESCRIPTION: SEQ ID NO:34:

| | | | | | | |
|---|---|---|---|---|---|---|
| GTAAGGCCAC | ATGCTGCCAT | GGGCTGGGGA | TCTAAGGTGT | CGGTTAAGGA | CTTAGCCACC | 60 |
| CCCGCGGGGA | AGATGGCCGT | CCATGACCGG | CTTCAGGAGA | TACTTGAAGG | GACTCCGGTC | 120 |
| CCCTTTACTC | TTACTGTGAA | AAAGGAGGTG | TTCTTCAAAG | ACCGGAAGGA | GGAGAAGGCC | 180 |
| CCCCGCCTCA | TTGTGTTCCC | CCCCCTGGAC | TTCCGGATAG | CTGAAAAGCT | CATCTTGGGA | 240 |

-continued

| | | | | | | |
|---|---|---|---|---|---|---|
| GACCCAGGCC | GGGTAGCCAA | GGCGGTGTTG | GGGGGGGCCT | ACGCCTTCCA | GTACACCCCA | 300 |
| AATCAGCGAG | TTAAGGAGAT | GCTCAAGCTA | TGGGAGTCTA | AGAAGACCCC | TTGCGCCATC | 360 |
| TGTGTGGACG | CCACCTGCTT | CGACAGTAGC | ATAACTGAAG | AGGACGTGGC | TTTGGAGACA | 420 |
| GAGTTATACG | CTCTGGCCTC | TGACCATCCA | GAATGGGTGC | GGGCACCTGG | GAAATACTAT | 480 |
| GCCTCAGGCA | CCATGGTCAC | CCCGGAAGGG | GTGCCCGTCG | GTGAGAGGTA | TTGCAGATCC | 540 |
| TCGGGTGTCC | TAACAACTAG | CGCGAGCAAC | TGCCTGACCT | GCTACATCAA | GGTGAAAGCT | 600 |
| GCCTGTGAGA | GAGTGGGGCT | GAAAAATGTC | TCTCTTCTCA | TAGCCGGCGA | TGACTGCTTG | 660 |
| ATCATATGTG | AGCGGCCAGT | GTGCGACCCA | AGCGACGCTT | TGGGCAGAGC | CCTAGCGAGC | 720 |
| TATGGGTACG | CGTGCGAGCC | CTCATATCAT | GCATCATTGG | ACACGGCCCC | CTTCTGCTCC | 780 |
| A | | | | | | 781 |

( 2 ) INFORMATION FOR SEQ ID NO:35:

( i ) SEQUENCE CHARACTERISTICS:
( A ) LENGTH: 27 base pairs
( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: PROBE 470- 201-1-142R ( x i ) SEQUENCE DESCRIPTION: SEQ ID NO:35:

TCGGTTACTG AGAGCAGCTC AGATGAG 27

( 2 ) INFORMATION FOR SEQ ID NO:36:

( i ) SEQUENCE CHARACTERISTICS:
( A ) LENGTH: 27 base pairs
( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: PROBE 470-20- 1-152F ( x i ) SEQUENCE DESCRIPTION: SEQ ID NO:36:

TCGGTTACTG AGAGCAGCTC AGATGAG 27

( 2 ) INFORMATION FOR SEQ ID NO:37:

( i ) SEQUENCE CHARACTERISTICS:
( A ) LENGTH: 570 base pairs
( B ) TYPE: nucleic acid
( C ) STRANDEDNESS: double
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:

(C) INDIVIDUAL ISOLATE: Clone 470EXP1

(ix) FEATURE:
    (A) NAME/KEY: CDS
    (B) LOCATION: 1..570

(xi) SEQUENCE DESCRIPTION: SEQ ID NO:37:

| GCT | GTA | TGG | TTC | TGG | ATT | TCC | ATC | TCA | CAC | AGG | CTA | GCA | ACA | TCA | GCC | 48 |
|---|---|---|---|---|---|---|---|---|---|---|---|---|---|---|---|---|
| Ala | Val | Trp | Phe | Trp | Ile | Ser | Ile | Ser | His | Arg | Leu | Ala | Thr | Ser | Ala | |
| 1 | | | | 5 | | | | | 10 | | | | | 15 | | |
| ACC | GTC | AAC | CCC | AAT | GAG | AAA | AAG | CGC | GTG | ACG | CTC | TTT | TCA | ACG | CAG | 96 |
| Thr | Val | Asn | Pro | Asn | Glu | Lys | Lys | Arg | Val | Thr | Leu | Phe | Ser | Thr | Gln | |
| | | | 20 | | | | | 25 | | | | | 30 | | | |
| CAC | GAC | ATC | TTG | ACG | GTA | AGC | TTC | CTG | GTC | GCG | TCG | CTC | TGT | GGA | AAT | 144 |
| His | Asp | Ile | Leu | Thr | Val | Ser | Phe | Leu | Val | Ala | Ser | Leu | Cys | Gly | Asn | |
| | | 35 | | | | | 40 | | | | | 45 | | | | |
| AAG | GCT | TTT | AAT | ACG | GAA | AGA | GCC | ACG | TTG | AAG | ACA | CTT | TCC | TCC | CCT | 192 |
| Lys | Ala | Phe | Asn | Thr | Glu | Arg | Ala | Thr | Leu | Lys | Thr | Leu | Ser | Ser | Pro | |
| | 50 | | | | | 55 | | | | | 60 | | | | | |
| TCG | GCT | GTC | TCG | GAC | TCT | TGG | ATG | ACC | TCG | AAT | GAG | TCA | GAG | GAC | GGG | 240 |
| Ser | Ala | Val | Ser | Asp | Ser | Trp | Met | Thr | Ser | Asn | Glu | Ser | Glu | Asp | Gly | |
| 65 | | | | | 70 | | | | | 75 | | | | | 80 | |
| GTA | TCC | TCC | TGC | GAG | GAG | GAC | ACC | GAC | GGG | GTC | TTC | TCA | TCT | GAG | CTG | 288 |
| Val | Ser | Ser | Cys | Glu | Glu | Asp | Thr | Asp | Gly | Val | Phe | Ser | Ser | Glu | Leu | |
| | | | | 85 | | | | | 90 | | | | | 95 | | |
| CTC | TCA | GTA | ACC | GAG | ATA | AGT | GCT | GGC | GAT | GGA | GTA | CGG | GGG | ATG | TCT | 336 |
| Leu | Ser | Val | Thr | Glu | Ile | Ser | Ala | Gly | Asp | Gly | Val | Arg | Gly | Met | Ser | |
| | | | 100 | | | | | 105 | | | | | 110 | | | |
| TCT | CCC | CAT | ACA | GGC | ATC | TCT | CGG | CTA | CTA | CCA | CAA | AGA | GAG | GGT | GTA | 384 |
| Ser | Pro | His | Thr | Gly | Ile | Ser | Arg | Leu | Leu | Pro | Gln | Arg | Glu | Gly | Val | |
| | | 115 | | | | | 120 | | | | | 125 | | | | |
| CTG | CAG | TCC | TCC | ATG | ATG | ACA | TCA | ATG | TGC | GGT | TCA | AGA | ATC | CTC | GCA | 432 |
| Leu | Gln | Ser | Ser | Met | Met | Thr | Ser | Met | Cys | Gly | Ser | Arg | Ile | Leu | Ala | |
| | 130 | | | | | 135 | | | | | 140 | | | | | |
| GCA | TTC | TCG | ATC | GCT | TGG | AGA | GCA | GCA | GCC | GCC | GGC | GGC | AGA | TCG | GCC | 480 |
| Ala | Phe | Ser | Ile | Ala | Trp | Arg | Ala | Ala | Ala | Ala | Gly | Gly | Arg | Ser | Ala | |
| 145 | | | | | 150 | | | | | 155 | | | | | 160 | |
| TCA | GTC | AGT | TCT | GAG | TCT | TCA | GTC | TCC | GTC | CCA | ATG | TCA | ATG | GAC | ACC | 528 |
| Ser | Val | Ser | Ser | Glu | Ser | Ser | Val | Ser | Val | Pro | Met | Ser | Met | Asp | Thr | |
| | | | | 165 | | | | | 170 | | | | | 175 | | |
| TCG | GAT | GAA | ACC | TCA | GAG | GGT | GCC | ACA | TTC | CTG | AGC | CTC | AGT | | | 570 |
| Ser | Asp | Glu | Thr | Ser | Glu | Gly | Ala | Thr | Phe | Leu | Ser | Leu | Ser | | | |
| | | | 180 | | | | | 185 | | | | | 190 | | | |

(2) INFORMATION FOR SEQ ID NO:38:

(i) SEQUENCE CHARACTERISTICS:
        (A) LENGTH: 190 amino acids
        (B) TYPE: amino acid
        (D) TOPOLOGY: linear (ii) MOLECULE TYPE: protein (xi) SEQUENCE DESCRIPTION: SEQ ID NO:38:

| Ala | Val | Trp | Phe | Trp | Ile | Ser | Ile | Ser | His | Arg | Leu | Ala | Thr | Ser | Ala |
|---|---|---|---|---|---|---|---|---|---|---|---|---|---|---|---|
| 1 | | | | 5 | | | | | 10 | | | | | 15 | |
| Thr | Val | Asn | Pro | Asn | Glu | Lys | Lys | Arg | Val | Thr | Leu | Phe | Ser | Thr | Gln |
| | | | 20 | | | | | 25 | | | | | 30 | | |
| His | Asp | Ile | Leu | Thr | Val | Ser | Phe | Leu | Val | Ala | Ser | Leu | Cys | Gly | Asn |
| | | 35 | | | | | 40 | | | | | 45 | | | |
| Lys | Ala | Phe | Asn | Thr | Glu | Arg | Ala | Thr | Leu | Lys | Thr | Leu | Ser | Ser | Pro |
| | 50 | | | | | 55 | | | | | 60 | | | | |

| Ser | Ala | Val | Ser | Asp | Ser | Trp | Met | Thr | Ser | Asn | Glu | Ser | Glu | Asp | Gly |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Val | Ser | Ser | Cys | Glu | Glu | Asp | Thr | Asp | Gly | Val | Phe | Ser | Ser | Glu | Leu |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Leu | Ser | Val | Thr | Glu | Ile | Ser | Ala | Gly | Asp | Gly | Val | Arg | Gly | Met | Ser |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Ser | Pro | His | Thr | Gly | Ile | Ser | Arg | Leu | Leu | Pro | Gln | Arg | Glu | Gly | Val |
|-----|-----|-----|-----|-----|-----|-----|-----|-----|-----|-----|-----|-----|-----|-----|-----|
|     |     | 115 |     |     |     |     |     | 120 |     |     |     |     | 125 |     |     |

| Leu | Gln | Ser | Ser | Met | Met | Thr | Ser | Met | Cys | Gly | Ser | Arg | Ile | Leu | Ala |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ala | Phe | Ser | Ile | Ala | Trp | Arg | Ala | Ala | Ala | Gly | Gly | Arg | Ser | Ala |
|-----|-----|-----|-----|-----|-----|-----|-----|-----|-----|-----|-----|-----|-----|-----|
| 145 |     |     |     |     | 150 |     |     |     |     | 155 |     |     |     | 160 |

| Ser | Val | Ser | Ser | Glu | Ser | Ser | Val | Ser | Val | Pro | Met | Ser | Met | Asp | Thr |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Ser | Asp | Glu | Thr | Ser | Glu | Gly | Ala | Thr | Phe | Leu | Ser | Leu | Ser |
|-----|-----|-----|-----|-----|-----|-----|-----|-----|-----|-----|-----|-----|-----|
|     |     |     | 180 |     |     |     |     | 185 |     |     |     |     | 190 |

( 2 ) INFORMATION FOR SEQ ID NO:39:

( i ) SEQUENCE CHARACTERISTICS:
        ( A ) LENGTH: 1288 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 5E3

( x i ) SEQUENCE DESCRIPTION: SEQ ID NO:39:

```
ACGGGTAGGG  GCAGGTCTGG  ACGCTACTAC  TACGCGGGGG  TGGGCAAAGC  CCCTGCGGGT      60
GTGGTGCGCT  CAGGTCCTGT  CTGGTCGGCG  GTGGAAGCTG  GAGTGACCTG  GTACGGAATG     120
GAACCTGACT  TGACAGCTAA  CCTACTGAGA  CTTTACGACG  ACTGCCCTTA  CACCGCAGCC     180
GTCGCGGCTG  ATATCGGAGA  AGCCGCGGTG  TTCTTCTCTG  GGCTCGCCCC  ATTGAGGATG     240
CACCCTGATG  TCAGCTGGGC  AAAAGTTCGC  GGCGTCAACT  GGCCCCTCTT  GGTGGGTGTT     300
CAGCGGACCA  TGTGTCGGGA  AACACTGTCT  CCCGGCCCAT  CGGATGACCC  CCAATGGGCA     360
GGTCTGAAGG  GCCCAAATCC  TGTCCCACTC  CTGCTGAGGT  GGGGCAATGA  TTTACCATCT     420
AAAGTGGCCG  GCCACCACAT  AGTGGACGAC  CTGGTCCGGA  GACTCGGTGT  GGCGGAGGGT     480
TACGTCCGCT  GCGACGCTGG  GCCGATCTTG  ATGATCGGTC  TAGCTATCGC  GGGGGGAATG     540
ATCTACGCGT  CATACACCGG  GTCGCTAGTG  GTGGTGACAG  ACTGGGATGT  GAAGGGGGT     600
GGCGCCCCCC  TTTATCGGCA  TGGAGACCAG  GCCACGCCTC  AGCCGGTGGT  GCAGGTTCCT     660
CCGGTAGACC  ATCGGCCGGG  GGGTGAATCA  GCACCATCGG  ATGCCAAGAC  AGTGACAGAT     720
GCGGTGGCAG  CCATCCAGGT  GGACTGCGAT  TGGACTATCA  TGACTCTGTC  GATCGGAGAA     780
GTGTTGTCCT  TGGCTCAGGC  TAAGACGGCC  GAGGCCTACA  CAGCAACCGC  CAAGTGGCTC     840
GCTGGCTGCT  ATACGGGGAC  GCGGGCCGTT  CCCACTGTAT  CCATTGTTGA  CAAGCTCTTC     900
GCCGGAGGGT  GGGCGGCTGT  GGTGGGCCAT  TGCCACAGCG  TGATTGCTGC  GGCGGTGGCG     960
GCCTACGGGG  CTTCAAGGAG  CCCGCCGTTG  GCAGCCGCGG  CTTCCTACCT  GATGGGGTTG    1020
GGCGTTGGAG  GCAACGCTCA  GACGCGCCTG  GCGTCTGCCC  TCCTATTGGG  GGCTGCTGGA    1080
```

```
ACCGCCTTGG  GCACTCCTGT  CGTGGGCTTG  ACCATGGCAG  GTGCGTTCAT  GGGGGGGGCC        1140

AGTGTCTCCC  CCTCCTTGGT  CACCATTTTA  TTGGGGGCCG  TCGGAGGTTG  GGAGGGTGTT        1200

GTCAACGCGG  CGAGCCTAGT  CTTTGACTTC  ATGGCGGGGA  AACTTTCATC  AGAAGATCTG        1260

TGGTATGCCA  TCCCGGTACT  GACCAGCC                                              1288
```

( 2 ) INFORMATION FOR SEQ ID NO:40:

( i ) SEQUENCE CHARACTERISTICS:
        ( A ) LENGTH: 862 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 6E3

( x i ) SEQUENCE DESCRIPTION: SEQ ID NO:40:

```
ACGGCAACAT  GGGGCACAAG  GTCTTAATCT  TGAACCCCTC  AGTGGCCACT  GTGCGGGCCA          60

TGGGCCCGTA  CATGGAGCGG  CTGGCGGGTA  AACATCCAAG  TATATACTGT  GGGCATGATA         120

CAACTGCTTT  CACAAGGATC  ACTGACTCCC  CCCTGACGTA  TTCAACCTAT  GGGAGGTTTT         180

TGGCCAACCC  TAGGCAGATG  CTACGGGGCG  TTTCGGTGGT  CATTTGTGAT  GAGTGCCACA         240

GTCATGACTC  AACCGTGCTG  TTAGGCATTG  GGAGAGTTCG  GGAGCTGGCG  CGTGGGTGCG         300

GAGTGCAACT  AGTGCTCTAC  GCCACCGCTA  CACCTCCCGG  ATCCCCTATG  ACGCAGCACC         360

CTTCCATAAT  TGAGACAAAA  TTGGACGTGG  GCGAGATTCC  CTTTTATGGG  CATGGAATAC         420

CCCTCGAGCG  GATGCGAACC  GGAAGGCACC  TCGTGTTCTG  CCATTCTAAG  GCTGAGTGCG         480

AGCGCCTTGC  TGGCCAGTTC  TCCGCTAGGG  GGGTCAATGC  CATTGCCTAT  TATAGGGGTA         540

AAGACAGTTC  TATCATCAAG  GATGGGGACC  TGGTGGTCTG  TGCTACAGAC  GCGCTTTCCA         600

CTGGGTACAC  TGGAAATTTC  GACTCCGTCA  CCGACTGTGG  ATTAGTGGTG  GAGGAGGTCG         660

TTGAGGTGAC  CCTTGATCCC  ACCATTACCA  TCTCCCTGCG  GACAGTGCCT  GCGTCGGCTG         720

AACTGTCGAT  GCAAAGACGA  GGACGCACGG  GTAGGGGCAG  GTCTGGACGC  TACTACTACG         780

CGGGGGTGGG  CAAAGCCCCT  GCGGGTGTGG  TGCGCTCAGG  TCCTGTCTGG  TCGGCGGTGG         840

AAGCTGGAGT  GACCTCGTAC  GG                                                    862
```

( 2 ) INFORMATION FOR SEQ ID NO:41:

( i ) SEQUENCE CHARACTERISTICS:
        ( A ) LENGTH: 865 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Individual Clone GE3L-11

( x i ) SEQUENCE DESCRIPTION: SEQ ID NO:41:

```
AGTACGGCAA  CATGGGGCAC  AAGGTCTTAA  TCTTGAACCC  CTCAGTGGCC  ACTGTGCGGG          60
```

| CCATGGGCCC | GTACATGGAG | CGGCTGGCGG | GTAAACATCC | AAGTATATAC | TGTGGGCATG | 120 |
| ATACAACTGC | TTTCACAAGG | ATCACTGACT | CCCCCCTGAC | GTATTCAACC | TATGGGAGGT | 180 |
| TTTTGGCCAA | CCCTAGGCAG | ATGCTACGGG | GCGTTTCGGT | GGTCATTTGT | GATGAGTGCC | 240 |
| ACAGTCATGA | CTCAACCGTG | CTGTTAGGCA | TTGGGAGAGT | CCGGGAGCTG | GCGCGTGGGT | 300 |
| GCGGGGTGCA | ACTAGTGCTC | TACGCCACCG | CTACACCTCC | CGGATCCCCT | ATGACGCAGC | 360 |
| ACCCTTCCAT | AATTGAGACA | AAATTGGACG | TGGGCGAGAT | TCCCTTTTAT | GGACATGGAA | 420 |
| TACCCCTCGA | GCGGATGCGA | ACCGGAAGGC | ACCTCGTGTT | CTGCCATTCT | AAGGCTGAGT | 480 |
| GCGAGCGCCT | TGCTGGCCAG | TTCTCCGCTA | GGGGGGTCAA | TGCCATTGCC | TATTATAGGG | 540 |
| GTAAAGACAG | TTCTATCATC | AAGGATGGGG | ACCTGGTGGT | CTGTGCTACA | GACGCGCTTT | 600 |
| CCACTGGGTA | CACTGGAAAT | TTCGACTCCG | TCACCGACTG | TGGATTAGTG | GTGGAGGAGG | 660 |
| TCGTTGAGGT | GACCCTTGAT | CCCACCATTA | CCATCTCCCT | GCGGACAGTG | CCTGCGTCGG | 720 |
| CTGAACTGTC | GATGCAAAGA | CGAGGACGCA | CGGGTAGGGG | CAGGTCTGGA | CGCTACTACT | 780 |
| ACGCGGGGGT | GGGCAAAGCC | CCTGCGGGTG | TGGTGCGCTC | AGGTCCTGTC | TGGTCGGCGG | 840 |
| TGGAAGCTGG | AGTGACCTCG | TACGG |  |  |  | 865 |

( 2 ) INFORMATION FOR SEQ ID NO:42:

( i ) SEQUENCE CHARACTERISTICS:
        ( A ) LENGTH: 596 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 7E3

( x i ) SEQUENCE DESCRIPTION: SEQ ID NO:42:

| AGCATGGGAA | CATGCTTGAA | CGGCCTGCTG | TTCACGACCT | TCCATGGGGC | TTCATCCCGA | 60 |
| ACCATCGCCA | CACCCGTGGG | GGCCCTTAAT | CCCAGATGGT | GGTCAGCCAG | TGATGATGTC | 120 |
| ACGGTGTATC | CACTCCCGGA | TGGGGCTACT | TCGTTAACAC | CTTGTACTTG | CCAGGCTGAG | 180 |
| TCCTGTTGGG | TCATCAGATC | CGACGGGGCC | CTATGCCATG | GCTTGAGCAA | GGGGACAAG | 240 |
| GTGGAGCTGG | ATGTGGCCAT | GGAGGTCTCT | GACTTCCGTG | GCTCGTCTGG | CTCACCGGTC | 300 |
| CTATGTGACG | AAGGGCACGC | AGTAGGAATG | CTCGTGTCTG | TGCTTCACTC | CGGTGGTAGG | 360 |
| GTCACCGCGG | CACGGTTCAC | TAGGCCGTGG | ACCCAAGTGC | CAACAGATGC | CAAAACCACT | 420 |
| ACTGAACCCC | CTCCGGTGCC | GGCCAAAGGA | GTTTTCAAAG | AGGCCCGTT | GTTTATGCCT | 480 |
| ACGGGAGCGG | GAAAGAGCAC | TCGCGTCCCG | TTGGAGTACG | ATAACATGGG | GCACAAGGTC | 540 |
| TTAATCTTGA | ACCCCTCAGT | GGCCACTGTG | CGGGCCATGG | GCCCGTACAT | GGAGCG | 596 |

( 2 ) INFORMATION FOR SEQ ID NO:43:

( i ) SEQUENCE CHARACTERISTICS:
        ( A ) LENGTH: 586 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( C ) INDIVIDUAL ISOLATE: Consensus Sequence 5E5

( x i ) SEQUENCE DESCRIPTION: SEQ ID NO:43:

| | | | | | | |
|---|---|---|---|---|---|---|
| GAGCTATGGG | TACGCGTGCG | AGCCCTCATA | TCATGCATCA | TTGGACACGG | CCCCCTTCTG | 60 |
| CTCCACTTGG | CTTGCTGAGT | GCAATGCAGA | TGGGAAGCGC | CATTTCTTCC | TGACCACGGA | 120 |
| CTTCCGGAGG | CCGCTCGCTC | GCATGTCGAG | TGAGTATAGT | GACCCGATGG | CTTCGGCGAT | 180 |
| CGGTTACATC | CTCCTTTATC | CTTGGCACCC | CATCACACGG | TGGGTCATCA | TCCCTCATGT | 240 |
| GCTAACGTGC | GCATTCAGGG | GTGGAGGCAC | ACCGTCTGAT | CCGGTTTGGT | GCCAGGTGCA | 300 |
| TGGTAACTAC | TACAAGTTTC | CACTGGACAA | ACTGCCTAAC | ATCATCGTGG | CCCTCCACGG | 360 |
| ACCAGCAGCG | TTGAGGGTTA | CCGCAGACAC | AACTAAAACA | AAGATGGAGG | CTGGTAAGGT | 420 |
| TCTGAGCGAC | CTCAAGCTCC | CTGGCTTAGC | AGTCCACCGA | AAGAAGGCCG | GGGCGTTGCG | 480 |
| AACACGCATG | CTCCGCTCGC | GCGGTTGGGC | TGAGTTGGCT | AGGGGCTTGT | TGTGGCATCC | 540 |
| AGGCCTACGG | CTTCCTCCCC | CTGAGATTGC | TGGTATCCCG | GGGGGT | | 586 |

( 2 ) INFORMATION FOR SEQ ID NO:44:

( i ) SEQUENCE CHARACTERISTICS:
        ( A ) LENGTH: 242 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 6E5 (44F)

( x i ) SEQUENCE DESCRIPTION: SEQ ID NO:44:

| | | | | | | |
|---|---|---|---|---|---|---|
| CGAACGCGCA | TGCTCCGCTC | GCGCGGTTGG | GCTGAGTTGG | CTAGGGGCTT | GTTGTGGCAT | 60 |
| CCAGGCCTAC | GGCTTCCTCC | CCCTGAGATT | GCTGGTATCC | CGGGGGGTTT | CCCTCTCTCC | 120 |
| CCCCCCTATA | TGGGGGTGGT | ACACCAATTG | GATTTCACAA | GCCAGAGGAG | TCGCTGGCGG | 180 |
| TGGTTGGGGT | TCTTAGCCCT | GCTCATCGTA | GCCCTCTTCG | GGTGAACTAA | ATTCATCTGT | 240 |
| TG | | | | | | 242 |

( 2 ) INFORMATION FOR SEQ ID NO:45:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer Gt11 rev-JL ( x i ) SEQUENCE DESCRIPTION: SEQ ID NO:45:

| | | | |
|---|---|---|---|
| TGGTAATGGT | AGCGACCGGC | GCTCAGC | 27 |

(2) INFORMATION FOR SEQ ID NO:46:

(i) SEQUENCE CHARACTERISTICS:
       (A) LENGTH: 45 base pairs
       (B) TYPE: nucleic acid
       (C) STRANDEDNESS: both
       (D) TOPOLOGY: linear (ii) MOLECULE TYPE: DNA (iii) HYPOTHETICAL: NO (iv) ANTI-SENSE: NO (vi) ORIGINAL SOURCE:
       (C) INDIVIDUAL ISOLATE: Primer GE- 3F (xi) SEQUENCE DESCRIPTION: SEQ ID NO:46:

GCCGCCATGG TCTCATGGGA CGCGGACGCT CGTGCGCCCG CGATG                45

(2) INFORMATION FOR SEQ ID NO:47:

(i) SEQUENCE CHARACTERISTICS:
       (A) LENGTH: 34 base pairs
       (B) TYPE: nucleic acid
       (C) STRANDEDNESS: both
       (D) TOPOLOGY: linear (ii) MOLECULE TYPE: DNA (iii) HYPOTHETICAL: NO (iv) ANTI-SENSE: NO (vi) ORIGINAL SOURCE:
       (C) INDIVIDUAL ISOLATE: Primer GE- 3R (xi) SEQUENCE DESCRIPTION: SEQ ID NO:47:

GCGCGGATCC GATAAGTGCT GGCGATGGAG TACG                            34

(2) INFORMATION FOR SEQ ID NO:48:

(i) SEQUENCE CHARACTERISTICS:
       (A) LENGTH: 22 base pairs
       (B) TYPE: nucleic acid
       (C) STRANDEDNESS: both
       (D) TOPOLOGY: linear (ii) MOLECULE TYPE: DNA (iii) HYPOTHETICAL: NO (iv) ANTI-SENSE: NO (vi) ORIGINAL SOURCE:
       (C) INDIVIDUAL ISOLATE: Primer GE- 9F (xi) SEQUENCE DESCRIPTION: SEQ ID NO:48:

GGCACCATGG TCACCCCGGA AG                                         22

(2) INFORMATION FOR SEQ ID NO:49:

(i) SEQUENCE CHARACTERISTICS:
       (A) LENGTH: 28 base pairs
       (B) TYPE: nucleic acid
       (C) STRANDEDNESS: both
       (D) TOPOLOGY: linear (ii) MOLECULE TYPE: DNA (iii) HYPOTHETICAL: NO (iv) ANTI-SENSE: NO ( v i ) ORIGINAL SOURCE:
        ( C ) INDIVIDUAL ISOLATE: Primer GE- 9R ( x i ) SEQUENCE DESCRIPTION: SEQ ID NO:49:

GCTCGGATCC GGAGCAGAAG GGGGCCGT                                                                28

( 2 ) INFORMATION FOR SEQ ID NO:50:

( i ) SEQUENCE CHARACTERISTICS:
        ( A ) LENGTH: 364 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: GE3-2

( i x ) FEATURE:
        ( A ) NAME/KEY: CDS
        ( B ) LOCATION: 2..364

( x i ) SEQUENCE DESCRIPTION: SEQ ID NO:50:

```
G GTC TCA TGG GAC GCG GAC GCT CGT GCG CCC GCG ATG GTC TAT GGC           46
  Val Ser Trp Asp Ala Asp Ala Arg Ala Pro Ala Met Val Tyr Gly
  1           5                   10                  15

CCT GGG CAA AGT GTT ACC ATT GAC GGG GAG CGC TAC ACC TTG CCT CAT         94
Pro Gly Gln Ser Val Thr Ile Asp Gly Glu Arg Tyr Thr Leu Pro His
            20                  25                  30

CAA CTG AGG CTC AGG AAT GTG GCA CCC TCT GAG GTT TCA TCC GAG GTG         142
Gln Leu Arg Leu Arg Asn Val Ala Pro Ser Glu Val Ser Ser Glu Val
            35                  40                  45

TCC ATT GAC ATT GGG ACG GAG ACT GAA GAC TCA GAA CTG ACT GAG GCC         190
Ser Ile Asp Ile Gly Thr Glu Thr Glu Asp Ser Glu Leu Thr Glu Ala
        50              55                  60

GAT CTG CCG CCG GCG GCT GCT GCT CTC CAA GCG ATC GAG AAT GCT GCG         238
Asp Leu Pro Pro Ala Ala Ala Ala Leu Gln Ala Ile Glu Asn Ala Ala
    65                  70                  75

AGG ATT CTT GAA CCG CAC ATT GAT GTC ATC ATG GAG GAC TGC AGT ACA         286
Arg Ile Leu Glu Pro His Ile Asp Val Ile Met Glu Asp Cys Ser Thr
80                  85                  90                  95

CCC TCT CTT TGT GGT AGT AGC CGA GAG ATG CCT GTA TGG GGA GAA GAC         334
Pro Ser Leu Cys Gly Ser Ser Arg Glu Met Pro Val Trp Gly Glu Asp
                100                 105                 110

ATC CCC CGT ACT CCA TCG CCA GCA CTT ATC                                 364
Ile Pro Arg Thr Pro Ser Pro Ala Leu Ile
            115                 120
```

( 2 ) INFORMATION FOR SEQ ID NO:51:

( i ) SEQUENCE CHARACTERISTICS:
        ( A ) LENGTH: 121 amino acids
        ( B ) TYPE: amino acid
        ( D ) TOPOLOGY: linear ( i i ) MOLECULE TYPE: protein ( x i ) SEQUENCE DESCRIPTION: SEQ ID NO:51:

```
Val Ser Trp Asp Ala Asp Ala Arg Ala Pro Ala Met Val Tyr Gly Pro
1               5                   10                  15

Gly Gln Ser Val Thr Ile Asp Gly Glu Arg Tyr Thr Leu Pro His Gln
```

|  | 20 |  |  |  | 25 |  |  |  | 30 |  |  |  |
|---|---|---|---|---|---|---|---|---|---|---|---|---|
| Leu | Arg | Leu | Arg | Asn | Val | Ala | Pro | Ser | Glu | Val | Ser | Ser | Glu | Val | Ser |
|  |  | 35 |  |  |  |  | 40 |  |  |  |  | 45 |  |  |  |
| Ile | Asp | Ile | Gly | Thr | Glu | Thr | Glu | Asp | Ser | Glu | Leu | Thr | Glu | Ala | Asp |
|  | 50 |  |  |  |  | 55 |  |  |  |  | 60 |  |  |  |  |
| Leu | Pro | Pro | Ala | Ala | Ala | Ala | Leu | Gln | Ala | Ile | Glu | Asn | Ala | Ala | Arg |
| 65 |  |  |  |  | 70 |  |  |  |  | 75 |  |  |  |  | 80 |
| Ile | Leu | Glu | Pro | His | Ile | Asp | Val | Ile | Met | Glu | Asp | Cys | Ser | Thr | Pro |
|  |  |  |  | 85 |  |  |  |  | 90 |  |  |  |  | 95 |  |
| Ser | Leu | Cys | Gly | Ser | Ser | Arg | Glu | Met | Pro | Val | Trp | Gly | Glu | Asp | Ile |
|  |  |  | 100 |  |  |  |  | 105 |  |  |  |  | 110 |  |  |
| Pro | Arg | Thr | Pro | Ser | Pro | Ala | Leu | Ile |  |  |  |  |  |  |  |
|  |  | 115 |  |  |  |  | 120 |  |  |  |  |  |  |  |  |

( 2 ) INFORMATION FOR SEQ ID NO:52:

( i ) SEQUENCE CHARACTERISTICS:
        ( A ) LENGTH: 290 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Clone GE9-2

( i x ) FEATURE:
        ( A ) NAME/KEY: CDS
        ( B ) LOCATION: 3..290

( x i ) SEQUENCE DESCRIPTION: SEQ ID NO:52:

| CC | ATG | GTC | ACC | CCG | GAA | GGG | GTG | CCC | GTT | GGT | GAG | AGG | TAT | TGC | AGA |  | 47 |
|---|---|---|---|---|---|---|---|---|---|---|---|---|---|---|---|---|---|
|  | Met | Val | Thr | Pro | Glu | Gly | Val | Pro | Val | Gly | Glu | Arg | Tyr | Cys | Arg |  |  |
|  | 1 |  |  |  | 5 |  |  |  |  | 10 |  |  |  |  | 15 |  |  |
| TCC | TCG | GGT | GTC | CTA | ACA | ACT | AGC | GCG | AGC | AAC | TGC | TTG | ACC | TGC | TAC |  | 95 |
| Ser | Ser | Gly | Val | Leu | Thr | Thr | Ser | Ala | Ser | Asn | Cys | Leu | Thr | Cys | Tyr |  |  |
|  |  |  |  | 20 |  |  |  |  | 25 |  |  |  |  | 30 |  |  |  |
| ATC | AAG | GTG | AAA | GCC | GCC | TGT | GAG | AGG | GTG | GGG | CTG | AAA | AAT | GTC | TCT |  | 143 |
| Ile | Lys | Val | Lys | Ala | Ala | Cys | Glu | Arg | Val | Gly | Leu | Lys | Asn | Val | Ser |  |  |
|  |  |  | 35 |  |  |  |  | 40 |  |  |  |  | 45 |  |  |  |  |
| CTT | CTC | ATA | GCC | GGC | GAT | GAC | TGC | TTG | ATC | ATA | TGT | GAG | CGG | CCA | GTG |  | 191 |
| Leu | Leu | Ile | Ala | Gly | Asp | Asp | Cys | Leu | Ile | Ile | Cys | Glu | Arg | Pro | Val |  |  |
|  |  | 50 |  |  |  |  | 55 |  |  |  |  | 60 |  |  |  |  |  |
| TGC | GAC | CCA | AGC | GAC | GCT | TTG | GGC | AGA | GCC | CTA | GCG | AGC | TAT | GGG | TAC |  | 239 |
| Cys | Asp | Pro | Ser | Asp | Ala | Leu | Gly | Arg | Ala | Leu | Ala | Ser | Tyr | Gly | Tyr |  |  |
|  | 65 |  |  |  |  | 70 |  |  |  |  | 75 |  |  |  |  |  |  |
| GCG | TGC | GAG | CCC | TCA | TAT | TAT | GCA | TGC | TCG | GAC | ACG | GCC | CCC | TTC | TGC |  | 287 |
| Ala | Cys | Glu | Pro | Ser | Tyr | Tyr | Ala | Cys | Ser | Asp | Thr | Ala | Pro | Phe | Cys |  |  |
| 80 |  |  |  |  | 85 |  |  |  |  | 90 |  |  |  |  | 95 |  |  |
| TCC |  |  |  |  |  |  |  |  |  |  |  |  |  |  |  |  | 290 |
| Ser |  |  |  |  |  |  |  |  |  |  |  |  |  |  |  |  |  |

( 2 ) INFORMATION FOR SEQ ID NO:53:

( i ) SEQUENCE CHARACTERISTICS:
        ( A ) LENGTH: 96 amino acids
        ( B ) TYPE: amino acid
        ( D ) TOPOLOGY: linear ( i i ) MOLECULE TYPE: protein ( x i ) SEQUENCE DESCRIPTION: SEQ ID NO:53:

| Met | Val | Thr | Pro | Glu | Gly | Val | Pro | Val | Gly | Glu | Arg | Tyr | Cys | Arg | Ser |
| 1 | | | | 5 | | | | | 10 | | | | | 15 | |

| Ser | Gly | Val | Leu | Thr | Thr | Ser | Ala | Ser | Asn | Cys | Leu | Thr | Cys | Tyr | Ile |
| | | | 20 | | | | | 25 | | | | | 30 | | |

| Lys | Val | Lys | Ala | Ala | Cys | Glu | Arg | Val | Gly | Leu | Lys | Asn | Val | Ser | Leu |
| | | 35 | | | | | 40 | | | | | 45 | | | |

| Leu | Ile | Ala | Gly | Asp | Asp | Cys | Leu | Ile | Ile | Cys | Glu | Arg | Pro | Val | Cys |
| | | 50 | | | | 55 | | | | | 60 | | | | |

| Asp | Pro | Ser | Asp | Ala | Leu | Gly | Arg | Ala | Leu | Ala | Ser | Tyr | Gly | Tyr | Ala |
| 65 | | | | | 70 | | | | 75 | | | | | | 80 |

| Cys | Glu | Pro | Ser | Tyr | Tyr | Ala | Cys | Ser | Asp | Thr | Ala | Pro | Phe | Cys | Ser |
| | | | | 85 | | | | | 90 | | | | | 95 | |

( 2 ) INFORMATION FOR SEQ ID NO:54:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: JML-A SISPA Primer ( x i ) SEQUENCE DESCRIPTION: SEQ ID NO:54:

AGGAATTCAG CGGCCGCGAG     20

( 2 ) INFORMATION FOR SEQ ID NO:55:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: JML-B SISPA Primer ( x i ) SEQUENCE DESCRIPTION: SEQ ID NO:55:

CTCGCGGCCG CTGAATTCCT TT     22

( 2 ) INFORMATION FOR SEQ ID NO:56:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO -continued ( v i ) ORIGINAL SOURCE:
( C ) INDIVIDUAL ISOLATE: 470ep-f1 Primer ( x i ) SEQUENCE DESCRIPTION: SEQ ID NO:56:

GCGAATTCGC CATGGCGGGG AGACTTTCAT CA  32

( 2 ) INFORMATION FOR SEQ ID NO:57:

( i ) SEQUENCE CHARACTERISTICS:
( A ) LENGTH: 35 base pairs
( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: 470ep-R1 Primer ( x i ) SEQUENCE DESCRIPTION: SEQ ID NO:57:

GCGAATTCGG ATCCAGGGCC ATAGACCATC GCGGG  35

( 2 ) INFORMATION FOR SEQ ID NO:58:

( i ) SEQUENCE CHARACTERISTICS:
( A ) LENGTH: 26 base pairs
( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: 470ep-f2 Primer ( x i ) SEQUENCE DESCRIPTION: SEQ ID NO:58:

GCGAATTCCG TGCGCCCGCC ATGGTC  26

( 2 ) INFORMATION FOR SEQ ID NO:59:

( i ) SEQUENCE CHARACTERISTICS:
( A ) LENGTH: 32 base pairs
( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: 470ep-R3 Primer ( x i ) SEQUENCE DESCRIPTION: SEQ ID NO:59:

GCGAATTCGG ATCCCAAGGT TTCTTGCCTA GC  32

( 2 ) INFORMATION FOR SEQ ID NO:60:

( i ) SEQUENCE CHARACTERISTICS:
( A ) LENGTH: 26 base pairs
( B ) TYPE: nucleic acid
( C ) STRANDEDNESS: both ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: 470ep-f4 Primer ( x i ) SEQUENCE DESCRIPTION: SEQ ID NO:60:

GCGAATTCAA GTGTGAGGCT AGGCAA     26

( 2 ) INFORMATION FOR SEQ ID NO:61:

( i ) SEQUENCE CHARACTERISTICS:
        ( A ) LENGTH: 35 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: 470ep-R4 Primer ( x i ) SEQUENCE DESCRIPTION: SEQ ID NO:61:

GCGAATTCGG ATCCCCACAC AGATGGCGCA AGGGG     35

( 2 ) INFORMATION FOR SEQ ID NO:62:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: KL-1 SISPA Primer ( x i ) SEQUENCE DESCRIPTION: SEQ ID NO:62:

GCAGGATCCG AATTCGCATC TAGAGAT     27

( 2 ) INFORMATION FOR SEQ ID NO:63:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: KL-2 SISPA Primer ( x i ) SEQUENCE DESCRIPTION: SEQ ID NO:63:

ATCTCTAGAT GCGAATTCGG ATCCTGCGA     29

( 2 ) INFORMATION FOR SEQ ID NO:64:

( i ) SEQUENCE CHARACTERISTICS:
    ( A ) LENGTH: 186 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( C ) INDIVIDUAL ISOLATE: Clone Y5-10

( i x ) FEATURE:
    ( A ) NAME/KEY: CDS
    ( B ) LOCATION: 1..186

( x i ) SEQUENCE DESCRIPTION: SEQ ID NO:64:

```
CGT  GCG  CCC  GCC  ATG  GTC  TAT  GGC  CCT  GGG  CAA  AGT  GTT  GCC  ATT  GAC        48
Arg  Ala  Pro  Ala  Met  Val  Tyr  Gly  Pro  Gly  Gln  Ser  Val  Ala  Ile  Asp
 1              5                        10                       15

GGG  GAG  CGC  TAC  ACC  TTG  CCT  CAT  CAA  CTG  AGG  CTC  AGG  AAT  GTG  GCA        96
Gly  Glu  Arg  Tyr  Thr  Leu  Pro  His  Gln  Leu  Arg  Leu  Arg  Asn  Val  Ala
              20                        25                       30

CCC  TCT  GAG  GTT  TCA  TCC  GAG  GTG  TCC  ATT  GAC  ATT  GGG  ACG  GAG  GCT       144
Pro  Ser  Glu  Val  Ser  Ser  Glu  Val  Ser  Ile  Asp  Ile  Gly  Thr  Glu  Ala
         35                        40                       45

GAA  AAC  TCA  GAA  CTG  ACT  GAG  GCC  GAT  CTG  CCG  CCG  GCG  GCT                 186
Glu  Asn  Ser  Glu  Leu  Thr  Glu  Ala  Asp  Leu  Pro  Pro  Ala  Ala
     50                        55                       60
```

( 2 ) INFORMATION FOR SEQ ID NO:65:

( i ) SEQUENCE CHARACTERISTICS:
    ( A ) LENGTH: 62 amino acids
    ( B ) TYPE: amino acid
    ( D ) TOPOLOGY: linear ( i i ) MOLECULE TYPE: protein ( x i ) SEQUENCE DESCRIPTION: SEQ ID NO:65:

```
Arg  Ala  Pro  Ala  Met  Val  Tyr  Gly  Pro  Gly  Gln  Ser  Val  Ala  Ile  Asp
 1              5                        10                       15

Gly  Glu  Arg  Tyr  Thr  Leu  Pro  His  Gln  Leu  Arg  Leu  Arg  Asn  Val  Ala
              20                        25                       30

Pro  Ser  Glu  Val  Ser  Ser  Glu  Val  Ser  Ile  Asp  Ile  Gly  Thr  Glu  Ala
         35                        40                       45

Glu  Asn  Ser  Glu  Leu  Thr  Glu  Ala  Asp  Leu  Pro  Pro  Ala  Ala
     50                        55                       60
```

( 2 ) INFORMATION FOR SEQ ID NO:66:

( i ) SEQUENCE CHARACTERISTICS:
    ( A ) LENGTH: 282 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO (v i) ORIGINAL SOURCE:
(C) INDIVIDUAL ISOLATE: Clone Y5-12

(i x) FEATURE:
(A) NAME/KEY: CDS
(B) LOCATION: 1..282

(x i) SEQUENCE DESCRIPTION: SEQ ID NO:66:

| CGT | GCG | CCC | GCC | ATG | GTC | TAT | GGC | CCT | GGG | CAA | AGT | GTT | ACC | ATT | GAC | 48 |
|---|---|---|---|---|---|---|---|---|---|---|---|---|---|---|---|---|
| Arg | Ala | Pro | Ala | Met | Val | Tyr | Gly | Pro | Gly | Gln | Ser | Val | Thr | Ile | Asp | |
| 1 | | | | 5 | | | | | 10 | | | | | 15 | | |
| GGG | GAG | CGC | TAC | ACC | TTG | CCT | CAT | CAA | CTG | AGG | CTC | AGG | AAT | GTG | GCA | 96 |
| Gly | Glu | Arg | Tyr | Thr | Leu | Pro | His | Gln | Leu | Arg | Leu | Arg | Asn | Val | Ala | |
| | | | 20 | | | | | 25 | | | | | 30 | | | |
| CCC | TCT | GAG | GTT | TCA | TCC | GAG | GTG | TCC | ATT | GAC | ATT | GGG | ACG | GAG | ACT | 144 |
| Pro | Ser | Glu | Val | Ser | Ser | Glu | Val | Ser | Ile | Asp | Ile | Gly | Thr | Glu | Thr | |
| | | 35 | | | | | 40 | | | | | 45 | | | | |
| GAA | GAC | TCA | GAA | CTG | ACT | GAG | GCC | GAT | CTG | CCG | CCG | GCG | GCT | GCT | GCT | 192 |
| Glu | Asp | Ser | Glu | Leu | Thr | Glu | Ala | Asp | Leu | Pro | Pro | Ala | Ala | Ala | Ala | |
| | 50 | | | | | 55 | | | | | 60 | | | | | |
| CTC | CAA | GCG | ATC | GAG | AAT | GCT | GCG | AGG | ATT | CTT | GAA | CCG | CAC | ATT | GAT | 240 |
| Leu | Gln | Ala | Ile | Glu | Asn | Ala | Ala | Arg | Ile | Leu | Glu | Pro | His | Ile | Asp | |
| 65 | | | | | 70 | | | | | 75 | | | | | 80 | |
| GTC | ATC | ATG | GAG | GAC | TGC | AGT | ACA | CCC | TCT | CTT | TGT | GGT | AGT | | | 282 |
| Val | Ile | Met | Glu | Asp | Cys | Ser | Thr | Pro | Ser | Leu | Cys | Gly | Ser | | | |
| | | | | 85 | | | | | 90 | | | | | | | |

(2) INFORMATION FOR SEQ ID NO:67:

(i) SEQUENCE CHARACTERISTICS:
(A) LENGTH: 94 amino acids
(B) TYPE: amino acid
(D) TOPOLOGY: linear (i i) MOLECULE TYPE: protein (x i) SEQUENCE DESCRIPTION: SEQ ID NO:67:

| Arg | Ala | Pro | Ala | Met | Val | Tyr | Gly | Pro | Gly | Gln | Ser | Val | Thr | Ile | Asp |
|---|---|---|---|---|---|---|---|---|---|---|---|---|---|---|---|
| 1 | | | | 5 | | | | | 10 | | | | | 15 | |
| Gly | Glu | Arg | Tyr | Thr | Leu | Pro | His | Gln | Leu | Arg | Leu | Arg | Asn | Val | Ala |
| | | | 20 | | | | | 25 | | | | | 30 | | |
| Pro | Ser | Glu | Val | Ser | Ser | Glu | Val | Ser | Ile | Asp | Ile | Gly | Thr | Glu | Thr |
| | | 35 | | | | | 40 | | | | | 45 | | | |
| Glu | Asp | Ser | Glu | Leu | Thr | Glu | Ala | Asp | Leu | Pro | Pro | Ala | Ala | Ala | Ala |
| | 50 | | | | | 55 | | | | | 60 | | | | |
| Leu | Gln | Ala | Ile | Glu | Asn | Ala | Ala | Arg | Ile | Leu | Glu | Pro | His | Ile | Asp |
| 65 | | | | | 70 | | | | | 75 | | | | | 80 |
| Val | Ile | Met | Glu | Asp | Cys | Ser | Thr | Pro | Ser | Leu | Cys | Gly | Ser | | |
| | | | | 85 | | | | | 90 | | | | | | |

(2) INFORMATION FOR SEQ ID NO:68:

(i) SEQUENCE CHARACTERISTICS:
(A) LENGTH: 279 base pairs
(B) TYPE: nucleic acid
(C) STRANDEDNESS: both
(D) TOPOLOGY: linear (i i) MOLECULE TYPE: cDNA (i i i) HYPOTHETICAL: NO (i v) ANTI-SENSE: NO (v i) ORIGINAL SOURCE:
(C) INDIVIDUAL ISOLATE: Clone Y5-26

( i x ) FEATURE:
  ( A ) NAME/KEY: CDS
  ( B ) LOCATION: 1..279

( x i ) SEQUENCE DESCRIPTION: SEQ ID NO:68:

| CGT | GCG | CCC | GCC | ATG | GTC | TAT | GGC | CCT | GGG | CAA | AGT | GTT | TCC | ATT | GAC | 48 |
| Arg | Ala | Pro | Ala | Met | Val | Tyr | Gly | Pro | Gly | Gln | Ser | Val | Ser | Ile | Asp | |
| 1 | | | | 5 | | | | | 10 | | | | | 15 | | |

| GGG | GAG | CGC | TAC | ACC | TTG | CCT | CAT | CAA | CTG | AGG | CTC | AGG | AAT | GTG | GCA | 96 |
| Gly | Glu | Arg | Tyr | Thr | Leu | Pro | His | Gln | Leu | Arg | Leu | Arg | Asn | Val | Ala | |
| | | | 20 | | | | | 25 | | | | | 30 | | | |

| CCC | TCT | GAG | GTT | TCA | TCC | GAG | GTG | TCC | ATT | GAC | ATT | GGG | ACG | GAG | ACT | 144 |
| Pro | Ser | Glu | Val | Ser | Ser | Glu | Val | Ser | Ile | Asp | Ile | Gly | Thr | Glu | Thr | |
| | | 35 | | | | | 40 | | | | | 45 | | | | |

| GAA | GAC | TCA | GAA | CTG | ACT | GAG | GCC | GAC | CTG | CCG | CCG | GCG | GCT | GCT | GCT | 192 |
| Glu | Asp | Ser | Glu | Leu | Thr | Glu | Ala | Asp | Leu | Pro | Pro | Ala | Ala | Ala | Ala | |
| | 50 | | | | | 55 | | | | | 60 | | | | | |

| CTC | CAA | GCG | ATC | GAG | AAT | GCT | GCG | AGG | ATT | CTT | GAA | CCG | CAC | ATC | GAT | 240 |
| Leu | Gln | Ala | Ile | Glu | Asn | Ala | Ala | Arg | Ile | Leu | Glu | Pro | His | Ile | Asp | |
| 65 | | | | | 70 | | | | | 75 | | | | | 80 | |

| GTC | ATC | ATG | GAG | GAC | TGC | AGT | ACA | CCC | TCT | CTT | TGT | GGT | | | | 279 |
| Val | Ile | Met | Glu | Asp | Cys | Ser | Thr | Pro | Ser | Leu | Cys | Gly | | | | |
| | | | | 85 | | | | | 90 | | | | | | | |

( 2 ) INFORMATION FOR SEQ ID NO:69:

( i ) SEQUENCE CHARACTERISTICS:
    ( A ) LENGTH: 93 amino acids
    ( B ) TYPE: amino acid
    ( D ) TOPOLOGY: linear ( i i ) MOLECULE TYPE: protein ( x i ) SEQUENCE DESCRIPTION: SEQ ID NO:69:

| Arg | Ala | Pro | Ala | Met | Val | Tyr | Gly | Pro | Gly | Gln | Ser | Val | Ser | Ile | Asp |
| 1 | | | | 5 | | | | | 10 | | | | | 15 | |

| Gly | Glu | Arg | Tyr | Thr | Leu | Pro | His | Gln | Leu | Arg | Leu | Arg | Asn | Val | Ala |
| | | | 20 | | | | | 25 | | | | | 30 | | |

| Pro | Ser | Glu | Val | Ser | Ser | Glu | Val | Ser | Ile | Asp | Ile | Gly | Thr | Glu | Thr |
| | | 35 | | | | | 40 | | | | | 45 | | | |

| Glu | Asp | Ser | Glu | Leu | Thr | Glu | Ala | Asp | Leu | Pro | Pro | Ala | Ala | Ala | Ala |
| | 50 | | | | | 55 | | | | | 60 | | | | |

| Leu | Gln | Ala | Ile | Glu | Asn | Ala | Ala | Arg | Ile | Leu | Glu | Pro | His | Ile | Asp |
| 65 | | | | | 70 | | | | | 75 | | | | | 80 |

| Val | Ile | Met | Glu | Asp | Cys | Ser | Thr | Pro | Ser | Leu | Cys | Gly |
| | | | | 85 | | | | | 90 | | | |

( 2 ) INFORMATION FOR SEQ ID NO:70:

( i ) SEQUENCE CHARACTERISTICS:
    ( A ) LENGTH: 108 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( C ) INDIVIDUAL ISOLATE: Clone Y5-5

( i x ) FEATURE:

( A ) NAME/KEY: CDS
        ( B ) LOCATION: 1..108

( x i ) SEQUENCE DESCRIPTION: SEQ ID NO:70:

| GCC | TAT | TGT | GAC | AAG | GTG | CGC | ACT | CCG | CTT | GAA | TTG | CAG | GTT | GGG | TGC | 48 |
|-----|-----|-----|-----|-----|-----|-----|-----|-----|-----|-----|-----|-----|-----|-----|-----|----|
| Ala | Tyr | Cys | Asp | Lys | Val | Arg | Thr | Pro | Leu | Glu | Leu | Gln | Val | Gly | Cys | |
| 1 | | | | 5 | | | | | 10 | | | | | 15 | | |

| TTG | GTG | GGC | AAT | GAA | CTT | ACC | TTT | GAA | TGT | GAC | AAG | TGT | GAG | GCT | AGG | 96 |
|-----|-----|-----|-----|-----|-----|-----|-----|-----|-----|-----|-----|-----|-----|-----|-----|----|
| Leu | Val | Gly | Asn | Glu | Leu | Thr | Phe | Glu | Cys | Asp | Lys | Cys | Glu | Ala | Arg | |
| | | | 20 | | | | | 25 | | | | | 30 | | | |

| CAA | GAA | ACC | TTG | 108 |
|-----|-----|-----|-----|-----|
| Gln | Glu | Thr | Leu | |
| | | 35 | | |

( 2 ) INFORMATION FOR SEQ ID NO:71:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: protein ( x i ) SEQUENCE DESCRIPTION: SEQ ID NO:71:

| Ala | Tyr | Cys | Asp | Lys | Val | Arg | Thr | Pro | Leu | Glu | Leu | Gln | Val | Gly | Cys |
|-----|-----|-----|-----|-----|-----|-----|-----|-----|-----|-----|-----|-----|-----|-----|-----|
| 1 | | | | 5 | | | | | 10 | | | | | 15 | |

| Leu | Val | Gly | Asn | Glu | Leu | Thr | Phe | Glu | Cys | Asp | Lys | Cys | Glu | Ala | Arg |
|-----|-----|-----|-----|-----|-----|-----|-----|-----|-----|-----|-----|-----|-----|-----|-----|
| | | | 20 | | | | | 25 | | | | | 30 | | |

| Gln | Glu | Thr | Leu |
|-----|-----|-----|-----|
| | | 35 | |

( 2 ) INFORMATION FOR SEQ ID NO:72:

( i ) SEQUENCE CHARACTERISTICS:
        ( A ) LENGTH: 132 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Clone Y5-3

( i x ) FEATURE:
        ( A ) NAME/KEY: CDS
        ( B ) LOCATION: 1..132

( x i ) SEQUENCE DESCRIPTION: SEQ ID NO:72:

| GAG | ATG | GAA | ATC | CAG | AAC | CAT | ACA | GCC | TAT | TGT | GAC | AAG | GTG | CGC | ACT | 48 |
|-----|-----|-----|-----|-----|-----|-----|-----|-----|-----|-----|-----|-----|-----|-----|-----|----|
| Glu | Met | Glu | Ile | Gln | Asn | His | Thr | Ala | Tyr | Cys | Asp | Lys | Val | Arg | Thr | |
| 1 | | | | 5 | | | | | 10 | | | | | 15 | | |

| CCG | CTT | GAA | TTG | CAG | GTT | GGG | TGC | TTG | GTG | GGC | AAT | GAA | CTT | ACC | TTT | 96 |
|-----|-----|-----|-----|-----|-----|-----|-----|-----|-----|-----|-----|-----|-----|-----|-----|----|
| Pro | Leu | Glu | Leu | Gln | Val | Gly | Cys | Leu | Val | Gly | Asn | Glu | Leu | Thr | Phe | |
| | | | 20 | | | | | 25 | | | | | 30 | | | |

| GAA | TGT | GAC | AAG | TGT | GAG | GCT | AGG | CAA | GAA | ACC | TTG | 132 |
|-----|-----|-----|-----|-----|-----|-----|-----|-----|-----|-----|-----|-----|
| Glu | Cys | Asp | Lys | Cys | Glu | Ala | Arg | Gln | Glu | Thr | Leu | |
| | | 35 | | | | 40 | | | | | | |

( 2 ) INFORMATION FOR SEQ ID NO:73:

( i ) SEQUENCE CHARACTERISTICS:
        ( A ) LENGTH: 44 amino acids
        ( B ) TYPE: amino acid (D) TOPOLOGY: linear (ii) MOLECULE TYPE: protein (xi) SEQUENCE DESCRIPTION: SEQ ID NO:73:

| Glu | Met | Glu | Ile | Gln | Asn | His | Thr | Ala | Tyr | Cys | Asp | Lys | Val | Arg | Thr |
|---|---|---|---|---|---|---|---|---|---|---|---|---|---|---|---|
| 1 | | | | 5 | | | | | 10 | | | | | 15 | |
| Pro | Leu | Glu | Leu | Gln | Val | Gly | Cys | Leu | Val | Gly | Asn | Glu | Leu | Thr | Phe |
| | | | 20 | | | | 25 | | | | | 30 | | | |
| Glu | Cys | Asp | Lys | Cys | Glu | Ala | Arg | Gln | Glu | Thr | Leu | | | | |
| | | 35 | | | | | 40 | | | | | | | | |

(2) INFORMATION FOR SEQ ID NO:74:

(i) SEQUENCE CHARACTERISTICS:
  (A) LENGTH: 258 base pairs
  (B) TYPE: nucleic acid
  (C) STRANDEDNESS: both
  (D) TOPOLOGY: linear (ii) MOLECULE TYPE: cDNA (iii) HYPOTHETICAL: NO (iv) ANTI-SENSE: NO (vi) ORIGINAL SOURCE:
  (C) INDIVIDUAL ISOLATE: Clone Y5-27

(ix) FEATURE:
  (A) NAME/KEY: CDS
  (B) LOCATION: 1..258

(xi) SEQUENCE DESCRIPTION: SEQ ID NO:74:

| AAA | GCC | TTA | TTT | CCA | CAG | AGC | GAC | GCG | ACC | AGG | AAG | CTT | ACC | GTC | AAG | 48 |
|---|---|---|---|---|---|---|---|---|---|---|---|---|---|---|---|---|
| Lys | Ala | Leu | Phe | Pro | Gln | Ser | Asp | Ala | Thr | Arg | Lys | Leu | Thr | Val | Lys | |
| 1 | | | | 5 | | | | | 10 | | | | | 15 | | |
| ATG | TCA | TGC | TGC | GTT | GAA | AAG | AGC | GTC | ACG | CGC | TTT | TTC | TCA | TTG | GGG | 96 |
| Met | Ser | Cys | Cys | Val | Glu | Lys | Ser | Val | Thr | Arg | Phe | Phe | Ser | Leu | Gly | |
| | | | 20 | | | | 25 | | | | | 30 | | | | |
| TTG | ACG | GTG | GCT | GAT | GTT | GCT | AGC | CTG | TGT | GAG | ATG | GAA | ATC | CAG | AAC | 144 |
| Leu | Thr | Val | Ala | Asp | Val | Ala | Ser | Leu | Cys | Glu | Met | Glu | Ile | Gln | Asn | |
| | | 35 | | | | | 40 | | | | | 45 | | | | |
| CAT | ATA | GCC | TAT | TGT | GAC | AAG | GTG | CGC | ACT | CCG | CTT | GAA | TTG | CAG | GTT | 192 |
| His | Ile | Ala | Tyr | Cys | Asp | Lys | Val | Arg | Thr | Pro | Leu | Glu | Leu | Gln | Val | |
| | 50 | | | | | 55 | | | | | 60 | | | | | |
| GGG | TGC | TTG | GTG | GGC | AAT | GAA | CTC | ACC | TTT | GAA | TGT | GAC | AAG | TGT | GAG | 240 |
| Gly | Cys | Leu | Val | Gly | Asn | Glu | Leu | Thr | Phe | Glu | Cys | Asp | Lys | Cys | Glu | |
| 65 | | | | | 70 | | | | 75 | | | | | | 80 | |
| GCT | AGG | CAA | GAA | ACC | TTG | | | | | | | | | | | 258 |
| Ala | Arg | Gln | Glu | Thr | Leu | | | | | | | | | | | |
| | | | | 85 | | | | | | | | | | | | |

(2) INFORMATION FOR SEQ ID NO:75:

(i) SEQUENCE CHARACTERISTICS:
  (A) LENGTH: 86 amino acids
  (B) TYPE: amino acid
  (D) TOPOLOGY: linear (ii) MOLECULE TYPE: protein (xi) SEQUENCE DESCRIPTION: SEQ ID NO:75:

| Lys | Ala | Leu | Phe | Pro | Gln | Ser | Asp | Ala | Thr | Arg | Lys | Leu | Thr | Val | Lys |
|---|---|---|---|---|---|---|---|---|---|---|---|---|---|---|---|
| 1 | | | | 5 | | | | | 10 | | | | | 15 | |
| Met | Ser | Cys | Cys | Val | Glu | Lys | Ser | Val | Thr | Arg | Phe | Phe | Ser | Leu | Gly |
| | | | 20 | | | | 25 | | | | | 30 | | | |

| Leu | Thr | Val | Ala | Asp | Val | Ala | Ser | Leu | Cys | Glu | Met | Glu | Ile | Gln | Asn |
|     |     | 35  |     |     |     |     | 40  |     |     |     |     | 45  |     |     |     |

| His | Ile | Ala | Tyr | Cys | Asp | Lys | Val | Arg | Thr | Pro | Leu | Glu | Leu | Gln | Val |
|     |     | 50  |     |     |     |     | 55  |     |     |     |     | 60  |     |     |     |

| Gly | Cys | Leu | Val | Gly | Asn | Glu | Leu | Thr | Phe | Glu | Cys | Asp | Lys | Cys | Glu |
| 65  |     |     |     |     | 70  |     |     |     |     | 75  |     |     |     |     | 80  |

| Ala | Arg | Gln | Glu | Thr | Leu |
|     |     |     |     | 85  |     |

( 2 ) INFORMATION FOR SEQ ID NO:76:

( i ) SEQUENCE CHARACTERISTICS:
        ( A ) LENGTH: 108 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Clone Y5- 25

( i x ) FEATURE:
        ( A ) NAME/KEY: CDS
        ( B ) LOCATION: 1..108

( x i ) SEQUENCE DESCRIPTION: SEQ ID NO:76:

| ACC | TAT | TGT | GAC | AAG | GTG | CGC | ACT | CCG | CTT | GAA | TTG | CAG | GTT | GGG | TGC | 48 |
| Thr | Tyr | Cys | Asp | Lys | Val | Arg | Thr | Pro | Leu | Glu | Leu | Gln | Val | Gly | Cys |    |
| 1   |     |     |     | 5   |     |     |     |     | 10  |     |     |     |     | 15  |     |    |

| TTG | GTG | GGC | AAT | GAA | CTT | ACC | TTT | GAA | TGT | GAC | AAG | TGT | GAG | GCT | AGG | 96 |
| Leu | Val | Gly | Asn | Glu | Leu | Thr | Phe | Glu | Cys | Asp | Lys | Cys | Glu | Ala | Arg |    |
|     |     |     | 20  |     |     |     |     | 25  |     |     |     |     | 30  |     |     |    |

| CAA | GAA | ACC | TTG | 108 |
| Gln | Glu | Thr | Leu |     |
|     |     | 35  |     |     |

( 2 ) INFORMATION FOR SEQ ID NO:77:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: protein ( x i ) SEQUENCE DESCRIPTION: SEQ ID NO:77:

| Thr | Tyr | Cys | Asp | Lys | Val | Arg | Thr | Pro | Leu | Glu | Leu | Gln | Val | Gly | Cys |
| 1   |     |     |     | 5   |     |     |     |     | 10  |     |     |     |     | 15  |     |

| Leu | Val | Gly | Asn | Glu | Leu | Thr | Phe | Glu | Cys | Asp | Lys | Cys | Glu | Ala | Arg |
|     |     |     | 20  |     |     |     |     | 25  |     |     |     |     | 30  |     |     |

| Gln | Glu | Thr | Leu |
|     |     | 35  |     |

( 2 ) INFORMATION FOR SEQ ID NO:78:

( i ) SEQUENCE CHARACTERISTICS:
        ( A ) LENGTH: 108 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
                ( C ) INDIVIDUAL ISOLATE: Clone Y5- 20

( i x ) FEATURE:
                ( A ) NAME/KEY: CDS
                ( B ) LOCATION: 52..108

( x i ) SEQUENCE DESCRIPTION: SEQ ID NO:78:

```
GCCGACACTA CTAAGGTGTA TGTTACCAAT CCAGACAATG TGGGACGAAG G GTG GGC         57
                                                         Val Gly
                                                           1

AAT GAA CTT ACC TTT GAA TGT GAC AAG TGT GAG GCT AGG CAA GAA ACC        105
Asn Glu Leu Thr Phe Glu Cys Asp Lys Cys Glu Ala Arg Gln Glu Thr
         5                   1 0                    1 5

T T G                                                                  108
L e u
```

( 2 ) INFORMATION FOR SEQ ID NO:79:

( i ) SEQUENCE CHARACTERISTICS:
                ( A ) LENGTH: 19 amino acids
                ( B ) TYPE: amino acid
                ( D ) TOPOLOGY: linear ( i i ) MOLECULE TYPE: protein ( x i ) SEQUENCE DESCRIPTION: SEQ ID NO:79:

```
Val Gly Asn Glu Leu Thr Phe Glu Cys Asp Lys Cys Glu Ala Arg Gln
 1               5                   1 0                    1 5

Glu Thr Leu
```

( 2 ) INFORMATION FOR SEQ ID NO:80:

( i ) SEQUENCE CHARACTERISTICS:
                ( A ) LENGTH: 168 base pairs
                ( B ) TYPE: nucleic acid
                ( C ) STRANDEDNESS: both
                ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
                ( C ) INDIVIDUAL ISOLATE: Clone Y5- 16

( i x ) FEATURE:
                ( A ) NAME/KEY: CDS
                ( B ) LOCATION: 1..168

( x i ) SEQUENCE DESCRIPTION: SEQ ID NO:80:

```
TTG GGG TTG ACG GTG GCT GAT GTT GCT AGC CTG TGT GAG ATG GAA ATC         48
Leu Gly Leu Thr Val Ala Asp Val Ala Ser Leu Cys Glu Met Glu Ile
 1               5                   1 0                    1 5

CAG AAC CAT ACA GCC TAT TGT GAC AAG GTG CGC ACT CCG CTT GAA TTG         96
Gln Asn His Thr Ala Tyr Cys Asp Lys Val Arg Thr Pro Leu Glu Leu
             2 0                    2 5                   3 0

CAG GTT GGG TGC TTG GTG GGC AAT GAA CTT ACC TTT GAA TGT GAC AAG        144
Gln Val Gly Cys Leu Val Gly Asn Glu Leu Thr Phe Glu Cys Asp Lys
         3 5                   4 0                    4 5

TGT GAG GCT AGG CAA GAA ACC TTG                                        168
Cys Glu Ala Arg Gln Glu Thr Leu
```

( 2 ) INFORMATION FOR SEQ ID NO:81:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: protein ( x i ) SEQUENCE DESCRIPTION: SEQ ID NO:81:

```
Leu  Gly  Leu  Thr  Val  Ala  Asp  Val  Ala  Ser  Leu  Cys  Glu  Met  Glu  Ile
 1                  5                        10                      15

Gln  Asn  His  Thr  Ala  Tyr  Cys  Asp  Lys  Val  Arg  Thr  Pro  Leu  Glu  Leu
               20                       25                      30

Gln  Val  Gly  Cys  Leu  Val  Gly  Asn  Glu  Leu  Thr  Phe  Glu  Cys  Asp  Lys
          35                       40                      45

Cys  Glu  Ala  Arg  Gln  Glu  Thr  Leu
     50                       55
```

( 2 ) INFORMATION FOR SEQ ID NO:82:

( i ) SEQUENCE CHARACTERISTICS:
        ( A ) LENGTH: 313 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Clone Y5-50

( i x ) FEATURE:
        ( A ) NAME/KEY: CDS
        ( B ) LOCATION: 1..313

( x i ) SEQUENCE DESCRIPTION: SEQ ID NO:82:

```
ATC  ACC  GTC  AAC  CCC  AAT  GAG  AAA  AAG  CGC  GTG  ACG  CTC  TTT  TCA  ACG      48
Ile  Thr  Val  Asn  Pro  Asn  Glu  Lys  Lys  Arg  Val  Thr  Leu  Phe  Ser  Thr
 1                  5                        10                      15

CAG  CAC  GAC  ATC  TTG  ACG  GTA  AGC  TTC  CTG  GTC  GCG  TCG  CTC  TGT  GGA      96
Gln  His  Asp  Ile  Leu  Thr  Val  Ser  Phe  Leu  Val  Ala  Ser  Leu  Cys  Gly
               20                       25                      30

AAT  AAG  GCT  TTT  AAT  ACG  GAA  AGA  GCC  ACG  TTG  AAG  ACA  CTT  TCC  TCC     144
Asn  Lys  Ala  Phe  Asn  Thr  Glu  Arg  Ala  Thr  Leu  Lys  Thr  Leu  Ser  Ser
          35                       40                      45

CCT  TCG  GCT  GTC  TCG  GAC  TCT  TGG  ATG  ACC  TCG  AAT  GAG  TCA  GAG  GAC     192
Pro  Ser  Ala  Val  Ser  Asp  Ser  Trp  Met  Thr  Ser  Asn  Glu  Ser  Glu  Asp
     50                       55                      60

GGG  GTA  TCC  TCC  TGC  GAG  GAG  GAC  ACC  GAC  GGG  GTC  TTC  TCA  TCT  GAG     240
Gly  Val  Ser  Ser  Cys  Glu  Glu  Asp  Thr  Asp  Gly  Val  Phe  Ser  Ser  Glu
 65                      70                       75                      80

CTG  CTC  TCA  GTA  ACC  GAG  ATA  AGT  GCT  GGC  GAT  GGA  GTA  CGG  GGG  ATG     288
Leu  Leu  Ser  Val  Thr  Glu  Ile  Ser  Ala  Gly  Asp  Gly  Val  Arg  Gly  Met
                    85                       90                      95

TCT  TCT  CCC  CAT  ACA  GGC  ATC  TCT  C                                          313
Ser  Ser  Pro  His  Thr  Gly  Ile  Ser
               100
```

( 2 ) INFORMATION FOR SEQ ID NO:83:

( i ) SEQUENCE CHARACTERISTICS:
  ( A ) LENGTH: 104 amino acids
  ( B ) TYPE: amino acid
  ( D ) TOPOLOGY: linear ( i i ) MOLECULE TYPE: protein ( x i ) SEQUENCE DESCRIPTION: SEQ ID NO:83:

| Ile | Thr | Val | Asn | Pro | Asn | Glu | Lys | Lys | Arg | Val | Thr | Leu | Phe | Ser | Thr |
|---|---|---|---|---|---|---|---|---|---|---|---|---|---|---|---|
| 1 | | | | 5 | | | | | 10 | | | | | 15 | |
| Gln | His | Asp | Ile | Leu | Thr | Val | Ser | Phe | Leu | Val | Ala | Ser | Leu | Cys | Gly |
| | | | 20 | | | | | 25 | | | | | 30 | | |
| Asn | Lys | Ala | Phe | Asn | Thr | Glu | Arg | Ala | Thr | Leu | Lys | Thr | Leu | Ser | Ser |
| | | 35 | | | | | 40 | | | | | 45 | | | |
| Pro | Ser | Ala | Val | Ser | Asp | Ser | Trp | Met | Thr | Ser | Asn | Glu | Ser | Glu | Asp |
| | 50 | | | | | 55 | | | | | 60 | | | | |
| Gly | Val | Ser | Ser | Cys | Glu | Glu | Asp | Thr | Asp | Gly | Val | Phe | Ser | Ser | Glu |
| 65 | | | | | 70 | | | | | 75 | | | | | 80 |
| Leu | Leu | Ser | Val | Thr | Glu | Ile | Ser | Ala | Gly | Asp | Gly | Val | Arg | Gly | Met |
| | | | | 85 | | | | | 90 | | | | | 95 | |
| Ser | Ser | Pro | His | Thr | Gly | Ile | Ser | | | | | | | | |
| | | | 100 | | | | | | | | | | | | |

( 2 ) INFORMATION FOR SEQ ID NO:84:

( i ) SEQUENCE CHARACTERISTICS:
    ( A ) LENGTH: 89 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( C ) INDIVIDUAL ISOLATE: Clone Y5- 52

( i x ) FEATURE:
    ( A ) NAME/KEY: CDS
    ( B ) LOCATION: 28..87

( x i ) SEQUENCE DESCRIPTION: SEQ ID NO:84:

```
ACTGAGAGCA GCTCAGATGA AAGACC CCT TCG GCT GTC TCG GAC TCT TGG        51
                              Pro Ser Ala Val Ser Asp Ser Trp
                               1               5
ATG ACC TCG AAT GAG TCA GAG GAC GGG GTA TCC TCG CA                  89
Met Thr Ser Asn Glu Ser Glu Asp Gly Val Ser Ser
     10              15              20
```

( 2 ) INFORMATION FOR SEQ ID NO:85:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: protein ( x i ) SEQUENCE DESCRIPTION: SEQ ID NO:85:

| Pro | Ser | Ala | Val | Ser | Asp | Ser | Trp | Met | Thr | Ser | Asn | Glu | Ser | Glu | Asp |
|---|---|---|---|---|---|---|---|---|---|---|---|---|---|---|---|
| 1 | | | | 5 | | | | | 10 | | | | | 15 | |
| Gly | Val | Ser | Ser | | | | | | | | | | | | |
| | | | 20 | | | | | | | | | | | | |

(2) INFORMATION FOR SEQ ID NO:86:

(i) SEQUENCE CHARACTERISTICS:
        (A) LENGTH: 214 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: Clone Y5-53

(ix) FEATURE:
        (A) NAME/KEY: CDS
        (B) LOCATION: 1..100

(xi) SEQUENCE DESCRIPTION: SEQ ID NO:86:

```
AAT  AAG  GCT  TTT  AAT  ACG  GAA  AGA  GCC  ACG  TTG  AAG  ACA  CTT  TCC  TCC        48
Asn  Lys  Ala  Phe  Asn  Thr  Glu  Arg  Ala  Thr  Leu  Lys  Thr  Leu  Ser  Ser
 1              5                        10                       15

CCT  TCG  GCT  GTC  TCG  GAC  TCT  TGG  ATG  ACC  TCG  AAT  GAG  TCA  GAG  GAC        96
Pro  Ser  Ala  Val  Ser  Asp  Ser  Trp  Met  Thr  Ser  Asn  Glu  Ser  Glu  Asp
              20                        25                       30

GGG  G ATCTCTAGAT  GCGAATTCAA  GTGTGAGGCT  AGGCAAGAAA  CCTTGGCCTC                     150
Gly

CTTCTCTTAC  ATTTGGTCTG  GAGTGCCGCT  GACTAGGGCC  ACGCCGGCCA  AGCCTCCGT                 210

GGTG                                                                                  214
```

(2) INFORMATION FOR SEQ ID NO:87:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:87:

```
Asn  Lys  Ala  Phe  Asn  Thr  Glu  Arg  Ala  Thr  Leu  Lys  Thr  Leu  Ser  Ser
 1              5                        10                       15

Pro  Ser  Ala  Val  Ser  Asp  Ser  Trp  Met  Thr  Ser  Asn  Glu  Ser  Glu  Asp
              20                        25                       30

Gly
```

(2) INFORMATION FOR SEQ ID NO:88:

(i) SEQUENCE CHARACTERISTICS:
        (A) LENGTH: 113 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: Clone Y5-55

(ix) FEATURE:
        (A) NAME/KEY: CDS (B) LOCATION: 52..113

(x i) SEQUENCE DESCRIPTION: SEQ ID NO:88:

```
CCATCGCCAG  CACTTATCTC  GGTTACTGAG  AGCAGCTCAG  ATCAGAAGAC  C  CCT  TCG        57
                                                               Pro  Ser
                                                                1

GCT  GTC  TCG  GAC  TCT  TGG  ATG  ACC  TCG  AAT  GAG  TCA  GAG  GAC  GGG  GTA   105
Ala  Val  Ser  Asp  Ser  Trp  Met  Thr  Ser  Asn  Glu  Ser  Glu  Asp  Gly  Val
          5                        10                       15

TCC  TCG  CA                                                                    113
Ser  Ser
     20
```

(2) INFORMATION FOR SEQ ID NO:89:

(i) SEQUENCE CHARACTERISTICS:
      (A) LENGTH: 20 amino acids
      (B) TYPE: amino acid
      (D) TOPOLOGY: linear (ii) MOLECULE TYPE: protein (x i) SEQUENCE DESCRIPTION: SEQ ID NO:89:

```
Pro  Ser  Ala  Val  Ser  Asp  Ser  Trp  Met  Thr  Ser  Asn  Glu  Ser  Glu  Asp
 1              5                        10                       15

Gly  Val  Ser  Ser
          20
```

(2) INFORMATION FOR SEQ ID NO:90:

(i) SEQUENCE CHARACTERISTICS:
      (A) LENGTH: 330 base pairs
      (B) TYPE: nucleic acid
      (C) STRANDEDNESS: both
      (D) TOPOLOGY: linear (ii) MOLECULE TYPE: cDNA (iii) HYPOTHETICAL: NO (iv) ANTI-SENSE: NO (v) ORIGINAL SOURCE:
      (C) INDIVIDUAL ISOLATE: Clone Y5-56

(ix) FEATURE:
      (A) NAME/KEY: CDS
      (B) LOCATION: 1..330

(x i) SEQUENCE DESCRIPTION: SEQ ID NO:90:

```
ACG  TTG  AAG  ACA  CTT  TCC  TCC  CCT  TCG  GCT  GTC  TCG  GAC  TCT  TGG  ATG    48
Thr  Leu  Lys  Thr  Leu  Ser  Ser  Pro  Ser  Ala  Val  Ser  Asp  Ser  Trp  Met
 1              5                        10                       15

ACC  TCG  AAT  GAG  TCA  GAG  GAC  GGG  GTA  TCC  TCC  TGC  GAG  GAG  GAC  ACC    96
Thr  Ser  Asn  Glu  Ser  Glu  Asp  Gly  Val  Ser  Ser  Cys  Glu  Glu  Asp  Thr
          20                        25                       30

GAC  GGG  GTC  TTC  TCA  TCT  GAG  CTG  CTC  TCA  GTA  ACC  GAG  ATA  AGT  GCT   144
Asp  Gly  Val  Phe  Ser  Ser  Glu  Leu  Leu  Ser  Val  Thr  Glu  Ile  Ser  Ala
          35                        40                       45

GGC  GAT  GGA  GTA  CGG  GGG  ATG  TCT  TCT  CCC  CAT  ACA  GGC  ATC  TCT  CGG   192
Gly  Asp  Gly  Val  Arg  Gly  Met  Ser  Ser  Pro  His  Thr  Gly  Ile  Ser  Arg
     50                        55                       60

CTA  CTA  CCA  CAA  AGA  GAG  GGT  GTA  CTG  CAG  TCC  TCC  ATG  ATG  ACA  TCA   240
Leu  Leu  Pro  Gln  Arg  Glu  Gly  Val  Leu  Gln  Ser  Ser  Met  Met  Thr  Ser
65                        70                       75                       80

ATG  TGC  GGT  TCA  AGA  ATC  CTC  GCA  GCA  TTC  TCG  ATC  GCT  TGG  AGA  GCA   288
Met  Cys  Gly  Ser  Arg  Ile  Leu  Ala  Ala  Phe  Ser  Ile  Ala  Trp  Arg  Ala
```

```
                                   85                          90                          95
GCA  GCC  GCC  GGC  GGC  AGA  TCG  GCC  TCA  GTC  AGT  TCT  GAG  TCT              330
Ala  Ala  Ala  Gly  Gly  Arg  Ser  Ala  Ser  Val  Ser  Ser  Glu  Ser
                    100                      105                      110
```

(2) INFORMATION FOR SEQ ID NO:91:

(i) SEQUENCE CHARACTERISTICS:
        (A) LENGTH: 110 amino acids
        (B) TYPE: amino acid
        (D) TOPOLOGY: linear (ii) MOLECULE TYPE: protein (xi) SEQUENCE DESCRIPTION: SEQ ID NO:91:

```
Thr  Leu  Lys  Thr  Leu  Ser  Ser  Pro  Ser  Ala  Val  Ser  Asp  Ser  Trp  Met
 1                    5                        10                       15

Thr  Ser  Asn  Glu  Ser  Glu  Asp  Gly  Val  Ser  Ser  Cys  Glu  Glu  Asp  Thr
               20                       25                       30

Asp  Gly  Val  Phe  Ser  Ser  Glu  Leu  Leu  Ser  Val  Thr  Glu  Ile  Ser  Ala
               35                       40                       45

Gly  Asp  Gly  Val  Arg  Gly  Met  Ser  Ser  Pro  His  Thr  Gly  Ile  Ser  Arg
          50                       55                       60

Leu  Leu  Pro  Gln  Arg  Glu  Gly  Val  Leu  Gln  Ser  Ser  Met  Met  Thr  Ser
 65                       70                       75                       80

Met  Cys  Gly  Ser  Arg  Ile  Leu  Ala  Ala  Phe  Ser  Ile  Ala  Trp  Arg  Ala
               85                       90                       95

Ala  Ala  Ala  Gly  Gly  Arg  Ser  Ala  Ser  Val  Ser  Ser  Glu  Ser
                    100                      105                      110
```

(2) INFORMATION FOR SEQ ID NO:92:

(i) SEQUENCE CHARACTERISTICS:
        (A) LENGTH: 195 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: Clone Y5-57

(ix) FEATURE:
        (A) NAME/KEY: CDS
        (B) LOCATION: 1..195

(xi) SEQUENCE DESCRIPTION: SEQ ID NO:92:

```
ACG  GAA  AGA  GCC  ACG  TTG  AAG  ACA  CTT  TCC  TCC  CCT  TCG  GCT  GCC  TCG    48
Thr  Glu  Arg  Ala  Thr  Leu  Lys  Thr  Leu  Ser  Ser  Pro  Ser  Ala  Ala  Ser
 1                    5                        10                       15

GAC  TCT  TGG  ATG  ACC  TCG  AAT  GAG  TCG  GAG  GAC  GGG  GTA  TCC  TCC  TGC    96
Asp  Ser  Trp  Met  Thr  Ser  Asn  Glu  Ser  Glu  Asp  Gly  Val  Ser  Ser  Cys
               20                       25                       30

GAA  GAG  GAC  ACC  GAC  GGG  GTC  TTC  TCA  TCT  GAG  CTG  CTC  TCA  GTA  ACC   144
Glu  Glu  Asp  Thr  Asp  Gly  Val  Phe  Ser  Ser  Glu  Leu  Leu  Ser  Val  Thr
               35                       40                       45

GAG  ATA  AGT  GCT  GGC  GGT  GGA  GTA  CGG  GGG  ATG  TCT  TCT  CCC  CAT  ACG   192
Glu  Ile  Ser  Ala  Gly  Gly  Gly  Val  Arg  Gly  Met  Ser  Ser  Pro  His  Thr
          50                       55                       60

GGC                                                                               195
```

Gly
65

(2) INFORMATION FOR SEQ ID NO:93:

(i) SEQUENCE CHARACTERISTICS:
        (A) LENGTH: 65 amino acids
        (B) TYPE: amino acid
        (D) TOPOLOGY: linear (ii) MOLECULE TYPE: protein (xi) SEQUENCE DESCRIPTION: SEQ ID NO:93:

```
Thr Glu Arg Ala Thr Leu Lys Thr Leu Ser Ser Pro Ser Ala Ala Ser
  1               5                  10                  15
Asp Ser Trp Met Thr Ser Asn Glu Ser Glu Asp Gly Val Ser Ser Cys
             20                  25                  30
Glu Glu Asp Thr Asp Gly Val Phe Ser Ser Glu Leu Leu Ser Val Thr
         35                  40                  45
Glu Ile Ser Ala Gly Gly Gly Val Arg Gly Met Ser Ser Pro His Thr
     50                  55                  60
Gly
 65
```

(2) INFORMATION FOR SEQ ID NO:94:

(i) SEQUENCE CHARACTERISTICS:
        (A) LENGTH: 115 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: Clone Y5-60

(ix) FEATURE:
        (A) NAME/KEY: CDS
        (B) LOCATION: 1..115

(xi) SEQUENCE DESCRIPTION: SEQ ID NO:94:

```
AAG ACA CTT TCC TCC CCT TCG GCT GTC TCG GAC TCT TGG ATG ACC TCG    48
Lys Thr Leu Ser Ser Pro Ser Ala Val Ser Asp Ser Trp Met Thr Ser
  1               5                  10                  15
AAT GAG TCA GAG GAC GGG GTA TCC TCC TGC GAG GAG GAC ACC GAC TGG    96
Asn Glu Ser Glu Asp Gly Val Ser Ser Cys Glu Glu Asp Thr Asp Trp
             20                  25                  30
GTC TTC TCA TCT GAG CTG C                                         115
Val Phe Ser Ser Glu Leu
             35
```

(2) INFORMATION FOR SEQ ID NO:95:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:95:

```
Lys Thr Leu Ser Ser Pro Ser Ala Val Ser Asp Ser Trp Met Thr Ser
```

| | | | | | | | | | | | | | | |
|---|---|---|---|---|---|---|---|---|---|---|---|---|---|---|
| 1 | | | | 5 | | | | | 10 | | | | | 15 |
| Asn | Glu | Ser | Glu | Asp | Gly | Val | Ser | Ser | Cys | Glu | Glu | Asp | Thr | Asp | Trp |
| | | | 20 | | | | | 25 | | | | 30 | | |
| Val | Phe | Ser | Ser | Glu | Leu | | | | | | | | | |
| | | | 35 | | | | | | | | | | | |

( 2 ) INFORMATION FOR SEQ ID NO:96:

( i ) SEQUENCE CHARACTERISTICS:
        ( A ) LENGTH: 93 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Clone Y5-63

( i x ) FEATURE:
        ( A ) NAME/KEY: CDS
        ( B ) LOCATION: 19..93

( x i ) SEQUENCE DESCRIPTION: SEQ ID NO:96:

```
GAGAGCAGCT CAGATGAG AAG ACA CTT TCC TCC CCT TCG GCT GTC TCG GAC         51
                    Lys Thr Leu Ser Ser Pro Ser Ala Val Ser Asp
                     1               5                      10

TCT TGG ATG ACC TCG AAT GAG TCA GAG GAC GGG GTA TCC TCG                93
Ser Trp Met Thr Ser Asn Glu Ser Glu Asp Gly Val Ser Ser
         15                  20                  25
```

( 2 ) INFORMATION FOR SEQ ID NO:97:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( x i ) SEQUENCE DESCRIPTION: SEQ ID NO:97:

| Lys | Thr | Leu | Ser | Ser | Pro | Ser | Ala | Val | Ser | Asp | Ser | Trp | Met | Thr | Ser |
|---|---|---|---|---|---|---|---|---|---|---|---|---|---|---|---|
| 1 | | | | 5 | | | | | 10 | | | | | 15 | |
| Asn | Glu | Ser | Glu | Asp | Gly | Val | Ser | Ser | | | | | | | |
| | | | 20 | | | | | 25 | | | | | | | |

( 2 ) INFORMATION FOR SEQ ID NO:98:

( i ) SEQUENCE CHARACTERISTICS:
        ( A ) LENGTH: 1181 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 8E3

( x i ) SEQUENCE DESCRIPTION: SEQ ID NO:98:

```
GCTGGCTGAG GCACGGTTGG TCCCGCTGAT CTTGCTGCTG CTATGGTGGT GGGTGAACCA        60
```

-continued

| | | | | | | |
|---|---|---|---|---|---|---|
| GCTGGCAGTC | CTAGGGCTGC | CGGCTGTGGA | AGCCGCCGTG | GCAGGTGAGG | TCTTCGCGGG | 120 |
| CCCTGCCCTG | TCCTGGTGTC | TGGGACTCCC | GGTCGTCAGT | ATGATATTGG | GTTTGGCAAA | 180 |
| CCTGGTGCTG | TACTTTAGAT | GGTTGGGACC | CCAACGCCTG | ATGTTCCTCG | TGTTGTGGAA | 240 |
| GCTTGCTCGG | GGAGCTTTCC | CGCTGGCCCT | CTTGATGGGG | ATTTCGGCGA | CCCGCGGGCG | 300 |
| CACCTCAGTG | CTCGGGGCCG | AGTTCTGCTT | CGATGCTACA | TTCGAGGTGG | ACACTTCGGT | 360 |
| GTTGGGCTGG | GTGGTGGCCA | GTGTGGTAGC | TTGGGCCATT | GCGCTCCTGA | GCTCGATGAG | 420 |
| CGCAGGGGGG | TGGAGGCACA | AAGCCGTGAT | CTATAGGACG | TGGTGTAAGG | GGTACCAGGC | 480 |
| AATCCGTCAA | AGGGTGGTGA | GGAGCCCCCT | CGGGGAGGGG | CGGCCTGCCA | AACCCCTGAC | 540 |
| CTTTGCCTGG | TGCTTGGCCT | CGTACATCTG | GCCAGATGCT | GTGATGATGG | TGGTGGTTGC | 600 |
| CTTGGTCCTT | CTCTTTGGCC | TGTTCGACGC | GTTGGATTGG | GCCTTGGAGG | AGATCTTGGT | 660 |
| GTCCCGGCCC | TCGTTGCGGC | GTTTGGCTCG | GGTGGTTGAG | TGCTGTGTGA | TGGCGGGTGA | 720 |
| GAAGGCCACA | ACCGTCCGGC | TGGTCTCCAA | GATGTGTGCG | AGAGGAGCTT | ATTTGTTCGA | 780 |
| TCATATGGGC | TCTTTTTCGC | GTGCTGTCAA | GGAGCGCCTG | TTGGAATGGG | ACGCAGCTCT | 840 |
| TGAACCTCTG | TCATTCACTA | GGACGGACTG | TCGCATCATA | CGGGATGCCG | CGAGGACTTT | 900 |
| GTCCTGCGGG | CAGTGCGTCA | TGGGTTTACC | CGTGGTTGCG | CGCCGTGGTG | ATGAGGTTCT | 960 |
| CATCGGCGTC | TTCCAGGATG | TGAATCATTT | GCCTCCCGGG | TTTGTTCCGA | CCGCGCCTGT | 1020 |
| TGTCATCCGA | CGGTGCGGAA | AGGGCTTCTT | GGGGGTCACA | AAGGCTGCCT | TGACAGGTCG | 1080 |
| GGATCCTGAC | TTACATCCAG | GGAACGTCAT | GGTGTTGGGG | ACGGCTACGT | CGCGAAGCAT | 1140 |
| GGGAACATGC | TTGAACGGCC | TGCTGTTCAC | GACCTTCCAT | G | | 1181 |

( 2 ) INFORMATION FOR SEQ ID NO:99:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer Y5-10- F1

( x i ) SEQUENCE DESCRIPTION: SEQ ID NO:99:

| | | |
|---|---|---|
| TCAGCCATGG | CTCGTGCGCC | CGCGATGGTC | 30 |

( 2 ) INFORMATION FOR SEQ ID NO:100:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer Y5-10- R1

( x i ) SEQUENCE DESCRIPTION: SEQ ID NO:100:

CGAGGATCCA GCCGCCGGCG GCAGATC 27

(2) INFORMATION FOR SEQ ID NO:101:

(i) SEQUENCE CHARACTERISTICS:
      (A) LENGTH: 32 base pairs
      (B) TYPE: nucleic acid
      (C) STRANDEDNESS: both
      (D) TOPOLOGY: linear (ii) MOLECULE TYPE: DNA (iii) HYPOTHETICAL: NO (iv) ANTI-SENSE: NO (vi) ORIGINAL SOURCE:
      (C) INDIVIDUAL ISOLATE: Primer Y5- 16F1

(xi) SEQUENCE DESCRIPTION: SEQ ID NO:101:

GATTCCATGG GTTTGGGGTT GACGGTGGCT GA 32

(2) INFORMATION FOR SEQ ID NO:102:

(i) SEQUENCE CHARACTERISTICS:
      (A) LENGTH: 32 base pairs
      (B) TYPE: nucleic acid
      (C) STRANDEDNESS: both
      (D) TOPOLOGY: linear (ii) MOLECULE TYPE: DNA (iii) HYPOTHETICAL: NO (iv) ANTI-SENSE: NO (vi) ORIGINAL SOURCE:
      (C) INDIVIDUAL ISOLATE: Primer 470EP- R3

(xi) SEQUENCE DESCRIPTION: SEQ ID NO:102:

GCGAATTCGG ATCCCAAGGT TTCTTGCCTA GC 32

(2) INFORMATION FOR SEQ ID NO:103:

(i) SEQUENCE CHARACTERISTICS:
      (A) LENGTH: 27 base pairs
      (B) TYPE: nucleic acid
      (C) STRANDEDNESS: both
      (D) TOPOLOGY: linear (ii) MOLECULE TYPE: DNA (iii) HYPOTHETICAL: NO (iv) ANTI-SENSE: NO (vi) ORIGINAL SOURCE:
      (C) INDIVIDUAL ISOLATE: Primer Y5-5- F1

(xi) SEQUENCE DESCRIPTION: SEQ ID NO:103:

GAGGCCATGG CCTATTGTGA CAAGGTG 27

(2) INFORMATION FOR SEQ ID NO:104:

(i) SEQUENCE CHARACTERISTICS:
      (A) LENGTH: 17 base pairs
      (B) TYPE: nucleic acid
      (C) STRANDEDNESS: both
      (D) TOPOLOGY: linear (ii) MOLECULE TYPE: DNA (iii) HYPOTHETICAL: NO ( i v ) ANTI-SENSE: NO ( v i ) ORIGINAL SOURCE:
    ( C ) INDIVIDUAL ISOLATE: Primer PGEX- R ( x i ) SEQUENCE DESCRIPTION: SEQ ID NO:104:

GACCGTCTCC GGGAGCT      17

( 2 ) INFORMATION FOR SEQ ID NO:105:

( i ) SEQUENCE CHARACTERISTICS:
        ( A ) LENGTH: 326 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Clone GE15

( i x ) FEATURE:
        ( A ) NAME/KEY: CDS
        ( B ) LOCATION: 3..326

( x i ) SEQUENCE DESCRIPTION: SEQ ID NO:105:

```
CC  ATG  GAG  GTC  TCT  GAC  TTC  CGT  GGC  TCG  TCT  GGC  TCA  CCG  GTC  CTA      47
    Met  Glu  Val  Ser  Asp  Phe  Arg  Gly  Ser  Ser  Gly  Ser  Pro  Val  Leu
     1              5                        10                       15

TGT  GAC  GAA  GGG  CAC  GCA  GTA  GGA  ATG  CTC  GTG  TCT  GTG  CTT  CAC  TCC      95
Cys  Asp  Glu  Gly  His  Ala  Val  Gly  Met  Leu  Val  Ser  Val  Leu  His  Ser
                    20                       25                       30

GGT  GGT  AGG  GTC  ACC  GCG  GCA  CGG  TTC  ACT  AGG  CCG  TGG  ACC  CAA  GTG     143
Gly  Gly  Arg  Val  Thr  Ala  Ala  Arg  Phe  Thr  Arg  Pro  Trp  Thr  Gln  Val
               35                       40                       45

CCA  ACA  GAT  GCC  AAA  ACC  ACC  ACT  GAA  CCC  CCT  CCG  GTG  CCG  GCC  AAA     191
Pro  Thr  Asp  Ala  Lys  Thr  Thr  Thr  Glu  Pro  Pro  Pro  Val  Pro  Ala  Lys
          50                       55                       60

GGA  GTT  TTC  AAA  GAG  GCC  CCG  TTG  TTT  ATG  CCT  ACG  GGA  GCG  GGA  AAG     239
Gly  Val  Phe  Lys  Glu  Ala  Pro  Leu  Phe  Met  Pro  Thr  Gly  Ala  Gly  Lys
     65                       70                       75

AGC  ACT  CGC  GTC  CCG  TTG  GAG  TAC  GGC  AAC  ATG  GGG  CAC  AAG  GTC  TTA     287
Ser  Thr  Arg  Val  Pro  Leu  Glu  Tyr  Gly  Asn  Met  Gly  His  Lys  Val  Leu
 80                       85                       90                       95

ATC  TTG  AAC  CCC  TCA  GTG  GCC  ACT  GTG  CGG  GCG  ATG  GGC                    326
Ile  Leu  Asn  Pro  Ser  Val  Ala  Thr  Val  Arg  Ala  Met  Gly
               100                      105
```

( 2 ) INFORMATION FOR SEQ ID NO:106:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:106:

```
Met  Glu  Val  Ser  Asp  Phe  Arg  Gly  Ser  Ser  Gly  Ser  Pro  Val  Leu  Cys
 1              5                        10                       15

Asp  Glu  Gly  His  Ala  Val  Gly  Met  Leu  Val  Ser  Val  Leu  His  Ser  Gly
               20                       25                       30
```

| | | | | | | | | | | | | | | |
|---|---|---|---|---|---|---|---|---|---|---|---|---|---|---|
| Gly | Arg | Val | Thr | Ala | Ala | Arg | Phe | Thr | Arg | Pro | Trp | Thr | Gln | Val | Pro |
| | | 35 | | | | | 40 | | | | | 45 | | | |
| Thr | Asp | Ala | Lys | Thr | Thr | Thr | Glu | Pro | Pro | Pro | Val | Pro | Ala | Lys | Gly |
| | | 50 | | | | 55 | | | | | 60 | | | | |
| Val | Phe | Lys | Glu | Ala | Pro | Leu | Phe | Met | Pro | Thr | Gly | Ala | Gly | Lys | Ser |
| 65 | | | | | 70 | | | | | 75 | | | | | 80 |
| Thr | Arg | Val | Pro | Leu | Glu | Tyr | Gly | Asn | Met | Gly | His | Lys | Val | Leu | Ile |
| | | | | 85 | | | | | 90 | | | | | 95 | |
| Leu | Asn | Pro | Ser | Val | Ala | Thr | Val | Arg | Ala | Met | Gly | | | | |
| | | | | 100 | | | | 105 | | | | | | | |

( 2 ) INFORMATION FOR SEQ ID NO:107:

( i ) SEQUENCE CHARACTERISTICS:
        ( A ) LENGTH: 138 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Clone GE17

( i x ) FEATURE:
        ( A ) NAME/KEY: CDS
        ( B ) LOCATION: 1..138

( x i ) SEQUENCE DESCRIPTION: SEQ ID NO:107:

| | | | | | | | | | | | | | | | | |
|---|---|---|---|---|---|---|---|---|---|---|---|---|---|---|---|---|
| GGT | GAT | GAG | GTT | CTC | ATC | GGC | GTC | TTC | CAG | GAT | GTG | AAT | CAT | TTG | CCT | 48 |
| Gly | Asp | Glu | Val | Leu | Ile | Gly | Val | Phe | Gln | Asp | Val | Asn | His | Leu | Pro | |
| 1 | | | | 5 | | | | | 10 | | | | | 15 | | |
| CCC | GGG | TTT | GTT | CCG | ACC | GCG | CCT | GTT | GTC | ATC | CGA | CGG | TGC | GGA | AAG | 96 |
| Pro | Gly | Phe | Val | Pro | Thr | Ala | Pro | Val | Val | Ile | Arg | Arg | Cys | Gly | Lys | |
| | | | 20 | | | | | 25 | | | | | 30 | | | |
| GGC | TTC | TTG | GGG | GTC | ACA | AAG | GCT | GCC | TTG | ACA | GGT | CGG | GAT | | | 138 |
| Gly | Phe | Leu | Gly | Val | Thr | Lys | Ala | Ala | Leu | Thr | Gly | Arg | Asp | | | |
| | | 35 | | | | 40 | | | | | 45 | | | | | |

( 2 ) INFORMATION FOR SEQ ID NO:108:

( i ) SEQUENCE CHARACTERISTICS:
        ( A ) LENGTH: 46 amino acids
        ( B ) TYPE: amino acid
        ( D ) TOPOLOGY: linear ( i i ) MOLECULE TYPE: protein ( x i ) SEQUENCE DESCRIPTION: SEQ ID NO:108:

| | | | | | | | | | | | | | | | |
|---|---|---|---|---|---|---|---|---|---|---|---|---|---|---|---|
| Gly | Asp | Glu | Val | Leu | Ile | Gly | Val | Phe | Gln | Asp | Val | Asn | His | Leu | Pro |
| 1 | | | | 5 | | | | | 10 | | | | | 15 | |
| Pro | Gly | Phe | Val | Pro | Thr | Ala | Pro | Val | Val | Ile | Arg | Arg | Cys | Gly | Lys |
| | | | 20 | | | | | 25 | | | | | 30 | | |
| Gly | Phe | Leu | Gly | Val | Thr | Lys | Ala | Ala | Leu | Thr | Gly | Arg | Asp | | |
| | | 35 | | | | 40 | | | | | 45 | | | | |

( 2 ) INFORMATION FOR SEQ ID NO:109:

( i ) SEQUENCE CHARACTERISTICS:
        ( A ) LENGTH: 395 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
 ( C ) INDIVIDUAL ISOLATE: Consensus Sequence 9E3

( x i ) SEQUENCE DESCRIPTION: SEQ ID NO:109:

| | | | | | | |
|---|---|---|---|---|---|---|
| TGTATTTGTC | CTGTTATACC | TGATGAAGCT | GGCTGAGGCA | CGGTTGGTCC | CGCTGATCTT | 60 |
| GCTGCTGCTA | TGGTGGTGGG | TGAACCAGCT | GGCAGTCCTA | GGGCTGCCGG | CTGTGGAAGC | 120 |
| CGCCGTGGCA | GGTGAGGTCT | TCGCGGGCCC | TGCCCTGTCC | TGGTGTCTGG | GACTCCCGGT | 180 |
| CGTCAGTATG | ATATTGGGTT | TGGCAAACCT | AGTGCTGTAC | TTTAGATGGT | TGGGACCCCA | 240 |
| ACGCCTGATG | TTCCTCGTGT | TGTGGAAGCT | TGCTCGGGGA | GCTTTCCCGC | TGGCCCTCTT | 300 |
| GATGGGGATT | TCGGCGACCC | GCGGGCGCAC | CTCAGTGCTC | GGGGCCGAGT | TCTGCTTCGA | 360 |
| TGCTACATTC | GAGGTGGACA | CTTCGGTGTT | GGGCT | | | 395 |

( 2 ) INFORMATION FOR SEQ ID NO:110:

( i ) SEQUENCE CHARACTERISTICS:
 ( A ) LENGTH: 460 base pairs
 ( B ) TYPE: nucleic acid
 ( C ) STRANDEDNESS: both
 ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
 ( C ) INDIVIDUAL ISOLATE: Consensus Sequence 10E3

( x i ) SEQUENCE DESCRIPTION: SEQ ID NO:110:

| | | | | | | |
|---|---|---|---|---|---|---|
| GCCCCTGGGC | AACCAGGGCC | GAGGCAACCC | GGTGCGGTCG | CCCTTGGGTT | TTGGGTCCTA | 60 |
| CGCCATGACC | AGGATCCGAG | ATACCCTACA | TCTGGTGGAG | TGTCCCACAC | CAGCCATTGA | 120 |
| GCCTCCCACC | GGGACGTTTG | GGTTCTTCCC | CGGGACGCCG | CCTCTCAACA | ACTGCATGCT | 180 |
| CTTGGGCACG | GAAGTGTCCG | AGGCACTTGG | GGGGGCTGGC | CTCACGGGGG | GGTTCTATGA | 240 |
| ACCCCTGGTG | CGCAGGTGTT | CGAAGCTGAT | GGGAAGCCGA | AATCCGGTTT | GTCCGGGGTT | 300 |
| TGCATGGCTC | TCTTCGGGCA | GGCCTGATGG | GTTTATACAT | GTCCAGGGTC | ACTTGCAGGA | 360 |
| GGTGGATGCA | GGCAACTTCA | TCCCGCCCCC | GCGCTGGTTG | CTCTTGGACT | TTGTATTTGT | 420 |
| CCTGTTATAC | CTGATGAAGC | TGGCTGAGGC | ACGGTTGGTC | | | 460 |

( 2 ) INFORMATION FOR SEQ ID NO:111:

( i ) SEQUENCE CHARACTERISTICS:
 ( A ) LENGTH: 28 base pairs
 ( B ) TYPE: nucleic acid
 ( C ) STRANDEDNESS: both
 ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
 ( C ) INDIVIDUAL ISOLATE: Primer GE15F ( x i ) SEQUENCE DESCRIPTION: SEQ ID NO:111:

GCCGCCATGG AGGTCTCTGA CTTCCGTG                                                                                28

( 2 ) INFORMATION FOR SEQ ID NO:112:

( i ) SEQUENCE CHARACTERISTICS:
                ( A ) LENGTH: 31 base pairs
                ( B ) TYPE: nucleic acid
                ( C ) STRANDEDNESS: both
                ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
                ( C ) INDIVIDUAL ISOLATE: Primer GE15R ( x i ) SEQUENCE DESCRIPTION: SEQ ID NO:112:

GCGCGGATCC GCCCATCGCC CGCACAGTGG C                                                                            31

( 2 ) INFORMATION FOR SEQ ID NO:113:

( i ) SEQUENCE CHARACTERISTICS:
                ( A ) LENGTH: 31 base pairs
                ( B ) TYPE: nucleic acid
                ( C ) STRANDEDNESS: both
                ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
                ( C ) INDIVIDUAL ISOLATE: Primer GE17F ( x i ) SEQUENCE DESCRIPTION: SEQ ID NO:113:

CGCTCCATGG GTGATGAGGT TCTCATCGGC G                                                                            31

( 2 ) INFORMATION FOR SEQ ID NO:114:

( i ) SEQUENCE CHARACTERISTICS:
                ( A ) LENGTH: 28 base pairs
                ( B ) TYPE: nucleic acid
                ( C ) STRANDEDNESS: both
                ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
                ( C ) INDIVIDUAL ISOLATE: Primer GE17R ( x i ) SEQUENCE DESCRIPTION: SEQ ID NO:114:

GTAAGTCAGG ATCCCGACCT GTCAAGGC                                                                                28

( 2 ) INFORMATION FOR SEQ ID NO:115:

( i ) SEQUENCE CHARACTERISTICS:
                ( A ) LENGTH: 452 base pairs
                ( B ) TYPE: nucleic acid
                ( C ) STRANDEDNESS: double
                ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( C ) INDIVIDUAL ISOLATE: NcoI/EcoRI- containing fragment of pGEX-HISb- GE3-s HGV plasmid ( x i ) SEQUENCE DESCRIPTION: SEQ ID NO:115:

| | | | | | | |
|---|---|---|---|---|---|---|
| CAAAATCGGA | TCTGGTTCCG | CGTGGTTCCA | TGGTCTCATG | GGACGCGGAC | GCTCGTGCGC | 60 |
| CCGCGATGGT | CTATGGCCCT | GGGCAAAGTG | TTACCATTGA | CGGGGAGCGC | TACACCTTGC | 120 |
| CTCATCAACT | GAGGCTCAGG | AATGTGGCAC | CCTCTGAGGT | TTCATCCGAG | GTGTCCATTG | 180 |
| ACATTGGGAC | GGAGACTGAA | GACTCAGAAC | TGACTGAGGC | CGATCTGCCG | CCGGCGGCTG | 240 |
| CTGCTCTCCA | AGCGATCGAG | AATGCTGCGA | GGATTCTTGA | ACCGCACATT | GATGTCATCA | 300 |
| TGGAGGACTG | CAGTACACCC | TCTCTTTGTG | GTAGTAGCCG | AGAGATGCCT | GTATGGGGAG | 360 |
| AAGACATCCC | CCGTACTCCA | TCGCCAGCAC | TTATCGGATC | CCACCATCAC | CATCACCATT | 420 |
| AGAATTCATC | GTGACTGACT | GACGATCTAC | CT | | | 452 |

( 2 ) INFORMATION FOR SEQ ID NO:116:

( i ) SEQUENCE CHARACTERISTICS:
        ( A ) LENGTH: 590 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 11E3

( x i ) SEQUENCE DESCRIPTION: SEQ ID NO:116:

| | | | | | | |
|---|---|---|---|---|---|---|
| AGCAATCGGC | TGGGGTGACC | CCATCACTTA | TTGGAGCCAC | GGGCAAAATC | AGTGGCCCCT | 60 |
| TTCATGCCCC | CAGTATGTCT | ATGGGTCTGC | TACAGTCACT | TGCGTGTGGG | GTTCCGCTTC | 120 |
| TTGGTTTGCC | TCCACCAGTG | GTCGCGACTC | GAAGATAGAT | GTGTGGAGTT | TAGTGCCAGT | 180 |
| TGGCTCTGCC | ACCTGCACCA | TAGCCGCACT | TGGATCATCG | GATCGCGACA | CGGTGCCTGG | 240 |
| GCTCTCCGAG | TGGGGAATCC | CGTGCGTGAC | GTGTGTTCTG | GACCGTCGGC | CTGCCTCCTG | 300 |
| CGGCACCTGT | GTGAGGGACT | GCTGGCCCGA | GACCGGGTCG | GTTAGGTTCC | CATTCCATCG | 360 |
| GTGCGGCGTG | GGGCCTCGGC | TGACAAAGGA | CTTGGAAGCT | GTGCCCTTCG | TCAACAGGAC | 420 |
| AACTCCCTTC | ACCATTAGGG | GGCCCCTGGG | CAACCAGGGC | CGAGGCAACC | CGGTGCGGTC | 480 |
| GCCCTTGGGT | TTTGGGTCCT | ACGCCATGAC | CAGGATCCGA | GATACCCTAC | ATCTGGTGGA | 540 |
| GTGTCCCACA | CCAGCCATCG | AGCCTCCCAC | CGGGACGTTT | GGGTTCTTCC | | 590 |

( 2 ) INFORMATION FOR SEQ ID NO:117:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO (iv) ANTI-SENSE: NO (vi) ORIGINAL SOURCE:
(C) INDIVIDUAL ISOLATE: Probe E3- 111PROB (xi) SEQUENCE DESCRIPTION: SEQ ID NO:117:

TGGTGAAGGG AGTTGTCCTA TTGACGAAG 29

(2) INFORMATION FOR SEQ ID NO:118:

(i) SEQUENCE CHARACTERISTICS:
(A) LENGTH: 735 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (vi) ORIGINAL SOURCE:
(C) INDIVIDUAL ISOLATE: Consensus Sequence 12E3

(xi) SEQUENCE DESCRIPTION: SEQ ID NO:118:

| ATTGTTGTGC | CCCGGAGGAC | ATCGGGTTCT | GCCTGGAGGG | TGGATGCCTG | GTGGCCCTGG | 60 |
| GGTGCACGAT | TTGCACTGAC | CAATGCTGGC | CACTGTATCA | GGCGGGTTTG | GCTGTGCGGC | 120 |
| CTGGCAAGTC | CGCGGCCCAA | CTGGTGGGGG | AGCTGGGTAG | CCTATACGGG | CCCCTGTCGG | 180 |
| TCTCGGCCTA | TGTGGCTGGG | ATCCTGGGCC | TGGGTGAGGT | GTACTCGGGT | GTCCTAACGG | 240 |
| TGGGAGTCGC | GTTGACGCGC | CGGGTCTACC | CGGTGCCTAA | CCTGACGTGT | GCAGTCGCGT | 300 |
| GTGAGCTAAA | GTGGGAAAGT | GAGTTTTGGA | GATGGACTGA | ACAGCTGGCC | TCCAACTACT | 360 |
| GGATTCTGGA | ATACCTCTGG | AAGGTCCCAT | TTGATTTCTG | GAGAGGCGTG | ATAAGCCTGA | 420 |
| CCCCCTTGTT | GGTTTGCGTG | GCCGCATTGC | TGCTGCTTGA | GCAACGGATT | GTCATGGTCT | 480 |
| TCCTGTTGGT | GACGATGGCC | GGGATGTCGC | AAGGCGCCCC | TGCCTCCGTT | TTGGGGTCAC | 540 |
| GCCCCTTTGA | CTACGGGTTG | ACTTGGCAGA | CCTGCTCTTG | CAGGGCCAAC | GGTTCGCGTT | 600 |
| TTTCGACTGG | GGAGAAGGTG | TGGGACCGTG | GGAACGTTAC | GCTTCAGTGT | GACTGCCCTA | 660 |
| ACGGCCCCTG | GGTGTGGTTG | CCAGCCTTTT | GCCAAGCAAT | CGGCTGGGGT | GACCCCATCA | 720 |
| CTTATTGGAG | CCACG |  |  |  |  | 735 |

(2) INFORMATION FOR SEQ ID NO:119:

(i) SEQUENCE CHARACTERISTICS:
(A) LENGTH: 22 base pairs
(B) TYPE: nucleic acid
(C) STRANDEDNESS: both
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer 470EXT4-2189R (xi) SEQUENCE DESCRIPTION: SEQ ID NO:119:

ATCTGTGGTA TGCCATCCCG GT 22

(2) INFORMATION FOR SEQ ID NO:120:

( i ) SEQUENCE CHARACTERISTICS:
( A ) LENGTH: 23 base pairs
( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Primer 470EXT4-29F ( x i ) SEQUENCE DESCRIPTION: SEQ ID NO:120:

GTTATGCTAC TGTCGAAGCA GGT  23

( 2 ) INFORMATION FOR SEQ ID NO:121:

( i ) SEQUENCE CHARACTERISTICS:
( A ) LENGTH: 24 base pairs
( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: NS5 Primer GV57-4512 MF ( x i ) SEQUENCE DESCRIPTION: SEQ ID NO:121:

GGACTTCCGG ATAGCTGARA AGCT  24

( 2 ) INFORMATION FOR SEQ ID NO:122:

( i ) SEQUENCE CHARACTERISTICS:
( A ) LENGTH: 20 base pairs
( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: NS5 Primer GV57-4657 MR ( x i ) SEQUENCE DESCRIPTION: SEQ ID NO:122:

GCRTCCACAC AGATGGCGCA  20

( 2 ) INFORMATION FOR SEQ ID NO:123:

( i ) SEQUENCE CHARACTERISTICS:
( A ) LENGTH: 28 base pairs
( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: NS5 Probe GV22dc-89 MF ( x i ) SEQUENCE DESCRIPTION: SEQ ID NO:123:

CYCGCTGRTT TGGGGTGTAC TGGAAGGC 28

( 2 ) INFORMATION FOR SEQ ID NO:124:

( i ) SEQUENCE CHARACTERISTICS:
        ( A ) LENGTH: 31 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: 5'-UTR Primer FV94-22F ( x i ) SEQUENCE DESCRIPTION: SEQ ID NO:124:

GAAAGCCCCA GAAACCGACG CCTATCTAAG T 31

( 2 ) INFORMATION FOR SEQ ID NO:125:

( i ) SEQUENCE CHARACTERISTICS:
        ( A ) LENGTH: 26 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: 5'UTR Primer FV94-724R ( x i ) SEQUENCE DESCRIPTION: SEQ ID NO:125:

GCACAGCCAA ACCCGCCTGA TACAGT 26

( 2 ) INFORMATION FOR SEQ ID NO:126:

( i ) SEQUENCE CHARACTERISTICS:
        ( A ) LENGTH: 28 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: 5'-UTR Primer FV94-94F ( x i ) SEQUENCE DESCRIPTION: SEQ ID NO:126:

GTGGTGGATG GGTGATGACA GGGTTGGT 28

( 2 ) INFORMATION FOR SEQ ID NO:127:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: linear (i i) MOLECULE TYPE: DNA (i i i) HYPOTHETICAL: NO (i v) ANTI-SENSE: NO (v i) ORIGINAL SOURCE:
(C) INDIVIDUAL ISOLATE: 5'-UTR Primer FV94-912R (x i) SEQUENCE DESCRIPTION: SEQ ID NO:127:

TAACTCACAC GCGACTGCAC ACGTCAGGT 29

(2) INFORMATION FOR SEQ ID NO:128:

(i) SEQUENCE CHARACTERISTICS:
(A) LENGTH: 30 base pairs
(B) TYPE: nucleic acid
(C) STRANDEDNESS: both
(D) TOPOLOGY: linear (i i) MOLECULE TYPE: DNA (i i i) HYPOTHETICAL: NO (i v) ANTI-SENSE: NO (v i) ORIGINAL SOURCE:
(C) INDIVIDUAL ISOLATE: ENV Library Primer GEP-F15

(x i) SEQUENCE DESCRIPTION: SEQ ID NO:128:

GCGGCCATGG TGCCCTTCGT CAATAGGACA 30

(2) INFORMATION FOR SEQ ID NO:129:

(i) SEQUENCE CHARACTERISTICS:
(A) LENGTH: 29 base pairs
(B) TYPE: nucleic acid
(C) STRANDEDNESS: both
(D) TOPOLOGY: linear (i i) MOLECULE TYPE: DNA (i i i) HYPOTHETICAL: NO (i v) ANTI-SENSE: NO (v i) ORIGINAL SOURCE:
(C) INDIVIDUAL ISOLATE: ENV Library Primer GEP-R15

(x i) SEQUENCE DESCRIPTION: SEQ ID NO:129:

CTTGCCATGG CCAGCTGGTT CACCCACCA 29

(2) INFORMATION FOR SEQ ID NO:130:

(i) SEQUENCE CHARACTERISTICS:
(A) LENGTH: 30 base pairs
(B) TYPE: nucleic acid
(C) STRANDEDNESS: both
(D) TOPOLOGY: linear (i i) MOLECULE TYPE: DNA (i i i) HYPOTHETICAL: NO (i v) ANTI-SENSE: NO (v i) ORIGINAL SOURCE:
(C) INDIVIDUAL ISOLATE: Primer GEP- F17

(x i) SEQUENCE DESCRIPTION: SEQ ID NO:130:

GCAGGATCCC CTCTGGAAGG TCCCATTTGA 30

(2) INFORMATION FOR SEQ ID NO:131:

(i) SEQUENCE CHARACTERISTICS:
        (A) LENGTH: 27 base pairs
        (B) TYPE: nucleic acid
        (C) STRANDEDNESS: both
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer GEP- R16

(xi) SEQUENCE DESCRIPTION: SEQ ID NO:131:

TGCGAATCCT CGGCCCTGGT TGCCCAG       27

(2) INFORMATION FOR SEQ ID NO:132:

(i) SEQUENCE CHARACTERISTICS:
        (A) LENGTH: 30 base pairs
        (B) TYPE: nucleic acid
        (C) STRANDEDNESS: both
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer 470ep- F9

(xi) SEQUENCE DESCRIPTION: SEQ ID NO:132:

GCTAGATCTG GCAACATGGG GCACAAGGTC       30

(2) INFORMATION FOR SEQ ID NO:133:

(i) SEQUENCE CHARACTERISTICS:
        (A) LENGTH: 30 base pairs
        (B) TYPE: nucleic acid
        (C) STRANDEDNESS: both
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer 470ep- R9

(xi) SEQUENCE DESCRIPTION: SEQ ID NO:133:

CACAGATCTC GCGTAGTAGT AGCGTCCAGA       30

(2) INFORMATION FOR SEQ ID NO:134:

(i) SEQUENCE CHARACTERISTICS:
        (A) LENGTH: 38 base pairs
        (B) TYPE: nucleic acid
        (C) STRANDEDNESS: both
        (D) TOPOLOGY: linear (ii) MOLECULE TYPE: DNA (iii) HYPOTHETICAL: NO (iv) ANTI-SENSE: NO ( v i ) ORIGINAL SOURCE:
( C ) INDIVIDUAL ISOLATE: AP Primer for Race PCR ( x i ) SEQUENCE DESCRIPTION: SEQ ID NO:134:

CTGGTTCGGC CCACCTCTGA AGGTTCCAGA ATCGATAG 38

( 2 ) INFORMATION FOR SEQ ID NO:135:

( i ) SEQUENCE CHARACTERISTICS:
( A ) LENGTH: 30 base pairs
( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Primer GEP- F10

( x i ) SEQUENCE DESCRIPTION: SEQ ID NO:135:

GCTGGATCCA GCATGGGAAC ATGCTTGAAC 30

( 2 ) INFORMATION FOR SEQ ID NO:136:

( i ) SEQUENCE CHARACTERISTICS:
( A ) LENGTH: 30 base pairs
( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Primer GEP- R10

( x i ) SEQUENCE DESCRIPTION: SEQ ID NO:136:

CGCGGATCCC ACAGTGGCCA CTGAGGGGTT 30

( 2 ) INFORMATION FOR SEQ ID NO:137:

( i ) SEQUENCE CHARACTERISTICS:
( A ) LENGTH: 27 base pairs
( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Primer EXY10- F1

( x i ) SEQUENCE DESCRIPTION: SEQ ID NO:137:

GCCCATATGG TGATCACTGG TGACGTT 27

( 2 ) INFORMATION FOR SEQ ID NO:138:

( i ) SEQUENCE CHARACTERISTICS:
( A ) LENGTH: 24 base pairs
( B ) TYPE: nucleic acid
( C ) STRANDEDNESS: both (D) TOPOLOGY: linear (ii) MOLECULE TYPE: DNA (iii) HYPOTHETICAL: NO (iv) ANTI-SENSE: NO (vi) ORIGINAL SOURCE:
    (C) INDIVIDUAL ISOLATE: Primer EXY10- F2

(xi) SEQUENCE DESCRIPTION: SEQ ID NO:138:

GCCCATATGC TGGGTTACGG TGAA  24

(2) INFORMATION FOR SEQ ID NO:139:

(i) SEQUENCE CHARACTERISTICS:
        (A) LENGTH: 27 base pairs
        (B) TYPE: nucleic acid
        (C) STRANDEDNESS: both
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer EXY10- F3

(xi) SEQUENCE DESCRIPTION: SEQ ID NO:139:

GCCCATATGA CCTCCGCCTA TAAGCTG  27

(2) INFORMATION FOR SEQ ID NO:140:

(i) SEQUENCE CHARACTERISTICS:
        (A) LENGTH: 27 base pairs
        (B) TYPE: nucleic acid
        (C) STRANDEDNESS: both
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer EXY10- R1

(xi) SEQUENCE DESCRIPTION: SEQ ID NO:140:

GCCCATATGA GCCGCCGGCG GCAGATC  27

(2) INFORMATION FOR SEQ ID NO:141:

(i) SEQUENCE CHARACTERISTICS:
        (A) LENGTH: 24 base pairs
        (B) TYPE: nucleic acid
        (C) STRANDEDNESS: both
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer EXY5- R1

(xi) SEQUENCE DESCRIPTION: SEQ ID NO:141:

TGCGGATCCC ACATTGTCTG GATT  24

( 2 ) INFORMATION FOR SEQ ID NO:142:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer Y5-5- F1

( x i ) SEQUENCE DESCRIPTION: SEQ ID NO:142:

TCGGCCATGG CCTATTGTGA CAAGGTG        27

( 2 ) INFORMATION FOR SEQ ID NO:143:

( i ) SEQUENCE CHARACTERISTICS:
        ( A ) LENGTH: 219 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Antigen Clone Q7-12-1

( i x ) FEATURE:
        ( A ) NAME/KEY: CDS
        ( B ) LOCATION: 1..219

( x i ) SEQUENCE DESCRIPTION: SEQ ID NO:143:

```
GTG  CCC  TTC  GTC  AAT  AGG  ACA  ACT  CTC  TTC  ACC  ATT  AGG  GGG  CCC  CTG      48
Val  Pro  Phe  Val  Asn  Arg  Thr  Thr  Leu  Phe  Thr  Ile  Arg  Gly  Pro  Leu
  1              5                        10                       15

GGC  AAC  CAG  GGC  CGA  GGC  AAC  CCG  GTG  CGG  TCG  CCC  TTG  GGT  TTT  GGG      96
Gly  Asn  Gln  Gly  Arg  Gly  Asn  Pro  Val  Arg  Ser  Pro  Leu  Gly  Phe  Gly
              20                       25                       30

TCC  TAC  GCC  ATG  ACC  AGG  ATC  CGA  GAT  ACC  CTA  CAT  CTG  GTG  GAG  TGT     144
Ser  Tyr  Ala  Met  Thr  Arg  Ile  Arg  Asp  Thr  Leu  His  Leu  Val  Glu  Cys
              35                       40                       45

CCC  ACA  CCA  GCC  ATC  GAG  CCT  CCC  ACC  GGG  ACG  TCT  GGG  TTC  TTC  CCC     192
Pro  Thr  Pro  Ala  Ile  Glu  Pro  Pro  Thr  Gly  Thr  Ser  Gly  Phe  Phe  Pro
              50                       55                       60

GGG  ACG  CCG  CCT  CTC  AAC  AGC  TGC  ATG                                         219
Gly  Thr  Pro  Pro  Leu  Asn  Ser  Cys  Met
 65                       70
```

( 2 ) INFORMATION FOR SEQ ID NO:144:

( i ) SEQUENCE CHARACTERISTICS:
        ( A ) LENGTH: 73 amino acids
        ( B ) TYPE: amino acid
        ( D ) TOPOLOGY: linear ( i i ) MOLECULE TYPE: protein ( x i ) SEQUENCE DESCRIPTION: SEQ ID NO:144:

Val Pro Phe Val Asn Arg Thr Thr Leu Phe Thr Ile Arg Gly Pro Leu

```
  1               5                        10                          15
Gly Asn Gln Gly Arg Gly Asn Pro Val Arg Ser Pro Leu Gly Phe Gly
             20                      25                      30

Ser Tyr Ala Met Thr Arg Ile Arg Asp Thr Leu His Leu Val Glu Cys
         35                  40                  45

Pro Thr Pro Ala Ile Glu Pro Pro Thr Gly Thr Ser Gly Phe Phe Pro
     50                  55                  60

Gly Thr Pro Pro Leu Asn Ser Cys Met
 65                      70
```

( 2 ) INFORMATION FOR SEQ ID NO:145:

( i ) SEQUENCE CHARACTERISTICS:
        ( A ) LENGTH: 264 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Antigen Clone Y12-10-3

( i x ) FEATURE:
        ( A ) NAME/KEY: CDS
        ( B ) LOCATION: 1..264

( x i ) SEQUENCE DESCRIPTION: SEQ ID NO:145:

```
CCC CTC GAG CGG ATG CGA ACC GGA AGG CAC CTC GTG TTC TGC CAT TCT      48
Pro Leu Glu Arg Met Arg Thr Gly Arg His Leu Val Phe Cys His Ser
 1               5                      10                      15

AAG GCT GAG TGC GAG CGC CTT GCT GGC CAG TTC TCC GCT AGG GGG GTC      96
Lys Ala Glu Cys Glu Arg Leu Ala Gly Gln Phe Ser Ala Arg Gly Val
             20                      25                      30

AAT GCC ATT GCC TAT TAT AGG GGT AAA GAC AGC TCT ATC ATC AAG GAT      144
Asn Ala Ile Ala Tyr Tyr Arg Gly Lys Asp Ser Ser Ile Ile Lys Asp
         35                      40                      45

GGG GAC CTG GTG GTC TGT GCT ACA GAC GCG CTT TCC ACT GGG TAC ACT      192
Gly Asp Leu Val Val Cys Ala Thr Asp Ala Leu Ser Thr Gly Tyr Thr
     50                      55                      60

GGA AAT TTC GAC TCC GTC ACC GAC TGT GGA TTA GTG GTG GAG GAG GTC      240
Gly Asn Phe Asp Ser Val Thr Asp Cys Gly Leu Val Val Glu Glu Val
 65                      70                      75                80

GTT GAG GTG ACC CTT GAT CCC ACC                                       264
Val Glu Val Thr Leu Asp Pro Thr
                     85
```

( 2 ) INFORMATION FOR SEQ ID NO:146:

( i ) SEQUENCE CHARACTERISTICS:
        ( A ) LENGTH: 88 amino acids
        ( B ) TYPE: amino acid
        ( D ) TOPOLOGY: linear ( i i ) MOLECULE TYPE: protein ( x i ) SEQUENCE DESCRIPTION: SEQ ID NO:146:

```
Pro Leu Glu Arg Met Arg Thr Gly Arg His Leu Val Phe Cys His Ser
 1               5                      10                      15

Lys Ala Glu Cys Glu Arg Leu Ala Gly Gln Phe Ser Ala Arg Gly Val
             20                      25                      30
```

| | | | | | | | | | | | | | | |
|---|---|---|---|---|---|---|---|---|---|---|---|---|---|---|
| Asn | Ala | Ile | Ala | Tyr | Tyr | Arg | Gly | Lys | Asp | Ser | Ser | Ile | Ile | Lys | Asp |
| | | 35 | | | | | 40 | | | | | 45 | | | |
| Gly | Asp | Leu | Val | Val | Cys | Ala | Thr | Asp | Ala | Leu | Ser | Thr | Gly | Tyr | Thr |
| | | 50 | | | | 55 | | | | | 60 | | | | |
| Gly | Asn | Phe | Asp | Ser | Val | Thr | Asp | Cys | Gly | Leu | Val | Val | Glu | Glu | Val |
| 65 | | | | | 70 | | | | 75 | | | | | | 80 |
| Val | Glu | Val | Thr | Leu | Asp | Pro | Thr |
| | | | | 85 | | | |

( 2 ) INFORMATION FOR SEQ ID NO:147:

( i ) SEQUENCE CHARACTERISTICS:
        ( A ) LENGTH: 205 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Antigen Clone Y12-15-1

( i x ) FEATURE:
        ( A ) NAME/KEY: CDS
        ( B ) LOCATION: 1..205

( x i ) SEQUENCE DESCRIPTION: SEQ ID NO:147:

| | | | | | | | | | | | | | | | | |
|---|---|---|---|---|---|---|---|---|---|---|---|---|---|---|---|---|
| GCT | AGA | TCT | GGC | AAC | ATG | GGG | CAC | AAG | GTC | TTA | ATC | TTG | AAC | CCC | TCA | 48 |
| Ala | Arg | Ser | Gly | Asn | Met | Gly | His | Lys | Val | Leu | Ile | Leu | Asn | Pro | Ser | |
| 1 | | | | 5 | | | | | 10 | | | | | 15 | | |
| GTG | GCC | ACT | GTG | CGG | GCC | ATG | GGC | CCG | TAC | ATG | GAG | CGG | CTG | GCG | GGT | 96 |
| Val | Ala | Thr | Val | Arg | Ala | Met | Gly | Pro | Tyr | Met | Glu | Arg | Leu | Ala | Gly | |
| | | | 20 | | | | | 25 | | | | | 30 | | | |
| AAA | CAT | CCA | AGT | ATA | TAC | TGT | GGG | CAT | GAT | ACA | ACT | GCT | TTC | ACA | AGG | 144 |
| Lys | His | Pro | Ser | Ile | Tyr | Cys | Gly | His | Asp | Thr | Thr | Ala | Phe | Thr | Arg | |
| | | | 35 | | | | 40 | | | | | 45 | | | | |
| ATC | ACT | GAC | TCC | CCC | CTG | ACG | TAT | TCA | ACC | TAT | GGG | AGG | TTT | TTG | GCC | 192 |
| Ile | Thr | Asp | Ser | Pro | Leu | Thr | Tyr | Ser | Thr | Tyr | Gly | Arg | Phe | Leu | Ala | |
| | 50 | | | | | 55 | | | | | 60 | | | | | |
| AAC | CCT | AGG | CAG | A | | | | | | | | | | | | 205 |
| Asn | Pro | Arg | Gln | | | | | | | | | | | | | |
| 65 | | | | | | | | | | | | | | | | |

( 2 ) INFORMATION FOR SEQ ID NO:148:

( i ) SEQUENCE CHARACTERISTICS:
        ( A ) LENGTH: 68 amino acids
        ( B ) TYPE: amino acid
        ( D ) TOPOLOGY: linear ( i i ) MOLECULE TYPE: protein ( x i ) SEQUENCE DESCRIPTION: SEQ ID NO:148:

| | | | | | | | | | | | | | | | |
|---|---|---|---|---|---|---|---|---|---|---|---|---|---|---|---|
| Ala | Arg | Ser | Gly | Asn | Met | Gly | His | Lys | Val | Leu | Ile | Leu | Asn | Pro | Ser |
| 1 | | | | 5 | | | | | 10 | | | | | 15 | |
| Val | Ala | Thr | Val | Arg | Ala | Met | Gly | Pro | Tyr | Met | Glu | Arg | Leu | Ala | Gly |
| | | | 20 | | | | | 25 | | | | | 30 | | |
| Lys | His | Pro | Ser | Ile | Tyr | Cys | Gly | His | Asp | Thr | Thr | Ala | Phe | Thr | Arg |
| | | | 35 | | | | 40 | | | | | 45 | | | |
| Ile | Thr | Asp | Ser | Pro | Leu | Thr | Tyr | Ser | Thr | Tyr | Gly | Arg | Phe | Leu | Ala |
| | 50 | | | | | 55 | | | | | 60 | | | | |

Asn Pro Arg Gln
65

( 2 ) INFORMATION FOR SEQ ID NO:149:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GE4F ( x i ) SEQUENCE DESCRIPTION: SEQ ID NO:149:

GCCGCCATGG CTCTCCAAGC GATCGAGAAT GC      32

( 2 ) INFORMATION FOR SEQ ID NO:150:

( i ) SEQUENCE CHARACTERISTICS:
        ( A ) LENGTH: 31 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GE4R ( x i ) SEQUENCE DESCRIPTION: SEQ ID NO:150:

GCGCGGATCC CAACCCCAAT GAGAAAAAGC G      31

( 2 ) INFORMATION FOR SEQ ID NO:151:

( i ) SEQUENCE CHARACTERISTICS:
        ( A ) LENGTH: 23 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer 470EXP3F ( x i ) SEQUENCE DESCRIPTION: SEQ ID NO:151:

CCGCCATGGG ACGCGGACGC TCG      23

( 2 ) INFORMATION FOR SEQ ID NO:152:

( i ) SEQUENCE CHARACTERISTICS:
        ( A ) LENGTH: 28 base pairs
        ( B ) TYPE: nucleic acid
        ( C ) STRANDEDNESS: both
        ( D ) TOPOLOGY: linear ( i i ) MOLECULE TYPE: DNA (　i　i　i　) HYPOTHETICAL: NO (　i　v　) ANTI-SENSE: NO (　v　i　) ORIGINAL SOURCE:
    (　C　) INDIVIDUAL ISOLATE: Primer 470EXP3R (　x　i　) SEQUENCE DESCRIPTION: SEQ ID NO:152:

C G C G G A T C C T　T A C T G T C T T A　T T G C T T C C　　　　　　　　　　　　　　　　　　　　　　　　　2 8

(　2　) INFORMATION FOR SEQ ID NO:153:

(　i　) SEQUENCE CHARACTERISTICS:
        (　A　) LENGTH: 34 base pairs
        (　B　) TYPE: nucleic acid
        (　C　) STRANDEDNESS: both
        (　D　) TOPOLOGY: linear (　i　i　) MOLECULE TYPE: DNA (　i　i　i　) HYPOTHETICAL: NO (　i　v　) ANTI-SENSE: NO (　v　i　) ORIGINAL SOURCE:
        (　C　) INDIVIDUAL ISOLATE: Primer FV94- 2888F (　x　i　) SEQUENCE DESCRIPTION: SEQ ID NO:153:

G C G G A A T T C T　T G G C T C G G G T　G G T T G A G T G C　T G T G　　　　　　　　　　　　　　　　　3 4

(　2　) INFORMATION FOR SEQ ID NO:154:

(　i　) SEQUENCE CHARACTERISTICS:
        (　A　) LENGTH: 32 base pairs
        (　B　) TYPE: nucleic acid
        (　C　) STRANDEDNESS: both
        (　D　) TOPOLOGY: linear (　i　i　) MOLECULE TYPE: DNA (　i　i　i　) HYPOTHETICAL: NO (　i　v　) ANTI-SENSE: NO (　v　i　) ORIGINAL SOURCE:
        (　C　) INDIVIDUAL ISOLATE: Primer FV94- 3216R (　x　i　) SEQUENCE DESCRIPTION: SEQ ID NO:154:

G C G A A G C T T C　C G T C G G A T G A　C A A C A G G C G C　G G　　　　　　　　　　　　　　　　　　　3 2

(　2　) INFORMATION FOR SEQ ID NO:155:

(　i　) SEQUENCE CHARACTERISTICS:
        (　A　) LENGTH: 36 base pairs
        (　B　) TYPE: nucleic acid
        (　C　) STRANDEDNESS: both
        (　D　) TOPOLOGY: linear (　i　i　) MOLECULE TYPE: DNA (　i　i　i　) HYPOTHETICAL: NO (　i　v　) ANTI-SENSE: NO (　v　i　) ORIGINAL SOURCE:
        (　C　) INDIVIDUAL ISOLATE: Primer FV94- 6521F (　x　i　) SEQUENCE DESCRIPTION: SEQ ID NO:155:

G C G G A A T T C A　C C T C C G C C T A　T A A G C T G C T G　C G C C A G　　　　　　　　　　　　　　　3 6

(　2　) INFORMATION FOR SEQ ID NO:156:

( i ) SEQUENCE CHARACTERISTICS:
    ( A ) LENGTH: 42 base pairs
    ( B ) TYPE: nucleic acid
    ( C ) STRANDEDNESS: both
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer FV94- 7483R ( x i ) SEQUENCE DESCRIPTION: SEQ ID NO:156:

GCTGCGGCCG CCCTCCGTCC CACATTGTCT GGATTGGTAA CA    42

( 2 ) INFORMATION FOR SEQ ID NO:157:

( i ) SEQUENCE CHARACTERISTICS:
    ( A ) LENGTH: 22 base pairs
    ( B ) TYPE: nucleic acid
    ( C ) STRANDEDNESS: both
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer T7F ( x i ) SEQUENCE DESCRIPTION: SEQ ID NO:157:

ATTAATACGA CTCACTATAG GG    22

( 2 ) INFORMATION FOR SEQ ID NO:158:

( i ) SEQUENCE CHARACTERISTICS:
    ( A ) LENGTH: 22 base pairs
    ( B ) TYPE: nucleic acid
    ( C ) STRANDEDNESS: both
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer T7R ( x i ) SEQUENCE DESCRIPTION: SEQ ID NO:158:

CAAGGGGTTA TGCTAGTTAT TG    22

( 2 ) INFORMATION FOR SEQ ID NO:159:

( i ) SEQUENCE CHARACTERISTICS:
    ( A ) LENGTH: 402 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( C ) INDIVIDUAL ISOLATE: Antigen Clone GE4-8

( i x ) FEATURE:
    ( A ) NAME/KEY: CDS
    ( B ) LOCATION: 1..402

( x i ) SEQUENCE DESCRIPTION: SEQ ID NO:159:

| GCT | CTC | CAA | GCG | ATC | GAG | AAT | GCT | GCG | AGG | ATT | CTT | GAA | CCG | CAC | ATT | 48 |
|---|---|---|---|---|---|---|---|---|---|---|---|---|---|---|---|---|
| Ala | Leu | Gln | Ala | Ile | Glu | Asn | Ala | Ala | Arg | Ile | Leu | Glu | Pro | His | Ile | |
| 1 | | | | 5 | | | | | 10 | | | | | 15 | | |
| GAT | GTC | ATC | ATG | GAG | GAC | TGC | AGT | ACA | CCC | TCT | CTT | TGT | GGT | AGT | AGC | 96 |
| Asp | Val | Ile | Met | Glu | Asp | Cys | Ser | Thr | Pro | Ser | Leu | Cys | Gly | Ser | Ser | |
| | | | 20 | | | | | 25 | | | | | 30 | | | |
| CGA | GAG | ATG | CCT | GTA | TGG | GGA | GAA | GAC | ATC | CCC | CGT | ACT | CCA | TCG | CCA | 144 |
| Arg | Glu | Met | Pro | Val | Trp | Gly | Glu | Asp | Ile | Pro | Arg | Thr | Pro | Ser | Pro | |
| | | 35 | | | | | 40 | | | | | 45 | | | | |
| GCA | CTT | ATC | TCG | GTT | ACT | GAG | AGC | AGC | TCA | GAT | GAG | AAG | ACC | CCG | TCG | 192 |
| Ala | Leu | Ile | Ser | Val | Thr | Glu | Ser | Ser | Ser | Asp | Glu | Lys | Thr | Pro | Ser | |
| | 50 | | | | | 55 | | | | | 60 | | | | | |
| GTG | TCC | TCC | TCG | CAG | GAG | GAT | ACC | CCG | TCC | TCT | GAC | TCA | TTC | GAG | GTC | 240 |
| Val | Ser | Ser | Ser | Gln | Glu | Asp | Thr | Pro | Ser | Ser | Asp | Ser | Phe | Glu | Val | |
| 65 | | | | | 70 | | | | | 75 | | | | | 80 | |
| ATC | CAA | GAG | TCC | GAG | ACA | GCC | GAA | GGG | GAG | GAA | AGT | GTC | TTC | AAC | GTG | 288 |
| Ile | Gln | Glu | Ser | Glu | Thr | Ala | Glu | Gly | Glu | Glu | Ser | Val | Phe | Asn | Val | |
| | | | | 85 | | | | | 90 | | | | | 95 | | |
| GCT | CTT | TCC | GTA | TTA | AAA | GCC | TTA | TTT | CCA | CAG | AGC | GAC | GCG | ACC | AGG | 336 |
| Ala | Leu | Ser | Val | Leu | Lys | Ala | Leu | Phe | Pro | Gln | Ser | Asp | Ala | Thr | Arg | |
| | | | 100 | | | | | 105 | | | | | 110 | | | |
| AAG | CTT | ACC | GTC | AAG | ATG | TCG | TGC | TGC | GTT | GAA | AAG | AGC | GTC | ACG | CGC | 384 |
| Lys | Leu | Thr | Val | Lys | Met | Ser | Cys | Cys | Val | Glu | Lys | Ser | Val | Thr | Arg | |
| | | 115 | | | | | 120 | | | | | 125 | | | | |
| TTT | TTC | TCA | TTG | GGG | TTG | | | | | | | | | | | 402 |
| Phe | Phe | Ser | Leu | Gly | Leu | | | | | | | | | | | |
| 130 | | | | | | | | | | | | | | | | |

( 2 ) INFORMATION FOR SEQ ID NO:160:

( i ) SEQUENCE CHARACTERISTICS:
        ( A ) LENGTH: 134 amino acids
        ( B ) TYPE: amino acid
        ( D ) TOPOLOGY: linear ( i i ) MOLECULE TYPE: protein ( x i ) SEQUENCE DESCRIPTION: SEQ ID NO:160:

| Ala | Leu | Gln | Ala | Ile | Glu | Asn | Ala | Ala | Arg | Ile | Leu | Glu | Pro | His | Ile |
|---|---|---|---|---|---|---|---|---|---|---|---|---|---|---|---|
| 1 | | | | 5 | | | | | 10 | | | | | 15 | |
| Asp | Val | Ile | Met | Glu | Asp | Cys | Ser | Thr | Pro | Ser | Leu | Cys | Gly | Ser | Ser |
| | | | 20 | | | | | 25 | | | | | 30 | | |
| Arg | Glu | Met | Pro | Val | Trp | Gly | Glu | Asp | Ile | Pro | Arg | Thr | Pro | Ser | Pro |
| | | 35 | | | | | 40 | | | | | 45 | | | |
| Ala | Leu | Ile | Ser | Val | Thr | Glu | Ser | Ser | Ser | Asp | Glu | Lys | Thr | Pro | Ser |
| | 50 | | | | | 55 | | | | | 60 | | | | |
| Val | Ser | Ser | Ser | Gln | Glu | Asp | Thr | Pro | Ser | Ser | Asp | Ser | Phe | Glu | Val |
| 65 | | | | | 70 | | | | | 75 | | | | | 80 |
| Ile | Gln | Glu | Ser | Glu | Thr | Ala | Glu | Gly | Glu | Glu | Ser | Val | Phe | Asn | Val |
| | | | | 85 | | | | | 90 | | | | | 95 | |
| Ala | Leu | Ser | Val | Leu | Lys | Ala | Leu | Phe | Pro | Gln | Ser | Asp | Ala | Thr | Arg |
| | | | 100 | | | | | 105 | | | | | 110 | | |
| Lys | Leu | Thr | Val | Lys | Met | Ser | Cys | Cys | Val | Glu | Lys | Ser | Val | Thr | Arg |
| | | 115 | | | | | 120 | | | | | 125 | | | |
| Phe | Phe | Ser | Leu | Gly | Leu | | | | | | | | | | |

(2) INFORMATION FOR SEQ ID NO:161:

(i) SEQUENCE CHARACTERISTICS:
(A) LENGTH: 1011 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (vi) ORIGINAL SOURCE:
(C) INDIVIDUAL ISOLATE: Antigen Clone EXP3-7

(ix) FEATURE:
(A) NAME/KEY: CDS
(B) LOCATION: 1..1011

(xi) SEQUENCE DESCRIPTION: SEQ ID NO:161:

```
ATG  GTC  TAT  GGC  CCT  GGG  CAA  AGT  GTT  ACC  ATT  GAC  GGG  GAG  CGC  TAC     48
Met  Val  Tyr  Gly  Pro  Gly  Gln  Ser  Val  Thr  Ile  Asp  Gly  Glu  Arg  Tyr
 1                   5                        10                       15

ACC  TTG  CCT  CAT  CAA  CTG  AGG  CTC  AGG  AAT  GTG  GCA  CCC  TCT  GAG  GTT     96
Thr  Leu  Pro  His  Gln  Leu  Arg  Leu  Arg  Asn  Val  Ala  Pro  Ser  Glu  Val
                    20                       25                  30

TCA  TCC  GAG  GTG  TCC  ATT  GAC  ATT  GGG  ACG  GAG  ACT  GAA  GAC  TCA  GAA    144
Ser  Ser  Glu  Val  Ser  Ile  Asp  Ile  Gly  Thr  Glu  Thr  Glu  Asp  Ser  Glu
               35                       40                  45

CTG  ACT  GAG  GCC  GAT  CTG  CCG  CCG  GCG  GCT  GCT  GCT  CTC  CAA  GCG  ATC    192
Leu  Thr  Glu  Ala  Asp  Leu  Pro  Pro  Ala  Ala  Ala  Ala  Leu  Gln  Ala  Ile
      50                       55                       60

GAG  AAT  GCT  GCG  AGG  ATT  CTT  GAA  CCG  CAC  ATT  GAT  GTC  ATC  ATG  GAG    240
Glu  Asn  Ala  Ala  Arg  Ile  Leu  Glu  Pro  His  Ile  Asp  Val  Ile  Met  Glu
 65                       70                  75                         80

GAC  TGC  AGT  ACA  CCC  TCT  CTT  TGT  GGT  AGT  AGC  CGA  GAG  ATG  CCT  GTA    288
Asp  Cys  Ser  Thr  Pro  Ser  Leu  Cys  Gly  Ser  Ser  Arg  Glu  Met  Pro  Val
                    85                       90                       95

TGG  GGA  GAA  GAC  ATC  CCC  CGT  ACT  CCA  TCG  CCA  GCA  CTT  ATC  TCG  GTT    336
Trp  Gly  Glu  Asp  Ile  Pro  Arg  Thr  Pro  Ser  Pro  Ala  Leu  Ile  Ser  Val
               100                      105                      110

ACT  GAG  AGC  AGC  TCA  GAT  GAG  AAG  ACC  CCG  TCG  GTG  TCC  TCC  TCG  CAG    384
Thr  Glu  Ser  Ser  Ser  Asp  Glu  Lys  Thr  Pro  Ser  Val  Ser  Ser  Ser  Gln
          115                      120                      125

GAG  GAT  ACC  CCG  TCC  TCT  GAC  TCA  TTC  GAG  GTC  ATC  CAA  GAG  TCC  GAG    432
Glu  Asp  Thr  Pro  Ser  Ser  Asp  Ser  Phe  Glu  Val  Ile  Gln  Glu  Ser  Glu
      130                      135                      140

ACA  GCC  GAA  GGG  GAG  GAA  AGT  GTC  TTC  AAC  GTG  GCT  CTT  TCC  GTA  TTA    480
Thr  Ala  Glu  Gly  Glu  Glu  Ser  Val  Phe  Asn  Val  Ala  Leu  Ser  Val  Leu
145                      150                      155                      160

AAA  GCC  TTA  TTT  CCA  CAG  AGC  GAC  GCG  ACC  AGG  AAG  CTT  ACC  GTC  AAG    528
Lys  Ala  Leu  Phe  Pro  Gln  Ser  Asp  Ala  Thr  Arg  Lys  Leu  Thr  Val  Lys
                    165                      170                      175

ATG  TCG  TGC  TGC  GTT  GAA  AAG  AGC  GTC  ACG  CGC  TTT  TTC  TCA  TTG  GGG    576
Met  Ser  Cys  Cys  Val  Glu  Lys  Ser  Val  Thr  Arg  Phe  Phe  Ser  Leu  Gly
               180                      185                      190

TTG  ACG  GTG  GCT  GAT  GTT  GCT  AGC  CTG  TGT  GAG  ATG  GAA  ATC  CAG  AAC    624
Leu  Thr  Val  Ala  Asp  Val  Ala  Ser  Leu  Cys  Glu  Met  Glu  Ile  Gln  Asn
          195                      200                      205

CAT  ACA  GCC  TAT  TGT  GAC  CAG  GTG  CGC  ACT  CCG  CTT  GAA  TTG  CAG  GTT    672
His  Thr  Ala  Tyr  Cys  Asp  Gln  Val  Arg  Thr  Pro  Leu  Glu  Leu  Gln  Val
```

|  |  |  |  |  |  |  |  |  |  |  |  |  |  |  |  |
|---|---|---|---|---|---|---|---|---|---|---|---|---|---|---|---|
|  | 210 |  |  |  | 215 |  |  |  |  | 220 |  |  |  |  |  |
| GGG | TGC | TTG | GTG | GGC | AAT | GAA | CTT | ACC | TTT | GAA | TGT | GAC | AAG | TGT | GAG | 720 |
| Gly | Cys | Leu | Val | Gly | Asn | Glu | Leu | Thr | Phe | Glu | Cys | Asp | Lys | Cys | Glu |  |
| 225 |  |  |  |  | 230 |  |  |  |  | 235 |  |  |  |  | 240 |  |
| GCT | AGG | CAA | GAA | ACC | TTG | GCC | TCC | TTC | TCT | TAC | ATT | TGG | TCT | GGA | GTG | 768 |
| Ala | Arg | Gln | Glu | Thr | Leu | Ala | Ser | Phe | Ser | Tyr | Ile | Trp | Ser | Gly | Val |  |
|  |  |  |  | 245 |  |  |  |  | 250 |  |  |  |  | 255 |  |  |
| CCG | CTG | ACT | AGG | GCC | ACG | CCG | GCC | AAG | CCT | CCC | GTG | GTG | AGG | CCG | GTT | 816 |
| Pro | Leu | Thr | Arg | Ala | Thr | Pro | Ala | Lys | Pro | Pro | Val | Val | Arg | Pro | Val |  |
|  |  |  | 260 |  |  |  |  | 265 |  |  |  |  | 270 |  |  |  |
| GGC | TCT | TTG | TTA | GTG | GCC | GAC | ACT | ACT | AAG | GTG | TAT | GTT | ACC | AAT | CCA | 864 |
| Gly | Ser | Leu | Leu | Val | Ala | Asp | Thr | Thr | Lys | Val | Tyr | Val | Thr | Asn | Pro |  |
|  |  | 275 |  |  |  |  | 280 |  |  |  |  | 285 |  |  |  |  |
| GAC | AAT | GTG | GGA | CGG | AGG | GTG | GAC | AAG | GTG | ACC | TTC | TGG | CGT | GCT | CCT | 912 |
| Asp | Asn | Val | Gly | Arg | Arg | Val | Asp | Lys | Val | Thr | Phe | Trp | Arg | Ala | Pro |  |
|  | 290 |  |  |  |  | 295 |  |  |  |  | 300 |  |  |  |  |  |
| AGG | GTT | CAT | GAT | AAG | TAC | CTC | GTG | GAC | TCT | ATT | GAG | CGC | GCT | AAG | AGG | 960 |
| Arg | Val | His | Asp | Lys | Tyr | Leu | Val | Asp | Ser | Ile | Glu | Arg | Ala | Lys | Arg |  |
| 305 |  |  |  |  | 310 |  |  |  |  | 315 |  |  |  |  | 320 |  |
| GCC | GCT | CAA | GCC | TGC | CTA | AGC | ATG | GGT | TAC | ACT | TAT | GAG | GAA | GCA | ATA | 1008 |
| Ala | Ala | Gln | Ala | Cys | Leu | Ser | Met | Gly | Tyr | Thr | Tyr | Glu | Glu | Ala | Ile |  |
|  |  |  |  | 325 |  |  |  | 330 |  |  |  |  |  | 335 |  |  |
| AGG |  |  |  |  |  |  |  |  |  |  |  |  |  |  |  | 1011 |
| Arg |  |  |  |  |  |  |  |  |  |  |  |  |  |  |  |  |

( 2 ) INFORMATION FOR SEQ ID NO:162:

( i ) SEQUENCE CHARACTERISTICS:
        ( A ) LENGTH: 337 amino acids
        ( B ) TYPE: amino acid
        ( D ) TOPOLOGY: linear ( i i ) MOLECULE TYPE: protein ( x i ) SEQUENCE DESCRIPTION: SEQ ID NO:162:

| Met | Val | Tyr | Gly | Pro | Gly | Gln | Ser | Val | Thr | Ile | Asp | Gly | Glu | Arg | Tyr |
|---|---|---|---|---|---|---|---|---|---|---|---|---|---|---|---|
| 1 |  |  |  | 5 |  |  |  |  | 10 |  |  |  |  | 15 |  |
| Thr | Leu | Pro | His | Gln | Leu | Arg | Leu | Arg | Asn | Val | Ala | Pro | Ser | Glu | Val |
|  |  |  | 20 |  |  |  |  | 25 |  |  |  |  | 30 |  |  |
| Ser | Ser | Glu | Val | Ser | Ile | Asp | Ile | Gly | Thr | Glu | Thr | Glu | Asp | Ser | Glu |
|  |  | 35 |  |  |  |  | 40 |  |  |  |  | 45 |  |  |  |
| Leu | Thr | Glu | Ala | Asp | Leu | Pro | Pro | Ala | Ala | Ala | Leu | Gln | Ala | Ile |  |
|  | 50 |  |  |  |  | 55 |  |  |  |  | 60 |  |  |  |  |
| Glu | Asn | Ala | Ala | Arg | Ile | Leu | Glu | Pro | His | Ile | Asp | Val | Ile | Met | Glu |
| 65 |  |  |  |  | 70 |  |  |  |  | 75 |  |  |  |  | 80 |
| Asp | Cys | Ser | Thr | Pro | Ser | Leu | Cys | Gly | Ser | Ser | Arg | Glu | Met | Pro | Val |
|  |  |  |  | 85 |  |  |  |  | 90 |  |  |  |  | 95 |  |
| Trp | Gly | Glu | Asp | Ile | Pro | Arg | Thr | Pro | Ser | Pro | Ala | Leu | Ile | Ser | Val |
|  |  |  | 100 |  |  |  |  | 105 |  |  |  |  | 110 |  |  |
| Thr | Glu | Ser | Ser | Ser | Asp | Glu | Lys | Thr | Pro | Ser | Val | Ser | Ser | Ser | Gln |
|  |  | 115 |  |  |  |  | 120 |  |  |  |  | 125 |  |  |  |
| Glu | Asp | Thr | Pro | Ser | Ser | Asp | Ser | Phe | Glu | Val | Ile | Gln | Glu | Ser | Glu |
|  | 130 |  |  |  |  | 135 |  |  |  |  | 140 |  |  |  |  |
| Thr | Ala | Glu | Gly | Glu | Glu | Ser | Val | Phe | Asn | Val | Ala | Leu | Ser | Val | Leu |
| 145 |  |  |  |  | 150 |  |  |  |  | 155 |  |  |  |  | 160 |
| Lys | Ala | Leu | Phe | Pro | Gln | Ser | Asp | Ala | Thr | Arg | Lys | Leu | Thr | Val | Lys |
|  |  |  |  | 165 |  |  |  |  | 170 |  |  |  |  | 175 |  |
| Met | Ser | Cys | Cys | Val | Glu | Lys | Ser | Val | Thr | Arg | Phe | Phe | Ser | Leu | Gly |
|  |  |  |  | 180 |  |  |  |  | 185 |  |  |  |  | 190 |  |

```
Leu  Thr  Val  Ala  Asp  Val  Ala  Ser  Leu  Cys  Glu  Met  Glu  Ile  Gln  Asn
          195                      200                     205

His  Thr  Ala  Tyr  Cys  Asp  Gln  Val  Arg  Thr  Pro  Leu  Glu  Leu  Gln  Val
          210                      215                     220

Gly  Cys  Leu  Val  Gly  Asn  Glu  Leu  Thr  Phe  Glu  Cys  Asp  Lys  Cys  Glu
225                      230                     235                     240

Ala  Arg  Gln  Glu  Thr  Leu  Ala  Ser  Phe  Ser  Tyr  Ile  Trp  Ser  Gly  Val
                245                      250                     255

Pro  Leu  Thr  Arg  Ala  Thr  Pro  Ala  Lys  Pro  Pro  Val  Val  Arg  Pro  Val
                260                      265                     270

Gly  Ser  Leu  Leu  Val  Ala  Asp  Thr  Thr  Lys  Val  Tyr  Val  Thr  Asn  Pro
          275                      280                     285

Asp  Asn  Val  Gly  Arg  Arg  Val  Asp  Lys  Val  Thr  Phe  Trp  Arg  Ala  Pro
          290                      295                     300

Arg  Val  His  Asp  Lys  Tyr  Leu  Val  Asp  Ser  Ile  Glu  Arg  Ala  Lys  Arg
305                      310                     315                     320

Ala  Ala  Gln  Ala  Cys  Leu  Ser  Met  Gly  Tyr  Thr  Tyr  Glu  Glu  Ala  Ile
                325                      330                     335

Arg
```

( 2 ) INFORMATION FOR SEQ ID NO:163:

( i ) SEQUENCE CHARACTERISTICS:
        ( A ) LENGTH: 351 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Antigen Clone GENS2b-1

( i x ) FEATURE:
        ( A ) NAME/KEY: CDS
        ( B ) LOCATION: 1..351

( x i ) SEQUENCE DESCRIPTION: SEQ ID NO:163:

```
TTG  GCT  CGG  GTG  GTT  GAG  TGC  TGT  GTG  ATG  GCG  GGT  GAG  AAG  GCC  ACA        48
Leu  Ala  Arg  Val  Val  Glu  Cys  Cys  Val  Met  Ala  Gly  Glu  Lys  Ala  Thr
  1                       5                        10                      15

ACC  GTC  CGG  CTG  GTC  TCC  AAG  ATG  TGT  GCG  AGA  GGA  GCT  TAT  TTG  TTC        96
Thr  Val  Arg  Leu  Val  Ser  Lys  Met  Cys  Ala  Arg  Gly  Ala  Tyr  Leu  Phe
                     20                       25                      30

GAT  CAT  ATG  GGC  TCT  TTT  TCG  CGT  GCT  GTC  AAG  GAG  CGC  CTG  TTG  GAA       144
Asp  His  Met  Gly  Ser  Phe  Ser  Arg  Ala  Val  Lys  Glu  Arg  Leu  Leu  Glu
          35                        40                      45

TGG  GAC  GCA  GCT  CTT  GAA  CCT  CTG  TCA  TTC  ACT  AGG  ACG  GAC  TGT  CGC       192
Trp  Asp  Ala  Ala  Leu  Glu  Pro  Leu  Ser  Phe  Thr  Arg  Thr  Asp  Cys  Arg
     50                       55                       60

ATC  ATA  CGG  GAT  GCC  GCG  AGG  ACT  TTG  TCC  TGC  GGG  CAG  TGC  GTC  ATG       240
Ile  Ile  Arg  Asp  Ala  Ala  Arg  Thr  Leu  Ser  Cys  Gly  Gln  Cys  Val  Met
 65                       70                       75                      80

GGT  TTA  CCC  GTG  GTT  GCG  CGC  CGT  GGT  GAT  GAG  GTT  CTC  ATC  GGC  GTC       288
Gly  Leu  Pro  Val  Val  Ala  Arg  Arg  Gly  Asp  Glu  Val  Leu  Ile  Gly  Val
                     85                       90                      95

TTC  CAG  GAT  GTG  AAT  CAT  TTG  CCT  CCC  GGG  TTT  GTT  CCG  ACC  GCG  CCT       336
Phe  Gln  Asp  Val  Asn  His  Leu  Pro  Pro  Gly  Phe  Val  Pro  Thr  Ala  Pro
```

|  | 100 |  |  |  |  | 105 |  |  |  | 110 |  |  |  |  |
|---|---|---|---|---|---|---|---|---|---|---|---|---|---|---|
| GTT | GTC | ATC | CGA | CGG |  |  |  |  |  |  |  |  |  | 351 |
| Val | Val | Ile | Arg | Arg |  |  |  |  |  |  |  |  |  |  |
|  |  | 115 |  |  |  |  |  |  |  |  |  |  |  |  |

( 2 ) INFORMATION FOR SEQ ID NO:164:

( i ) SEQUENCE CHARACTERISTICS:
        ( A ) LENGTH: 117 amino acids
        ( B ) TYPE: amino acid
        ( D ) TOPOLOGY: linear ( i i ) MOLECULE TYPE: protein ( x i ) SEQUENCE DESCRIPTION: SEQ ID NO:164:

| Leu | Ala | Arg | Val | Val | Glu | Cys | Cys | Val | Met | Ala | Gly | Glu | Lys | Ala | Thr |
|---|---|---|---|---|---|---|---|---|---|---|---|---|---|---|---|
| 1 |  |  |  | 5 |  |  |  |  | 10 |  |  |  |  | 15 |  |
| Thr | Val | Arg | Leu | Val | Ser | Lys | Met | Cys | Ala | Arg | Gly | Ala | Tyr | Leu | Phe |
|  |  |  | 20 |  |  |  |  | 25 |  |  |  |  | 30 |  |  |
| Asp | His | Met | Gly | Ser | Phe | Ser | Arg | Ala | Val | Lys | Glu | Arg | Leu | Leu | Glu |
|  |  | 35 |  |  |  |  | 40 |  |  |  |  | 45 |  |  |  |
| Trp | Asp | Ala | Ala | Leu | Glu | Pro | Leu | Ser | Phe | Thr | Arg | Thr | Asp | Cys | Arg |
|  | 50 |  |  |  |  | 55 |  |  |  |  | 60 |  |  |  |  |
| Ile | Ile | Arg | Asp | Ala | Ala | Arg | Thr | Leu | Ser | Cys | Gly | Gln | Cys | Val | Met |
| 65 |  |  |  |  | 70 |  |  |  |  | 75 |  |  |  |  | 80 |
| Gly | Leu | Pro | Val | Val | Ala | Arg | Arg | Gly | Asp | Glu | Val | Leu | Ile | Gly | Val |
|  |  |  |  | 85 |  |  |  |  | 90 |  |  |  |  | 95 |  |
| Phe | Gln | Asp | Val | Asn | His | Leu | Pro | Pro | Gly | Phe | Val | Pro | Thr | Ala | Pro |
|  |  |  | 100 |  |  |  |  | 105 |  |  |  |  | 110 |  |  |
| Val | Val | Ile | Arg | Arg |  |  |  |  |  |  |  |  |  |  |  |
|  |  | 115 |  |  |  |  |  |  |  |  |  |  |  |  |  |

( 2 ) INFORMATION FOR SEQ ID NO:165:

( i ) SEQUENCE CHARACTERISTICS:
        ( A ) LENGTH: 993 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Antigen Clone GENS5a-3

( i x ) FEATURE:
        ( A ) NAME/KEY: CDS
        ( B ) LOCATION: 1..993

( x i ) SEQUENCE DESCRIPTION: SEQ ID NO:165:

| ACC | TCC | GCC | TAT | AAG | CTG | CTG | CGC | CAG | CAA | ATC | CTA | TCG | GCT | GCT | GTA | 48 |
|---|---|---|---|---|---|---|---|---|---|---|---|---|---|---|---|---|
| Thr | Ser | Ala | Tyr | Lys | Leu | Leu | Arg | Gln | Gln | Ile | Leu | Ser | Ala | Ala | Val |  |
| 1 |  |  |  | 5 |  |  |  |  | 10 |  |  |  |  | 15 |  |  |
| GCT | GAG | CCC | TAC | TAC | GTC | GAC | GGC | ATT | CCG | GTC | TCA | TGG | GAC | GCG | GAC | 96 |
| Ala | Glu | Pro | Tyr | Tyr | Val | Asp | Gly | Ile | Pro | Val | Ser | Trp | Asp | Ala | Asp |  |
|  |  |  | 20 |  |  |  |  | 25 |  |  |  |  | 30 |  |  |  |
| GCT | CGT | GCG | CCC | GCC | ATG | GTC | TAT | GGC | CCT | GGG | CAA | AGT | GTT | ACC | ATT | 144 |
| Ala | Arg | Ala | Pro | Ala | Met | Val | Tyr | Gly | Pro | Gly | Gln | Ser | Val | Thr | Ile |  |
|  |  |  | 35 |  |  |  |  | 40 |  |  |  |  | 45 |  |  |  |
| GAC | GGG | GAG | CGC | TAC | ACC | TTG | CCT | CAT | CAA | CTG | AGG | CTC | AGG | AAT | GTG | 192 |
| Asp | Gly | Glu | Arg | Tyr | Thr | Leu | Pro | His | Gln | Leu | Arg | Leu | Arg | Asn | Val |  |

```
                    50                      55                           60
GCA  CCC  TCT  GAG  GTT  TCA  TCC  GAG  GTG  TCC  ATT  GAC  ATT  GGG  ACG  GAG      240
Ala  Pro  Ser  Glu  Val  Ser  Ser  Glu  Val  Ser  Ile  Asp  Ile  Gly  Thr  Glu
 65            70                       75                            80

ACT  GAA  GAC  TCA  GAA  CTG  ACT  GAG  GCC  GAT  CTG  CCG  CCG  GCG  GCT  GCT      288
Thr  Glu  Asp  Ser  Glu  Leu  Thr  Glu  Ala  Asp  Leu  Pro  Pro  Ala  Ala  Ala
               85                         90                          95

GCT  CTC  CAA  GCG  ATC  GAG  AAT  GCT  GCG  AGG  ATT  CTT  GAA  CCG  CAC  ATT      336
Ala  Leu  Gln  Ala  Ile  Glu  Asn  Ala  Ala  Arg  Ile  Leu  Glu  Pro  His  Ile
              100                      105                    110

GAT  GTC  ATC  ATG  GAG  GAC  TGC  AGT  ACA  CCC  TCT  CTT  TGT  GGT  AGT  AGC      384
Asp  Val  Ile  Met  Glu  Asp  Cys  Ser  Thr  Pro  Ser  Leu  Cys  Gly  Ser  Ser
              115                      120                    125

CGA  GAG  ATG  CCT  GTA  TGG  GGA  GAA  GAC  ATC  CCC  CGT  ACT  CCA  TCG  CCA      432
Arg  Glu  Met  Pro  Val  Trp  Gly  Glu  Asp  Ile  Pro  Arg  Thr  Pro  Ser  Pro
130                      135                      140

GCA  CTT  ATC  TCG  GTT  ACT  GAG  AGC  AGC  TCA  GAT  GAG  AAG  ACC  CCG  TCG      480
Ala  Leu  Ile  Ser  Val  Thr  Glu  Ser  Ser  Ser  Asp  Glu  Lys  Thr  Pro  Ser
145                      150                      155                    160

GTG  TCC  TCC  TCG  CAG  GAG  GAT  ACC  CCG  TCC  TCT  GAC  TCA  TTC  GAG  GTC      528
Val  Ser  Ser  Ser  Gln  Glu  Asp  Thr  Pro  Ser  Ser  Asp  Ser  Phe  Glu  Val
                    165                      170                    175

ATC  CAA  GAG  TCC  GAG  ACA  GCC  GAA  GGG  GAG  GAA  AGT  GTC  TTC  AAC  GTG      576
Ile  Gln  Glu  Ser  Glu  Thr  Ala  Glu  Gly  Glu  Glu  Ser  Val  Phe  Asn  Val
               180                      185                    190

GCT  CTT  TCC  GTA  TTA  AAA  GCC  TTA  TTT  CCA  CAG  AGC  GAC  GCG  ACC  AGG      624
Ala  Leu  Ser  Val  Leu  Lys  Ala  Leu  Phe  Pro  Gln  Ser  Asp  Ala  Thr  Arg
               195                      200                    205

AAG  CTT  ACC  GTC  AAG  ATG  TCG  TGC  TGC  GTT  GAA  AAG  AGC  GTC  ACG  CGC      672
Lys  Leu  Thr  Val  Lys  Met  Ser  Cys  Cys  Val  Glu  Lys  Ser  Val  Thr  Arg
210                      215                      220

TTT  TTC  TCA  TTG  GGG  TTG  ACG  GTG  GCT  GAT  GTT  GCT  AGC  CTG  TGT  GAG      720
Phe  Phe  Ser  Leu  Gly  Leu  Thr  Val  Ala  Asp  Val  Ala  Ser  Leu  Cys  Glu
225                      230                      235                    240

ATG  GAA  ATC  CAG  AAC  CAT  ACA  GCC  TAT  TGT  GAC  CAG  GTG  CGC  ACT  CCG      768
Met  Glu  Ile  Gln  Asn  His  Thr  Ala  Tyr  Cys  Asp  Gln  Val  Arg  Thr  Pro
               245                      250                    255

CTT  GAA  TTG  CAG  GTT  GGG  TGC  TTG  GTG  GGC  AAT  GAA  CTT  ACC  TTT  GAA      816
Leu  Glu  Leu  Gln  Val  Gly  Cys  Leu  Val  Gly  Asn  Glu  Leu  Thr  Phe  Glu
               260                      265                    270

TGT  GAC  AAG  TGT  GAG  GCT  AGG  CAA  GAA  ACC  TTG  GCC  TCC  TTC  TCT  TAC      864
Cys  Asp  Lys  Cys  Glu  Ala  Arg  Gln  Glu  Thr  Leu  Ala  Ser  Phe  Ser  Tyr
               275                      280                    285

ATT  TGG  TCT  GGA  GTG  CCG  CTG  ACT  AGG  GCC  ACG  CCG  GCC  AAG  CCT  CCC      912
Ile  Trp  Ser  Gly  Val  Pro  Leu  Thr  Arg  Ala  Thr  Pro  Ala  Lys  Pro  Pro
               290                      295                    300

GTG  GTG  AGG  CCG  GTT  GGC  TCT  TTG  TTA  GTG  GCC  GAC  ACT  ACT  AAG  GTG      960
Val  Val  Arg  Pro  Val  Gly  Ser  Leu  Leu  Val  Ala  Asp  Thr  Thr  Lys  Val
305                      310                      315                    320

TAT  GTT  ACC  AAT  CCA  GAC  AAT  GTG  GGA  CGG  AGG                                993
Tyr  Val  Thr  Asn  Pro  Asp  Asn  Val  Gly  Arg  Arg
               325                      330
```

( 2 ) INFORMATION FOR SEQ ID NO:166:

( i ) SEQUENCE CHARACTERISTICS:
        ( A ) LENGTH: 331 amino acids
        ( B ) TYPE: amino acid
        ( D ) TOPOLOGY: linear ( i i ) MOLECULE TYPE: protein ( x i ) SEQUENCE DESCRIPTION: SEQ ID NO:166:

Thr Ser Ala Tyr Lys Leu Leu Arg Gln Gln Ile Leu Ser Ala Ala Val
1               5                   10                  15

Ala Glu Pro Tyr Tyr Val Asp Gly Ile Pro Val Ser Trp Asp Ala Asp
            20                  25                  30

Ala Arg Ala Pro Ala Met Val Tyr Gly Pro Gly Gln Ser Val Thr Ile
            35                  40                  45

Asp Gly Glu Arg Tyr Thr Leu Pro His Gln Leu Arg Leu Arg Asn Val
        50                  55              60

Ala Pro Ser Glu Val Ser Ser Glu Val Ser Ile Asp Ile Gly Thr Glu
65                      70                  75                  80

Thr Glu Asp Ser Glu Leu Thr Glu Ala Asp Leu Pro Pro Ala Ala Ala
                85                  90                  95

Ala Leu Gln Ala Ile Glu Asn Ala Ala Arg Ile Leu Glu Pro His Ile
                100                 105                 110

Asp Val Ile Met Glu Asp Cys Ser Thr Pro Ser Leu Cys Gly Ser Ser
            115                 120                 125

Arg Glu Met Pro Val Trp Gly Glu Asp Ile Pro Arg Thr Pro Ser Pro
            130                 135                 140

Ala Leu Ile Ser Val Thr Glu Ser Ser Ser Asp Glu Lys Thr Pro Ser
145                 150                 155                 160

Val Ser Ser Ser Gln Glu Asp Thr Pro Ser Ser Asp Ser Phe Glu Val
                165                 170                 175

Ile Gln Glu Ser Glu Thr Ala Glu Gly Glu Glu Ser Val Phe Asn Val
            180                 185                 190

Ala Leu Ser Val Leu Lys Ala Leu Phe Pro Gln Ser Asp Ala Thr Arg
            195                 200                 205

Lys Leu Thr Val Lys Met Ser Cys Cys Val Glu Lys Ser Val Thr Arg
    210                 215                 220

Phe Phe Ser Leu Gly Leu Thr Val Ala Asp Val Ala Ser Leu Cys Glu
225                 230                 235                 240

Met Glu Ile Gln Asn His Thr Ala Tyr Cys Asp Gln Val Arg Thr Pro
            245                 250                 255

Leu Glu Leu Gln Val Gly Cys Leu Val Gly Asn Glu Leu Thr Phe Glu
            260                 265                 270

Cys Asp Lys Cys Glu Ala Arg Gln Glu Thr Leu Ala Ser Phe Ser Tyr
            275                 280                 285

Ile Trp Ser Gly Val Pro Leu Thr Arg Ala Thr Pro Ala Lys Pro Pro
    290                 295                 300

Val Val Arg Pro Val Gly Ser Leu Leu Val Ala Asp Thr Thr Lys Val
305                 310                 315                 320

Tyr Val Thr Asn Pro Asp Asn Val Gly Arg Arg
                325                 330

( 2 ) INFORMATION FOR SEQ ID NO:167:

( i ) SEQUENCE CHARACTERISTICS:
        ( A ) LENGTH: 536 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO (v i) ORIGINAL SOURCE:
  (C) INDIVIDUAL ISOLATE: Consensus Sequence 3'-end (x i) SEQUENCE DESCRIPTION: SEQ ID NO:167:

```
CTGAGCGACC  TCAAGCTCCC  TGGCTTAGCA  GTCCACCGAA  AGAAGGCCGG  GGCGTTGCGA   60
ACACGCATGC  TCCGCTCGCG  CGGTTGGGCT  GAGTTGGCTA  GGGGCTTGTT  GTGGCATCCA  120
GGCCTACGGC  TTCCTCCCCC  TGAGATTGCT  GGTATCCCGG  GGGGTTTCCC  TCTCTCCCCC  180
CCCTATATGG  GGGTGGTACA  TCAATTGGAT  TTCACAAGCC  AGAGGAGTCG  CTGGCGGTGG  240
TTGGGGTTCT  TAGCCCTGCT  CATCGTAGCC  CTCTTCGGGT  GAACTAAATT  CATCTGTTGC  300
GGCAAGGTCT  GGTGACTGAT  CATCACCGGA  GGAGGTTCCC  GCCCTCCCCG  CCCCAGGGGT  360
CTCCCCGCTG  GGTAAAAAGG  GCCCGGCCTT  GGGAGGCATG  GTGGTTACTA  ACCCCCTGGC  420
AGGGTCAAAG  CCTGATGGTG  CTAATGCACT  GCCACTTCGG  TGGCGGGTCG  CTACCTTATA  480
GCGTAATCCG  TGACTACGGG  CTGCTCGCAG  AGCCCTCCCC  GGATGGGGCA  CAGTGC      536
```

(2) INFORMATION FOR SEQ ID NO:168:

(i) SEQUENCE CHARACTERISTICS:
    (A) LENGTH: 594 base pairs
    (B) TYPE: nucleic acid
    (C) STRANDEDNESS: both
    (D) TOPOLOGY: linear (i i) MOLECULE TYPE: cDNA (i i i) HYPOTHETICAL: NO (i v) ANTI-SENSE: NO (v i) ORIGINAL SOURCE:
    (C) INDIVIDUAL ISOLATE: Individual Clone MP3-3

(x i) SEQUENCE DESCRIPTION: SEQ ID NO:168:

```
CTGAGCGACC  TCAAGCTCCC  TGGCTTAGCA  GTCCACCGAA  AGAAGGCCGG  GGCGTTGCGA   60
ACACGCATGC  TCCGCTCGCG  CGGTTGGGCT  GAGTTGGCTA  GGGGCTTGTT  GTGGCATCCA  120
GGCCTACGGC  TTCCTCCCCC  TGAGATTGCT  GGTATCCCGG  GGGGTTTCCC  TCTCTCCCCC  180
CCCTATATGG  GGGTGGTACA  CCAATTGGAT  TTCACAAGCC  AGAGGAGTCG  CTGGCGGTGG  240
TTGGGGTTCT  TAGCCCTGCT  CATCGTAGCC  CTCTTCGGGT  GAACTAAATT  CATCTGTTGC  300
GGCAAGGTCT  GGTGACTGAT  CATCACCGGA  GGAGGTTCCC  GCCCTCCCCG  CCCCAGGGGT  360
CTCCCCGCTG  GGTAAAAAGG  GCCCGGCCTT  GGGAGGCATG  GTGGTTACTA  ACCCCCTGGC  420
AGGGTCAAAG  CCTGATGGTG  CTAATGCACT  GCCACTTCGG  TGGCGGGTCG  CTACCTTATA  480
GCGTAATCCG  TGACTACGGG  CTGCTCGCAG  AGCCCTCCCC  GGATGGGGCA  CAGTGCACTG  540
TGATCTGAAG  GGGTGCACCC  CGGGAAGAGC  TCGGCCCGAA  GGCCGGCTTC  TACT        594
```

(2) INFORMATION FOR SEQ ID NO:169:

(i) SEQUENCE CHARACTERISTICS:
    (A) LENGTH: 594 base pairs
    (B) TYPE: nucleic acid
    (C) STRANDEDNESS: both
    (D) TOPOLOGY: linear (i i) MOLECULE TYPE: cDNA (i i i) HYPOTHETICAL: NO (i v) ANTI-SENSE: NO (v i) ORIGINAL SOURCE:
    (C) INDIVIDUAL ISOLATE: Individual Clone MP3-7

( x i ) SEQUENCE DESCRIPTION: SEQ ID NO:169:

| | | | | | |
|---|---|---|---|---|---|
| CTGAGCGACC | TCAAGCTCCC | TGGCTTAGCA | GTCCACCGAA | AGAAGGCCGG | GGCGTTGCGA | 60
| ACACGCATGC | TCCGCTCGCG | CGGTTGGGCT | GAGTTGGCTA | GGGGCTTGTT | GTGGCATCCA | 120
| GGCCTACGGC | TTCCTCCCCC | TGAGATTGCT | GGTGTCCCGG | GGGGTTTCCC | TCTCTCCCCC | 180
| CCCTATATGG | GGGTGGTACA | CCAATTGGAT | TTCACAAGCC | AGAGGAGTCG | CTGGCGGTGG | 240
| TTGGGGTTCT | TAGCCCTGCT | CATCGTAGCC | CTCTTCGGGT | GAACTAAATT | CATCTGTTGC | 300
| GGCAAGGTCT | GGTGACTGAT | CATCACCGGA | GGAGGTTCCC | GCCCTCCCCG | CCCCAGGGGT | 360
| CTCCCCGCTG | GGTAAAAAGG | GCCCGGCCTT | GGGAGGCATG | GTGGTTACTA | ACCCCCTGGC | 420
| AGGGTCAAAG | CCTGATGGTG | CTAATGCACT | GCCACTTCGG | TGGCGGGTCG | CTACCTTATA | 480
| GCGTAATCCG | TGACTACGGG | CTGCTCGCAG | AGCCCTCCCC | GGATGGGGCA | CAGTGCACTG | 540
| TGATCTGAAG | GGGTGCACCC | CGGTAAGAGC | TCGGCCCGAA | GGCCGGGTTC | TACT | 594

( 2 ) INFORMATION FOR SEQ ID NO:170:

( i ) SEQUENCE CHARACTERISTICS:
        ( A ) LENGTH: 39 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GV5446IRT ( x i ) SEQUENCE DESCRIPTION: SEQ ID NO:170:

| | | | |
|---|---|---|---|
| CGGTCCCTCG | AACTCCAGCG | AGTCTTTTTT | TTTTTTTTT | 39

( 2 ) INFORMATION FOR SEQ ID NO:171:

( i ) SEQUENCE CHARACTERISTICS:
        ( A ) LENGTH: 24 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GV59- 5446F ( x i ) SEQUENCE DESCRIPTION: SEQ ID NO:171:

| | | |
|---|---|---|
| CTGAGCGACC | TCAAGCTCCC | TGGC | 24

( 2 ) INFORMATION FOR SEQ ID NO:172:

( i ) SEQUENCE CHARACTERISTICS:
        ( A ) LENGTH: 24 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
   ( C ) INDIVIDUAL ISOLATE: Primer GV- 5446IR ( x i ) SEQUENCE DESCRIPTION: SEQ ID NO:172:

CGGTCCCTCG AACTCCAGCG AGTC                    24

( 2 ) INFORMATION FOR SEQ ID NO:173:

( i ) SEQUENCE CHARACTERISTICS:
      ( A ) LENGTH: 23 base pairs
      ( B ) TYPE: nucleic acid
      ( C ) STRANDEDNESS: both
      ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
      ( C ) INDIVIDUAL ISOLATE: Probe E5-7- PRB ( x i ) SEQUENCE DESCRIPTION: SEQ ID NO:173:

CGTAGCCCTC GGGTGAACTA AAT                     23

( 2 ) INFORMATION FOR SEQ ID NO:174:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
      ( C ) INDIVIDUAL ISOLATE: Race Anchor Sequence ( x i ) SEQUENCE DESCRIPTION: SEQ ID NO:174:

CACGAATTCA CTATCGATTC TGGAACCTTC AGAGG         35

( 2 ) INFORMATION FOR SEQ ID NO:175:

( i ) SEQUENCE CHARACTERISTICS:
      ( A ) LENGTH: 736 base pairs
      ( B ) TYPE: nucleic acid
      ( C ) STRANDEDNESS: both
      ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
      ( C ) INDIVIDUAL ISOLATE: Consensus Sequence 5'-end ( x i ) SEQUENCE DESCRIPTION: SEQ ID NO:175:

ACGTGGGGA  GTTGATCCCC  CCCCCCCGGC  ACTGGGTGCA  AGCCCCAGAA  ACCGACGCCT    60
ATCTAAGTAG  ACGCAATGAC  TCGGCGCCGA  CTCGGCGACC  GGCCAAAAGG  TGGTGGATGG   120
GTGATGACAG  GGTTGGTAGG  TCGTAAATCC  CGGTCACCTT  GGTAGCCACT  ATAGGTGGGT   180
CTTAAGAGAA  GGTTAAGATT  CCTCTTGTGC  CTGCGGCGAG  ACCGCGCACG  GTCCACAGGT   240

| | | | | | |
|---|---|---|---|---|---|
|GTTGGCCCTA|CCGGTGGGAA|TAAGGGCCCG|ACGTCAGGCT|CGTCGTTAAA|CCGAGCCCGT|300|
|TACCCACCTG|GGCAAACGAC|GCCCACGTAC|GGTCCACGTC|GCCCTTCAAT|GTCTCTCTTG|360|
|ACCAATAGGC|GTAGCCGGCG|AGTTGACAAG|GACCAGTGGG|GGCCGGGGGC|TTGGAGAGGG|420|
|ACTCCAAGTC|CCGCCCTTCC|CGGTGGGCCG|GGAAATGCAT|GGGGCCACCC|AGCTCCGCGG|480|
|CGGCCTGCAG|CCGGGGTAGC|CCAAGAATCC|TTCGGGTGAG|GGCGGGTGGC|ATTTCCTTTT|540|
|TCTATACCAT|CATGGCAGTC|CTTCTGCTCC|TTCTCGTGGT|TGAGGCCGGG|GCCATTCTGG|600|
|CCCCGGCCAC|CCACGCTTGT|CGAGCGAATG|GGCAATATTT|CCTCACAAAT|TGTTGTGCCC|660|
|CGGAGGACAT|CGGGTTCTGC|CTGGAGGGTG|GATGCCTGGT|GGCCCTGGGG|TGCACGATTT|720|
|GCACTGACCA|ATGCTG| | | | |736|

( 2 ) INFORMATION FOR SEQ ID NO:176:

( i ) SEQUENCE CHARACTERISTICS:
        ( A ) LENGTH: 688 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: HGV Variant BG34

( i x ) FEATURE:
        ( A ) NAME/KEY: CDS
        ( B ) LOCATION: 272..688

( x i ) SEQUENCE DESCRIPTION: SEQ ID NO:176:

```
GACTCGGCGC  CGACTCGGCG  ACCGGCCAAA  AGGTGGTGGA  TGGGTGATGA  CAGGGTTGGT               60

AGGTCGTAAA  TCCCGGTCAC  CTTGGTAGCC  ACTATAGGTG  GGTCTTAAGA  GAAGGTTAAG              120

ATTCCTCTTG  TGCCTGCGGC  GAGACCGCGC  ACGGTCCACA  GGTGTTGGCC  CTACCGGTGT              180

GAATAAGGGC  CCGACGTCAG  GCTCGTCGTT  AAACCGAGCC  CGTCACCCAC  CTGGGCAAAC              240

GACGCCCACG  TACGGTCCAC  GTCGCCCTTC  A  ATG  CCT  CTC  TTG  GCC  AAT  AGG            292
                                      Met  Pro  Leu  Leu  Ala  Asn  Arg
                                       1                    5

AGT  ATC  CGG  CGA  GTT  GAC  AAG  GAC  CAG  TGG  GGG  CCG  GGA  GTC  ACG  GGG      340
Ser  Ile  Arg  Arg  Val  Asp  Lys  Asp  Gln  Trp  Gly  Pro  Gly  Val  Thr  Gly
              10                    15                    20

ATG  GAC  CCC  GGG  CTC  TGC  CCT  TCC  CGG  TGG  AAC  GGG  AAA  CGC  ATG  GGG      388
Met  Asp  Pro  Gly  Leu  Cys  Pro  Ser  Arg  Trp  Asn  Gly  Lys  Arg  Met  Gly
       25                    30                    35

CCA  CCC  AGC  TCC  GCG  GCG  GCC  TGC  AGC  CGG  GGT  AGC  CCA  AGA  ACC  CTT      436
Pro  Pro  Ser  Ser  Ala  Ala  Ala  Cys  Ser  Arg  Gly  Ser  Pro  Arg  Thr  Leu
 40                    45                    50                    55

CGG  GTG  AGG  GCG  GGT  GGC  ATT  TCT  CTT  TTC  TGT  ATC  ATC  ATG  GCA  GTC      484
Arg  Val  Arg  Ala  Gly  Gly  Ile  Ser  Leu  Phe  Cys  Ile  Ile  Met  Ala  Val
              60                    65                    70

CTC  CTG  CTC  CTT  CTC  GTG  GTT  GAG  GCC  GGG  GCC  ATT  CTG  GCC  CCG  GCC      532
Leu  Leu  Leu  Leu  Leu  Val  Val  Glu  Ala  Gly  Ala  Ile  Leu  Ala  Pro  Ala
                     75                    80                    85

ACC  CAC  GCT  TGT  CGA  GCG  AAT  GGA  CAA  TAT  TTC  CTC  ACA  AAC  TGT  TGC      580
Thr  His  Ala  Cys  Arg  Ala  Asn  Gly  Gln  Tyr  Phe  Leu  Thr  Asn  Cys  Cys
              90                    95                   100

GCC  CTC  GAG  GAC  ATC  GGG  TTC  TGC  CTG  GAA  GGC  GGG  TGC  CTG  GTG  GCC      628
```

```
Ala  Leu  Glu  Asp  Ile  Gly  Phe  Cys  Leu  Glu  Gly  Gly  Cys  Leu  Val  Ala
     105                 110                 115

TTA  GGG  TGC  ACC  ATT  TGC  ACT  GAC  CGT  TGC  TGG  CCA  CTG  TAT  CAG  GCG        676
Leu  Gly  Cys  Thr  Ile  Cys  Thr  Asp  Arg  Cys  Trp  Pro  Leu  Tyr  Gln  Ala
120                      125                 130                      135

GGT  TTG  GCT  GTG                                                                    688
Gly  Leu  Ala  Val
```

( 2 ) INFORMATION FOR SEQ ID NO:177:

( i ) SEQUENCE CHARACTERISTICS:
        ( A ) LENGTH: 139 amino acids
        ( B ) TYPE: amino acid
        ( D ) TOPOLOGY: linear ( i i ) MOLECULE TYPE: protein ( x i ) SEQUENCE DESCRIPTION: SEQ ID NO:177:

```
Met  Pro  Leu  Leu  Ala  Asn  Arg  Ser  Ile  Arg  Arg  Val  Asp  Lys  Asp  Gln
 1                   5                       10                      15

Trp  Gly  Pro  Gly  Val  Thr  Gly  Met  Asp  Pro  Gly  Leu  Cys  Pro  Ser  Arg
               20                       25                      30

Trp  Asn  Gly  Lys  Arg  Met  Gly  Pro  Pro  Ser  Ser  Ala  Ala  Ala  Cys  Ser
          35                       40                      45

Arg  Gly  Ser  Pro  Arg  Thr  Leu  Arg  Val  Arg  Ala  Gly  Gly  Ile  Ser  Leu
     50                       55                      60

Phe  Cys  Ile  Ile  Met  Ala  Val  Leu  Leu  Leu  Leu  Val  Val  Glu  Ala
65                       70                      75                      80

Gly  Ala  Ile  Leu  Ala  Pro  Ala  Thr  His  Ala  Cys  Arg  Ala  Asn  Gly  Gln
               85                       90                      95

Tyr  Phe  Leu  Thr  Asn  Cys  Cys  Ala  Leu  Glu  Asp  Ile  Gly  Phe  Cys  Leu
               100                      105                     110

Glu  Gly  Gly  Cys  Leu  Val  Ala  Leu  Gly  Cys  Thr  Ile  Cys  Thr  Asp  Arg
          115                      120                     125

Cys  Trp  Pro  Leu  Tyr  Gln  Ala  Gly  Leu  Ala  Val
     130                      135
```

( 2 ) INFORMATION FOR SEQ ID NO:178:

( i ) SEQUENCE CHARACTERISTICS:
        ( A ) LENGTH: 663 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: HGV Variant T55806

( i x ) FEATURE:
        ( A ) NAME/KEY: CDS
        ( B ) LOCATION: 271..663

( x i ) SEQUENCE DESCRIPTION: SEQ ID NO:178:

```
GACTCGGCGC  CGACTCGGCG  ACCGGCCAAA  AGGTGGTGGA  TGGGTGATGC  CAGGGTTGGT      60

AGGTCGTAAA  TCCCGGTCAT  CTTGGTAGCC  ACTATAGGTG  GGTCTTAAGA  GAAGGTTAAG     120

ATTCCTCTTG  TGCCTGCGGC  GAGACCGCGC  ACGGTCCACA  GGTGTTGGCC  CTACCGGTGG     180

AATAAGGGCC  CGACGTCAGG  CTCGTCGTTA  AACCGAGCCC  GTCACCCACC  TGGGCAAACG     240
```

```
ACGCTCACGT ACGGTCCACG TCGCCCTTCA ATG TCT CTC TTG ACC AAT AGG TTT          294
                                 Met Ser Leu Leu Thr Asn Arg Phe
                                  1               5

ATC CGG CGA GTT GAC AAG GAC CAG TGG GGG CCG GGG GTT ACG GGG ACG          342
Ile Arg Arg Val Asp Lys Asp Gln Trp Gly Pro Gly Val Thr Gly Thr
     10              15                       20

GAC CCC GAA CCC TGC CCT TCC CGG TGG GCC GGG AAA TGC ATG GGG CCA          390
Asp Pro Glu Pro Cys Pro Ser Arg Trp Ala Gly Lys Cys Met Gly Pro
 25              30                  35                       40

CCC AGC TCC GCG GCG GCC TGC AGC CGG GGT AGC CCA AGA ATC CTT CGG          438
Pro Ser Ser Ala Ala Ala Cys Ser Arg Gly Ser Pro Arg Ile Leu Arg
                 45                  50                       55

GTG AGG GCG GGT GGC ATT TCT CTT TTC TAT ACC ATC ATG GCA GTC CTT          486
Val Arg Ala Gly Gly Ile Ser Leu Phe Tyr Thr Ile Met Ala Val Leu
                 60              65                  70

CTG CTC TTC TTC GTG GTT GAG GCC GGG GCG ATT CTC GCC CCG GCC ACC          534
Leu Leu Phe Phe Val Val Glu Ala Gly Ala Ile Leu Ala Pro Ala Thr
         75                  80                  85

CAC GCT TGT CGG GCG AAT GGG CAA TAT TTC CTC ACA AAT TGT TGC GCC          582
His Ala Cys Arg Ala Asn Gly Gln Tyr Phe Leu Thr Asn Cys Cys Ala
         90                  95                 100

CCA GAG GAT GTT GGG TTC TGC CTG GAG GGC GGA TGC CTG GTG GCT CTG          630
Pro Glu Asp Val Gly Phe Cys Leu Glu Gly Gly Cys Leu Val Ala Leu
105              110                 115                      120

GGG TGT ACG ATT TGC ACT GAC CGT TGC TGG CCA                              663
Gly Cys Thr Ile Cys Thr Asp Arg Cys Trp Pro
                 125                 130
```

( 2 ) INFORMATION FOR SEQ ID NO:179:

( i ) SEQUENCE CHARACTERISTICS:
        ( A ) LENGTH: 131 amino acids
        ( B ) TYPE: amino acid
        ( D ) TOPOLOGY: linear ( i i ) MOLECULE TYPE: protein ( x i ) SEQUENCE DESCRIPTION: SEQ ID NO:179:

```
Met Ser Leu Leu Thr Asn Arg Phe Ile Arg Arg Val Asp Lys Asp Gln
 1               5                  10                      15

Trp Gly Pro Gly Val Thr Gly Thr Asp Pro Glu Pro Cys Pro Ser Arg
             20                  25                  30

Trp Ala Gly Lys Cys Met Gly Pro Pro Ser Ser Ala Ala Ala Cys Ser
         35                  40                  45

Arg Gly Ser Pro Arg Ile Leu Arg Val Arg Ala Gly Gly Ile Ser Leu
         50              55                  60

Phe Tyr Thr Ile Met Ala Val Leu Leu Leu Phe Phe Val Val Glu Ala
 65                  70                  75                  80

Gly Ala Ile Leu Ala Pro Ala Thr His Ala Cys Arg Ala Asn Gly Gln
                 85                  90                  95

Tyr Phe Leu Thr Asn Cys Cys Ala Pro Glu Asp Val Gly Phe Cys Leu
             100                 105                 110

Glu Gly Gly Cys Leu Val Ala Leu Gly Cys Thr Ile Cys Thr Asp Arg
             115                 120                 125

Cys Trp Pro
         130
```

( 2 ) INFORMATION FOR SEQ ID NO:180:

( i ) SEQUENCE CHARACTERISTICS:

(A) LENGTH: 632 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: HGV Variant EB20-2

(ix) FEATURE:
        (A) NAME/KEY: CDS
        (B) LOCATION: 271..632

(xi) SEQUENCE DESCRIPTION: SEQ ID NO:180:

| | | |
|---|---|---|
| GACTCGGCGC CGACTCGGCG ACCGGCCAAA AGGTGGTGGA TGGGTGATGC CAGGGTTGGT | 60 |
| AGGTCGTAAA TCCCGGTCAT CTTGGTAGCC ACTATAGGTG GGTCTTAAGA GAAGGTTAAG | 120 |
| ATTCCTCTTG TGCCTGCGGC GAGACCGCGC ACGGTCCACA GGTGTTGGCC CTACCGGTGT | 180 |
| AATAAGGGCC CGACGTCAGG CTCGTCGTTA AACCGAGCCC GTCACCCACC TGGGCAAACG | 240 |
| ACGCCCACGT ACGGTCCACG TCGCCCTTCA ATG CCT CTC TTG GCC AAT AGG AGT | 294 |
|                                  Met Pro Leu Leu Ala Asn Arg Ser |
|                                   1                5              |

```
TAT CTC CGG CGA GTT GGC AAG GAC CAG TGG GGG CCG GGG GTT ACG GGG      342
Tyr Leu Arg Arg Val Gly Lys Asp Gln Trp Gly Pro Gly Val Thr Gly
         10                  15                  20

AAG GAC CCC GAA CCC TGC CCT TCC CGG TGG GCC GGG AAA TGC ATG GGG      390
Lys Asp Pro Glu Pro Cys Pro Ser Arg Trp Ala Gly Lys Cys Met Gly
 25                  30                  35                  40

CCA CCC AGC TCC GCG GCG GCC TGC AGC CGG GGT AGC CCA AAA AAC CTT      438
Pro Pro Ser Ser Ala Ala Ala Cys Ser Arg Gly Ser Pro Lys Asn Leu
                 45                  50                  55

CGG GTG AGG GCG GGT GGC ATT TTC TTT TCC TAT ACC ATC ATG GCA GTC      486
Arg Val Arg Ala Gly Gly Ile Phe Phe Ser Tyr Thr Ile Met Ala Val
                 60                  65                  70

CTT CTG CTC CTT CTC GTG GTT GAG GCC GGG GCC ATT TTG GCC CCG GCC      534
Leu Leu Leu Leu Leu Val Val Glu Ala Gly Ala Ile Leu Ala Pro Ala
             75                  80                  85

ACC CAC GCT TGC AGA GCT AAT GGG CAA TAT TTC CTC ACA AAC TGT TGT      582
Thr His Ala Cys Arg Ala Asn Gly Gln Tyr Phe Leu Thr Asn Cys Cys
         90                  95                 100

GCC TTG GAG GAC ATC GGG TTC TGC CTG GAA GGC GGA TGC TTG GTG GCG CT  632
Ala Leu Glu Asp Ile Gly Phe Cys Leu Glu Gly Gly Cys Leu Val Ala
105                 110                 115                 120
```

(2) INFORMATION FOR SEQ ID NO:181:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO:181:

```
Met Pro Leu Leu Ala Asn Arg Ser Tyr Leu Arg Arg Val Gly Lys Asp
 1               5                  10                  15

Gln Trp Gly Pro Gly Val Thr Gly Lys Asp Pro Glu Pro Cys Pro Ser
                 20                  25                  30

Arg Trp Ala Gly Lys Cys Met Gly Pro Pro Ser Ser Ala Ala Ala Cys
             35                  40                  45
```

```
Ser  Arg  Gly  Ser  Pro  Lys  Asn  Leu  Arg  Val  Arg  Ala  Gly  Gly  Ile  Phe
      50                  55                       60

Phe  Ser  Tyr  Thr  Ile  Met  Ala  Val  Leu  Leu  Leu  Leu  Leu  Val  Val  Glu
 65                 70                       75                            80

Ala  Gly  Ala  Ile  Leu  Ala  Pro  Ala  Thr  His  Ala  Cys  Arg  Ala  Asn  Gly
                85                       90                            95

Gln  Tyr  Phe  Leu  Thr  Asn  Cys  Cys  Ala  Leu  Glu  Asp  Ile  Gly  Phe  Cys
               100                      105                      110

Leu  Glu  Gly  Gly  Cys  Leu  Val  Ala
          115                     120
```

( 2 ) INFORMATION FOR SEQ ID NO:182:

( i ) SEQUENCE CHARACTERISTICS:
        ( A ) LENGTH: 9103 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: HGV-JC Variant ( i x ) FEATURE:
        ( A ) NAME/KEY: CDS
        ( B ) LOCATION: 276..9005

( x i ) SEQUENCE DESCRIPTION: SEQ ID NO:182:

```
CAATGACTCG  GCGCCGACTC  GGCGACCGGC  CAAAAGGTGG  TGGATGGGTG  ATGACAGGGT         60

TGGTAGGTCG  TAAATCCCGG  TCACCTTGGT  AGCCACTATA  GGTGGGTCTT  AAGAGAAGGT        120

TAAGATTCCT  CTTGTGCCTG  CGGCGAGACC  GCGCACGGTC  CACAGGTGTT  GGCCCTACCG        180

GTGGGAATAA  GGGCCCGACG  TCAGGCTCGT  CGTTAAACCG  AGCCCGTAAC  CCGCCTGGGC        240

AAACGACGCC  CACGTACGGT  CCACGTCGCC  CTTCA ATG TCG CTC TTG ACC AAT             293
                                         Met Ser Leu Leu Thr Asn
                                          1               5

AGG CTT AGC CGG CGA GTT GAC AAG GAC CAG TGG GGG CCG GGG TTT ATG              341
Arg Leu Ser Arg Arg Val Asp Lys Asp Gln Trp Gly Pro Gly Phe Met
            10                  15                      20

GGG AAG GAC CCC AAA CCC TGC CCT TCC CGG CGG ACC GGG AAA TGC ATG              389
Gly Lys Asp Pro Lys Pro Cys Pro Ser Arg Arg Thr Gly Lys Cys Met
        25                  30                      35

GGG CCA CCC AGC TCC GCG GCG GCC TGC AGC CGG GGT AGC CCA AGA ATC              437
Gly Pro Pro Ser Ser Ala Ala Ala Cys Ser Arg Gly Ser Pro Arg Ile
    40                  45                      50

CTT CGG GTG AGG GCG GGT GGC ATT TCT CTT CCT TAT ACC ATC ATG GAA              485
Leu Arg Val Arg Ala Gly Gly Ile Ser Leu Pro Tyr Thr Ile Met Glu
 55                  60                      65                      70

GCC CTC CTG TTC CTC CTC GGG GTG GAG GCC GGG GCC ATT CTG GCC CCG              533
Ala Leu Leu Phe Leu Leu Gly Val Glu Ala Gly Ala Ile Leu Ala Pro
                 75                      80                      85

GCC ACC CAC GCT TGT CGA GCG AAT GGG CAA TAT TTC CTC ACA AAC TGT              581
Ala Thr His Ala Cys Arg Ala Asn Gly Gln Tyr Phe Leu Thr Asn Cys
             90                      95                     100

TGT GCT CCA GAG GAC ATT GGG TTC TGC CTC GAA GGC GGT TGC CTT GTG              629
Cys Ala Pro Glu Asp Ile Gly Phe Cys Leu Glu Gly Gly Cys Leu Val
            105                     110                     115
```

-continued

| | | | | | | | | | | | | | | | | |
|---|---|---|---|---|---|---|---|---|---|---|---|---|---|---|---|---|
| GCC | CTG | GGG | TGC | ACA | GTT | TGC | ACT | GAC | CGA | TGC | TGG | CCG | CTG | TAT | CAG | 677 |
| Ala | Leu | Gly | Cys | Thr | Val | Cys | Thr | Asp | Arg | Cys | Trp | Pro | Leu | Tyr | Gln | |
| 120 | | | | | 125 | | | | | 130 | | | | | | |
| GCG | GGC | TTG | GCT | GTG | CGG | CCT | GGC | AAG | TCC | GCA | GCC | CAG | CTG | GTG | GGG | 725 |
| Ala | Gly | Leu | Ala | Val | Arg | Pro | Gly | Lys | Ser | Ala | Ala | Gln | Leu | Val | Gly | |
| 135 | | | | | 140 | | | | | 145 | | | | | 150 | |
| CAA | CTG | GGT | GGC | CTC | TAC | GGG | CCC | TTG | TCG | GTG | TCG | GCC | TAC | GTG | GCC | 773 |
| Gln | Leu | Gly | Gly | Leu | Tyr | Gly | Pro | Leu | Ser | Val | Ser | Ala | Tyr | Val | Ala | |
| | | | | 155 | | | | | 160 | | | | | 165 | | |
| GGC | ATC | CTG | GGC | CTG | GGT | GAG | GTG | TAC | TCG | GGT | GTC | CTA | ACA | GTT | GGT | 821 |
| Gly | Ile | Leu | Gly | Leu | Gly | Glu | Val | Tyr | Ser | Gly | Val | Leu | Thr | Val | Gly | |
| | | | 170 | | | | | 175 | | | | | 180 | | | |
| GTT | GCG | TTG | ACG | CGC | CGG | GTC | TAC | CCG | ATG | CCC | AAC | CTG | ACG | TGT | GCA | 869 |
| Val | Ala | Leu | Thr | Arg | Arg | Val | Tyr | Pro | Met | Pro | Asn | Leu | Thr | Cys | Ala | |
| | | 185 | | | | | 190 | | | | | 195 | | | | |
| GTA | GAG | TGT | GAG | CTT | AAG | TGG | GAA | AGT | GAG | TTT | TGG | AGA | TGG | ACT | GAG | 917 |
| Val | Glu | Cys | Glu | Leu | Lys | Trp | Glu | Ser | Glu | Phe | Trp | Arg | Trp | Thr | Glu | |
| 200 | | | | | 205 | | | | | 210 | | | | | | |
| CAG | CTG | GCC | TCC | AAT | TAC | TGG | ATT | CTG | GAA | TAC | CTT | TGG | AAG | GTC | CCG | 965 |
| Gln | Leu | Ala | Ser | Asn | Tyr | Trp | Ile | Leu | Glu | Tyr | Leu | Trp | Lys | Val | Pro | |
| 215 | | | | | 220 | | | | | 225 | | | | | 230 | |
| TTT | GAC | TTC | TGG | AGA | GGC | GTG | CTA | AGC | CTG | ACT | CCC | TTG | CTG | GTT | TGC | 1013 |
| Phe | Asp | Phe | Trp | Arg | Gly | Val | Leu | Ser | Leu | Thr | Pro | Leu | Leu | Val | Cys | |
| | | | | 235 | | | | | 240 | | | | | 245 | | |
| GTG | GCC | GCG | TTG | CTG | CTG | CTG | GAG | CAA | CGG | ATT | GTC | ATG | GTC | TTC | CTG | 1061 |
| Val | Ala | Ala | Leu | Leu | Leu | Leu | Glu | Gln | Arg | Ile | Val | Met | Val | Phe | Leu | |
| | | | | 250 | | | | | 255 | | | | | 260 | | |
| TTG | GTG | ACG | ATG | GCC | GGG | ATG | TCG | CAA | GGC | GCT | CCG | GCC | TCC | GTT | TTG | 1109 |
| Leu | Val | Thr | Met | Ala | Gly | Met | Ser | Gln | Gly | Ala | Pro | Ala | Ser | Val | Leu | |
| | | 265 | | | | | 270 | | | | | 275 | | | | |
| GGG | TCT | CGC | CCC | TTT | GAC | TAC | GGG | TTG | ACA | TGG | CAG | TCT | TGT | TCC | TGC | 1157 |
| Gly | Ser | Arg | Pro | Phe | Asp | Tyr | Gly | Leu | Thr | Trp | Gln | Ser | Cys | Ser | Cys | |
| | 280 | | | | | 285 | | | | | 290 | | | | | |
| AGG | GCT | AAT | GGG | TCG | CGC | TAT | ACT | ACT | GGG | GAG | AAG | GTG | TGG | GAC | CGT | 1205 |
| Arg | Ala | Asn | Gly | Ser | Arg | Tyr | Thr | Thr | Gly | Glu | Lys | Val | Trp | Asp | Arg | |
| 295 | | | | | 300 | | | | | 305 | | | | | 310 | |
| GGG | AAC | GTC | ACG | CTC | CTG | TGT | GAC | TGC | CCC | AAC | GGC | CCC | TGG | GTG | TGG | 1253 |
| Gly | Asn | Val | Thr | Leu | Leu | Cys | Asp | Cys | Pro | Asn | Gly | Pro | Trp | Val | Trp | |
| | | | | 315 | | | | | 320 | | | | | 325 | | |
| TTG | CCG | GCC | TTT | TGC | CAA | GCA | ATC | GGC | TGG | GGC | GAT | CCC | ATC | ACT | CAT | 1301 |
| Leu | Pro | Ala | Phe | Cys | Gln | Ala | Ile | Gly | Trp | Gly | Asp | Pro | Ile | Thr | His | |
| | | | 330 | | | | | 335 | | | | | 340 | | | |
| TGG | AGC | CAC | GGC | CAA | AAT | CGG | TGG | CCC | CTC | TCA | TGC | CCC | CAG | TAT | GTC | 1349 |
| Trp | Ser | His | Gly | Gln | Asn | Arg | Trp | Pro | Leu | Ser | Cys | Pro | Gln | Tyr | Val | |
| | | 345 | | | | | 350 | | | | | 355 | | | | |
| TAT | GGG | TCT | GTT | TCA | GTC | ACT | TGC | GTG | TGG | GGT | TCC | GTC | TCT | TGG | TTT | 1397 |
| Tyr | Gly | Ser | Val | Ser | Val | Thr | Cys | Val | Trp | Gly | Ser | Val | Ser | Trp | Phe | |
| | 360 | | | | | 365 | | | | | 370 | | | | | |
| GCC | TCG | ACT | GGC | GGT | CGC | GAC | TCG | AAG | ATC | GAT | GTG | TGG | AGT | CTG | GTG | 1445 |
| Ala | Ser | Thr | Gly | Gly | Arg | Asp | Ser | Lys | Ile | Asp | Val | Trp | Ser | Leu | Val | |
| 375 | | | | | 380 | | | | | 385 | | | | | 390 | |
| CCG | GTT | GGT | TCC | GCC | AGC | TGC | ACC | ATA | GCC | GCT | CTT | GGA | TCG | TCG | GAT | 1493 |
| Pro | Val | Gly | Ser | Ala | Ser | Cys | Thr | Ile | Ala | Ala | Leu | Gly | Ser | Ser | Asp | |
| | | | | 395 | | | | | 400 | | | | | 405 | | |
| CGG | GAC | ACG | GTA | GTT | GAG | CTC | TCC | GAG | TGG | GGA | GTC | CCG | TGC | GCA | ACG | 1541 |
| Arg | Asp | Thr | Val | Val | Glu | Leu | Ser | Glu | Trp | Gly | Val | Pro | Cys | Ala | Thr | |
| | | | 410 | | | | | 415 | | | | | 420 | | | |
| TGC | ATT | CTG | GAT | CGT | CGG | CCG | GCC | TCG | TGC | GGC | ACC | TGT | GTG | AGA | GAC | 1589 |
| Cys | Ile | Leu | Asp | Arg | Arg | Pro | Ala | Ser | Cys | Gly | Thr | Cys | Val | Arg | Asp | |
| | | 425 | | | | | 430 | | | | | 435 | | | | |

| | | | | | | | | | | | | | | | | |
|---|---|---|---|---|---|---|---|---|---|---|---|---|---|---|---|---|
| TGC | TGG | CCC | GAA | ACC | GGG | TCG | GTT | AGG | TTT | CCA | TTC | CAT | CGG | TGC | GGC | 1637 |
| Cys | Trp | Pro | Glu | Thr | Gly | Ser | Val | Arg | Phe | Pro | Phe | His | Arg | Cys | Gly | |
| | 440 | | | | 445 | | | | | | 450 | | | | | |
| GCG | GGG | CCT | AAG | CTG | ACA | AAG | GAC | TTG | GAA | GCT | GTG | CCC | TTC | GTC | AAT | 1685 |
| Ala | Gly | Pro | Lys | Leu | Thr | Lys | Asp | Leu | Glu | Ala | Val | Pro | Phe | Val | Asn | |
| 455 | | | | | 460 | | | | | 465 | | | | | 470 | |
| AGG | ACA | ACT | CCC | TTC | ACC | ATA | AGG | GGC | CCC | CTG | GGC | AAC | CAG | GGG | AGA | 1733 |
| Arg | Thr | Thr | Pro | Phe | Thr | Ile | Arg | Gly | Pro | Leu | Gly | Asn | Gln | Gly | Arg | |
| | | | | 475 | | | | | 480 | | | | | 485 | | |
| GGC | AAC | CCG | GTG | CGG | TCG | CCC | TTG | GGT | TTT | GGG | TCC | TAC | GCC | ATG | ACC | 1781 |
| Gly | Asn | Pro | Val | Arg | Ser | Pro | Leu | Gly | Phe | Gly | Ser | Tyr | Ala | Met | Thr | |
| | | | 490 | | | | | 495 | | | | | 500 | | | |
| AAG | ATC | CGA | GAC | TCC | TTA | CAT | TTG | GTG | AAA | TGT | CCC | ACA | CCA | GCC | ATT | 1829 |
| Lys | Ile | Arg | Asp | Ser | Leu | His | Leu | Val | Lys | Cys | Pro | Thr | Pro | Ala | Ile | |
| | | 505 | | | | | 510 | | | | | 515 | | | | |
| GAG | CCT | CCC | ACC | GGG | ACG | TTT | GGG | TTC | TTC | CCC | GGA | GTG | CCG | CCT | CTT | 1877 |
| Glu | Pro | Pro | Thr | Gly | Thr | Phe | Gly | Phe | Phe | Pro | Gly | Val | Pro | Pro | Leu | |
| 520 | | | | | 525 | | | | | 530 | | | | | | |
| AAC | AAC | TGC | CTG | CTG | TTG | GGC | ACG | GAA | GTG | TCC | GAA | GCG | CTG | GGC | GGG | 1925 |
| Asn | Asn | Cys | Leu | Leu | Leu | Gly | Thr | Glu | Val | Ser | Glu | Ala | Leu | Gly | Gly | |
| 535 | | | | | 540 | | | | | 545 | | | | | 550 | |
| GCC | GGC | CTC | ACG | GGG | GGG | TTC | TAT | GAA | CCC | CTG | GTG | CGC | AGG | CGT | TCG | 1973 |
| Ala | Gly | Leu | Thr | Gly | Gly | Phe | Tyr | Glu | Pro | Leu | Val | Arg | Arg | Arg | Ser | |
| | | | | 555 | | | | | 560 | | | | | 565 | | |
| GAG | CTG | ATG | GGG | CGC | CGA | AAT | CCG | GTT | TGC | CCG | GGG | TTT | GCA | TGG | CTG | 2021 |
| Glu | Leu | Met | Gly | Arg | Arg | Asn | Pro | Val | Cys | Pro | Gly | Phe | Ala | Trp | Leu | |
| | | | 570 | | | | | 575 | | | | | 580 | | | |
| TCC | TCG | GGT | CGA | CCT | GAC | GGG | TTT | ATA | CAC | GTC | CAG | GGC | CAC | TTG | CAG | 2069 |
| Ser | Ser | Gly | Arg | Pro | Asp | Gly | Phe | Ile | His | Val | Gln | Gly | His | Leu | Gln | |
| | | 585 | | | | | 590 | | | | | 595 | | | | |
| GAG | GTC | GAT | GCT | GGC | AAC | TTC | ATC | CCT | CCA | CCT | CGC | TGG | TTG | CTC | TTG | 2117 |
| Glu | Val | Asp | Ala | Gly | Asn | Phe | Ile | Pro | Pro | Pro | Arg | Trp | Leu | Leu | Leu | |
| | 600 | | | | | 605 | | | | | 610 | | | | | |
| GAC | TTT | GTG | TTT | GTC | CTG | TTA | TAC | CTG | ATG | AAG | CTG | GCT | GAG | GCA | CGG | 2165 |
| Asp | Phe | Val | Phe | Val | Leu | Leu | Tyr | Leu | Met | Lys | Leu | Ala | Glu | Ala | Arg | |
| 615 | | | | | 620 | | | | | 625 | | | | | 630 | |
| CTG | GTC | CCG | TTG | ATC | TTG | CTT | CTG | CTG | TGG | TGG | TGG | GTG | AAC | CAG | TTG | 2213 |
| Leu | Val | Pro | Leu | Ile | Leu | Leu | Leu | Leu | Trp | Trp | Trp | Val | Asn | Gln | Leu | |
| | | | | 635 | | | | | 640 | | | | | 645 | | |
| GCA | GTC | CTT | GGA | CTG | CCG | GCT | GTG | GAC | GCC | GCC | GTG | GCT | GGT | GAG | GTC | 2261 |
| Ala | Val | Leu | Gly | Leu | Pro | Ala | Val | Asp | Ala | Ala | Val | Ala | Gly | Glu | Val | |
| | | | 650 | | | | | 655 | | | | | 660 | | | |
| TTC | GCG | GGC | CCG | GCC | CTG | TCG | TGG | TGT | CTG | GGC | CTC | CCC | ACC | GTT | AGT | 2309 |
| Phe | Ala | Gly | Pro | Ala | Leu | Ser | Trp | Cys | Leu | Gly | Leu | Pro | Thr | Val | Ser | |
| | | 665 | | | | | 670 | | | | | 675 | | | | |
| ATG | ATC | CTG | GGC | TTA | GCA | AAC | CTG | GTG | TTG | TAT | TTC | CGG | TGG | ATG | GGT | 2357 |
| Met | Ile | Leu | Gly | Leu | Ala | Asn | Leu | Val | Leu | Tyr | Phe | Arg | Trp | Met | Gly | |
| | | 680 | | | | | 685 | | | | | 690 | | | | |
| CCC | CAA | CGC | CTC | ATG | TTC | CTC | GTG | TTG | TGG | AAG | CTC | GCT | CGG | GGA | GCC | 2405 |
| Pro | Gln | Arg | Leu | Met | Phe | Leu | Val | Leu | Trp | Lys | Leu | Ala | Arg | Gly | Ala | |
| 695 | | | | | 700 | | | | | 705 | | | | | 710 | |
| TTC | CCG | CTG | GCA | CTT | CTG | ATG | GGG | ATC | TCG | GCA | ACC | CGG | GGC | CGC | ACC | 2453 |
| Phe | Pro | Leu | Ala | Leu | Leu | Met | Gly | Ile | Ser | Ala | Thr | Arg | Gly | Arg | Thr | |
| | | | | 715 | | | | | 720 | | | | | 725 | | |
| TCG | GTG | CTC | GGG | GCC | GAG | TTC | TGC | TTC | GAT | GTC | ACA | TTC | GAG | GTG | GAC | 2501 |
| Ser | Val | Leu | Gly | Ala | Glu | Phe | Cys | Phe | Asp | Val | Thr | Phe | Glu | Val | Asp | |
| | | | | 730 | | | | | 735 | | | | | 740 | | |
| ACG | TCG | GTT | TTG | GGC | TGG | GTG | GTG | GCC | AGT | GTG | GTA | GCC | TGG | GCC | ATT | 2549 |
| Thr | Ser | Val | Leu | Gly | Trp | Val | Val | Ala | Ser | Val | Val | Ala | Trp | Ala | Ile | |
| | | 745 | | | | | 750 | | | | | 755 | | | | |

```
GCG CTC CTG AGC TCG ATG AGC GCG GGA GGG TGG AGG CAC AAG GCC GTG      2597
Ala Leu Leu Ser Ser Met Ser Ala Gly Gly Trp Arg His Lys Ala Val
    760             765             770

ATC TAT AGG ACG TGG TGT AAG GGG TAC CAG GCA ATA CGC CAA CGG GTG      2645
Ile Tyr Arg Thr Trp Cys Lys Gly Tyr Gln Ala Ile Arg Gln Arg Val
775             780             785                         790

GTG CGG AGC CCC CTC GGG GAG GGG CGG CCC ACC AAA CCC TTG ACG TTT      2693
Val Arg Ser Pro Leu Gly Glu Gly Arg Pro Thr Lys Pro Leu Thr Phe
                795             800             805

GCT TGG TGC TTG GCC TCA TAC ATC TGG CCG GAT GCT GTG ATG ATG GTG      2741
Ala Trp Cys Leu Ala Ser Tyr Ile Trp Pro Asp Ala Val Met Met Val
            810             815             820

GTG GTA GCC TTG GTG CTC CTC TTT GGC CTG TTC GAC GCG TTG GAC TGG      2789
Val Val Ala Leu Val Leu Leu Phe Gly Leu Phe Asp Ala Leu Asp Trp
        825             830             835

GCT TTG GAG GAG CTC TTG GTG TCC CGG CCC TCG TTA CGG CGT CTG GCC      2837
Ala Leu Glu Glu Leu Leu Val Ser Arg Pro Ser Leu Arg Arg Leu Ala
    840             845             850

CGG GTG GTT GAG TGC TGT GTG ATG GCG GGA GAG AAG GCC ACA ACC GTC      2885
Arg Val Val Glu Cys Cys Val Met Ala Gly Glu Lys Ala Thr Thr Val
855             860             865             870

CGG CTG GTC TCC AAG ATG TGC GCG AGA GGG GCC TAT TTG TTT GAC CAT      2933
Arg Leu Val Ser Lys Met Cys Ala Arg Gly Ala Tyr Leu Phe Asp His
                875             880             885

ATG GGC TCT TTT TCG CGC GCT GTC AAG GAG CGC CTG CTG GAG TGG GAC      2981
Met Gly Ser Phe Ser Arg Ala Val Lys Glu Arg Leu Leu Glu Trp Asp
            890             895             900

GCG GCT TTG GAA CCC CTG TCA TTC ACT AGG ACG GAC TGT CGC ATC ATT      3029
Ala Ala Leu Glu Pro Leu Ser Phe Thr Arg Thr Asp Cys Arg Ile Ile
        905             910             915

AGA GAT GCT GCG AGG ACC TTG GCC TGC GGG CAG TGC GTC ATG GGC TTG      3077
Arg Asp Ala Ala Arg Thr Leu Ala Cys Gly Gln Cys Val Met Gly Leu
    920             925             930

CCT GTG GTA GCG CGC CGT GGT GAC GAG GTT CTT ATC GGT GTC TTT CAG      3125
Pro Val Val Ala Arg Arg Gly Asp Glu Val Leu Ile Gly Val Phe Gln
935             940             945             950

GAT GTG AAC CAT TTG CCT CCC GGA TTC GTC CCG ACC GCA CCC GTT GTC      3173
Asp Val Asn His Leu Pro Pro Gly Phe Val Pro Thr Ala Pro Val Val
                955             960             965

ATC CGG CGG TGC GGG AAG GGG TTT CTG GGG GTC ACT AAG GCT GCC TTG      3221
Ile Arg Arg Cys Gly Lys Gly Phe Leu Gly Val Thr Lys Ala Ala Leu
            970             975             980

ACT GGT CGG GAT CCT GAC TTA CAT CCA GGG AAC GTC ATG GTG TTG GGG      3269
Thr Gly Arg Asp Pro Asp Leu His Pro Gly Asn Val Met Val Leu Gly
        985             990             995

ACG GCT ACG TCG CGA AGC ATG GGG ACA TGC CTG AAC GGC CTG CTG TTC      3317
Thr Ala Thr Ser Arg Ser Met Gly Thr Cys Leu Asn Gly Leu Leu Phe
    1000            1005            1010

ACG ACT TTC CAT GGG GCT TCA TCC CGA ACC ATC GCC ACG CCC GTG GGG      3365
Thr Thr Phe His Gly Ala Ser Ser Arg Thr Ile Ala Thr Pro Val Gly
1015            1020            1025            1030

GCC CTT AAT CCC AGG TGG TGG TCC GCC AGT GAT GAC GTC ACG GTG TAC      3413
Ala Leu Asn Pro Arg Trp Trp Ser Ala Ser Asp Asp Val Thr Val Tyr
                1035            1040            1045

CCG CTC CCG GAT GGG GCA ACC TCG TTG ACG CCC TGC ACT TGC CAG GCT      3461
Pro Leu Pro Asp Gly Ala Thr Ser Leu Thr Pro Cys Thr Cys Gln Ala
            1050            1055            1060

GAG TCC TGT TGG GTC ATA CGG TCC GAC GGG GCT TTG TGC CAT GGC TTG      3509
Glu Ser Cys Trp Val Ile Arg Ser Asp Gly Ala Leu Cys His Gly Leu
        1065            1070            1075
```

| | | | | | | | | | | | | | | | | |
|---|---|---|---|---|---|---|---|---|---|---|---|---|---|---|---|---|
| AGT | AAG | GGA | GAC | AAG | GTG | GAG | CTA | GAT | GTG | GCC | ATG | GAG | GTC | TCA | GAT | 3557 |
| Ser | Lys | Gly | Asp | Lys | Val | Glu | Leu | Asp | Val | Ala | Met | Glu | Val | Ser | Asp | |
| | 1080 | | | | 1085 | | | | 1090 | | | | | | | |
| TTC | CGT | GGC | TCG | TCC | GGC | TCA | CCT | GTC | CTG | TGC | GAC | GAG | GGG | CAC | GCA | 3605 |
| Phe | Arg | Gly | Ser | Ser | Gly | Ser | Pro | Val | Leu | Cys | Asp | Glu | Gly | His | Ala | |
| 1095 | | | | | 1100 | | | | 1105 | | | | | | 1110 | |
| GTA | GGA | ATG | CTC | GTG | TCG | GTG | CTC | CAC | TCG | GGT | GGT | CGG | GTC | ACC | GCG | 3653 |
| Val | Gly | Met | Leu | Val | Ser | Val | Leu | His | Ser | Gly | Gly | Arg | Val | Thr | Ala | |
| | | | | 1115 | | | | | 1120 | | | | | 1125 | | |
| GCT | CGA | TTC | ACC | AGG | CCG | TGG | ACC | CAG | GTC | CCA | ACA | GAT | GCT | AAG | ACC | 3701 |
| Ala | Arg | Phe | Thr | Arg | Pro | Trp | Thr | Gln | Val | Pro | Thr | Asp | Ala | Lys | Thr | |
| | | | 1130 | | | | | 1135 | | | | | 1140 | | | |
| ACC | ACT | GAA | CCC | CCT | CCG | GTG | CCG | GCA | AAG | GGA | GTT | TTC | AAG | GAA | GCC | 3749 |
| Thr | Thr | Glu | Pro | Pro | Pro | Val | Pro | Ala | Lys | Gly | Val | Phe | Lys | Glu | Ala | |
| | | 1145 | | | | | 1150 | | | | | 1155 | | | | |
| CCA | CTG | TTT | ATG | CCC | ACG | GGC | GCA | GGA | AAG | AGC | ACG | CGC | GTC | CCG | TTG | 3797 |
| Pro | Leu | Phe | Met | Pro | Thr | Gly | Ala | Gly | Lys | Ser | Thr | Arg | Val | Pro | Leu | |
| | 1160 | | | | | 1165 | | | | | 1170 | | | | | |
| GAG | TAT | GGC | AAC | ATG | GGG | CAC | AAG | GTC | CTG | ATT | TTG | AAC | CCC | TCG | GTG | 3845 |
| Glu | Tyr | Gly | Asn | Met | Gly | His | Lys | Val | Leu | Ile | Leu | Asn | Pro | Ser | Val | |
| 1175 | | | | | 1180 | | | | | 1185 | | | | | 1190 | |
| GCG | ACA | GTG | AGG | GCC | ATG | GGC | CCT | TAC | ATG | GAG | CGA | CTG | GCG | GGA | AAA | 3893 |
| Ala | Thr | Val | Arg | Ala | Met | Gly | Pro | Tyr | Met | Glu | Arg | Leu | Ala | Gly | Lys | |
| | | | | 1195 | | | | | 1200 | | | | | 1205 | | |
| CAT | CCA | AGT | ATC | TAC | TGT | GGC | CAT | GAC | ACC | ACT | GCC | TTC | ACA | AGG | ATC | 3941 |
| His | Pro | Ser | Ile | Tyr | Cys | Gly | His | Asp | Thr | Thr | Ala | Phe | Thr | Arg | Ile | |
| | | | 1210 | | | | | 1215 | | | | | 1220 | | | |
| ACT | GAT | TCC | CCC | TTA | ACG | TAC | TCT | ACC | TAT | GGG | AGG | TTT | CTG | GCC | AAC | 3989 |
| Thr | Asp | Ser | Pro | Leu | Thr | Tyr | Ser | Thr | Tyr | Gly | Arg | Phe | Leu | Ala | Asn | |
| | | 1225 | | | | | 1230 | | | | | 1235 | | | | |
| CCT | AGG | CAG | ATG | CTG | CGA | GGT | GTG | TCG | GTG | GTC | ATT | TGC | GAT | GAA | TGC | 4037 |
| Pro | Arg | Gln | Met | Leu | Arg | Gly | Val | Ser | Val | Val | Ile | Cys | Asp | Glu | Cys | |
| | 1240 | | | | | 1245 | | | | | 1250 | | | | | |
| CAC | AGT | CAT | GAT | TCC | ACT | GTG | TTG | TTG | GGG | ATT | GGA | CGG | GTC | CGG | GAG | 4085 |
| His | Ser | His | Asp | Ser | Thr | Val | Leu | Leu | Gly | Ile | Gly | Arg | Val | Arg | Glu | |
| 1255 | | | | | 1260 | | | | | 1265 | | | | | 1270 | |
| CTG | GCA | CGA | GAG | TGT | GGG | GTG | CAG | CTT | GTG | CTC | TAC | GCC | ACT | GCC | ACG | 4133 |
| Leu | Ala | Arg | Glu | Cys | Gly | Val | Gln | Leu | Val | Leu | Tyr | Ala | Thr | Ala | Thr | |
| | | | | 1275 | | | | | 1280 | | | | | 1285 | | |
| CCT | CCT | GGG | TCC | CCC | ATG | ACT | CAG | CAT | CCG | TCA | ATC | ATT | GAG | ACC | AAA | 4181 |
| Pro | Pro | Gly | Ser | Pro | Met | Thr | Gln | His | Pro | Ser | Ile | Ile | Glu | Thr | Lys | |
| | | | 1290 | | | | | 1295 | | | | | 1300 | | | |
| TTG | GAT | GTG | GGT | GAG | ATT | CCC | TTC | TAT | GGG | CAT | GGC | ATA | CCC | CTC | GAG | 4229 |
| Leu | Asp | Val | Gly | Glu | Ile | Pro | Phe | Tyr | Gly | His | Gly | Ile | Pro | Leu | Glu | |
| | | | 1305 | | | | | 1310 | | | | | 1315 | | | |
| CGG | ATG | CGG | ACC | GGT | AGG | CAC | CTC | GTA | TTC | TGC | TAC | TCT | AAG | GCA | GAG | 4277 |
| Arg | Met | Arg | Thr | Gly | Arg | His | Leu | Val | Phe | Cys | Tyr | Ser | Lys | Ala | Glu | |
| | 1320 | | | | | 1325 | | | | | 1330 | | | | | |
| TGT | GAG | CGG | CTA | GCC | GGT | CAG | TTT | TCT | GCT | AGG | GGA | GTT | AAC | GCC | ATA | 4325 |
| Cys | Glu | Arg | Leu | Ala | Gly | Gln | Phe | Ser | Ala | Arg | Gly | Val | Asn | Ala | Ile | |
| 1335 | | | | | 1340 | | | | | 1345 | | | | | 1350 | |
| GCC | TAT | TAC | AGG | GGA | AAA | GAC | AGT | TCT | ATC | ATC | AAG | GAC | GGA | GAT | CTG | 4373 |
| Ala | Tyr | Tyr | Arg | Gly | Lys | Asp | Ser | Ser | Ile | Ile | Lys | Asp | Gly | Asp | Leu | |
| | | | | 1355 | | | | | 1360 | | | | | 1365 | | |
| GTG | GTG | TGC | GCG | ACC | GAC | GCG | CTA | TCC | ACT | GGA | TAC | ACT | GGG | AAC | TTC | 4421 |
| Val | Val | Cys | Ala | Thr | Asp | Ala | Leu | Ser | Thr | Gly | Tyr | Thr | Gly | Asn | Phe | |
| | | | | 1370 | | | | | 1375 | | | | | 1380 | | |
| GAT | TCT | GTC | ACC | GAC | TGT | GGG | TTA | GTG | GTG | GAG | GAG | GTC | GTC | GAG | GTG | 4469 |
| Asp | Ser | Val | Thr | Asp | Cys | Gly | Leu | Val | Val | Glu | Glu | Val | Val | Glu | Val | |
| | | | 1385 | | | | | 1390 | | | | | 1395 | | | |

| | | | | | | | | | | | | | | | | |
|---|---|---|---|---|---|---|---|---|---|---|---|---|---|---|---|---|
| ACC | CTT | GAT | CCC | ACC | ATT | ACC | ATC | TCC | CTG | CGG | ACA | GTG | CCC | GCG | TCG | 4517 |
| Thr | Leu | Asp | Pro | Thr | Ile | Thr | Ile | Ser | Leu | Arg | Thr | Val | Pro | Ala | Ser | |
| | | | 1400 | | | 1405 | | | | | 1410 | | | | | |
| GCA | GAA | CTG | TCG | ATG | CAG | AGA | CGA | GGA | CGC | ACG | GGT | AGA | GGC | AGG | TCT | 4565 |
| Ala | Glu | Leu | Ser | Met | Gln | Arg | Arg | Gly | Arg | Thr | Gly | Arg | Gly | Arg | Ser | |
| 1415 | | | | | 1420 | | | | | 1425 | | | | | 1430 | |
| GGG | CGC | TAC | TAC | TAC | GCC | GGG | GTC | GGA | AAG | GCC | CCC | GCG | GGT | GTG | GTG | 4613 |
| Gly | Arg | Tyr | Tyr | Tyr | Ala | Gly | Val | Gly | Lys | Ala | Pro | Ala | Gly | Val | Val | |
| | | | | 1435 | | | | | 1440 | | | | | 1445 | | |
| CGC | TCG | GGT | CCT | GTC | TGG | TCG | GCG | GTG | GAG | GCC | GGA | GTG | ACC | TGG | TAT | 4661 |
| Arg | Ser | Gly | Pro | Val | Trp | Ser | Ala | Val | Glu | Ala | Gly | Val | Thr | Trp | Tyr | |
| | | | 1450 | | | | | 1455 | | | | | 1460 | | | |
| GGA | ATG | GAA | CCT | GAC | TTG | ACA | GCT | AAC | CTA | TTG | AGA | CTT | TAC | GAC | GAC | 4709 |
| Gly | Met | Glu | Pro | Asp | Leu | Thr | Ala | Asn | Leu | Leu | Arg | Leu | Tyr | Asp | Asp | |
| | | 1465 | | | | | 1470 | | | | | 1475 | | | | |
| TGC | CCT | TAC | ACC | GCA | GCC | GTC | GCA | GCT | GAC | ATC | GGT | GAA | GCC | GCG | GTG | 4757 |
| Cys | Pro | Tyr | Thr | Ala | Ala | Val | Ala | Ala | Asp | Ile | Gly | Glu | Ala | Ala | Val | |
| | 1480 | | | | | 1485 | | | | | 1490 | | | | | |
| TTT | TTC | TCC | GGG | CTA | GCC | CCG | TTG | AGG | ATG | CAT | CCC | GAT | GTT | AGC | TGG | 4805 |
| Phe | Phe | Ser | Gly | Leu | Ala | Pro | Leu | Arg | Met | His | Pro | Asp | Val | Ser | Trp | |
| 1495 | | | | 1500 | | | | | 1505 | | | | | 1510 | | |
| GCA | AAA | GTG | CGC | GGC | GTC | AAC | TGG | CCC | CTC | TTG | GTG | GGT | GTT | CAG | CGG | 4853 |
| Ala | Lys | Val | Arg | Gly | Val | Asn | Trp | Pro | Leu | Leu | Val | Gly | Val | Gln | Arg | |
| | | | | 1515 | | | | | 1520 | | | | | 1525 | | |
| ACC | ATG | TGC | CGG | GAA | ACA | CTG | TCT | CCC | GGA | CCA | TCG | GAC | GAC | CCC | CAA | 4901 |
| Thr | Met | Cys | Arg | Glu | Thr | Leu | Ser | Pro | Gly | Pro | Ser | Asp | Asp | Pro | Gln | |
| | | | 1530 | | | | | 1535 | | | | | 1540 | | | |
| TGG | GCA | GGT | CTG | AAG | GGC | CCG | AAT | CCT | GTT | CCA | CTA | CTG | CTG | AGG | TGG | 4949 |
| Trp | Ala | Gly | Leu | Lys | Gly | Pro | Asn | Pro | Val | Pro | Leu | Leu | Leu | Arg | Trp | |
| | | 1545 | | | | | 1550 | | | | | 1555 | | | | |
| GGC | AAT | GAT | TTA | CCA | TCA | AAA | GTG | GCC | GGC | CAC | CAC | ATT | GTT | GAC | GAC | 4997 |
| Gly | Asn | Asp | Leu | Pro | Ser | Lys | Val | Ala | Gly | His | His | Ile | Val | Asp | Asp | |
| | 1560 | | | | | 1565 | | | | | 1570 | | | | | |
| CTG | GTT | CGT | AGG | CTT | GGT | GTG | GCG | GAG | GGT | TAT | GTC | CGC | TGC | GAT | GCG | 5045 |
| Leu | Val | Arg | Arg | Leu | Gly | Val | Ala | Glu | Gly | Tyr | Val | Arg | Cys | Asp | Ala | |
| 1575 | | | | 1580 | | | | | 1585 | | | | | 1590 | | |
| GGG | CCG | ATC | TTA | ATG | GTC | GGC | CTC | GCT | ATC | GCG | GGG | GGG | ATG | ATC | TAC | 5093 |
| Gly | Pro | Ile | Leu | Met | Val | Gly | Leu | Ala | Ile | Ala | Gly | Gly | Met | Ile | Tyr | |
| | | | | 1595 | | | | | 1600 | | | | | 1605 | | |
| GCA | TCT | TAC | ACC | GGG | TCT | TTA | GTG | GTG | GTG | ACA | GAC | TGG | GAT | GTA | AAG | 5141 |
| Ala | Ser | Tyr | Thr | Gly | Ser | Leu | Val | Val | Val | Thr | Asp | Trp | Asp | Val | Lys | |
| | | | 1610 | | | | | 1615 | | | | | 1620 | | | |
| GGG | GGT | GGC | AGC | CCT | CTT | TAT | CGG | CAT | GGA | GAC | CAG | GCC | ACG | CCA | CAG | 5189 |
| Gly | Gly | Gly | Ser | Pro | Leu | Tyr | Arg | His | Gly | Asp | Gln | Ala | Thr | Pro | Gln | |
| | | 1625 | | | | | 1630 | | | | | 1635 | | | | |
| CCG | GTT | GTG | CAG | GTC | CCC | CCG | GTA | GAC | CAT | CGG | CCG | GGG | GGG | GAG | TCT | 5237 |
| Pro | Val | Val | Gln | Val | Pro | Pro | Val | Asp | His | Arg | Pro | Gly | Gly | Glu | Ser | |
| 1640 | | | | | 1645 | | | | | 1650 | | | | | | |
| GCG | CCT | TCG | GAT | GCC | AAG | ACA | GTG | ACA | GAT | GCG | GTG | GCG | GCC | ATC | CAG | 5285 |
| Ala | Pro | Ser | Asp | Ala | Lys | Thr | Val | Thr | Asp | Ala | Val | Ala | Ala | Ile | Gln | |
| 1655 | | | | | 1660 | | | | | 1665 | | | | | 1670 | |
| GTG | GAT | TGC | GAT | TGG | TCA | GTC | ATG | ACC | CTG | TCG | ATC | GGG | GAA | GTG | CTG | 5333 |
| Val | Asp | Cys | Asp | Trp | Ser | Val | Met | Thr | Leu | Ser | Ile | Gly | Glu | Val | Leu | |
| | | | | 1675 | | | | | 1680 | | | | | 1685 | | |
| TCC | TTG | GCT | CAG | GCT | AAA | ACA | GCT | GAG | GCC | TAC | ACG | GCA | ACC | GCC | AAG | 5381 |
| Ser | Leu | Ala | Gln | Ala | Lys | Thr | Ala | Glu | Ala | Tyr | Thr | Ala | Thr | Ala | Lys | |
| | | | 1690 | | | | | 1695 | | | | | 1700 | | | |
| TGG | CTC | GCT | GGC | TGC | TAC | ACG | GGG | ACG | CGG | GCC | GTT | CCC | ACT | GTT | TCA | 5429 |
| Trp | Leu | Ala | Gly | Cys | Tyr | Thr | Gly | Thr | Arg | Ala | Val | Pro | Thr | Val | Ser | |
| | | 1705 | | | | | 1710 | | | | | 1715 | | | | |

```
ATT GTT GAC AAG CTC TTT GCC GGA GGG TGG GCG GCT GTG GTT GGC CAC        5477
Ile Val Asp Lys Leu Phe Ala Gly Gly Trp Ala Ala Val Val Gly His
    1720            1725                1730

TGT CAC AGC GTC ATA GCT GCG GCG GTG GCT GCC TAC GGG GCT TCC AGG        5525
Cys His Ser Val Ile Ala Ala Ala Val Ala Ala Tyr Gly Ala Ser Arg
1735                1740                1745                1750

AGT CCG CCG TTG GCA GCC GCG GCT TCC TAC CTG ATG GGA CTG GGC GTC        5573
Ser Pro Pro Leu Ala Ala Ala Ala Ser Tyr Leu Met Gly Leu Gly Val
                1755                1760                1765

GGA GGC AAC GCT CAG ACG CGT TTG GCG TCT GCC CTC CTG TTG GGG GCC        5621
Gly Gly Asn Ala Gln Thr Arg Leu Ala Ser Ala Leu Leu Leu Gly Ala
            1770                1775                1780

GCT GGC ACC GCC CTG GGC ACT CCC GTC GTG GGT TTA ACC ATG GCG GGG        5669
Ala Gly Thr Ala Leu Gly Thr Pro Val Val Gly Leu Thr Met Ala Gly
        1785                1790                1795

GCG TTC ATG GGG GGT GCT AGC GTC TCT CCC TCC TTG GTC ACC ATC TTG        5717
Ala Phe Met Gly Gly Ala Ser Val Ser Pro Ser Leu Val Thr Ile Leu
1800                1805                1810

TTG GGG GCC GTG GGA GGC TGG GAG GGC GTC GTC AAC GCT GCT AGC CTT        5765
Leu Gly Ala Val Gly Gly Trp Glu Gly Val Val Asn Ala Ala Ser Leu
1815                1820                1825                1830

GTC TTT GAC TTC ATG GCG GGG AAA CTA TCG TCA GAA GAT CTG TGG TAC        5813
Val Phe Asp Phe Met Ala Gly Lys Leu Ser Ser Glu Asp Leu Trp Tyr
                1835                1840                1845

GCC ATC CCA GTG CTC ACC AGC CCG GGG GCG GGC CTT GCG GGG ATC GCC        5861
Ala Ile Pro Val Leu Thr Ser Pro Gly Ala Gly Leu Ala Gly Ile Ala
            1850                1855                1860

CTT GGG TTG GTG CTG TAC TCA GCT AAC AAC TCT GGT ACT ACC ACT TGG        5909
Leu Gly Leu Val Leu Tyr Ser Ala Asn Asn Ser Gly Thr Thr Thr Trp
        1865                1870                1875

TTG AAC CGT CTG CTG ACT ACG TTA CCT AGG TCT TCT TGC ATC CCT GAC        5957
Leu Asn Arg Leu Leu Thr Thr Leu Pro Arg Ser Ser Cys Ile Pro Asp
1880                1885                1890

AGC TAT TTC CAA CAG GCC GAT TAC TGT GAC AAG GTC TCG GCC GTG CTT        6005
Ser Tyr Phe Gln Gln Ala Asp Tyr Cys Asp Lys Val Ser Ala Val Leu
1895                1900                1905                1910

CGC CGA CTG AGC CTC ACC CGC ACT GTG GTG GCC CTA GTC AAT AGG GAA        6053
Arg Arg Leu Ser Leu Thr Arg Thr Val Val Ala Leu Val Asn Arg Glu
                1915                1920                1925

CCC AAG GTG GAC GAG GTA CAG GTG GGG TAC GTC TGG GAT CTC TGG GAG        6101
Pro Lys Val Asp Glu Val Gln Val Gly Tyr Val Trp Asp Leu Trp Glu
            1930                1935                1940

TGG ATC ATG CGT CAA GTG CGC ATG GTC ATG GCC AGG CTC CGG GCT CTC        6149
Trp Ile Met Arg Gln Val Arg Met Val Met Ala Arg Leu Arg Ala Leu
        1945                1950                1955

TGC CCC GTG GTG TCA CTG CCT TTG TGG CAC TGC GGG GAG GGG TGG TCC        6197
Cys Pro Val Val Ser Leu Pro Leu Trp His Cys Gly Glu Gly Trp Ser
1960                1965                1970

GGA GAG TGG TTG TTG GAC GGC CAT GTG GAG AGT CGC TGT CTT TGC GGG        6245
Gly Glu Trp Leu Leu Asp Gly His Val Glu Ser Arg Cys Leu Cys Gly
1975                1980                1985                1990

TGC GTG ATC ACC GGC GAT GTT TTC AAT GGG CAA CTC AAA GAG CCA GTT        6293
Cys Val Ile Thr Gly Asp Val Phe Asn Gly Gln Leu Lys Glu Pro Val
                1995                2000                2005

TAC TCT ACA AAG TTG TGC CGG CAC TAT TGG ATG GGG ACC GTT CCT GTG        6341
Tyr Ser Thr Lys Leu Cys Arg His Tyr Trp Met Gly Thr Val Pro Val
            2010                2015                2020

AAC ATG CTG GGT TAC GGC GAA ACA TCA CCC CTC TTG GCC TCT GAC ACC        6389
Asn Met Leu Gly Tyr Gly Glu Thr Ser Pro Leu Leu Ala Ser Asp Thr
        2025                2030                2035
```

```
CCG  AAG  GTG  GTG  CCT  TTT  GGG  ACG  TCG  GGC  TGG  GCT  GAG  GTG  GTG  GTG              6437
Pro  Lys  Val  Val  Pro  Phe  Gly  Thr  Ser  Gly  Trp  Ala  Glu  Val  Val  Val
     2040                    2045                     2050

ACC  CCT  ACC  CAC  GTG  GTG  ATC  AGG  AGA  ACC  TCT  CCC  TAC  GAG  TTG  CTG              6485
Thr  Pro  Thr  His  Val  Val  Ile  Arg  Arg  Thr  Ser  Pro  Tyr  Glu  Leu  Leu
2055                     2060                    2065                     2070

CGC  CAA  CAA  ATC  CTA  TCA  GCT  GCA  GTT  GCT  GAG  CCC  TAT  TAT  GTC  GAC              6533
Arg  Gln  Gln  Ile  Leu  Ser  Ala  Ala  Val  Ala  Glu  Pro  Tyr  Tyr  Val  Asp
               2075                     2080                     2085

GGC  ATA  CCG  GTC  TCA  TGG  GAC  GCG  GAC  GCT  CGT  GCG  CCT  GCT  ATG  GTT              6581
Gly  Ile  Pro  Val  Ser  Trp  Asp  Ala  Asp  Ala  Arg  Ala  Pro  Ala  Met  Val
          2090                     2095                     2100

TAT  GGC  CCT  GGG  CAA  AGT  GTT  ACC  ATT  GAC  GGG  GAG  CGC  TAC  ACC  CTG              6629
Tyr  Gly  Pro  Gly  Gln  Ser  Val  Thr  Ile  Asp  Gly  Glu  Arg  Tyr  Thr  Leu
     2105                     2110                     2115

CCG  CAT  CAA  CTG  CGG  CTC  AGG  AAT  GTA  GCG  CCC  TCT  GAG  GTT  TCA  TCC              6677
Pro  His  Gln  Leu  Arg  Leu  Arg  Asn  Val  Ala  Pro  Ser  Glu  Val  Ser  Ser
2120                     2125                     2130

GAG  GTG  TCC  ATA  GAC  ATT  GGG  ACG  GAG  ACT  GAA  GAC  TCA  GAA  CTG  ACT              6725
Glu  Val  Ser  Ile  Asp  Ile  Gly  Thr  Glu  Thr  Glu  Asp  Ser  Glu  Leu  Thr
2135                     2140                     2145                     2150

GAG  GCC  GAC  CTG  CCG  CCG  GCA  GCT  GCA  GCC  CTC  CAG  GCT  ATC  GAG  AAT              6773
Glu  Ala  Asp  Leu  Pro  Pro  Ala  Ala  Ala  Ala  Leu  Gln  Ala  Ile  Glu  Asn
               2155                     2160                     2165

GCT  GCG  AGG  ATT  CTT  GAG  CCT  CAT  ATT  GAT  GTC  ATC  ATG  GAG  GAT  TGC              6821
Ala  Ala  Arg  Ile  Leu  Glu  Pro  His  Ile  Asp  Val  Ile  Met  Glu  Asp  Cys
          2170                     2175                     2180

AGT  ACA  CCC  TCT  CTT  TGT  GGT  AGT  AGC  CGA  GAG  ATG  CCT  GTG  TGG  GGA              6869
Ser  Thr  Pro  Ser  Leu  Cys  Gly  Ser  Ser  Arg  Glu  Met  Pro  Val  Trp  Gly
     2185                     2190                     2195

GAA  GAC  ATC  CCC  CGC  ACT  CCA  TCG  CCA  GCA  CTT  ATC  TCG  GTT  ACC  GAG              6917
Glu  Asp  Ile  Pro  Arg  Thr  Pro  Ser  Pro  Ala  Leu  Ile  Ser  Val  Thr  Glu
2200                     2205                     2210

AGC  AGC  TCA  GAT  GAG  AAG  ACC  CCG  TCG  GTG  TCC  TCC  TCG  CAG  GAG  GAT              6965
Ser  Ser  Ser  Asp  Glu  Lys  Thr  Pro  Ser  Val  Ser  Ser  Ser  Gln  Glu  Asp
2215                     2220                     2225                     2230

ACC  CCG  TCC  TCT  GAC  TCA  TTC  GAA  GTC  ATC  CAA  GAG  TCT  GAG  ACA  GCT              7013
Thr  Pro  Ser  Ser  Asp  Ser  Phe  Glu  Val  Ile  Gln  Glu  Ser  Glu  Thr  Ala
               2235                     2240                     2245

GAA  GGA  GAG  GAA  AGT  GTC  TTC  AAC  GTG  GCT  CTT  TCC  GTA  CTA  GAA  GCC              7061
Glu  Gly  Glu  Glu  Ser  Val  Phe  Asn  Val  Ala  Leu  Ser  Val  Leu  Glu  Ala
          2250                     2255                     2260

TTG  TTT  CCA  CAG  AGT  GAT  GCC  ACT  AGA  AAG  CTT  ACC  GTC  AGG  ATG  AAT              7109
Leu  Phe  Pro  Gln  Ser  Asp  Ala  Thr  Arg  Lys  Leu  Thr  Val  Arg  Met  Asn
     2265                     2270                     2275

TGC  TGC  GTT  GAG  AAG  AGC  GTC  ACG  CGC  TTC  TTT  TCT  TTG  GGG  CTG  ACG              7157
Cys  Cys  Val  Glu  Lys  Ser  Val  Thr  Arg  Phe  Phe  Ser  Leu  Gly  Leu  Thr
2280                     2285                     2290

GTG  GCT  GAT  GTG  GCC  AGT  CTG  TGT  GAG  ATG  GAG  ATC  CAG  AAC  CAT  ACA              7205
Val  Ala  Asp  Val  Ala  Ser  Leu  Cys  Glu  Met  Glu  Ile  Gln  Asn  His  Thr
2295                     2300                     2305                     2310

GCC  TAT  TGT  GAC  AAG  GTG  CGC  ACT  CCG  CTC  GAA  TTG  CAA  GTT  GGG  TGC              7253
Ala  Tyr  Cys  Asp  Lys  Val  Arg  Thr  Pro  Leu  Glu  Leu  Gln  Val  Gly  Cys
               2315                     2320                     2325

TTG  GTG  GGC  AAT  GAA  CTT  ACC  TTT  GAA  TGT  GAT  AAG  TGT  GAG  GCT  AGG              7301
Leu  Val  Gly  Asn  Glu  Leu  Thr  Phe  Glu  Cys  Asp  Lys  Cys  Glu  Ala  Arg
          2330                     2335                     2340

CAA  GAG  ACT  TTG  GCC  TCC  TTC  TCC  TAT  ATT  TGG  TCT  GGG  GTG  CCA  TTG              7349
Gln  Glu  Thr  Leu  Ala  Ser  Phe  Ser  Tyr  Ile  Trp  Ser  Gly  Val  Pro  Leu
     2345                     2350                     2355
```

```
ACT AGG GCC ACA CCG GCT AAA CCA CCT GTG GTG AGG CCG GTG GGG TCC       7397
Thr Arg Ala Thr Pro Ala Lys Pro Pro Val Val Arg Pro Val Gly Ser
    2360            2365                2370

TTG TTG GTG GCT GAC ACC ACG AAA GTG TAT GTC ACA AAC CCG GAC AAT       7445
Leu Leu Val Ala Asp Thr Thr Lys Val Tyr Val Thr Asn Pro Asp Asn
2375            2380                2385                2390

GTT GGG AGA AGA GTG GAC AAG GTG ACC TTC TGG CGC GCC CCC AGG GTC       7493
Val Gly Arg Arg Val Asp Lys Val Thr Phe Trp Arg Ala Pro Arg Val
                2395            2400                2405

CAT GAC AAA TAT CTC GTG GAC TCC ATC GAG CGT GCC AGG AGG GCG GCT       7541
His Asp Lys Tyr Leu Val Asp Ser Ile Glu Arg Ala Arg Arg Ala Ala
            2410            2415                2420

CAA GCC TGC CAA AGC ATG GGT TAC ACT TAT GAG GAA GCA ATA AGG ACT       7589
Gln Ala Cys Gln Ser Met Gly Tyr Thr Tyr Glu Glu Ala Ile Arg Thr
        2425            2430                2435

GTT AGG CCA CAT GCT GCC ATG GGC TGG GGA TCT AAG GTG TCG GTC AAG       7637
Val Arg Pro His Ala Ala Met Gly Trp Gly Ser Lys Val Ser Val Lys
    2440            2445                2450

GAC TTG GCC ACC CCT GCG GGG AAG ATG GCC GTC CAC GAC CGA CTT CAG       7685
Asp Leu Ala Thr Pro Ala Gly Lys Met Ala Val His Asp Arg Leu Gln
2455            2460                2465                2470

GAG ATA CTT GAG GGG ACT CCG GTC CCT TTT ACT CTT ACT GTG AAA AAG       7733
Glu Ile Leu Glu Gly Thr Pro Val Pro Phe Thr Leu Thr Val Lys Lys
                2475            2480                2485

GAG GTG TTC TTC AAA GAC CGT AAG GAG GAG AAG GCC CCC CGC CTC ATT       7781
Glu Val Phe Phe Lys Asp Arg Lys Glu Glu Lys Ala Pro Arg Leu Ile
            2490            2495                2500

GTG TTC CCC CCC CTG GAC TTC CGG ATA GCT GAG AAG CTT ATC CTG GGA       7829
Val Phe Pro Pro Leu Asp Phe Arg Ile Ala Glu Lys Leu Ile Leu Gly
        2505            2510                2515

GAC CCG GGG CGG GTG GCC AAG GCG GTG TTG GGG GGG GCT TAC GCC TTC       7877
Asp Pro Gly Arg Val Ala Lys Ala Val Leu Gly Gly Ala Tyr Ala Phe
2520            2525                2530

CAG TAC ACC CCA AAT CAG CGA GTT AAG GAG ATG CTC AAA CTG TGG GAG       7925
Gln Tyr Thr Pro Asn Gln Arg Val Lys Glu Met Leu Lys Leu Trp Glu
2535            2540                2545                2550

TCA AAG AAA ACA CCT TGC GCC ATC TGT GTG GAC GCC ACT TGC TTC GAC       7973
Ser Lys Lys Thr Pro Cys Ala Ile Cys Val Asp Ala Thr Cys Phe Asp
            2555            2560                2565

AGT AGC ATT ACT GAA GAG GAC GTG GCG CTG GAG ACA GAG CTG TAC GCT       8021
Ser Ser Ile Thr Glu Glu Asp Val Ala Leu Glu Thr Glu Leu Tyr Ala
        2570            2575                2580

CTG GCC TCT GAC CAT CCA GAG TGG GTG CGA GCT TTG GGG AAG TAC TAT       8069
Leu Ala Ser Asp His Pro Glu Trp Val Arg Ala Leu Gly Lys Tyr Tyr
    2585            2590                2595

GCC TCA GGA ACC ATG GTC ACC CCT GAG GGG GTT CCC GTA GGT GAG AGG       8117
Ala Ser Gly Thr Met Val Thr Pro Glu Gly Val Pro Val Gly Glu Arg
2600            2605                2610

TAT TGT AGA TCC TCA GGC GTT TTG ACT ACC AGC GCG AGT AAC TGC CTG       8165
Tyr Cys Arg Ser Ser Gly Val Leu Thr Thr Ser Ala Ser Asn Cys Leu
2615            2620                2625            2630

ACC TGC TAC ATC AAG GTG AAA GCC GCT TGT GAG AGA GTG GGG CTG AAA       8213
Thr Cys Tyr Ile Lys Val Lys Ala Ala Cys Glu Arg Val Gly Leu Lys
            2635            2640                2645

AAT GTC TCG CTT CTC ATA GCC GGC GAT GAC TGT TTG ATC ATA TGC GAA       8261
Asn Val Ser Leu Leu Ile Ala Gly Asp Asp Cys Leu Ile Ile Cys Glu
        2650            2655                2660

CGG CCA GTG TGC GAC CCT TGT GAC GCC TTG GGC AGA GCC CTG GCG AGC       8309
Arg Pro Val Cys Asp Pro Cys Asp Ala Leu Gly Arg Ala Leu Ala Ser
    2665            2670                2675
```

| | | | | | | | | | | | | | | | | |
|---|---|---|---|---|---|---|---|---|---|---|---|---|---|---|---|---|
| TAT | GGG | TAT | GCT | TGC | GAG | CCT | TCG | TAT | CAT | GCA | TCA | CTG | GAC | ACG | GCC | 8357 |
| Tyr | Gly | Tyr | Ala | Cys | Glu | Pro | Ser | Tyr | His | Ala | Ser | Leu | Asp | Thr | Ala | |
| | | 2680 | | | 2685 | | | | | 2690 | | | | | | |
| CCC | TTC | TGC | TCC | ACT | TGG | CTC | GCT | GAG | TGC | AAC | GCA | GAT | GGG | AAA | CGC | 8405 |
| Pro | Phe | Cys | Ser | Thr | Trp | Leu | Ala | Glu | Cys | Asn | Ala | Asp | Gly | Lys | Arg | |
| 2695 | | | | 2700 | | | | | 2705 | | | | | 2710 | | |
| CAT | TTC | TTC | CTG | ACC | ACG | GAC | TTT | CGG | AGG | CCG | CTT | GCT | CGC | ATG | TCG | 8453 |
| His | Phe | Phe | Leu | Thr | Thr | Asp | Phe | Arg | Arg | Pro | Leu | Ala | Arg | Met | Ser | |
| | | | 2715 | | | | | 2720 | | | | | 2725 | | | |
| AGC | GAG | TAT | AGT | GAC | CCA | ATG | GCT | TCG | GCC | ATA | GGT | TAC | ATC | CTC | CTG | 8501 |
| Ser | Glu | Tyr | Ser | Asp | Pro | Met | Ala | Ser | Ala | Ile | Gly | Tyr | Ile | Leu | Leu | |
| | | | 2730 | | | | 2735 | | | | | 2740 | | | | |
| TAT | CCC | TGG | CAT | CCC | ATC | ACA | CGG | TGG | GTC | ATC | ATC | CCT | CAT | GTG | CTA | 8549 |
| Tyr | Pro | Trp | His | Pro | Ile | Thr | Arg | Trp | Val | Ile | Ile | Pro | His | Val | Leu | |
| | | 2745 | | | | 2750 | | | | | 2755 | | | | | |
| ACG | TGC | GCA | TTC | AGG | GGT | GGT | GGT | ACA | CCG | TCT | GAT | CCG | GTT | TGG | TGT | 8597 |
| Thr | Cys | Ala | Phe | Arg | Gly | Gly | Gly | Thr | Pro | Ser | Asp | Pro | Val | Trp | Cys | |
| | 2760 | | | | | 2765 | | | | | 2770 | | | | | |
| CAG | GTG | CAT | GGT | AAC | TAC | TAC | AAG | TTT | CCA | CTG | GAC | AAA | CTG | CCT | AAC | 8645 |
| Gln | Val | His | Gly | Asn | Tyr | Tyr | Lys | Phe | Pro | Leu | Asp | Lys | Leu | Pro | Asn | |
| 2775 | | | | | 2780 | | | | | 2785 | | | | | 2790 | |
| ATC | ATC | GTG | GCC | CTC | CAC | GGA | CCA | GCA | GCG | TTG | AGG | GTT | ACC | GCA | GAC | 8693 |
| Ile | Ile | Val | Ala | Leu | His | Gly | Pro | Ala | Ala | Leu | Arg | Val | Thr | Ala | Asp | |
| | | | | 2795 | | | | | 2800 | | | | | 2805 | | |
| ACA | ACT | AAG | ACA | AAA | ATG | GAA | GCT | GGG | AAG | GTG | CTG | AGT | GAC | CTC | AAG | 8741 |
| Thr | Thr | Lys | Thr | Lys | Met | Glu | Ala | Gly | Lys | Val | Leu | Ser | Asp | Leu | Lys | |
| | | | 2810 | | | | 2815 | | | | | 2820 | | | | |
| CTC | CCT | GGC | CTA | GCG | GTC | CAC | CGA | AAG | AAG | GCC | GGA | GCA | CTG | CGA | ACA | 8789 |
| Leu | Pro | Gly | Leu | Ala | Val | His | Arg | Lys | Lys | Ala | Gly | Ala | Leu | Arg | Thr | |
| | | 2825 | | | | 2830 | | | | | 2835 | | | | | |
| CGC | ATG | CTT | CGG | TCG | CGC | GGT | TGG | GCC | GAG | TTG | GCG | AGG | GGC | CTG | TTG | 8837 |
| Arg | Met | Leu | Arg | Ser | Arg | Gly | Trp | Ala | Glu | Leu | Ala | Arg | Gly | Leu | Leu | |
| | 2840 | | | | | 2845 | | | | | 2850 | | | | | |
| TGG | CAT | CCA | GGC | CTC | CGG | CTC | CCT | CCC | CCT | GAG | ATT | GCT | GGT | ATC | CCG | 8885 |
| Trp | His | Pro | Gly | Leu | Arg | Leu | Pro | Pro | Pro | Glu | Ile | Ala | Gly | Ile | Pro | |
| 2855 | | | | | 2860 | | | | | 2865 | | | | | 2870 | |
| GGG | GGT | TTC | CCC | CTC | TCC | CCC | CCC | TAC | ATG | GGG | GTG | GTG | CAT | CAA | TTG | 8933 |
| Gly | Gly | Phe | Pro | Leu | Ser | Pro | Pro | Tyr | Met | Gly | Val | Val | His | Gln | Leu | |
| | | | | 2875 | | | | | 2880 | | | | | 2885 | | |
| GAT | TTT | ACA | AGC | CAG | AGG | AGT | CGC | TGG | CGG | TGG | CTG | GGG | TTC | TTA | GCC | 8981 |
| Asp | Phe | Thr | Ser | Gln | Arg | Ser | Arg | Trp | Arg | Trp | Leu | Gly | Phe | Leu | Ala | |
| | | | 2890 | | | | 2895 | | | | | 2900 | | | | |
| CTG | CTC | ATC | GTA | GCC | CTC | TTC | GGG | TGAACTAAAT | | TCATCTGTTG | | CGGCAAGGTC | | | | 9035 |
| Leu | Leu | Ile | Val | Ala | Leu | Phe | Gly | | | | | | | | | |
| | | 2905 | | | | | 2910 | | | | | | | | | |

CAGTGACTGA TCATCACTGG AGGAGGTTCC CGCCCTCCCC GCCCCAGGGG TCTCCCCGCT 9095

GGGTAAAA 9103

( 2 ) INFORMATION FOR SEQ ID NO:183:

( i ) SEQUENCE CHARACTERISTICS:
        ( A ) LENGTH: 2910 amino acids
        ( B ) TYPE: amino acid
        ( D ) TOPOLOGY: linear ( i i ) MOLECULE TYPE: protein ( x i ) SEQUENCE DESCRIPTION: SEQ ID NO:183:

| Met | Ser | Leu | Leu | Thr | Asn | Arg | Leu | Ser | Arg | Arg | Val | Asp | Lys | Asp | Gln |
|---|---|---|---|---|---|---|---|---|---|---|---|---|---|---|---|
| 1 | | | | 5 | | | | | 10 | | | | | 15 | |
| Trp | Gly | Pro | Gly | Phe | Met | Gly | Lys | Asp | Pro | Lys | Pro | Cys | Pro | Ser | Arg |

-continued

|  | 20 | 25 | 30 |
|---|---|---|---|

Arg Thr Gly Lys Cys Met Gly Pro Ser Ser Ala Ala Cys Ser
         35              40             45

Arg Gly Ser Pro Arg Ile Leu Arg Val Arg Ala Gly Gly Ile Ser Leu
         50              55             60

Pro Tyr Thr Ile Met Glu Ala Leu Leu Phe Leu Leu Gly Val Glu Ala
65               70              75                            80

Gly Ala Ile Leu Ala Pro Ala Thr His Ala Cys Arg Ala Asn Gly Gln
             85              90                       95

Tyr Phe Leu Thr Asn Cys Cys Ala Pro Glu Asp Ile Gly Phe Cys Leu
             100             105              110

Glu Gly Gly Cys Leu Val Ala Leu Gly Cys Thr Val Cys Thr Asp Arg
         115             120              125

Cys Trp Pro Leu Tyr Gln Ala Gly Leu Ala Val Arg Pro Gly Lys Ser
         130             135              140

Ala Ala Gln Leu Val Gly Gln Leu Gly Gly Leu Tyr Gly Pro Leu Ser
145              150              155                           160

Val Ser Ala Tyr Val Ala Gly Ile Leu Gly Leu Gly Glu Val Tyr Ser
             165             170              175

Gly Val Leu Thr Val Gly Val Ala Leu Thr Arg Arg Val Tyr Pro Met
         180             185              190

Pro Asn Leu Thr Cys Ala Val Glu Cys Glu Leu Lys Trp Glu Ser Glu
         195             200              205

Phe Trp Arg Trp Thr Glu Gln Leu Ala Ser Asn Tyr Trp Ile Leu Glu
         210             215              220

Tyr Leu Trp Lys Val Pro Phe Asp Phe Trp Arg Gly Val Leu Ser Leu
225              230             235                           240

Thr Pro Leu Leu Val Cys Val Ala Ala Leu Leu Leu Glu Gln Arg
             245             250              255

Ile Val Met Val Phe Leu Leu Val Thr Met Ala Gly Met Ser Gln Gly
             260             265              270

Ala Pro Ala Ser Val Leu Gly Ser Arg Pro Phe Asp Tyr Gly Leu Thr
         275             280              285

Trp Gln Ser Cys Ser Cys Arg Ala Asn Gly Ser Arg Tyr Thr Thr Gly
         290             295              300

Glu Lys Val Trp Asp Arg Gly Asn Val Thr Leu Leu Cys Asp Cys Pro
305              310             315                           320

Asn Gly Pro Trp Val Trp Leu Pro Ala Phe Cys Gln Ala Ile Gly Trp
             325             330              335

Gly Asp Pro Ile Thr His Trp Ser His Gly Gln Asn Arg Trp Pro Leu
         340             345              350

Ser Cys Pro Gln Tyr Val Tyr Gly Ser Val Ser Val Thr Cys Val Trp
         355             360              365

Gly Ser Val Ser Trp Phe Ala Ser Thr Gly Gly Arg Asp Ser Lys Ile
         370             375              380

Asp Val Trp Ser Leu Val Pro Val Gly Ser Ala Ser Cys Thr Ile Ala
385              390             395                           400

Ala Leu Gly Ser Ser Asp Arg Asp Thr Val Val Glu Leu Ser Glu Trp
             405             410              415

Gly Val Pro Cys Ala Thr Cys Ile Leu Asp Arg Arg Pro Ala Ser Cys
         420             425              430

Gly Thr Cys Val Arg Asp Cys Trp Pro Glu Thr Gly Ser Val Arg Phe
         435             440              445

```
Pro Phe His Arg Cys Gly Ala Gly Pro Lys Leu Thr Lys Asp Leu Glu
    450                 455                 460

Ala Val Pro Phe Val Asn Arg Thr Thr Pro Phe Thr Ile Arg Gly Pro
465                 470                 475                 480

Leu Gly Asn Gln Gly Arg Gly Asn Pro Val Arg Ser Pro Leu Gly Phe
                485                 490                 495

Gly Ser Tyr Ala Met Thr Lys Ile Arg Asp Ser Leu His Leu Val Lys
            500                 505                 510

Cys Pro Thr Pro Ala Ile Glu Pro Pro Thr Gly Thr Phe Gly Phe Phe
            515                 520                 525

Pro Gly Val Pro Pro Leu Asn Asn Cys Leu Leu Leu Gly Thr Glu Val
    530                 535                 540

Ser Glu Ala Leu Gly Gly Ala Gly Leu Thr Gly Gly Phe Tyr Glu Pro
545                 550                 555                 560

Leu Val Arg Arg Arg Ser Glu Leu Met Gly Arg Arg Asn Pro Val Cys
                565                 570                 575

Pro Gly Phe Ala Trp Leu Ser Ser Gly Arg Pro Asp Gly Phe Ile His
            580                 585                 590

Val Gln Gly His Leu Gln Glu Val Asp Ala Gly Asn Phe Ile Pro Pro
            595                 600                 605

Pro Arg Trp Leu Leu Leu Asp Phe Val Phe Val Leu Leu Tyr Leu Met
    610                 615                 620

Lys Leu Ala Glu Ala Arg Leu Val Pro Leu Ile Leu Leu Leu Leu Trp
625                 630                 635                 640

Trp Trp Val Asn Gln Leu Ala Val Leu Gly Leu Pro Ala Val Asp Ala
                645                 650                 655

Ala Val Ala Gly Glu Val Phe Ala Gly Pro Ala Leu Ser Trp Cys Leu
            660                 665                 670

Gly Leu Pro Thr Val Ser Met Ile Leu Gly Leu Ala Asn Leu Val Leu
            675                 680                 685

Tyr Phe Arg Trp Met Gly Pro Gln Arg Leu Met Phe Leu Val Leu Trp
    690                 695                 700

Lys Leu Ala Arg Gly Ala Phe Pro Leu Ala Leu Leu Met Gly Ile Ser
705                 710                 715                 720

Ala Thr Arg Gly Arg Thr Ser Val Leu Gly Ala Glu Phe Cys Phe Asp
                725                 730                 735

Val Thr Phe Glu Val Asp Thr Ser Val Leu Gly Trp Val Val Ala Ser
            740                 745                 750

Val Val Ala Trp Ala Ile Ala Leu Leu Ser Ser Met Ser Ala Gly Gly
            755                 760                 765

Trp Arg His Lys Ala Val Ile Tyr Arg Thr Trp Cys Lys Gly Tyr Gln
    770                 775                 780

Ala Ile Arg Gln Arg Val Val Arg Ser Pro Leu Gly Glu Gly Arg Pro
785                 790                 795                 800

Thr Lys Pro Leu Thr Phe Ala Trp Cys Leu Ala Ser Tyr Ile Trp Pro
                805                 810                 815

Asp Ala Val Met Met Val Val Val Ala Leu Val Leu Leu Phe Gly Leu
            820                 825                 830

Phe Asp Ala Leu Asp Trp Ala Leu Glu Glu Leu Leu Val Ser Arg Pro
    835                 840                 845

Ser Leu Arg Arg Leu Ala Arg Val Val Glu Cys Cys Val Met Ala Gly
    850                 855                 860

Glu Lys Ala Thr Thr Val Arg Leu Val Ser Lys Met Cys Ala Arg Gly
865                 870                 875                 880
```

Ala Tyr Leu Phe Asp His Met Gly Ser Phe Ser Arg Ala Val Lys Glu
                885                 890                 895

Arg Leu Leu Glu Trp Asp Ala Ala Leu Glu Pro Leu Ser Phe Thr Arg
                900                 905                 910

Thr Asp Cys Arg Ile Ile Arg Asp Ala Ala Arg Thr Leu Ala Cys Gly
                915                 920                 925

Gln Cys Val Met Gly Leu Pro Val Val Ala Arg Arg Gly Asp Glu Val
            930                 935                 940

Leu Ile Gly Val Phe Gln Asp Val Asn His Leu Pro Pro Gly Phe Val
945                 950                 955                 960

Pro Thr Ala Pro Val Val Ile Arg Arg Cys Gly Lys Gly Phe Leu Gly
                965                 970                 975

Val Thr Lys Ala Ala Leu Thr Gly Arg Asp Pro Asp Leu His Pro Gly
            980                 985                 990

Asn Val Met Val Leu Gly Thr Ala Thr Ser Arg Ser Met Gly Thr Cys
            995                 1000                1005

Leu Asn Gly Leu Leu Phe Thr Thr Phe His Gly Ala Ser Ser Arg Thr
            1010                1015                1020

Ile Ala Thr Pro Val Gly Ala Leu Asn Pro Arg Trp Trp Ser Ala Ser
1025                1030                1035                1040

Asp Asp Val Thr Val Tyr Pro Leu Pro Asp Gly Ala Thr Ser Leu Thr
                1045                1050                1055

Pro Cys Thr Cys Gln Ala Glu Ser Cys Trp Val Ile Arg Ser Asp Gly
            1060                1065                1070

Ala Leu Cys His Gly Leu Ser Lys Gly Asp Lys Val Glu Leu Asp Val
            1075                1080                1085

Ala Met Glu Val Ser Asp Phe Arg Gly Ser Ser Gly Ser Pro Val Leu
            1090                1095                1100

Cys Asp Glu Gly His Ala Val Gly Met Leu Val Ser Val Leu His Ser
1105                1110                1115                1120

Gly Gly Arg Val Thr Ala Ala Arg Phe Thr Arg Pro Trp Thr Gln Val
                1125                1130                1135

Pro Thr Asp Ala Lys Thr Thr Thr Glu Pro Pro Pro Val Pro Ala Lys
                1140                1145                1150

Gly Val Phe Lys Glu Ala Pro Leu Phe Met Pro Thr Gly Ala Gly Lys
            1155                1160                1165

Ser Thr Arg Val Pro Leu Glu Tyr Gly Asn Met Gly His Lys Val Leu
            1170                1175                1180

Ile Leu Asn Pro Ser Val Ala Thr Val Arg Ala Met Gly Pro Tyr Met
1185                1190                1195                1200

Glu Arg Leu Ala Gly Lys His Pro Ser Ile Tyr Cys Gly His Asp Thr
                1205                1210                1215

Thr Ala Phe Thr Arg Ile Thr Asp Ser Pro Leu Thr Tyr Ser Thr Tyr
                1220                1225                1230

Gly Arg Phe Leu Ala Asn Pro Arg Gln Met Leu Arg Gly Val Ser Val
            1235                1240                1245

Val Ile Cys Asp Glu Cys His Ser His Asp Ser Thr Val Leu Leu Gly
            1250                1255                1260

Ile Gly Arg Val Arg Glu Leu Ala Arg Glu Cys Gly Val Gln Leu Val
1265                1270                1275                1280

Leu Tyr Ala Thr Ala Thr Pro Pro Gly Ser Pro Met Thr Gln His Pro
                1285                1290                1295

Ser Ile Ile Glu Thr Lys Leu Asp Val Gly Glu Ile Pro Phe Tyr Gly

-continued

His Gly Ile Pro Leu Glu Arg Met Arg Thr Gly Arg His Leu Val Phe
1300                     1305                     1310

Cys Tyr Ser Lys Ala Glu Cys Glu Arg Leu Ala Gly Gln Phe Ser Ala
        1315                     1320                    1325

Arg Gly Val Asn Ala Ile Ala Tyr Tyr Arg Gly Lys Asp Ser Ser Ile
1330                    1335                    1340

Ile Lys Asp Gly Asp Leu Val Val Cys Ala Thr Asp Ala Leu Ser Thr
1345                    1350                    1355                    1360

Gly Tyr Thr Gly Asn Phe Asp Ser Val Thr Asp Cys Gly Leu Val Val
            1365                    1370                    1375

Glu Glu Val Val Glu Val Thr Leu Asp Pro Thr Ile Thr Ile Ser Leu
            1380                    1385                    1390

Arg Thr Val Pro Ala Ser Ala Glu Leu Ser Met Gln Arg Arg Gly Arg
    1395                    1400                    1405

Thr Gly Arg Gly Arg Ser Gly Arg Tyr Tyr Ala Gly Val Gly Lys
        1410                    1415                    1420

Ala Pro Ala Gly Val Val Arg Ser Gly Pro Val Trp Ser Ala Val Glu
1425                    1430                    1435                    1440

Ala Gly Val Thr Trp Tyr Gly Met Glu Pro Asp Leu Thr Ala Asn Leu
            1445                    1450                    1455

Leu Arg Leu Tyr Asp Asp Cys Pro Tyr Thr Ala Ala Val Ala Ala Asp
            1460                    1465                    1470

Ile Gly Glu Ala Ala Val Phe Phe Ser Gly Leu Ala Pro Leu Arg Met
    1475                    1480                    1485

His Pro Asp Val Ser Trp Ala Lys Val Arg Gly Val Asn Trp Pro Leu
        1490                    1495                    1500

Leu Val Gly Val Gln Arg Thr Met Cys Arg Glu Thr Leu Ser Pro Gly
1505                    1510                    1515                    1520

Pro Ser Asp Asp Pro Gln Trp Ala Gly Leu Lys Gly Pro Asn Pro Val
            1525                    1530                    1535

Pro Leu Leu Leu Arg Trp Gly Asn Asp Leu Pro Ser Lys Val Ala Gly
            1540                    1545                    1550

His His Ile Val Asp Asp Leu Val Arg Arg Leu Gly Val Ala Glu Gly
        1555                    1560                    1565

Tyr Val Arg Cys Asp Ala Gly Pro Ile Leu Met Val Gly Leu Ala Ile
1570                    1575                    1580

Ala Gly Gly Met Ile Tyr Ala Ser Tyr Thr Gly Ser Leu Val Val Val
1585                    1590                    1595                    1600

Thr Asp Trp Asp Val Lys Gly Gly Gly Ser Pro Leu Tyr Arg His Gly
            1605                    1610                    1615

Asp Gln Ala Thr Pro Gln Pro Val Val Gln Val Pro Pro Val Asp His
            1620                    1625                    1630

Arg Pro Gly Gly Glu Ser Ala Pro Ser Asp Ala Lys Thr Val Thr Asp
    1635                    1640                    1645

Ala Val Ala Ala Ile Gln Val Asp Cys Asp Trp Ser Val Met Thr Leu
1650                    1655                    1660

Ser Ile Gly Glu Val Leu Ser Leu Ala Gln Ala Lys Thr Ala Glu Ala
1665                    1670                    1675                    1680

Tyr Thr Ala Thr Ala Lys Trp Leu Ala Gly Cys Tyr Thr Gly Thr Arg
            1685                    1690                    1695

Ala Val Pro Thr Val Ser Ile Val Asp Lys Leu Phe Ala Gly Gly Trp
            1700                    1705                    1710

1715                    1720                    1725

```
Ala  Ala  Val  Val  Gly  His  Cys  His  Ser  Val  Ile  Ala  Ala  Ala  Val  Ala
     1730                1735                     1740

Ala  Tyr  Gly  Ala  Ser  Arg  Ser  Pro  Pro  Leu  Ala  Ala  Ala  Ala  Ser  Tyr
1745                1750                     1755                     1760

Leu  Met  Gly  Leu  Gly  Val  Gly  Gly  Asn  Ala  Gln  Thr  Arg  Leu  Ala  Ser
               1765                     1770                     1775

Ala  Leu  Leu  Leu  Gly  Ala  Ala  Gly  Thr  Ala  Leu  Gly  Thr  Pro  Val  Val
               1780                     1785                     1790

Gly  Leu  Thr  Met  Ala  Gly  Ala  Phe  Met  Gly  Gly  Ala  Ser  Val  Ser  Pro
               1795                     1800                     1805

Ser  Leu  Val  Thr  Ile  Leu  Leu  Gly  Ala  Val  Gly  Gly  Trp  Glu  Gly  Val
     1810                     1815                     1820

Val  Asn  Ala  Ala  Ser  Leu  Val  Phe  Asp  Phe  Met  Ala  Gly  Lys  Leu  Ser
1825                1830                     1835                     1840

Ser  Glu  Asp  Leu  Trp  Tyr  Ala  Ile  Pro  Val  Leu  Thr  Ser  Pro  Gly  Ala
               1845                     1850                     1855

Gly  Leu  Ala  Gly  Ile  Ala  Leu  Gly  Leu  Val  Leu  Tyr  Ser  Ala  Asn  Asn
               1860                     1865                     1870

Ser  Gly  Thr  Thr  Thr  Trp  Leu  Asn  Arg  Leu  Leu  Thr  Thr  Leu  Pro  Arg
               1875                     1880                     1885

Ser  Ser  Cys  Ile  Pro  Asp  Ser  Tyr  Phe  Gln  Gln  Ala  Asp  Tyr  Cys  Asp
     1890                     1895                     1900

Lys  Val  Ser  Ala  Val  Leu  Arg  Arg  Leu  Ser  Leu  Thr  Arg  Thr  Val  Val
1905                     1910                     1915                     1920

Ala  Leu  Val  Asn  Arg  Glu  Pro  Lys  Val  Asp  Glu  Val  Gln  Val  Gly  Tyr
               1925                     1930                     1935

Val  Trp  Asp  Leu  Trp  Glu  Trp  Ile  Met  Arg  Gln  Val  Arg  Met  Val  Met
               1940                     1945                     1950

Ala  Arg  Leu  Arg  Ala  Leu  Cys  Pro  Val  Val  Ser  Leu  Pro  Leu  Trp  His
          1955                     1960                     1965

Cys  Gly  Glu  Gly  Trp  Ser  Gly  Glu  Trp  Leu  Leu  Asp  Gly  His  Val  Glu
          1970                     1975                     1980

Ser  Arg  Cys  Leu  Cys  Gly  Cys  Val  Ile  Thr  Gly  Asp  Val  Phe  Asn  Gly
1985                     1990                     1995                     2000

Gln  Leu  Lys  Glu  Pro  Val  Tyr  Ser  Thr  Lys  Leu  Cys  Arg  His  Tyr  Trp
               2005                     2010                     2015

Met  Gly  Thr  Val  Pro  Val  Asn  Met  Leu  Gly  Tyr  Gly  Glu  Thr  Ser  Pro
               2020                     2025                     2030

Leu  Leu  Ala  Ser  Asp  Thr  Pro  Lys  Val  Val  Pro  Phe  Gly  Thr  Ser  Gly
               2035                     2040                     2045

Trp  Ala  Glu  Val  Val  Val  Thr  Pro  Thr  His  Val  Val  Ile  Arg  Arg  Thr
     2050                     2055                     2060

Ser  Pro  Tyr  Glu  Leu  Leu  Arg  Gln  Gln  Ile  Leu  Ser  Ala  Ala  Val  Ala
2065                     2070                     2075                     2080

Glu  Pro  Tyr  Tyr  Val  Asp  Gly  Ile  Pro  Val  Ser  Trp  Asp  Ala  Asp  Ala
               2085                     2090                     2095

Arg  Ala  Pro  Ala  Met  Val  Tyr  Gly  Pro  Gly  Gln  Ser  Val  Thr  Ile  Asp
               2100                     2105                     2110

Gly  Glu  Arg  Tyr  Thr  Leu  Pro  His  Gln  Leu  Arg  Leu  Arg  Asn  Val  Ala
          2115                     2120                     2125

Pro  Ser  Glu  Val  Ser  Ser  Glu  Val  Ser  Ile  Asp  Ile  Gly  Thr  Glu  Thr
          2130                     2135                     2140

Glu  Asp  Ser  Glu  Leu  Thr  Glu  Ala  Asp  Leu  Pro  Pro  Ala  Ala  Ala  Ala
2145                     2150                     2155                     2160
```

| | | | | | | | | | | | | | | |
|---|---|---|---|---|---|---|---|---|---|---|---|---|---|---|
|Leu|Gln|Ala|Ile|Glu|Asn|Ala|Ala|Arg|Ile|Leu|Glu|Pro|His|Ile|Asp|
| | | | |2165| | | |2170| | | |2175| | |
|Val|Ile|Met|Glu|Asp|Cys|Ser|Thr|Pro|Ser|Leu|Cys|Gly|Ser|Ser|Arg|
| | | |2180| | | |2185| | | |2190| | | |
|Glu|Met|Pro|Val|Trp|Gly|Glu|Asp|Ile|Pro|Arg|Thr|Pro|Ser|Pro|Ala|
| | |2195| | | |2200| | | |2205| | | | |
|Leu|Ile|Ser|Val|Thr|Glu|Ser|Ser|Asp|Glu|Lys|Thr|Pro|Ser|Val|
| |2210| | | |2215| | | |2220| | | | | |
|Ser|Ser|Ser|Gln|Glu|Asp|Thr|Pro|Ser|Ser|Asp|Ser|Phe|Glu|Val|Ile|
|2225| | | |2230| | | |2235| | | | |2240| | |
|Gln|Glu|Ser|Glu|Thr|Ala|Glu|Gly|Glu|Glu|Ser|Val|Phe|Asn|Val|Ala|
| | | |2245| | | |2250| | | | |2255| | | |
|Leu|Ser|Val|Leu|Glu|Ala|Leu|Phe|Pro|Gln|Ser|Asp|Ala|Thr|Arg|Lys|
| | | |2260| | | |2265| | | |2270| | | | |
|Leu|Thr|Val|Arg|Met|Asn|Cys|Cys|Val|Glu|Lys|Ser|Val|Thr|Arg|Phe|
| | |2275| | | |2280| | | |2285| | | | | |
|Phe|Ser|Leu|Gly|Leu|Thr|Val|Ala|Asp|Val|Ala|Ser|Leu|Cys|Glu|Met|
| | |2290| | | |2295| | | |2300| | | | | |
|Glu|Ile|Gln|Asn|His|Thr|Ala|Tyr|Cys|Asp|Lys|Val|Arg|Thr|Pro|Leu|
|2305| | | |2310| | | |2315| | | |2320| | | |
|Glu|Leu|Gln|Val|Gly|Cys|Leu|Val|Gly|Asn|Glu|Leu|Thr|Phe|Glu|Cys|
| | | |2325| | | |2330| | | | |2335| | | |
|Asp|Lys|Cys|Glu|Ala|Arg|Gln|Glu|Thr|Leu|Ala|Ser|Phe|Ser|Tyr|Ile|
| | | |2340| | | |2345| | | | |2350| | | |
|Trp|Ser|Gly|Val|Pro|Leu|Thr|Arg|Ala|Thr|Pro|Ala|Lys|Pro|Pro|Val|
| | |2355| | | |2360| | | | |2365| | | | |
|Val|Arg|Pro|Val|Gly|Ser|Leu|Leu|Val|Ala|Asp|Thr|Thr|Lys|Val|Tyr|
| |2370| | | |2375| | | | |2380| | | | | |
|Val|Thr|Asn|Pro|Asp|Asn|Val|Gly|Arg|Arg|Val|Asp|Lys|Val|Thr|Phe|
|2385| | | |2390| | | |2395| | | | |2400| | |
|Trp|Arg|Ala|Pro|Arg|Val|His|Asp|Lys|Tyr|Leu|Val|Asp|Ser|Ile|Glu|
| | | |2405| | | |2410| | | | |2415| | | |
|Arg|Ala|Arg|Arg|Ala|Ala|Gln|Ala|Cys|Gln|Ser|Met|Gly|Tyr|Thr|Tyr|
| | | |2420| | | |2425| | | | |2430| | | |
|Glu|Glu|Ala|Ile|Arg|Thr|Val|Arg|Pro|His|Ala|Ala|Met|Gly|Trp|Gly|
| | |2435| | | |2440| | | | |2445| | | | |
|Ser|Lys|Val|Ser|Val|Lys|Asp|Leu|Ala|Thr|Pro|Ala|Gly|Lys|Met|Ala|
| |2450| | | |2455| | | | |2460| | | | | |
|Val|His|Asp|Arg|Leu|Gln|Glu|Ile|Leu|Glu|Gly|Thr|Pro|Val|Pro|Phe|
|2465| | | |2470| | | |2475| | | | |2480| | |
|Thr|Leu|Thr|Val|Lys|Lys|Glu|Val|Phe|Phe|Lys|Asp|Arg|Lys|Glu|Glu|
| | | |2485| | | |2490| | | | |2495| | | |
|Lys|Ala|Pro|Arg|Leu|Ile|Val|Phe|Pro|Pro|Leu|Asp|Phe|Arg|Ile|Ala|
| | |2500| | | |2505| | | | |2510| | | | |
|Glu|Lys|Leu|Ile|Leu|Gly|Asp|Pro|Gly|Arg|Val|Ala|Lys|Ala|Val|Leu|
| | |2515| | | |2520| | | | |2525| | | | |
|Gly|Gly|Ala|Tyr|Ala|Phe|Gln|Tyr|Thr|Pro|Asn|Gln|Arg|Val|Lys|Glu|
| |2530| | | |2535| | | | |2540| | | | | |
|Met|Leu|Lys|Leu|Trp|Glu|Ser|Lys|Lys|Thr|Pro|Cys|Ala|Ile|Cys|Val|
|2545| | | |2550| | | |2555| | | | |2560| | |
|Asp|Ala|Thr|Cys|Phe|Asp|Ser|Ser|Ile|Thr|Glu|Glu|Asp|Val|Ala|Leu|
| | | |2565| | | |2570| | | | |2575| | | |
|Glu|Thr|Glu|Leu|Tyr|Ala|Leu|Ala|Ser|Asp|His|Pro|Glu|Trp|Val|Arg|

|  | 2580 |  |  |  |  | 2585 |  |  |  |  | 2590 |  |  |
|---|---|---|---|---|---|---|---|---|---|---|---|---|---|
| Ala | Leu | Gly | Lys | Tyr | Tyr | Ala | Ser | Gly | Thr | Met | Val | Thr | Pro | Glu | Gly |
|  |  | 2595 |  |  |  |  | 2600 |  |  |  |  | 2605 |  |  |

Val Pro Val Gly Glu Arg Tyr Cys Arg Ser Ser Gly Val Leu Thr Thr
2610 2615 2620

Ser Ala Ser Asn Cys Leu Thr Cys Tyr Ile Lys Val Lys Ala Ala Cys
2625 2630 2635 2640

Glu Arg Val Gly Leu Lys Asn Val Ser Leu Leu Ile Ala Gly Asp Asp
2645 2650 2655

Cys Leu Ile Ile Cys Glu Arg Pro Val Cys Asp Pro Cys Asp Ala Leu
2660 2665 2670

Gly Arg Ala Leu Ala Ser Tyr Gly Tyr Ala Cys Glu Pro Ser Tyr His
2675 2680 2685

Ala Ser Leu Asp Thr Ala Pro Phe Cys Ser Thr Trp Leu Ala Glu Cys
2690 2695 2700

Asn Ala Asp Gly Lys Arg His Phe Phe Leu Thr Thr Asp Phe Arg Arg
2705 2710 2715 2720

Pro Leu Ala Arg Met Ser Ser Glu Tyr Ser Asp Pro Met Ala Ser Ala
2725 2730 2735

Ile Gly Tyr Ile Leu Leu Tyr Pro Trp His Pro Ile Thr Arg Trp Val
2740 2745 2750

Ile Ile Pro His Val Leu Thr Cys Ala Phe Arg Gly Gly Gly Thr Pro
2755 2760 2765

Ser Asp Pro Val Trp Cys Gln Val His Gly Asn Tyr Tyr Lys Phe Pro
2770 2775 2780

Leu Asp Lys Leu Pro Asn Ile Ile Val Ala Leu His Gly Pro Ala Ala
2785 2790 2795 2800

Leu Arg Val Thr Ala Asp Thr Thr Lys Thr Lys Met Glu Ala Gly Lys
2805 2810 2815

Val Leu Ser Asp Leu Lys Leu Pro Gly Leu Ala Val His Arg Lys Lys
2820 2825 2830

Ala Gly Ala Leu Arg Thr Arg Met Leu Arg Ser Arg Gly Trp Ala Glu
2835 2840 2845

Leu Ala Arg Gly Leu Leu Trp His Pro Gly Leu Arg Leu Pro Pro Pro
2850 2855 2860

Glu Ile Ala Gly Ile Pro Gly Gly Phe Pro Leu Ser Pro Pro Tyr Met
2865 2870 2875 2880

Gly Val Val His Gln Leu Asp Phe Thr Ser Gln Arg Ser Arg Trp Arg
2885 2890 2895

Trp Leu Gly Phe Leu Ala Leu Leu Ile Val Ala Leu Phe Gly
2900 2905 2910

( 2 ) INFORMATION FOR SEQ ID NO:184:

( i ) SEQUENCE CHARACTERISTICS:
        ( A ) LENGTH: 39 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GV5446IRT ( x i ) SEQUENCE DESCRIPTION: SEQ ID NO:184:

CGGTCCCTCG AACTCCAGCG AGTCTTTTTT TTTTTTTT            39

( 2 ) INFORMATION FOR SEQ ID NO:185:

( i ) SEQUENCE CHARACTERISTICS:
        ( A ) LENGTH: 70 amino acids
        ( B ) TYPE: amino acid
        ( C ) STRANDEDNESS: double
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( C ) INDIVIDUAL ISOLATE: GE-CAP from T55806

( x i ) SEQUENCE DESCRIPTION: SEQ ID NO:185:

```
Met Ser Leu Leu Thr Asn Arg Phe Ile Arg Arg Val Asp Lys Asp Gln
 1               5                  10                  15
Trp Gly Pro Gly Val Thr Gly Thr Asp Pro Glu Pro Cys Pro Ser Arg
            20                  25                  30
Trp Ala Gly Lys Cys Met Gly Pro Pro Ser Ser Ala Ala Ala Cys Ser
         35                  40                  45
Arg Gly Ser Pro Arg Ile Leu Arg Val Arg Ala Gly Gly Ile Ser Leu
         50                  55                  60
Phe Tyr Thr Ile Met Ala
 65                  70
```

( 2 ) INFORMATION FOR SEQ ID NO:186:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-S59 Variant ( x i ) SEQUENCE DESCRIPTION: SEQ ID NO:186:

AGACGCAATG ACTCGGCGCC GACTCGGCGA CCGGCCAAAA GGTGGTGGAT GGGTGATGAC            60
AGGGTTGGTA GGTCGTAAAT CCCGGTCACC TTGGTAGCCA CTATAGGTGG GTCTTAAGAG           120
AAGGTTAAGA TTCCTCTTGT GCCTGCGGCG AGACCGCGCA CGGTCCACAG GTGTTGGCCC           180
TACCGGTGTG AATAAGGGCC CGACGTCAGG CTCGTCGTTA AACCGAGCCC GTTACCCACC           240
TGGGCAAACG ACGCCCACGT ACGGTCCACG TCGCCCTTCA ATGCCTCTCT TGGCCAATAG           300
GTTTATCCGG CGAGTTGACA AGGACCAGTG GGGGCCGGGG GCTTGGGAA GGACCTCAAG           360
CCCTGCCCTT CCCGGTGGGG CGGGAAATGC ATGGGCCAC C                               401

( 2 ) INFORMATION FOR SEQ ID NO:187:

( i ) SEQUENCE CHARACTERISTICS:
        ( A ) LENGTH: 401 base pairs
        ( B ) TYPE: nucleic acid
        ( C ) STRANDEDNESS: double (D) TOPOLOGY: unknown (ii) MOLECULE TYPE: DNA (iii) HYPOTHETICAL: NO (iv) ANTI-SENSE: NO (vi) ORIGINAL SOURCE:
  (C) INDIVIDUAL ISOLATE: HGV-S368 Variant (xi) SEQUENCE DESCRIPTION: SEQ ID NO:187:

```
AGACGCAATG ACTCGGCGCC AACTCGGCGA CCGGCCAAAA GGTGGTGGAT GGGTGATGAC      60
AGGGTTGGTA GGTCGTAAAT CCCGGTCACC TTGGTAGCCA CTATAGGTGG GTCTTAAGAG     120
AAGGTTAAGA TTCCTCTTGT GCCTGCGGCG AGACCGCGCA CGGTCCACAG GTGTTGGCCC     180
TACCGGTGTG AATAAGGGCC CGACGTCAGG CTCGTCGTTA AACCGAGCCC GTTACCCACC     240
CGGGCAAACG ACGCCCACGT ACGGTCCACG TCGCCCTTCA ATGTCTCTCT TGACCAATAG     300
GCTTAGCCGG CGAGTTGACA AGGACCAGTG GGGGCCGGGG GCTTGGAGAG GGACTCCAAG     360
TCCTGCCCTT CCCGGTGGGC CGGGAAATGC ATGGGCCAC C                          401
```

(2) INFORMATION FOR SEQ ID NO:188:

(i) SEQUENCE CHARACTERISTICS:
    (A) LENGTH: 402 base pairs
    (B) TYPE: nucleic acid
    (C) STRANDEDNESS: double
    (D) TOPOLOGY: unknown (ii) MOLECULE TYPE: DNA (iii) HYPOTHETICAL: NO (iv) ANTI-SENSE: NO (vi) ORIGINAL SOURCE:
    (C) INDIVIDUAL ISOLATE: HGV-S309 VARIANT (xi) SEQUENCE DESCRIPTION: SEQ ID NO:188:

```
AGACGCAATG ACTCGGCGCC GACTCGGCGA CCGGCCAAAA GGTGGTGGAT GGGTGATGAC      60
AGGGTTGGTA GGTCGTAAAT CCCGGTCATC CTGGTAGCCA CTATAGGTGG GTCTTAAGAG     120
AAGGTTAAGA TTCCTCTTGT GCATGCGGCG AGAACGCGCA CGGTCCACAG GTGTTGGCCC     180
TACCGGTGTG AATAAGGGCC CGACGTCAGG CTCGTCGTTA AACCGAGCCC GTTACCCACC     240
TGGGCAAACG ACGCCCACGT ACGGTCCACG TCGCCCTTCA ATGTCTCTCT TGACCAATAG     300
GTTTATCCGG CGAGTTGACA AGGACCAGTG GGGGCCGGGG GTCACGGGGA AGGACCCCGG     360
ATCCTGCCCT TCCCGGTGGG CCGGGAAATG CATGGGCCA CC                         402
```

(2) INFORMATION FOR SEQ ID NO:189:

(i) SEQUENCE CHARACTERISTICS:
    (A) LENGTH: 402 base pairs
    (B) TYPE: nucleic acid
    (C) STRANDEDNESS: double
    (D) TOPOLOGY: unknown (ii) MOLECULE TYPE: DNA (iii) HYPOTHETICAL: NO (iv) ANTI-SENSE: NO (vi) ORIGINAL SOURCE:
    (C) INDIVIDUAL ISOLATE: HGV-FZ VARIANT (xi) SEQUENCE DESCRIPTION: SEQ ID NO:189:

```
AGACGCAATG  ACTCGGCGCC  GACTCGGCGA  CCGGCCAAAA  GGTGGTGG

| ACCCTGCCCT | TCCCGGCGGA | CCGGGAAATG | CATGGGGCCA | CC | | 402 |

( 2 ) INFORMATION FOR SEQ ID NO:192:

( i ) SEQUENCE CHARACTERISTICS:
        ( A ) LENGTH: 405 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-G59 VARIANT ( x i ) SEQUENCE DESCRIPTION: SEQ ID NO:192:

| AGACGCAATG | ACTCGGCGCC | GACTCGGCGA | CCGGCCAAAA | GGTGGTGGAT | GGGTGATGCC | 60 |
| AGGGTTGGTA | GGTCGTAAAT | CCCGGTCATC | TTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGCCC | 180 |
| TACCGGTGGG | AATAAGGGCC | CGACGTCAGG | CTCGTCGTTA | AACTGAGCCC | GTAACCCACC | 240 |
| TGGGCAAACG | ACGCCCACGT | ACGGTCCACG | TCGCCCTTCA | ATGCCTCTCT | TGGCCAATAG | 300 |
| GGATTATTCC | CGGCGAGTTG | GCAAGGACCA | GTGGGGGCCG | GGAGCTACAG | AGAAGGACTC | 360 |
| TGAGCTCTGC | CCTTCCCGGT | GGAACGGGAA | ATGCATGGGG | CCACC | | 405 |

( 2 ) INFORMATION FOR SEQ ID NO:193:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-E36 VARIANT ( x i ) SEQUENCE DESCRIPTION: SEQ ID NO:193:

| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGGCG | AGACCGCGCA | CGGCCCACAG | GTGTTGGCCC | 180 |
| TACCGGTGTG | AATAAGGGCC | CGACGTCAGG | CTCGTCGTTA | AACCGAGCCC | ACTACCCACC | 240 |
| TGGGCAAACG | ACGCCCACGT | ACGGTCTACG | TCGCCCTTCA | ATGTCTCTCT | TGACCAATAG | 300 |
| GCTAAGCCGG | CGAGTTGACA | AAGACCAGTG | GGGGCCGGGG | GTCACAGGGA | TGGACCCTGG | 360 |
| ACCCTGCCCT | TCCCGGTGGA | GTGGGAAATG | CATGGGGCCA | CC | | 402 |

( 2 ) INFORMATION FOR SEQ ID NO:194:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
            ( C ) INDIVIDUAL ISOLATE: HGV-R38730 VARIANT ( x i ) SEQUENCE DESCRIPTION: SEQ ID NO:194:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGG | ATCCTCTTGT | GCCTGCGGCG | AGACCGCGCA | CGGTCCACAG | GTGTTGGCCC | 180 |
| TACCGGTGTG | AATAAGGGCC | CGACGTCAGG | CTCGTCGTTA | AACCGAGCCC | GTATCCCACC | 240 |
| TGGGCAAACG | ACGCCCACGT | ACGGTCCACG | TCGCCCTTCA | ATGTCTCTCT | TGACCAATAG | 300 |
| GTTCGTCCGG | CGAGTTGACA | AGGACCAGTG | GGGGCCGGGG | GTTGCGGGGA | AGGACCCCGA | 360 |
| ACTCTGCCCT | TCCCGGTGGG | CCGGGAAATG | CATGGGCCA | CC | | 402 |

( 2 ) INFORMATION FOR SEQ ID NO:195:

( i ) SEQUENCE CHARACTERISTICS:
            ( A ) LENGTH: 401 base pairs
            ( B ) TYPE: nucleic acid
            ( C ) STRANDEDNESS: double
            ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
            ( C ) INDIVIDUAL ISOLATE: HGV-G281 VARIANT ( x i ) SEQUENCE DESCRIPTION: SEQ ID NO:195:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGTCC | 180 |
| TACCGGTGTG | AATAAGGACC | CGACGTCAGG | CTCGTCGTTA | AACCGAGCCC | GTTACCCACC | 240 |
| TGGGCAAACG | ACGCCCACGT | ACGGTCCACG | TCGCCCTTCA | ATGTCTCTCT | TGACCAATAG | 300 |
| GCTTAGCCGG | CGAGTTGACA | AGGACCAGTG | GGGGCCGGGG | GCTTGGGGAA | GGACCCCAAG | 360 |
| CCCTGCCCTT | CCCGGTGGGC | CGGGAAATGC | ATGGGCCAC | C | | 401 |

( 2 ) INFORMATION FOR SEQ ID NO:196:

( i ) SEQUENCE CHARACTERISTICS:
            ( A ) LENGTH: 402 base pairs
            ( B ) TYPE: nucleic acid
            ( C ) STRANDEDNESS: double
            ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
            ( C ) INDIVIDUAL ISOLATE: HGV-G157 VARIANT ( x i ) SEQUENCE DESCRIPTION: SEQ ID NO:196:

| | | | | | | |
|---|---|---|---|---|---|---|
| AGACGCAATG | ACTCGGCGCC | GACCCGGCGA | CCGGCCAAAA | GGTGGTGGAT | GGGTGATGCC | 60 |

| | | | | | |
|---|---|---|---|---|---|
|AGGGTTGGTA|GGTCGTAAAT|CCCGGTCATC|TTGGTAGCCA|CTATAGGTGG|GTCTTAAGGG|120|
|AAGGTTAAGA|TTCCTCTTGT|GCCTGTGGCG|AGACAGCGCA|CGGTCCACAG|GTGTTGGCCC|180|
|TACCGGTGTG|AATAAGGGCC|CGACGTCAGG|CTCGTCGTTA|AACCGAGACC|GACACCCACC|240|
|TGGGCAAACG|ACGCCCACGT|ACGGTCCACG|TCGCCCTTCA|ATGTCTCTCT|TGACCAATAG|300|
|GCTTTGCCGG|CGAGTTGACA|AGGACCAGTG|GGGGCCGGGT|GCTGGGGGAA|GGACCCCCTT|360|
|GCACCGCCCT|TCCCGGTGGG|ACGGGAAATG|CATGGGGCCA|CC| |402|

( 2 ) INFORMATION FOR SEQ ID NO:197:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-G154 VARIANT ( x i ) SEQUENCE DESCRIPTION: SEQ ID NO:197:

| | | | | | |
|---|---|---|---|---|---|
|AGACGCAATG|ACTCGGCGCC|GACTCGGCGA|CCGGCCAAAA|GGTGGTGGAT|GGGTGATGAC|60|
|AGGGTTGGTA|GGTCGTAAAT|CCCGGTCATC|CTGGTAGCCA|CTATAGGTGG|GTCTTAAGAG|120|
|AAGGTTAAGA|TTCCTCTTAC|GCCTGCGGCG|AGACCGCGCA|CGGTCCACAG|GTGCTGGCCT|180|
|TACCGGTGTG|AATAAGGCC|CGACGTCAGG|CTCGTCGTTA|AACCGAGCCC|GTCACCCACC|240|
|TGGGCAAACG|ACGCCCACGT|ACGGTCCACG|TCGCCCTTCA|ATGTCTCTCT|TGACCAGTAG|300|
|GTTTAACCGG|CGAGTTGACA|AGGACCAGTG|GGGGCCGGGG|CCTTGGAGAT|GGACTCCAAG|360|
|TCCTGCCCTT|CCCGGTGGGC|CGGGAAATGC|ATGGGCCAC|C| |401|

( 2 ) INFORMATION FOR SEQ ID NO:198:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-G213 VARIANT ( x i ) SEQUENCE DESCRIPTION: SEQ ID NO:198:

| | | | | | |
|---|---|---|---|---|---|
|AGACGCAATG|ACTCGGCGCC|AACTCGGCGA|CCGGCCAAAA|GGTGGTGGAT|GGGTGATGAC|60|
|AGGGTTGGTA|GGTCGTAAAT|CCCGGTCACC|TTGGTAGCCA|CTATAGGTGG|GTCTTAAGAG|120|
|AAGGTTAAGA|TTCCTCTTGT|GCCTGCGGCG|AGACCGCGCA|CGGTCCACAG|GTGTTGGTCC|180|
|TACCGGTGGG|AATAAGGGCC|CGACGTCAGG|CTCGTCGTTA|AACCGAGCCC|GTCACCCACC|240|
|TGGGCAAACG|ACGCCCACGT|ATGGTCCACG|TCGCCCTTCA|ATGCCTCTCT|TGGCCAATAG|300|
|GTTTATCCGG|CGAGTTGACA|AGGACCAGTG|GGGGCCGGGG|GTTCGGGGAA|GGACCCCGTA|360|
|CCCTGCCCTT|CCCGGTGGAA|CGGGAAATGC|ATGGGCCAC|C| |401|

( 2 ) INFORMATION FOR SEQ ID NO:199:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-G204 VARIANT ( x i ) SEQUENCE DESCRIPTION: SEQ ID NO:199:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGCCC | 180 |
| TACCGGTGTT | AATAAGGGCC | CGACGTCAGG | CTCGTCGTTA | AACCGAGCCC | GTCACCCACC | 240 |
| TGGGCAAACG | ACGCCCACGT | ACGGTCCACG | TCGCCCTTCA | ATGTCTCTCT | TGACCAATAG | 300 |
| GCTTAGCCGG | CGAGTTGACA | AGGACCAGTG | GGGGCCGGGG | GCCTGGAGAG | GGACTCCAGG | 360 |
| TCCTGCCCTT | CCCGGTGGGC | CGGGAAATGC | ATGGGCCAC | C | | 401 |

( 2 ) INFORMATION FOR SEQ ID NO:200:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-G191 VARIANT ( x i ) SEQUENCE DESCRIPTION: SEQ ID NO:200:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCATC | CTGGTAGCCA | CTATAGGTGG | GTCTTAAGAG | 120 |
| AAGGTTAAGG | ATCCTCTTGT | GCCTGCGGCG | AGACCGCGCA | CGGTCCACAG | GTGTTGGCCC | 180 |
| TACCGGTGTG | AATAAGGGCC | CGACGTCAGG | CTCGTCGCTA | AACCGAGCCC | GTATCCCACC | 240 |
| TGGGCAAACG | ACGCCCACGT | ACGGTCCACG | TCGCCCTTCA | ATGTCTCTCT | TGACCAATAG | 300 |
| GTTTATCCGG | CGAGTTGACA | AGGACCAGTG | GGGGCCGGAG | GTTACGGGA | AGGACCCCGA | 360 |
| GCCTCGCCCT | TCCCGGTGGG | CCGGGAAATG | CATGGGCCA | CC | | 402 |

( 2 ) INFORMATION FOR SEQ ID NO:201:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
                    ( C ) INDIVIDUAL ISOLATE: HGV-G299 VARIANT ( x i ) SEQUENCE DESCRIPTION: SEQ ID NO:201:

```
AGACGCAATG  ACTCGGCGCC  GACTCGGCGA  CCGGCCAAAA  GGTGGTGGAT  GGGTGATGAC      60

AGGGTTGGTA  GGTCGTAAAT  CCCGGTCACC  TTGGTAGCCA  CTATAGGTGG  GTCTTAAGAG     120

AAGGTTAAGA  TTCCTCTTGT  GCCTGCGGCG  AGACCGCGCA  CGGTCCACAG  GTGTTGGCCC     180

TACCGGTGTG  AATAAGGGCC  CGACGTCAGG  CTCGTCGTTA  AACCGAGCCC  GTCACCCACC     240

TGGGCAAACG  ACGCCCACGC  ACGGTCCACG  TCGCCCTTCA  ATGCCTCTCT  TGGCCAATAG     300

GAGTATCCGG  CGAGTTGACA  AGGACCAGTG  GGGGCCGGGA  GTCACGGGGA  TGGACCCCGG     360

GCTCTGCCCT  TCCCGGTGGA  ACGGGAAATG  CATGGGGCCA  CC                         402
```

( 2 ) INFORMATION FOR SEQ ID NO:202:

( i ) SEQUENCE CHARACTERISTICS:
                    ( A ) LENGTH: 402 base pairs
                    ( B ) TYPE: nucleic acid
                    ( C ) STRANDEDNESS: double
                    ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
                    ( C ) INDIVIDUAL ISOLATE: HGV-T56957 VARIANT ( x i ) SEQUENCE DESCRIPTION: SEQ ID NO:202:

```
AGACGCAATG  ACTCGGCGCC  GACTCGGCGA  CCGGCCAAAA  GGTGGTGGAT  GGGTGATGAC      60

AGGGTTGGTA  GGTCGTAAAT  CCCGGTCACC  TTGGTAGCCA  CTATAGGTGG  GTCTTAAGAG     120

AAGGTTAAGA  TTCCTCTTGT  GCCTGCGGCG  AGACCGCGCA  CGGTCCACAG  GTGTTGGCCC     180

TACCGGTGTG  AATAAGGGCC  CGACGTCAGG  CTCGTCGTTA  AACCGAGCCC  ATCACCCACC     240

TGGGCAAACG  ACGCCCACGT  ACGGTCCACG  TCGCCCTACA  ATGTCTCTCT  TGACCAATAG     300

GCTTAGCCGG  CGAGTTGACA  AGGACCAGTG  GGGGCCGGGG  GTCACAGGGA  TGGACCCTGG     360

GCCCTGCCCT  TCCCGGTGGG  GTGGGAAATG  CATGGGGCCA  CC                         402
```

( 2 ) INFORMATION FOR SEQ ID NO:203:

( i ) SEQUENCE CHARACTERISTICS:
                    ( A ) LENGTH: 401 base pairs
                    ( B ) TYPE: nucleic acid
                    ( C ) STRANDEDNESS: double
                    ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
                    ( C ) INDIVIDUAL ISOLATE: HGV-C01698 VARIANT ( x i ) SEQUENCE DESCRIPTION: SEQ ID NO:203:

```
AGACGCAATG  ACTCGGCGCC  GACTCGGCGA  CCGGCCAAAA  GGTGGTGGAT  GGGTGATGAC      60

AGGGTTGGTA  GGTCGTAAAT  CCCGGTCACC  TTGGTAGCCA  CTATAGGTGG  GTCTTAAGAG     120
```

```
AAGGTTAAGA  TTCCTCTTGT  GCCTGCGGCG  AGACCGCGCA  CGGTCCACAG  GTGTTGGCCC      180

TACCGGTGTG  AATAAGGGCC  CGACGTCAGG  CTCGTCGTTA  AACCGAGCCC  GTCACCCACC      240

TGGGCAAACG  ACGCCCACGT  ACGGTCCACG  TCGCCCTTCA  ATGTCTCTCT  TGACCAATAG      300

GCTTAGCCGG  CGAGTTGACA  AGGACCAGTG  GGGGCCGGGG  GCTTGGAGAT  GGACTCCAAG      360

TCCTGCCCTT  CCCGGTGGGC  CGGGAAATGC  ATGGGGCCAC  C                           401
```

( 2 ) INFORMATION FOR SEQ ID NO:204:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-T27034 VARIANT ( x i ) SEQUENCE DESCRIPTION: SEQ ID NO:204:

```
AGACGCAATG  ACTCGGCGCC  GACTCGGCGA  CCGGCCAAAA  GGTGGTGGAT  GGGTGATGAC       60

AGGGTTGGTA  GGTCGTAAAT  CCCGGTCACC  TTGGTAGCCA  CTATAGGTGG  GTCTTAAGAG      120

AAGGTTAAGA  TTCCTCTTGT  GCCTGCGGCG  AGACCGCGCA  CGGTCCACAG  GTGTTGGCCC      180

TACCGGTGTG  AATAAGGGCC  CGACGTCAGG  CTCGTCGTTA  AACCGAGCCC  ATTTCCCGCC      240

TGGGCTAACG  ACGCCCACGT  ACGGTCCACG  TCGCCCTTCA  ATGTCTCTCT  TGACCAATAG      300

GTTTATCCGG  CGAGTTGACA  AGGACCAGTG  GGGGCCGGGA  GTCACTGGGA  TGGACCCAGG      360

GCTCTGCCCT  TCCCGGCGGG  GTGGGAAAAG  CATGGGCCA  CC                          402
```

( 2 ) INFORMATION FOR SEQ ID NO:205:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-E57963 VARIANT ( x i ) SEQUENCE DESCRIPTION: SEQ ID NO:205:

```
AGACGCAATG  ACTCGGCGCC  GACTCGGCGA  CCGGCCAAAA  GGTGGTGGAT  GGGTGATGAC       60

AGGGTTGGTA  GGTCGTAAAT  CCCGGTCACC  TTGGTAGCCA  CTATAGGTGG  GTCTTAAGAG      120

AAGGTTAAGA  TTCCTCTTGT  GCCTGCGGCG  AGACCGCGCA  CGGTCCGCAG  GTGTTGGCCC      180

TACCGGTGTG  AATAAGGGCC  CGACGTCAGG  CTCGTCGTTA  AACCGAGCCC  GTCACCCACC      240

TGGGCAAACG  ACGCCCACGT  ACGGTCCACG  TCGCCCTTCA  ATGTCTCTCT  TGACCAATAG      300

GCTTAGCCGG  CGAGTTGACA  AGGACCAGTG  GGGGCCGGGG  GCTTGGAGAA  GGACTCCAAG      360

TCCTGCCCTT  CCCGGTGGGC  CGGGAAATGC  ATGGGGCCAC  C                           401
```

( 2 ) INFORMATION FOR SEQ ID NO:206:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-R37166 VARIANT ( x i ) SEQUENCE DESCRIPTION: SEQ ID NO:206:

```
AGACGCAATG ACTCGGCGCC GACTCGGCGA CCGGCCAAAA GGTGGTGGAT GGGTGATGAC      60
AGGGTTGGTA GGTCGTAAAT CCCGGTCACC TTGGTAGCCA CTATAGGTGG GTCTTAAGAG     120
AAGGTTAAGA TTCCTCTTGT GCCTGCGGCG AGACCGCGCA CGGTCCACAG GTGTTGGCCC     180
TACCGGTGTG AATAAGGGCC CGACGTCAGG CTCGTCGTTA AACCGAGCCC GTAACCCGCC     240
TGGGCAAACG ACGCCCACGT ACGGTCCACG TCGCCCTTCA ATGTCTCTCT TGACCAATAG     300
GTTTAACCGG CGAGTTGACA AGGACCAGTG GGGGCCGGGG CCTTGGAGAT GGACTCCAAG     360
TCCTGCCCTT CCCGGCGGGC CGGGAAATGC ATGGGCCAC C                          401
```

( 2 ) INFORMATION FOR SEQ ID NO:207:

( i ) SEQUENCE CHARACTERISTICS:
        ( A ) LENGTH: 404 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-B5 VARIANT ( x i ) SEQUENCE DESCRIPTION: SEQ ID NO:207:

```
AGACGCAATG ACTCGGCGCC GACTCGGCGA CCGGCCAAAA GGTGGTGGAT GGGTGATGAC      60
AGGGTTGGTA GGTCGTAAAT CCCGGTCATC CTGGTAGCCA CTATAGGTGG GTCTTAAGGG     120
AAGGTTAAGA TTCCTCTTGT GCCTGCGGCG AGACCGCGCA CGGTCCACAG GTGTTGGCCC     180
TACCGGTGTG AATAAGGGCC CGACGTCAGG CTCGTCGTTA AACCGAGCCC GTCACCCACC     240
TGGGCTAACG ACGCCCACGT ACGGTCCACG TCGCCCTTCA ATGTCTCTCT TGACCAATAG     300
GCTTTTTGCC GGCGAGTTGA CAAGGACCAG TGGGGCCGG GGGTTATGGG GAAGGACCCC     360
AAACCCTGCC CTTCCCGGTG GGCCGGGAAA TGCATGGGGC CACC                      404
```

( 2 ) INFORMATION FOR SEQ ID NO:208:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: HGV-B33 VARIANT ( x i ) SEQUENCE DESCRIPTION: SEQ ID NO:208:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCATC | CTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGCCC | 180 |
| TACCGGTGTG | AATAAGGGCC | CGACGTCAGG | CTCGTCGTTA | AACCGAGCCC | GTTCCCCGCC | 240 |
| TGGGCAAACG | ACGCCACGT  | ACGGTCCACG | TCGCCCTTCA | ATGTCTCTCT | TGACCAATAG | 300 |
| GTTTATCCGG | CGAGTTGACA | AGGACCAGTG | GGGGCCGGGG | ATCATGGGGA | AGGACCCCAG | 360 |
| ATCCTGCCCT | TCCCGGCGGG | CCGGGAAATG | CATGGGGCCA | CC | | 402 |

( 2 ) INFORMATION FOR SEQ ID NO:209:

( i ) SEQUENCE CHARACTERISTICS:
    ( A ) LENGTH: 401 base pairs
    ( B ) TYPE: nucleic acid
    ( C ) STRANDEDNESS: double
    ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: HGV-FH010 VARIANT ( x i ) SEQUENCE DESCRIPTION: SEQ ID NO:209:

| | | | | | | |
|---|---|---|---|---|---|---|
| AGACGCAATG | ACTCGGCGCC | GACCCGGCGA | CCGGCCAAAA | GGTGGTGGAT | GGGTGATGCC | 60 |
| AGGGTTGGTA | GGTCGTAAAT | CCCGGTCATC | TTGGTAGCCA | CTATAGGTGG | GTCTTAAGGG | 120 |
| AAGGTTAAGA | TTCCTCTTGT | GCCTGTGGCG | AGACAGCGCA | CGGTCCACAG | GTGTTGGCCC | 180 |
| TACCGGTGTG | AATAAGGGCC | CGACGTCAGG | CTCGTCGTTA | AACTGAGACC | GACACCCACC | 240 |
| TGGGCAAACG | ACGCCACGT  | ACGGTCCACG | TCGCCCTTCA | ATGTCTCTCT | TGACCAATAG | 300 |
| GCTTTGCCGG | CGAGTTGACA | AGGACCAGTG | GGGGCCGGGG | GCTGGGGGAA | GGACCCCCAG | 360 |
| TCCTGCCCTT | CCCGGTGGGA | CGGGAAATGC | ATGGGCCAC | C | | 401 |

( 2 ) INFORMATION FOR SEQ ID NO:210:

( i ) SEQUENCE CHARACTERISTICS:
    ( A ) LENGTH: 401 base pairs
    ( B ) TYPE: nucleic acid
    ( C ) STRANDEDNESS: double
    ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: HGV-PNF2161 VARIANT ( x i ) SEQUENCE DESCRIPTION: SEQ ID NO:210:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGCCC | 180 |

| | | | | | | |
|---|---|---|---|---|---|---|
| TACCGGTGGG | AATAAGGGCC | CGACGTCAGG | CTCGTCGTTA | AACCGAGCCC | GTTACCCACC | 240 |
| TGGGCAAACG | ACGCCCACGT | ACGGTCCACG | TCGCCCTTCA | ATGTCTCTCT | TGACCAATAG | 300 |
| GCGTAGCCGG | CGAGTTGACA | AGGACCAGTG | GGGGCCGGGG | GCTTGGAGAG | GGACTCCAAG | 360 |
| TCCCGCCCTT | CCCGGTGGGC | CGGGAAATGC | ATGGGGCCAC | C | | 401 |

(2) INFORMATION FOR SEQ ID NO:211:

(i) SEQUENCE CHARACTERISTICS:
        (A) LENGTH: 402 base pairs
        (B) TYPE: nucleic acid
        (C) STRANDEDNESS: double
        (D) TOPOLOGY: unknown (ii) MOLECULE TYPE: DNA (iii) HYPOTHETICAL: NO (iv) ANTI-SENSE: NO (v) ORIGINAL SOURCE:
        (C) INDIVIDUAL ISOLATE: HGV-JC VARIANT (xi) SEQUENCE DESCRIPTION: SEQ ID NO:211:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGCCC | 180 |
| TACCGGTGGG | AATAAGGGCC | CGACGTCAGG | CTCGTCGTTA | AACCGAGCCC | GTAACCCGCC | 240 |
| TGGGCAAACG | ACGCCCACGT | ACGGTCCACG | TCGCCCTTCA | ATGTCGCTCT | TGACCAATAG | 300 |
| GCTTAGCCGG | CGAGTTGACA | AGGACCAGTG | GGGGCCGGGG | TTTATGGGGA | AGGACCCCAA | 360 |
| ACCCTGCCCT | TCCCGGCGGA | CCGGGAAATG | CATGGGGCCA | CC | | 402 |

(2) INFORMATION FOR SEQ ID NO:212:

(i) SEQUENCE CHARACTERISTICS:
        (A) LENGTH: 401 base pairs
        (B) TYPE: nucleic acid
        (C) STRANDEDNESS: double
        (D) TOPOLOGY: unknown (ii) MOLECULE TYPE: DNA (iii) HYPOTHETICAL: NO (iv) ANTI-SENSE: NO (v) ORIGINAL SOURCE:
        (C) INDIVIDUAL ISOLATE: HGV-7155 VARIANT (xi) SEQUENCE DESCRIPTION: SEQ ID NO:212:

| | | | | | | |
|---|---|---|---|---|---|---|
| AGACGTTATG | AACCGGCGCC | GCCCGGCGA | CCGGCCAAAA | GGTGGTGGAT | GGGTGATGCC | 60 |
| AGGGTTGGTA | GGTCGTAAAT | CCCGGTCATC | TTGGTAGCCA | CTATAGGTGG | GTCTTAAGGG | 120 |
| GTGGTCAAGG | TCCCTCTAGC | GCTTGTGGCG | AGAAAGCGCA | CGGTCCACAG | GTGTTGGCCC | 180 |
| TACCGGTGTG | AATAAGGGCC | CGACGTCAGG | CTCGTCGTTA | AACCGAGCCC | ATTATCCTCC | 240 |
| TGGGCAAACG | ACGCCCACGT | ACGGTCCACG | TCGCCCTTCA | ATGTCTCTCT | TGACCAATAG | 300 |
| GCTTTGCCGG | CGAGTTGACA | AGGACCAGTG | GGGGCCGGGT | GCCGGGGAA | GGACCCCGG | 360 |
| TACTGCCCCT | CCCGGAGGAG | TGGGAAATGC | ATGGGGCCAC | C | | 401 |

(2) INFORMATION FOR SEQ ID NO:213:

( i ) SEQUENCE CHARACTERISTICS:
    ( A ) LENGTH: 401 base pairs
    ( B ) TYPE: nucleic acid
    ( C ) STRANDEDNESS: double
    ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: HGV-7244 VARIANT ( x i ) SEQUENCE DESCRIPTION: SEQ ID NO:213:

```
AGACGTTAAG AACCGGCGCC GCCCCGGCGA CCGGCCAAAA GGTGGTGGAT GGGTGATGCC      60
AGGGTTGGTA GGTCGTAAAT CCCGGTCATC TTGGTAGCCA CTATAGGTGG GTCTTAAGGG     120
GTGGTCAAGG TCCCTCTGGC GCTTGTGGCG AGAAAGCGCA CGGTCCACAG GTGTTGGCCC     180
TACCGGTGTG AATAAGGGCC CGACGTCAGG CTCGTCGTTA AACCGAGCCC ATTACCCTCC     240
TGGGCAAACG ACGCCCATGT ACGGTCCACG TCGCCCTTCA ATGTCTCTCT TGACCAATAG     300
GCTTTGCCGG CGAGTTGACA AGGACCAGTG GGGGCCGGGT GGCGGGGGAA GGACCCCCGT     360
CACTGCCCTT CCCGGAGGGG TGGGAAATGC ATGGGCCAC C                          401
```

( 2 ) INFORMATION FOR SEQ ID NO:214:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-K27 VARIANT ( x i ) SEQUENCE DESCRIPTION: SEQ ID NO:214:

```
AGACGTTAAG TACCGGCGCC GACCCGGCGA CCGGCCAAAA GGTGGTGGAT GGGTGATGCC      60
AGGGTTGGTA GGTCGTAAAT CCCGGTCATC TTGGTAGCCA CTATAGGTGG GTCTTAAGGG     120
TTGGTCAAGG TCCCTCTGGC GCTTGTGGCG AGAAAGCGCA CGGTCCACAG GTGTTGGCCC     180
TACCGGTGTG AATAAGGGCC CGACGTCAGG CTCGTCGTTA AACCGAGCCC ATTACCCACC     240
TGGGCAAACA ACGCCACGT  ACGGTCCACG TCGCCCTACA ATGTCTCTCT TGACCAATAG     300
GCTTTGCCGG CGAGTTGACA AGGACCAGTG GGGGCTGGGC GGCGAGGGAA GGACCCTCGT     360
CGCTGCCCTT CCCGGCGGGG TGGGAATGC  ATGGGCCAC C                          401
```

( 2 ) INFORMATION FOR SEQ ID NO:215:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO (v i) ORIGINAL SOURCE:
(C) INDIVIDUAL ISOLATE: HGV-K30 VARIANT (x i) SEQUENCE DESCRIPTION: SEQ ID NO:215:

| | | | | | | |
|---|---|---|---|---|---|---|
| AGACGTTAAG | AACCGGCGCC | TTCCCGGCGA | CCGGCCAAAA | GGTGGTGGAT | GGGTGATGCC | 60 |
| AGGGTTGGTA | GGTCGTAAGT | CCCGGTCATC | TTGGTAGCCA | CTATAGGTGG | GTCTTAAGGG | 120 |
| AGGGTTAAGG | TCCCTCTGGC | GCTTGTGGCG | AGAAAGCGCA | CGGTCCACAG | GTGTTGGCCC | 180 |
| TACCGGTGTG | AATAAGGGCC | CGACGTCAGG | CTCGTCGTTA | AACCGAGCCC | ATTACCCACC | 240 |
| TGGGCAAACA | ACGCCCACGT | ACGGTCCACG | TCGCCCTTCA | ATGTCTCTCT | TGACCAATAG | 300 |
| GCTTTGCCGG | CGAGTTGACA | AGGACCAGTG | GGGGCTGGGC | GGTAGGGGAA | GGACCCTTGC | 360 |
| CGCTGCCCTT | CCCGGTGGGG | TGGGAAATGC | ATGGGCCAC | C | | 401 |

(2) INFORMATION FOR SEQ ID NO:216:

(i) SEQUENCE CHARACTERISTICS:
(A) LENGTH: 401 base pairs
(B) TYPE: nucleic acid
(C) STRANDEDNESS: double
(D) TOPOLOGY: unknown (i i) MOLECULE TYPE: DNA (i i i) HYPOTHETICAL: NO (i v) ANTI-SENSE: NO (v i) ORIGINAL SOURCE:
(C) INDIVIDUAL ISOLATE: HGV-T55875 VARIANT (x i) SEQUENCE DESCRIPTION: SEQ ID NO:216:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGACG | AGACCGCGCA | CGGTCCGCAG | GTGTTGGCCC | 180 |
| TACCGGTGTG | AATAAGGGCC | CGACGTCAGG | CTCGTCGTTA | AACCGAGCCC | GTCACCCACC | 240 |
| TGGGCAAACG | ACGCCCACGT | ACGGTCCACG | TCGCCCTTCA | ATGCCTCTCT | TGGCCAATAG | 300 |
| GTTTAACCGG | CGAGTTGGCA | AGGACCAGTG | GGGGCCGGGG | GCTTGGAGAG | GGACTCCAAG | 360 |
| TCCTGCCCTT | CCCGGTGGGC | CGGGAAATGC | ATGGGCCAC | C | | 401 |

(2) INFORMATION FOR SEQ ID NO:217:

(i) SEQUENCE CHARACTERISTICS:
(A) LENGTH: 402 base pairs
(B) TYPE: nucleic acid
(C) STRANDEDNESS: double
(D) TOPOLOGY: unknown (i i) MOLECULE TYPE: DNA (i i i) HYPOTHETICAL: NO (i v) ANTI-SENSE: NO (v i) ORIGINAL SOURCE:
(C) INDIVIDUAL ISOLATE: HGV-T56633 VARIANT (x i) SEQUENCE DESCRIPTION: SEQ ID NO:217:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGCCC | 180 |
| TACCGGTGTG | AATAAGGGCC | CGACGTCAGG | CTCGTCGTTA | AACCGAGCCC | ACTACCCACC | 240 |

| | | | | | | |
|---|---|---|---|---|---|---|
| TGGGCTAACG | ACGCCCACGT | ACGGTCCACG | TCGCCCTTCA | ATGTCTCTCT | TGACCAATAG | 300 |
| GCTAGTCCGG | CGAGTTGACA | AGGACCAGTG | GGGGCCGGAG | GTCACAGGGA | TGGACCCTGG | 360 |
| GCCTTGCCCT | TCCCGGTGGA | GTGGGAAAAG | CATGGGGCCA | CC | | 402 |

( 2 ) INFORMATION FOR SEQ ID NO:218:

( i ) SEQUENCE CHARACTERISTICS:
        ( A ) LENGTH: 404 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-EB20 VARIANT ( x i ) SEQUENCE DESCRIPTION: SEQ ID NO:218:

| | | | | | | |
|---|---|---|---|---|---|---|
| AGACGCAATG | ACTCGGCGCC | GACTCGGCGA | CCGGCCAAAA | GGTGGTGGAT | GGGTGATGCC | 60 |
| AGGGTTGGTA | GGTCGTAAAT | CCCGGTCATC | TTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGCCC | 180 |
| TACCGGTGTA | ATAAGGGCCC | GACGTCAGGC | TCGTCGTTAA | ACCGAGCCCG | TCACCCACCT | 240 |
| GGGCAAACGA | CGCCCACGTA | CGGTCCACGT | CGCCCTTCAA | TGCCTCTCTT | GGCCAATAGG | 300 |
| AGTTATCTCC | GGCGAGTTGG | CAAGGACCAG | TGGGGCCGG | GGGTTACGGG | GAAGGACCCC | 360 |
| GAACCCTGCC | CTTCCCGGTG | GGCCGGGAAA | TGCATGGGGC | CACC | | 404 |

( 2 ) INFORMATION FOR SEQ ID NO:219:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-T55806 VARIANT ( x i ) SEQUENCE DESCRIPTION: SEQ ID NO:219:

| | | | | | | |
|---|---|---|---|---|---|---|
| AGACGCAATG | ACTCGGCGCC | GACTCGGCGA | CCGGCCAAAA | GGTGGTGGAT | GGGTGATGCC | 60 |
| AGGGTTGGTA | GGTCGTAAAT | CCCGGTCATC | TTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGCCC | 180 |
| TACCGGTGGA | ATAAGGGCCC | GACGTCAGGC | TCGTCGTTAA | ACCGAGCCCG | TCACCCACCT | 240 |
| GGGCAAACGA | CGCTCACGTA | CGGTCCACGT | CGCCCTTCAA | TGTCTCTCTT | GACCAATAGG | 300 |
| TTTATCCGGC | GAGTTGACAA | GGACCAGTGG | GGCCGGGG | TTACGGGAC | GGACCCCGAA | 360 |
| CCCTGCCCTT | CCCGGTGGGC | CGGGAAATGC | ATGGGCCAC | C | | 401 |

( 2 ) INFORMATION FOR SEQ ID NO:220:

( i ) SEQUENCE CHARACTERISTICS:
        ( A ) LENGTH: 402 base pairs ( B ) TYPE: nucleic acid
( C ) STRANDEDNESS: double
( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: HGV-BG34 VARIANT ( x i ) SEQUENCE DESCRIPTION: SEQ ID NO:220:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGCCC | 180 |
| TACCGGTGTG | AATAAGGGCC | CGACGTCAGG | CTCGTCGTTA | AACCGAGCCC | GTCACCCACC | 240 |
| TGGGCAAACG | ACGCCCACGT | ACGGTCCACG | TCGCCCTTCA | ATGCCTCTCT | TGGCCAATAG | 300 |
| GAGTATCCGG | CGAGTTGACA | AGGACCAGTG | GGGGCCGGGA | GTCACGGGGA | TGGACCCCGG | 360 |
| GCTCTGCCCT | TCCCGGTGGA | ACGGAAACG | CATGGGGCCA | CC | | 402 |

( 2 ) INFORMATION FOR SEQ ID NO:221:

( i ) SEQUENCE CHARACTERISTICS:
( A ) LENGTH: 402 base pairs
( B ) TYPE: nucleic acid
( C ) STRANDEDNESS: double
( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: HGV-BE12 VARIANT ( x i ) SEQUENCE DESCRIPTION: SEQ ID NO:221:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGGCG | AGACCGCGCA | CGGTCCGCAG | GTGTTGGTCC | 180 |
| TACCGGTGTG | AATAAGGACC | CGACGTCAGG | CTCGTCGTTA | AACCGAGCCC | GCCACCCACC | 240 |
| TGGGCAAACG | ACGCCCACGT | ACGGTCCACG | TCGCCCTTCA | ATGCCTCTCT | TGGCCAATAG | 300 |
| GTTTATCCGG | CGAGTTGACA | AGGACCAGTG | GGGGCCGGGG | GCTCCGGGGA | AGAACCCCGA | 360 |
| GCCCCGCCCT | TCCCGGTGGG | ACGGAAATG | CATGGGGCCA | CC | | 402 |

( 2 ) INFORMATION FOR SEQ ID NO:222:

( i ) SEQUENCE CHARACTERISTICS:
( A ) LENGTH: 24 base pairs
( B ) TYPE: nucleic acid
( C ) STRANDEDNESS: single
( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: HGV-FORWARD PRIMER ( x i ) SEQUENCE DESCRIPTION: SEQ ID NO:222:

CCAAAAGGTG GTGGATGGGT GATG 24

( 2 ) INFORMATION FOR SEQ ID NO:223:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-FORWARD PRIMER ( x i ) SEQUENCE DESCRIPTION: SEQ ID NO:223:

GTGATGMCAG GGTTGGTAGG TCGT 24

( 2 ) INFORMATION FOR SEQ ID NO:224:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-FORWARD PRIMER ( x i ) SEQUENCE DESCRIPTION: SEQ ID NO:224:

GGTAGCCACT ATAGGTGGGT CTTAAG 26

( 2 ) INFORMATION FOR SEQ ID NO:225:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-REVERSE PRIMER ( x i ) SEQUENCE DESCRIPTION: SEQ ID NO:225:

GAGMGRCATT GWAGGGCGAC GTRGA 25

( 2 ) INFORMATION FOR SEQ ID NO:226:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: unknown (  i i  ) MOLECULE TYPE: DNA (  i i i  ) HYPOTHETICAL: NO (  i v  ) ANTI-SENSE: NO (  v i  ) ORIGINAL SOURCE:
       ( C ) INDIVIDUAL ISOLATE: HGV-REVERSE PRIMER (  x i  ) SEQUENCE DESCRIPTION: SEQ ID NO:226:

GRCATTGWAG GGCGACGTRG A                                                   21

( 2 ) INFORMATION FOR SEQ ID NO:227:

(  i  ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: unknown (  i i  ) MOLECULE TYPE: DNA (  i i i  ) HYPOTHETICAL: NO (  i v  ) ANTI-SENSE: NO (  v i  ) ORIGINAL SOURCE:
       ( C ) INDIVIDUAL ISOLATE: HGV-REVERSE PRIMER (  x i  ) SEQUENCE DESCRIPTION: SEQ ID NO:227:

CCCCACTGGT CYTTGYCAAC TC                                                 22

( 2 ) INFORMATION FOR SEQ ID NO:228:

(  i  ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: unknown (  i i  ) MOLECULE TYPE: DNA (  i i i  ) HYPOTHETICAL: NO (  i v  ) ANTI-SENSE: NO (  v i  ) ORIGINAL SOURCE:
       ( C ) INDIVIDUAL ISOLATE: PRIMER GV75- 36FE (  x i  ) SEQUENCE DESCRIPTION: SEQ ID NO:228:

GCGAGATCTA AAATGCAGGC CTGATGGGT                                     29

( 2 ) INFORMATION FOR SEQ ID NO:229:

(  i  ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: unknown (  i i  ) MOLECULE TYPE: DNA (  i i i  ) HYPOTHETICAL: NO (  i v  ) ANTI-SENSE: NO (  v i  ) ORIGINAL SOURCE:
       ( C ) INDIVIDUAL ISOLATE: PRIMER GV75- 7064RLE (  x i  ) SEQUENCE DESCRIPTION: SEQ ID NO:229:

GCGAGATCTA AAATGTGGAC TGCTAAGCC                                     29

( 2 ) INFORMATION FOR SEQ ID NO:230:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: PRIMER FV94- 28F ( x i ) SEQUENCE DESCRIPTION: SEQ ID NO:230:

GCGAGATCTA AAATGGCAAG CCCCAGAAAC CGACGCCTAT CTAAGT    46

( 2 ) INFORMATION FOR SEQ ID NO:231:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: PRIMER FV94- 2864R ( x i ) SEQUENCE DESCRIPTION: SEQ ID NO:231:

GGCATGATGA ATTCGCAACG AGGGCCGGGA CACCAAGAT    39

( 2 ) INFORMATION FOR SEQ ID NO:232:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: PRIMER FV94- 6439F ( x i ) SEQUENCE DESCRIPTION: SEQ ID NO:232:

GCGAGATCTA AAATGGGCCT CCGACACCCC GAAGGTTGT    39

( 2 ) INFORMATION FOR SEQ ID NO:233:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: PRIMER FV94- 9331R ( x i ) SEQUENCE DESCRIPTION: SEQ ID NO:233:

GCGAGATCTG AATTCTTCCC GGGGTGCACC CCTTCAGAT 39

( 2 ) INFORMATION FOR SEQ ID NO:234:

( i ) SEQUENCE CHARACTERISTICS:
    ( A ) LENGTH: 9327 base pairs
    ( B ) TYPE: nucleic acid
    ( C ) STRANDEDNESS: double
    ( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
    ( C ) INDIVIDUAL ISOLATE: 3ZHGV-6, HGV FROM PNF2161

( x i ) SEQUENCE DESCRIPTION: SEQ ID NO:234:

GCAAGCCCCA GAAACCGACG CCTATCTAAG TAGACGCAAT GACTCGGCGC CGACTCGGCG 60

ACCGGCCAAA AGGTGGTGGA TGGGTGATGA CAGGGTTGGT AGGTCGTAAA TCCCGGTCAC 120

CTTGGTAGCC ACTATAGGTG GGTCTTAAGA GAAGGTTAAG ATTCCTCTTG TGCCTGCGGC 180

GAGACCGCGC ACGGTCCACA GGTGTTGGCC CTACCGGTGG GAATAAGGGC CCGACGTCAG 240

GCTCGTCGTT AAACCGAGCC CGTTACCCAC CTGGGCAAAC GACGCCCACG TACGGTCCAC 300

GTCGCCCTTC AATGTCTCTC TTGACCAATA GGCGTAGCCG GCGAGTTGAC AAGGACCAGT 360

GGGGGCCGGG GGCTTGGAGA GGGACTCCAA GTCCCGCCCT TCCCGGTGGG CCGGGAAATG 420

CATGGGGCCA CCCAGCTCCG CGGCGGCCTG CAGCCGGGGT AGCCCAAGAA TCCTTCGGGT 480

GAGGGCGGGT GGCATTTCCT TTTTCTATAC CATCATGGCA GTCCTTCTGC TCCTTCTCGT 540

GGTTGAGGCC GGGGCCATTC TGGCCCCGGC CACCCACGCT TGTCGAGCGA ATGGGCAATA 600

TTTCCTCACA AATTGTTGTG CCCCGGAGGA CATCGGGTTC TGCCTGGAGG GTGGATGCCT 660

GGTGGCCCTG GGGTGCACGA TTTGCACTGA CCAATGCTGG CCACTGTATC AGGCGGGTTT 720

GGCTGTGCGG CCTGGCAAGT CCGCGGCCCA ACTGGTGGGG GAGCTGGGTA GCCTATACGG 780

GCCCCTGTCG GTCTCGGCCT ATGTGGCTGG GATCCTGGGC CTGGGTGAGG TGTACTCGGG 840

TGTCCTAACG GTGGGAGTCG CGTTGACGCG CCGGATCTAC CCGGTGCCTA ACCTGACGTG 900

TGCAGTCGCG TGTGAGTTAA AGTGGGAAAG TGAGTTTTGG AGATGGACTG AACAGCTGGC 960

CTCCAACTAC TGGATTCTGG AATACCTCTG GAAGGTCCCA TTTGATTTCT GGAGAGGCGT 1020

GATAAGCCTG ACCCCCTTGT TGGTTTGCGT GGCCGCATTG CTGCTGCTTG AGCAACGGGT 1080

TGTCATGGTC TTCCTGTTGG TGACGATGGC CGGGATGTCG CAAGGCGCCC CTGCCTCCGT 1140

TTTGGGGTCA CGCCCCTTTG ACTACGGGTT GACTTGGCAG ACCTGCTCTT GCAGGGCCAA 1200

CGGTTCGCGT TTTTCGACTG GGAGAAGGT GTGGGACCGT GGGAACGTTA CGCTTCAGTG 1260

TGACTGCCCT AACGGCCCCT GGGTGTGGTT GCCAGCCTTT TGCCAAGCAA TCGGCTGGGG 1320

TGACCCCATC ACTTATTGGA GCCACGGGCA AAATCAGTGG CCCCTTTCAT GCCCCCAGTA 1380

TGTCTATGGG TCTGCTACAG TCACTTGCGT GTGGGGTTCC GCTTCTTGGT ATGCCTCCAC 1440

CAGTGGTCGC GACTCGAAGA TAGATGTGTG GAGTTTAGTG CCAGTTGGCT CTGCCACCTG 1500

CACCATAGCC GCACTTGGAT CATCGGATCG CGACACGGTG CCTGGGCTCT CCGAGTGGGG 1560

AATCCCGTGC GTGACGTGTG TTCTGGACCG TCGGCCTGCT TCATGCGGCA CCTGTGTGAG 1620

-continued

| | | | | | | |
|---|---|---|---|---|---|---|
| GGACTGCTGG | CCCGAGACCG | GGTCGGTTAG | GTTCCCATTC | CATCGGTGCG | GCGTGGGGCC | 1680 |
| TCGGCTGACA | AAGGACTTGG | AAGCTGTGCC | CTTCGTCAAT | AGGACAACTC | CCTTCACCAT | 1740 |
| TAGGGGGCCC | CTGGGCAACC | AGGGCCGAGG | CAACCCGGTG | CGGTCGCCCT | TGGGTTTTGG | 1800 |
| GTCCTACGCC | ATGACCAGGA | TCCGAGATAC | CCTACATCTG | GTGGAGTGTC | CCACACCAGC | 1860 |
| CATCGAGCCT | CCCACCGGGA | CGTTTGGGTT | CTTCCCCGGG | ACGCCGCCTC | TCAACAACTG | 1920 |
| CATGCTCTTG | GGCACGGAAG | TGTCCGAGGC | ACTTGGGGGG | GCTGGCCTCA | CGGGGGGGTT | 1980 |
| CTATGAACCC | CTGGTGCGCA | GGTGTTCGGA | GCTGATGGGA | AGCCGAAATC | CGGTTTGTCC | 2040 |
| GGGGTTTGCA | TGGCTCTCTT | CGGGCAGGCC | TGATGGGTTT | ATACATGTCC | AGGGTCACTT | 2100 |
| GCAGGAGGTG | GATGCAGGCA | ACTTCATCCC | GCCCCGCGC | TGGTTGCTCT | TGGACTTTGT | 2160 |
| ATTTGTCCTG | TTATACCTGA | TGAAGCTGGC | TGAGGCACGG | TTGGTCCCGC | TGATCTTGCT | 2220 |
| GCTGCTATGG | TGGTGGGTGA | ACCAGCTGGC | AGTCCTAGGG | CTGCCGGCTG | TGGAAGCCGC | 2280 |
| CGTGGCAGGT | GAGGTCTTCG | CGGGCCCTGC | CCTGTCCTGG | TGTCTGGGAC | TCCCGGTCGT | 2340 |
| CAGTATGATA | TTGGGTTTGG | CAAACCTGGT | GCTGTACTTT | AGATGGTTGG | GACCCCAACG | 2400 |
| CCTGATGTTC | CTCGTGTTGT | GGAAGCTTGC | TCGGGGAGCT | TTCCCGCTGG | CCCTCTTGAT | 2460 |
| GGGGATTTCG | GCGACCCGCG | GGCGCACCTC | AGTGCTCGGG | GCCGAGTTCT | GCTTCGATGC | 2520 |
| TACATTCGAG | GTGGACACTT | CGGTGTTGGG | CTGGGTGGTG | GCCAATGTGG | TAGCTTGGGC | 2580 |
| CATTGCGCTC | CTGAGCTCGA | TGAGCGCAGG | GGGGTGGAGG | CACAAAGCCG | TGATCTATAG | 2640 |
| GACGTGGTGT | AAGGGGTACC | AGGCAATCCG | TCAAAGGGTG | GTGAGGAGCC | CCCTCGGGGA | 2700 |
| GGGGCGGCCT | GCCAAACCCC | TGACCTTTGC | CTGGTGCTTG | GCCTCGTACA | TCTGGCCAGA | 2760 |
| TGCTGTGATG | ATGGTGGTGG | TTGCCTTGGT | TCTTCTCTTT | GGCCTGTTCG | ACGCGTTGGA | 2820 |
| TTGGGCCTTG | GAGGAGATCT | TGGTGTCCCG | GCCCTCGCTG | CGGCGTTTGG | CTCGGGTGGT | 2880 |
| TGAGTGCTGT | GTGATGGCGG | GTGAGAAGGC | CACAACCGTC | CGGCTGGTCT | CCAAGATGTG | 2940 |
| TGCGAGAGGA | GCTTATTTGT | TCGATCATAT | GGGCTCATTT | TCGCGTGCTG | TCAAGGAGCG | 3000 |
| CCTGTTGGAA | TGGGACGCGG | CTCTTGAACC | TCTGTCATTC | ACTAGGACGG | ACTGTCGCAT | 3060 |
| CATACGGGAT | GCCGCGAGGA | CTTTGTCCTG | CGGGCAATGC | GTCATGGGTT | TACCCGTGGT | 3120 |
| TGCGCGCCGT | GGTGATGAGG | TTCTCATCGG | CGTCTTCCAG | GATGTGAATC | ATTTGCCTCC | 3180 |
| CGGGTTTGTT | CCGACCGCGC | CTGTTGTCAT | CCGACGGTGC | GGAAAGGGCT | TCTTGGGGGT | 3240 |
| CACAAAGGCT | GCCTTGACAG | GTCGGGATCC | TGACTTACAT | CCAGGGAACG | TCATGGTGTT | 3300 |
| GGGGACGGCT | ACGTCGCGAA | GCATGGGAAC | ATGCTTGAAC | GGCCTGCTGT | TCACGACCTT | 3360 |
| CCATGGGGCT | TCATCCCGAA | CCATCGCCAC | ACCCGTGGGG | GCCCTTAATC | CCAGATGGTG | 3420 |
| GTCAGCCAGT | GATGATGTCA | CGGTGTATCC | ACTCCCGGAT | GGGGCTACTT | CGTTAACGCC | 3480 |
| TTGTACTTGC | CAGGCTGAGT | CCTGTTGGGT | CATCAGATCC | GACGGGCCC | TATGCCATGG | 3540 |
| CTTGAGCAAG | GGGACAAGG | TGGAGCTGGA | TGTGGCCATG | GAGGTCCCTG | ATTTCCGTGG | 3600 |
| CTCGTCTGGC | TCACCGGTCC | TATGTGACGA | GGGGCACGCA | GTAGGAATGC | TCGTGTCTGT | 3660 |
| GCTTCACTCC | GGTGGTAGGG | TCACCGCGGC | ACGGTTCACT | AGGCCGTGGA | CCCAAGTGCC | 3720 |
| AACAGATGCC | AAAACCACCA | CTGAACCCCC | TCCGGTGCCG | GCCAAAGGAG | TTTTCAAAGA | 3780 |
| GGCCCCGTTG | TTTATGCCTA | CGGGAGCGGG | AAAGAGCACT | CGCGTCCCGT | TGGAGTACGG | 3840 |
| CAACATGGGG | CACAAGGTCT | TAGTCTTGAA | CCCCTCAGTG | GCCACTGTGC | GGGCCATGGG | 3900 |
| CCCGTACATG | GAGCGGCTGG | CGGGTAAACA | TCCAAGTATA | TACTGTGGGC | ATGATACAAC | 3960 |
| TGCTTTCACA | AGGATCACTG | ACTCCCCCCT | GACGTATTCA | ACCTATGGGA | GGTTTTTGGC | 4020 |

```
CAACCCTAGG  CAGATGCTAC  GGGGCGTTTC  GGTGGTCATT  TGTGATGAGT  GCCACAGTTA   4080

TGACTCAACC  GTGCTGTTAG  GCATTGGGAG  GGTTCGGGAG  CTGGCGCGTG  GGTGCGGAGT   4140

GCAACTAGTG  CTCTACGCCA  CCGCTACGCC  TCCCGGATCC  CCTATGACGC  AGCACCCTTC   4200

CATAATTGAG  ACAAAATTGG  ACGTGGGCGA  GATTCCCTTT  TATGGGCACG  GAATACCCCT   4260

CGAGCGGATG  CGAACCGGAA  GGCACCTCGT  GTTCTGCCAT  TCTAAGGCTG  AGTGCGAGCG   4320

CCTTGCTGGC  CAGTTCTCCG  CTAGGGGGGT  CAATGCCATT  GCCTATTATA  GGGGTAAAGA   4380

CAGTTCTATC  ATCAAGGATG  GGACCTGGT   GGTCTGTGCC  ACAGACGCGC  TTTCCACTGG   4440

GTACACTGGA  AATTTCGACT  CCGTCACCGA  CTGTGGATTA  GTGGTGGAGG  AGGTCGTTGA   4500

GGTGACCCTT  GATCCTACCA  TTACCATCTC  CCTGCGGACA  GTGCCTGCGT  CGGCTGAACT   4560

GTCGATGCAA  AGACGAGGAC  GCACGGGTAG  GGGCAGGTCT  GGACGCTACT  ACTACGCGGG   4620

GGTGGGCAAA  GCCCTGCGG   GTGTGGTGCG  CTCAGGTCCT  GTCTGGTCGG  CGGTGGAAGC   4680

TGGAGTGACC  TGGTACGGAA  TGGAACCTGA  CTTGACAGCT  AACCTACTGA  GACTTTACGA   4740

CGACTGCCCT  TACACCGCAG  CCGTCGCGGC  TGATATCGGA  GAAGCCGCGG  TGTTCTTCTC   4800

TGGGCTCGCC  CCATTGAGGA  TGCACCCTGA  TGTCAGCTGG  GCAAAAGTTC  GCGGCGTCAA   4860

CTGGCCCCTC  TTGGTGGGTG  TTCAGCGGAC  CATGTGTCGG  GAAACACTGT  CTCCCGGCCC   4920

ATCGGATGAC  CCCCAATGGG  CAGGTCTGAA  GGGCCCAAAT  CCTGTCCCAC  TCCTGCTGAG   4980

GTGGGGCAAT  GATTTACCAT  CTAAAGTGGC  CGGCCACCAC  ATAGTGGACG  ACCTGGTCCG   5040

GAGACTCGGT  GTGGCGGAGG  GTTACGCCCG  CTGCGACGCT  GGGCCGATCT  TGATGATCGG   5100

TCTAGCTATC  GCGGGGGGAA  TGATCTACGC  GTCGTACACC  GGGTCGCTAG  TGGTGGTGAC   5160

AGACTGGGAT  GTGAAGGGGG  GTGGCGCCCC  CCTTTATCGG  CATGGAGACC  AGGCCACGCC   5220

TCAGCCGGTG  GTGCAGGTTC  CTCCGGTAGA  CCATCGGCCG  GGGGGTGAAT  CAGCACCATC   5280

GGATGCCAAG  ACAGTGACAG  ATGCGGTGGC  AGCGATCCAG  GTGGACTGCG  ATTGGACTAT   5340

CATGACTCTG  TCGATCGGAG  AAGTGTTGTC  CTTGGCTCAG  GCTAAGACGG  CCGAGGCCTA   5400

CACAGCAGCC  ACCAAGTGGC  TCGCTGGCTG  CTATACGGGG  ACGCGGGCCG  TTCCCACTGT   5460

ATCCATTGTT  GACAAGCTCT  TCGCCGGAGG  GTGGGCGGCT  GTGGTGGGCC  ATTGCCACAA   5520

CGTGATTGCT  GCGGCGGTGG  CGGCCTACGG  GGCTTCAAAG  AGCCCGCCGT  TGGCAGCCGC   5580

GGCTTCCTAC  CTGATGGGGT  TGGGCGTTGG  AGGCAACGCT  CAGACGCGTC  TGGCATCTGC   5640

CCTCCTATTG  GGGGCTGCTG  GAACCGCCTT  GGGCACTCCT  GTCGTGGGCT  TGACCATGGC   5700

AGGTGCGTTC  ATGGGGGGCG  CCAGTGTCTC  CCCCTCCTTG  GTCACCATTT  TATTGGGGGC   5760

CGTCGGAGGT  TGGGAGGGTG  TTGTCAACGC  GGCGAGCCTA  GTCTTTGACT  TCATGGCGGG   5820

GAAACTTTCA  TCAGAAGATC  TGTGGTATGC  CATCCCGGTA  CTGACCAGCC  CGGGGGCGGG   5880

CCTTGCGGGG  ATCGCTCTCG  GGTTGGTTTT  GTATTCAGCT  AACAACTCTG  GCACTACCAC   5940

TTGGTTGAAC  CGTCTGCTGA  CTACGTTACC  AAGGTCTTCA  TGTATCCCGG  ACAGTTACTT   6000

TCAGCAAGTT  GACTATTGCG  ACAAGGTCTC  AGCCGTGCTC  CGGCGCCTGA  GCCTCACCCG   6060

CACAGTGGTT  GCCCTGGTCA  ACAGGGAGCC  TAAGGTGGAT  GAGGTACAGG  TGGGGTATGT   6120

CTGGGACCTG  TGGGAGTGGA  TCATGCGCCA  AGTGCGCGTG  GTCATGGCCA  GACTCAGGGC   6180

CCTCTGCCCC  GTGGTGTCAT  TACCCTTGTG  GCACTGCGGG  GAGGGTGGT   CCGGGGAATG   6240

GTTGCTTGAC  GGTCATGTTG  AGAGTCGCTG  CCTCTGTGGC  TGCGCGATCA  CTGGTGACGT   6300

TCTGAATGGG  CAACTCAAAG  AACCAGTTTA  CTCTACCAAG  CTGTGCCGGC  ACTATTGGAT   6360

GGGGACTGTC  CCTGTGAACA  TGCTGGGTTA  CGGTGAAACG  TCGCCTCTCC  TGGCCTCCGA   6420
```

```
CACCCCGAAG  GTTGTGCCCT  TCGGGACGTC  TGGCTGGGCT  GAGGTGGTGG  TGACCACTAC    6480
CCACGTGGTA  ATCAGGAGAA  CCTCCGCCTA  TAAGCTGCTG  CGCCAGCAAA  TCCTATCGGC    6540
TGCTGTAGCT  GAGCCCTACT  ACGTCGACGG  CATTCCGGTC  TCATGGACG   CGGACGCTCG    6600
TGCGCCCGCC  ATGGTCTATG  GCCCTGGGCA  AAGTGTTACC  ATTGACGGGG  AGCGCTACAC    6660
CCTGCCTCAT  CAACTGAGGC  TCAGGAATGT  GGCGCCCTCT  GAGGTTTCAT  CCGAGGTGTC    6720
CATTGACATT  GGGACGGAGA  CTGGAGACTC  AGAACTGACT  GAGGCCGATC  TGCCGCCGGC    6780
GGCTGCTGCT  CTCCAAGCGA  TCGAGAATGC  TGCGAGGATT  CTTGAACCGC  ACATTGATGC    6840
CATCATGGAG  GACTGCAGTA  CACCCTCTCT  TTGTGGTAGT  AGCCGAGAGA  TGCCTGTATG    6900
GGGAGAAGAC  ATCCCCGTA   CTCCATCGCC  AGCACTTATC  TCGGTTACTG  AGAGCAGCTC    6960
AGATGAGAAG  ACCCCGTCGG  TGTCCTCCTC  GCAGGAGGAT  ACCCCGTCCT  CTGACTCATT    7020
CGAGGTCATC  CAAGAGTCCG  AGACAGCCGA  AGGGGAGGAA  AGCGTCTTCA  ACGTGGCTCT    7080
TTCCGTATTA  GAAGCCTCAT  TTCCACAGAG  CGACGCGACC  AGGAAGCTTA  CCGTCAAGAT    7140
GTCGTGCTGC  GTTGAAAAGA  GCGTCACGCG  CTTTTTCTCA  TTGGGGTTGA  CGGTGGCTGA    7200
TGTTGCTAGC  CTGTGTGAGA  TGGAAATCCA  GAACCATACA  GCCTATTGTG  ACAAGGTGCG    7260
CACTCCGCTT  GAATTGCAGG  TTGGGTGCTT  GGTGGGCAAT  GAACTTACCT  TTGAATGTGA    7320
CAAGTGTGAG  GCTAGGCAAG  AAACCTTGGC  CTCCTTCTCT  TACATTTGGT  CTGGAGTGCC    7380
GCTGACTAGG  GCCACGCCGG  CCAAGCCTCC  CGTGGTGAGG  CCGGTTGGCT  CTTTATTAGT    7440
GGCCGACACT  ACTAAGGTGT  ATGTTACCAA  TCCAGACAAT  GTGGGACGGA  GGGTGGACAA    7500
GGTGACCTTC  TGGCGTGCTC  CTAGGGTTCA  TGATAAGTAC  CTCGTGGACT  CTATTGAGCG    7560
CGCTAAGAGG  GCCGCTCAAG  CCTGCCTAAG  CATGGGTTAC  ACTTATGAGG  AAGCAATAAG    7620
GACTGTAAGG  CCACATGCTG  CCATGGGCTG  GGGATCTAAG  GTGTCGGTTA  AGGACTTAGC    7680
CACCCCCGCG  GGGAAGATGG  CCGTCCATGA  CCGGCTCCAG  GAGATACTTG  AAGGGACTCC    7740
GGTCCCCTTT  ACTCTTACTG  TGAAAAAGGA  GGTGTTCTTC  AAAGACCGGA  AGGAGGAGGA    7800
GGCCCCCCGC  CTCATTGTGT  TCCCCCCCCT  GGACTTCCGG  ATAGCTGAAA  AGCTCATCTT    7860
GGGAGACCCA  GACCGGGTAG  CCAAGGCGGT  GTTGGGGGGG  GCCTACGCCT  TCCAGTACAC    7920
CCCAAATCAG  CGAGTTAAGG  AGATGCTCAA  GCTATGGGAG  TCTAAGAAGA  CCCCTTGCGC    7980
CATCTGTGTG  GACGCCACCT  GCTTCGACAG  TAGCATAACT  GAAGAGGACG  TGGCTTTGGA    8040
GACAGAGCTG  TACGCTCTGG  CCTCTGACCA  TCCAGAATGG  GTGCGGGCAC  TTGGGAAATA    8100
CTATGCCTCA  GGCACCATGG  TCACCCCGGA  AGGGGTGCCC  GTCGGTGAGA  GGTATTGCAG    8160
ATCCTCGGGT  GTCCTAACAA  CTAGCGCGAG  CAACTGCTTG  ACCTGCTACA  TCAAGGTGAA    8220
AGCCGCCTGT  GAGAGGGTGG  GGCTGAAGAA  TGTCTCTCTT  CTCATAGCCG  GCGATGACTG    8280
CTTGATCATA  TGTGAGCGGC  CAGTGTGCGA  CCCAAGCGAC  GCTTGGGCA   GAGCCCTAGC    8340
GAGCTATGGG  TACGCGTGCG  AGCCCTCATA  TCATGCATCC  TTGGACACGG  CCCCCTTCTG    8400
CTCCACTTGG  CTTGCTGAGT  GCAATGCAGA  TGGGAAGCGC  CATTTCTTCC  TGACCACGGA    8460
CTTCCGGAGG  CCGCTCGCTC  GCATGTCGAG  TGAGTATAGT  GACCCGATGG  CTTCGGCGAT    8520
CGGTTACATC  CTCCTTTATC  CTTGGCACCC  CATCACACGG  TGGGTCATCA  TCCCTCATGT    8580
GCTAACGTGC  GCATTCAGGG  GTGGAGGCAC  ACCGTCTGAT  CCGGTTTGGT  GCCAGGTACA    8640
TGGTAACTAC  TACAAGTTTC  CACTGGACAA  ACTGCCTAAC  ATCATCGTGG  CCCTCCACGG    8700
ACCAGCAGCG  TTGAGGGTTA  CCGCAGACAC  AACTAAAACA  AAGATGGAGG  CTGGTAAGGT    8760
TCTGAGCGAC  CTCAAGCTCC  CTGGCTTAGC  AGTCCACCGA  AAGAAGGCCG  GGGCGTTGCG    8820
```

```
AACACGCATG  CTCCGCTCGC  GCGGTTGGGC  TGAGTTGGCT  AGGGGCTTGT  TGTGGCATCC    8880

AGGCCTACGG  CTTCCTCCCC  CTGAGATTGC  TGGTATCCCG  GGGGGTTTCC  CTCTCTCCCC    8940

CCCCTATATG  GGGGTGGTAC  ACCAATTGGA  TTTTACAAGC  CAGAGGAGTC  GCTGGCGGTG    9000

GTTGGGGTTC  TTAGCCCTGC  TCATCGTAGC  CCTCTTCGGG  TGAACTAAAT  TCATCTGTTG    9060

CGGCGAGGTC  TGGTGACTGA  TCGTCACCGG  AGGAGGTTCC  CGCCCTCCCC  GCCCAGGGG    9120

TCTCCCCGCT  GGGTAAAAAG  GGCCCGGCCT  TGGGAGGCAT  GGTGGTTACT  AACCCCTGG    9180

CAGGGTTAAA  GCCTGATGGT  GCTAATGCAC  TGCCACTTCG  GTGGCGGGTC  GCTACCTTAT    9240

AGCGTAATCC  GTGACTACGG  GCTGCTCGCA  GAGCCCTCCC  CGGATGGGGC  ACAGTGCACT    9300

GAGATCTGAA  GGGGTGCACC  CCGGGAA                                          9327
```

(2) INFORMATION FOR SEQ ID NO:235:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer GLI-F (xi) SEQUENCE DESCRIPTION: SEQ ID NO:235:

```
TAGCATGGCC  TTTGCAGGGC  TG                                                 22
```

(2) INFORMATION FOR SEQ ID NO:236:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer GLI-R (xi) SEQUENCE DESCRIPTION: SEQ ID NO:236:

```
AAGCTGTGAC  CGTCTCCG                                                       18
```

(2) INFORMATION FOR SEQ ID NO:237:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer GE1-NF ( x i ) SEQUENCE DESCRIPTION: SEQ ID NO:237:

GCCGCCATGG CGGGGAAACT TTCATCAGAA G 31

( 2 ) INFORMATION FOR SEQ ID NO:238:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GE1- NR ( x i ) SEQUENCE DESCRIPTION: SEQ ID NO:238:

GCGCGGATCC TAGTGACACC ACGGGGCAGA GG 32

( 2 ) INFORMATION FOR SEQ ID NO:239:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GE57F ( x i ) SEQUENCE DESCRIPTION: SEQ ID NO:239:

GCCGCCATGG CTCTCTTGAC CAATAGGTTT ATC 33

( 2 ) INFORMATION FOR SEQ ID NO:240:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GE57R ( x i ) SEQUENCE DESCRIPTION: SEQ ID NO:240:

GCGCGGATCC AGAAATGCCA CCCGCCCTCA C 31

( 2 ) INFORMATION FOR SEQ ID NO:241:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
    ( C ) INDIVIDUAL ISOLATE: GE57 amino acid sequence ( x i ) SEQUENCE DESCRIPTION: SEQ ID NO:241:

```
Met  Ser  Leu  Leu  Thr  Asn  Arg  Phe  Ile  Arg  Arg  Val  Asp  Lys  Asp  Gln
 1                   5                        10                       15

Trp  Gly  Pro  Gly  Val  Thr  Gly  Thr  Asp  Pro  Glu  Pro  Cys  Pro  Ser  Arg
              20                        25                       30

Trp  Ala  Gly  Lys  Cys  Met  Gly  Pro  Pro  Ser  Ser  Ala  Ala  Ala  Cys  Ser
              35                        40                       45

Arg  Gly  Ser  Pro  Arg  Ile  Leu  Arg  Val  Arg  Ala  Gly  Gly
              50                        55                       60
```

( 2 ) INFORMATION FOR SEQ ID NO:242:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Forward Primer for E1

( x i ) SEQUENCE DESCRIPTION: SEQ ID NO:242:

GCGCAGATCT AAAATGAGCC GTGGTGGCAT TTCCTTTTTC TATACCATCA TG    52

( 2 ) INFORMATION FOR SEQ ID NO:243:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Reverse Primer for E1

( x i ) SEQUENCE DESCRIPTION: SEQ ID NO:243:

GCGCAGATCT CCAGAAATCA AATGGGACCT TCCAGAGG    38

( 2 ) INFORMATION FOR SEQ ID NO:244:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Forward Primer for E2 with insect
signal sequence ( x i ) SEQUENCE DESCRIPTION: SEQ ID NO:244:

CGCGAGATCT GTCGCAAGGC GCCCCT 26

( 2 ) INFORMATION FOR SEQ ID NO:245:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Reverse Primer for E2 with insect
signal sequence ( x i ) SEQUENCE DESCRIPTION: SEQ ID NO:245:

GCGCAGATCT AGTTGCCTGC ATCCACCT 28

( 2 ) INFORMATION FOR SEQ ID NO:246:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Forward Primer for E2 with HGV
signal sequence ( x i ) SEQUENCE DESCRIPTION: SEQ ID NO:246:

CGCGAGATCT AAAATGAAAC TGCTTGTCAT GGTCTTCCTG TT 42

( 2 ) INFORMATION FOR SEQ ID NO:247:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Reverse Primer for E2 with HGV
signal sequence ( x i ) SEQUENCE DESCRIPTION: SEQ ID NO:247:

GCGCAGATCT AGTTGCCTGC ATCCACCT 28

( 2 ) INFORMATION FOR SEQ ID NO:248:

(i) SEQUENCE CHARACTERISTICS:
    (A) LENGTH: 34 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: NO (vi) ORIGINAL SOURCE:
    (C) INDIVIDUAL ISOLATE: Forward Primer for NS2a (xi) SEQUENCE DESCRIPTION: SEQ ID NO:248:

GCGCAGATCT GGCCGTGGCA GGTGAGGTCT TCGC      34

(2) INFORMATION FOR SEQ ID NO:249:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: NO (vi) ORIGINAL SOURCE:
    (C) INDIVIDUAL ISOLATE: Reverse Primer for NS2a (xi) SEQUENCE DESCRIPTION: SEQ ID NO:249:

GCGCAGATCT TAACGCCGCA ACGAGGGCCG G      31

(2) INFORMATION FOR SEQ ID NO:250:

(i) SEQUENCE CHARACTERISTICS:
    (A) LENGTH: 46 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: NO (vi) ORIGINAL SOURCE:
    (C) INDIVIDUAL ISOLATE: Forward Primer for NS2b (xi) SEQUENCE DESCRIPTION: SEQ ID NO:250:

GCGCGGATCC AAAATGATCG CTCGGGTGGT TGAGTGCTGT GTGATG      46

(2) INFORMATION FOR SEQ ID NO:251:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: NO (vi) ORIGINAL SOURCE:

(C) INDIVIDUAL ISOLATE: Reverse Primer for NS2b (xi) SEQUENCE DESCRIPTION: SEQ ID NO:251:

GCGCGGATCC AGGCGCGGTC GGAACAAACC CG 32

(2) INFORMATION FOR SEQ ID NO:252:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Forward Primer NS3

(xi) SEQUENCE DESCRIPTION: SEQ ID NO:252:

GCGAGATCTA AAATGTGCGG AAAGGGCTTC TTGGGGGTC 39

(2) INFORMATION FOR SEQ ID NO:253:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Reverse Primer NS3

(xi) SEQUENCE DESCRIPTION: SEQ ID NO:253:

GCGAGATCTC ATCTCCGGAC CAGGTCGTCC ACTATGTGG 39

(2) INFORMATION FOR SEQ ID NO:254:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Forward Primer NS4a (xi) SEQUENCE DESCRIPTION: SEQ ID NO:254:

GGCGGATCCA AAATGATCGG TGTGGCGGAG G 31

(2) INFORMATION FOR SEQ ID NO:255:

(i) SEQUENCE CHARACTERISTICS:
        (A) LENGTH: 26 base pairs
        (B) TYPE: nucleic acid
        (C) STRANDEDNESS: single
        (D) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Reverse Primer NS4a ( x i ) SEQUENCE DESCRIPTION: SEQ ID NO:255:

GGCGGGATCC ATGCGCCGGA GCACGG 26

( 2 ) INFORMATION FOR SEQ ID NO:256:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Forward Primer NS4b ( x i ) SEQUENCE DESCRIPTION: SEQ ID NO:256:

GCGGGATCCA AAATGATCAG CCTCACCCGC ACAG 34

( 2 ) INFORMATION FOR SEQ ID NO:257:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Reverse Primer NS5a ( x i ) SEQUENCE DESCRIPTION: SEQ ID NO:257:

GGCGGGATCC TACCTCCTGA TTACCACGT 29

( 2 ) INFORMATION FOR SEQ ID NO:258:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Forward Primer NS5a ( x i ) SEQUENCE DESCRIPTION: SEQ ID NO:258:

GCGAGATCTA AAATGACCTC CGCCTATAAG CTGCTGCGCC AG 42

( 2 ) INFORMATION FOR SEQ ID NO:259:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Reverse Primer NS5a ( x i ) SEQUENCE DESCRIPTION: SEQ ID NO:259:

GGCAGATCTA CCTCCGTCCC ACATTGTCTG GATTGGTAAC     40

( 2 ) INFORMATION FOR SEQ ID NO:260:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Forward Primer NS5b ( x i ) SEQUENCE DESCRIPTION: SEQ ID NO:260:

GCGAGATCTA AAATGGTGGA CAAGGTGACC TTCTGGCGTG CTC     43

( 2 ) INFORMATION FOR SEQ ID NO:261:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Reverse Primer NS5b ( x i ) SEQUENCE DESCRIPTION: SEQ ID NO:261:

GCGAGATCTC ACCCGAAGAG GGCTACGATG AGCAGG     36

( 2 ) INFORMATION FOR SEQ ID NO:262:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO (v i) ORIGINAL SOURCE:
(C) INDIVIDUAL ISOLATE: Forward Primer E1-E2-NS2a (x i) SEQUENCE DESCRIPTION: SEQ ID NO:262:

GCGCAGATCT AAAATGAGCC GTGGTGGCAT TTCCTTTTTC TATACCATCA TG          52

(2) INFORMATION FOR SEQ ID NO:263:

(i) SEQUENCE CHARACTERISTICS:
(A) LENGTH: 31 base pairs
(B) TYPE: nucleic acid
(C) STRANDEDNESS: single
(D) TOPOLOGY: linear (i i) MOLECULE TYPE: DNA (i i i) HYPOTHETICAL: NO (i v) ANTI-SENSE: NO (v i) ORIGINAL SOURCE:
(C) INDIVIDUAL ISOLATE: Reverse Primer E1-E2-NS2a (x i) SEQUENCE DESCRIPTION: SEQ ID NO:263:

GCGCAGATCT TAACGCCGCA ACGAGGGCCG G          31

(2) INFORMATION FOR SEQ ID NO:264:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: DNA (i i i) HYPOTHETICAL: NO (i v) ANTI-SENSE: NO (v i) ORIGINAL SOURCE:
(C) INDIVIDUAL ISOLATE: Primer 9E3- REV (x i) SEQUENCE DESCRIPTION: SEQ ID NO:264:

GCTGGCTGAG GCACGGTTGG TC          22

(2) INFORMATION FOR SEQ ID NO:265:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: DNA (i i i) HYPOTHETICAL: NO (i v) ANTI-SENSE: NO (v i) ORIGINAL SOURCE:
(C) INDIVIDUAL ISOLATE: Primer E39- 94PR (x i) SEQUENCE DESCRIPTION: SEQ ID NO:265:

CACCATCATC ACAGCATCTG GC          22

(2) INFORMATION FOR SEQ ID NO:266:

(i) SEQUENCE CHARACTERISTICS:
(A) LENGTH: 32 base pairs
(B) TYPE: nucleic acid (C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer GEP-F12

(xi) SEQUENCE DESCRIPTION: SEQ ID NO:266:

GCAACCATGG AACCTGCCAA ACCCCTGACC TT 32

(2) INFORMATION FOR SEQ ID NO:267:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer GEP-R12

(xi) SEQUENCE DESCRIPTION: SEQ ID NO:267:

AGCCCCATGG AAGGTCGTGA A 21

(2) INFORMATION FOR SEQ ID NO:268:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer GEP-F14

(xi) SEQUENCE DESCRIPTION: SEQ ID NO:268:

TTGGGATCCC TCGTGTTCCG CCATTCTAAG 30

(2) INFORMATION FOR SEQ ID NO:269:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer GEP-R13

(xi) SEQUENCE DESCRIPTION: SEQ ID NO:269:

TATGGATCCT GGTAAATCAT TGCCCCACCT 30

(2) INFORMATION FOR SEQ ID NO:270:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer 470EP- F8

(xi) SEQUENCE DESCRIPTION: SEQ ID NO:270:

GCTGAATTCG CCATGGCGAC GTGCGCATTC AGGGGTGGA 39

(2) INFORMATION FOR SEQ ID NO:271:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer GEP- R14

(xi) SEQUENCE DESCRIPTION: SEQ ID NO:271:

GGAGGATCCG CGACCCGCCA CCGAAGT 27

(2) INFORMATION FOR SEQ ID NO:272:

(i) SEQUENCE CHARACTERISTICS:
        (A) LENGTH: 48 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (C) INDIVIDUAL ISOLATE: Y5 epitope (xi) SEQUENCE DESCRIPTION: SEQ ID NO:272:

```
Ile Asp Gly Glu Arg Tyr Thr Leu Pro His Gln Leu Arg Leu Arg Asn
 1               5                  10                  15
Val Ala Pro Ser Glu Val Ser Ser Glu Val Ser Ile Asp Ile Gly Thr
             20                  25                  30
Glu Ala Glu Asn Ser Glu Leu Thr Glu Ala Asp Leu Pro Pro Ala Ala
         35                  40                  45
```

(2) INFORMATION FOR SEQ ID NO:273:

(i) SEQUENCE CHARACTERISTICS:
        (A) LENGTH: 55 amino acids
        (B) TYPE: amino acid ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
                ( C ) INDIVIDUAL ISOLATE: Q9 Epitope ( x i ) SEQUENCE DESCRIPTION: SEQ ID NO:273:

| Cys | Gly | Leu | Leu | Thr | Arg | His | His | Thr | Ala | Leu | Asn | His | Pro | Ser | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Thr | Pro | Gln | Arg | Gly | Pro | Gly | His | Gln | Asp | Leu | Leu | Gln | Gly | Pro | Ile |
|     |     |     | 20  |     |     |     |     | 25  |     |     |     |     | 30  |     |     |
| Gln | Arg | Val | Glu | Gln | Ala | Lys | Glu | Lys | Asp | Gln | Gly | Asn | His | His | His |
|     |     | 35  |     |     |     |     | 40  |     |     |     |     | 45  |     |     |     |
| His | His | Ser | Ile | Trp | Pro | Asp |     |     |     |     |     |     |     |     |     |
|     | 50  |     |     |     |     | 55  |     |     |     |     |     |     |     |     |     |

( 2 ) INFORMATION FOR SEQ ID NO:274:

( i ) SEQUENCE CHARACTERISTICS:
                ( A ) LENGTH: 35 amino acids
                ( B ) TYPE: amino acid
                ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
                ( C ) INDIVIDUAL ISOLATE: Q11 Epitope ( x i ) SEQUENCE DESCRIPTION: SEQ ID NO:274:

| Ala | Ala | Val | Ala | Glu | Pro | Tyr | Tyr | Val | Asp | Gly | Ile | Pro | Val | Ser | Trp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Asp | Ala | Asp | Ala | Arg | Ala | Pro | Ala | Met | Val | Tyr | Gly | Pro | Gly | Gln | Ser |
|     |     |     | 20  |     |     |     |     | 25  |     |     |     |     | 30  |     |     |
| Val | Thr | Ile |     |     |     |     |     |     |     |     |     |     |     |     |     |
|     |     | 35  |     |     |     |     |     |     |     |     |     |     |     |     |     |

( 2 ) INFORMATION FOR SEQ ID NO:275:

( i ) SEQUENCE CHARACTERISTICS:
                ( A ) LENGTH: 225 base pairs
                ( B ) TYPE: nucleic acid
                ( C ) STRANDEDNESS: both
                ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
                ( C ) INDIVIDUAL ISOLATE: Q7-12-1 env clone ( x i ) SEQUENCE DESCRIPTION: SEQ ID NO:275:

| GTGCCCTTCG | TCAACAGGAC | AACTCTCTTC | ACCATTAGGG | GGCCCCTGGG | CAACCAGGGC | 60 |
| CGAGGCAACC | CGGTGCGGTC | GCCCTTGGGT | TTTGGGTCCT | ACGCCATGAC | CAGGATCCGA | 120 |
| GATACCCTAC | ATCTGGTGGA | GTGTCCCACA | CCAGCCATCG | AGCCTCCCAC | CGGGACGTCT | 180 |
| GGGTTCTTCC | CCGGGACGCC | GCCTCTCAAC | AACTGCATGC | ATATG | | 225 |

( 2 ) INFORMATION FOR SEQ ID NO:276:

( i ) SEQUENCE CHARACTERISTICS:
        ( A ) LENGTH: 192 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Y12-15-1 NS3 clone DNA ( x i ) SEQUENCE DESCRIPTION: SEQ ID NO:276:

```
AACATGGGGC ACAAGGTCTT AATCTTGAAC CCCTCAGTGG CCACTGTGCG GGCCATGGGC     60
CCGTACATGG AGCGGCTGGC GGGTAAACAT CCAAGTATAT ACTGTGGGCA TGATACAACT    120
GCTTTCACAA GGATCACTGA CTCCCCCCTG ACGTATTCAA CCTATGGGAG GTTTTTGGCC    180
AACCCTAGGC AA                                                        192
```

( 2 ) INFORMATION FOR SEQ ID NO:277:

( i ) SEQUENCE CHARACTERISTICS:
        ( A ) LENGTH: 264 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Y12-10-2 NS3 clone ( x i ) SEQUENCE DESCRIPTION: SEQ ID NO:277:

```
CCCCTCGAGC GGATGCGAAC CGGAAGGCAC CTCGTGTTCT GCCATTCTAA GGCTGAGTGC     60
GAGCGCCTTG CTGGCCAGTT CTCCGCTAGG GGGGTCAATG CCATTGCCTA TTATAGGGGT    120
AAAGACAGCT CTATCATCAA GGATGGGGAC CTGGTGGTCT GTGCTACAGA CGCGCTTTCC    180
ACTGGGTACA CTGGAAATTT CGACTCCGTC ACCGACTGTG GATTAGTGGT GGAGGAGGTC    240
GTTGAGGTGA CCCTTGATCC CACC                                           264
```

It is claimed:

1. A Non-A Non-B Non-C Non-D Non-E Hepatitis Virus (HGV) immunogenic composition, comprising a purified HGV polypeptide antigen at least 10 amino acids in length which is specifically immunoreactive with HGV-positive sera, present in a suitable carrier, where HGV is characterized by:(i) production of elevated serum alanine aminotransferase levels in an infected primate, (ii) its serological distinction from hepatitis A virus (HAV), hepatitis B virus (HBV), hepatitis C virus (HCV), hepatitis D virus, and hepatitis E virus (HEV), (iii) membership in the virus family Flaviviridae and (iv) a viral genome comprising a polynucleotide region that is selectively hybridizable with SEQ ID NO:19.

2. A composition of claim 1, where said polypeptide antigen is recombinantly produced.

3. A composition of claim 1, where said polypeptide antigen is chemically synthesized.

4. A composition of claim 1, where said antigen is encoded by a series of polynucleotides contained within the region extending from base 1149 to base 2183 of SEQ ID NO:14.

5. A composition of claim 1, where the amino acid sequence of said antigen is contained within the region extending from amino acids 231 to 575 of SEQ ID NO:15.

6. A composition of claim 1, where the amino acid sequence of said antigen has at least 65% sequence identity to the 2873 amino acid sequence of SEQ ID NO:15.

\* \* \* \* \*